US012655347B2

(12) United States Patent
Doh et al.

(10) Patent No.: US 12,655,347 B2
(45) Date of Patent: Jun. 16, 2026

(54) PLURALITY OF LIGHT-EMITTING MATERIALS, ORGANIC ELECTROLUMINESCENT COMPOUND, AND ORGANIC ELECTROLUMINESCENT DEVICE COMPRISING THE SAME

(71) Applicants: DuPont Specialty Materials Korea Ltd., Chungcheongnam-do (KR); DuPont Electronics, Inc, Wilmington, DE (US)

(72) Inventors: Yoo-Jin Doh, Gyeonggi-do (KR); Chi-Sik Kim, Gyeonggi-do (KR); Soo-Yong Lee, Gyeonggi-do (KR); Seung-Hoon Yoo, Gyeonggi-do (KR); Viacheslav V Diev, Wilmington, DE (US); Charles D McLaren, Landenberg, PA (US); Yunlong Zou, Newark, DE (US); Mi-Ran Seo, Gyeonggi-do (KR); Denis Yurievich Kondakov, Wilmington, DE (US)

(73) Assignees: DuPont Specialty Materials Korea Ltd. (KR); DuPont Electronics, Inc

( * ) Notice: Subject to any disclaimer, the term of this patent is extended or adjusted under 35 U.S.C. 154(b) by 0 days.

(21) Appl. No.: 18/745,074

(22) Filed: Jun. 17, 2024

(65) Prior Publication Data

US 2024/0349606 A1 Oct. 17, 2024

Related U.S. Application Data

(62) Division of application No. 17/347,249, filed on Jun. 14, 2021, now Pat. No. 12,096,687.

(60) Provisional application No. 63/054,910, filed on Jul. 22, 2020.

(51) Int. Cl.
*C09K 11/06* (2006.01)
*C07D 307/77* (2006.01)
*H10K 85/60* (2023.01)
*H10K 50/11* (2023.01)

(52) U.S. Cl.
CPC ............ *C09K 11/06* (2013.01); *C07D 307/77* (2013.01); *H10K 85/615* (2023.02); *H10K 85/6574* (2023.02); *H10K 85/658* (2023.02); *C09K 2211/1018* (2013.01); *H10K 50/11* (2023.02)

(58) Field of Classification Search
CPC ............ C09K 11/06; C09K 2211/1018; C09K 2211/1011; C09K 2211/1014; C09K 2211/1029; C09K 2211/1033; C09K 2211/1037; C09K 2211/1085; C09K 2211/1088; C09K 2211/1092; C09K 2211/1048; C09K 2211/1051; C07D 307/77; H10K 85/615; H10K 85/6574; H10K 85/658; H10K 50/11; H10K 85/657; H10K 85/6576; H10K 85/633; H10K 85/636; H10K 85/40; H10K 85/622; H10K 85/624; H10K 85/6572; H10K 85/631; H10K 50/12; C07C 2603/24; C07C 2603/40
USPC .................................................... 252/301.16
See application file for complete search history.

(56) References Cited

U.S. PATENT DOCUMENTS

2014/0239273 A1* 8/2014 Mizutani ............. H10K 85/626
544/242

FOREIGN PATENT DOCUMENTS

WO 2020071479 A1 4/2020

OTHER PUBLICATIONS

Notice of the 1st Office Action from China National Intellectual Property Administration for Chinese patent application No. 202110827798.7; Application Date: Jul. 21, 2021.

* cited by examiner

*Primary Examiner* — Prem C Singh
*Assistant Examiner* — Francis C Campanell
(74) *Attorney, Agent, or Firm* — G. Creston Campbell

(57) ABSTRACT

The present disclosure relates to a plurality of light-emitting materials, an organic electroluminescent compound, and an organic electroluminescent device comprising the same. By comprising the organic electroluminescent compound or a specific combination of compounds according to the present disclosure as a host material and/or a dopant material, it is possible to provide an organic electroluminescent device having improved driving voltage, luminous efficiency and/or lifetime properties compared to conventional organic electroluminescent devices.

8 Claims, No Drawings

PLURALITY OF LIGHT-EMITTING MATERIALS, ORGANIC ELECTROLUMINESCENT COMPOUND, AND ORGANIC ELECTROLUMINESCENT DEVICE COMPRISING THE SAME

CLAIM OF BENEFIT OF PRIOR APPLICATION

This application is a divisional of prior application Ser. No. 17/347,249 filed Jun. 14, 2021 which claims the benefit of U.S. Provisional application No. 63/054,910 filed Jul. 22, 2020; both of which are incorporated by reference herein in their entirety.

TECHNICAL FIELD

The present disclosure relates to a plurality of light-emitting materials, an organic electroluminescent compound, and an organic electroluminescent device comprising the same.

BACKGROUND ART

An electroluminescent device (EL device) is a self-light-emitting display device which has advantages in that it provides a wider viewing angle, a greater contrast ratio, and a faster response time. The first organic EL device was developed by Eastman Kodak in 1987, by using small aromatic diamine molecules and aluminum complexes as materials for forming a light-emitting layer (see Appl. Phys. Lett. 51, 913, 1987).

An organic electroluminescent device (OLED) changes electric energy into light by applying electricity to an organic electroluminescent material, and commonly comprises an anode, a cathode, and an organic layer formed between the two electrodes. The organic layer of the OLED may comprise a hole injection layer, a hole transport layer, a hole auxiliary layer, a light-emitting auxiliary layer, an electron blocking layer, a light-emitting layer, an electron buffer layer, a hole blocking layer, an electron transport layer, an electron injection layer, etc. The materials used in the organic layer can be classified into a hole injection material, a hole transport material, a hole auxiliary material, a light-emitting auxiliary material, an electron blocking material, a light-emitting material (including a host material and a dopant material), an electron buffer material, a hole blocking material, an electron transport material, an electron injection material, etc., depending on their functions. In the OLED, holes from the anode and electrons from the cathode are injected into a light-emitting layer by the application of electric voltage, and excitons having high energy are produced by the recombination of the holes and electrons. The organic light-emitting compound moves into an excited state by the energy and emits light using the energy when the organic light-emitting compound returns to the ground state from the excited state.

Recently, as displays have become large-scale, there is a need for light-emitting materials capable of exhibiting more delicate and vivid colors. Particularly, in the case of blue light-emitting materials, materials such as ADN and DPVBi are used as host materials, and materials such as aromatic amine-based compounds, copper phthalocyanine compounds, carbazole-based derivatives, perylene-based derivatives, coumarin-based derivatives, pyrene-based derivatives are used as dopant materials, but it is difficult to obtain a deep blue with high color purity, and as the wavelength becomes shorter, the light emission lifetime becomes shorter.

Accordingly, in order to implement a full color display, there is a demand for the development of a deep blue light-emitting material having a long lifetime and development of other organic materials having energy levels matched with the blue light-emitting material.

Chinese Patent Appl. Laid-Open No. 110294663 A (published on Oct. 1, 2019) and Korean Patent Appl. Laid-Open No. 2019-0094038 A (published on Aug. 12, 2019) disclose anthracene derivative compounds. However, the development for improving performance of an OLED is still required.

DISCLOSURE OF INVENTION

Technical Problem

The objective of the present disclosure is to provide an organic electroluminescent material capable of providing an organic electroluminescent device having improved luminous efficiency and/or longer lifetime properties. Another objective of the present disclosure is to provide an organic electroluminescent compound having a new structure suitable to an organic electroluminescent device. A further objective of the present disclosure is to provide an organic electroluminescent device having improved driving voltage, luminous efficiency and/or lifetime properties by comprising a specific compound or a specific combination of compounds as a host material and/or a dopant material.

Solution to Problem

As a result of intensive studies to solve the technical problem above, the present inventors found that the above objective can be achieved by using an organic electroluminescent compound represented by the following formula 1 or 11. In addition, the present inventors found that the above objective can be achieved by a plurality of light-emitting materials comprising at least one first compound represented by the following formula 1 and at least one second compound represented by the following formula 2.

(1)

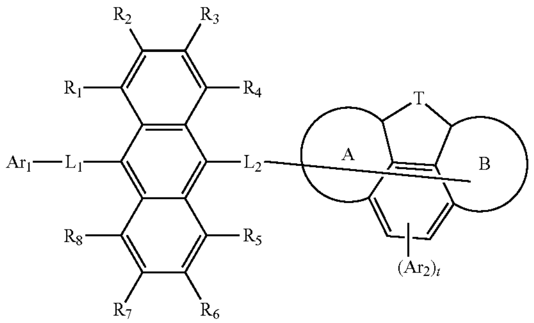

In formula 1,

T represents O, S, or $CR_9R_{10}$;

ring A and ring B, each independently, represent a substituted or unsubstituted (C6-C30)aryl, or a substituted or unsubstituted (3- to 30-membered) heteroaryl;

$R_1$ to $R_{10}$, each independently, represent hydrogen, deuterium, a halogen, a cyano, a substituted or unsubstituted (C1-C30)alkyl, a substituted or unsubstituted (C6-C30)aryl, a substituted or unsubstituted (3- to 30-membered) heteroaryl, a substituted or unsubstituted (C3-C30)cycloalkyl, a substituted or unsubstituted (C1-C30)alkoxy, a substituted or unsubstituted tri (C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri (C6-C30)arylsilyl, a substituted or unsubstituted fused ring group of a (C3-C30) aliphatic ring(s) and a (C6-C30) aromatic ring(s), or -$L_3$-N($Ar_{11}$)($Ar_{12}$);

$L_1$ to $L_3$, each independently, represent a single bond, a substituted or unsubstituted (C6-C30)arylene, or a substituted or unsubstituted (3- to 30-membered) heteroarylene;

$Ar_1$ represents a substituted or unsubstituted (C6-C30) aryl, or a substituted or unsubstituted (3- to 30-membered) heteroaryl;

$Ar_2$, $Ar_{11}$, and $Ar_{12}$, each independently, represent hydrogen, deuterium, a halogen, a cyano, a substituted or unsubstituted (C1-C30)alkyl, a substituted or unsubstituted (C2-C30)alkenyl, a substituted or unsubstituted (C6-C30)aryl, a substituted or unsubstituted (3- to 30-membered) heteroaryl, a substituted or unsubstituted (C3-C30)cycloalkyl, a substituted or unsubstituted (C1-C30)alkoxy, a substituted or unsubstituted fused ring group of a (C3-C30) aliphatic ring(s) and a (C6-C30) aromatic ring(s), a substituted or unsubstituted tri (C1-C30)alkylsilyl, a substituted or unsubstituted di(C1-C30)alkyl(C6-C30)arylsilyl, a substituted or unsubstituted (C1-C30)alkyldi(C6-C30)arylsilyl, or a substituted or unsubstituted tri (C6-C30)arylsilyl; and t represents an integer of 1 or 2, in which if t is 2, each of $Ar_2$ may be the same or different.

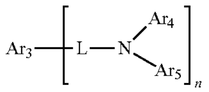

(2)

In formula 2,

L, each independently, represents a single bond, a substituted or unsubstituted (C6-C30)arylene, or a substituted or unsubstituted (3- to 30-membered) heteroarylene;

$Ar_4$ and $Ar_5$, each independently, represent a substituted or unsubstituted (C1-C30)alkyl, a substituted or unsubstituted (C6-C30)aryl, a substituted or unsubstituted (3- to 30-membered) heteroaryl, a substituted or unsubstituted (C3-C30)cycloalkyl, a substituted or unsubstituted (C1-C30)alkoxy, a substituted or unsubstituted tri (C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri (C6-C30)arylsilyl, a substituted or unsubstituted fused ring group of a (C3-C30) aliphatic ring(s) and a (C6-C30) aromatic ring(s), or -$L_4$-N($Ar_{13}$)($Ar_{14}$); or $Ar_4$ and $Ar_5$ may be linked to each other to form a ring(s);

n represents an integer of 0 to 2, in which if n is 0, $Ar_3$ is represented by the following formula 2-1, and if n is 2,

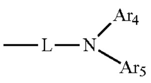

may be the same or different; and $Ar_3$ is represented by any one of the following formulas 2-1 to 2-5, with the proviso that if in formula 1, both ring A and ring B represent a C6 aryl, $L_2$ represents a single bond, and T represents $CR_9R_{10}$, $Ar_3$ is represented by any one of the following formulas 2-1, 2-3, 2-4 and 2-5:

(2-1)

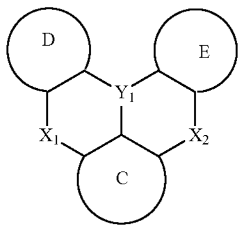

(2-2)

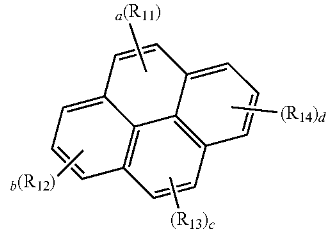

(2-3)

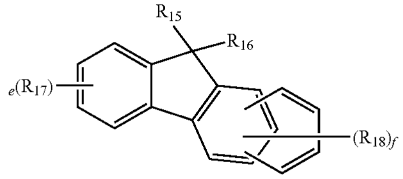

(2-4)

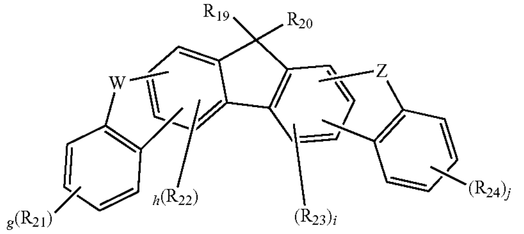

(2-5)

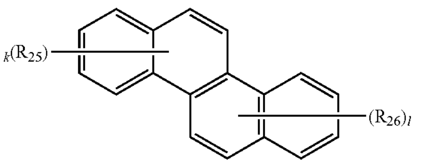

wherein, $Y_1$ represents B;

$X_1$ and $X_2$, each independently, represent NR', O or S;

W and Z, each independently, represent O, S, NR' or $CR_{27}R_{28}$;

R', each independently, represents hydrogen, deuterium, a halogen, a cyano, a substituted or unsubstituted (C1-C30)alkyl, a substituted or unsubstituted (C6-C30)aryl, a substituted or unsubstituted (3- to 30-membered) heteroaryl, a substituted or unsubstituted (C3-C30) cycloalkyl, a substituted or unsubstituted (C1-C30) alkoxy, a substituted or unsubstituted tri (C1-C30) alkylsilyl, a substituted or unsubstituted di(C1-C30) alkyl(C6-C30)arylsilyl, a substituted or unsubstituted (C1-C30)alkyldi(C6-C30)arylsilyl, a substituted or unsubstituted tri (C6-C30)arylsilyl, a substituted or unsubstituted fused ring group of a (C3-C30) aliphatic ring(s) and a (C6-C30) aromatic ring(s), or $-L_4-N(Ar_{13})(Ar_{14})$; and R' may be linked to at least one of ring C, ring D and ring E, directly or via B, O, S or $CR_{27}R_{28}$ as a linker, to form a ring(s);

ring C, ring D, and ring E, each independently, represent a substituted or unsubstituted (C6-C30)aryl, or a substituted or unsubstituted (3- to 50-membered) heteroaryl; and ring D and ring E may be linked to each other directly or via B, O, S or $CR_{27}R_{28}$ as a linker to form a ring(s);

$R_{11}$ to $R_{14}$. $R_{17}$, $R_{18}$, and $R_{21}$ to $R_{26}$, each independently, represent hydrogen, deuterium, a halogen, a cyano, a substituted or unsubstituted (C1-C30)alkyl, a substituted or unsubstituted (C6-C30)aryl, a substituted or unsubstituted (3- to 30-membered) heteroaryl, a substituted or unsubstituted (C3-C30)cycloalkyl, a substituted or unsubstituted (C1-C30)alkoxy, a substituted or unsubstituted tri (C1-C30)alkylsilyl, a substituted or unsubstituted di(C1-C30)alkyl(C6-C30)arylsilyl, a substituted or unsubstituted (C1-C30)alkyldi(C6-C30) arylsilyl, a substituted or unsubstituted tri (C6-C30) arylsilyl, a substituted or unsubstituted fused ring group of a (C3-C30) aliphatic ring(s) and a (C6-C30) aromatic ring(s), or $-L_4-N(Ar_{13})(Ar_{14})$;

$R_{15}$, $R_{16}$, $R_{19}$, $R_{20}$, $R_{27}$, and $R_{28}$, each independently, represent a substituted or unsubstituted (C1-C30)alkyl, a substituted or unsubstituted (C6-C30)aryl, or a substituted or unsubstituted (3- to 30-membered) heteroaryl; and at least one of $R_{15}$ and $R_{16}$, $R_{19}$ and $R_{20}$, and $R_{27}$ and $R_{28}$ may be fused to each other to form a spiro structure;

$L_4$, each independently, represents a single bond, a substituted or unsubstituted (C6-C30)arylene, a substituted or unsubstituted (3- to 30-membered) heteroarylene, a substituted or unsubstituted divalent (C2-C30) aliphatic hydrocarbon group, or a substituted or unsubstituted divalent fused ring group of a (C3-C30) aliphatic ring(s) and a (C6-C30) aromatic ring(s);

$Ar_{13}$ and $Ar_{14}$, each independently, represent a substituted or unsubstituted (C1-C30)alkyl, a substituted or unsubstituted (C2-C30)alkenyl, a substituted or unsubstituted (C6-C30)aryl, or a substituted or unsubstituted (3- to 30-membered) heteroaryl; and a, c, h, and i, each independently, represent an integer of 1 or 2; b and d, each independently, represent an integer of 1 to 3; f, k, and l, each independently, represent an integer of 1 to 6; and e, g, and j, each independently, represent an integer of 1 to 4, in which if a to l, each independently, are an integer of 2 or more, each of $R_{11}$, each of $R_{12}$, each of $R_{13}$, each of $R_{14}$, each of $R_{17}$, each of $R_{18}$, each of $R_{21}$, each of $R_{22}$, each of $R_{23}$, each of $R_{24}$, each of $R_{25}$, or each of $R_{26}$ may be the same or different.

Advantageous Effects of Invention

The organic electroluminescent compound according to the present disclosure can exhibit performances suitable to be used in an organic electroluminescent device. In addition, by comprising the plurality of light-emitting materials according to the present disclosure, it is possible to provide an organic electroluminescent device having higher luminous efficiency and/or longer lifetime properties compared to conventional organic electroluminescent devices.

Mode for the Invention

Hereinafter, the present disclosure will be described in detail. However, the following description is intended to explain the disclosure, and is not meant in any way to restrict the scope of the disclosure.

The term "an organic electroluminescent compound" in the present disclosure means a compound that may be used in an organic electroluminescent device. If necessary, the organic electroluminescent compound may be comprised in any layers constituting an organic electroluminescent device.

The term "an organic electroluminescent material" in the present disclosure means a material that may be used in an organic electroluminescent device, and may comprise at least one compound. If necessary, the organic electroluminescent material may be comprised in any layers constituting an organic electroluminescent device. For example, the organic electroluminescent material may be a hole injection material, a hole transport material, a hole auxiliary material, a light-emitting auxiliary material, an electron blocking material, a light-emitting material (including a host material and a dopant material), an electron buffer material, a hole blocking material, an electron transport material, an electron injection material, etc.

The term "a plurality of light-emitting materials" in the present disclosure means a host material(s) and/or a dopant material(s), comprising a combination of at least two compounds, which may be comprised in any light-emitting layer constituting an organic electroluminescent device. It may mean both a material before being comprised in an organic electroluminescent device (for example, before vapor deposition) and a material after being comprised in an organic electroluminescent device (for example, after vapor deposition). For example, the plurality of light-emitting materials of the present disclosure may be a combination of one or more host materials and one or more dopant materials, and may optionally further include a conventional material comprised in organic electroluminescent materials. The two or more compounds comprised in the plurality of light-emitting materials of the present disclosure may be included in one light-emitting layer or may be respectively included in different light-emitting layers by means of the methods used in the art. For example, the two or more compounds may be mixture-evaporated or co-evaporated, or individually deposited.

Herein, the term "(C1-C30)alkyl" is meant to be a linear or branched alkyl having 1 to 30 carbon atoms constituting the chain, in which the number of carbon atoms is preferably 1 to 20, and more preferably 1 to 10. The above alkyl may include methyl, ethyl, n-propyl, isopropyl, n-butyl, isobutyl, tert-butyl, sec-butyl, etc. The term "(C2-C30)alkenyl" is meant to be a linear or branched alkenyl having 2 to 30 carbon atoms constituting the chain, in which the number of carbon atoms is preferably 2 to 20, and more preferably 2 to 10. The above alkenyl may include vinyl, 1-propenyl, 2-propenyl, 1-butenyl, 2-butenyl, 3-butenyl, 2-methylbut-2-enyl, etc. The term "(C2-C30)alkynyl" is meant to be a linear or branched alkynyl having 2 to 30 carbon atoms constituting the chain, in which the number of carbon atoms is preferably 2 to 20, and more preferably 2 to 10. The above alkynyl may include ethynyl, 1-propynyl, 2-propynyl, 1-butynyl, 2-butynyl, 3-butynyl, 1-methylpent-2-ynyl, etc. The term "(C3-C30)cycloalkyl" is meant to be a mono- or polycyclic hydrocarbon having 3 to 30 ring backbone carbon atoms, in which the number of carbon atoms is preferably 3 to 20, and more preferably 3 to 7. The above cycloalkyl may include cyclopropyl, cyclobutyl, cyclopentyl, cyclohexyl, cyclopentylmethyl, cyclohexylmethyl, etc. The term "(3- to 7-membered) heterocycloalkyl" is meant to be a cycloalkyl having 3 to 7, preferably 5 to 7, ring backbone atoms, and including at least one heteroatom selected from the group consisting of B, N, O, S, Si, and P, and preferably the group consisting of O, S, and N. The above heterocycloalkyl may include tetrahydrofuran, pyrrolidine, thiolan, tetrahydropyran, etc. The term "(C6-C30)aryl(ene)" is meant to be a monocyclic or fused ring radical derived from an aromatic hydrocarbon having 6 to 30 ring backbone carbon atoms. The above aryl(ene) may be partially saturated, and may comprise a spiro structure. The number of ring backbone carbon atoms is preferably 6 to 25, and more preferably 6 to 18. The above aryl may include phenyl, biphenyl, terphenyl, naphthyl, binaphthyl, phenylnaphthyl, naphthylphenyl, phenylterphenyl, fluorenyl, phenylfluorenyl, benzofluorenyl, dibenzofluorenyl, phenanthrenyl, phenylphenanthrenyl, anthracenyl, indenyl, triphenylenyl, pyrenyl, tetracenyl, perylenyl, chrysenyl, naphthacenyl, fluoranthenyl, spirobifluorenyl, azulenyl, tetramethyldihydrophenanthrenyl, etc. More specifically, the aryl may include phenyl, 1-naphthyl, 2-naphthyl, 1-anthryl, 2-anthryl, 9-anthryl, benzanthryl, 1-phenanthryl, 2-phenanthryl, 3-phenanthryl, 4-phenanthryl, 9-phenanthryl, naphthacenyl, pyrenyl, 1-chrysenyl, 2-chrysenyl, 3-chrysenyl, 4-chrysenyl, 5-chrysenyl, 6-chrysenyl, benzo[c]phenanthryl, benzo[g]chrysenyl, 1-triphenylenyl, 2-triphenylenyl, 3-triphenylenyl, 4-triphenylenyl, 1-fluorenyl, 2-fluorenyl, 3-fluorenyl, 4-fluorenyl, 9-fluorenyl, benzo[a]fluorenyl, benzo[b]fluorenyl, benzo[c]fluorenyl, dibenzofluorenyl, 2-biphenylyl, 3-biphenylyl, 4-biphenylyl, o-terphenyl, m-terphenyl-4-yl, m-terphenyl-3-yl, m-terphenyl-2-yl, p-terphenyl-4-yl, p-terphenyl-3-yl, p-terphenyl-2-yl, m-quaterphenyl, 3-fluoranthenyl, 4-fluoranthenyl, 8-fluoranthenyl, 9-fluoranthenyl, benzofluoranthenyl, o-tolyl, m-tolyl, p-tolyl, 2,3-xylyl, 3,4-xylyl, 2,5-xylyl, mesityl, o-cumenyl, m-cumenyl, p-cumenyl, p-tert-butylphenyl, p-(2-phenylpropyl)phenyl, 4'-methylbiphenylyl, 4"-tert-butyl-p-terphenyl-4-yl, 9,9-dimethyl-1-fluorenyl, 9,9-dimethyl-2-fluorenyl, 9,9-dimethyl-3-fluorenyl, 9,9-dimethyl-4-fluorenyl, 9,9-diphenyl-1-fluorenyl, 9,9-diphenyl-2-fluorenyl, 9,9-diphenyl-3-fluorenyl, 9,9-diphenyl-4-fluorenyl, 11,11-dimethyl-1-benzo[a]fluorenyl, 11,11-dimethyl-2-benzo[a]fluorenyl, 11,11-dimethyl-3-benzo[a]fluorenyl, 11,11-dimethyl-4-benzo[a]fluorenyl, 11,11-dimethyl-5-benzo[a]fluorenyl, 11,11-dimethyl-6-benzo[a]fluorenyl, 11,11-dimethyl-7-benzo[a]fluorenyl, 11,11-dimethyl-8-benzo[a]fluorenyl, 11,11-dimethyl-9-benzo[a]fluorenyl, 11,11-dimethyl-10-benzo[a]fluorenyl, 11,11-dimethyl-1-benzo[b]fluorenyl, 11,11-dimethyl-2-benzo[b]fluorenyl, 11,11-dimethyl-3-benzo[b]fluorenyl, 11,11-dimethyl-4-benzo[b]fluorenyl, 11,11-dimethyl-5-benzo[b]fluorenyl, 11,11-dimethyl-6-benzo[b]fluorenyl, 11,11-dimethyl-7-benzo[b]fluorenyl, 11,11-dimethyl-8-benzo[b]fluorenyl, 11,11-dimethyl-9-benzo[b]fluorenyl, 11,11-dimethyl-10-benzo[b]fluorenyl, 11,11-dimethyl-1-benzo[c]fluorenyl, 11,11-dimethyl-2-benzo[c]fluorenyl, 11,11-dimethyl-3-benzo[c]fluorenyl, 11,11-dimethyl-4-benzo[c]fluorenyl, 11,11-dimethyl-5-benzo[c]fluorenyl, 11,11-dimethyl-6-benzo[c]fluorenyl, 11,11-dimethyl-7-benzo[c]fluorenyl, 11,11-dimethyl-8-benzo[c]fluorenyl, 11,11-dimethyl-9-benzo[c]fluorenyl, 11,11-dimethyl-10-benzo[c]fluorenyl, 11,11-diphenyl-1-benzo[a]fluorenyl, 11,11-diphenyl-2-benzo[a]fluorenyl, 11,11-diphenyl-3-benzo[a]fluorenyl, 11,11-diphenyl-4-benzo[a]fluorenyl, 11,11-diphenyl-5-benzo[a]fluorenyl, 11,11-diphenyl-6-benzo[a]fluorenyl, 11,11-diphenyl-7-benzo[a]fluorenyl, 11,11-diphenyl-8-benzo[a]fluorenyl, 11,11-diphenyl-9-benzo[a]fluorenyl, 11,11-diphenyl-10-benzo[a]fluorenyl, 11,11-diphenyl-1-benzo[b]fluorenyl, 11,11-diphenyl-2-benzo[b]fluorenyl, 11,11-diphenyl-3-benzo[b]fluorenyl, 11,11-diphenyl-4-benzo[b]fluorenyl, 11,11-diphenyl-5-benzo[b]fluorenyl, 11,11-diphenyl-6-benzo[b]fluorenyl, 11,11-diphenyl-7-benzo[b]fluorenyl, 11,11-diphenyl-8-benzo[b]fluorenyl, 11,11-diphenyl-9-benzo[b]fluorenyl, 11,11-diphenyl-10-benzo[b]fluorenyl, 11,11-diphenyl-1-benzo[c]fluorenyl, 11,11-diphenyl-2-benzo[c]fluorenyl, 11,11-diphenyl-3-benzo[c]fluorenyl, 11,11-diphenyl-4-benzo[c]fluorenyl, 11,11-diphenyl-5-benzo[c]fluorenyl, 11,11-diphenyl-6-benzo[c]fluorenyl, 11,11-diphenyl-7-benzo[c]fluorenyl, 11,11-diphenyl-8-benzo[c]fluorenyl, 11,11-diphenyl-9-benzo[c]fluorenyl, 11,11-diphenyl-10-benzo[c]fluorenyl, 9,9,10,10-tetramethyl-9,10-dihydro-1-phenanthrenyl, 9,9,10,10-tetramethyl-9,10-dihydro-2-phenanthrenyl, 9,9,10,10-tetramethyl-9,10-dihydro-3-phenanthrenyl, 9,9,10,10-tetramethyl-9,10-dihydro-4-phenanthrenyl, etc.

The term "(3- to 30-membered) heteroaryl(ene)" or "(3- to 50-membered) heteroaryl(ene)" is an aryl(ene) having 3 to 30 ring backbone atoms or 3 to 50 ring backbone atoms, and including at least one, preferably 1 to 4 heteroatoms selected from the group consisting of B, N, O, S, Si, and P. The above heteroaryl(ene) may be a monocyclic ring, or a fused ring condensed with at least one benzene ring; may be partially saturated; may be one formed by linking at least one heteroaryl or aryl group to a heteroaryl group via a single bond(s); and may comprise a spiro structure. The above heteroaryl may include a monocyclic ring-type heteroaryl such as furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl, etc., and a fused ring-type heteroaryl such as benzofuranyl, benzothiophenyl, isobenzofuranyl, dibenzofuranyl, dibenzothiophenyl, dibenzoselenophenyl, naphthobenzofuranyl, naphthobenzothiophenyl, benzofuroquinolinyl, benzofuroquinazolinyl, benzofuronaphthyridinyl, benzofuropyrimidinyl, naphthofuropyrimidinyl, benzothienoquinolinyl, benzothienoquinazolinyl, benzothienonaphthyridinyl, benzothienopyrimidinyl, naphthothienopyrimidinyl, pyrimidoindolyl, benzopyrimidoindolyl, benzofuropyrazinyl, naphthofuropyrazinyl, benzothienopyrazinyl, naphthothienopyrazinyl, pyrazinoindolyl, benzopyrazinoindolyl, benzimidazolyl, benzothiazolyl, benzoisothiazolyl, benzoisoxazolyl, benzoxazolyl, isoindolyl, indolyl, benzoindolyl, indazolyl, benzothiadiazolyl, quinolyl, isoquinolyl, cinnolinyl, quinazolinyl, benzoquinazolinyl, quinoxalinyl, benzoquinoxalinyl, naphthyridinyl, carbazolyl, benzocarbazolyl, dibenzocarbazolyl, phenoxazinyl, phenothiazinyl, phenanthridinyl, benzodioxolyl, dihydroacridinyl, benzotriazolphenazinyl, imidazopyridyl, chromenoquinazolinyl, thiochromenoquinazolinyl, dimethylbenzoperimidinyl, indolocarbazolyl, indenocarbazolyl, etc. More specifically, the heteroaryl may include 1-pyrrolyl, 2-pyrrolyl, 3-pyrrolyl, pyrazinyl, 2-pyridyl, 2-pyrimidinyl, 4-pyrimidinyl, 5-pyrimidinyl, 6-pyrimidinyl, 1,2,3-triazin-4-yl, 1,2,4-triazin-3-yl, 1,3,5-triazin-2-yl, 1-imidazolyl, 2-imidazolyl, 1-pyrazolyl, 1-indolidinyl, 2-indolidinyl, 3-indolidinyl, 5-indolidinyl, 6-indolidinyl, 7-indolidinyl, 8-indolidinyl, 2-imidazopyridyl, 3-imidazopyridyl, 5-imidazopyridyl, 6-imidazopyridyl, 7-imidazopyridyl, 8-imidazopyridyl, 3-pyridyl, 4-pyridyl, 1-indolyl, 2-indolyl, 3-indolyl, 4-indolyl, 5-indolyl, 6-indolyl, 7-indolyl, 1-isoindolyl, 2-isoindolyl, 3-isoindolyl, 4-isoindolyl, 5-isoindolyl, 6-isoindolyl, 7-isoindolyl, 2-furyl, 3-furyl, 2-benzofuranyl, 3-benzofuranyl, 4-benzofuranyl, 5-benzofuranyl, 6-benzofuranyl, 7-benzofuranyl, 1-isobenzofuranyl, 3-isobenzofuranyl, 4-isobenzofuranyl, 5-isobenzofuranyl, 6-isobenzofuranyl, 7-isobenzofuranyl, 2-quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 2-quinoxalinyl, 5-quinoxalinyl, 6-quinoxalinyl, 1-carbazolyl, 2-carbazolyl, 3-carbazolyl, 4-carbazolyl, 9-carbazolyl, azacarbazolyl-1-yl, azacarbazolyl-2-yl, azacarbazolyl-3-yl, azacarbazolyl-4-yl, azacarbazolyl-5-yl, azacarbazolyl-6-yl, azacarbazolyl-7-yl, azacarbazolyl-8-yl, azacarbazolyl-9-yl, 1-phenanthridinyl, 2-phenanthridinyl, 3-phenanthridinyl, 4-phenanthridinyl, 6-phenanthridinyl, 7-phenanthridinyl, 8-phenanthridinyl, 9-phenanthridinyl, 10-phenanthridinyl, 1-acridinyl, 2-acridinyl, 3-acridinyl, 4-acridinyl, 9-acridinyl, 2-oxazolyl, 4-oxazolyl, 5-oxazolyl, 2-oxadiazolyl, 5-oxadiazolyl, 3-furazanyl, 2-thienyl, 3-thienyl, 2-methylpyrrol-1-yl, 2-methylpyrrol-3-yl, 2-methylpyrrol-4-yl, 2-methylpyrrol-5-yl, 3-methylpyrrol-1-yl, 3-methylpyrrol-2-yl, 3-methylpyrrol-4-yl, 3-methylpyrrol-5-yl, 2-tert-butylpyrrol-4-yl, 3-(2-phenylpropyl) pyrrol-1-yl, 2-methyl-1-indolyl, 4-methyl-1-indolyl, 2-methyl-3-indolyl, 4-methyl-3-indolyl, 2-tert-butyl-1-indolyl, 4-tert-butyl-1-indolyl, 2-tert-butyl-3-indolyl, 4-tert-butyl-3-indolyl, 1-dibenzofuranyl, 2-dibenzofuranyl, 3-dibenzofuranyl, 4-dibenzofuranyl, 1-dibenzothiophenyl, 2-dibenzothiophenyl, 3-dibenzothiophenyl, 4-dibenzothiophenyl, 1-naphtho-[1,2-b]-benzofuranyl, 2-naphtho-[1,2-b]-benzofuranyl, 3-naphtho-[1,2-b]-benzofuranyl, 4-naphtho-[1,2-b]-benzofuranyl, 5-naphtho-[1,2-b]-benzofuranyl, 6-naphtho-[1,2-b]-benzofuranyl, 7-naphtho-[1,2-b]-benzofuranyl, 8-naphtho-[1,2-b]-benzofuranyl, 9-naphtho-[1,2-b]-benzofuranyl, 10-naphtho-[1,2-b]-benzofuranyl, 1-naphtho-[2,3-b]-benzofuranyl, 2-naphtho-[2,3-b]-benzofuranyl, 3-naphtho-[2,3-b]-benzofuranyl, 4-naphtho-[2,3-b]-benzofuranyl, 5-naphtho-[2,3-b]-benzofuranyl, 6-naphtho-[2,3-b]-benzofuranyl, 7-naphtho-[2,3-b]-benzofuranyl, 8-naphtho-[2,3-b]-benzofuranyl, 9-naphtho-[2,3-b]-benzofuranyl, 10-naphtho-[2,3-b]-benzofuranyl, 1-naphtho-[2,1-b]-benzofuranyl, 2-naphtho-[2,1-b]-benzofuranyl, 3-naphtho-[2,1-b]-benzofuranyl, 4-naphtho-[2,1-b]-benzofuranyl, 5-naphtho-[2,1-b]-benzofuranyl, 6-naphtho-[2,1-b]-benzofuranyl, 7-naphtho-[2,1-b]-benzofuranyl, 8-naphtho-[2,1-b]-benzofuranyl, 9-naphtho-[2,1-b]-benzofuranyl, 10-naphtho-[2,1-b]-benzofuranyl, 1-naphtho-[1,2-b]-benzothiophenyl, 2-naphtho-[1,2-b]-benzothiophenyl, 3-naphtho-[1,2-b]-benzothiophenyl, 4-naphtho-[1,2-b]-benzothiophenyl, 5-naphtho-[1,2-b]-benzothiophenyl, 6-naphtho-[1,2-b]-benzothiophenyl, 7-naphtho-[1,2-b]-benzothiophenyl, 8-naphtho-[1,2-b]-benzothiophenyl, 9-naphtho-[1,2-b]-benzothiophenyl, 10-naphtho-[1,2-b]-benzothiophenyl, 1-naphtho-[2,3-b]-benzothiophenyl, 2-naphtho-[2,3-b]-benzothiophenyl, 3-naphtho-[2,3-b]-benzothiophenyl, 4-naphtho-[2,3-b]-benzothiophenyl, 5-naphtho-[2,3-b]-benzothiophenyl, 1-naphtho-[2,1-b]-benzothiophenyl, 2-naphtho-[2,1-b]-benzothiophenyl, 3-naphtho-[2,1-b]-benzothiophenyl, 4-naphtho-[2,1-b]-benzothiophenyl, 5-naphtho-[2,1-b]-benzothiophenyl, 6-naphtho-[2,1-b]-benzothiophenyl, 7-naphtho-[2,1-b]-benzothiophenyl, 8-naphtho-[2,1-b]-benzothiophenyl, 9-naphtho-[2,1-b]-benzothiophenyl, 10-naphtho-[2,1-b]-benzothiophenyl, 2-benzofuro[3,2-d]pyrimidinyl, 6-benzofuro[3,2-d]pyrimidinyl, 7-benzofuro[3,2-d]pyrimidinyl, 8-benzofuro[3,2-d]pyrimidinyl, 9-benzofuro[3,2-d]pyrimidinyl, 2-benzothio[3,2-d]pyrimidinyl, 6-benzothio[3,2-d]pyrimidinyl, 7-benzothio[3,2-d]pyrimidinyl, 8-benzothio[3,2-d]pyrimidinyl, 9-benzothio[3,2-d]pyrimidinyl, 2-benzofuro[3,2-d]pyrazinyl, 6-benzofuro[3,2-d]pyrazinyl, 7-benzofuro[3,2-d]pyrazinyl, 8-benzofuro[3,2-d]pyrazinyl, 9-benzofuro[3,2-d]pyrazinyl, 2-benzothio[3,2-d]pyrazinyl, 6-benzothio[3,2-d]pyrazinyl, 7-benzothio[3,2-d]pyrazinyl, 8-benzothio[3,2-d]pyrazinyl, 9-benzothio[3,2-d]pyrazinyl, 1-silafluorenyl, 2-silafluorenyl, 3-silafluorenyl, 4-silafluorenyl, 1-germafluorenyl, 2-germafluorenyl, 3-germafluorenyl, 4-germafluorenyl, 1-dibenzoselenophenyl, 2-dibenzoselenophenyl, 3-dibenzoselenophenyl, 4-dibenzoselenophenyl, etc. "Halogen" includes F, Cl, Br, and I.

In addition, "ortho (o-)," "meta (m-)," and "para (p-)" are prefixes, which represent the relative positions of substituents, respectively. Ortho indicates that two substituents are adjacent to each other, and for example, when two substituents in a benzene derivative occupy positions 1 and 2, it is called an ortho position. Meta indicates that two substituents are at positions 1 and 3, and for example, when two substituents in a benzene derivative occupy positions 1 and 3, it is called a meta position. Para indicates that two substituents are at positions 1 and 4, and for example, when two substituents in a benzene derivative occupy positions 1 and 4, it is called a para position.

In the formulas of the present disclosure, a ring formed by a linkage of adjacent substituents means that at least two adjacent substituents are linked to or fused with each other to form a substituted or unsubstituted mono- or polycyclic (3- to 30-membered) alicyclic or aromatic ring, or the combination thereof; preferably, a substituted or unsubstituted mono- or polycyclic (5- to 25-membered) alicyclic or aromatic ring, or the combination thereof; more preferably, a substituted or unsubstituted mono- or polycyclic (5- to 18-membered) alicyclic or aromatic ring, or the combination thereof. Also, the ring may contain at least one heteroatom selected from B, N, O, S, Si, and P, preferably at least one heteroatom selected from N, O, and S.

Herein, "substituted" in the expression "substituted or unsubstituted" means that a hydrogen atom in a certain functional group is replaced with another atom or another functional group, i.e., a substituent, and also includes that the hydrogen atom is replaced with a group formed by a linkage of two or more substituents. For example, the group formed by a linkage of two or more substituents may be pyridine-triazine. That is, pyridine-triazine may be interpreted as a heteroaryl substituent, or as a substituent in which two heteroaryls are linked. In the present disclosure, the substituents of the substituted alkyl, the substituted alkenyl, the substituted aryl(ene), the substituted heteroaryl (ene), the substituted cycloalkyl, the substituted alkoxy, the substituted trialkylsilyl, the substituted dialkylarylsilyl, the substituted alkyldiarylsilyl, the substituted triarylsilyl, the substituted aliphatic hydrocarbon group, and the substituted fused ring group of a aliphatic ring(s) and a aromatic ring(s), each independently, are at least one selected from the group consisting of deuterium; a halogen; a cyano; a carboxyl; a nitro; a hydroxyl; a phosphineoxide; a (C1-C30)alkyl unsubstituted or substituted with at least one of deuterium(s) and a halogen(s); a halo(C1-C30)alkyl; a (C2-C30)alkenyl; a (C2-C30)alkynyl; a (C1-C30)alkoxy; a (C1-C30)alkylthio; a (C3-C30)cycloalkyl; a (C3-C30)cycloalkenyl; a (3- to 7-membered) heterocycloalkyl; a (C6-C30)aryloxy; a (C6-C30)arylthio; a (3- to 30-membered) heteroaryl unsubstituted or substituted with at least one of a (C1-C30)alkyl(s), a (C6-C30)aryl(s) and a di(C6-C30)arylamino(s); a (C6-C30)aryl unsubstituted or substituted with at least one of deuterium(s), a (C1-C30)alkyl(s), a (3- to 30-membered) heteroaryl(s) and a di(C6-C30)arylamino(s); a tri (C1-C30) alkylsilyl; a tri (C6-C30)arylsilyl; a di(C1-C30)alkyl(C6-C30)arylsilyl; a (C1-C30)alkyldi(C6-C30)arylsilyl; an amino; a mono- or di-(C1-C30)alkylamino; a mono- or di-(C2-C30)alkenylamino; a mono- or di-(C6-C30)arylamino unsubstituted or substituted with at least one of a (C1-C30)alkyl(s), a (3- to 30-membered) heteroaryl(s) and a di(C6-C30)arylamino(s); a mono- or di-(3- to 30-membered) heteroarylamino; a (C1-C30)alkyl(C2-C30)alkenylamino; a (C1-C30)alkyl(C6-C30)arylamino; a (C1-C30)alkyl(3- to 30-membered) heteroarylamino; a (C2-C30) alkenyl(C6-C30)arylamino; a (C2-C30)alkenyl(3- to 30-membered) heteroarylamino; a (C6-C30)aryl(3- to 30-membered) heteroarylamino unsubstituted or substituted with a (C6-C30)aryl(s); a (C1-C30)alkylcarbonyl; a (C1-C30)alkoxycarbonyl; a (C6-C30)arylcarbonyl; a (C6-C30) arylphosphine; a di(C6-C30)arylboronyl; a di(C1-C30)alkylboronyl; a (C1-C30)alkyl(C6-C30)arylboronyl; a (C6-C30)aryl(C1-C30)alkyl; and a (C1-C30)alkyl(C6-C30)aryl. According to one embodiment of the present disclosure, the substituents, each independently, are at least one selected from the group consisting of deuterium; a halogen; a cyano; a (C1-C20)alkyl unsubstituted or substituted with at least one of deuterium(s) and a halogen(s); a (5- to 25-membered) heteroaryl unsubstituted or substituted with a (C1-C20) alkyl(s); a (C6-C25)aryl unsubstituted or substituted with at least one of deuterium(s), a (C1-C20)alkyl(s), a (5- to 20-membered) heteroaryl(s) and a di(C6-C25)arylamino(s); a tri (C1-C20)alkylsilyl; a tri (C6-C25)arylsilyl; a (C1-C20) alkyldi(C6-C30)arylsilyl; a mono- or di-(C6-C25)arylamino unsubstituted or substituted with at least one of a (C1-C20) alkyl(s) and a di(C6-C25)arylamino(s); and a (C6-C25)aryl (5- to 20-membered) heteroarylamino unsubstituted or substituted with a (C6-C18)aryl(s). According to another embodiment of the present disclosure, the substituents, each independently, are at least one selected from the group consisting of deuterium; a halogen; a cyano; a (C1-C10) alkyl unsubstituted or substituted with at least one of deuterium(s) and a halogen(s); a (5- to 20-membered) heteroaryl unsubstituted or substituted with a (C1-C10)alkyl(s); a (C6-C18)aryl unsubstituted or substituted with at least one of deuterium(s), a (C1-C10)alkyl(s), a (5- to 20-membered) heteroaryl(s) and a di(C6-C18)arylamino(s); a tri (C1-C10) alkylsilyl; a tri (C6-C18)arylsilyl; a (C1-C10)alkyldi(C6-C18)arylsilyl; a mono- or di-(C6-C18)arylamino unsubstituted or substituted with at least one of a (C1-C10)alkyl(s) and a di(C6-C18)arylamino(s); and a (C6-C18)aryl(5- to 20-membered) heteroarylamino unsubstituted or substituted with a (C6-C18)aryl(s). For example, the substituents, each independently, may be at least one selected from the group consisting of deuterium; a cyano; a fluorine; a methyl unsubstituted or substituted with at least one of deuterium(s) and a fluorine(s); an ethyl; tert-butyl; a phenyl unsubstituted or substituted with at least one of deuterium(s), a methyl(s), a tert-butyl(s), a carbazolyl(s), a dibenzofuranyl(s), a diphenylamino(s), a phenoxazinyl(s), a phenothiazinyl(s), and a dihydroacridinyl(s) substituted with a methyl(s); a naphthyl; a biphenyl; a terphenyl; a triphenylenyl; a carbazolyl; a dibenzofuranyl; a phenoxazinyl; a phenothiazinyl; a dihydroacridinyl substituted with a methyl(s); a xanthenyl substituted with a methyl(s); a trimethylsilyl; a triphenylsilyl; a diphenylmethylsilyl; a diphenylamino unsubstituted or substituted with at least one of a methyl(s), a tert-butyl(s), and a diphenylamino(s); a phenylnaphthylamino; a phenylbiphenylamino unsubstituted or substituted with a tert-butyl(s); a dinaphthylamino; a dibiphenylamino; a phenyldibenzofuranylamino; and a carbazolylphenylamino substituted with a phenyl(s).

Herein, the heteroaryl, the heteroarylene, and the heterocycloalkyl, each independently, may contain at least one heteroatom selected from B, N, O, S, Si, and P. Also, the heteroatom may be bonded to at least one selected from the group consisting of hydrogen, deuterium, a halogen, a cyano, a substituted or unsubstituted (C1-C30)alkyl, a substituted or unsubstituted (C6-C30)aryl, a substituted or unsubstituted (3- to 30-membered) heteroaryl, a substituted or unsubstituted (C3-C30)cycloalkyl, a substituted or unsubstituted (C1-C30)alkoxy, a substituted or unsubstituted tri (C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri (C6-C30)arylsilyl, a substituted or unsubstituted mono- or di-(C1-C30)alkylamino, a substituted or unsubstituted mono- or di-(C6-C30)arylamino, and a substituted or unsubstituted (C1-C30)alkyl(C6-C30)arylamino.

Hereinafter, a plurality of light-emitting materials according to one embodiment will be explained.

A plurality of light-emitting materials according to one embodiment comprises at least one first compound represented by formula 1 and at least one second compound represented by formula 2. Specifically, the present disclosure provides an organic electroluminescent device exhibiting high luminous efficiency and/or long lifetime properties by comprising the plurality of light-emitting materials in at least one organic layer, for example, at least one light-emitting layer of the organic electroluminescent device. More specifically, the first compound and the second compound may be used together in the light-emitting layer to increase charge mobility and stability, thereby improving device efficiency such as external quantum efficiency and lifetime properties.

According to one embodiment, the present disclosure provides a host/dopant combination, i.e., a combination of the host compound represented by formula 1 and the dopant compound represented by formula 2. In addition, the present disclosure provides an organic electroluminescent device comprising the host/dopant combination.

The light-emitting material according to one embodiment includes at least one anthracene derivative represented by formula 1. For example, the compound represented by formula 1 may be a fluorescent host, and further, it may be a blue light-emitting fluorescent host.

In formula 1, T represents O, S, or $CR_9R_{10}$.

In formula 1, ring A and ring B, each independently, represent a substituted or unsubstituted (C6-C30)aryl, or a substituted or unsubstituted (3- to 30-membered) heteroaryl. According to one embodiment of the present disclosure, ring A and ring B, each independently, represent a substituted or unsubstituted (C6-C25)aryl, or a substituted or unsubstituted (5- to 25-membered) heteroaryl. According to another embodiment of the present disclosure, ring A and ring B, each independently, represent a (C6-C18)aryl unsubstituted or substituted with at least one of deuterium(s) and a (C1-C10)alkyl(s); or a (5- to 20-membered) heteroaryl unsubstituted or substituted with at least one of deuterium(s) and a (C6-C18)aryl(s). For example, ring A and ring B, each independently, may be a benzene ring unsubstituted or substituted with deuterium(s); a naphthalene ring unsubstituted or substituted with deuterium(s); a fluorene ring substituted with at least one of deuterium(s) and a methyl(s); a dibenzofurane ring substituted with deuterium(s); a carbazole ring substituted with at least one of deuterium(s) and a phenyl(s), etc.

In formula 1, $R_1$ to $R_{10}$, each independently, represent hydrogen, deuterium, a halogen, a cyano, a substituted or unsubstituted (C1-C30)alkyl, a substituted or unsubstituted (C6-C30)aryl, a substituted or unsubstituted (3- to 30-membered) heteroaryl, a substituted or unsubstituted (C3-C30) cycloalkyl, a substituted or unsubstituted (C1-C30)alkoxy, a substituted or unsubstituted tri (C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri (C6-C30)arylsilyl, a substituted or unsubstituted fused ring group of a (C3-C30) aliphatic ring(s) and a (C6-C30) aromatic ring(s), or $-L_3-N(Ar_{11})(Ar_{12})$. According to one embodiment of the present disclosure, $R_1$ to $R_{10}$, each independently, represent hydrogen, deuterium, a substituted or unsubstituted (C1-C20) alkyl, a substituted or unsubstituted (C6-C18)aryl, or a substituted or unsubstituted (5- to 20-membered) heteroaryl. According to another embodiment of the present disclosure, $R_1$ to $R_{10}$, each independently, represent hydrogen, deuterium, or a (C1-C10)alkyl unsubstituted or substituted with deuterium(s). For example, $R_1$ to $R_8$, each independently, may be hydrogen or deuterium; and $R_9$ and $R_{10}$, each independently, may be a methyl unsubstituted or substituted with deuterium(s).

In formula 1, $L_1$ to $L_3$, each independently, represent a single bond, a substituted or unsubstituted (C6-C30)arylene, or a substituted or unsubstituted (3- to 30-membered) heteroarylene. According to one embodiment of the present disclosure, $L_1$ to $L_3$, each independently, represent a single bond, a substituted or unsubstituted (C6-C25)arylene, or a substituted or unsubstituted (5- to 25-membered) heteroarylene. According to another embodiment of the present disclosure, $L_1$ to $L_3$, each independently, represent a single bond; a (C6-C18)arylene unsubstituted or substituted with at least one of deuterium(s) and a (C6-C18)aryl(s); or a (5- to 20-membered) heteroarylene unsubstituted or substituted with deuterium(s). For example, $L_1$ to $L_3$, each independently, may be a single bond; a phenylene unsubstituted or substituted with at least one of deuterium(s) and a phenyl(s); or a naphthylene unsubstituted or substituted with deuterium(s); a carbazolylene unsubstituted or substituted with deuterium(s), etc.

In formula 1, $Ar_1$, each independently, represents a substituted or unsubstituted (C6-C30)aryl, or a substituted or unsubstituted (3- to 30-membered) heteroaryl. According to one embodiment of the present disclosure, $Ar_1$, each independently, represents a substituted or unsubstituted (C6-C25)aryl, or a substituted or unsubstituted (5- to 25-membered) heteroaryl. According to another embodiment of the present disclosure, $Ar_1$, each independently, represents a (C6-C25)aryl unsubstituted or substituted with at least one of deuterium(s) and a (C1-C10)alkyl; or a (5- to 20-membered) heteroaryl unsubstituted or substituted with at least one of deuterium(s) and a (C6-C18)aryl(s). For example, $Ar_1$, each independently, may be a phenyl, a naphthyl, a biphenyl, a dimethylfluorenyl, a phenanthrenyl, a dimethylbenzofluorenyl, a terphenyl, a triphenylenyl, a spirobifluorenyl, a dibenzofuranyl, a dibenzothiophenyl, a carbazolyl, a phenylcarbazolyl, a benzonaphthofuranyl or a benzonaphthothiophenyl, unsubstituted or substituted with deuterium(s).

In formula 1, $Ar_2$, $Ar_{11}$, and $Ar_{12}$, each independently, represent hydrogen, deuterium, a halogen, a cyano, a substituted or unsubstituted (C1-C30)alkyl, a substituted or unsubstituted (C2-C30)alkenyl, a substituted or unsubstituted (C6-C30)aryl, a substituted or unsubstituted (3- to 30-membered) heteroaryl, a substituted or unsubstituted (C3-C30)cycloalkyl, a substituted or unsubstituted (C1-C30)alkoxy, a substituted or unsubstituted fused ring group of a (C3-C30) aliphatic ring(s) and a (C6-C30) aromatic ring(s), a substituted or unsubstituted tri (C1-C30)alkylsilyl, a substituted or unsubstituted di(C1-C30)alkyl(C6-C30)arylsilyl, a substituted or unsubstituted (C1-C30)alkyldi(C6-C30)arylsilyl, or a substituted or unsubstituted tri (C6-C30) arylsilyl. For example, $Ar_2$ may be hydrogen or deuterium.

In formula 1, t represents an integer of 1 or 2, in which if t is 2, each of $Ar_2$ may be the same or different.

According to one embodiment of the present disclosure, the formula 1 may be represented by at least one of the following formulas 1-1 and 1-2:

(1-1)

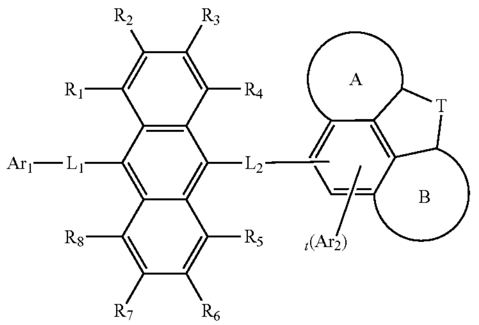

(1-2)

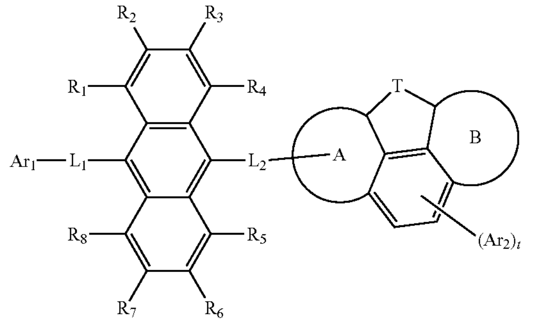

wherein $L_1$, $L_2$, $Ar_1$, $Ar_2$, T, ring A, ring B, $R_1$ to $R_8$, and t are as defined in formula 1.

In formula 2, L, each independently, represents a single bond, a substituted or unsubstituted (C6-C30)arylene, or a substituted or unsubstituted (3- to 30-membered) heteroarylene. According to one embodiment of the present disclosure, L, each independently, represents a single bond, or a substituted or unsubstituted (C6-C25)arylene. According to another embodiment of the present disclosure, L, each independently, represents a single bond, or a (C6-C25) arylene unsubstituted or substituted with a (C1-C10)alkyl(s). For example, L, each independently, may be a single bond; a phenylene; a naphthylene; or a fluorenylene substituted with an ethyl(s).

In formula 2, $Ar_4$ and $Ar_5$, each independently, represent a substituted or unsubstituted (C1-C30)alkyl, a substituted or unsubstituted (C6-C30)aryl, a substituted or unsubstituted (3- to 30-membered) heteroaryl, a substituted or unsubstituted (C3-C30)cycloalkyl, a substituted or unsubstituted (C1-C30)alkoxy, a substituted or unsubstituted tri (C1-C30) alkylsilyl, a substituted or unsubstituted di(C1-C30)alkyl (C6-C30)arylsilyl, a substituted or unsubstituted (C1-C30) alkyldi(C6-C30)arylsilyl, a substituted or unsubstituted tri (C6-C30)arylsilyl, a substituted or unsubstituted fused ring group of a (C3-C30) aliphatic ring(s) and a (C6-C30) aromatic ring(s), or $-L_4-N(Ar_{13})(Ar_{14})$; or $Ar_4$ and $Ar_5$ may be linked to each other to form a ring(s). According to one embodiment of the present disclosure, $Ar_4$ and $Ar_5$, each independently, represent a substituted or unsubstituted (C6-C25)aryl, or a substituted or unsubstituted (5- to 25-membered) heteroaryl; or $Ar_4$ and $Ar_5$ may be linked to each other to form a ring(s). According to another embodiment of the present disclosure, $Ar_4$ and $Ar_5$, each independently, represent a (C6-C18)aryl unsubstituted or substituted with at least one of deuterium(s), a halogen(s), a cyano(s), a (C1-C10) alkyl(s), a tri (C1-C10)alkylsilyl(s), a (C1-C30)alkyldi(C6-C30)arylsilyl(s), and a tri (C6-C30)arylsilyl(s); or a (5- to 20-membered) heteroaryl unsubstituted or substituted with a (C6-C18)aryl(s); or $Ar_4$ and $Ar_5$ may be linked to each other to form a ring(s). For example, Ara and $Ar_5$, each independently, may be a phenyl unsubstituted or substituted with at least one of deuterium(s), a fluorine(s), a cyano(s), a methyl(s), a methyl substituted with a fluorine(s), a tert-butyl(s), a trimethylsilyl(s), a triphenylsilyl(s), and a diphenylmethylsiliyl(s); a naphthyl; a biphenyl unsubstituted or substituted with at least one of deuterium(s), a fluorine(s), and a cyano(s); a naphthylphenyl unsubstituted or substituted with at least one of a fluorine(s) and a cyano(s); a dimethylfluorenyl; a terphenyl unsubstituted or substituted with at least one of a fluorine(s), a cyano(s), and a methyl(s); or a carbazolyl substituted with a phenyl(s), etc.; or $Ar_4$ and $Ar_5$ may be linked to each other to form a indoline ring unsubstituted or substituted with at least one of a fluorine(s), a cyano(s), and a methyl(s); a tetrahydroquinoline ring unsubstituted or substituted with at least one of a cyano(s) and a methyl(s); or an unsubstituted carbazole ring.

In formula 2, n represents an integer of 0 to 2, in which if n is 0, $Ar_3$ is represented by the formula 2-1, and if n is 2,

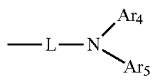

may be the same or different.

In formula 2, $Ar_3$ is represented by any one of the formulas 2-1 to 2-5. If in formula 1, both ring A and ring B represent a C6 aryl, $L_2$ represents a single bond, and T represents $CR_9R_{10}$, $Ar_3$ is represented by any one of the formulas 2-1, 2-3, 2-4 and 2-5. In addition, if $Ar_3$ is represented by the formula 2-1, n is 0.

In formula 2-1, $Y_1$ represents B; $X_1$ and $X_2$, each independently, represent NR', O or S. According to one embodiment of the present disclosure, $X_1$ and $X_2$, each independently, represent NR' or O.

In formula 2-1, ring C, ring D, and ring E, each independently, represent a substituted or unsubstituted (C6-C30) aryl, or a substituted or unsubstituted (3- to 50-membered) heteroaryl. According to one embodiment of the present disclosure, ring C, ring D, and ring E, each independently, represent a substituted or unsubstituted (C6-C25)aryl, or a substituted or unsubstituted (5- to 30-membered) heteroaryl; and at least one of ring C, ring D, and ring E may be linked to R' directly or via B, O, S or $CR_{27}R_{28}$ as a linker to form a ring(s); and ring D and ring E may be linked to each other directly or via B, O, S or $CR_{27}R_{28}$ as a linker to form a ring(s). According to another embodiment of the present disclosure, ring C, ring D, and ring E, each independently, represent a (C6-C18)aryl unsubstituted or substituted with at least one of deuterium(s), a (C1-C10)alkyl(s), a (C6-C18) aryl(s), a (5- to 20-membered) heteroaryl(s), a di(C6-C18) arylamino(s), and a (C6-C18)aryl(5- to 20-membered) heteroaryl(s); or a (5- to 25-membered) heteroaryl(s) unsubstituted or substituted with at least one of a (C6-C18) aryl(s) and di(C6-C18)arylamino(s). For example, ring C may be a substituted or unsubstituted benzene ring, or an unsubstituted naphthyl ring, in which the substituent of the substituted benzene ring may be at least one selected from the group consisting of deuterium; a methyl unsubstituted or substituted with deuterium(s); a tert-butyl; a phenyl unsubstituted or substituted with at least one of a methyl(s), a carbazolyl(s), a dibenzofuranyl(s), a phenoxazinyl(s), a phenothiazinyl(s), a 9,10-dihydro-9,9-dimethylacridinyl(s), and a diphenylamino(s); a naphthyl; a biphenyl; a terphenyl; a triphenylenyl; a carbazolyl; a phenoxazinyl; a phenothiazinyl; a 9,10-dihydro-9,9-dimethylacridinyl; a diphenylamino unsubstituted or substituted with at least one of deuterium(s), a methyl(s), and a tert-butyl(s); a phenylnaphthylamino; a phenylbiphenylamino unsubstituted or substituted with a tert-butyl(s); a dinaphthylamino; a dibiphenylamino; and a phenyldibenzofuranylamino. For example, ring D and ring E, each independently, may be a substituted or unsubstituted benzene ring; a naphthalene ring; a dibenzofuran ring; a carbazole ring substituted with at least one of a phenyl(s) and a diphenylamino(s); or a 21-membered heteroaryl ring substituted with at least one of a methyl(s) and a phenyl(s); and ring D and ring E may be linked to each other directly or via B, O, S or $CR_{27}R_{28}$ as a linker to form a ring(s). The substituents of the substituted benzene ring may be at least one selected from the group consisting of deuterium; a methyl; a tert-butyl; a phenyl; a naphthyl; a diphenylamino unsubstituted or substituted with a diphenylamino(s); a phenylnaphthylamino; a dibiphenylamino; a phenylcarbazolylphenylamino, and a dibenzofuranylphenylamino.

R', each independently, represents hydrogen, deuterium, a halogen, a cyano, a substituted or unsubstituted (C1-C30) alkyl, a substituted or unsubstituted (C6-C30)aryl, a substituted or unsubstituted (3- to 30-membered) heteroaryl, a substituted or unsubstituted (C3-C30)cycloalkyl, a substituted or unsubstituted (C1-C30)alkoxy, a substituted or unsubstituted tri (C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri (C6-C30)arylsilyl, a substituted or unsubstituted fused ring group of a (C3-C30) aliphatic ring(s) and a (C6-C30) aromatic ring(s), or $-L_4-N(Ar_{13})(Ar_{14})$; or R' may be linked to at least one of ring C, ring D, and ring E directly or via B, O, S or $CR_{27}R_{28}$ as a linker to form a ring(s). According to one embodiment of the present disclosure, R', each independently, represents a substituted or unsubstituted (C1-C20)alkyl, a substituted or unsubstituted (C6-C25)aryl, or a substituted or unsubstituted (5- to 25-membered) heteroaryl. According to another embodiment of the present disclosure, R', each independently, represents an unsubstituted (C1-C10)alkyl; a (C6-C18)aryl unsubstituted or substituted with at least one of deuterium(s), a (C1-C10)alkyl(s), and a di(C6-C18)arylamino(s); or a (5- to 20-membered) heteroaryl unsubstituted or substituted with a (C6-C18)aryl(s). For example, R', each independently, may be a methyl; a phenyl unsubstituted or substituted with at least one of deuterium(s), a methyl(s), a tert-butyl(s), and a diphenylamino(s); a naphthyl; a biphenyl; or a carbazolyl substituted with a phenyl(s); and R' may be linked to at least one of ring C, ring D, and ring E directly or via B, O, S or $CR_{27}R_{28}$ as a linker to form a ring(s).

In formula 2-4, W and Z, each independently, represent O, S, NR' or $CR_{27}R_{28}$. According to one embodiment of the present disclosure, W and Z, each independently, represent O and S.

In formulas 2-2 to 2-5, $R_{11}$ to $R_{14}$. $R_{17}$, $R_{18}$, and $R_{21}$ to $R_{26}$, each independently, represent hydrogen, deuterium, a halogen, a cyano, a substituted or unsubstituted (C1-C30) alkyl, a substituted or unsubstituted (C6-C30)aryl, a substituted or unsubstituted (3- to 30-membered) heteroaryl, a substituted or unsubstituted (C3-C30)cycloalkyl, a substituted or unsubstituted (C1-C30)alkoxy, a substituted or unsubstituted tri (C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri (C6-C30)arylsilyl, a substituted or unsubstituted fused ring group of a (C3-C30) aliphatic ring(s) and a (C6-C30) aromatic ring(s), or $-L_4-N(Ar_{13})(Ar_{14})$. According to one embodiment of the present disclosure, $R_{11}$ to $R_{14}$. $R_{17}$, $R_{18}$, and $R_{21}$ to $R_{26}$, each independently, represent hydrogen, a substituted or unsubstituted (C6-C25)aryl, or a substituted or unsubstituted (5- to 25-membered) heteroaryl. According to another embodiment of the present disclosure, $R_{11}$ to $R_{14}$. $R_{17}$, $R_{18}$, and $R_{21}$ to $R_{26}$, each independently, represent hydrogen; a (C6-C18) aryl unsubstituted or substituted with deuterium(s); or a (5- to 20-membered) heteroaryl unsubstituted or substituted with a (C6-C18)aryl(s). For example, $R_{17}$, $R_{18}$, and $R_{21}$ to $R_{26}$ may be hydrogen; and $R_{11}$ to $R_{14}$, each independently, represent hydrogen; a phenyl unsubstituted or substituted with deuterium(s); or a substituted carbazolyl, in which the substituent of the substituted carbazolyl may be a phenyl substituted with a tert-butyl(s), etc.

In formulas 2-1 to 2-5, $R_{15}$, $R_{16}$, $R_{19}$, $R_{20}$, $R_{27}$, and $R_{28}$, each independently, represent a substituted or unsubstituted (C1-C30)alkyl, a substituted or unsubstituted (C6-C30)aryl, or a substituted or unsubstituted (3- to 30-membered) heteroaryl; and at least one of $R_{15}$ and $R_{16}$, $R_{19}$ and $R_{20}$, and $R_{27}$ and $R_{28}$ may be fused to each other to form a spiro structure. According to one embodiment of the present disclosure, $R_{15}$, $R_{16}$, $R_{19}$, $R_{20}$, $R_{27}$, and $R_{28}$, each independently, represent a substituted or unsubstituted (C1-C20)alkyl, or a substituted or unsubstituted (C6-C25)aryl; and at least one of $R_{15}$ and $R_{16}$, $R_{19}$ and $R_{20}$, and $R_{27}$ and $R_{28}$ may be fused to each other to form a spiro structure. According to another embodiment of the present disclosure, $R_{15}$, $R_{16}$, $R_{19}$, $R_{20}$, $R_{27}$, and $R_{28}$, each independently, represent an unsubstituted (C1-C10)alkyl, or an unsubstituted (C6-C18)aryl; and at least one of $R_{15}$ and $R_{16}$, $R_{19}$ and $R_{20}$, and $R_{27}$ and $R_{28}$ may be fused to each other to form a spiro structure. For example, $R_{15}$ and $R_{16}$, each independently, may be a methyl or a phenyl; or $R_{15}$ and $R_{16}$ may be fused to each other to form a spiro structure, e.g., a fluorene ring. For example, $R_{19}$ and $R_{20}$, each independently, may be a phenyl; or $R_{19}$ and $R_{20}$ may be fused to each other to form a spiro structure, e.g., a fluorene ring. For example, $R_{27}$ and $R_{28}$, each independently, may be a methyl.

$L_4$, each independently, represents a single bond, a substituted or unsubstituted (C6-C30)arylene, a substituted or unsubstituted (3- to 30-membered) heteroarylene, a substituted or unsubstituted divalent (C2-C30) aliphatic hydrocarbon group, or a substituted or unsubstituted divalent fused ring group of a (C3-C30) aliphatic ring(s) and a (C6-C30) aromatic ring(s). For example, $L_4$, each independently, may be a single bond.

$Ar_{13}$ and $Ar_{14}$, each independently, represent a substituted or unsubstituted (C1-C30)alkyl, a substituted or unsubstituted (C2-C30)alkenyl, a substituted or unsubstituted (C6-C30)aryl, or a substituted or unsubstituted (3- to 30-membered) heteroaryl. According to one embodiment of the present disclosure, $Ar_{13}$ and $Ar_{14}$, each independently, represent a substituted or unsubstituted (C6-C25)aryl, or a substituted or unsubstituted (5- to 25-membered) heteroaryl. According to another embodiment of the present disclosure, $Ar_{13}$ and $Ar_{14}$, each independently, represent a (C6-C18)aryl unsubstituted or substituted with at least one of deuterium (s), a (C1-C10)alkyl(s), and a di(C6-C18)arylamino(s); or a (5- to 20-membered) heteroaryl unsubstituted or substituted with a (C6-C18)aryl(s). For example, $Ar_{13}$ and $Ar_{14}$, each independently, may be a phenyl unsubstituted or substituted with at least one of deuterium(s), a methyl(s), a tert-butyl(s), and a diphenylamino(s); a naphthyl; a biphenyl unsubstituted or substituted with a tert-butyl(s); a carbazolyl substituted with a phenyl(s); or a dibenzofuranyl.

In formulas 2-2 to 2-5, a, c, h, and i, each independently, represent an integer of 1 or 2; b and d, each independently, represent an integer of 1 to 3; f, k, and l, each independently, represent an integer of 1 to 6; and e, g, and j, each independently, represent an integer of 1 to 4, in which if a to l, each independently, are an integer of 2 or more, each of $R_{11}$, each of $R_{12}$, each of $R_{13}$, each of $R_{14}$, each of $R_{17}$, each of $R_{18}$, each of $R_{21}$, each of $R_{22}$, each of $R_{23}$, each of $R_{24}$, each of $R_{25}$, or each of $R_{26}$ may be the same or different.

According to one embodiment of the present disclosure, the formula 2 may be represented by at least one of the following formulas 2-11 to 2-18.

(2-11)

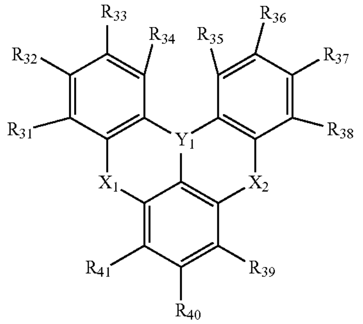

(2-12)

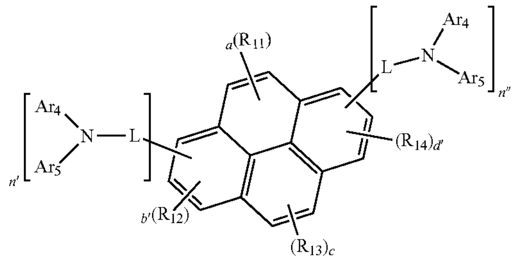

(2-13)

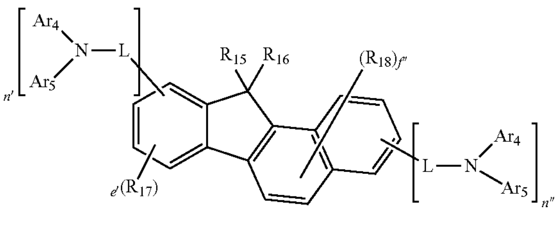

-continued (2-14)

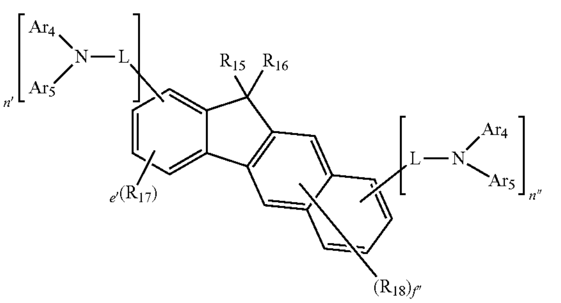

(2-15)

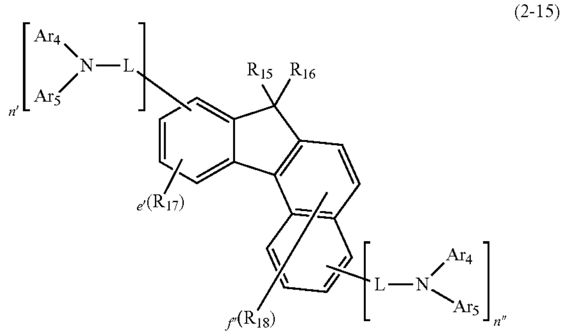

(2-16)

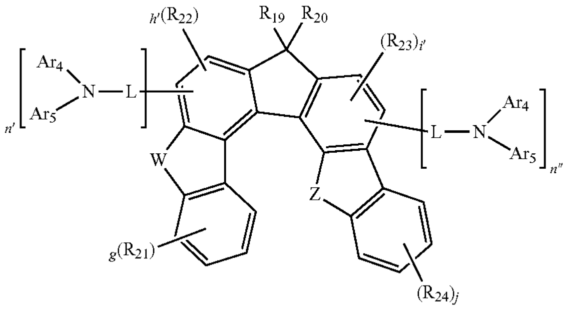

(2-17)

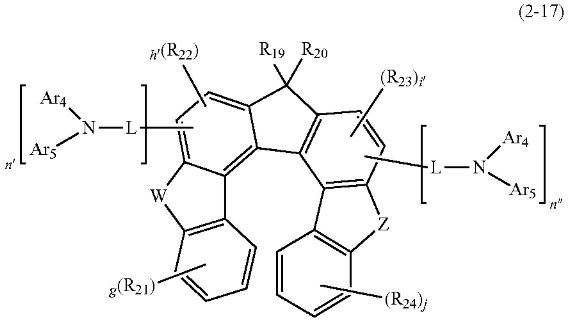

-continued (2-18)

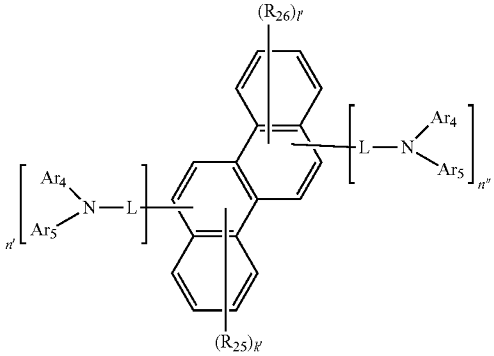

In formula 2-11, $R_{31}$ to $R_{41}$, each independently, represent hydrogen, deuterium, a halogen, a cyano, a substituted or unsubstituted (C1-C30)alkyl, a substituted or unsubstituted (C6-C30)aryl, a substituted or unsubstituted (3- to 30-membered) heteroaryl, a substituted or unsubstituted (C3-C30) cycloalkyl, a substituted or unsubstituted (C1-C30)alkoxy, a substituted or unsubstituted tri (C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri (C6-C30)arylsilyl, a substituted or unsubstituted fused ring group of a (C3-C30) aliphatic ring(s) and a (C6-C30) aromatic ring(s), or $-L_4-N(Ar_{13})(Ar_{14})$; or at least two adjacent ones of $R_{31}$ to $R_{41}$ and R' may be linked to each other directly or via B, O, S or $CR_{27}R_{28}$ as a linker to form a ring(s). According to one embodiment of the present disclosure, $R_{31}$ to $R_{41}$, each independently, represent hydrogen, deuterium, a substituted or unsubstituted (C1-C20)alkyl, a substituted or unsubstituted (C6-C25)aryl, a substituted or unsubstituted (5- to 25-membered) heteroaryl, or $-L_4-N(Ar_{13})(Ar_{14})$; or at least two adjacent ones of $R_{31}$ to $R_{41}$ and R' may be linked to each other directly or via B, O, S or $CR_{27}R_{28}$ as a linker to form a ring(s). According to another embodiment of the present disclosure, $R_{31}$ to $R_{41}$, each independently, represent hydrogen; deuterium; a (C1-C10)alkyl unsubstituted or substituted with deuterium(s); a (C6-C18)aryl unsubstituted or substituted with at least one of a (C1-C10)alkyl(s), a (5- to 20-membered) heteroaryl(s), and a di(C6-C18)arylamino(s); or $-L_4-N(Ar_{13})(Ar_{14})$; or at least two adjacent ones of $R_{31}$ to $R_{41}$ and R' may be linked to each other directly or via B, O, S or $CR_{27}R_{28}$ as a linker to form a ring(s). For example, $R_{31}$ to $R_{41}$, each independently, may be hydrogen; deuterium; a methyl unsubstituted or substituted with deuterium(s); a tert-butyl; a substituted or unsubstituted phenyl; a naphthyl; a biphenyl; a terphenyl; a triphenylenyl; a carbazolyl; a phenoxazinyl; a phenothiazinyl; a 9,10-dihydro-9,9-dimethylacridinyl; or $-L_4-N(Ar_{13})(Ar_{14})$; or at least two adjacent ones of $R_{31}$ to $R_{41}$ and R' may be linked to each other directly or via B, O, S or $CR_{27}R_{28}$ as a linker to form a benzene ring; an indole ring substituted with at least one of a phenyl(s) and a diphenylamino(s); a benzofuran ring; a benzoxazine ring; a benzothiazine ring; or a (17- to 18-membered) heteroaryl ring substituted with a methyl(s) and a phenyl(s), in which the substituent of the substituted phenyl may be at least one of a methyl, a carbazolyl, a dibenzofuranyl, a phenoxazinyl, a phenothiazinyl, a 9,10-dihydro-9,9-dimethylacridinyl, and a diphenylamino.

In formulas 2-12 to 2-18, n' and n", each independently, represent 0 or 1, in which at least one of n' and n" is 1.

In formulas 2-12 to 2-18, b' and d', each independently, represent an integer of 1 or 2; e', each independently, represents an integer of 1 to 3; f, k', and l', each independently, represent an integer of 1 to 5; and h' and i', each independently, represent an integer of 1.

In formulas 2-11 to 2-18, $Y_1$, $X_1$, $X_2$, $R_{11}$ to $R_{28}$, $L_4$, $Ar_{13}$, $Ar_{14}$, a, c, g, and j, each independently, are as defined in formula 2.

Specifically, the compound represented by formula 1 may be at least one selected from the group consisting of the following compounds, but is not limited thereto.

H1-1

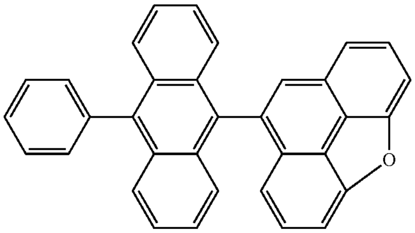

H1-2

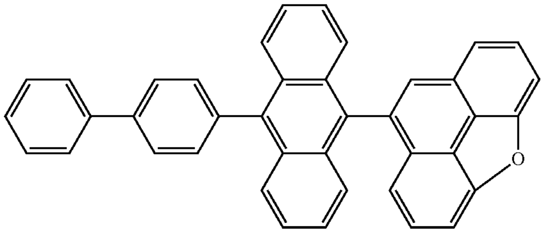

H1-3

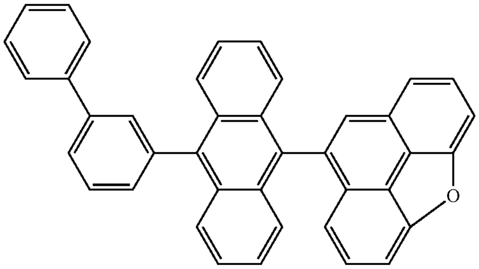

H1-4

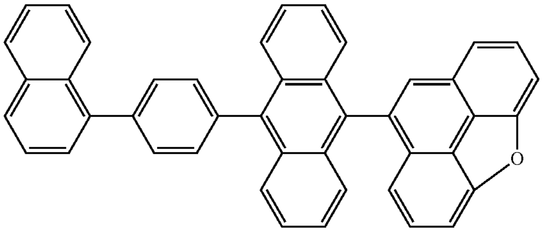

H1-5

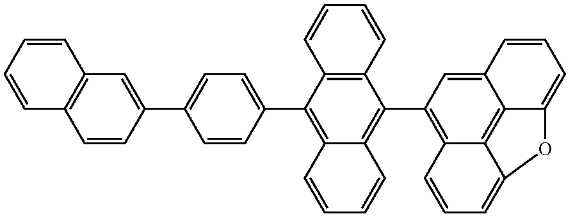

-continued

H1-6

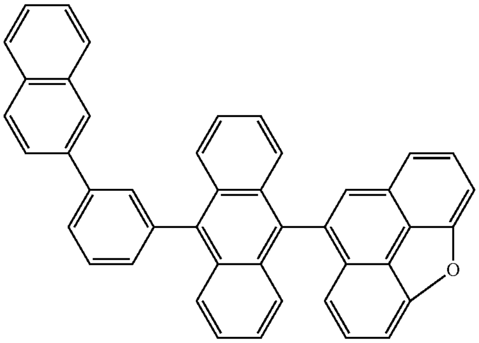

H1-7

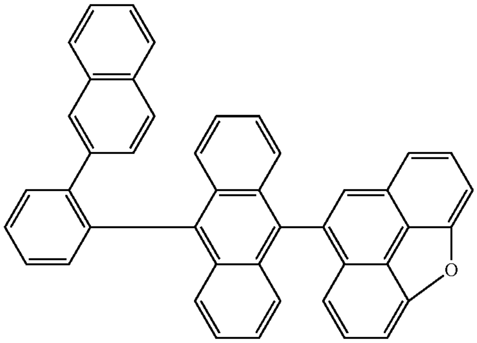

H1-8

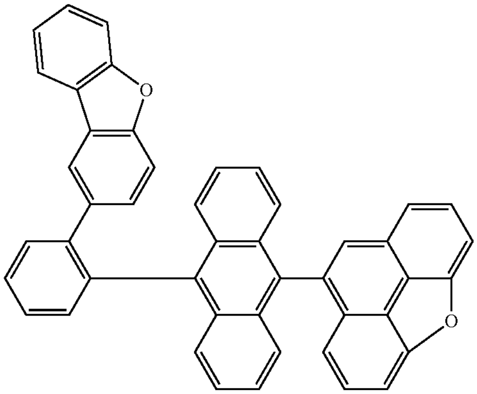

H1-9

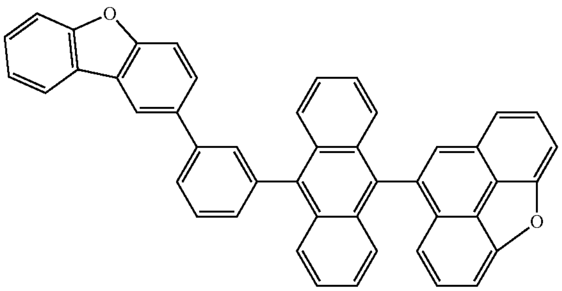

-continued
H1-10
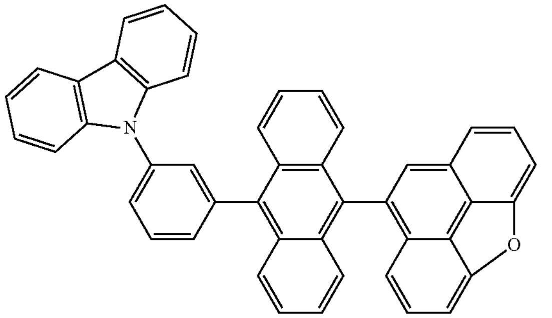
H1-11
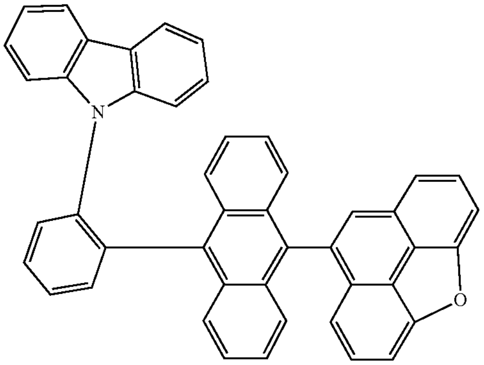
H1-12
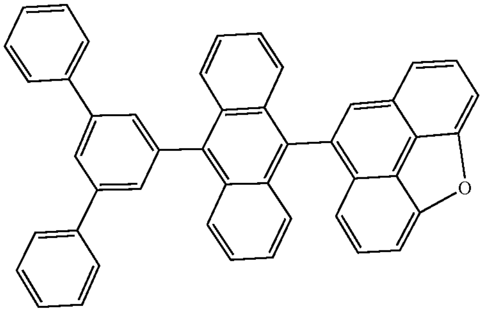
H1-13
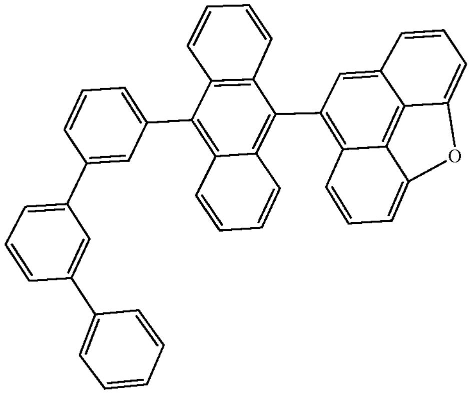
-continued
H1-14
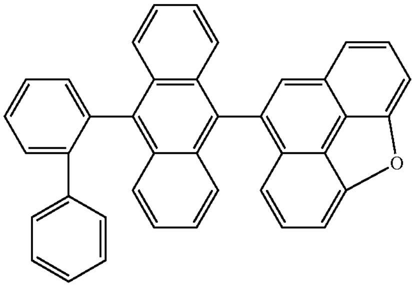
H1-15
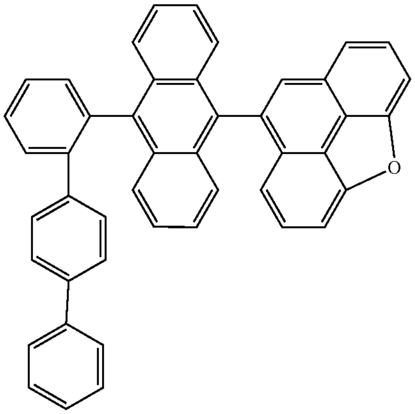
H1-16
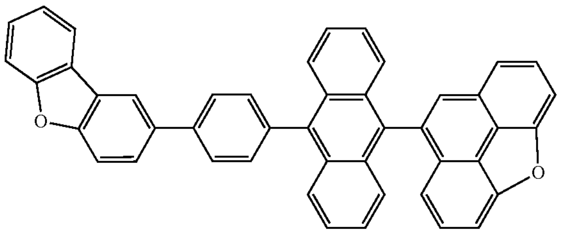
H1-17
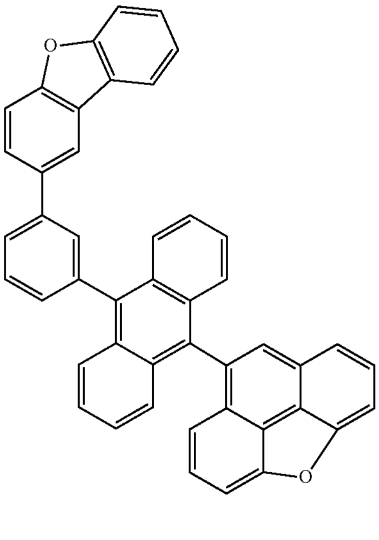

-continued
H1-18
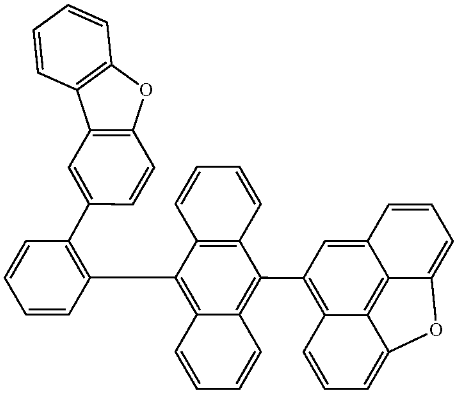
H1-19
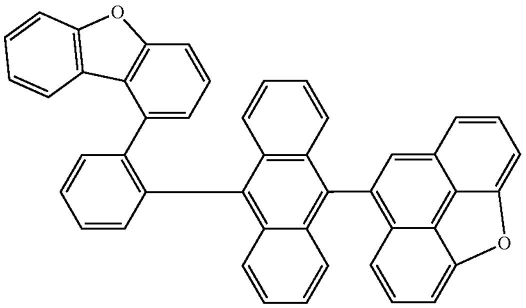
H1-20
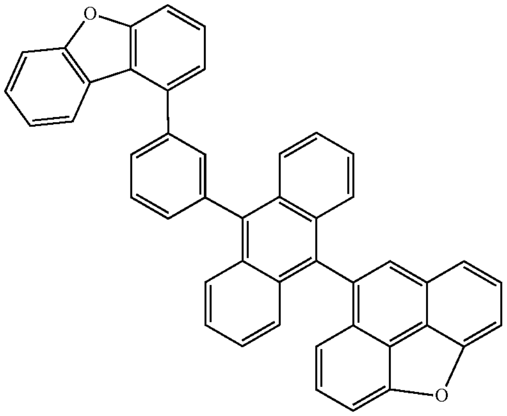
H1-21
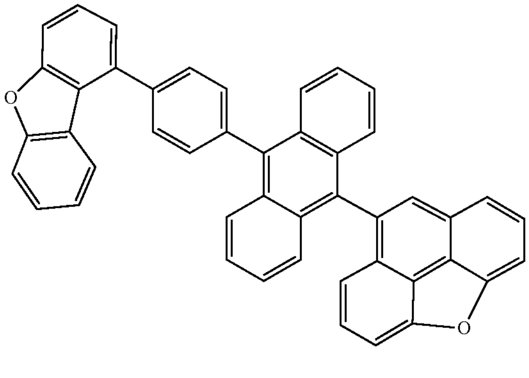
-continued
H1-22
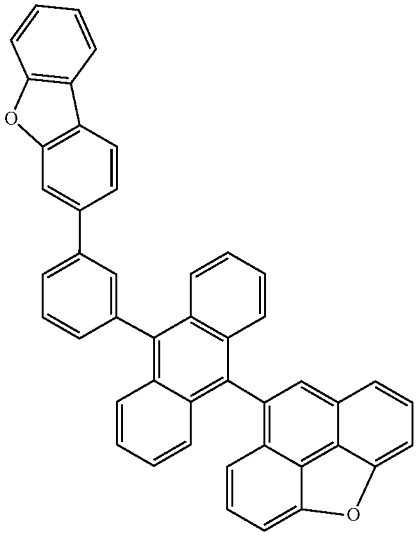
H1-23
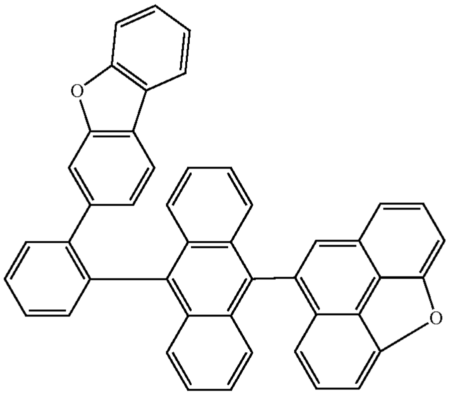
H1-24
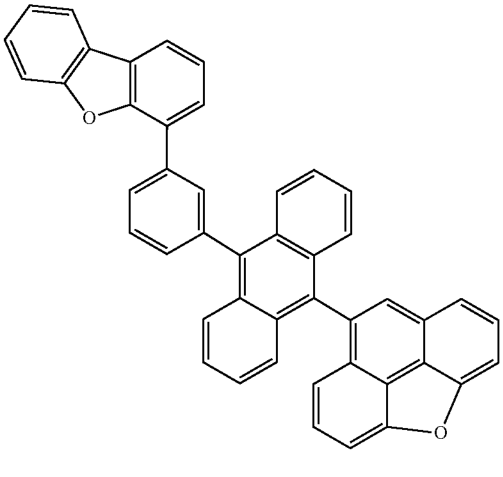

-continued
H1-25
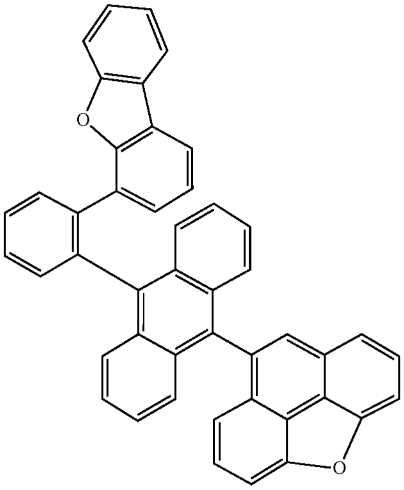
H1-26
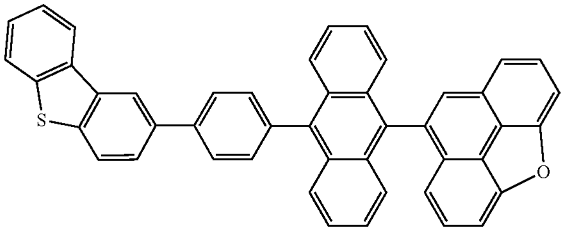
H1-27
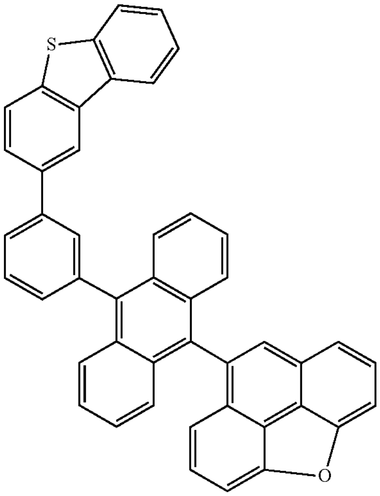
H1-28
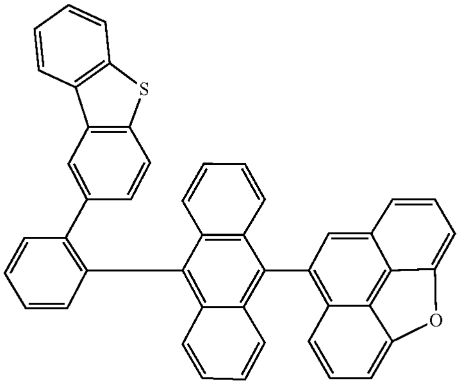
-continued
H1-29
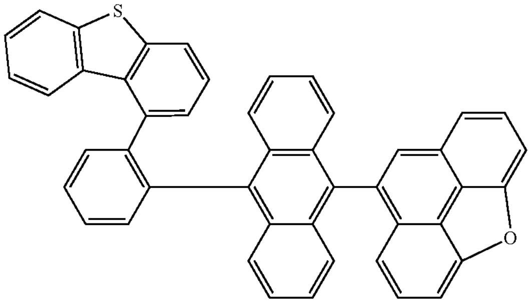
H1-30
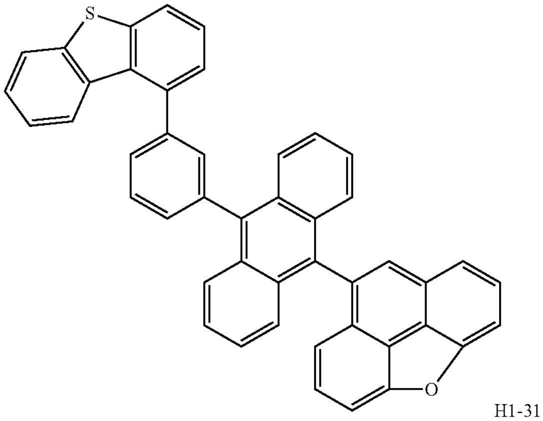
H1-31
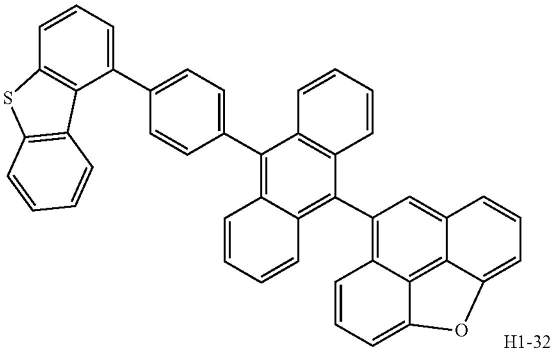
H1-32
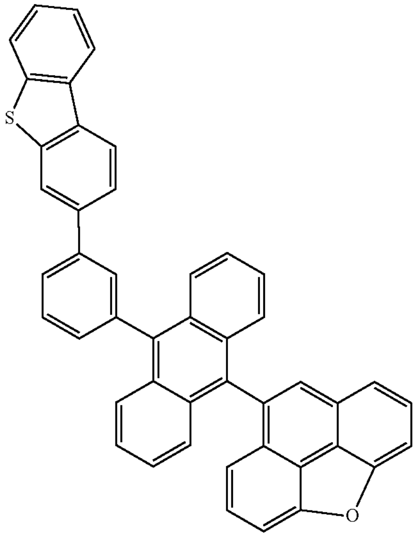

-continued
H1-33
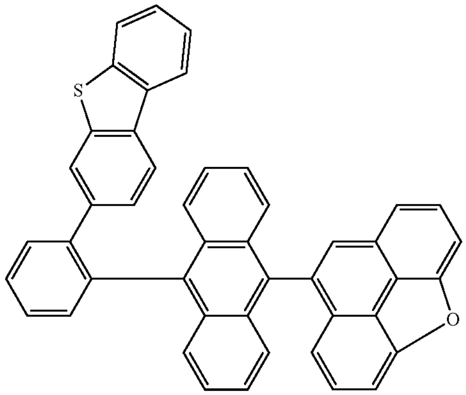
H1-34
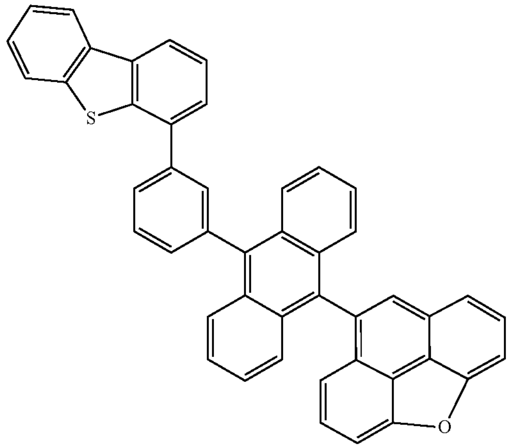
H1-35
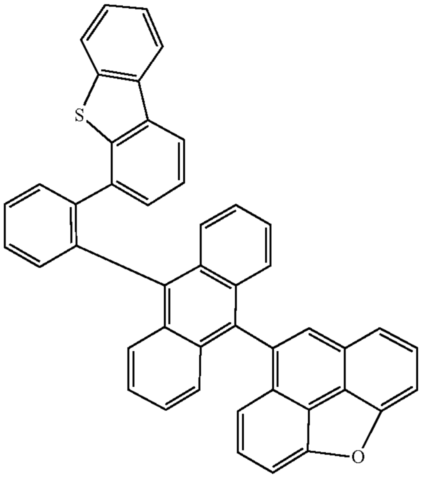
-continued
H1-36
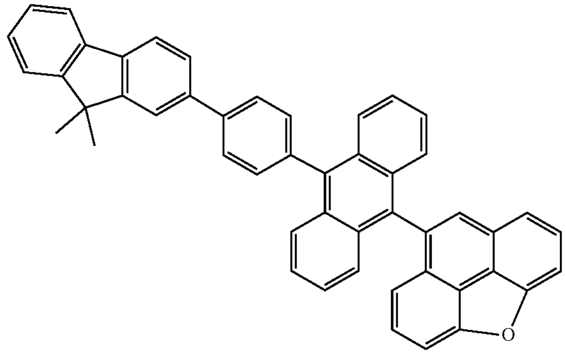
H1-37
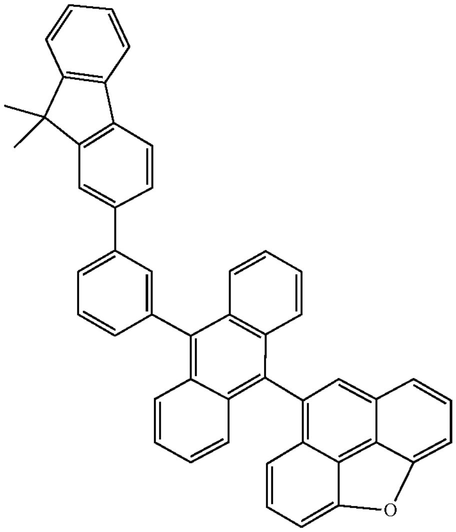
H1-38
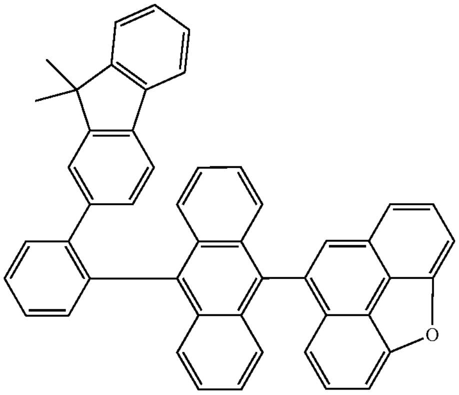

-continued
H1-39
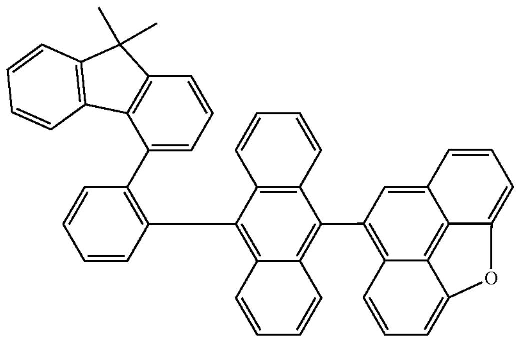
H1-40
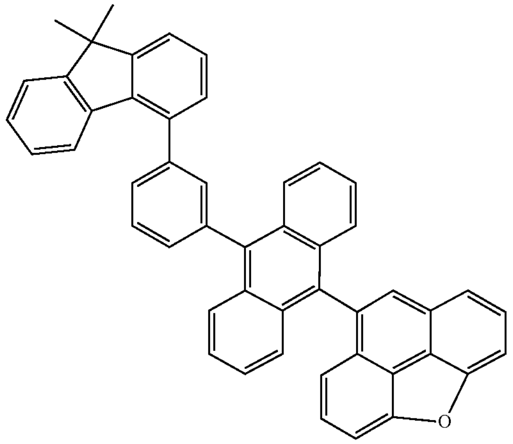
H1-41
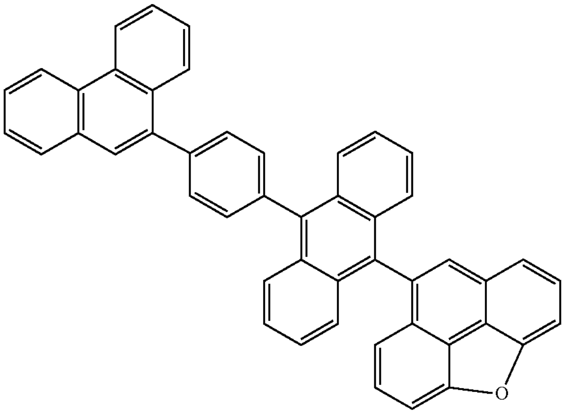
-continued
H1-42
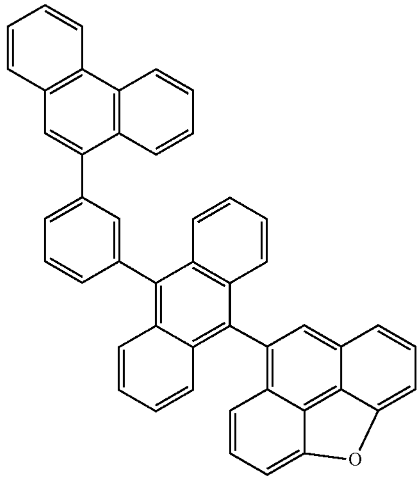
H1-43
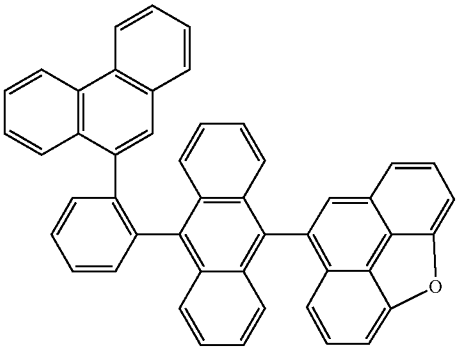
H1-44
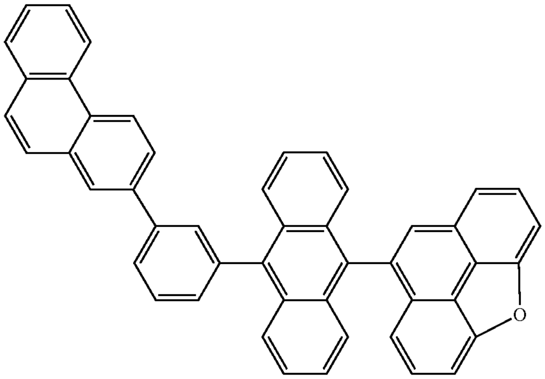

-continued
H1-45
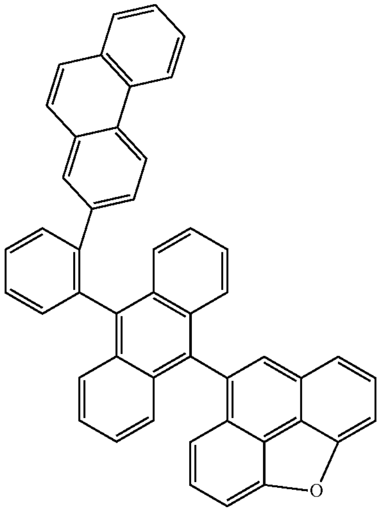
H1-46
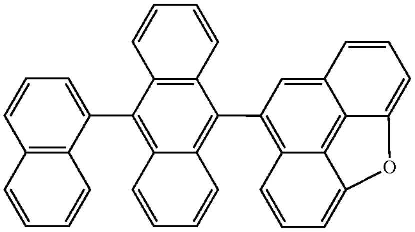
H1-47
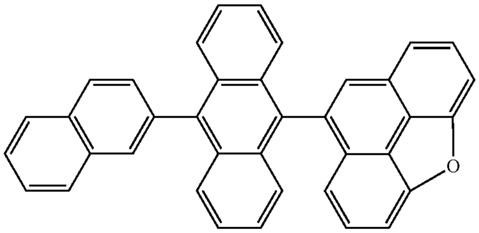
H1-48
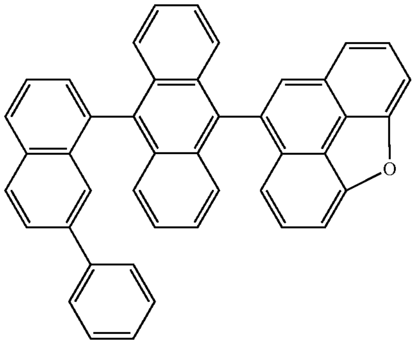
-continued
H1-49
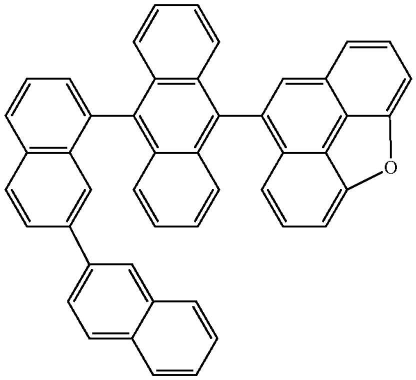
H1-50
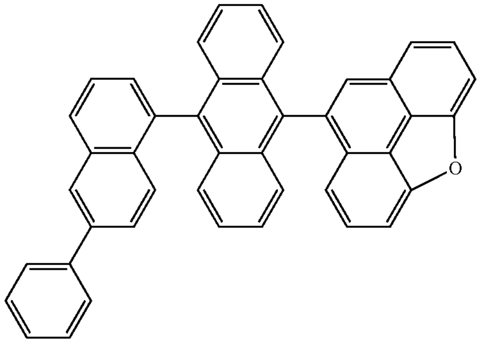
H1-51
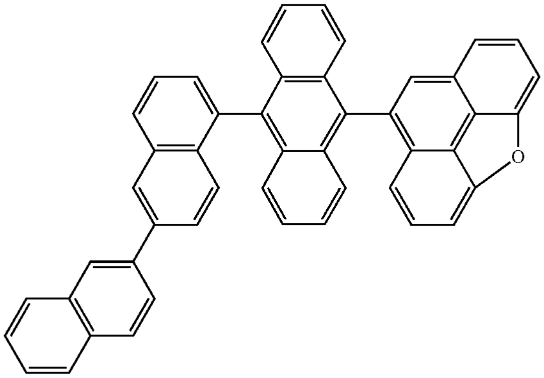
H1-52
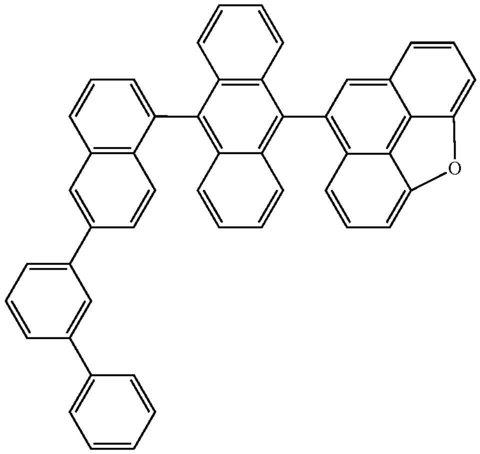

-continued
H1-53
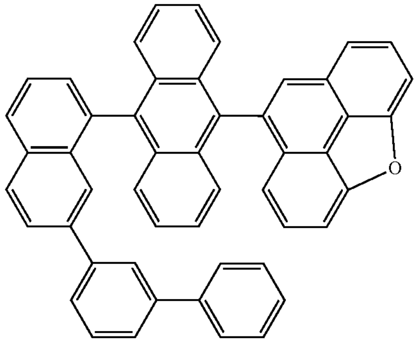
H1-54
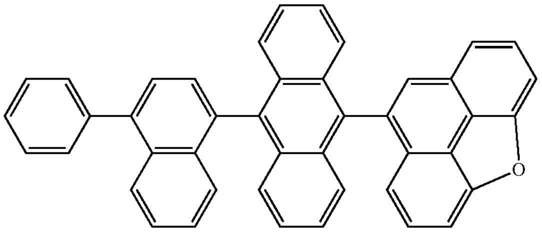
H1-55
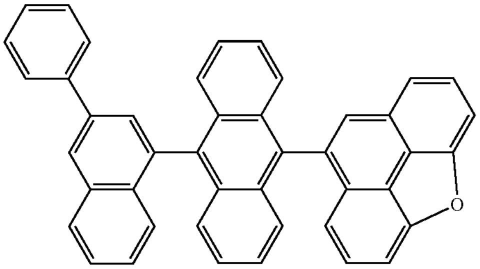
H1-56
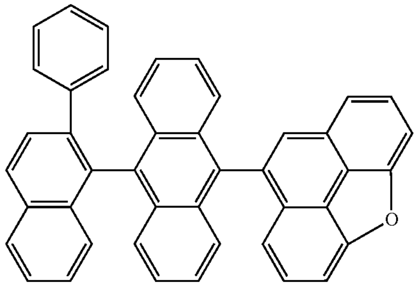
H1-57
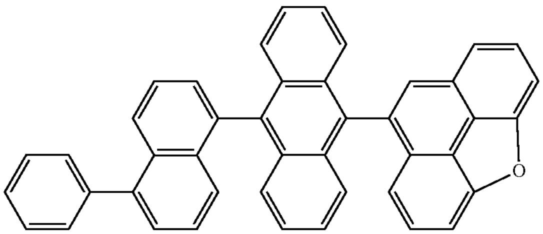
-continued
H1-58
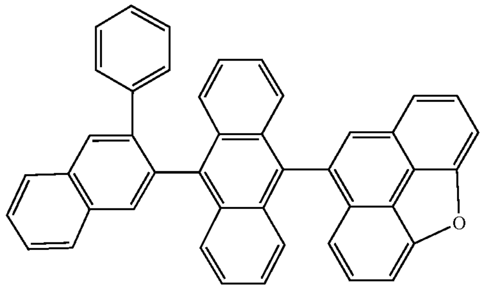
H1-59
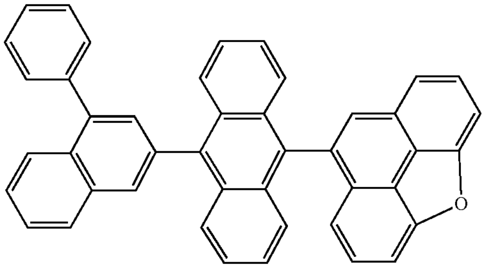
H1-60
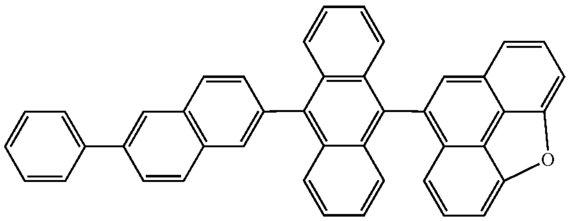
H1-61
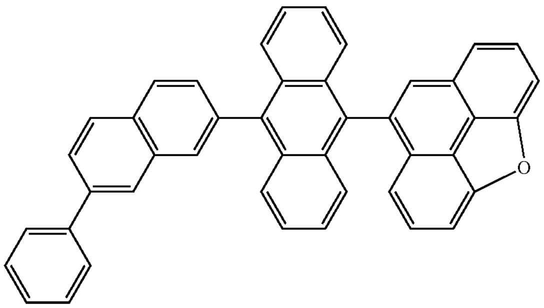
H1-62
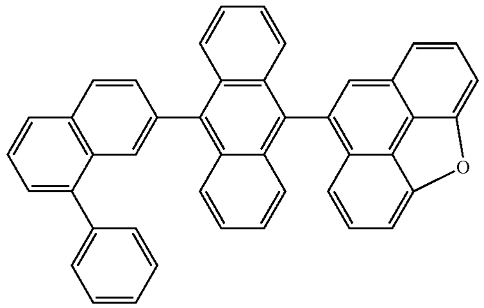

-continued
H1-63
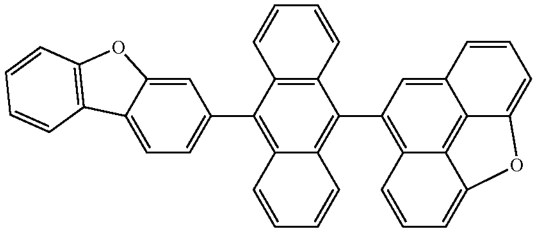
H1-64
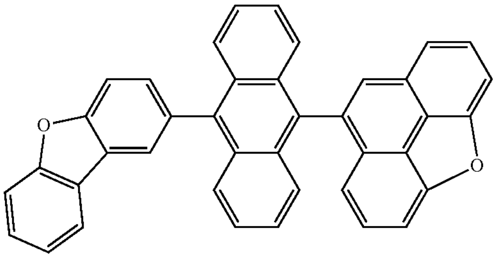
H1-65
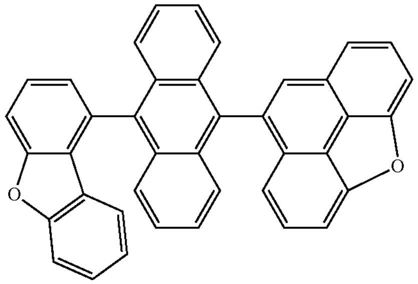
H1-66
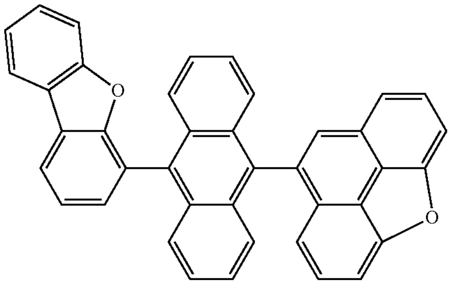
H1-67
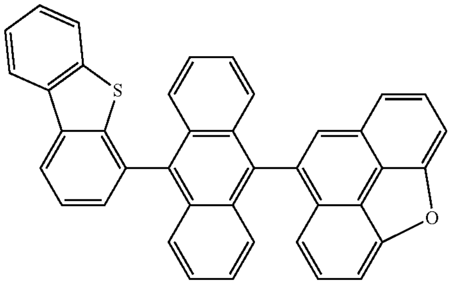
-continued
H1-68
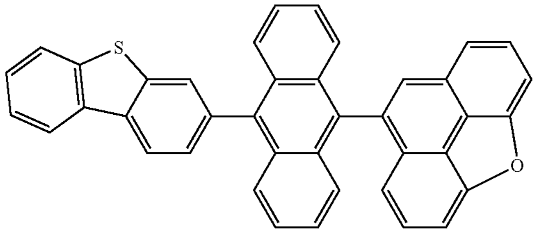
H1-69
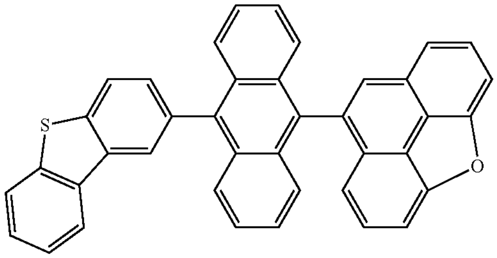
H1-70
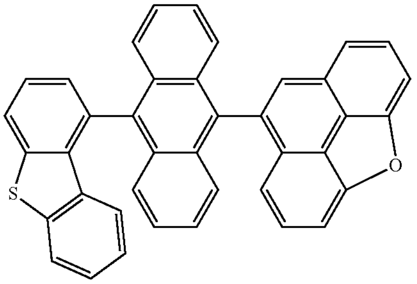
H1-71
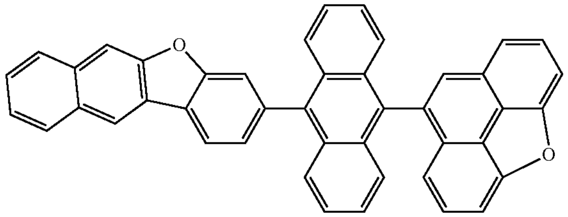
H1-72
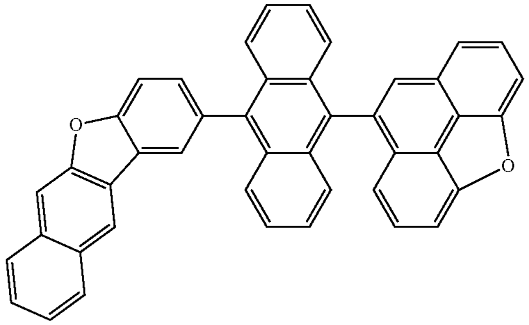

-continued
H1-73
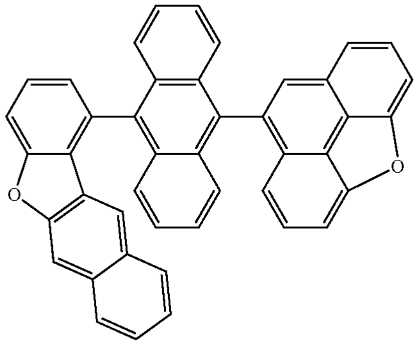
H1-74
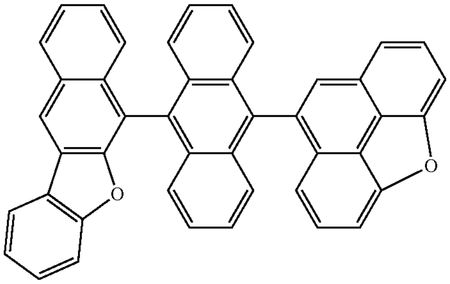
H1-75
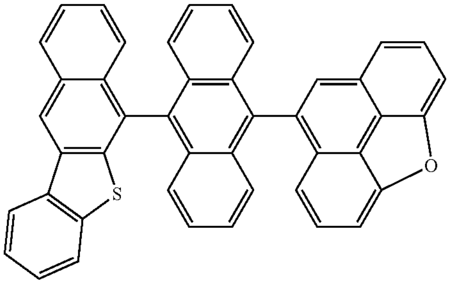
H1-76
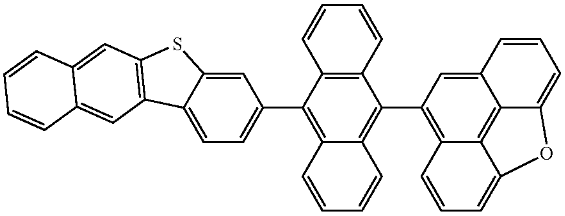
H1-77
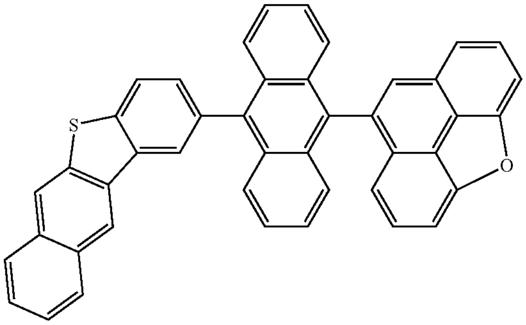
-continued
H1-78
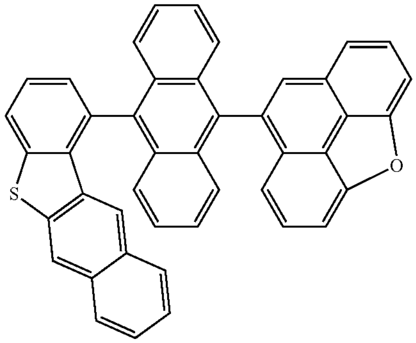
H1-79
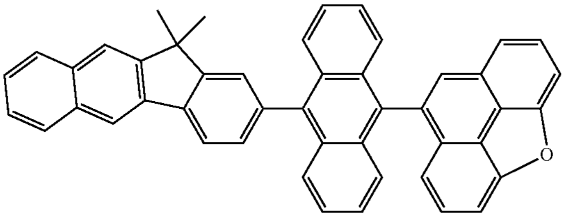
H1-80
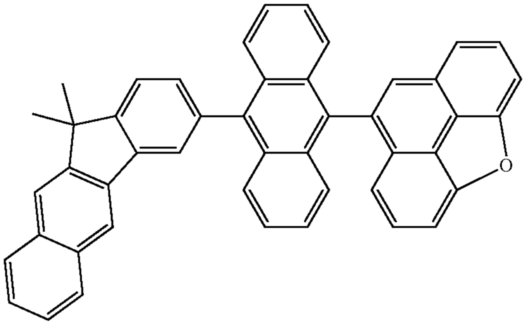
H1-81
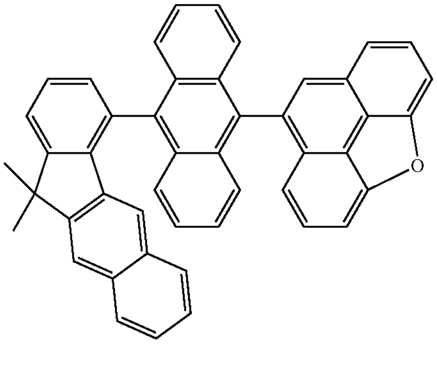
H1-82
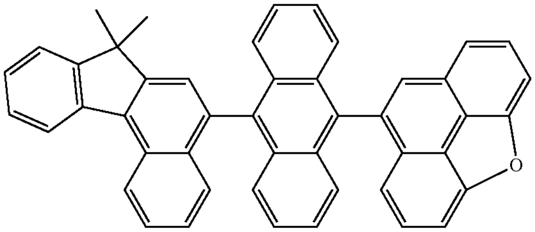

-continued
H1-83
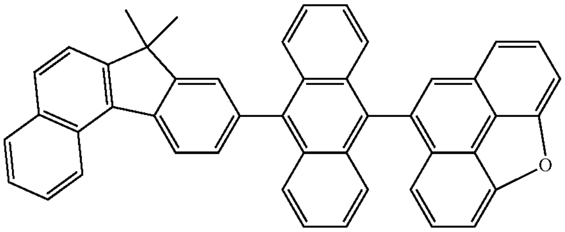
H1-84
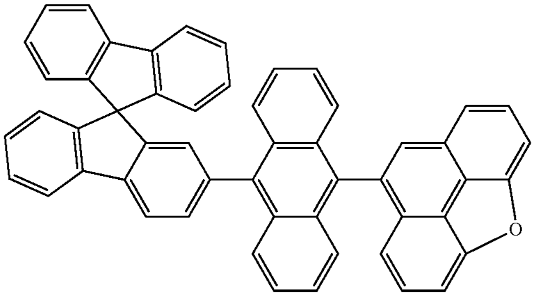
H1-85
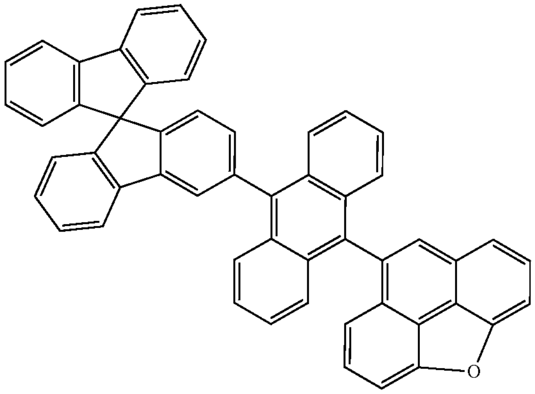
H1-86
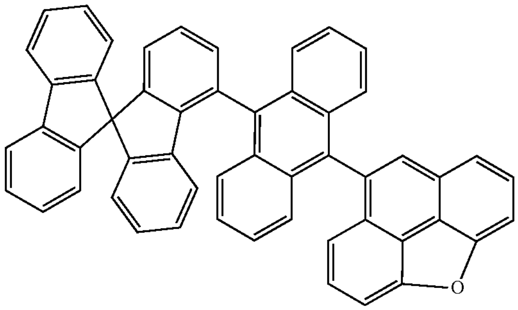
H1-87
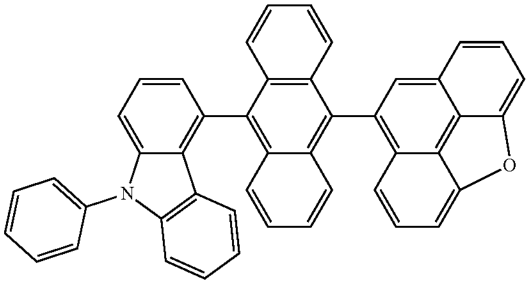
-continued
H1-88
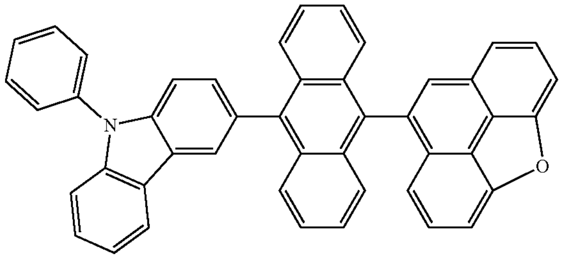
H1-89
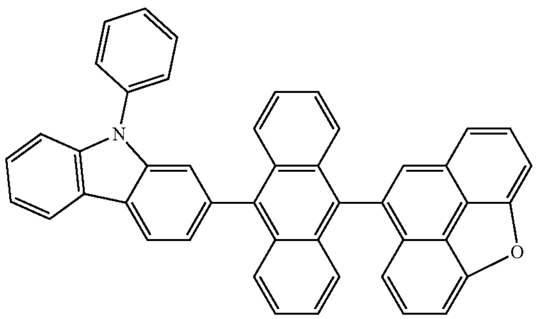
H1-90
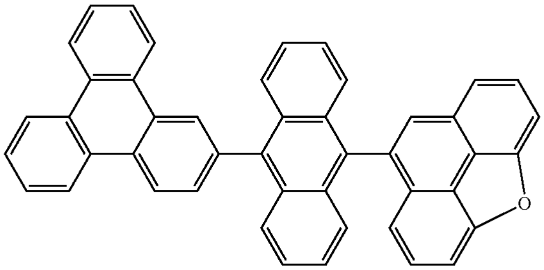
H1-91
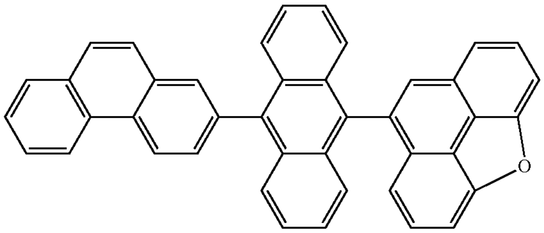
H1-92
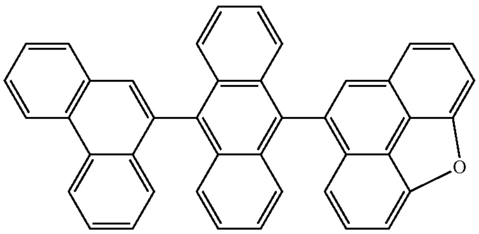

H1-93
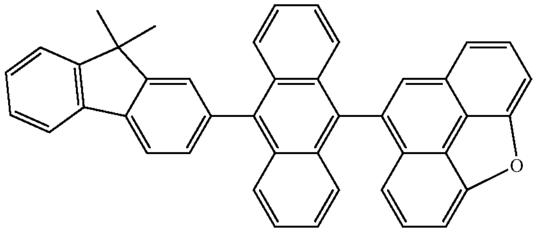
H1-94
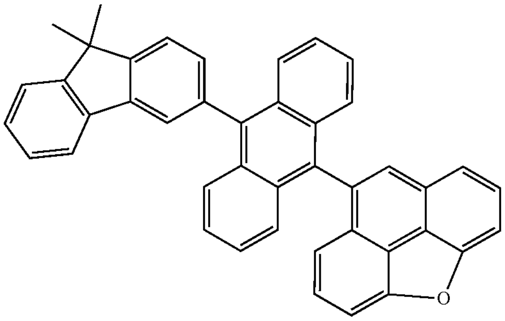
H1-95
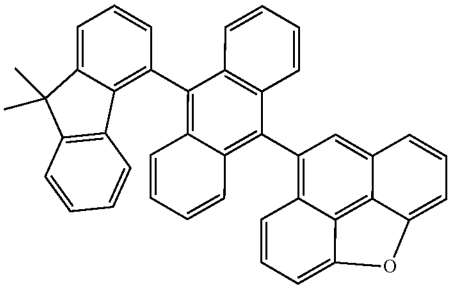
H1-96
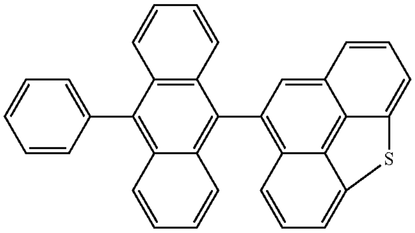
H1-97
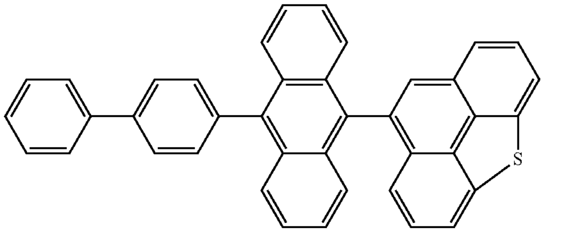
H1-98
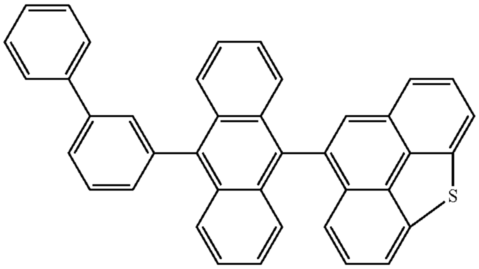
H1-99
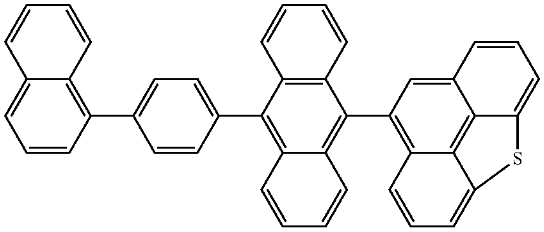
H1-100
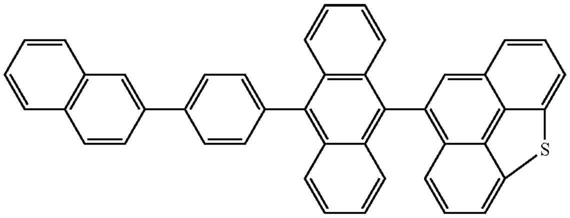
H1-101
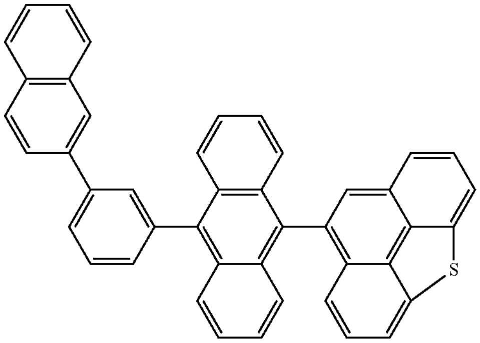
H1-102
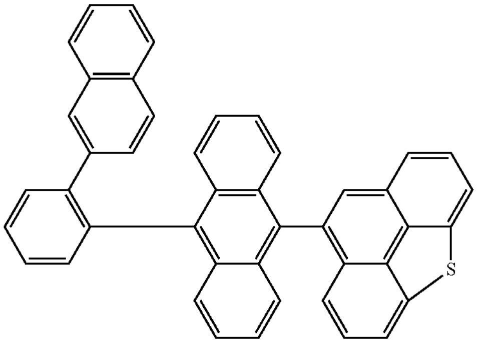

-continued
H1-103
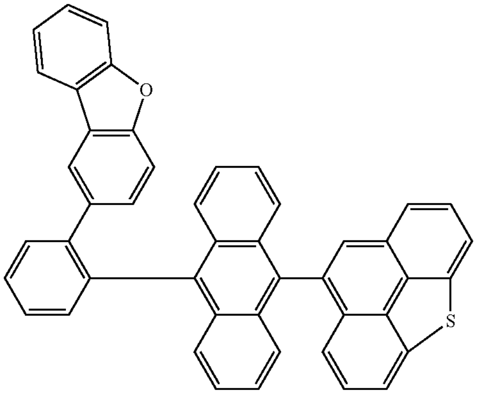
H1-104
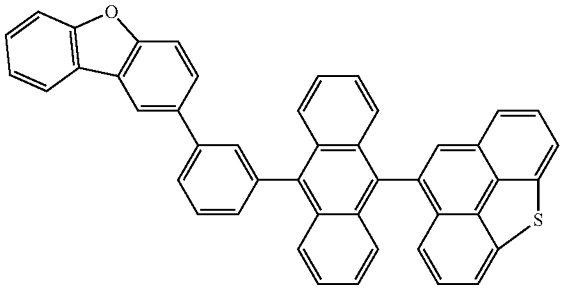
H1-105
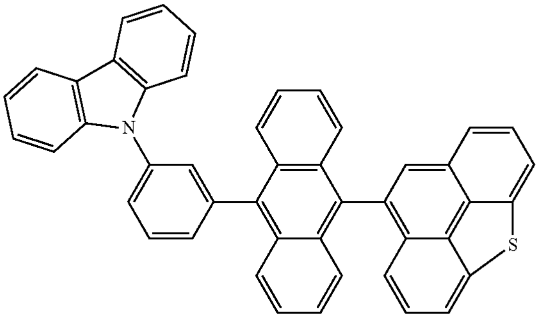
H1-106
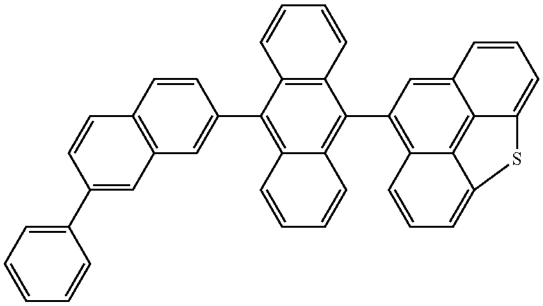
-continued
H1-107
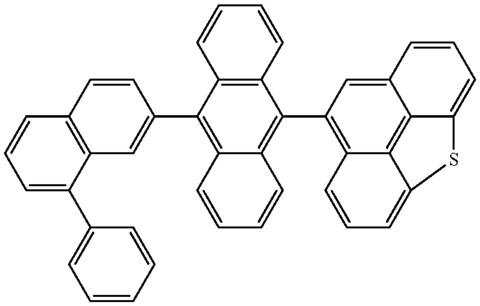
H1-108
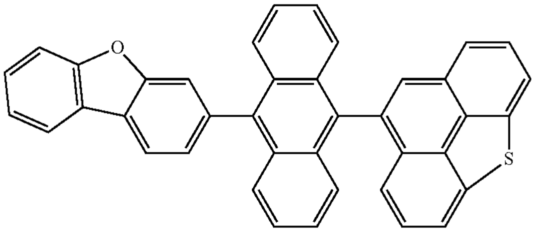
H1-109
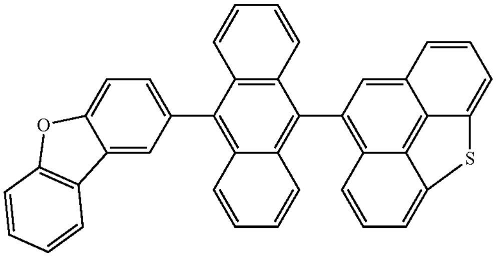
H1-110
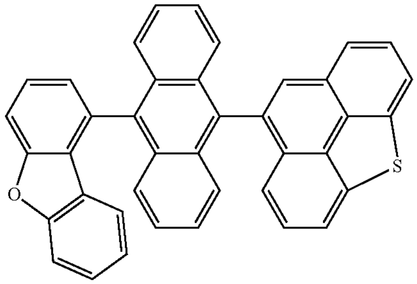
H1-111
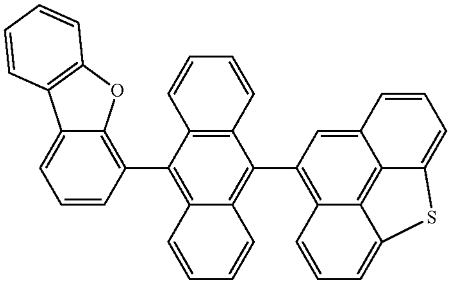

-continued
H1-112
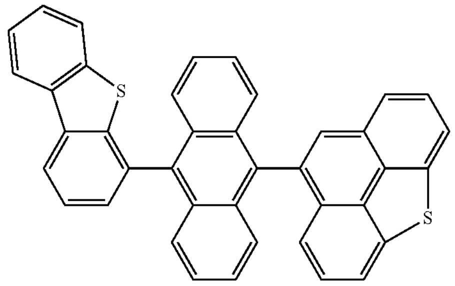
H1-113
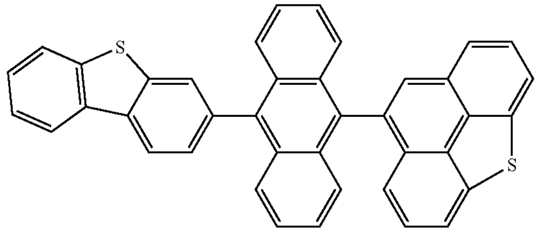
H1-114
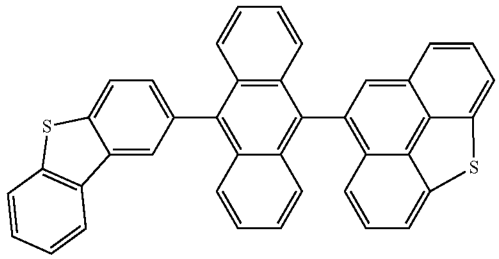
H1-115
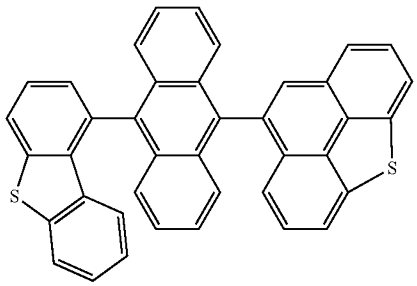
H1-116
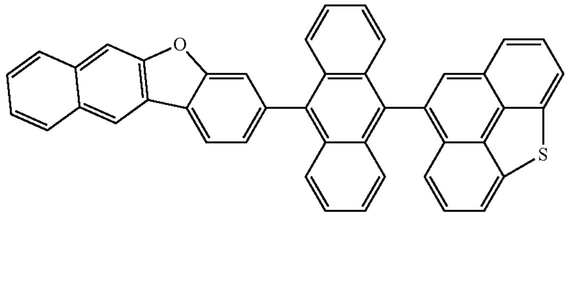
-continued
H1-117
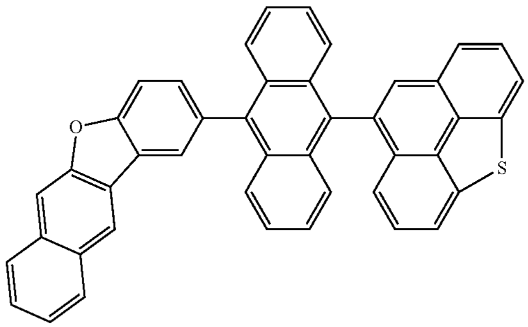
H1-118
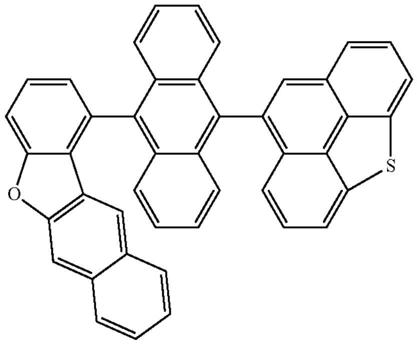
H1-119
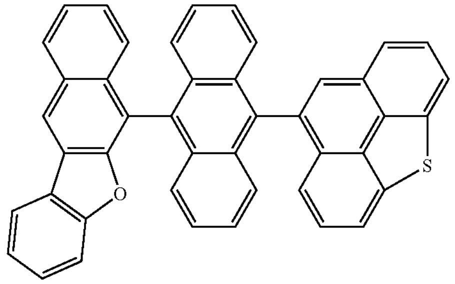
H1-120
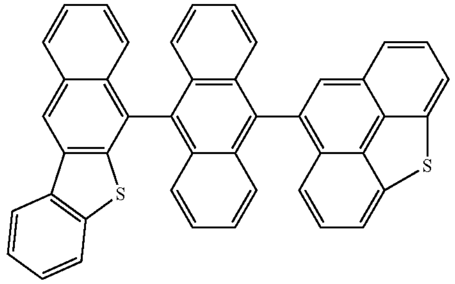
H1-121
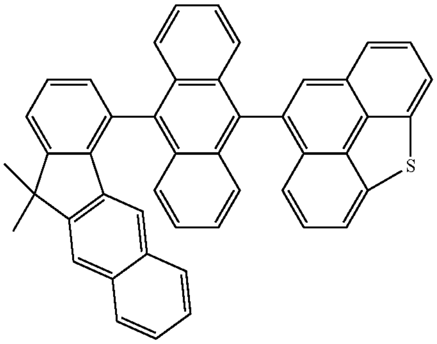

-continued
H1-122
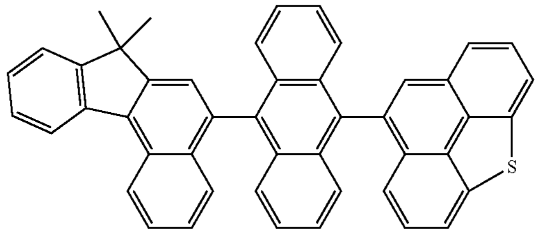
H1-123
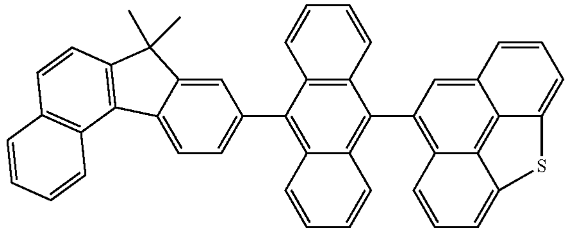
H1-124
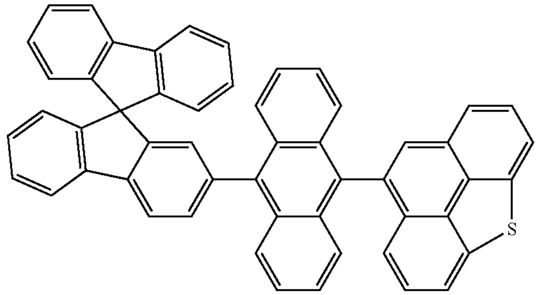
H1-125
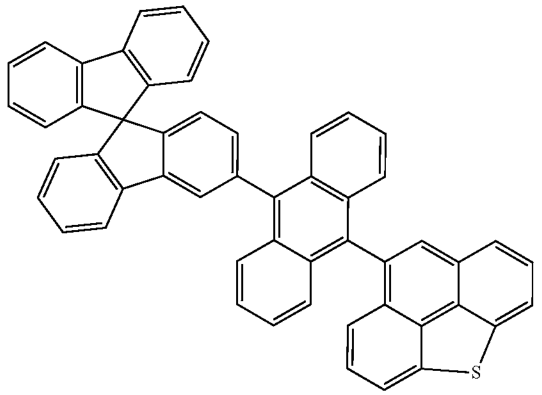
H1-126
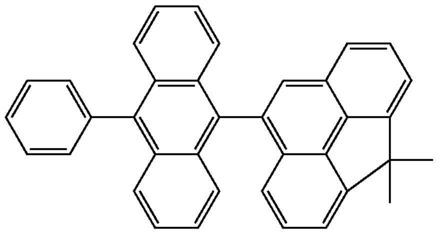
-continued
H1-127
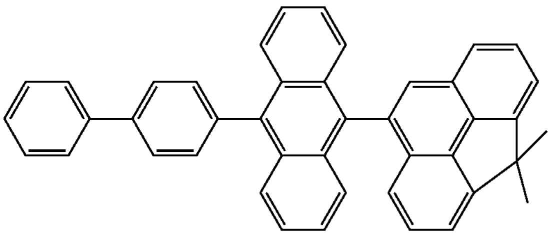
H1-128
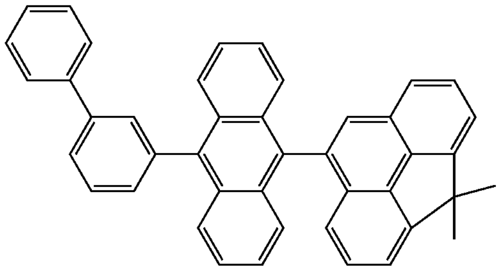
H1-129
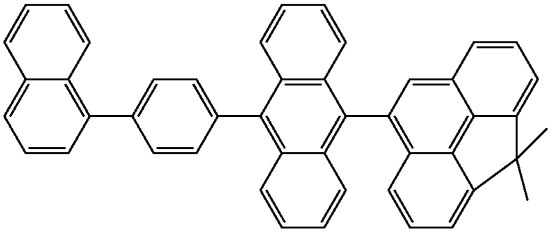
H1-130
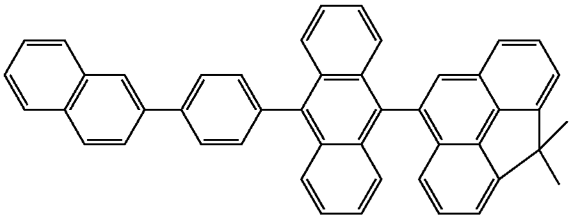
H1-131
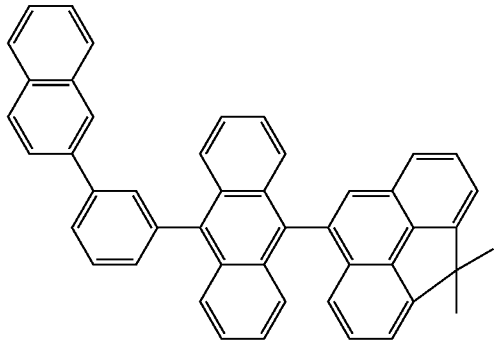

-continued
H1-132
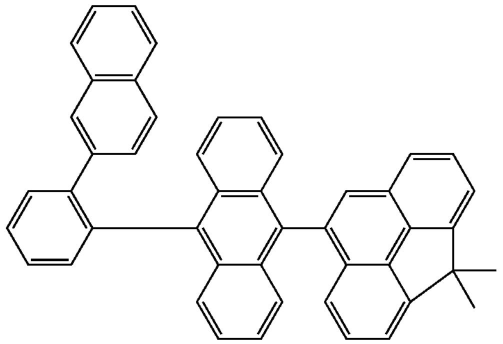
H1-133
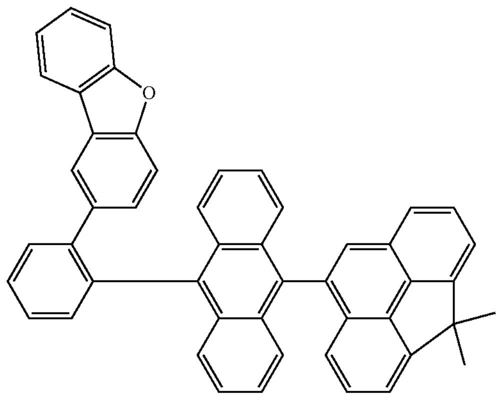
H1-134
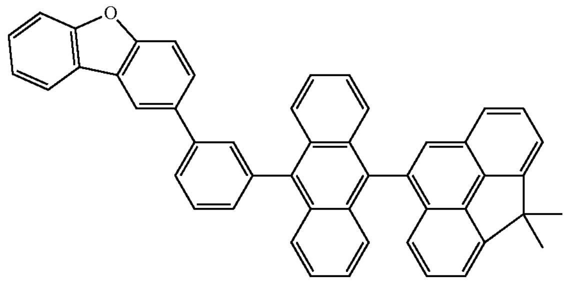
H1-135
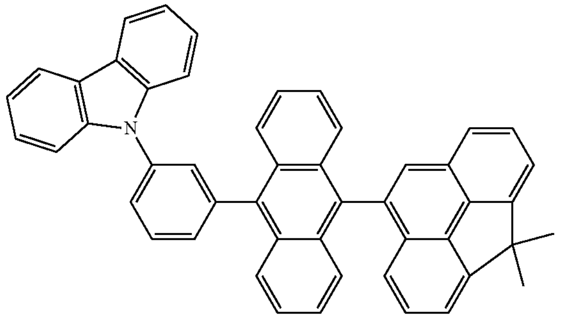
-continued
H1-136
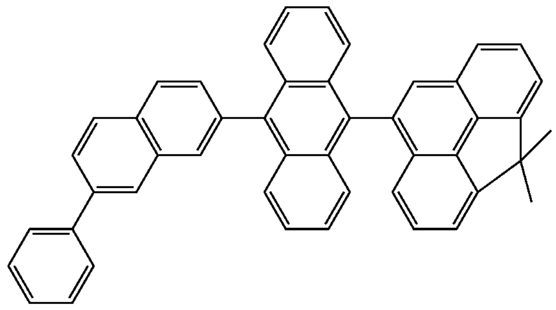
H1-137
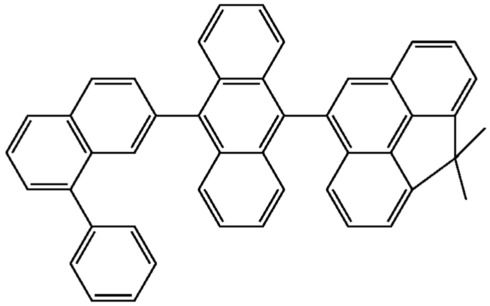
H1-138
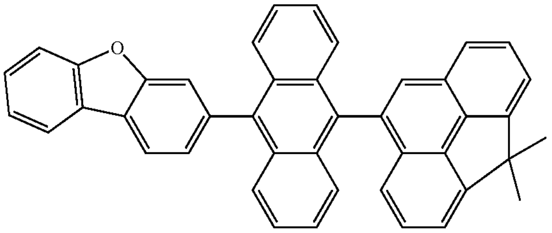
H1-139
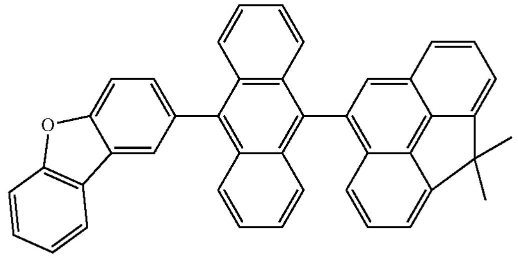
H1-140
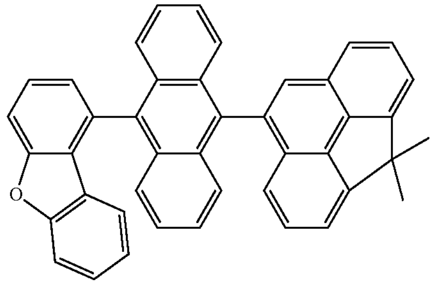

-continued
H1-141
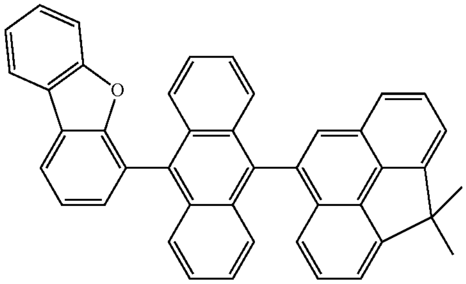
H1-142
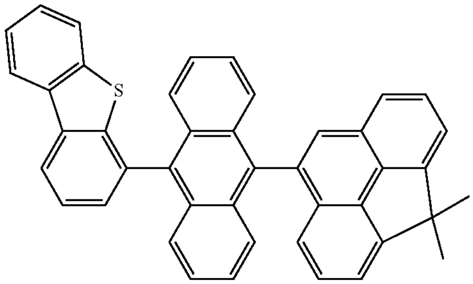
H1-143
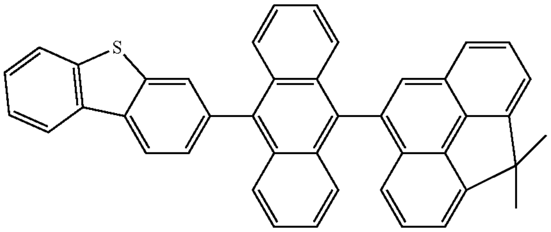
H1-144
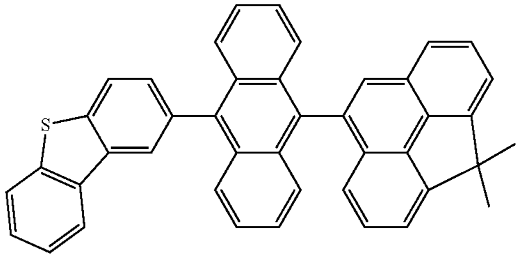
H1-145
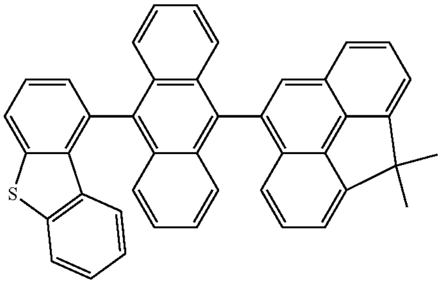
-continued
H1-146
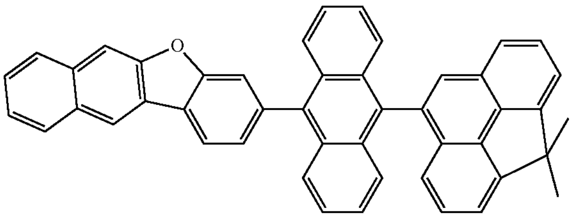
H1-147
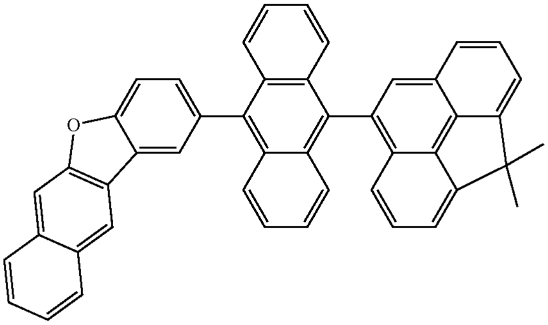
H1-148
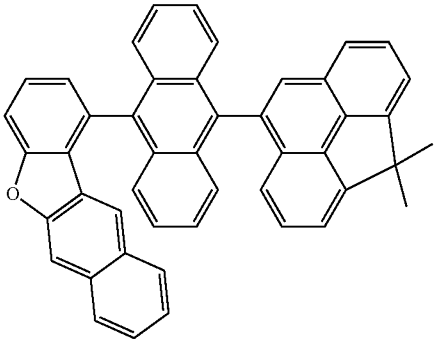
H1-149
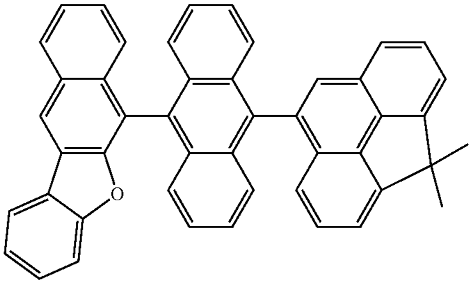
H1-150
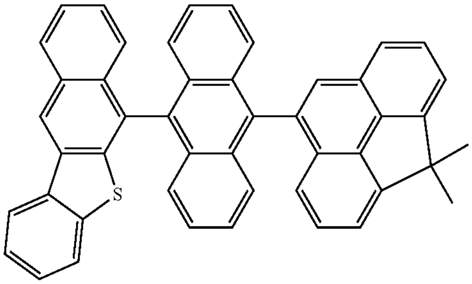

-continued
H1-151
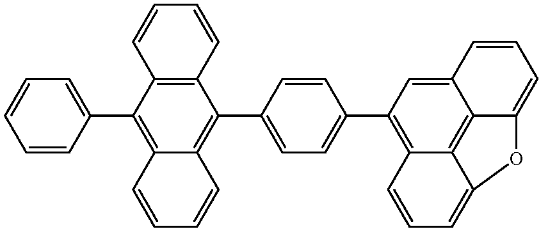
H1-152
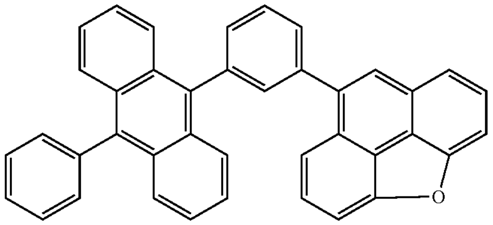
H1-153
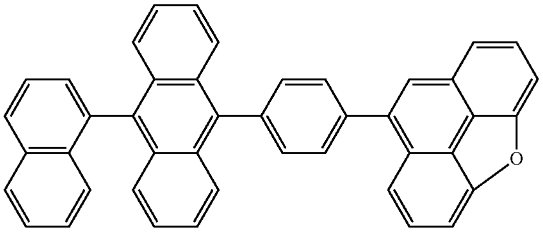
H1-154
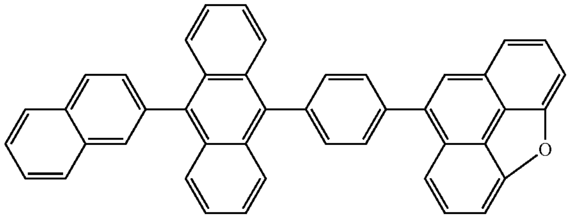
H1-155
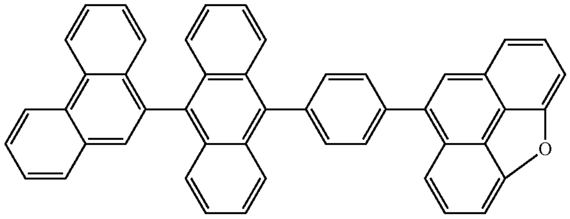
H1-156
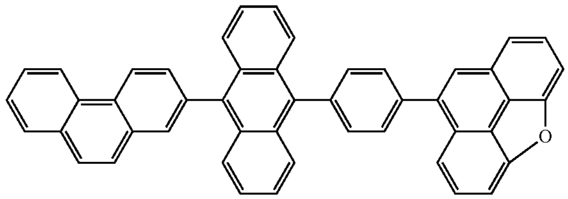
-continued
H1-157
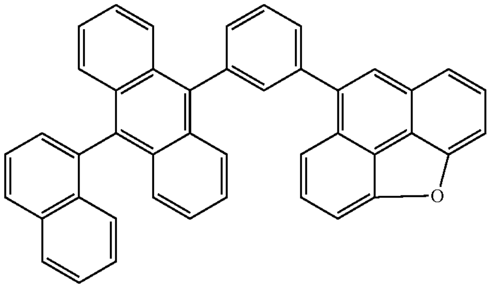
H1-158
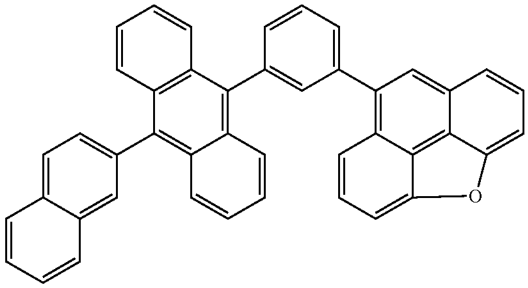
H1-159
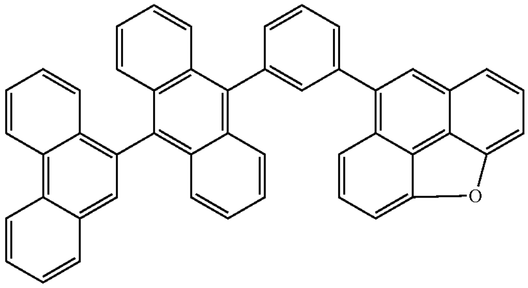
H1-160
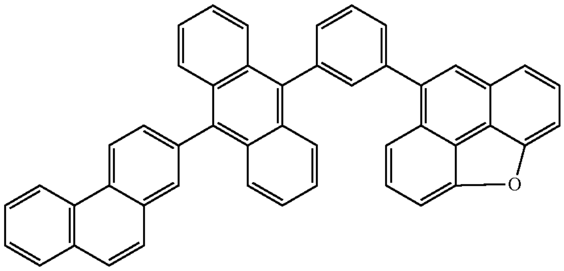
H1-161
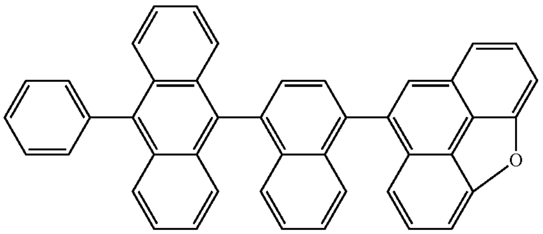

-continued
H1-162
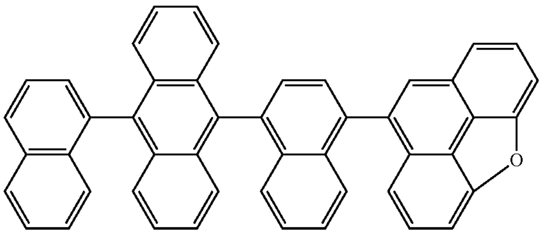
H1-163
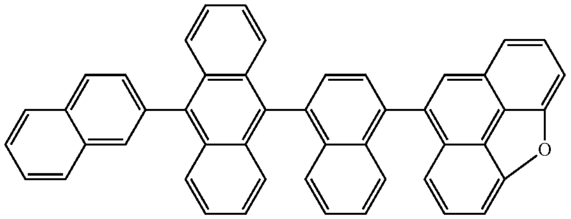
H1-164
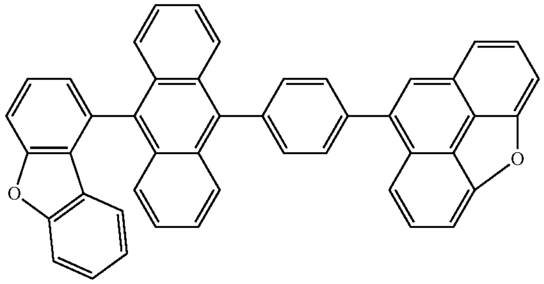
H1-165
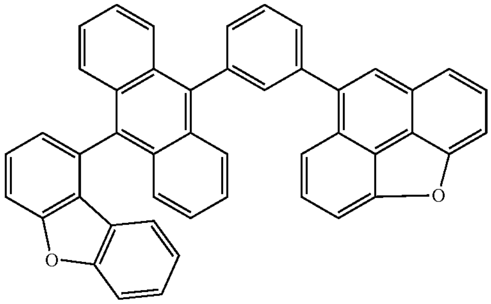
H1-166
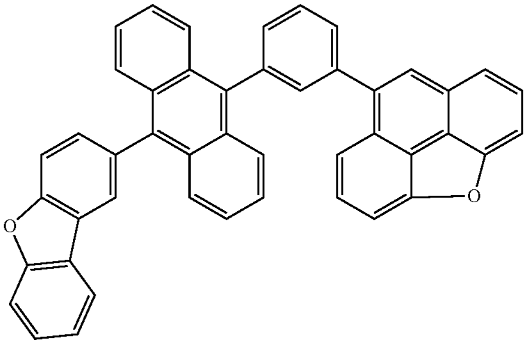
-continued
H1-167
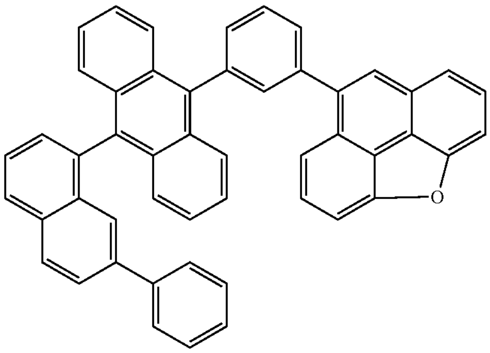
H1-168
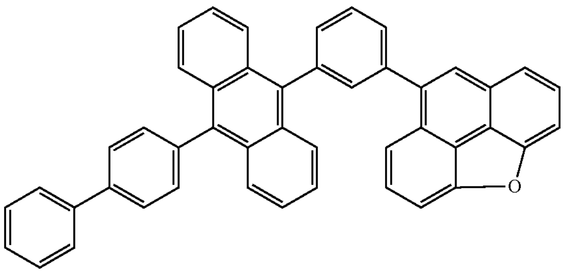
H1-169
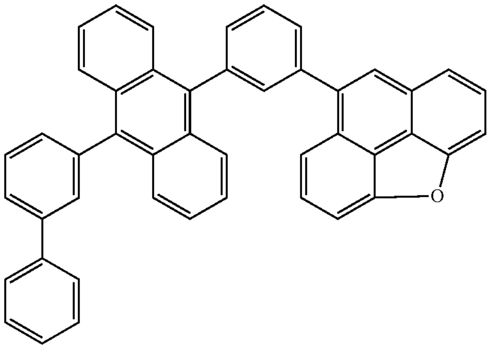
H1-170
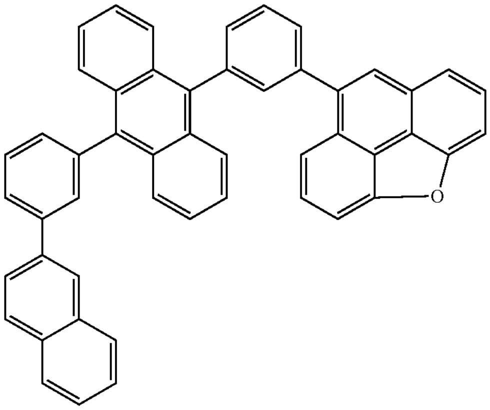

-continued
H1-171
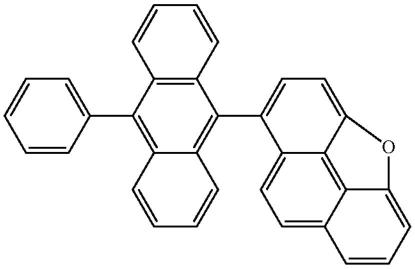
H1-172
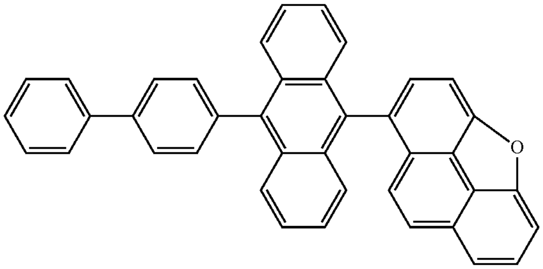
H1-173
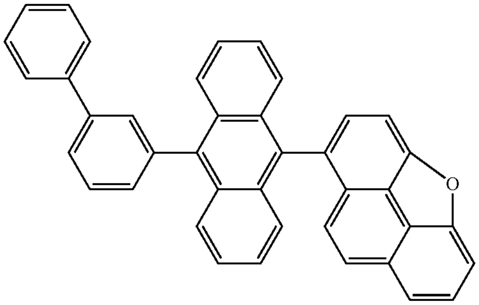
H1-174
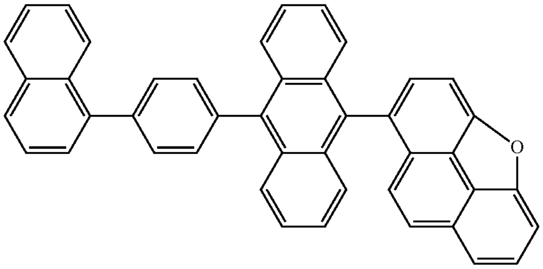
H1-175
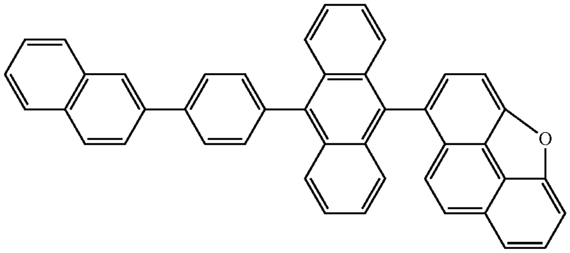
-continued
H1-176
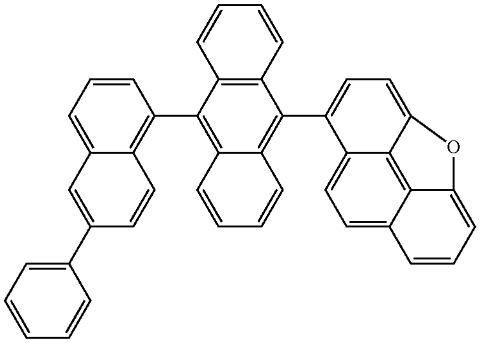
H1-177
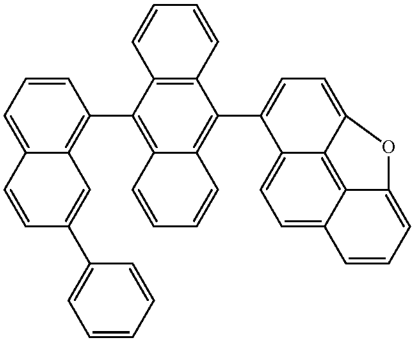
H1-178
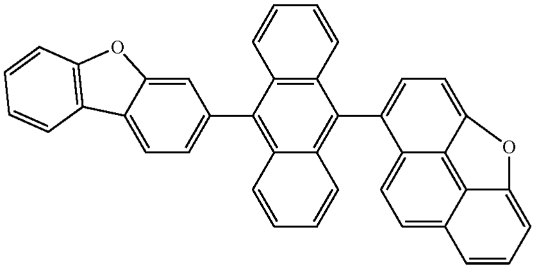
H1-179
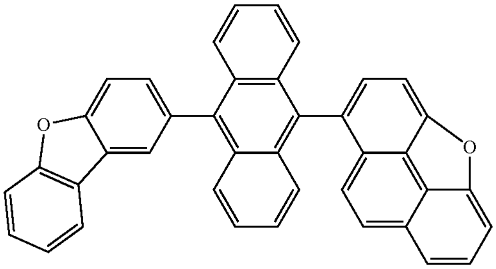
H1-180
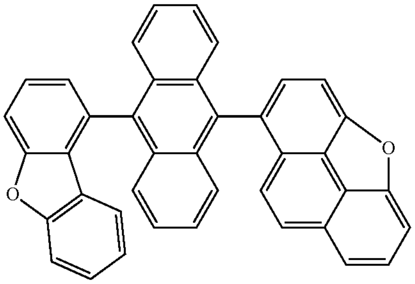

-continued
H1-181
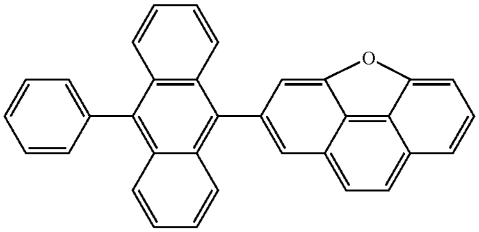
H1-182
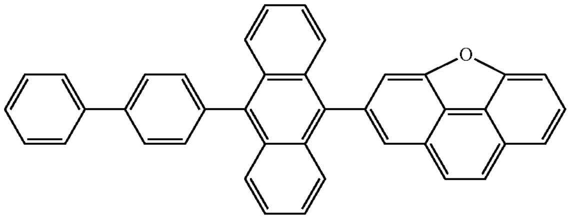
H1-183
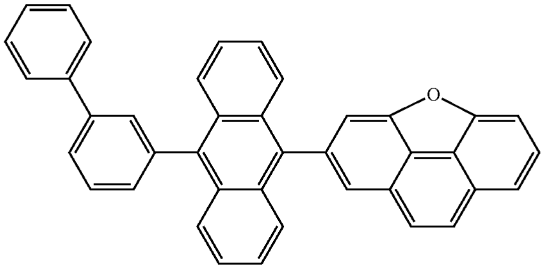
H1-184
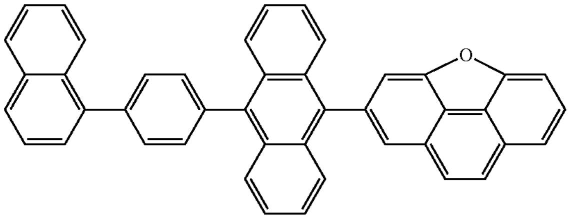
H1-185
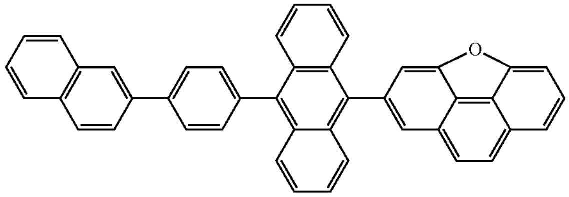
H1-186
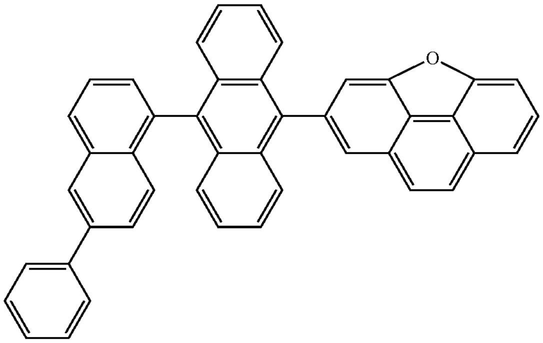
-continued
H1-187
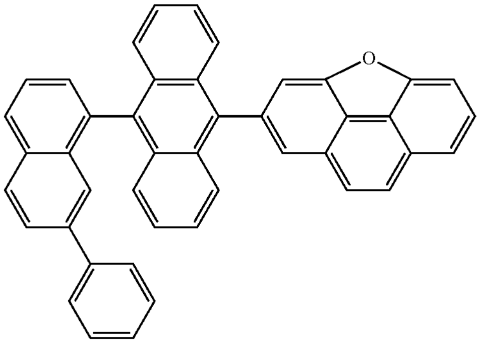
H1-188
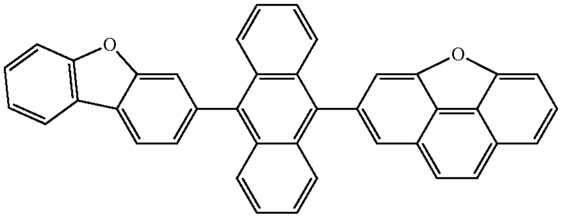
H1-189
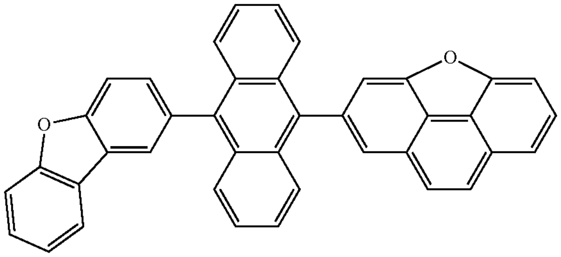
H1-190
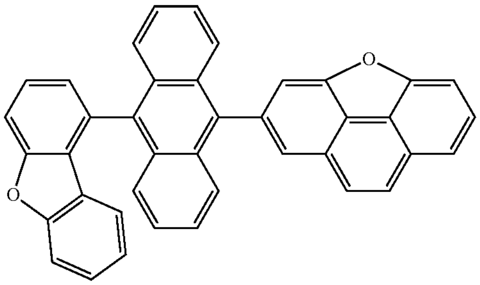
H1-191
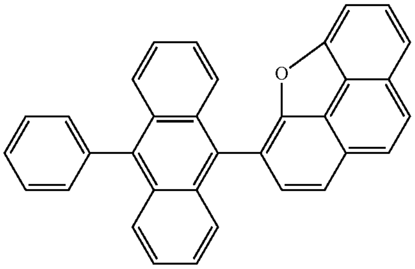

-continued
H1-192
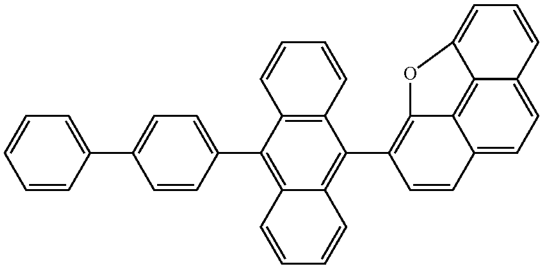
H1-193
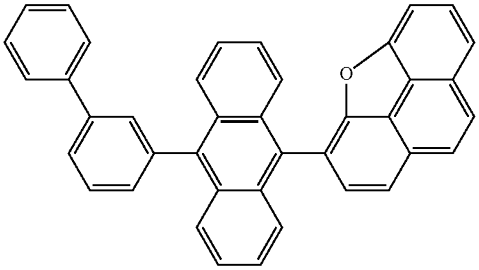
H1-194
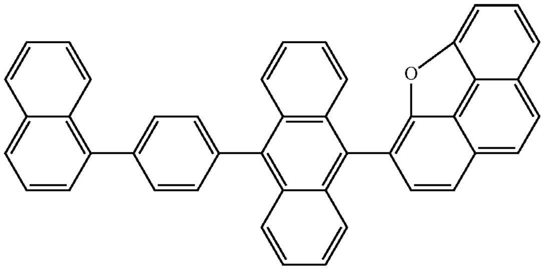
H1-195
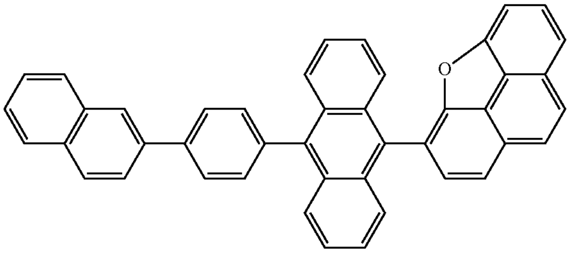
H1-196
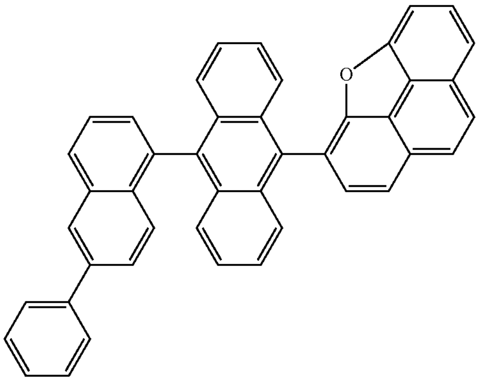
-continued
H1-197
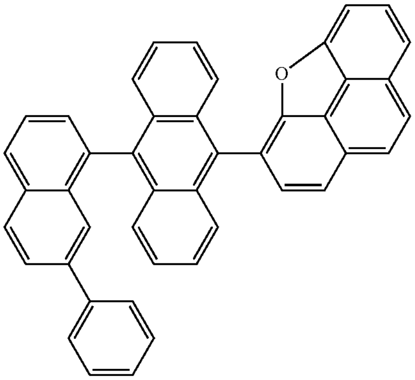
H1-198
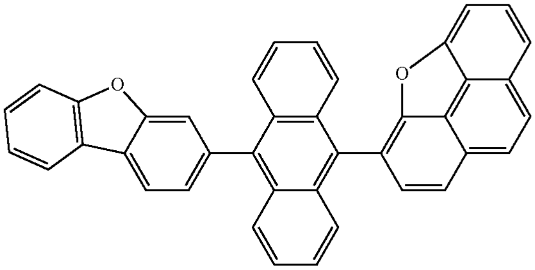
H1-199
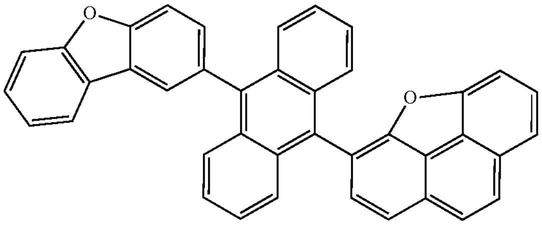
H1-200
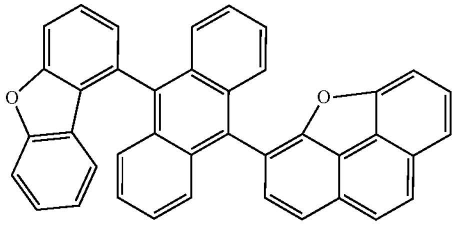
H1-201
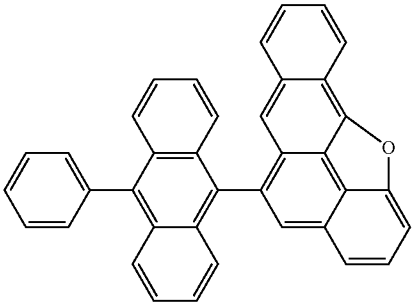

-continued
H1-202
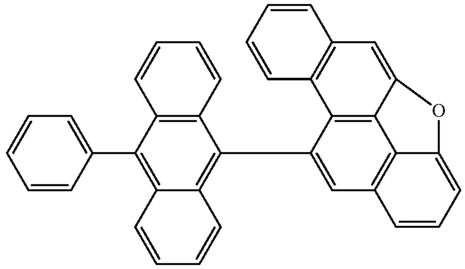
H1-203
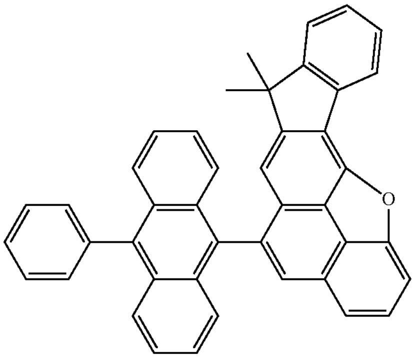
H1-204
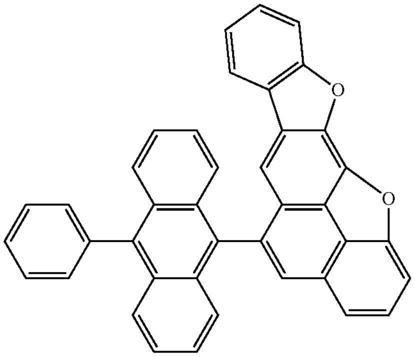
H1-205
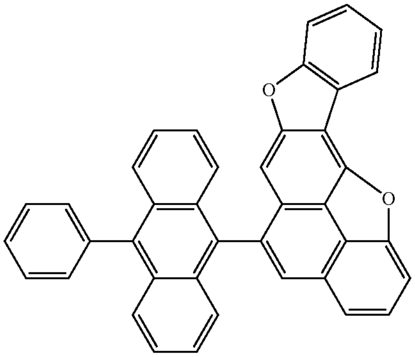
-continued
H1-206
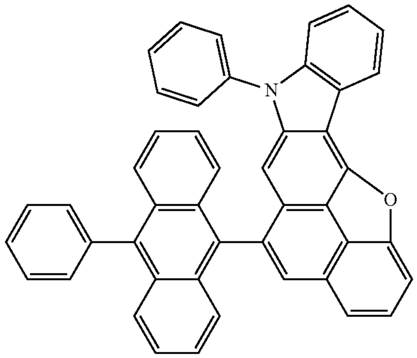
H1-207
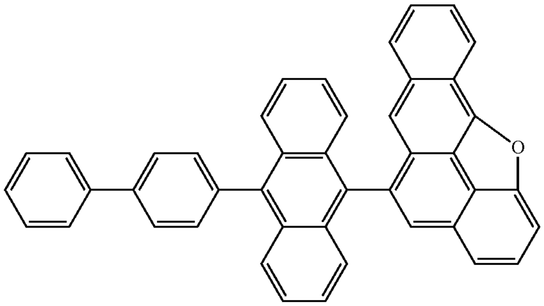
H1-208
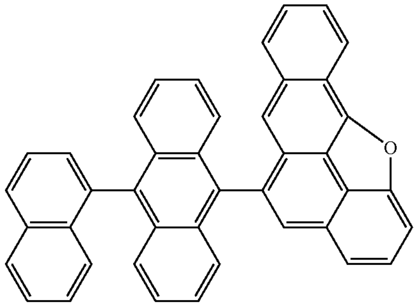
H1-209
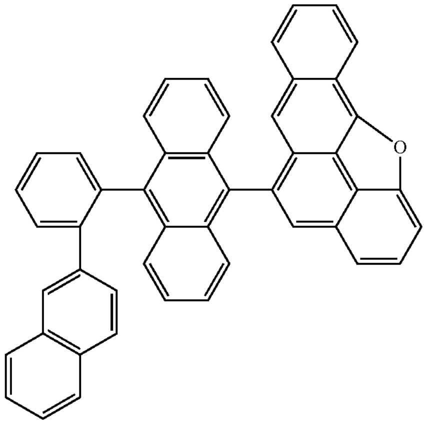

-continued
H1-210
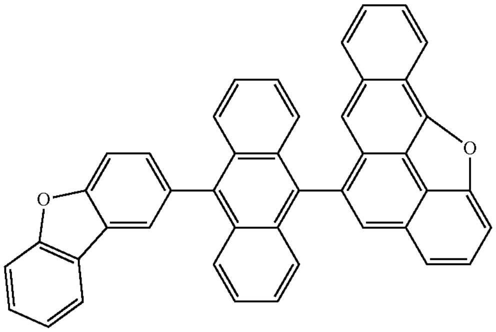
H1-211
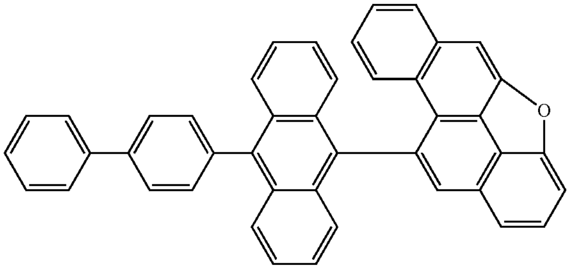
H1-212
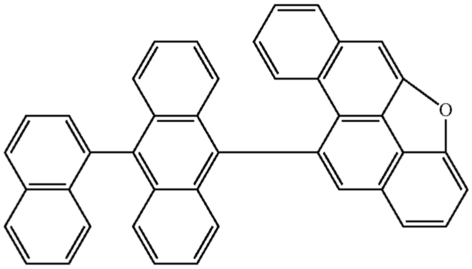
H1-213
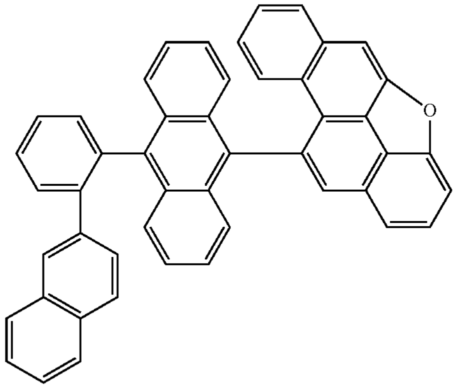
H1-214
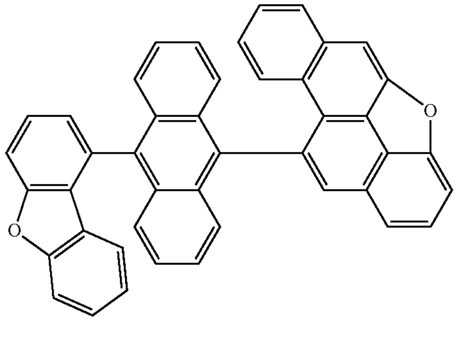
-continued
H1-215
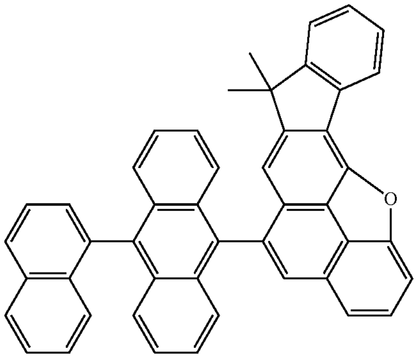
H1-216
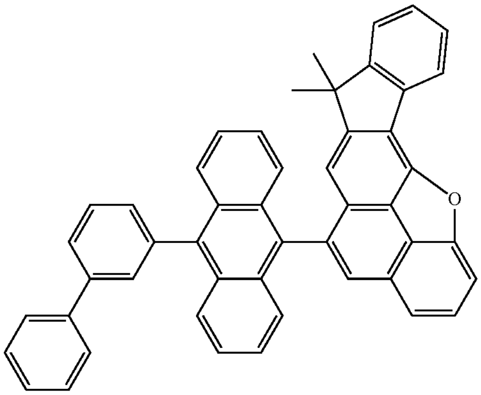
H1-217
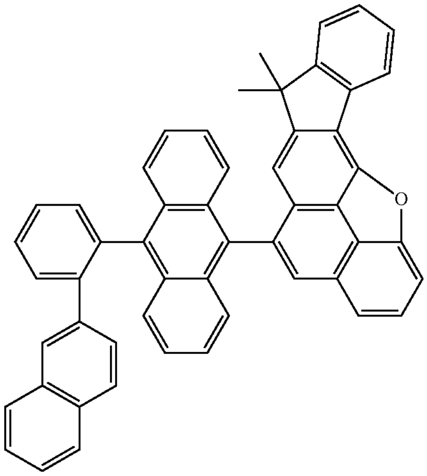
H1-218
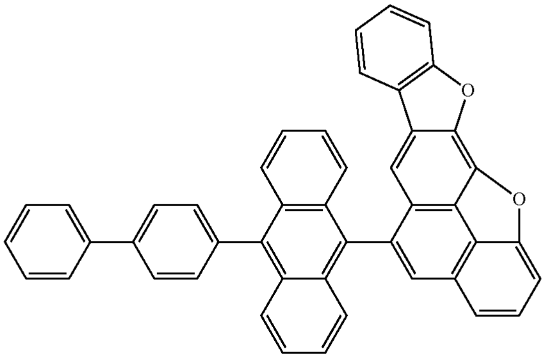

-continued
H1-219
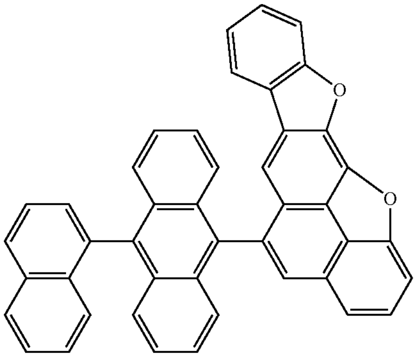
H1-220
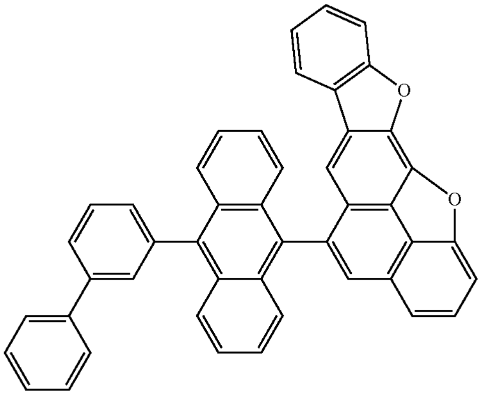
H1-221
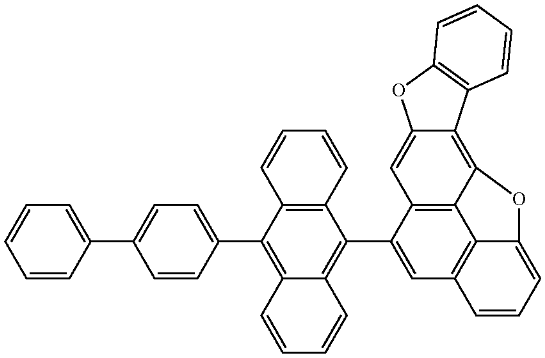
H1-222
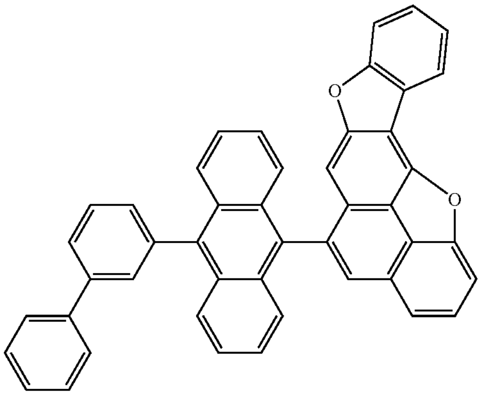
-continued
H1-223
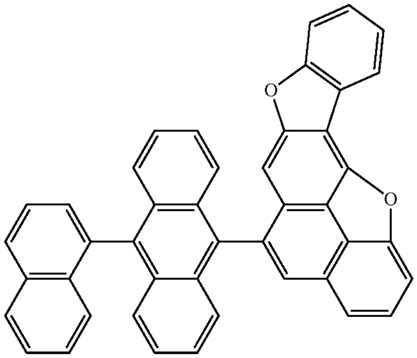
H1-224
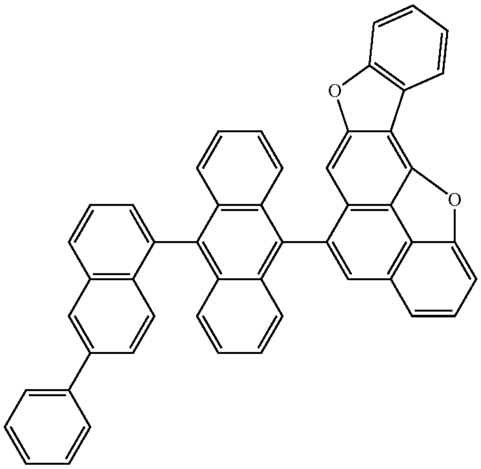
H1-225
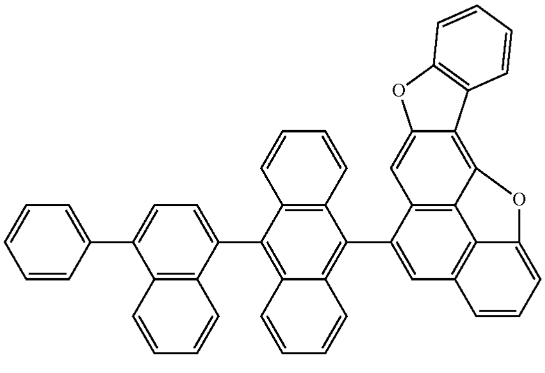
H1-226
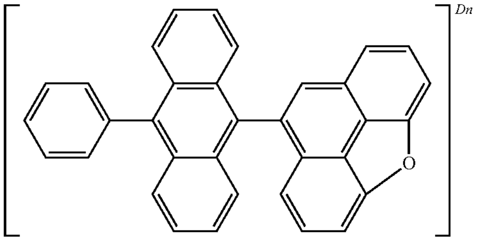

-continued
H1-227
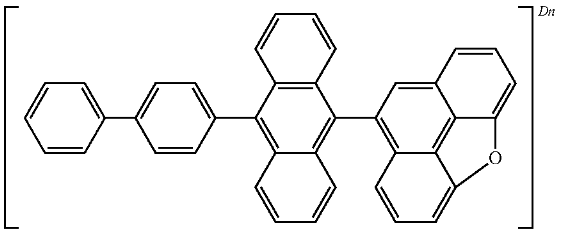
H1-228
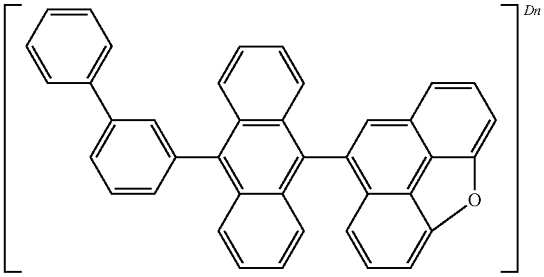
H1-229
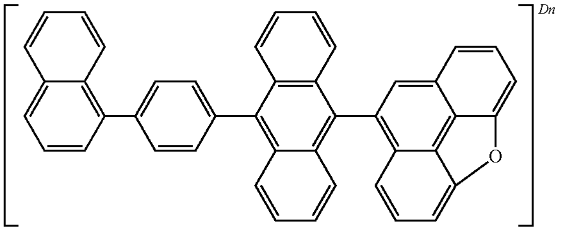
H1-230
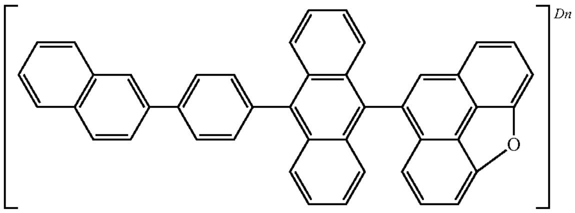
H1-231
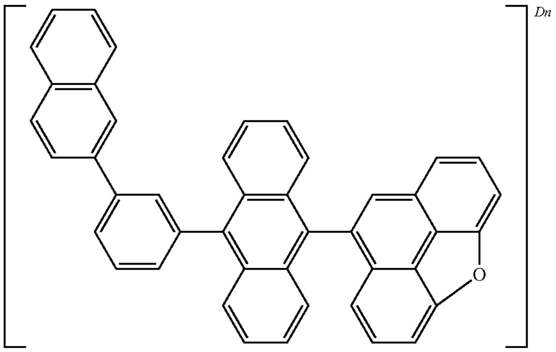
-continued
H1-232
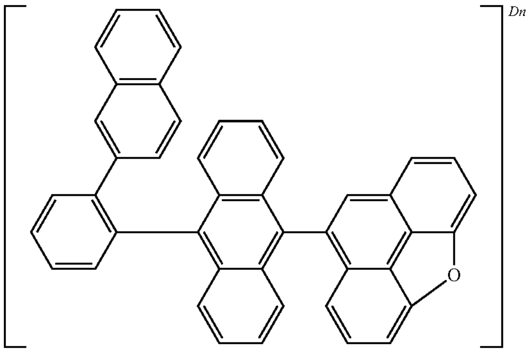
H1-233
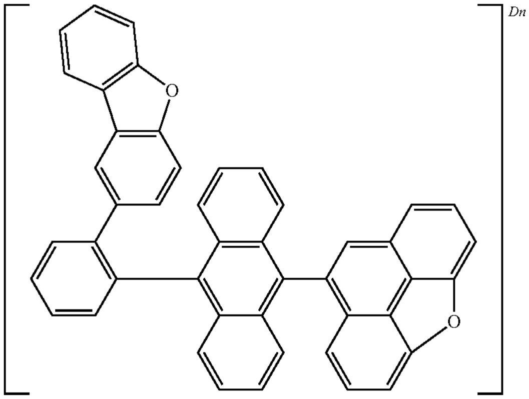
H1-234
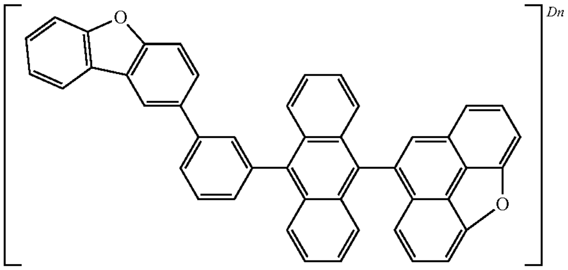
H1-235
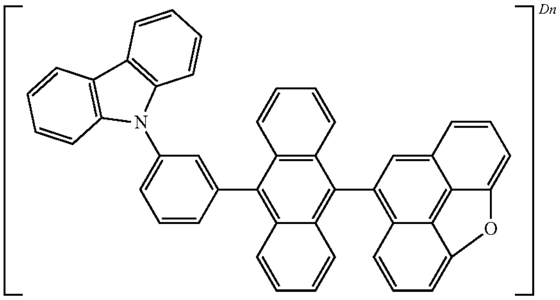

-continued
H1-236
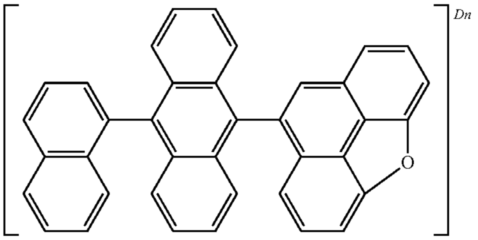
H1-237
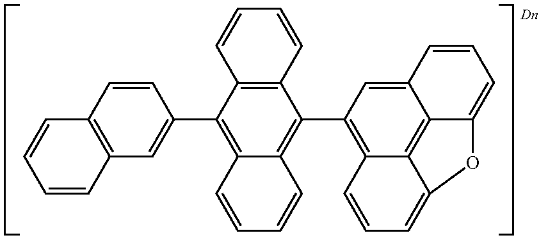
H1-238
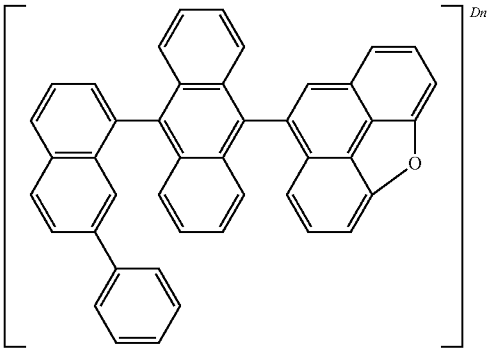
H1-239
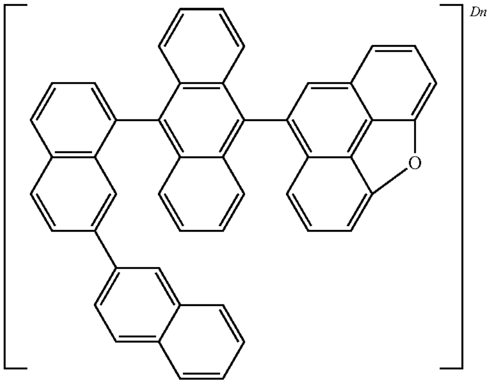
-continued
H1-240
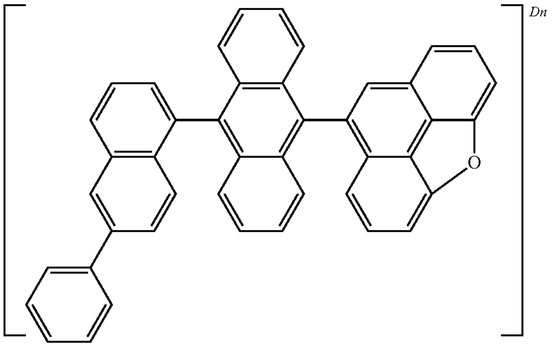
H1-241
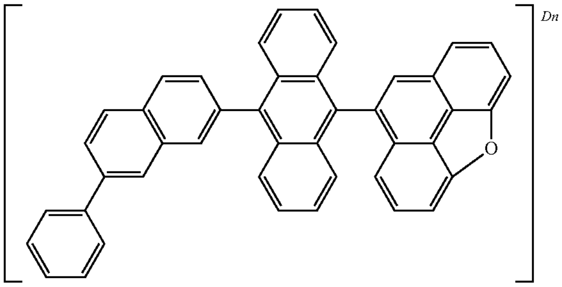
H1-242
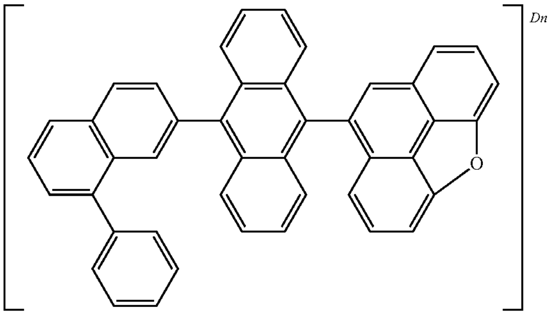
H1-243
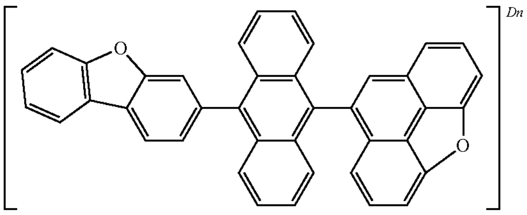
H1-244
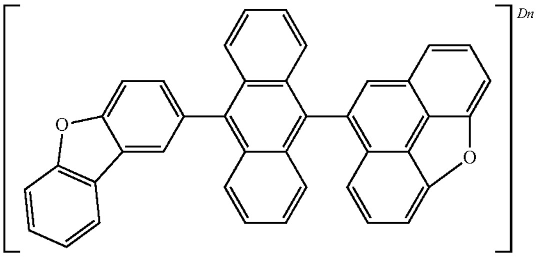

-continued
H1-245
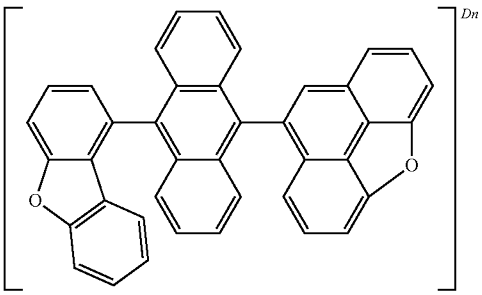
H1-246
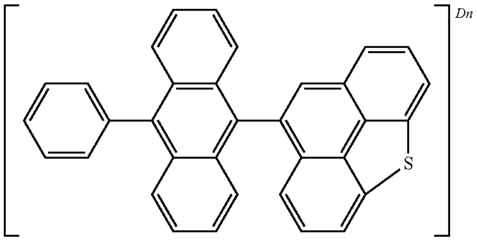
H1-247
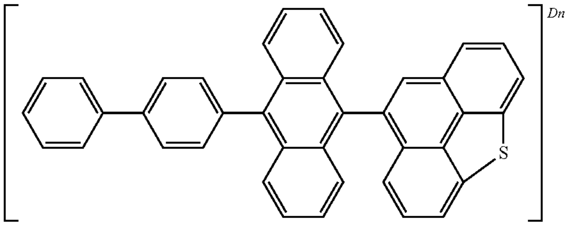
H1-248
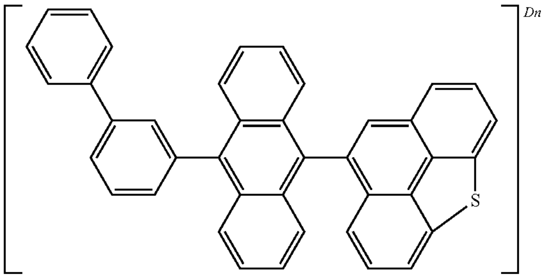
H1-249
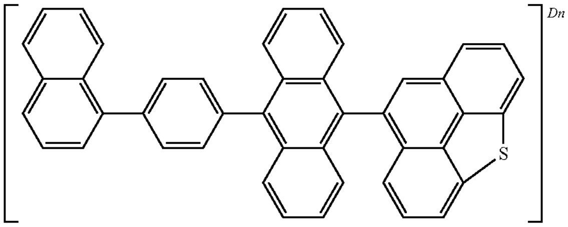
H1-250
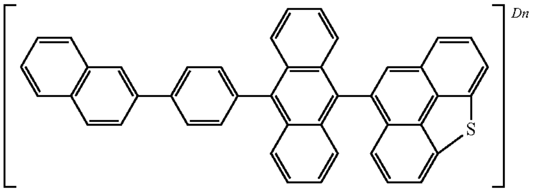
-continued
H1-251
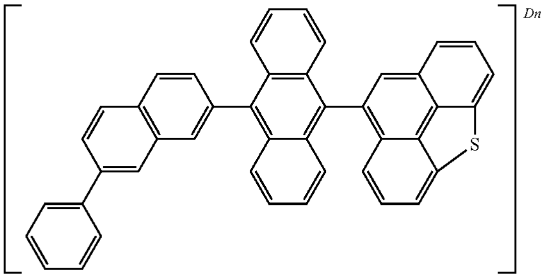
H1-252
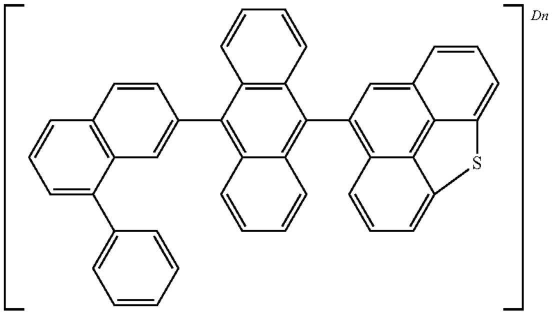
H1-253
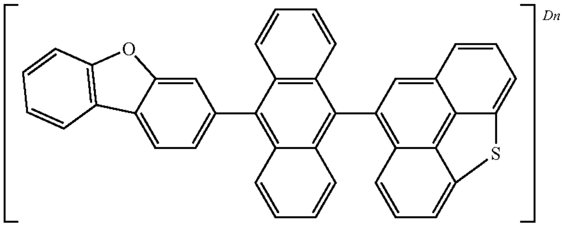
H1-254
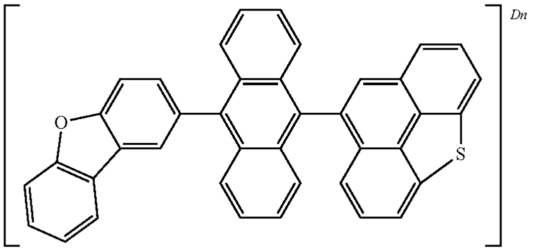
H1-255
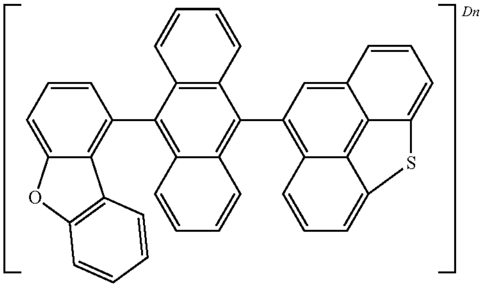

-continued
H1-256
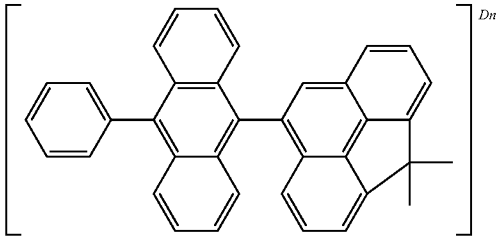
H1-257
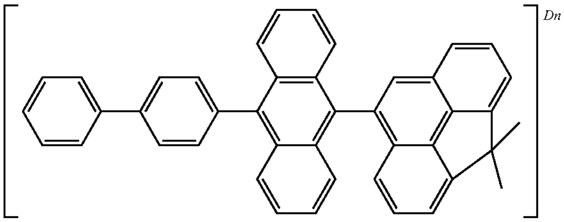
H1-258
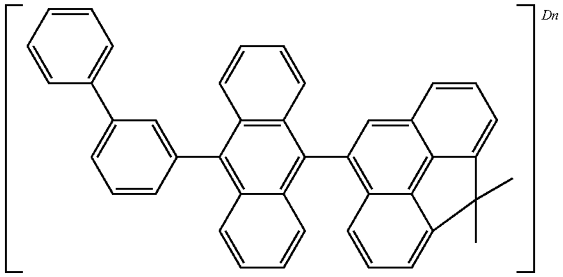
H1-259
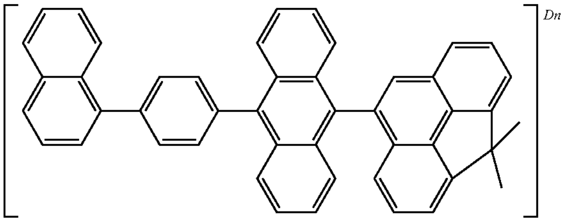
H1-260
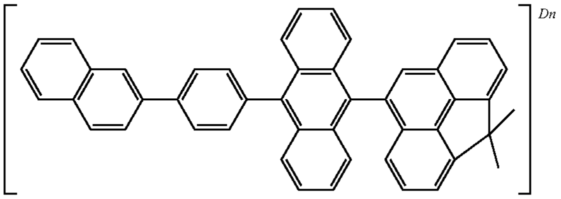
H1-261
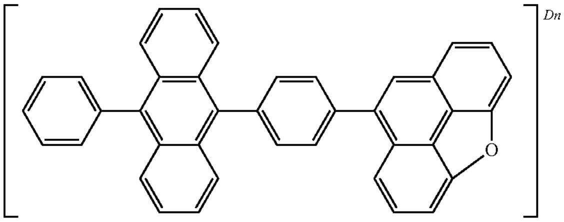
-continued
H1-262
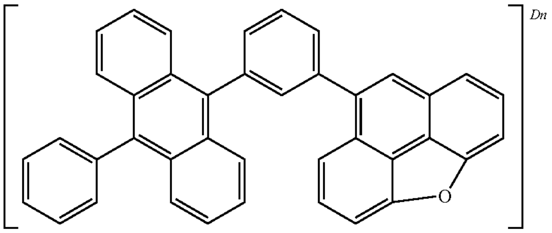
H1-263
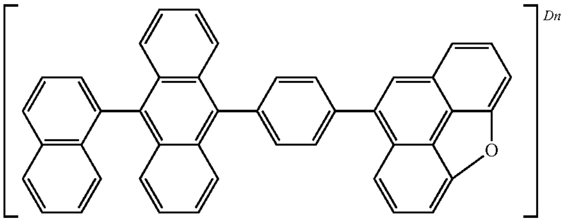
H1-264
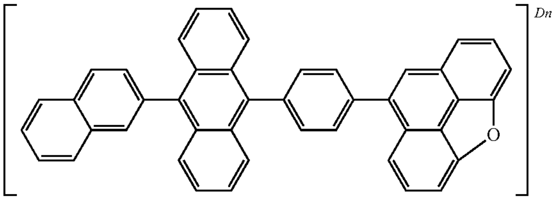
H1-265
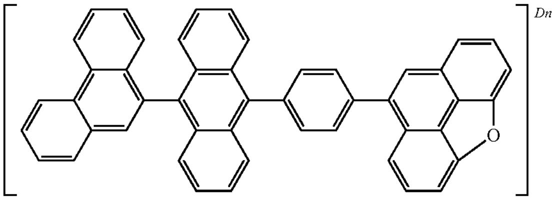
H1-266
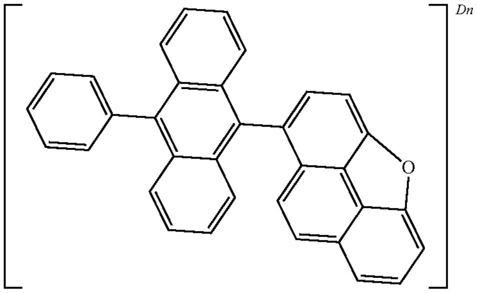
H1-267
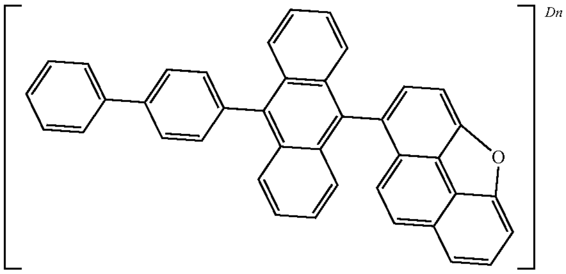

-continued
H1-268
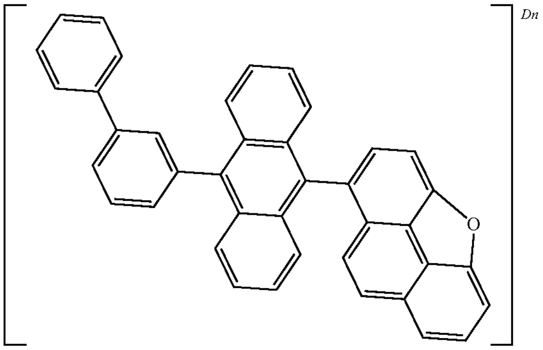
H1-269
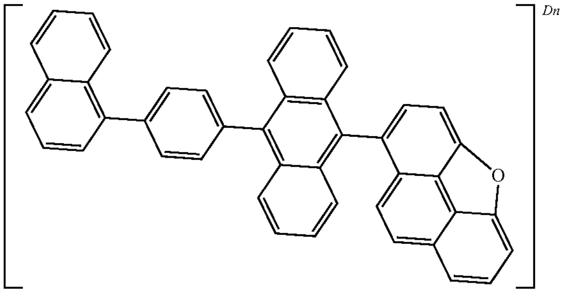
H1-270
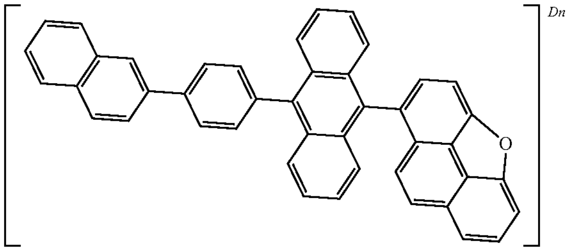
H1-271
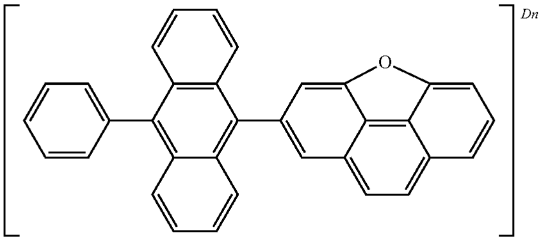
H1-272
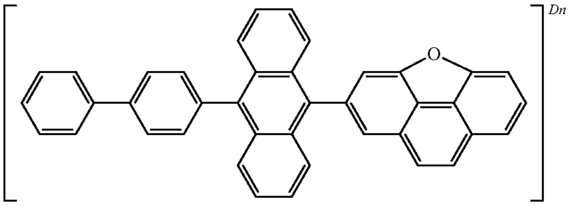
-continued
H1-273
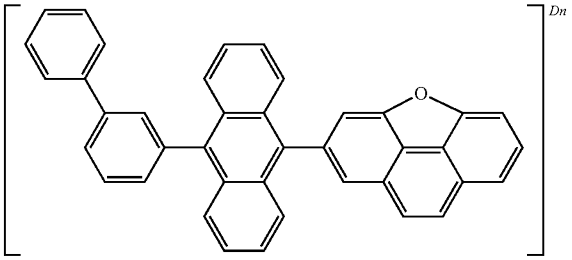
H1-274
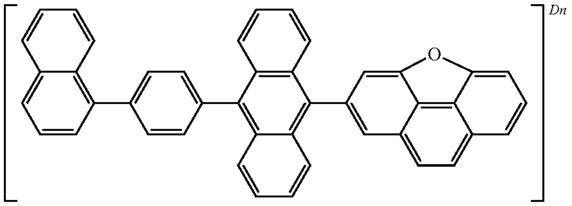
H1-275
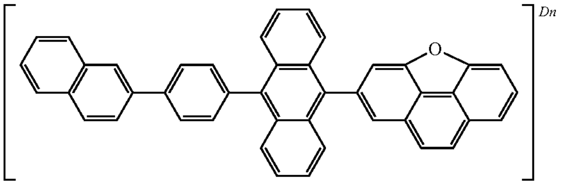
H1-276
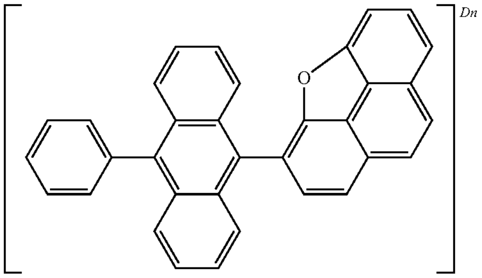
H1-277
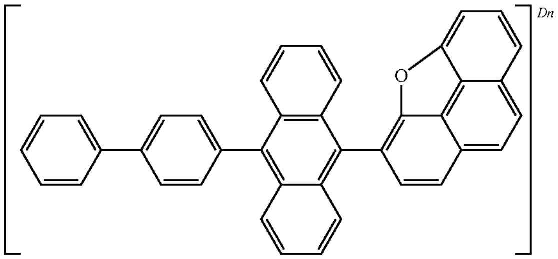

-continued
H1-278
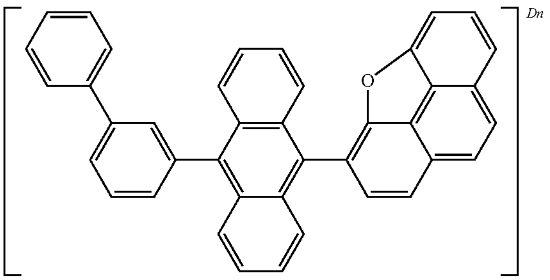
H1-279
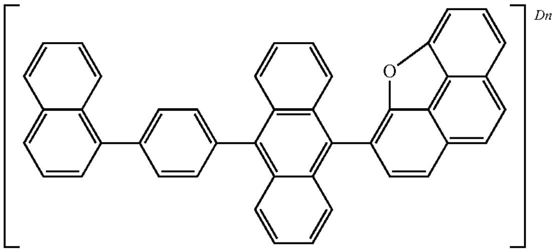
H1-280
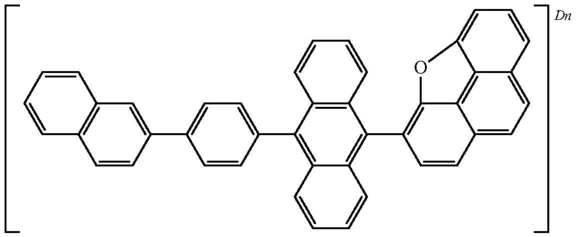
H1-281
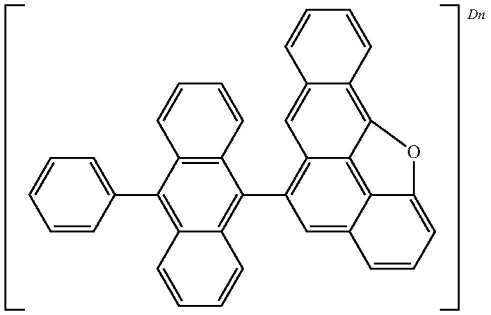
H1-282
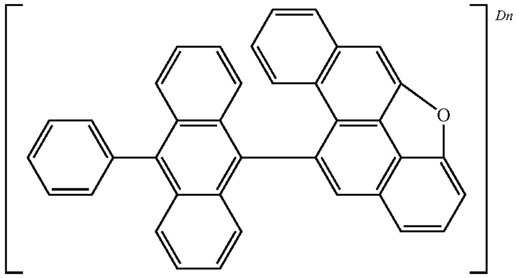
-continued
H1-283
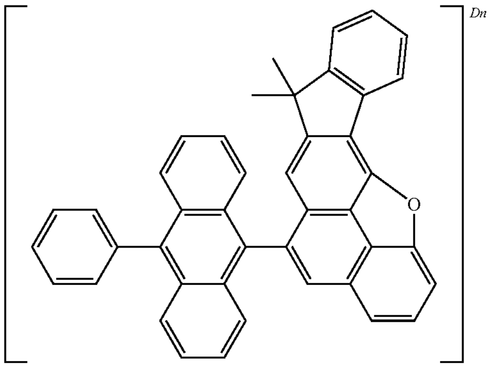
H1-284
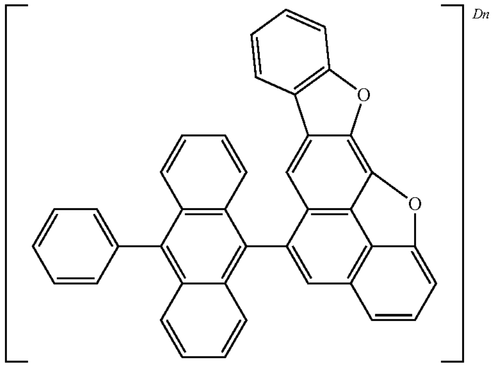
H1-285
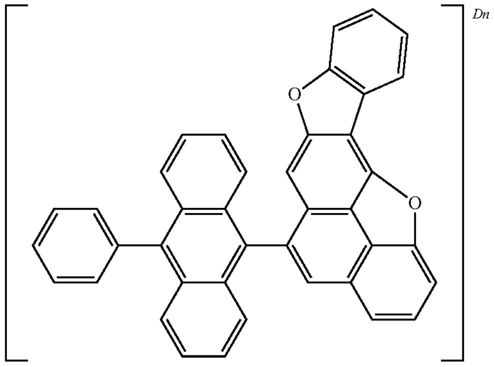

-continued
H1-286
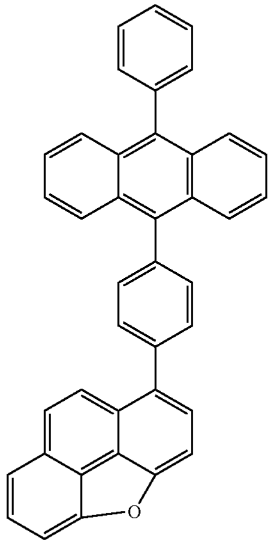
H1-287
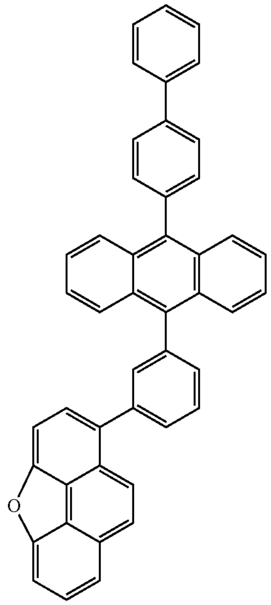
-continued
H1-288
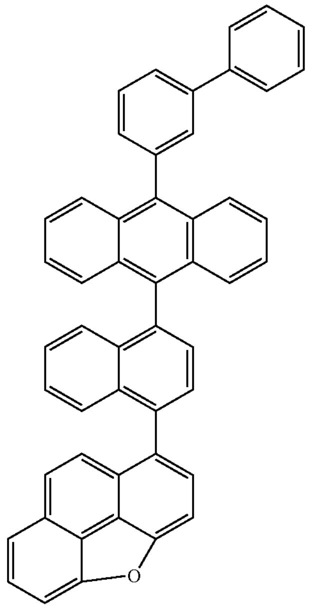
H1-289
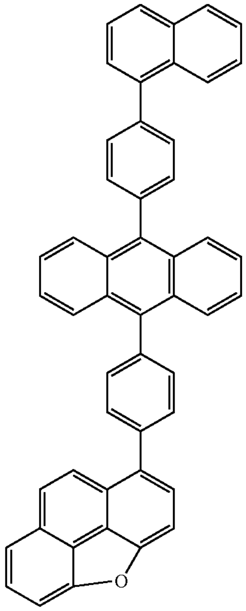

-continued
H1-290
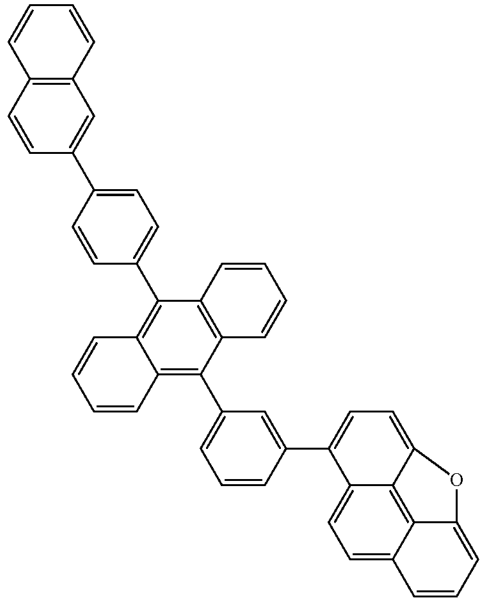
H1-291
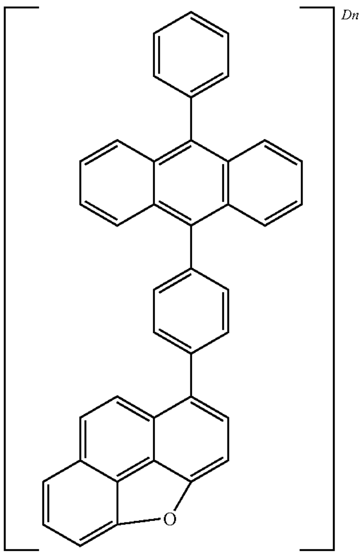
-continued
H1-292
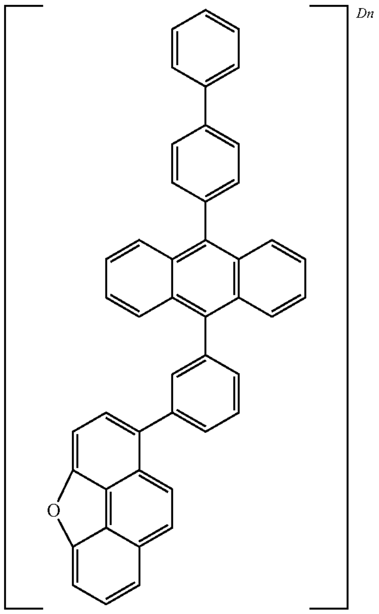
H1-293
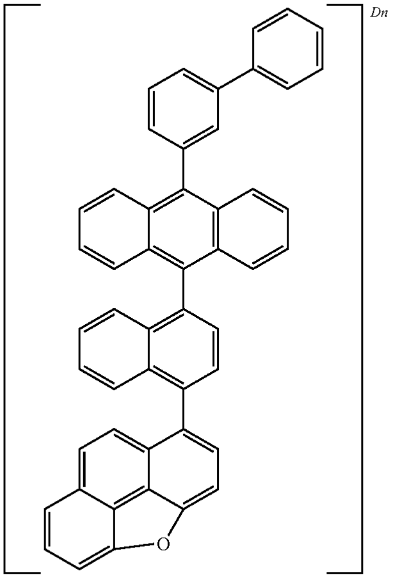

-continued

H1-294

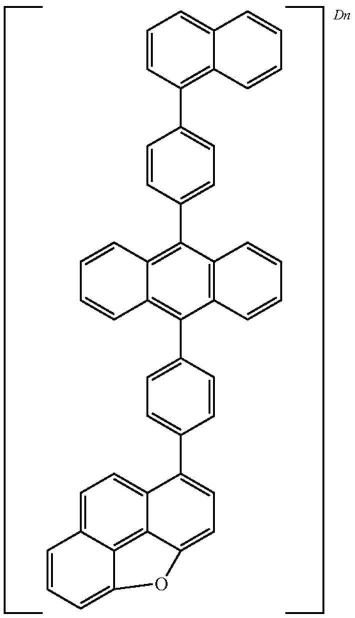

H1-295

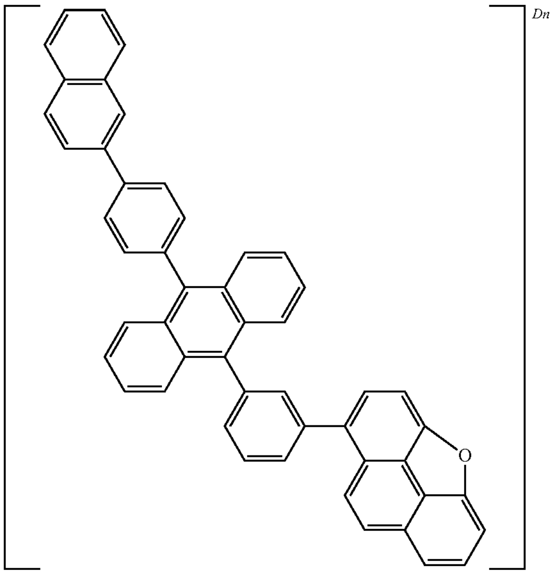

In the compounds above, $D_n$ represents that n hydrogens are replaced with deuterium; and n represents an integer of 1 to 50. According to one embodiment of the present disclosure, n, each independently, represents an integer of 4 to 45. According to another embodiment of the present disclosure, n, each independently, represents an integer of 6 to 40. For example, n may be an integer of 1 to 32. When being deuterated to the number of the lower limit or more, the bond dissociation energy related to deuteration may increase to exhibit improved lifetime properties. The upper limit of n is determined by the number of hydrogens capable of being substituted in each compound.

Specifically, the compound represented by formula 2 may be at least one selected from the group consisting of the following compounds, but is not limited thereto.

C-1

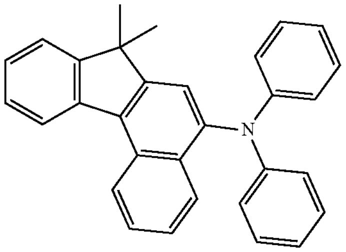

C-2

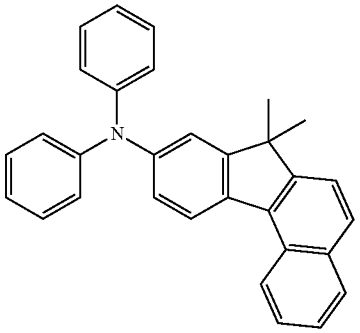

C-3

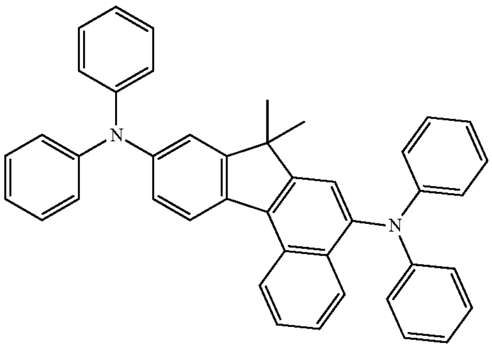

C-4

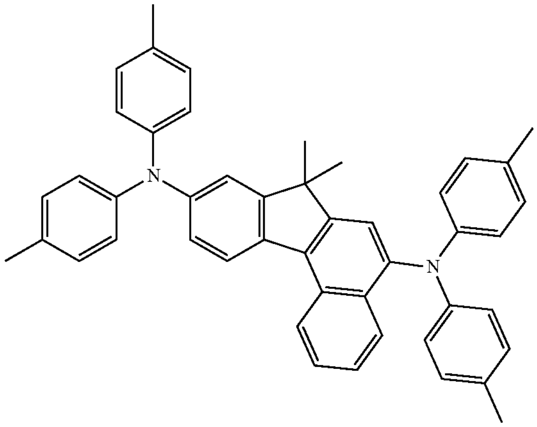

-continued
C-5
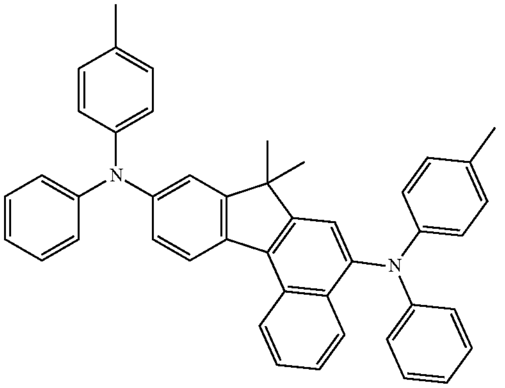
C-6
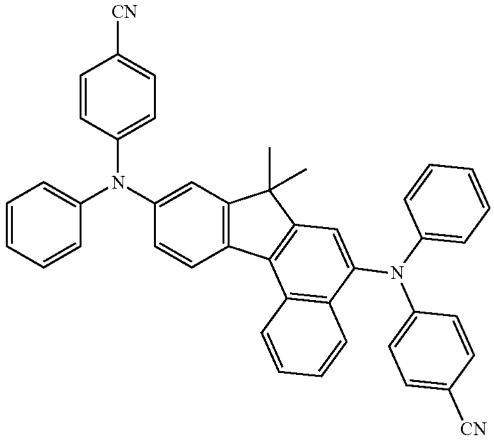
C-7
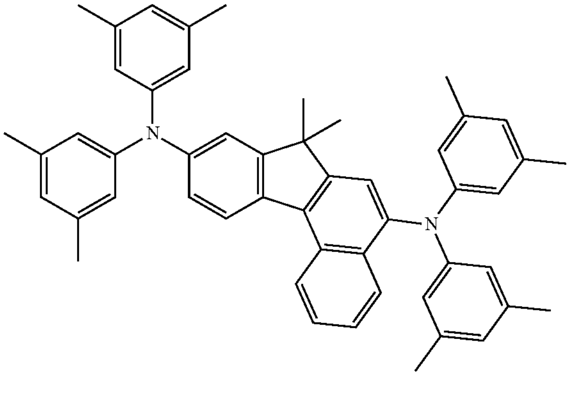
-continued
C-8
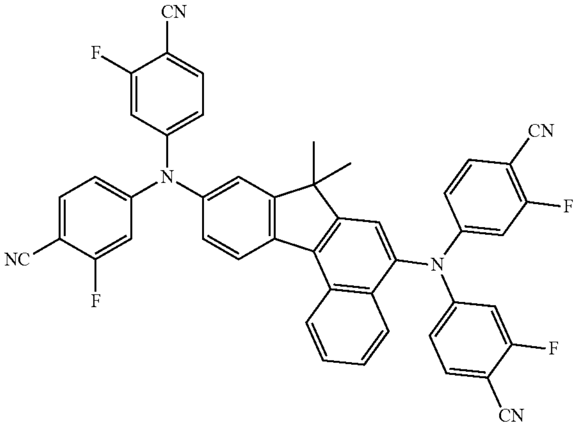
C-9
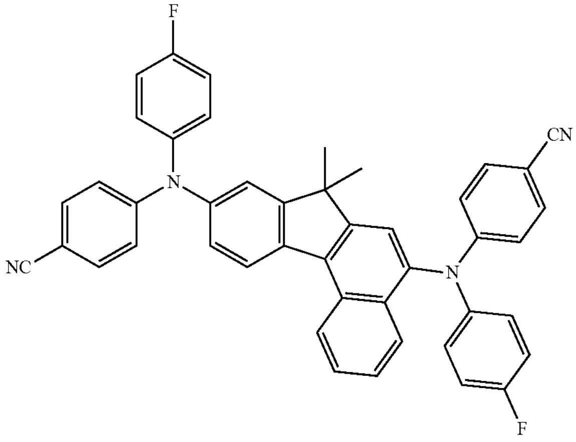
C-10
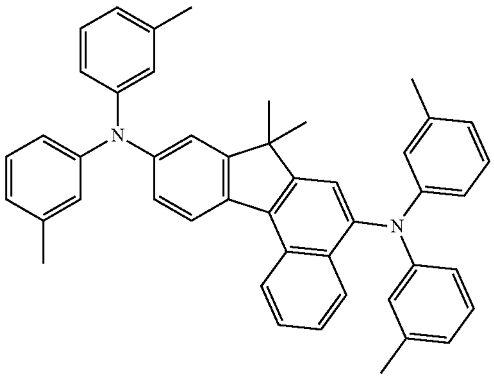
C-11
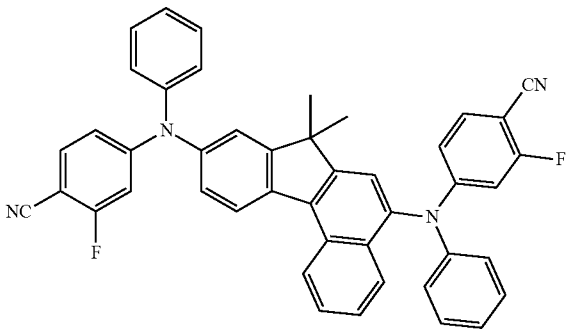

-continued
C-12
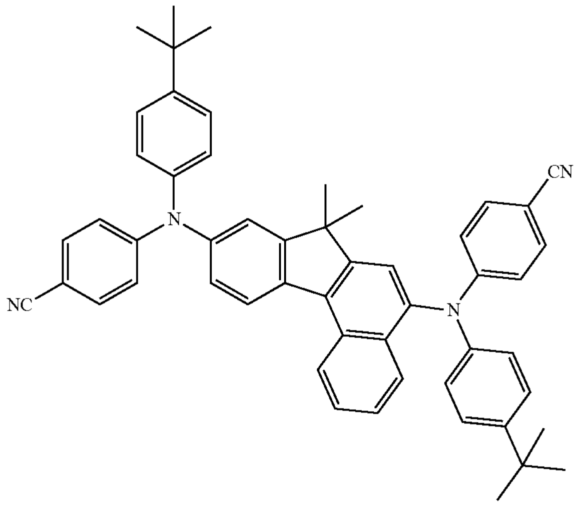
C-13
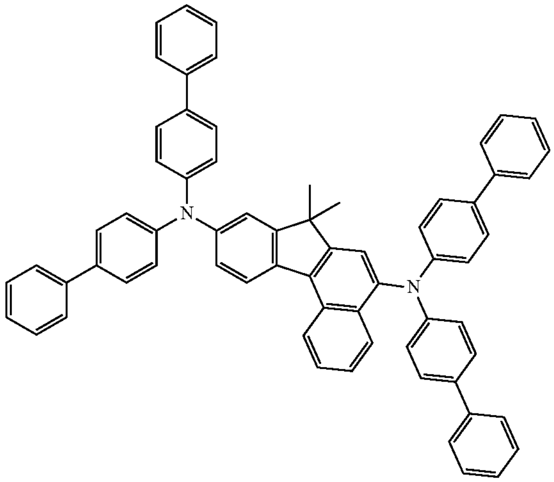
C-14
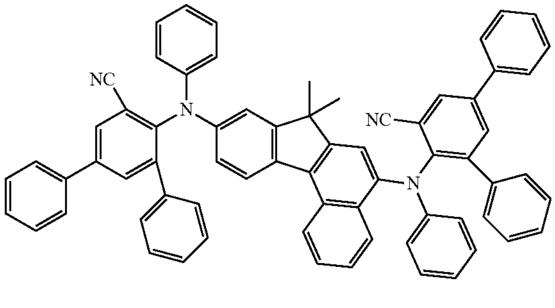
-continued
C-15
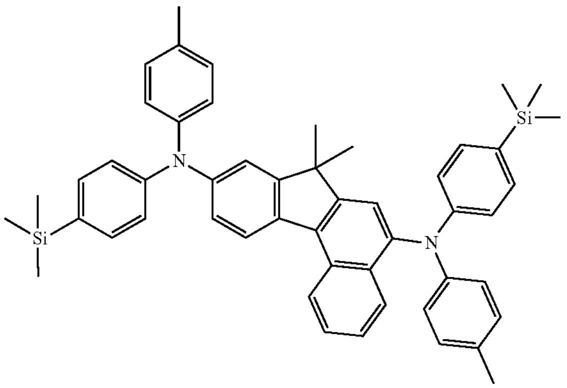
C-16
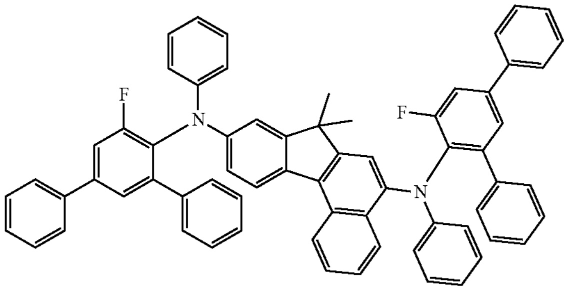
C-17
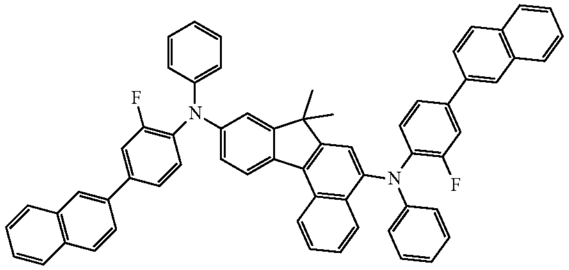
C-18
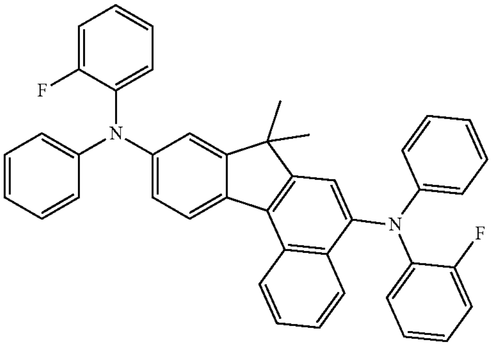

-continued
C-19
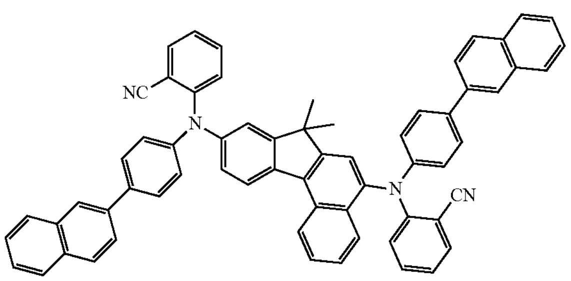
C-20
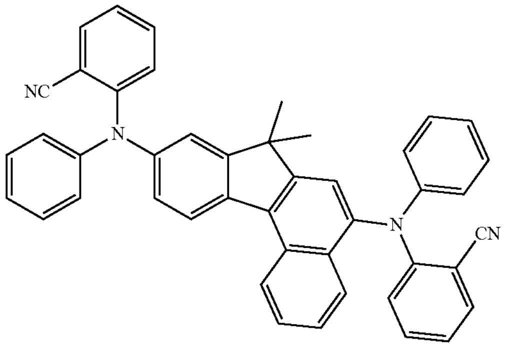
C-21
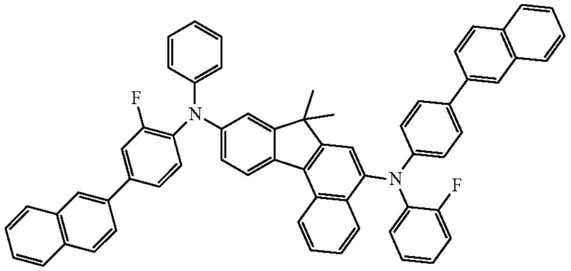
C-22
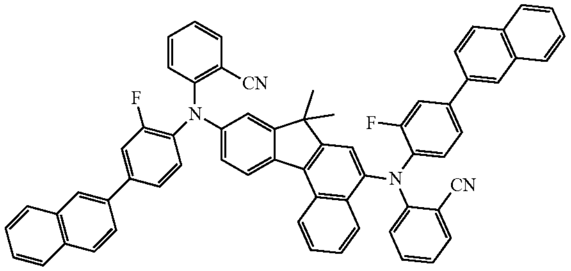
-continued
C-23
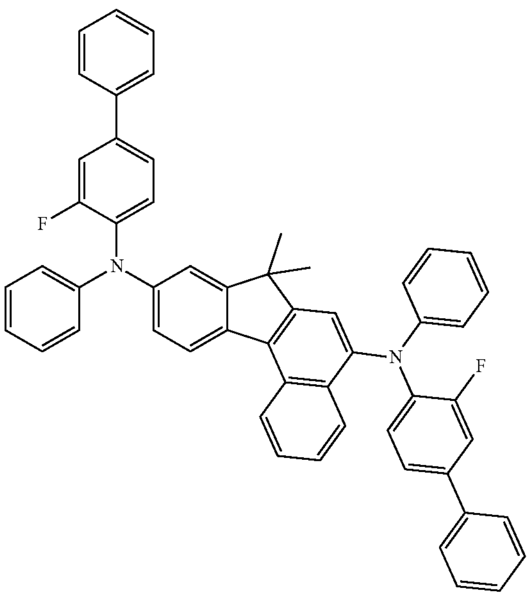
C-24
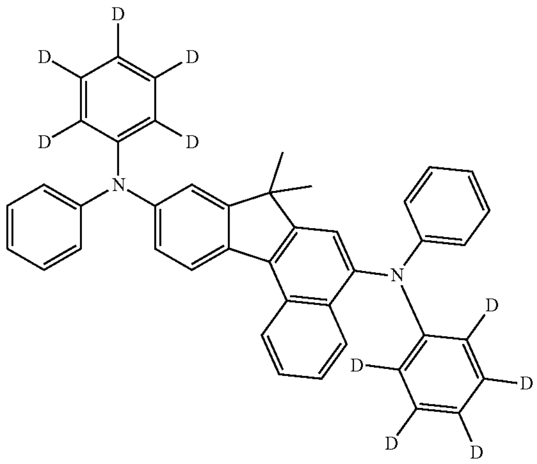
C-25
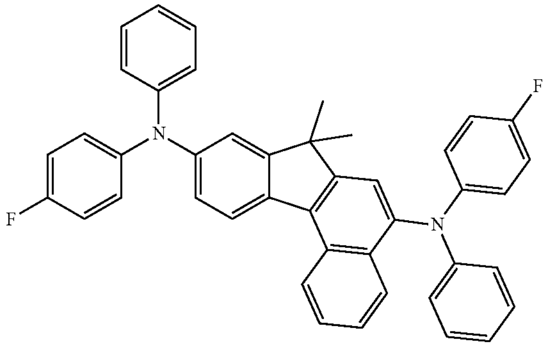

-continued
C-26
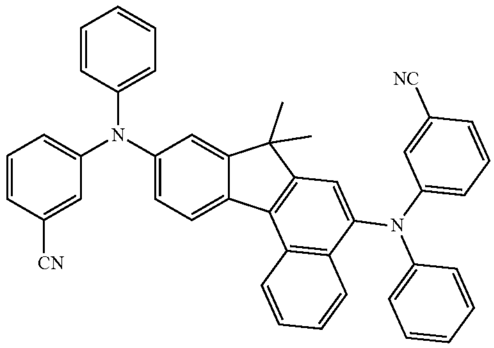
C-27
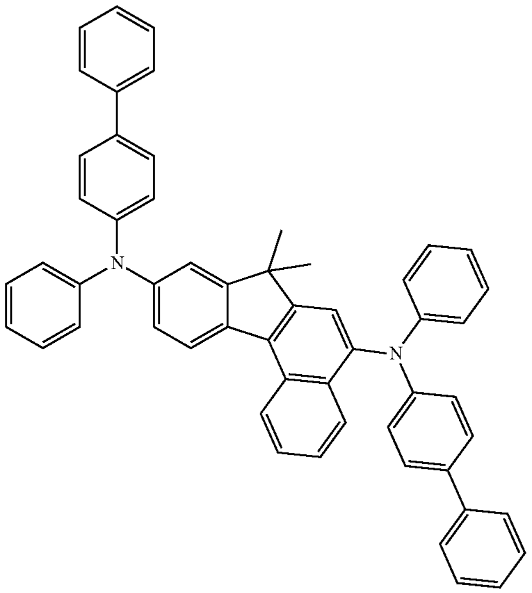
C-28
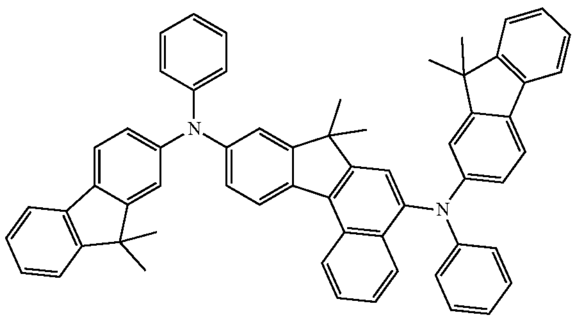
-continued
C-29
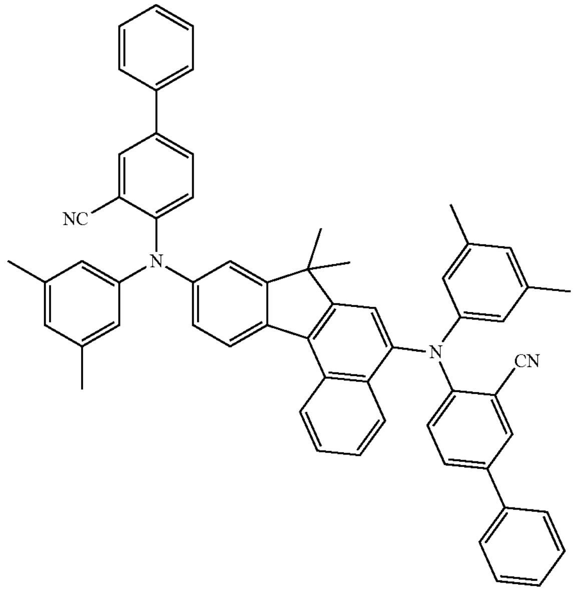
C-30
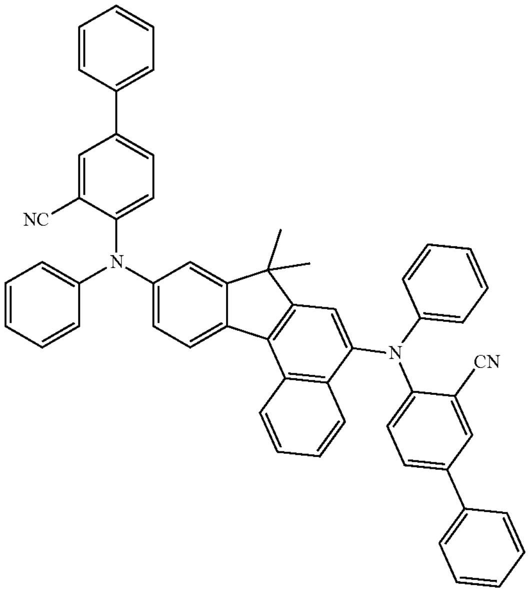
C-31
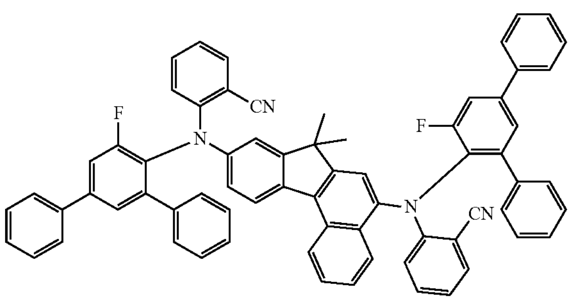

-continued
C-32
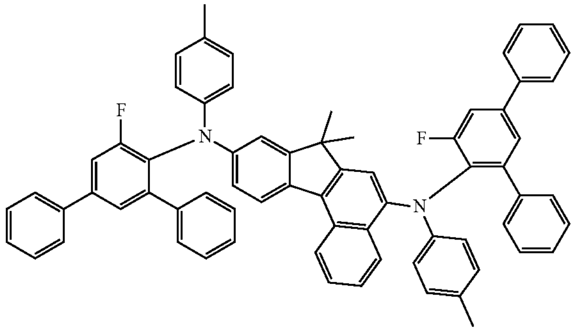
C-33
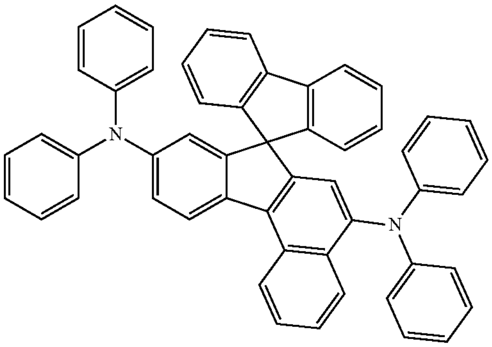
C-34
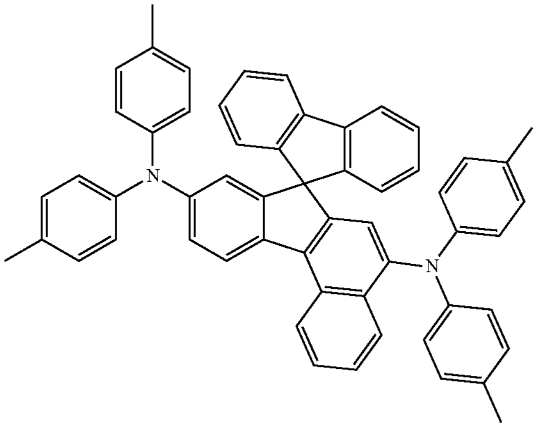
C-35
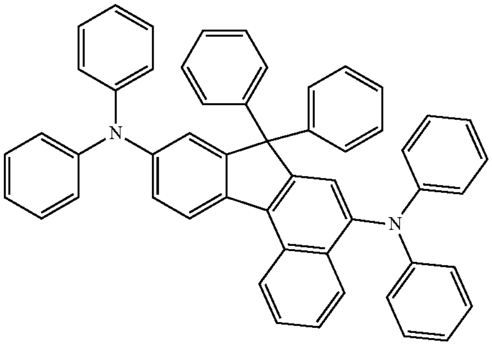
-continued
C-36
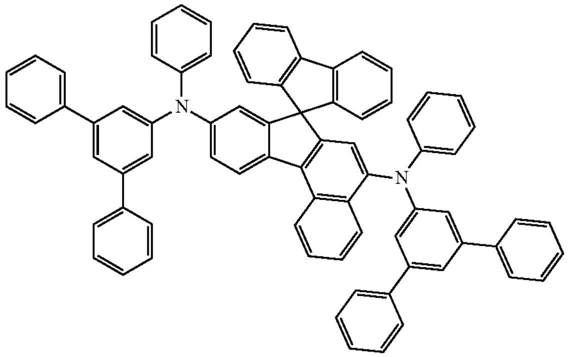
C-37
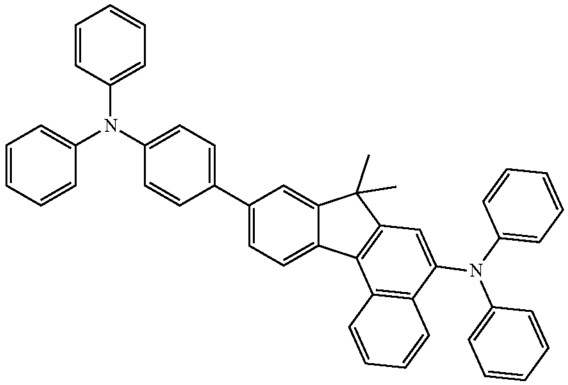
C-38
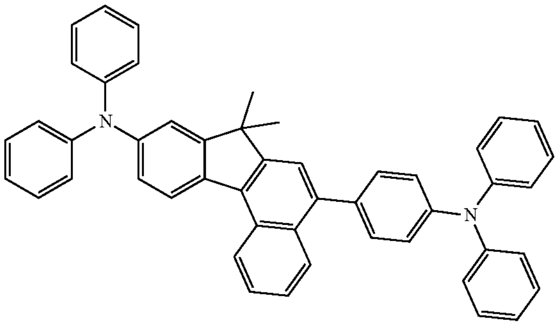
C-39
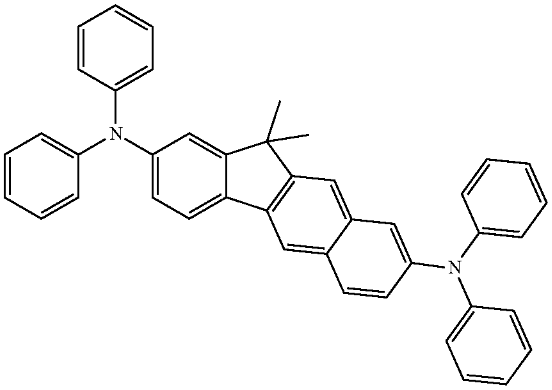

-continued
C-40
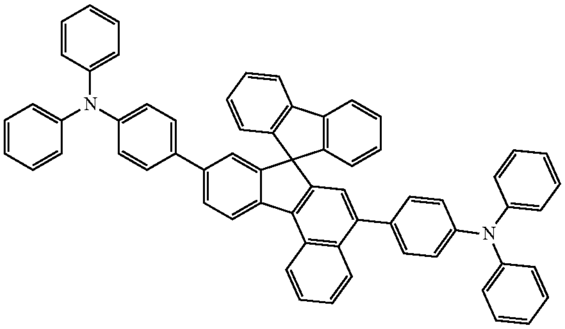
C-41
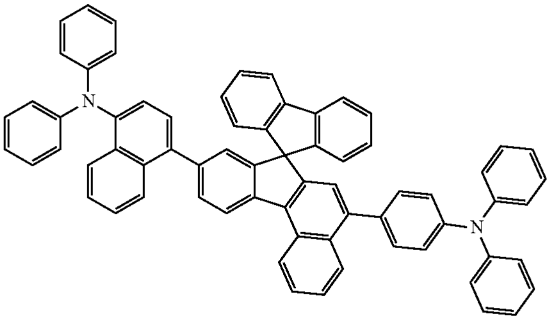
C-42
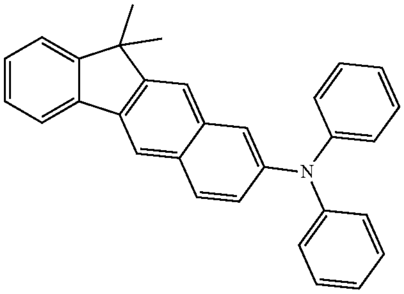
C-43
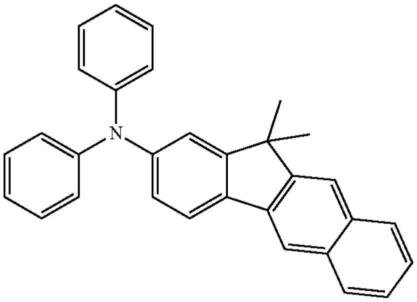
-continued
C-44
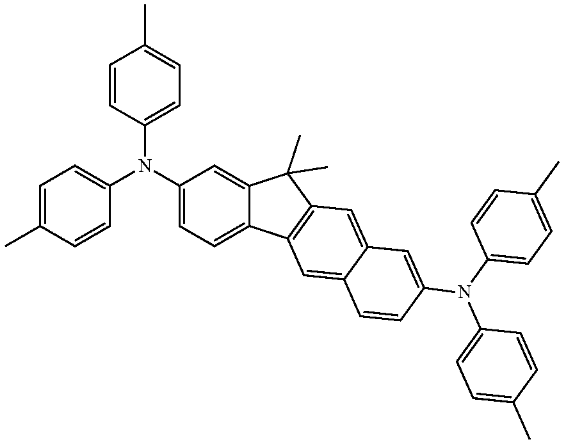
C-45
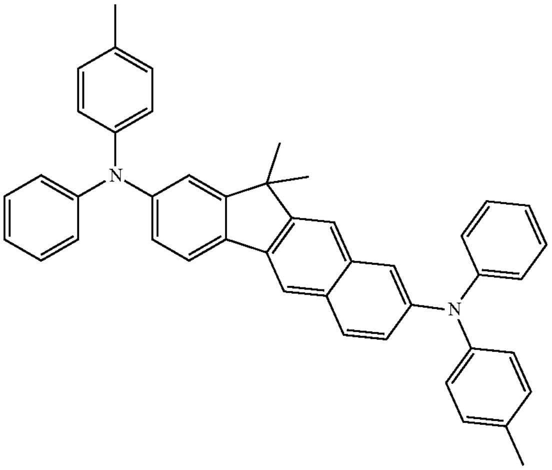
C-46
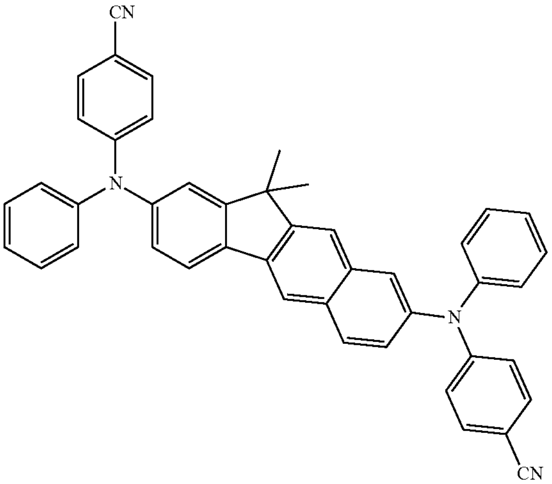

-continued
C-47
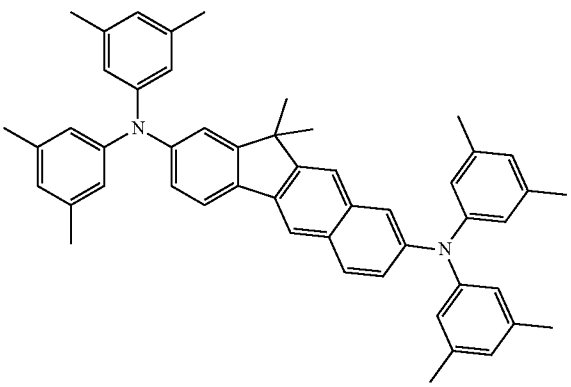
C-48
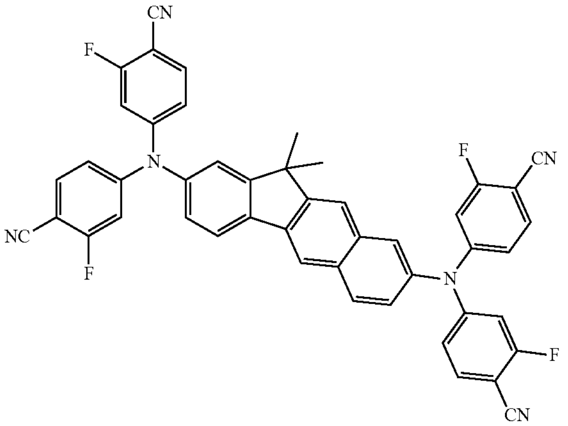
C-49
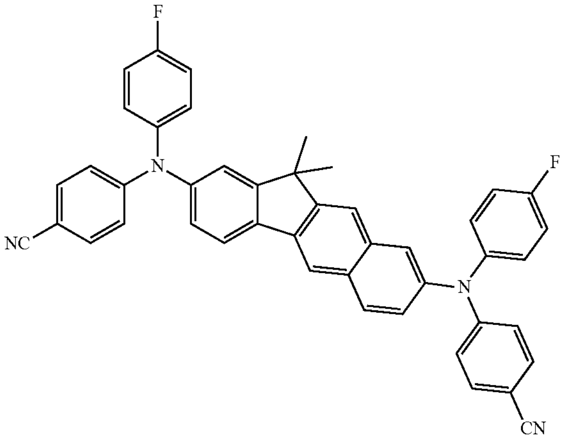
-continued
C-50
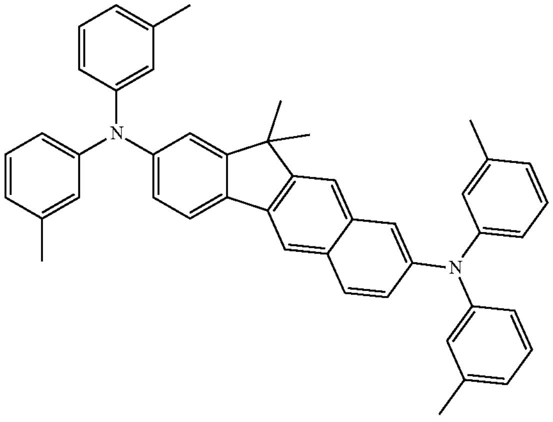
C-51
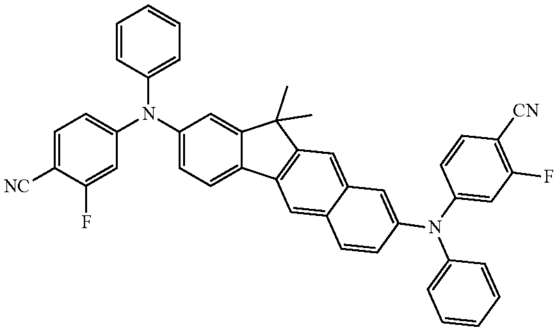
C-52
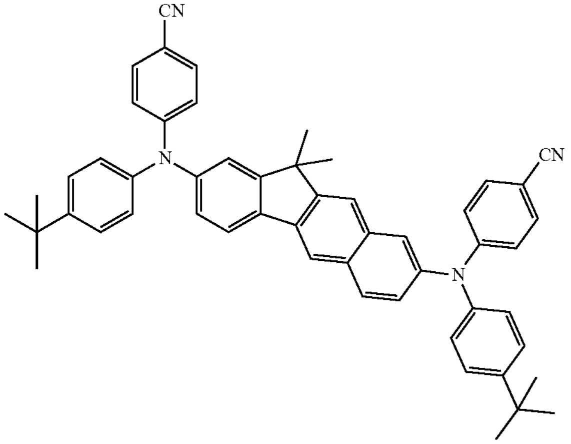

-continued
C-53
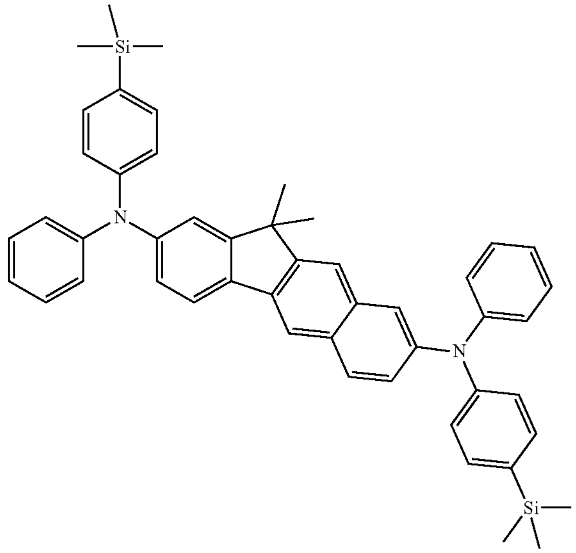
C-54
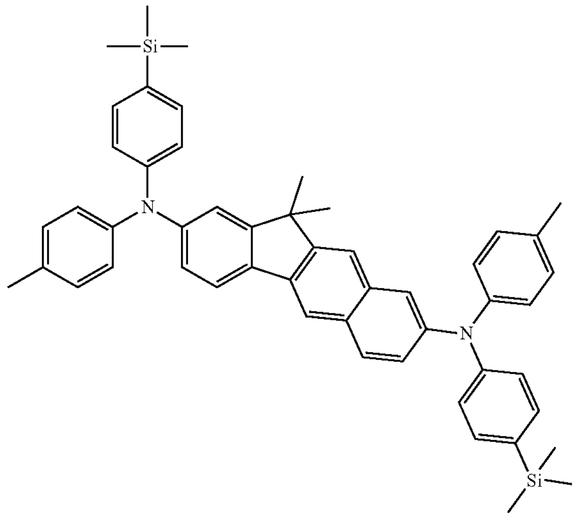
C-55
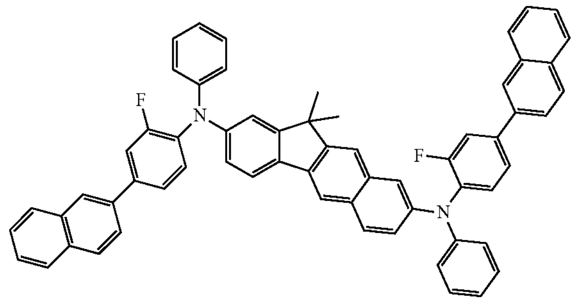
-continued
C-56
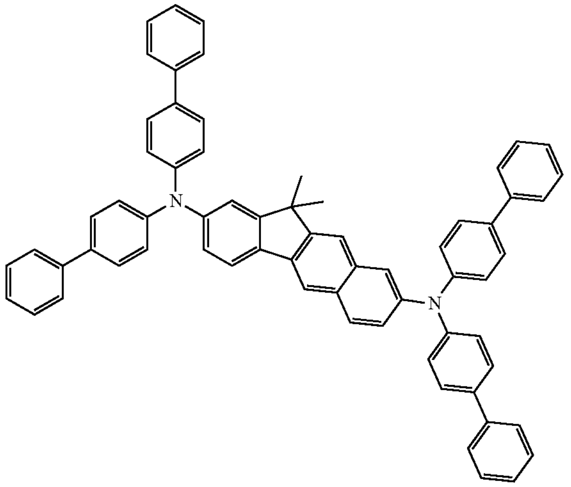
C-57
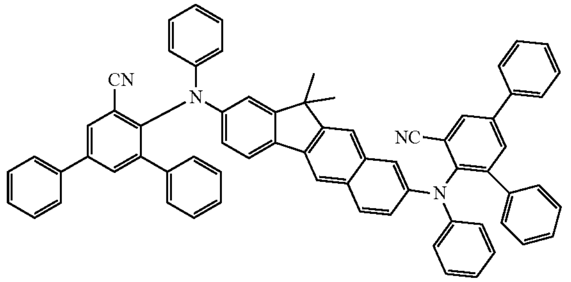
C-58
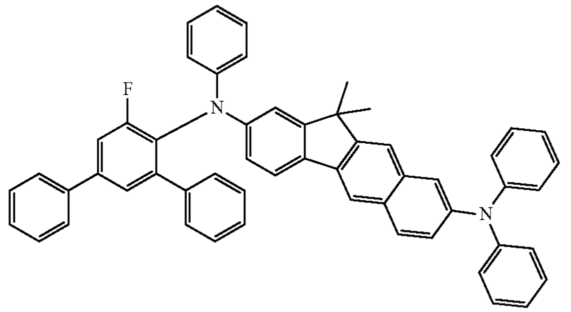
C-59
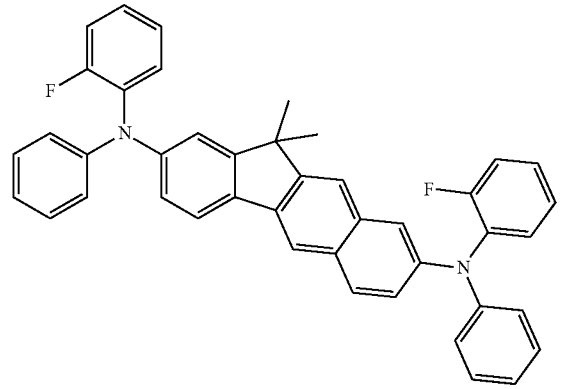

-continued
C-60
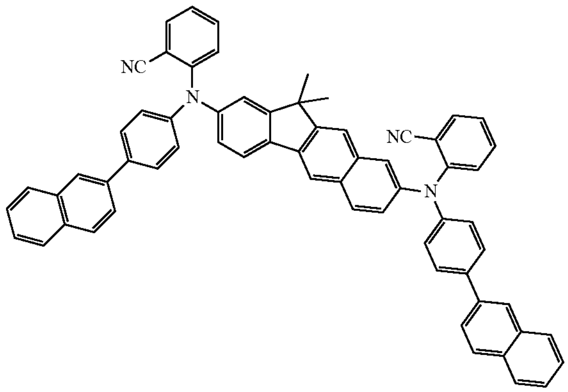
C-61
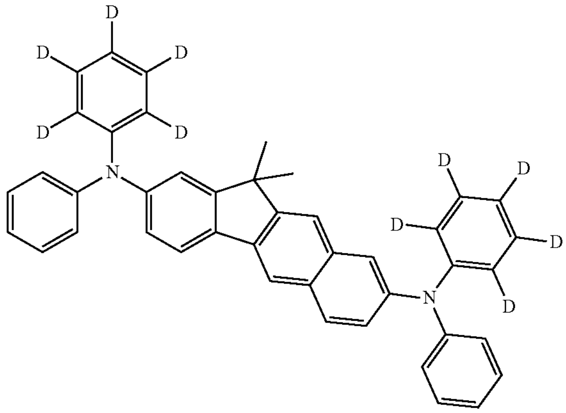
C-62
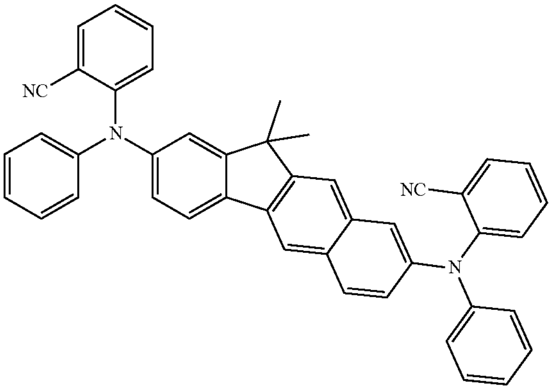
C-63
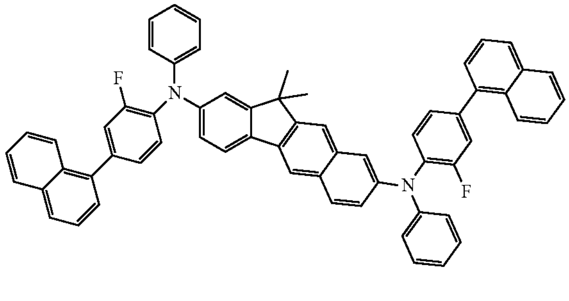
-continued
C-64
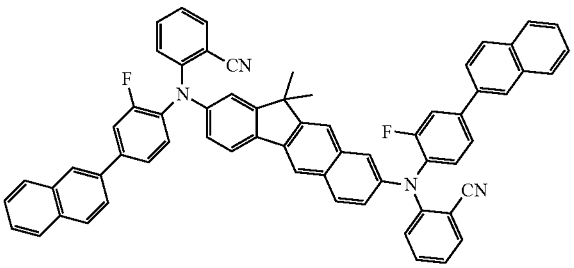
C-65
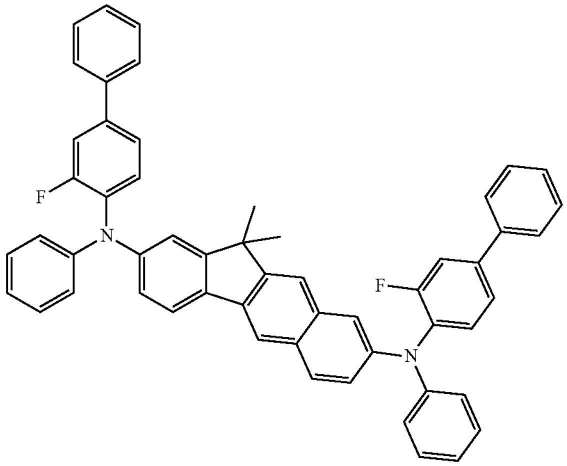
C-66
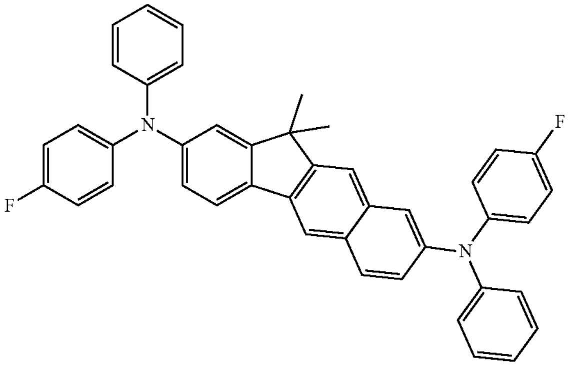
C-67
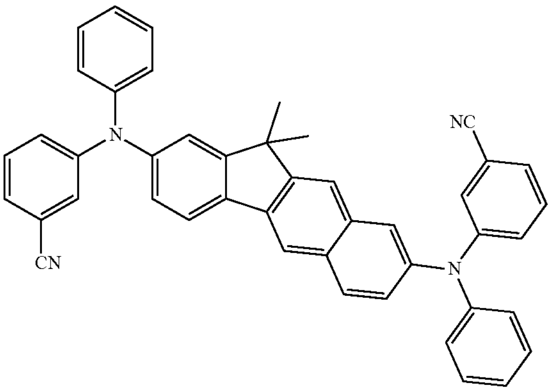

-continued
C-68
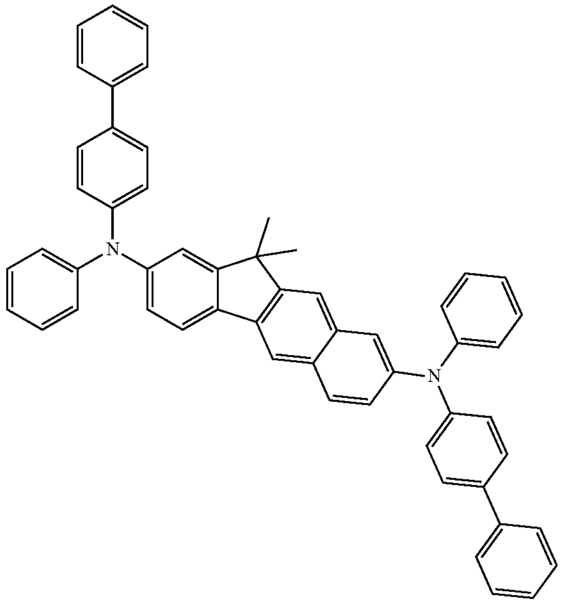
C-69
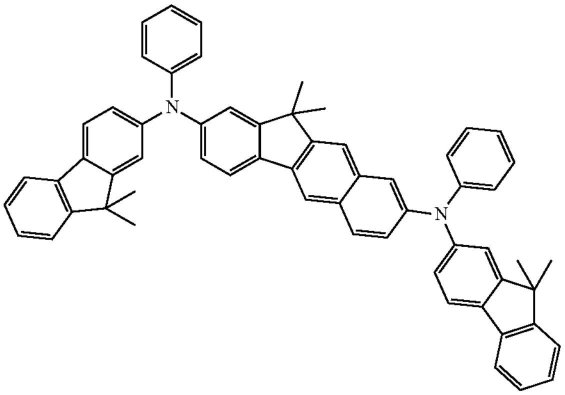
C-70
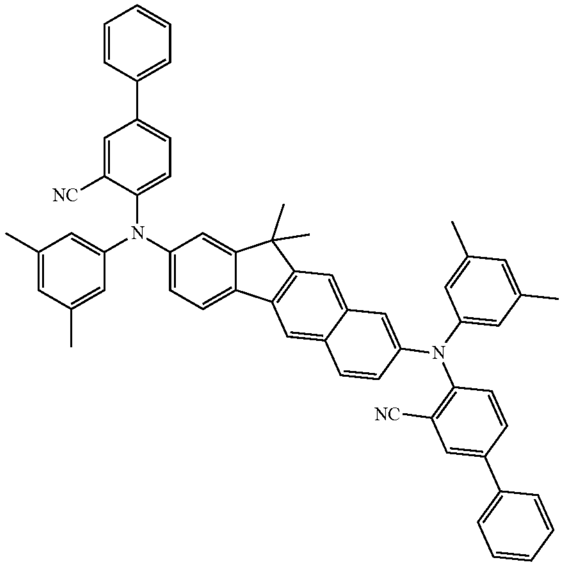
-continued
C-71
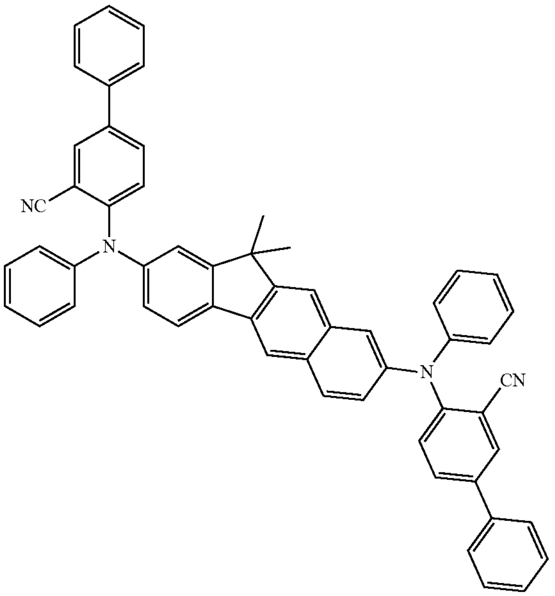
C-72
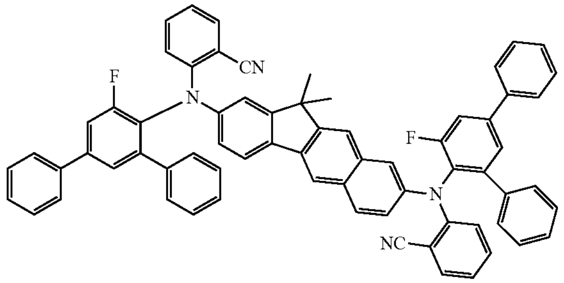
C-73
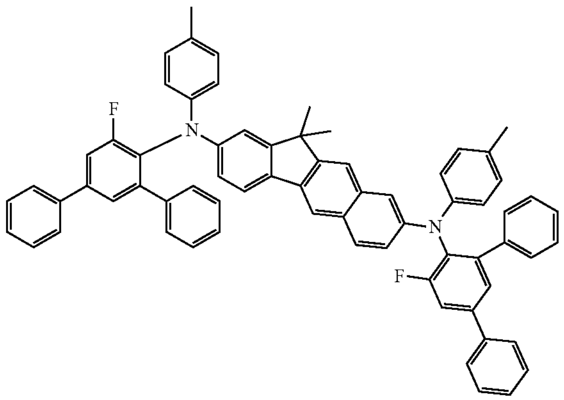

-continued
C-74
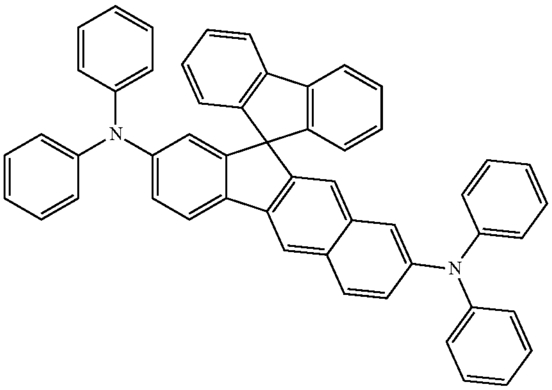
C-75
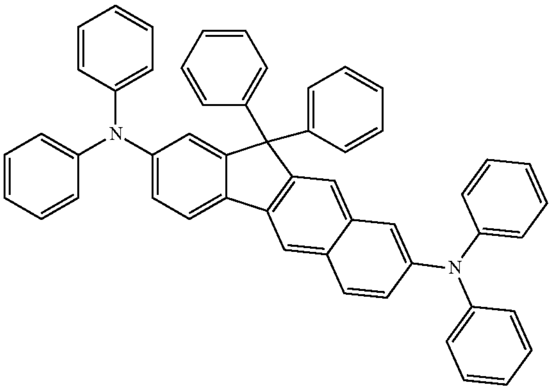
C-76
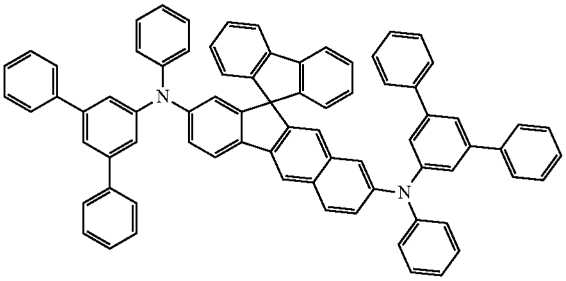
C-77
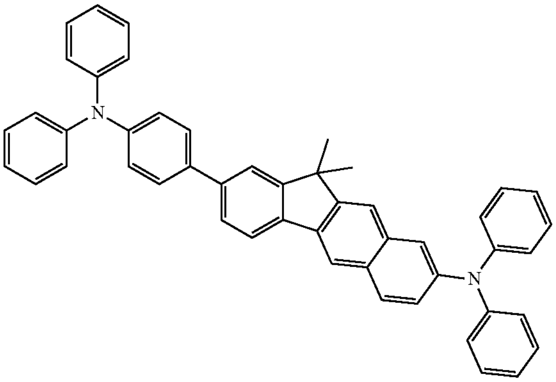
-continued
C-78
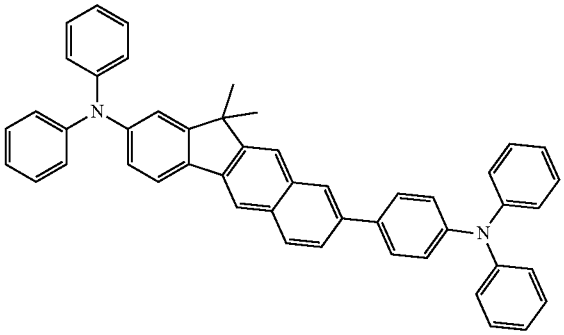
C-79
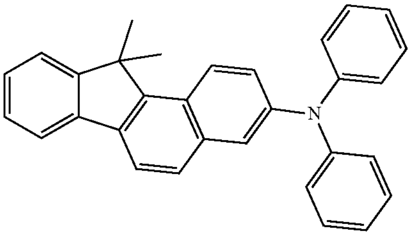
C-80
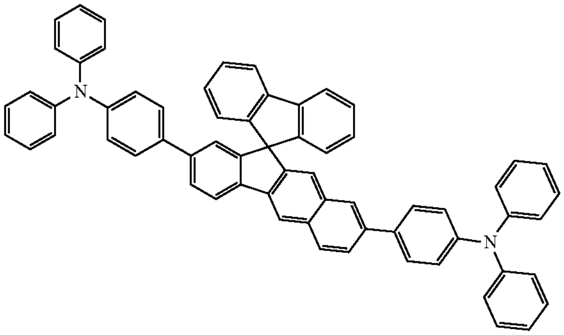
C-81
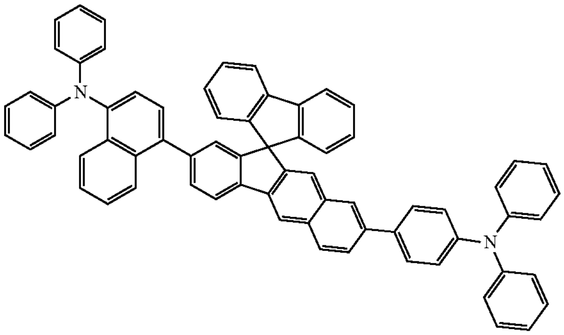

C-82
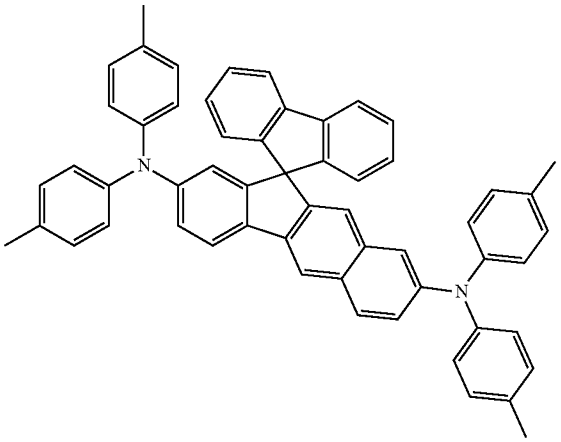
C-83
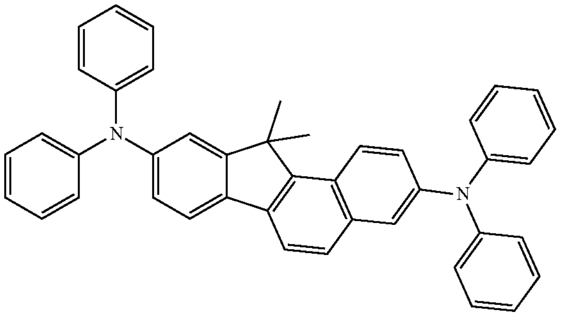
C-84
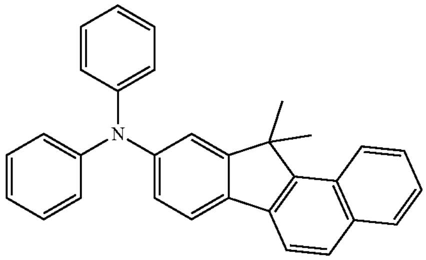
C-85
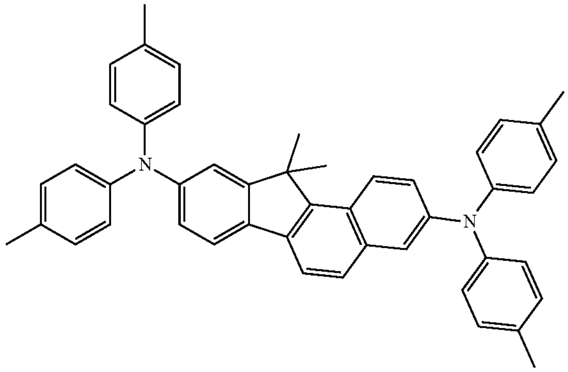
C-86
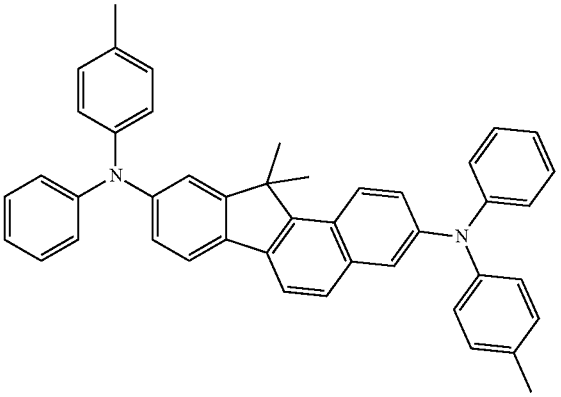
C-87
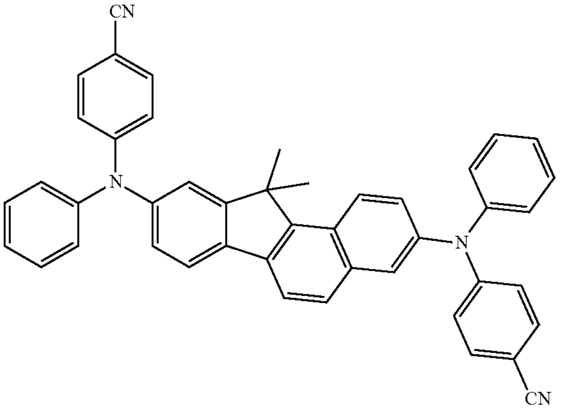
C-88
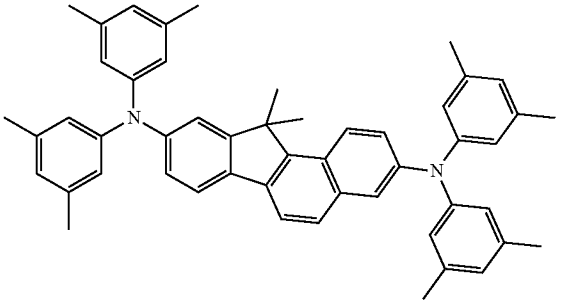
C-89
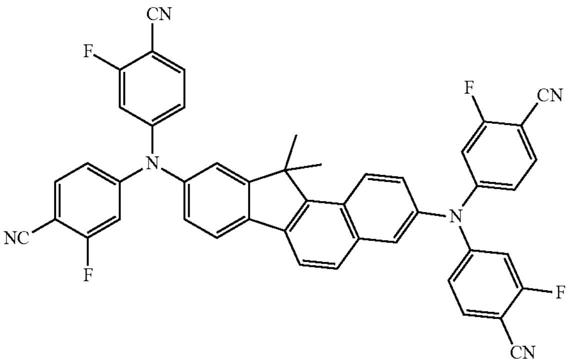

-continued
C-90
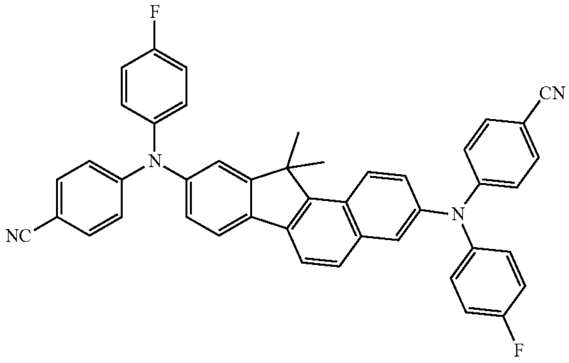
C-91
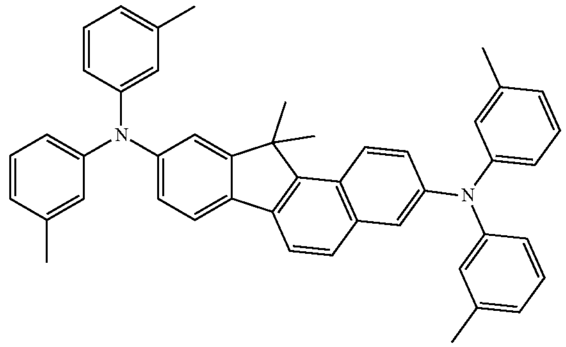
C-92
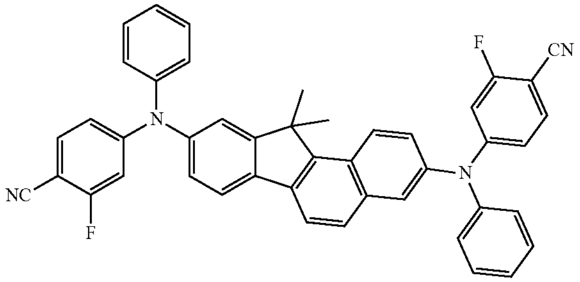
C-93
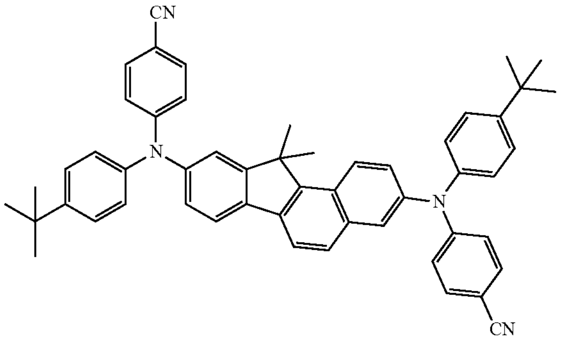
-continued
C-94
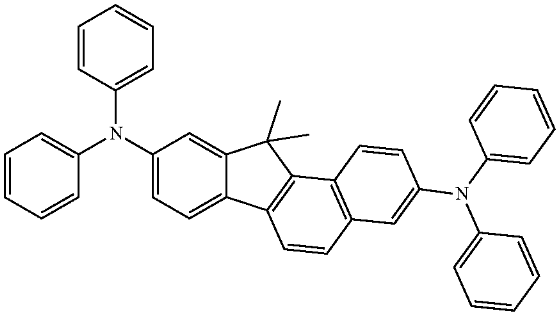
C-95
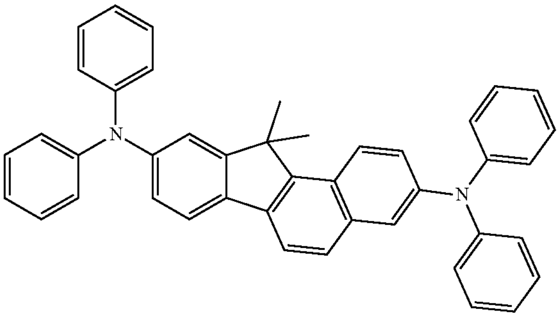
C-96
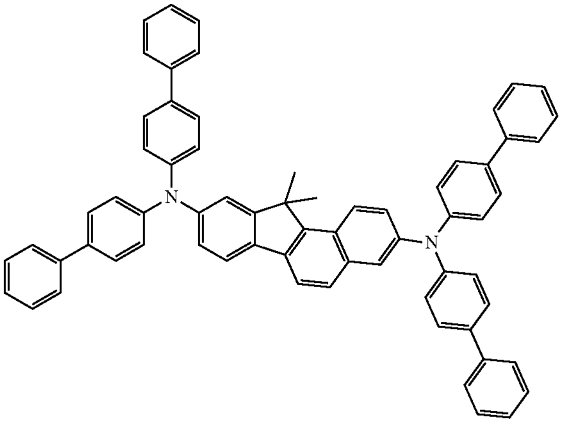
C-97
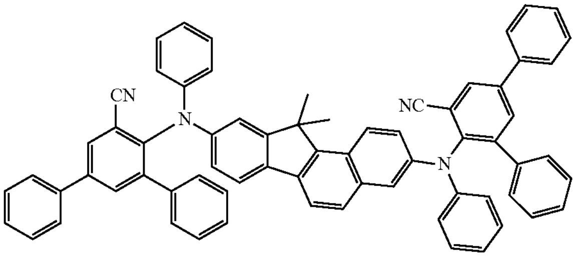

-continued
C-98
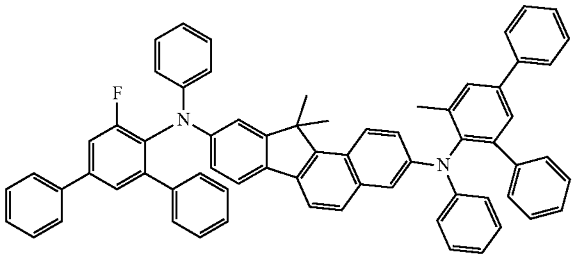
C-99
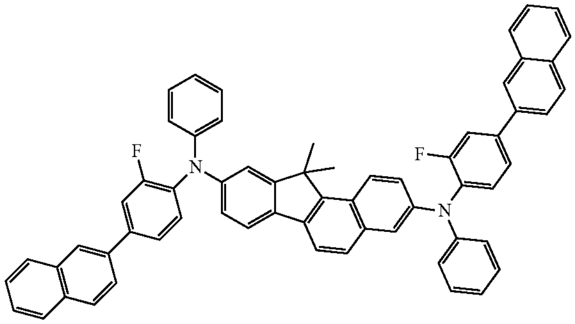
C-100
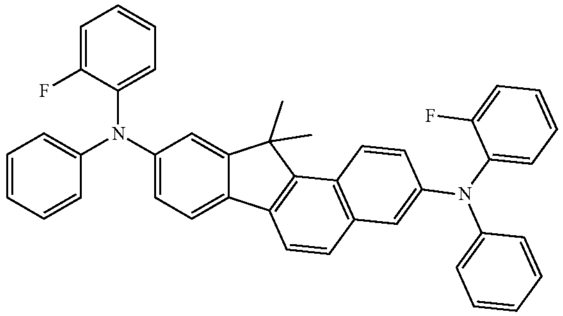
C-101
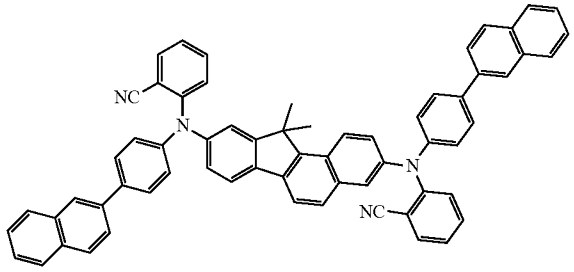
C-102
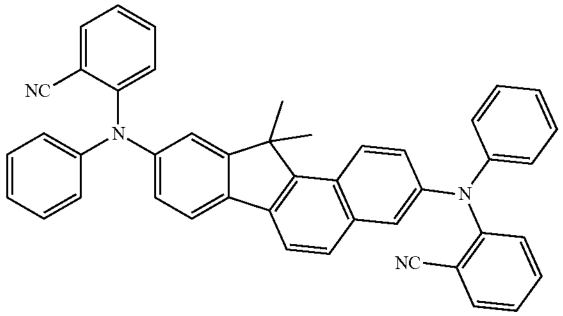
-continued
C-103
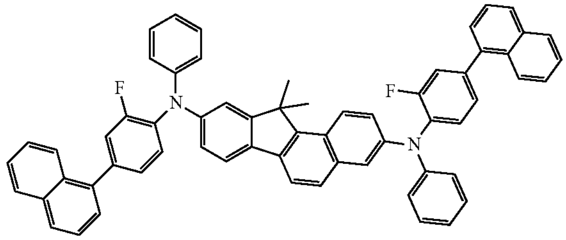
C-104
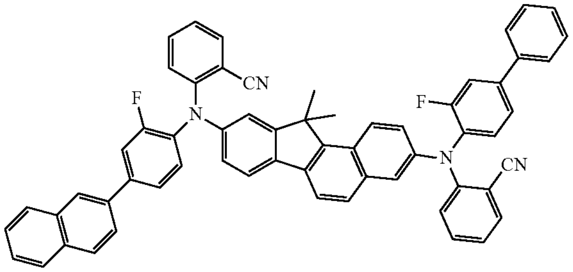
C-105
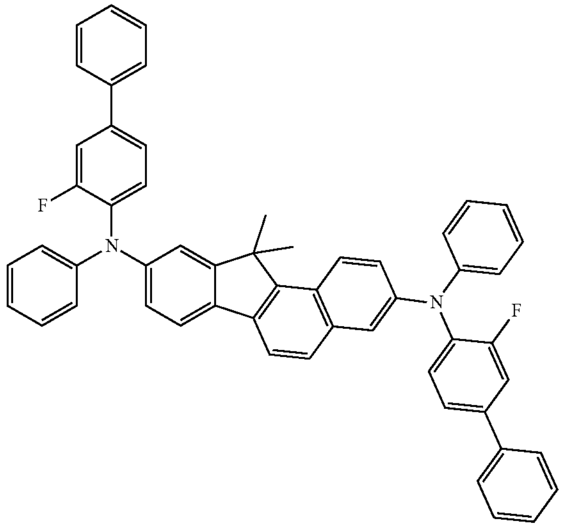
C-105
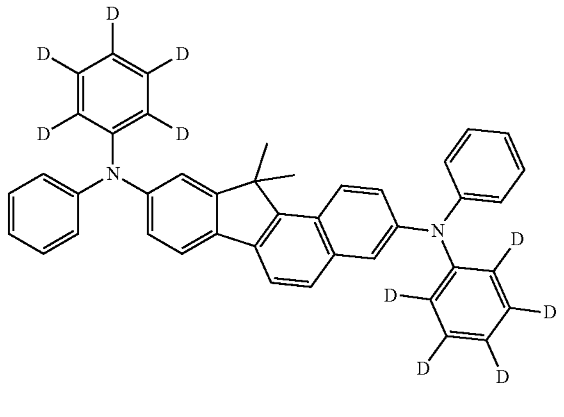

-continued
C-107
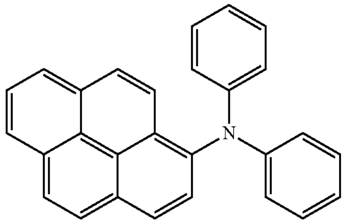
C-108
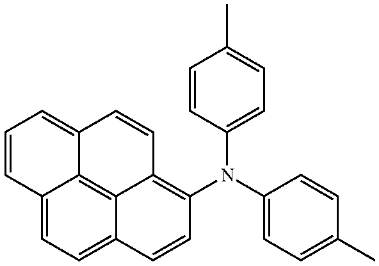
C-109
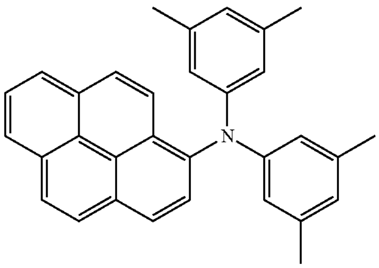
C-110
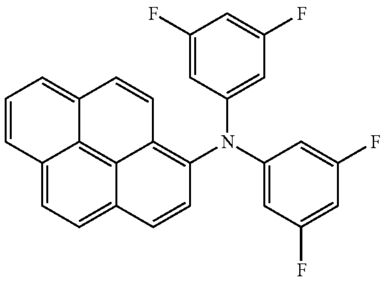
C-111
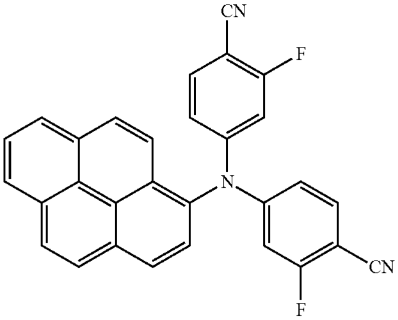
-continued
C-112
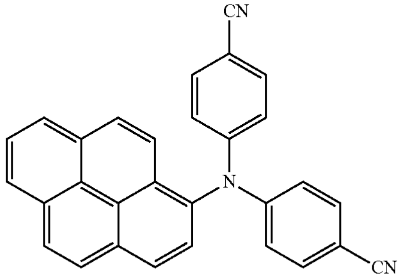
C-113
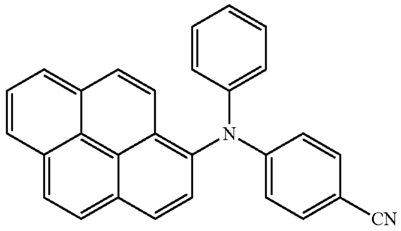
C-114
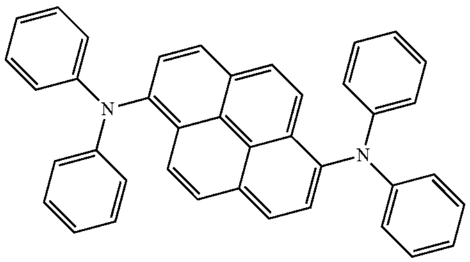
C-115
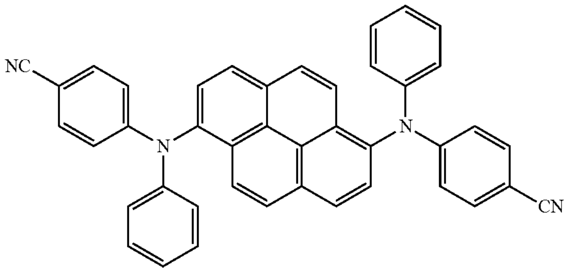
C-116
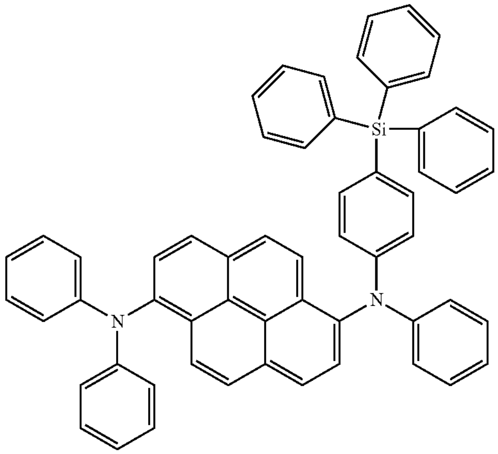

-continued
C-117
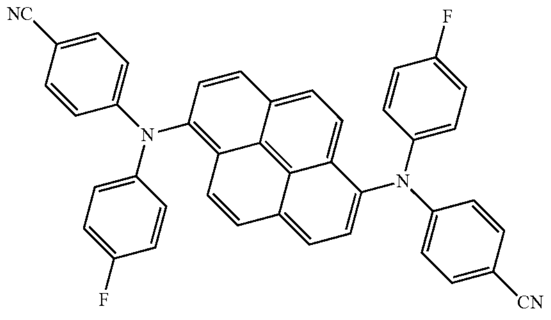
C-118
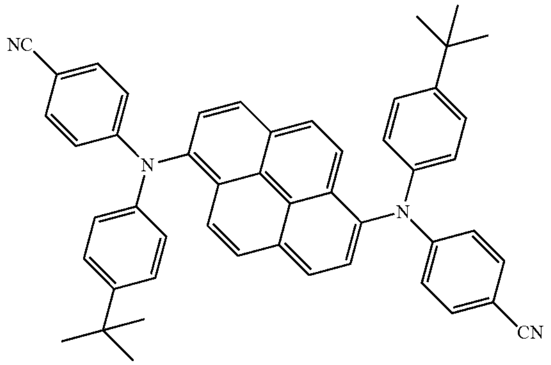
C-119
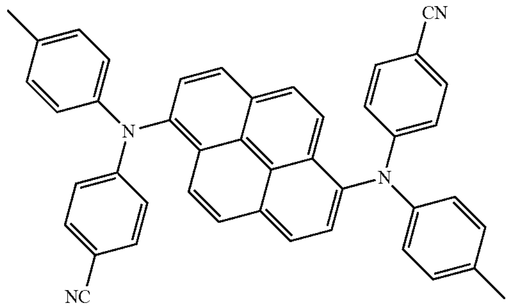
C-120
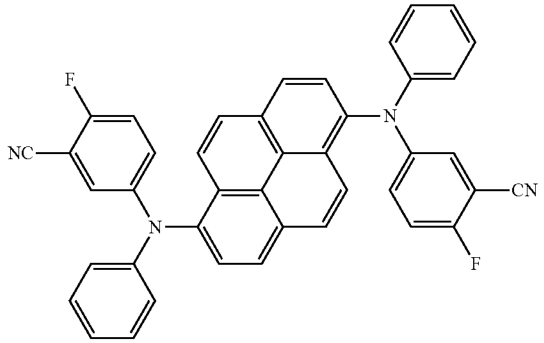
-continued
C-121
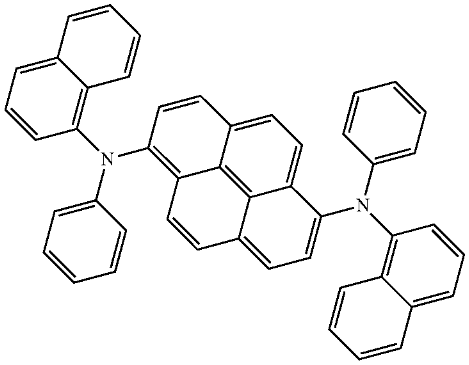
C-122
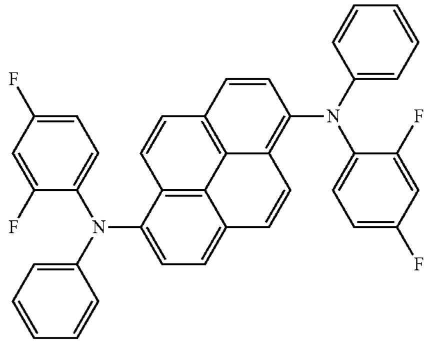
C-123
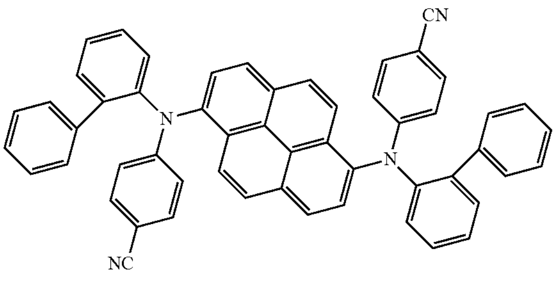
C-124
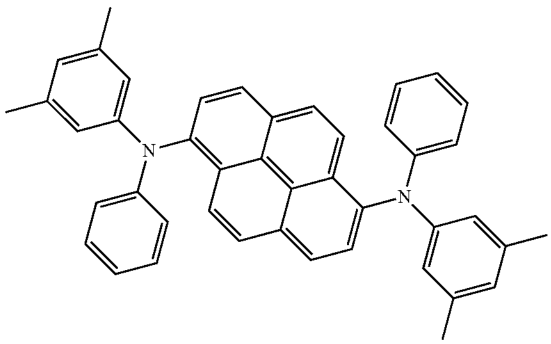

-continued
C-125
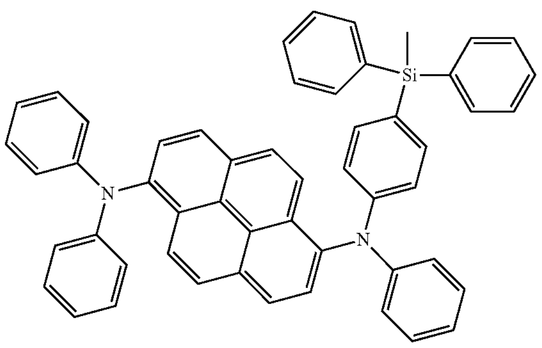
C-126
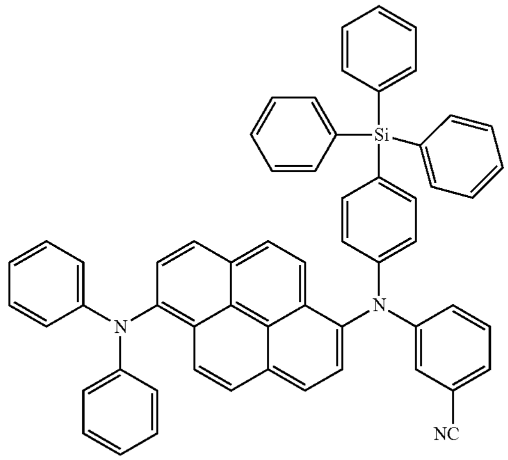
C-127
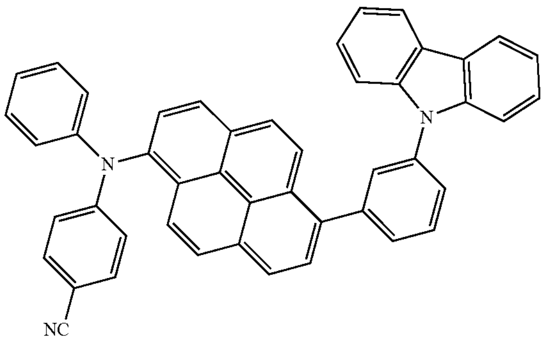
C-128
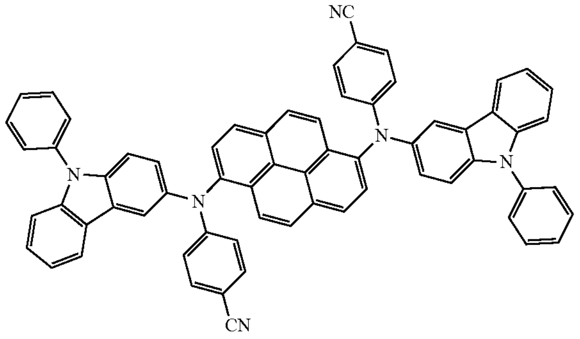
-continued
C-129
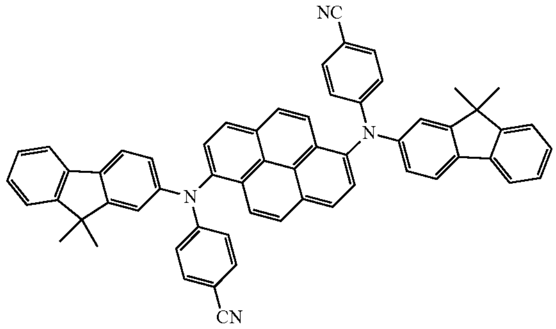
C-130
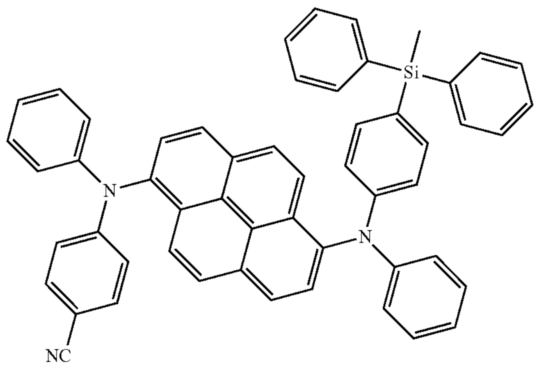
C-131
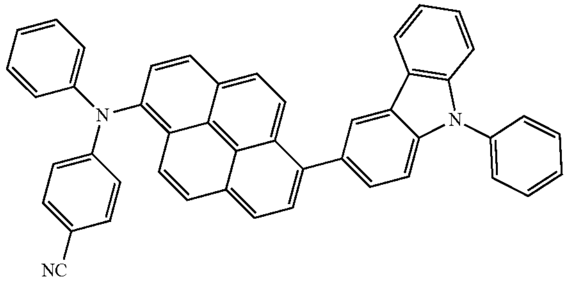
C-132
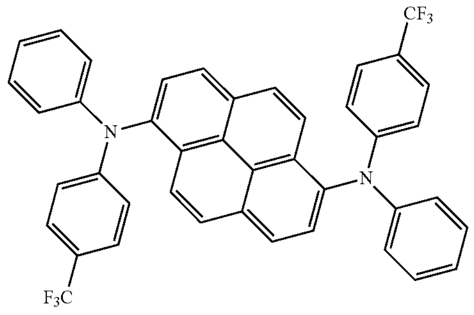

C-133
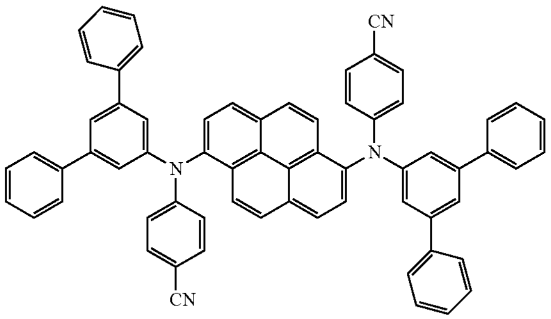
C-134
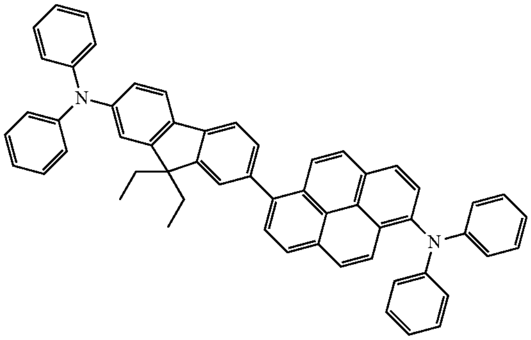
C-135
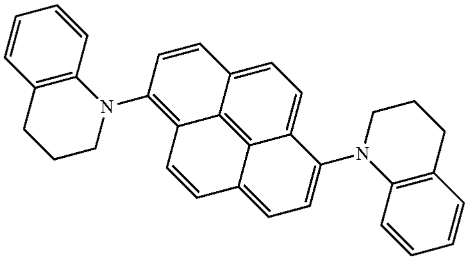
C-136
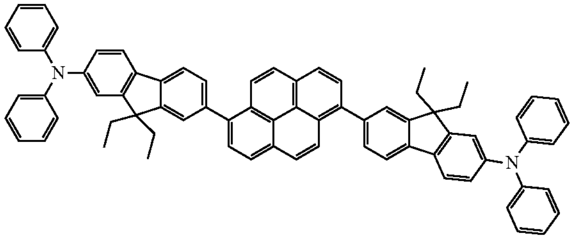
C-137
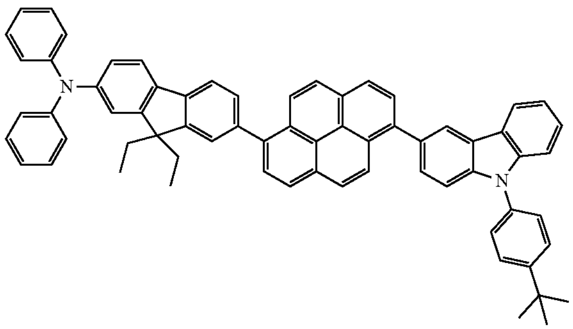
C-138
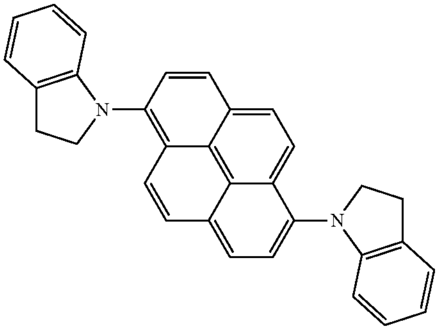
C-139
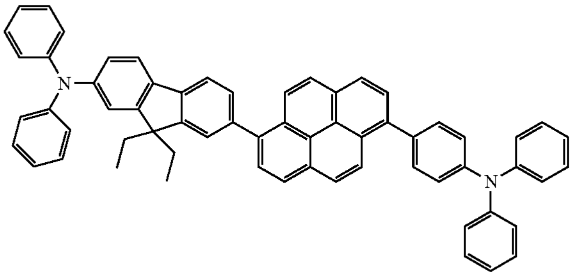
C-140
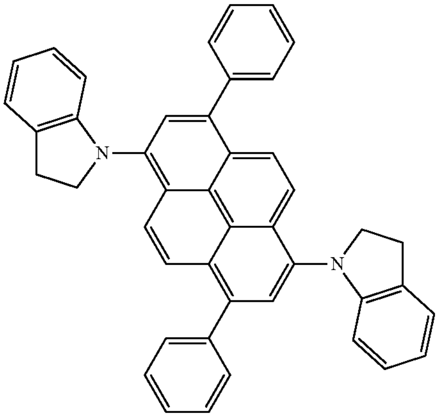
C-141
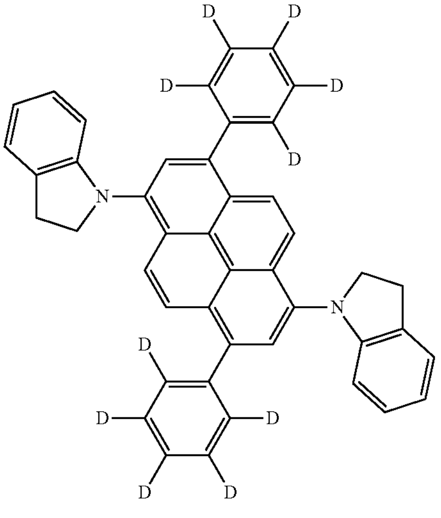

-continued
C-142
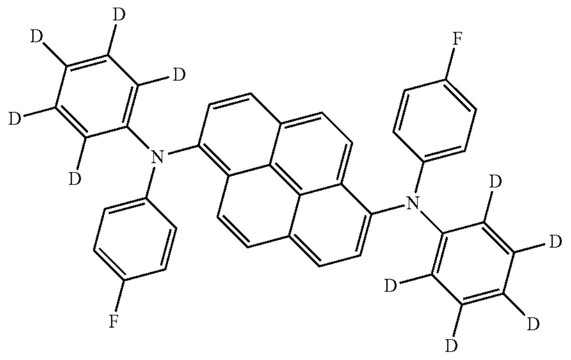
C-143
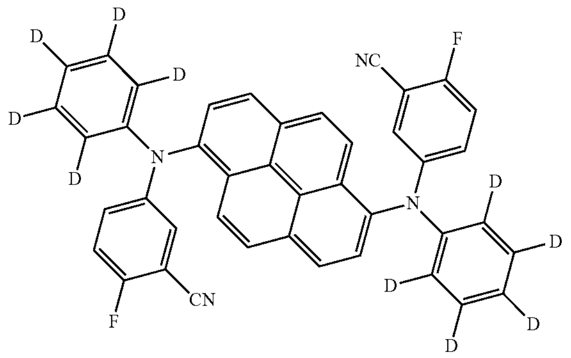
C-144
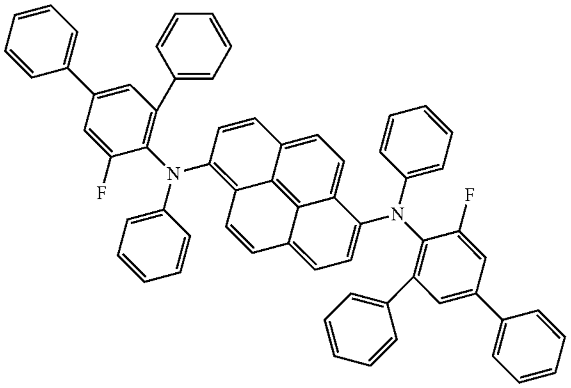
C-145
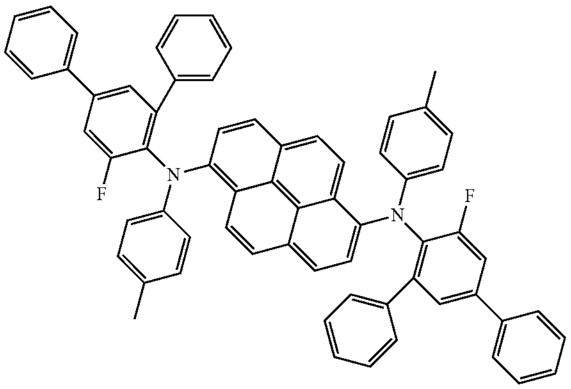
-continued
C-146
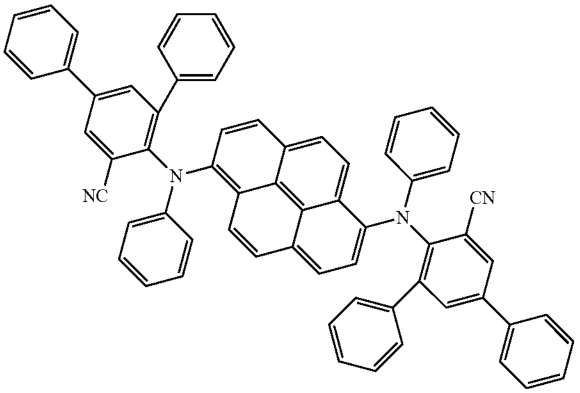
C-147
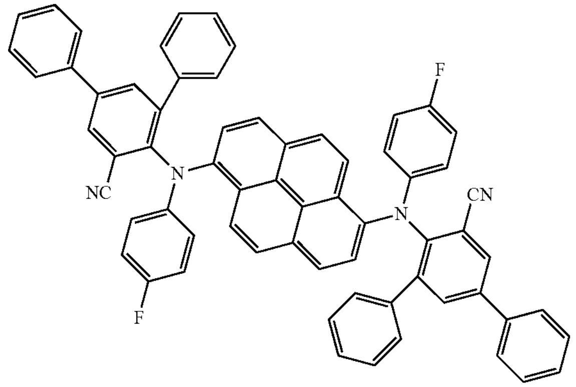
C-148
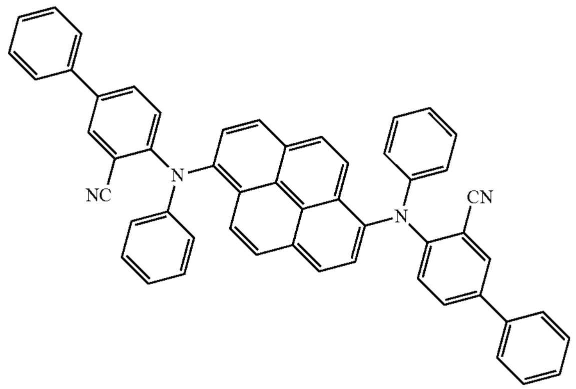
C-149
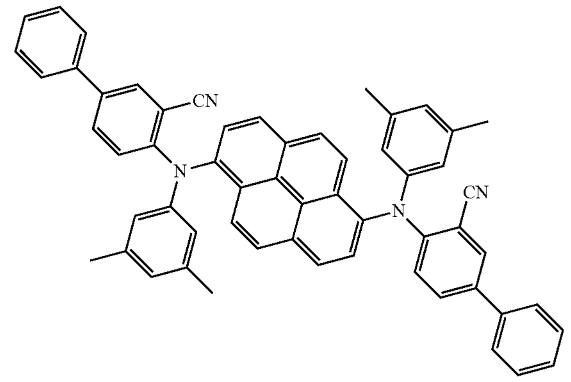

-continued
C-150
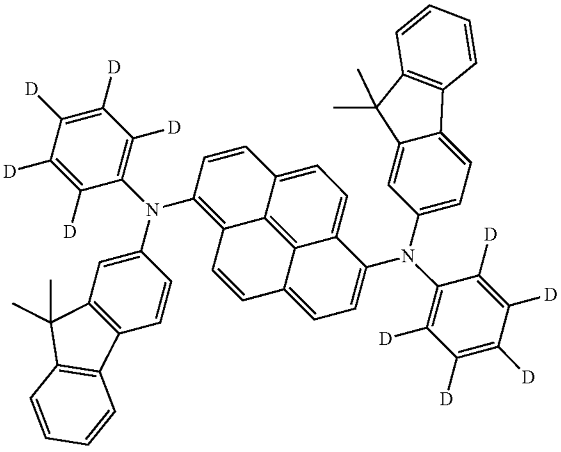
C-151
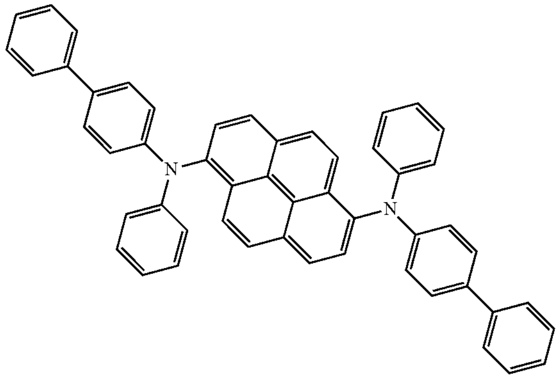
C-152
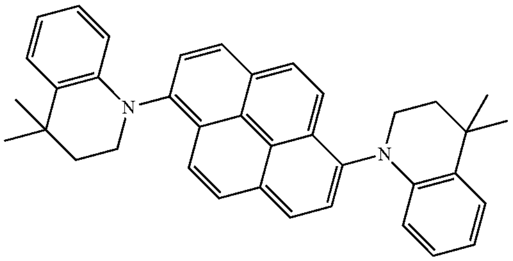
C-153
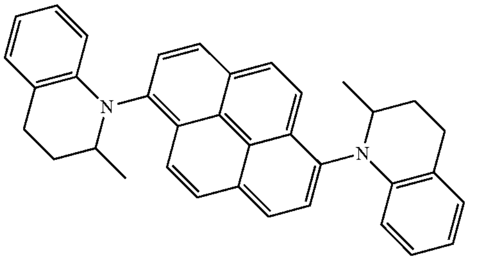
-continued
C-154
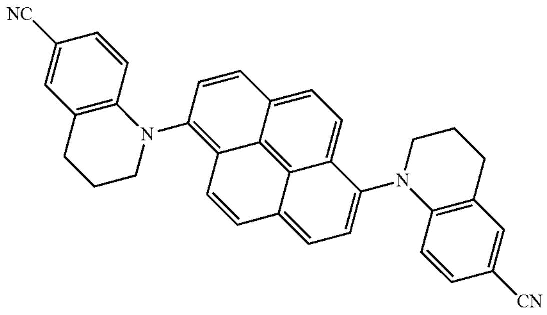
C-155
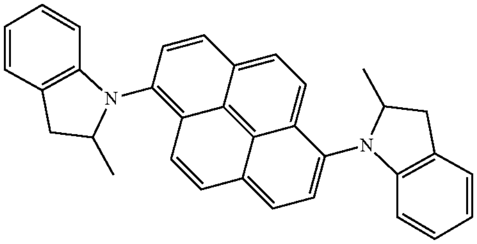
C-156
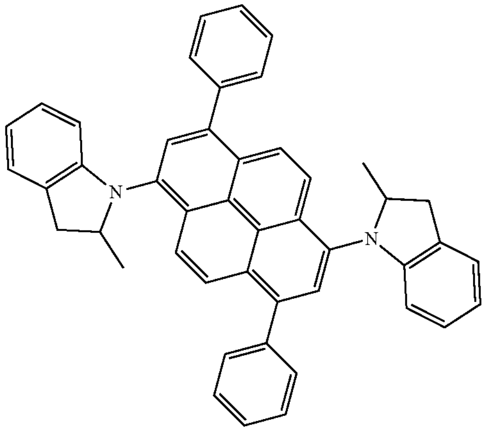
C-157
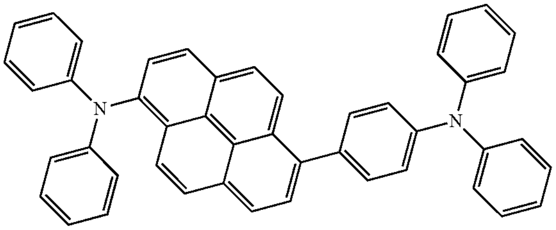
C-158
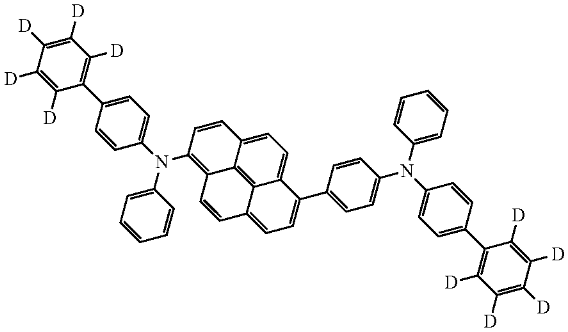

-continued
C-159
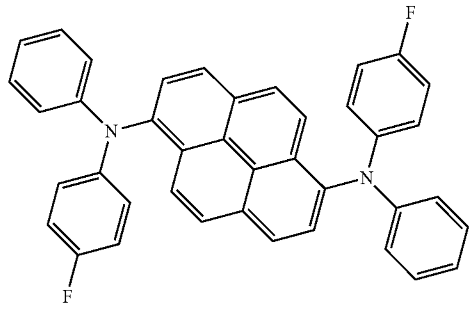
C-160
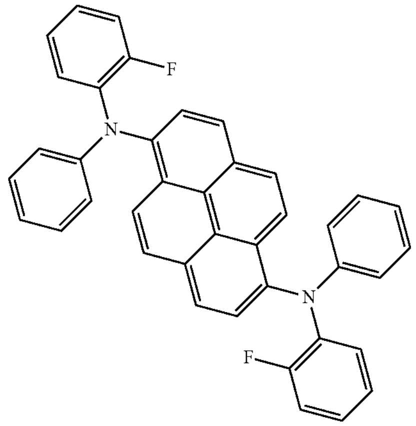
C-161
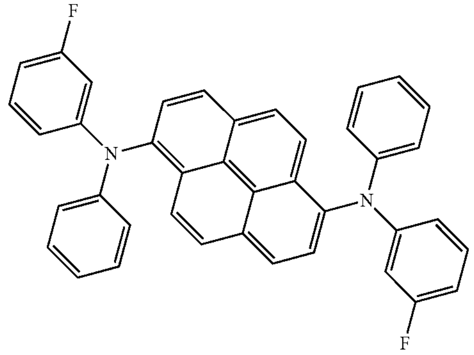
C-162
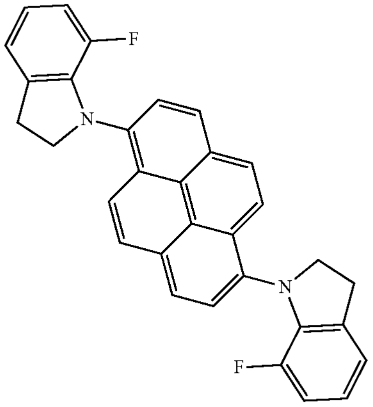
-continued
C-163
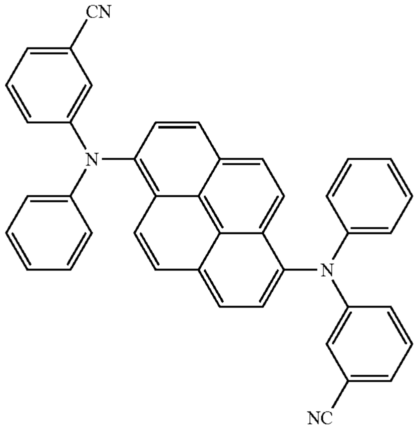
C-164
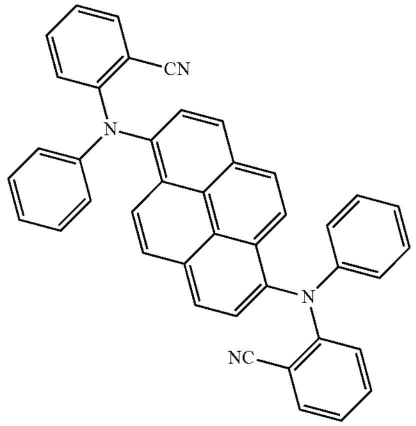
C-165
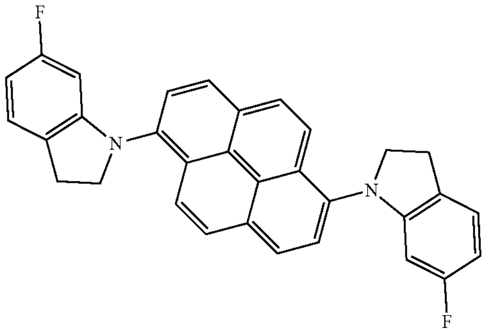
C-166
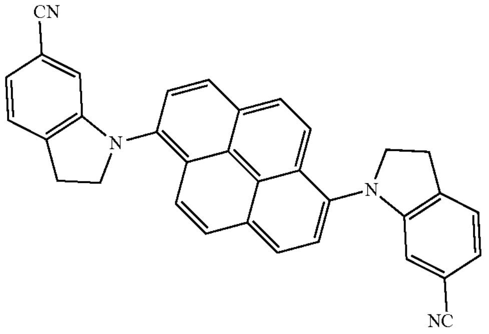

-continued
C-167
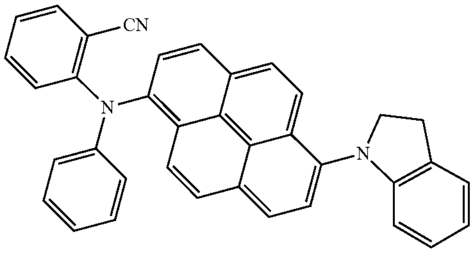
C-168
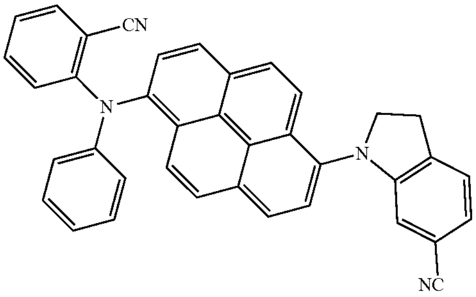
C-169
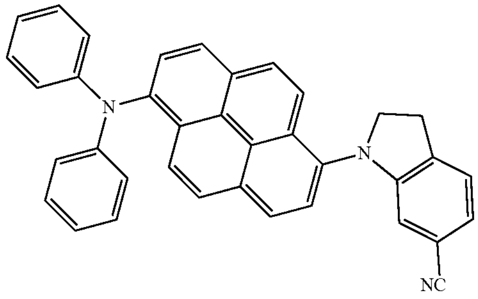
C-170
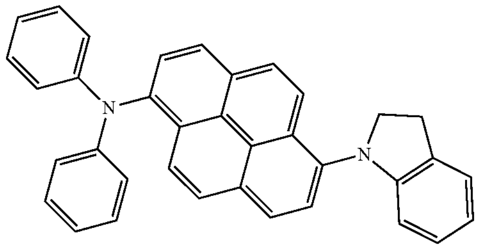
C-171
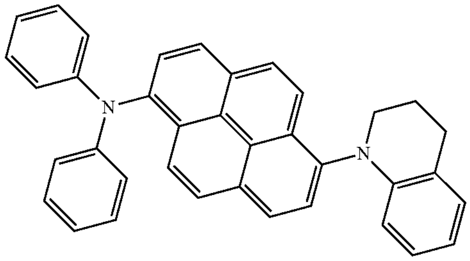
C-172
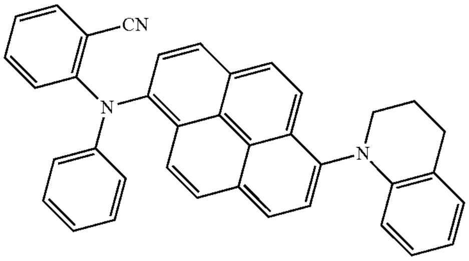
C-173
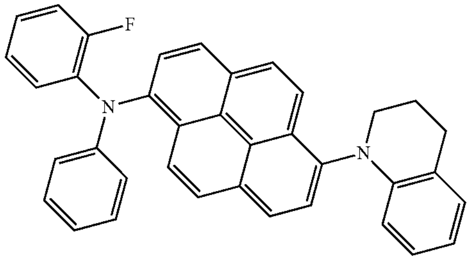
C-174
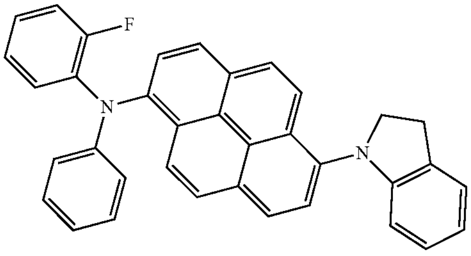
C-175
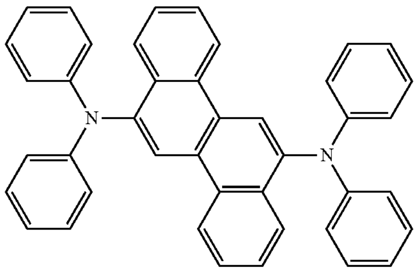
C-176
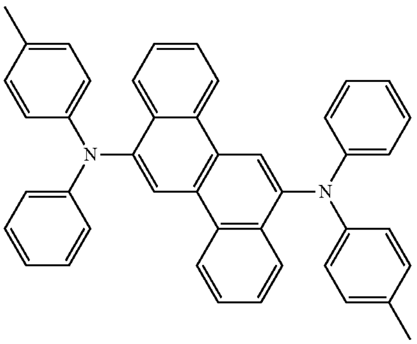

-continued
C-177
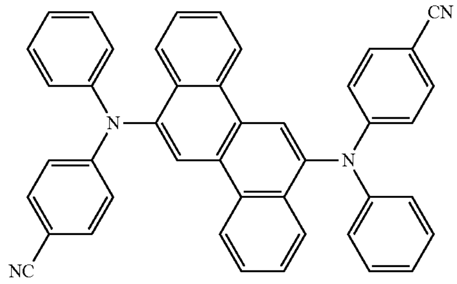
C-178
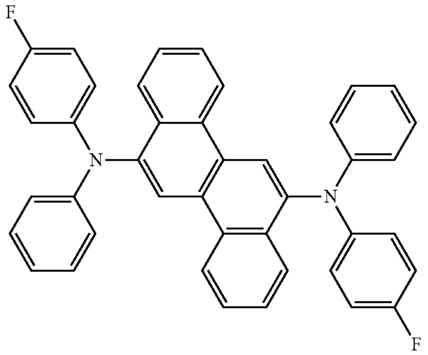
C-179
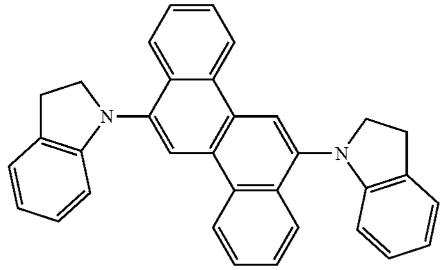
C-180
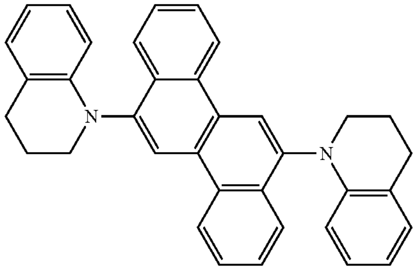
C-181
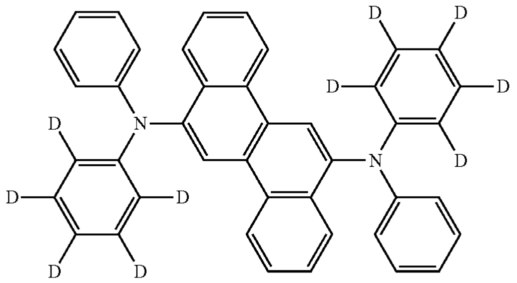
C-182
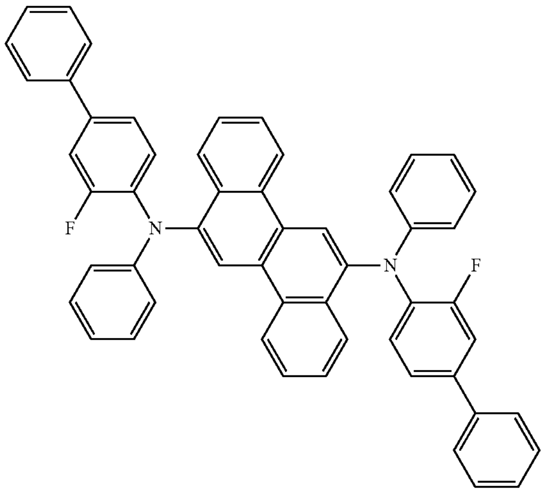
C-183
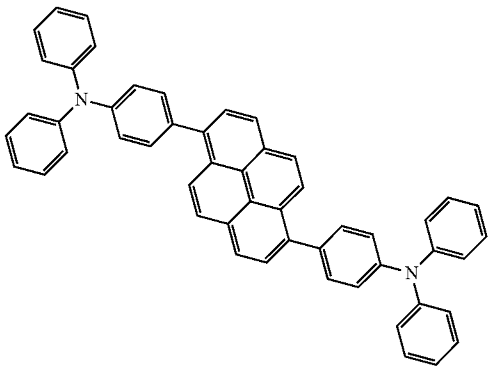
C-184
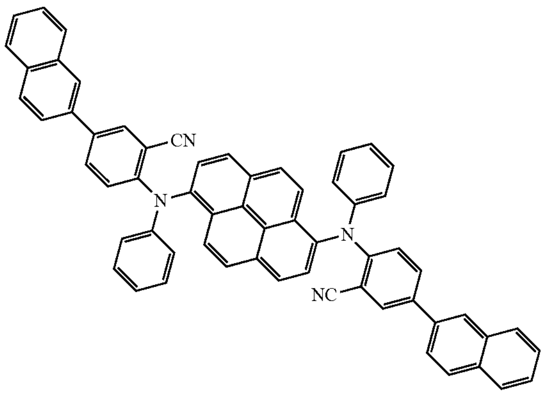

-continued
C-185
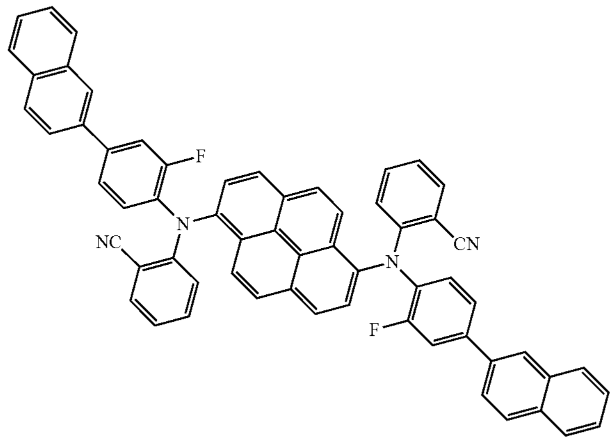
C-186
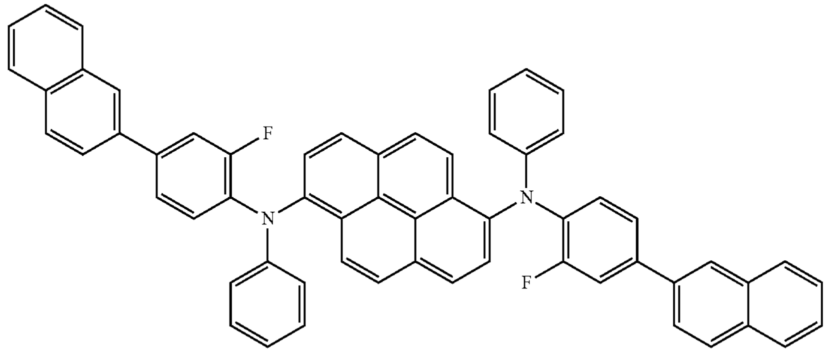
C-187
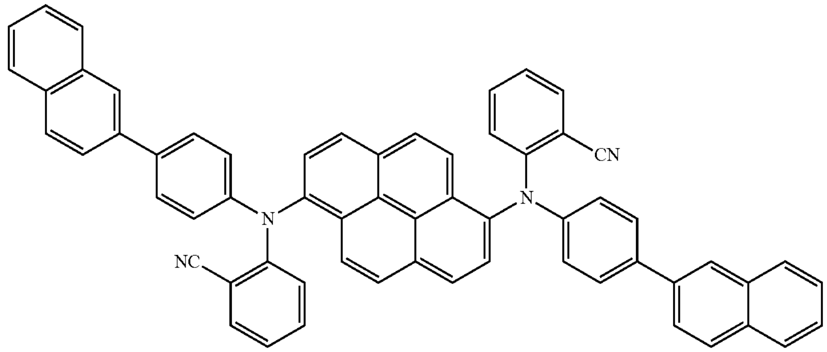
C-188
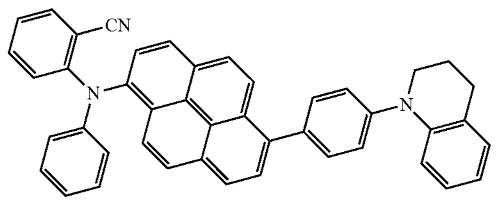
C-189
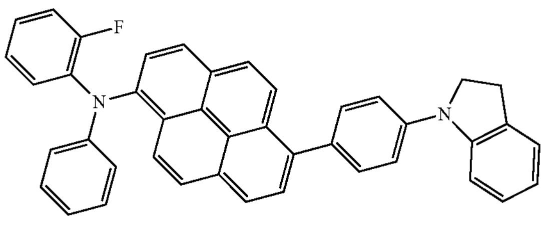
C-190
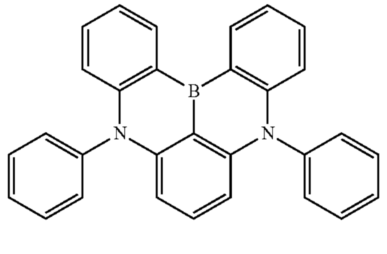
C-191
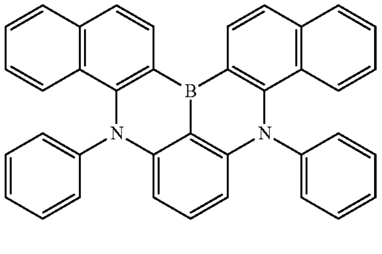

-continued
C-192
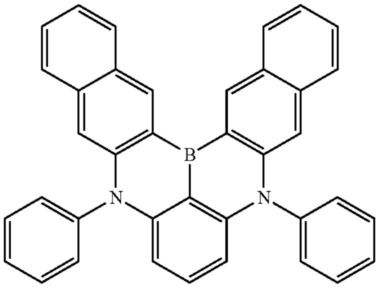
C-193
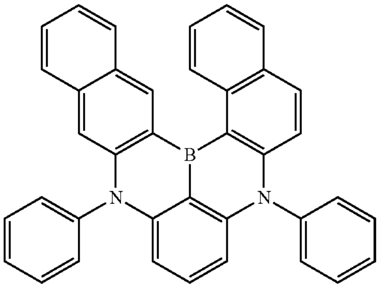
C-194
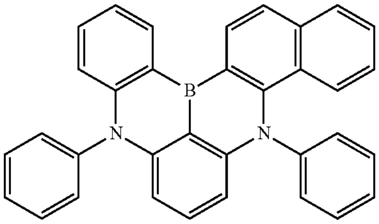
C-195
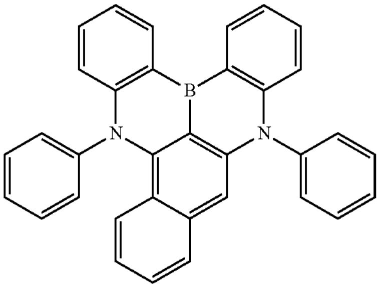
C-196
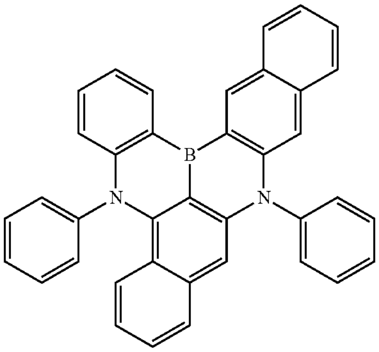
C-197
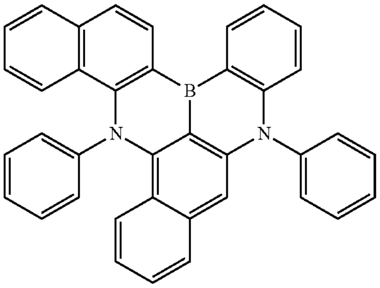
C-198
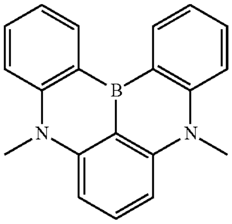
C-199
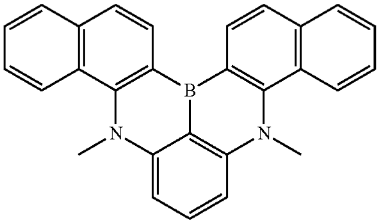
C-200
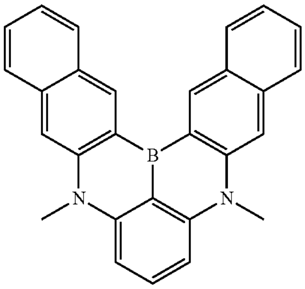
C-201
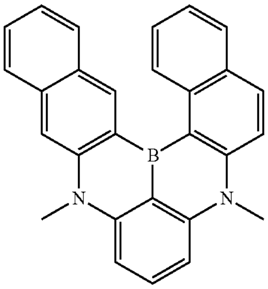

-continued
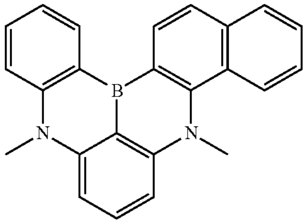
C-202
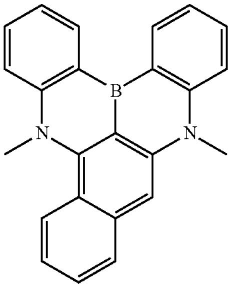
C-203
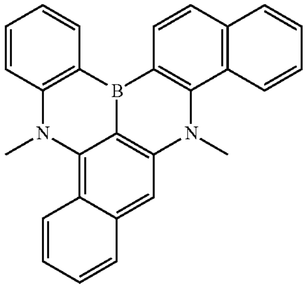
C-204
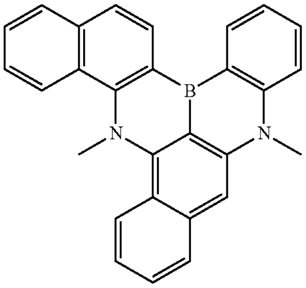
C-205
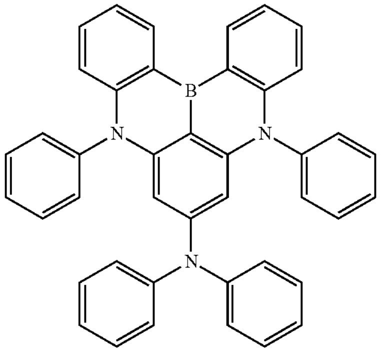
C-206
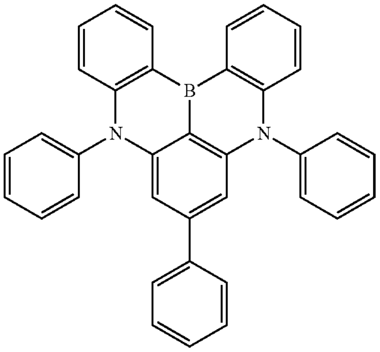
C-207
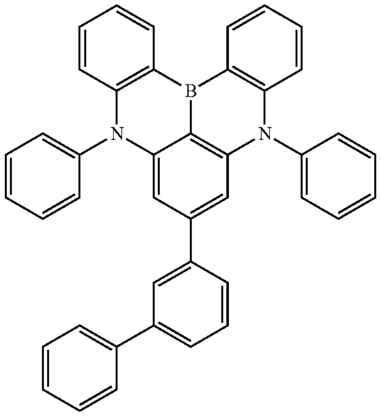
C-208
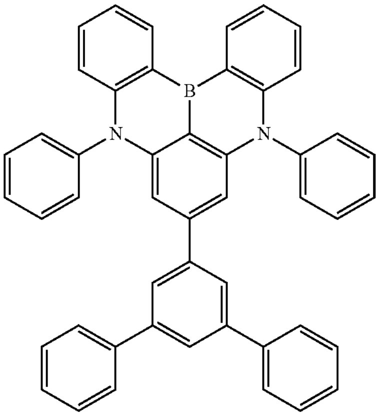
C-209

-continued
C-210
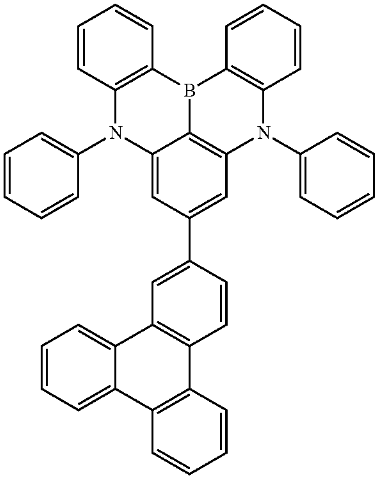
C-211
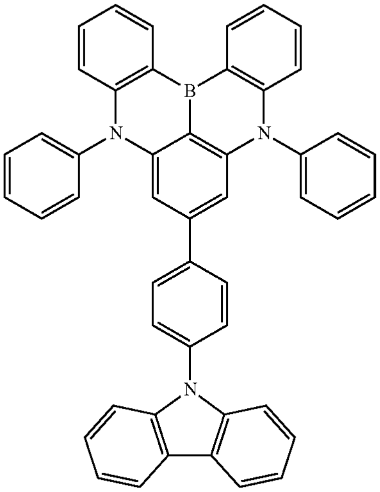
C-212
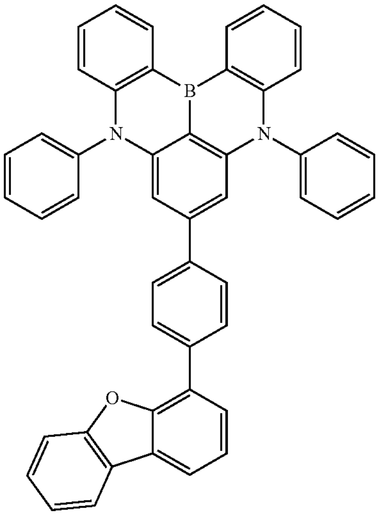
C-213
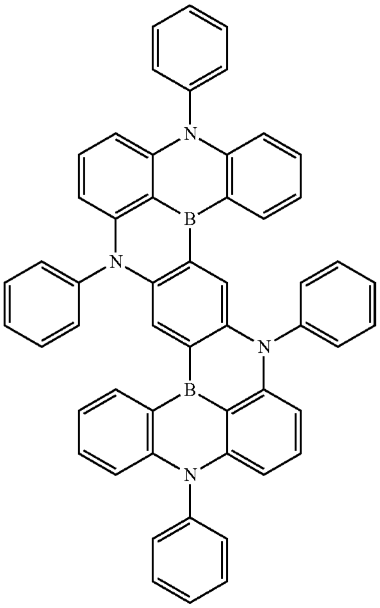
C-214
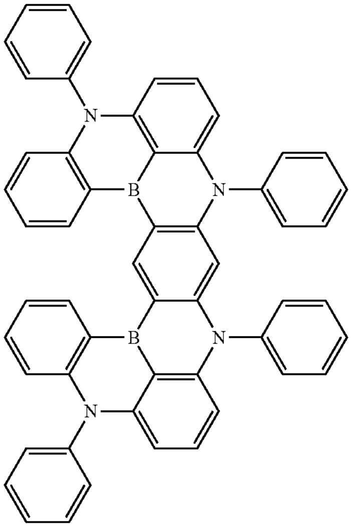
C-215
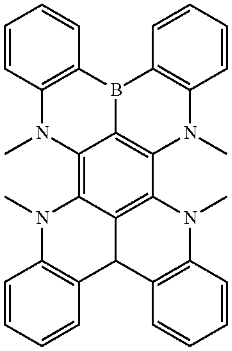

-continued
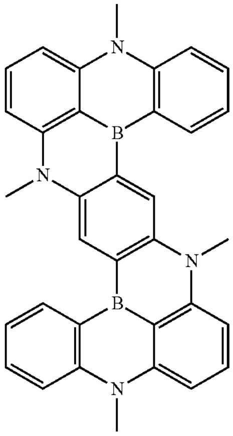
C-216
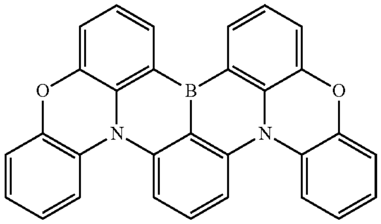
C-217
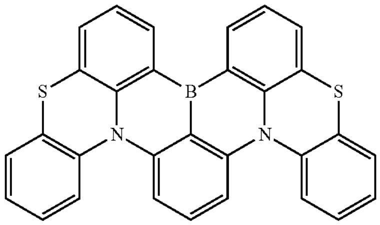
C-218
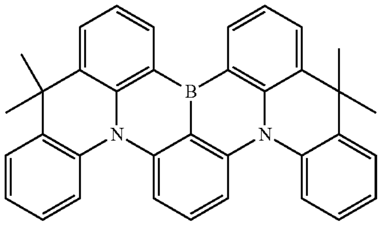
C-219
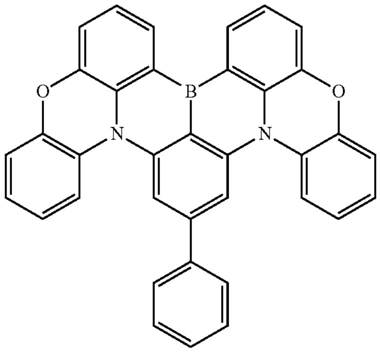
C-220
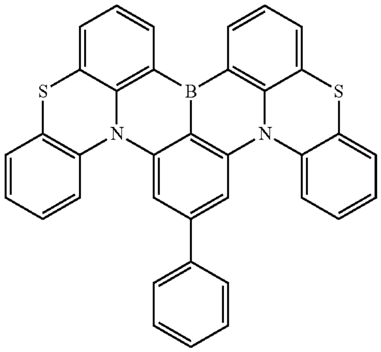
C-221
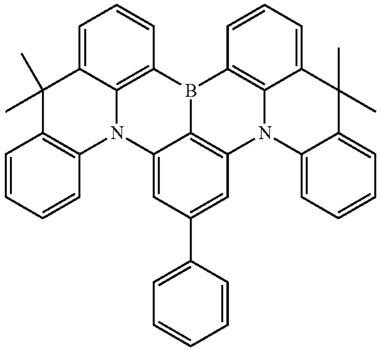
C-222
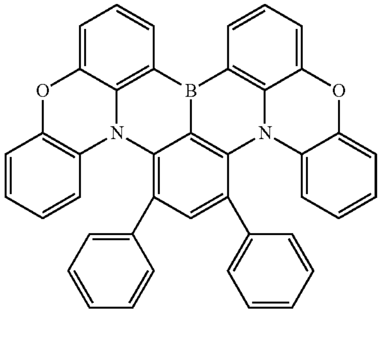
C-223

-continued
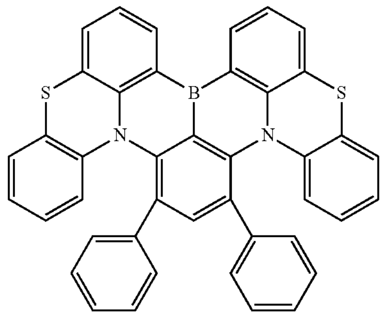
C-224
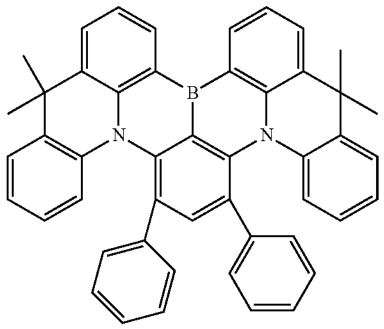
C-225
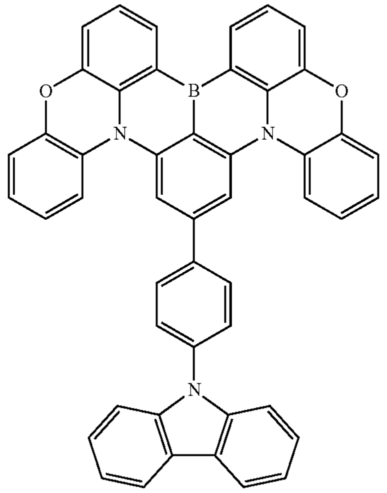
C-226
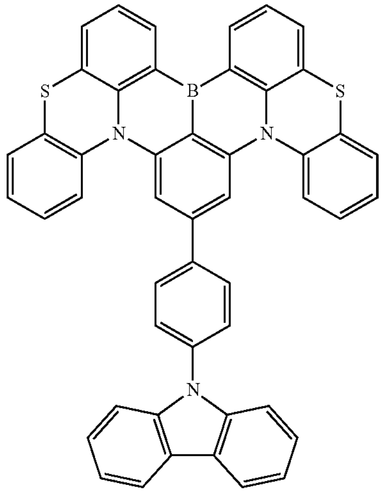
C-227
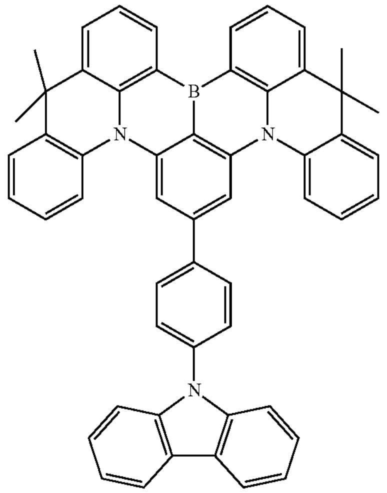
C-228
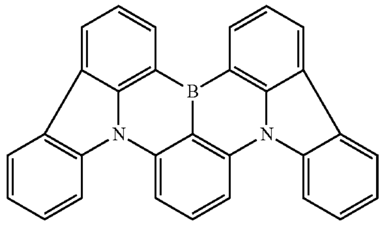
C-229

-continued
C-230
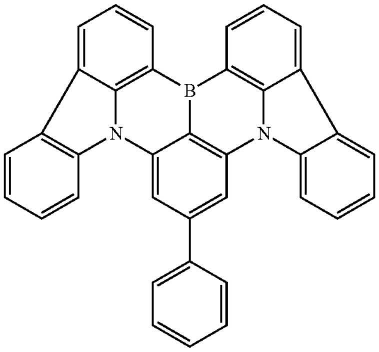
C-231
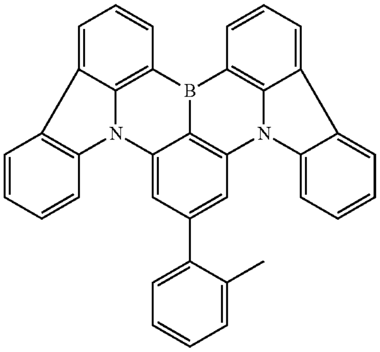
C-232
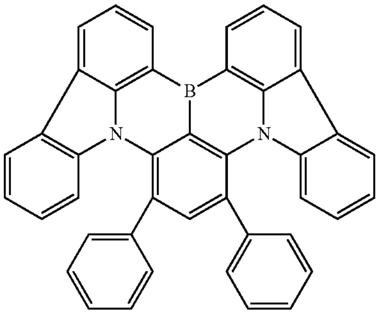
C-233
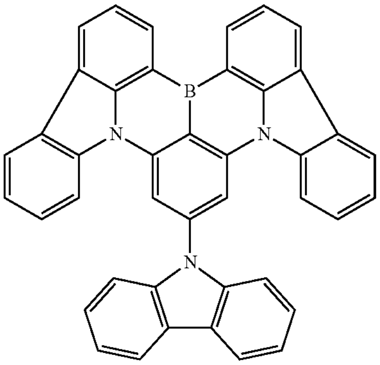
C-234
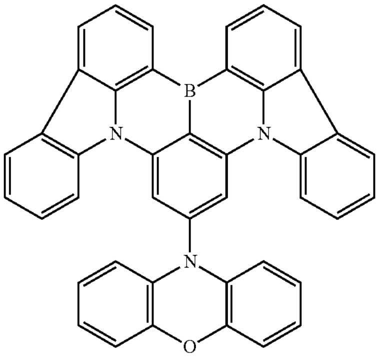
C-235
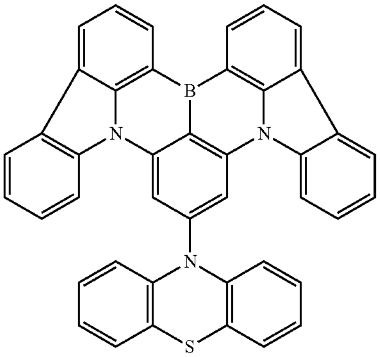
C-236
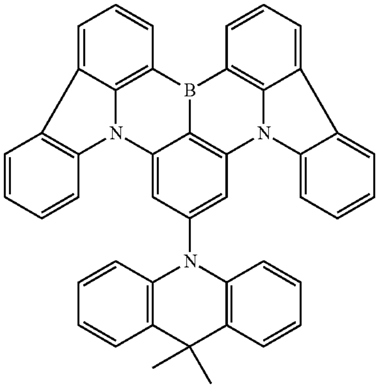
C-237
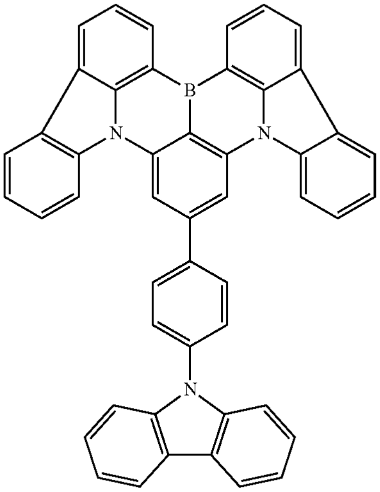

-continued
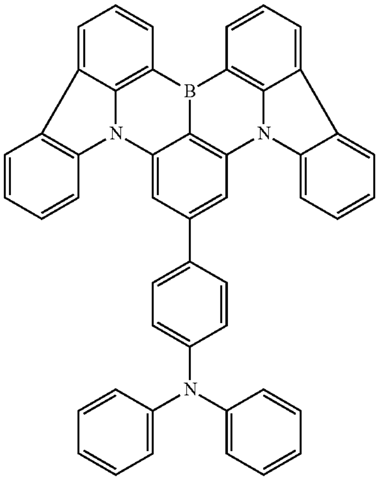
C-238
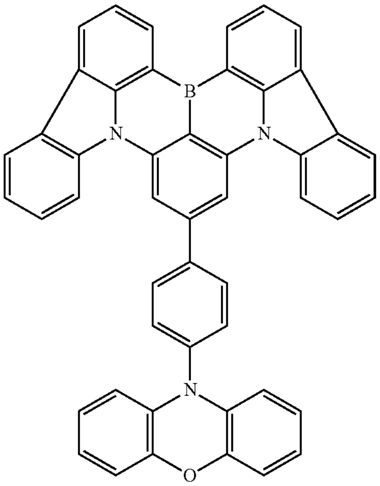
C-239
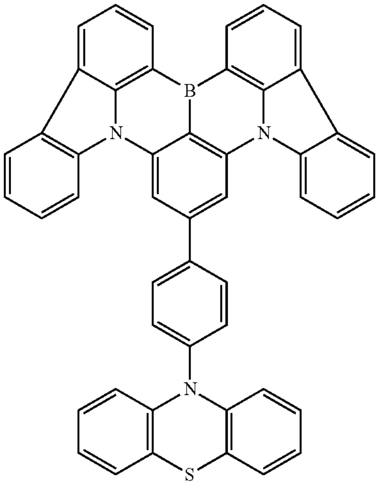
C-240
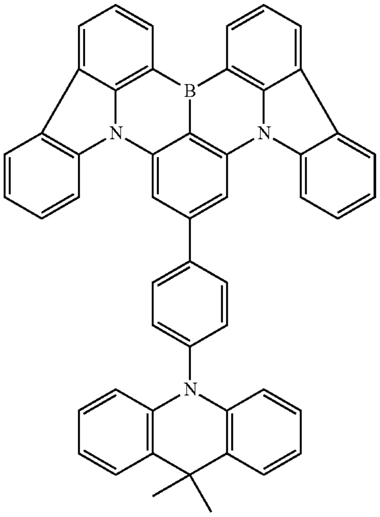
C-241
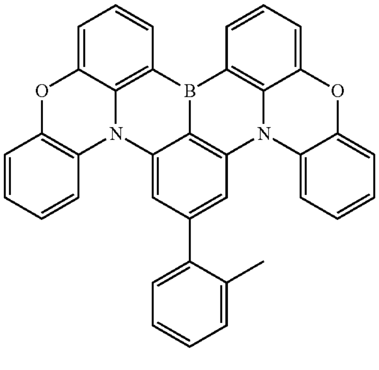
C-242
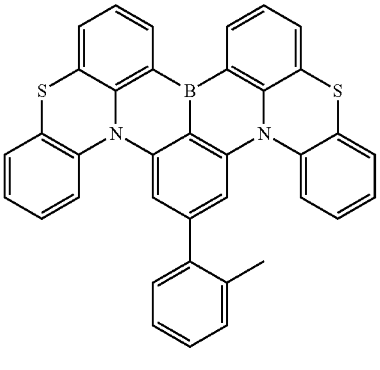
C-243

-continued
C-244
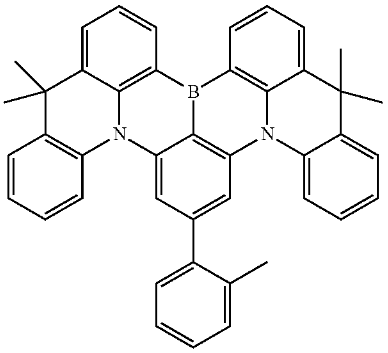
C-245
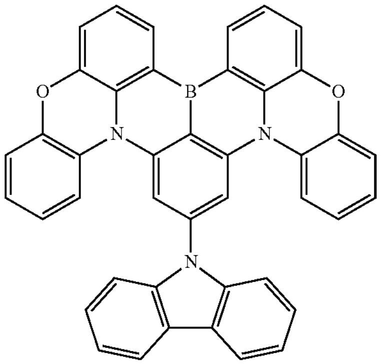
C-246
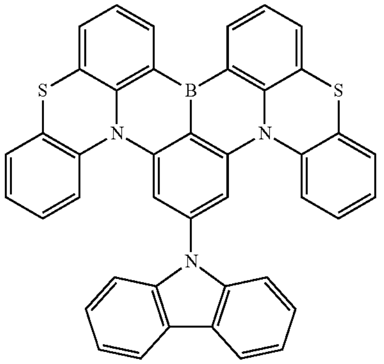
C-247
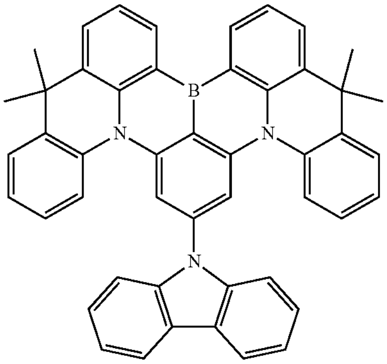
C-248
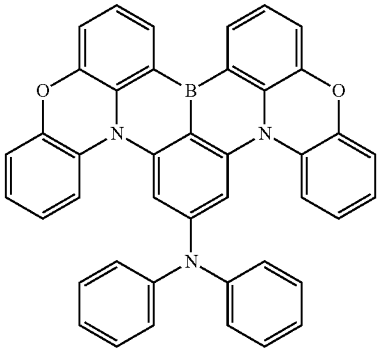
C-249
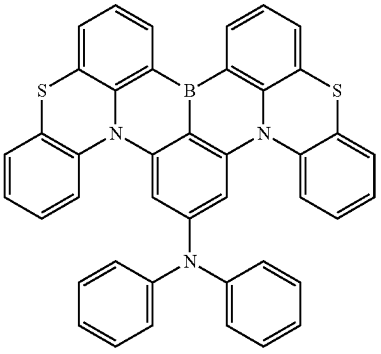
C-250
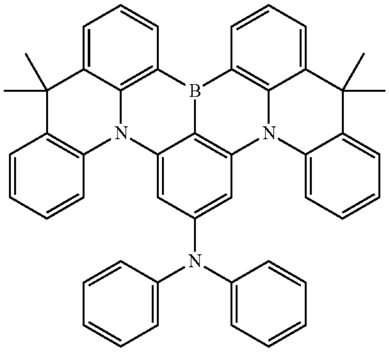
C-251
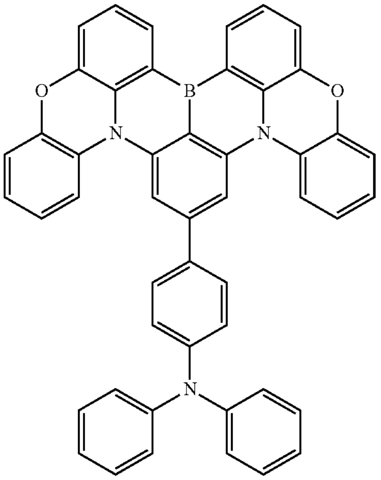

-continued
C-252
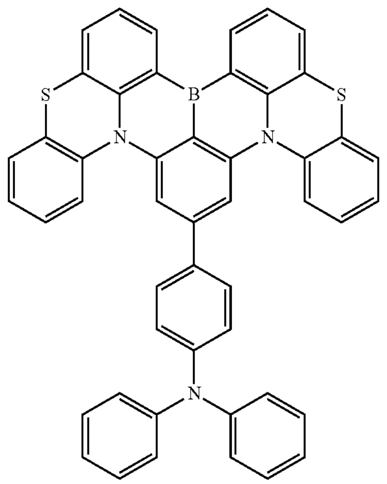
C-253
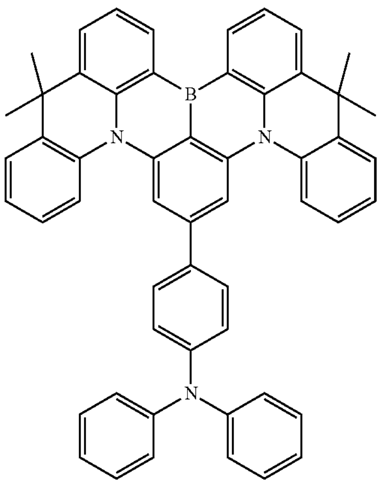
C-254
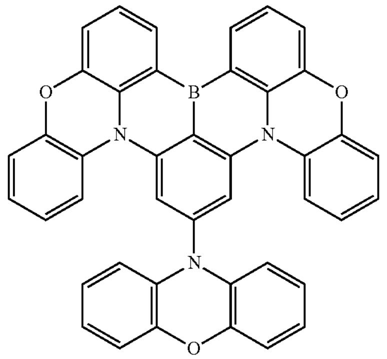
C-255
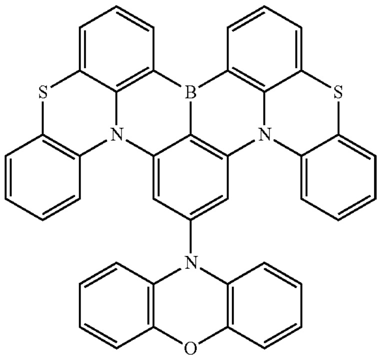
C-256
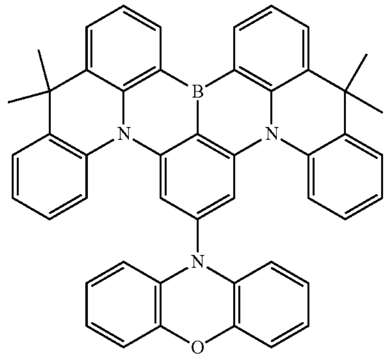
C-257
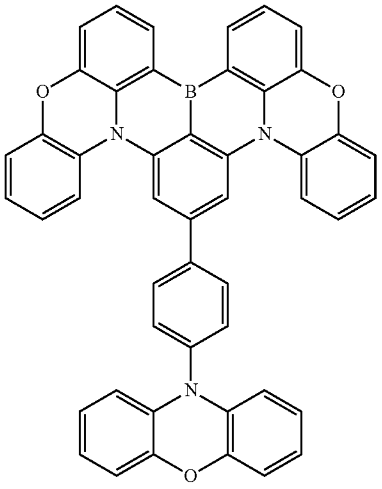

-continued
C-258
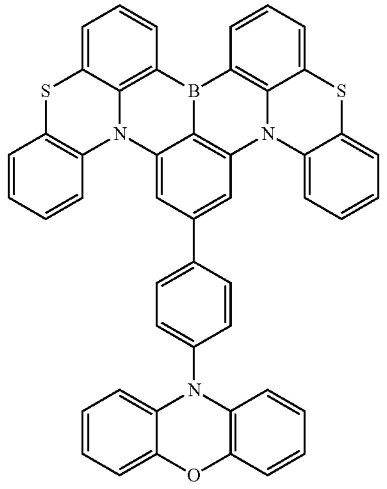
C-259
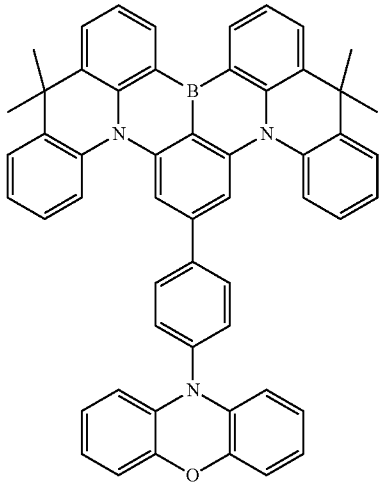
C-260
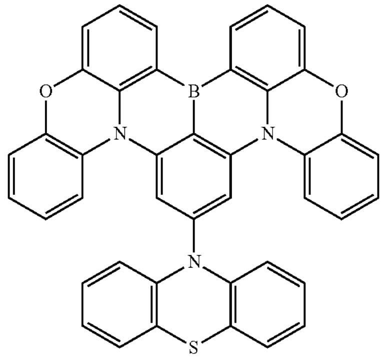
C-261
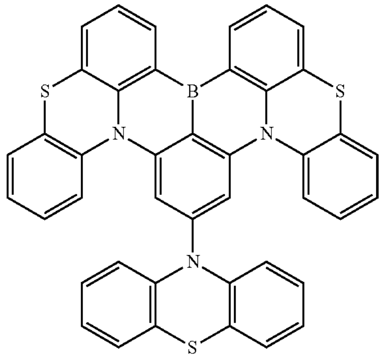
C-262
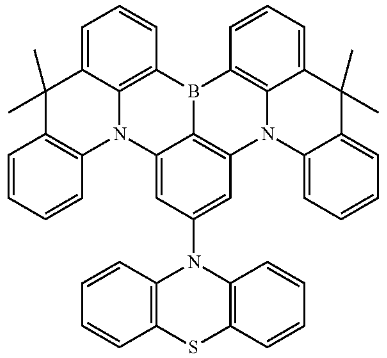
C-263
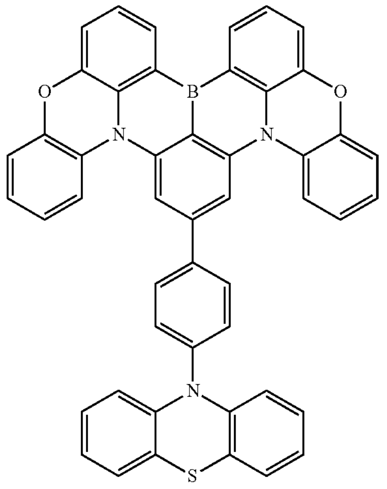

-continued
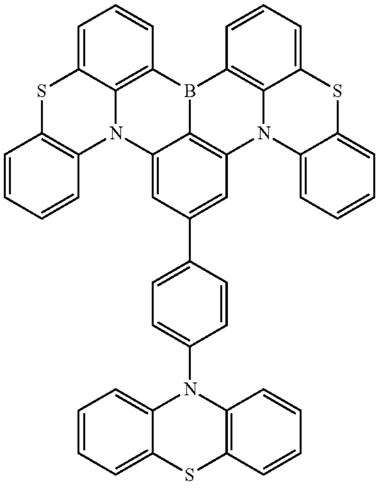
C-264
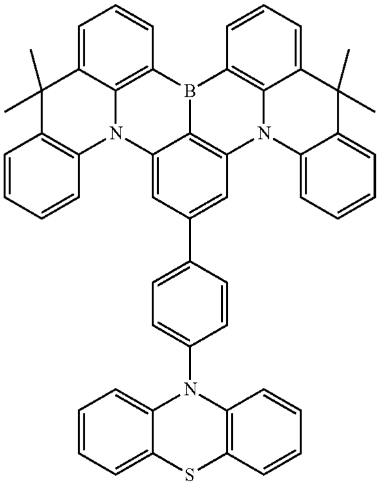
C-265
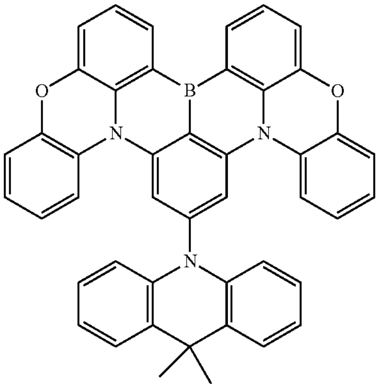
C-266
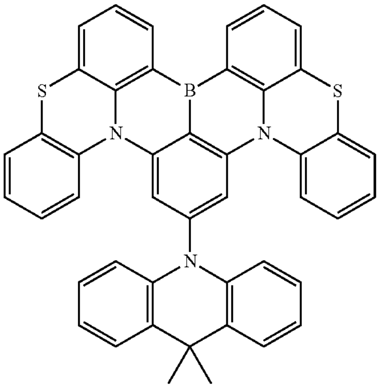
C-267
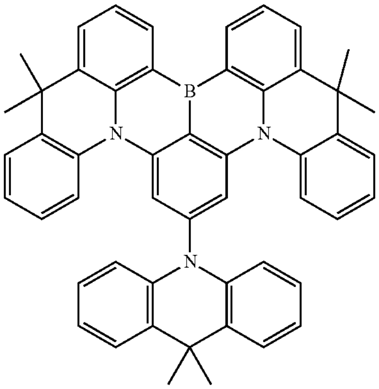
C-268
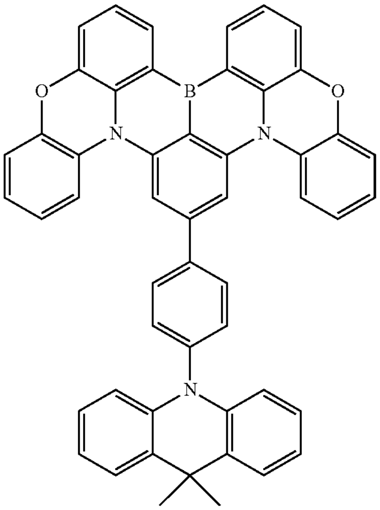
C-269

-continued
C-270
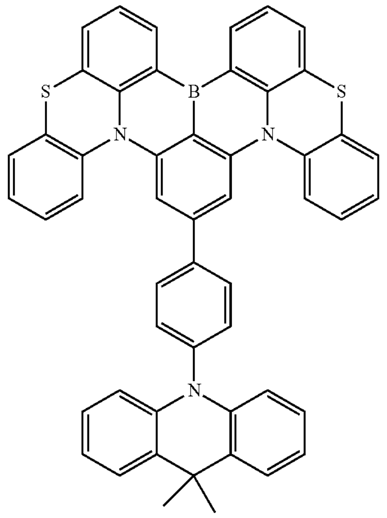
C-271
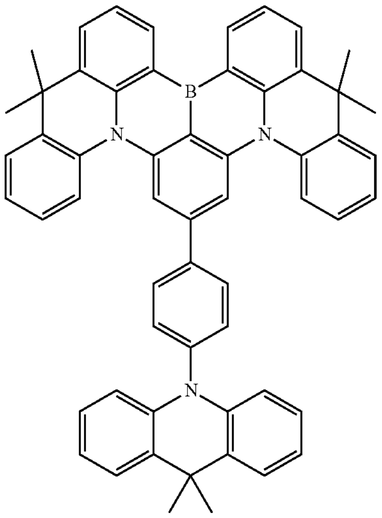
C-272
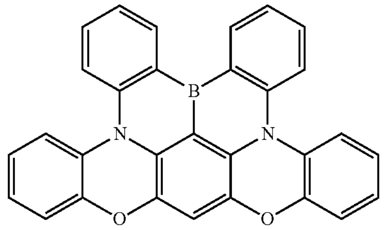
C-273
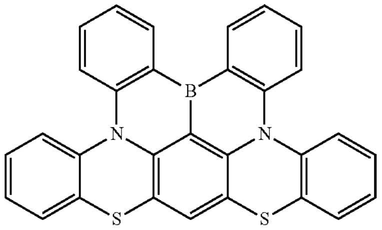
C-274
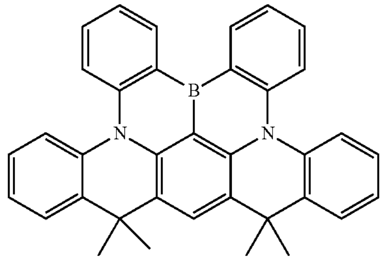
C-275
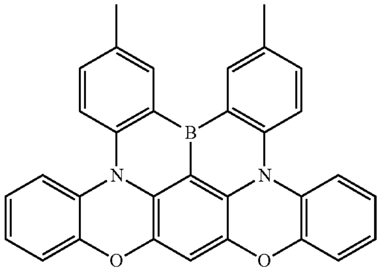
C-276
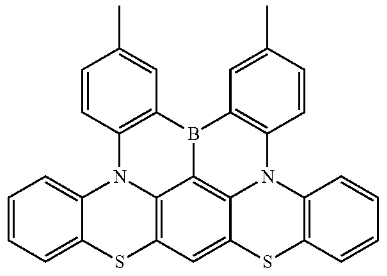
C-277
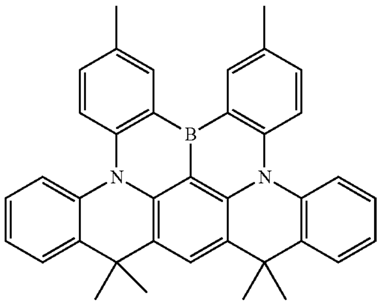

-continued
C-278
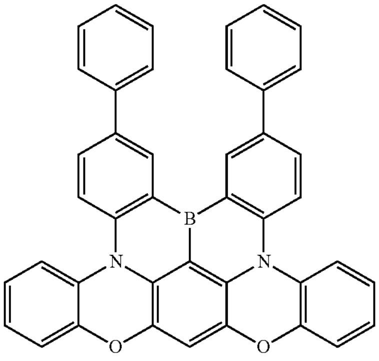
C-279
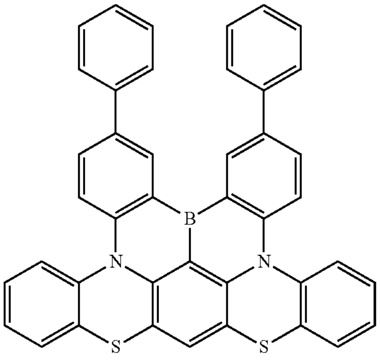
C-280
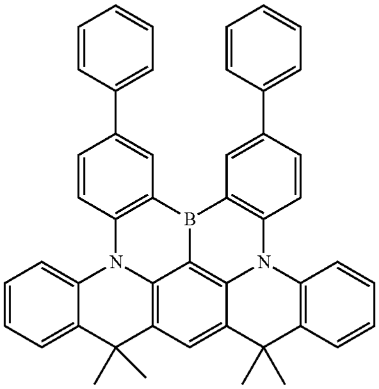
C-281
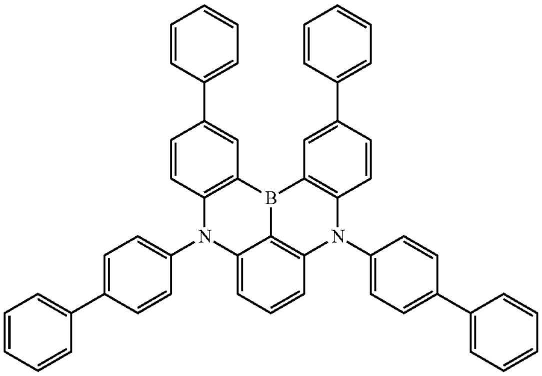
C-282
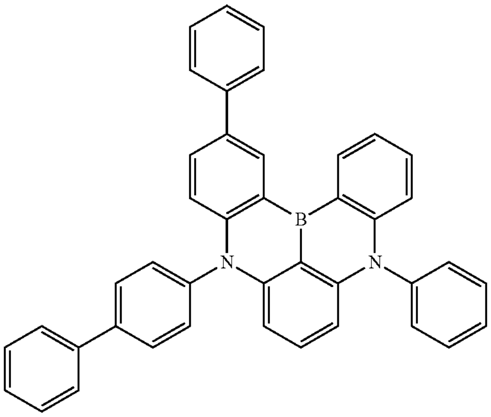
C-283
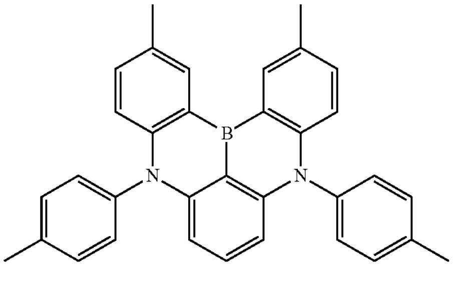
C-284
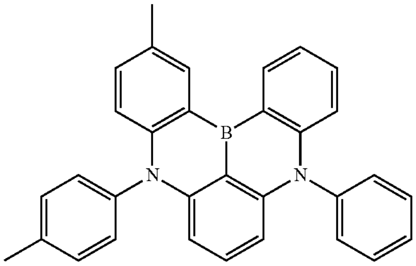
C-285
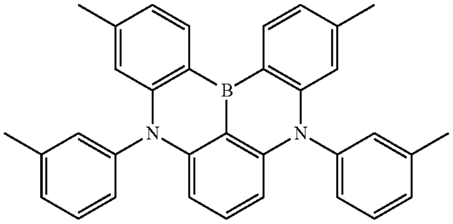

-continued
C-286
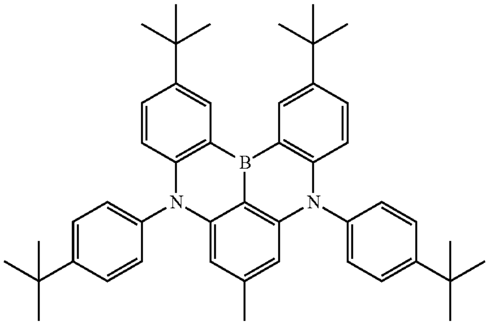
C-287
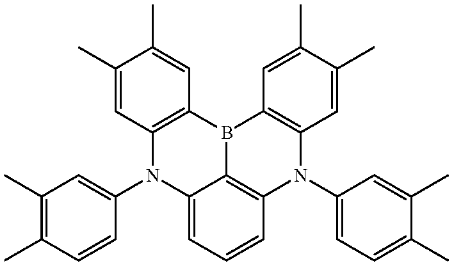
C-288
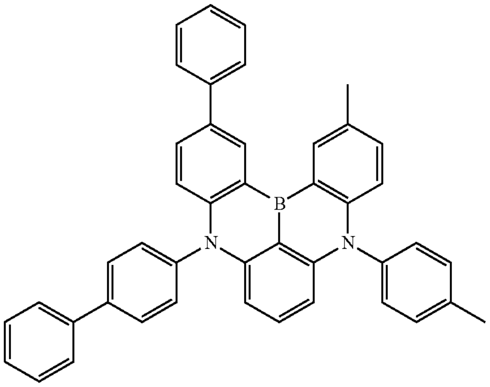
C-289
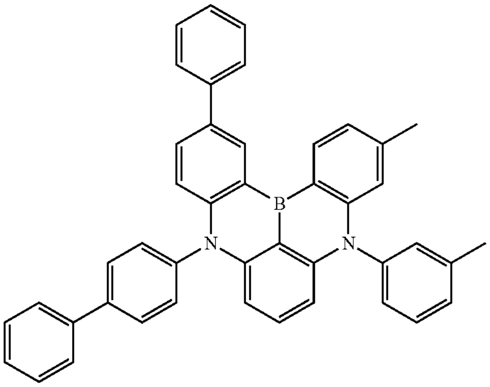
C-290
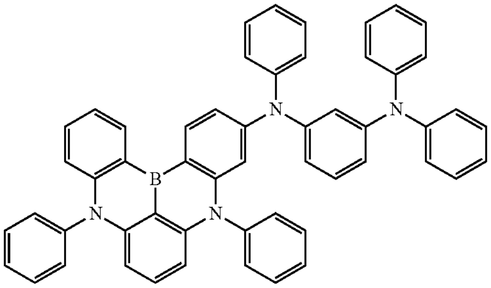
C-291
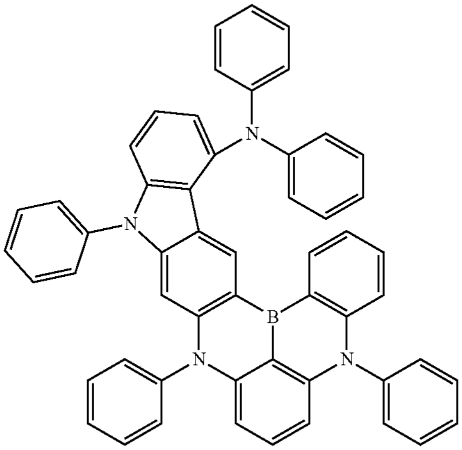
C-292
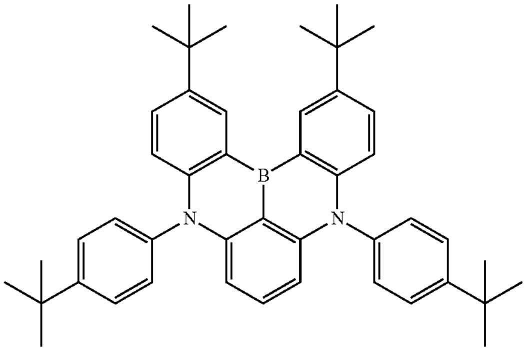
C-293
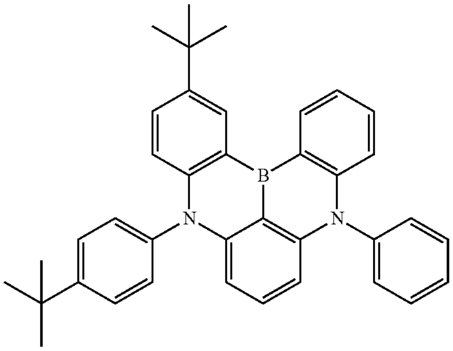

-continued
C-294
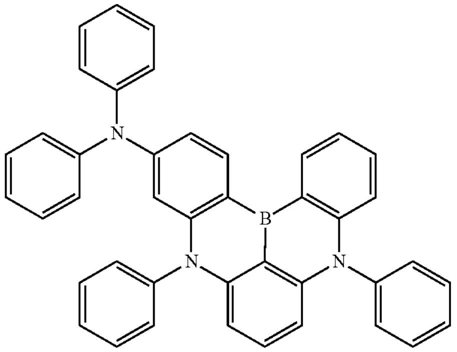
C-295
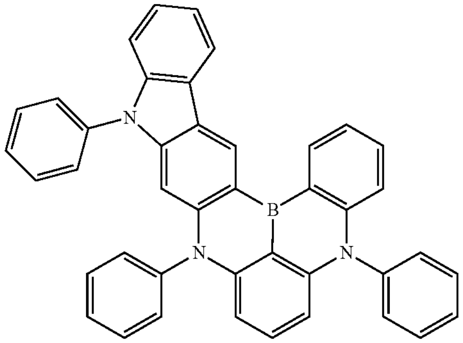
C-296
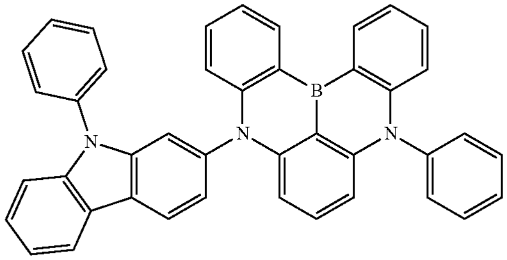
C-297
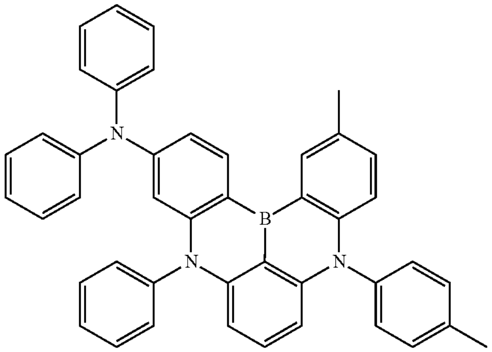
C-298
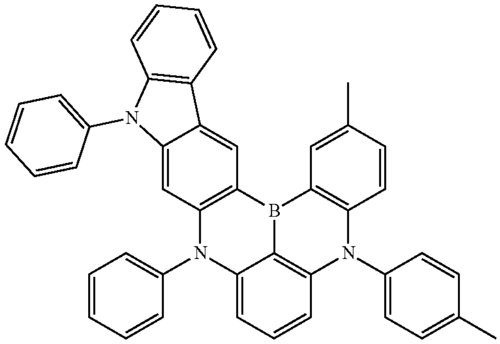
C-299
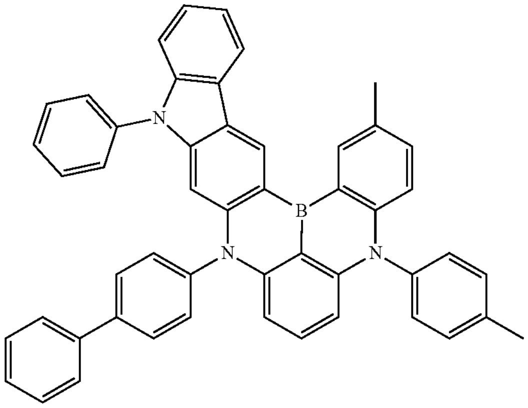
C-300
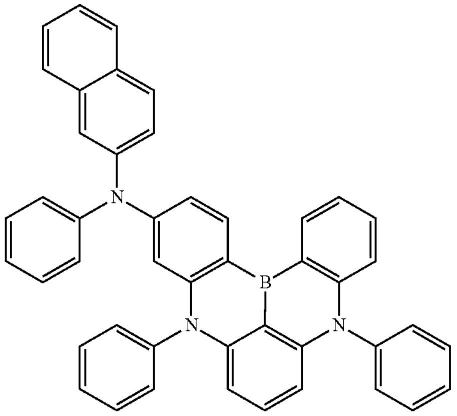

-continued
C-301
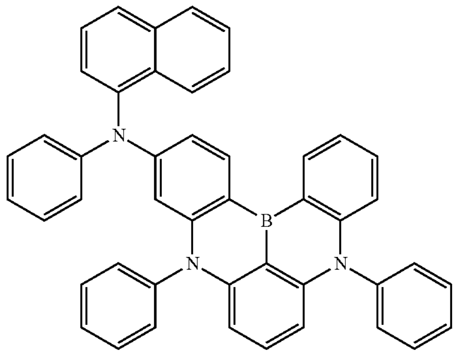
C-302
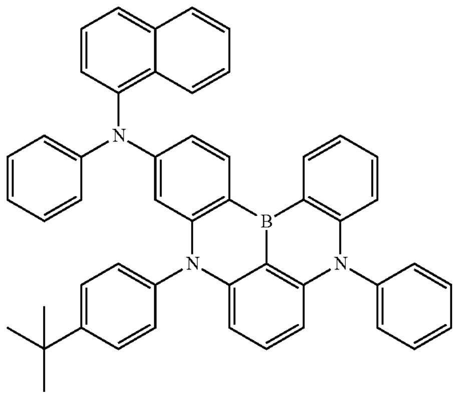
C-303
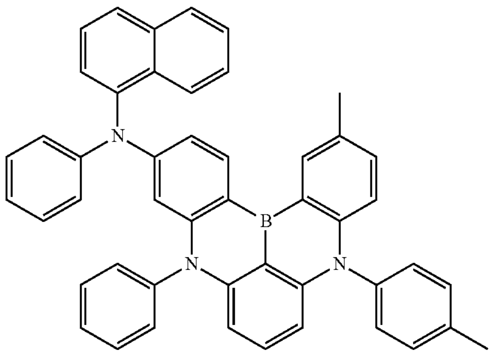
C-304
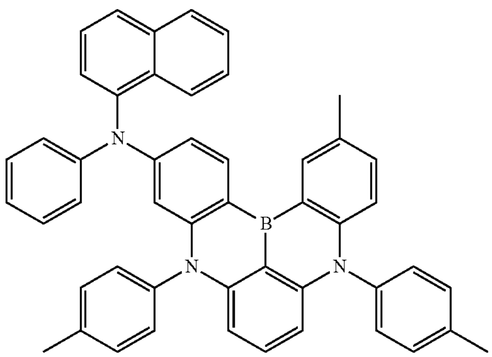
C-305
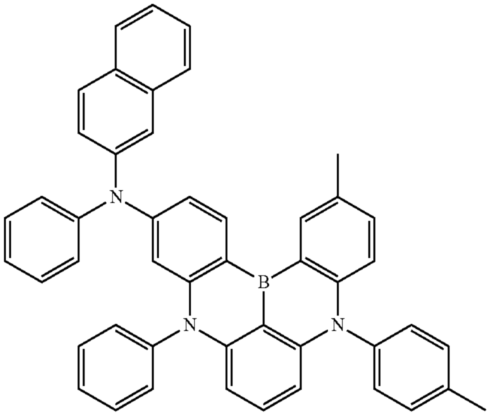
C-306
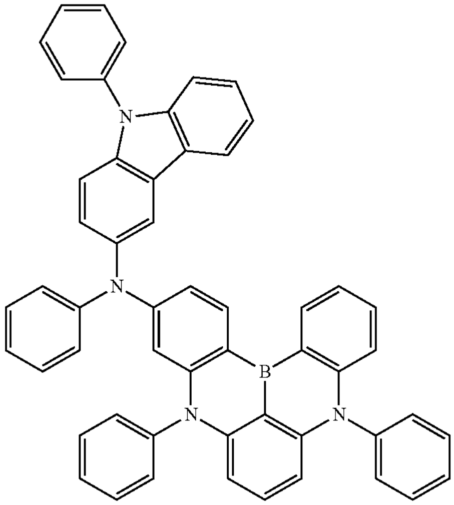
C-307
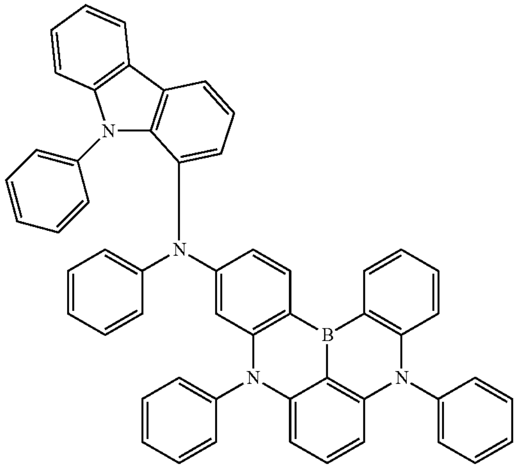

-continued
C-308
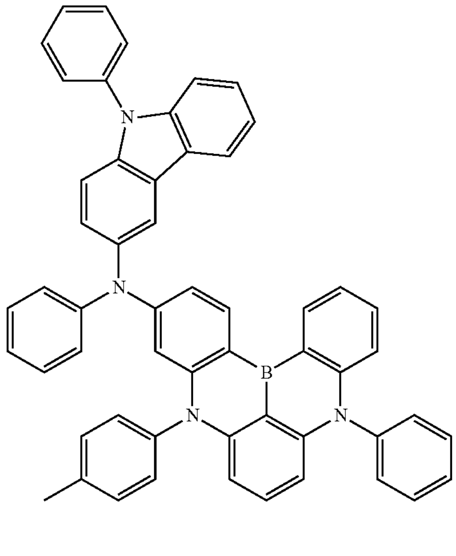
C-309
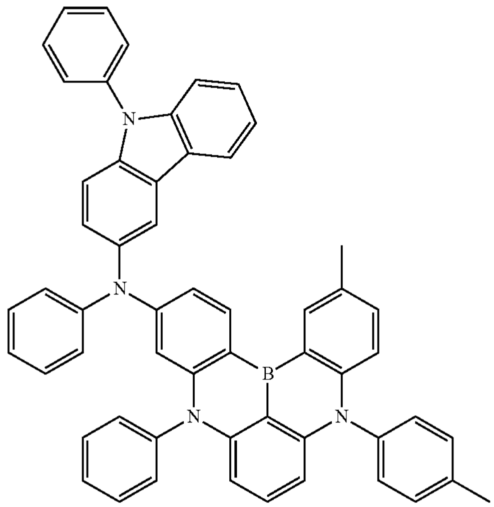
C-310
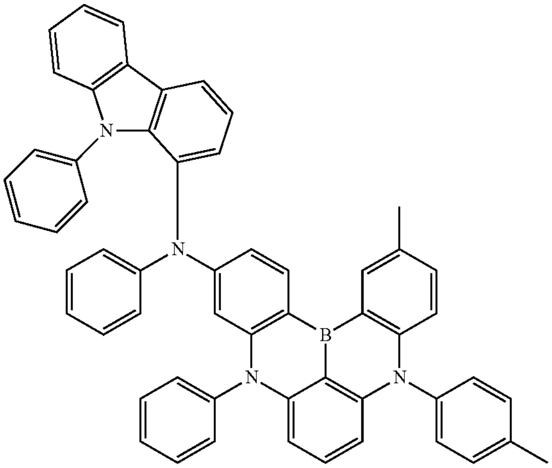
-continued
C-311
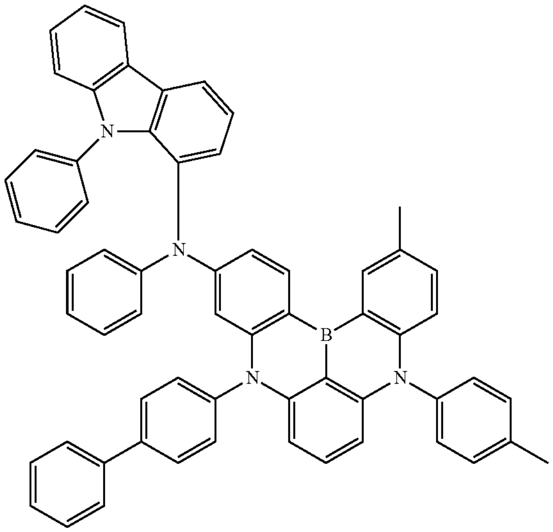
C-312
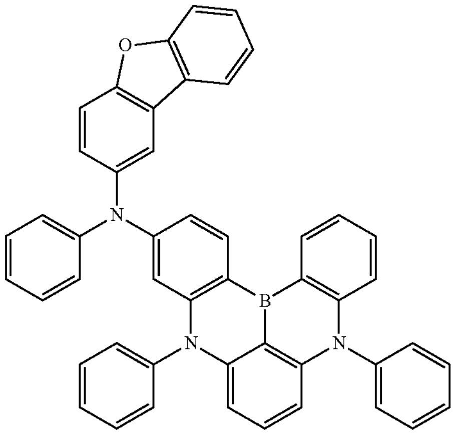
C-313
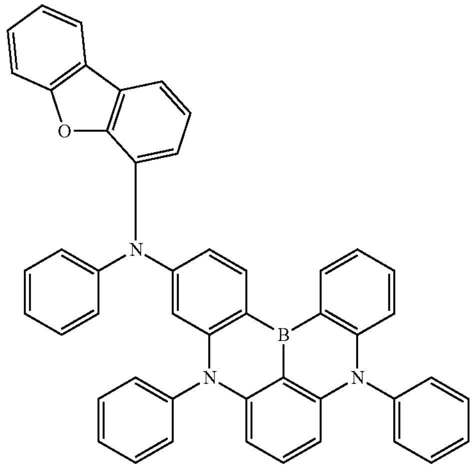

-continued
C-314
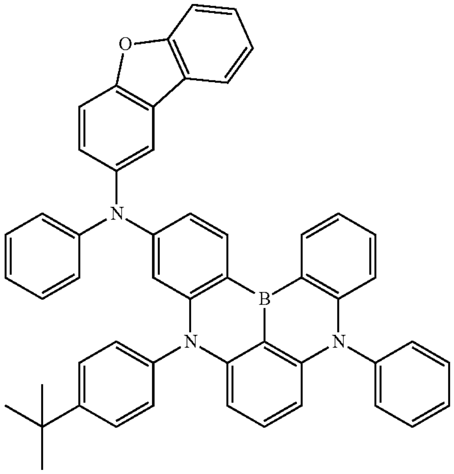
C-315
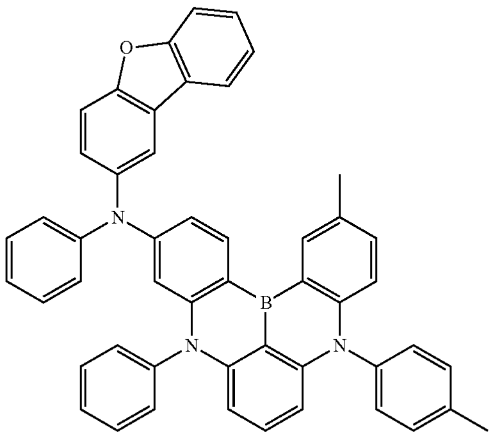
C-316
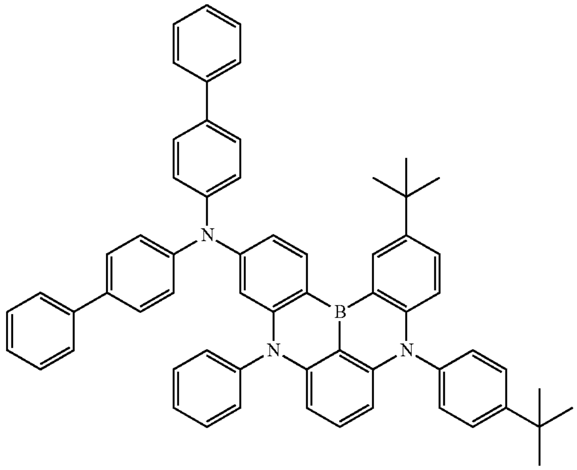
-continued
C-317
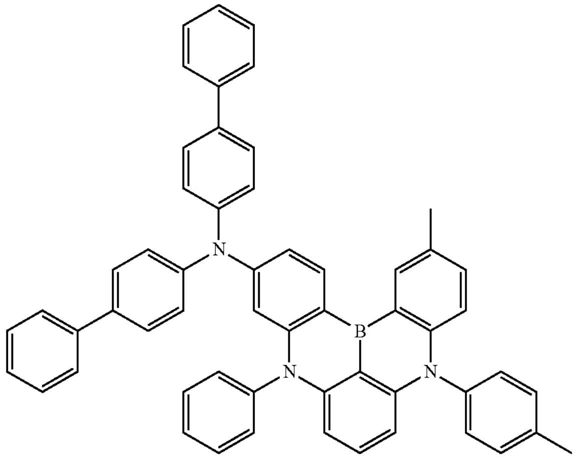
C-318
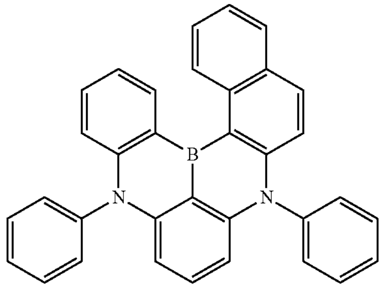
C-319
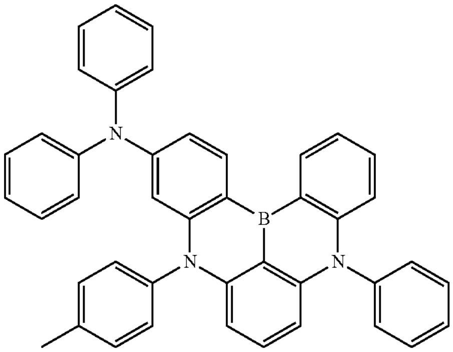
C-320
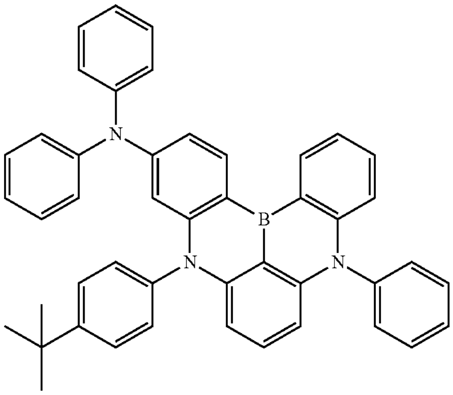

-continued
C-321
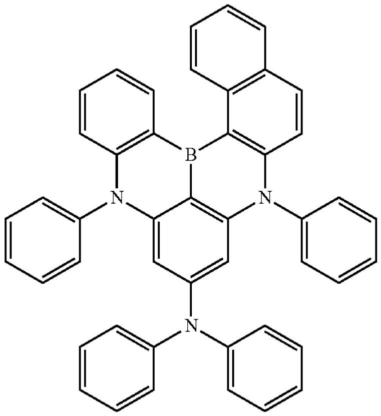
C-322
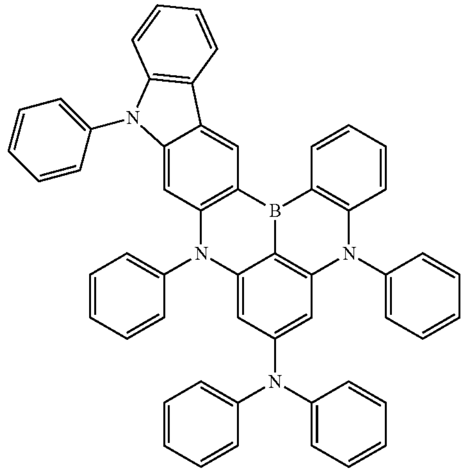
C-323
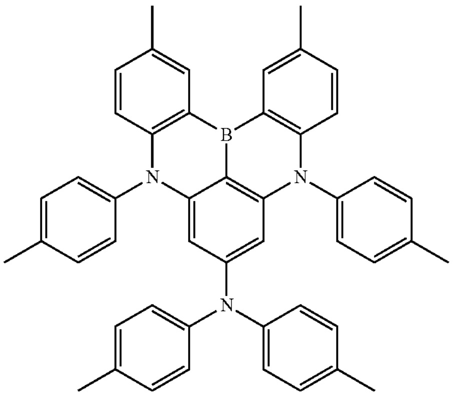
-continued
C-324
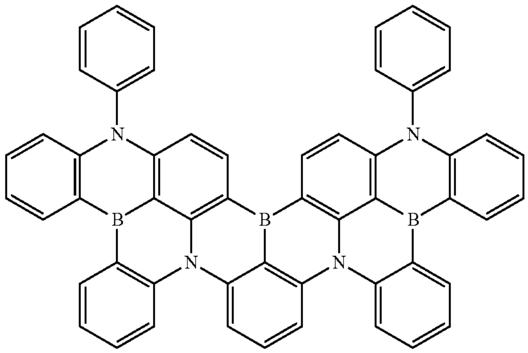
C-325
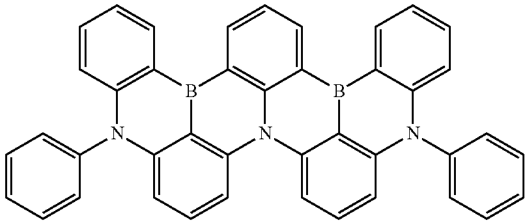
C-326
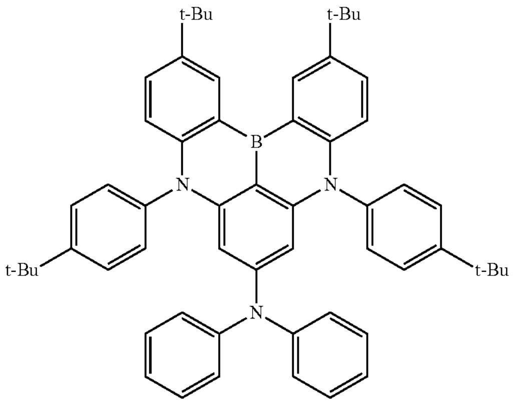
C-327
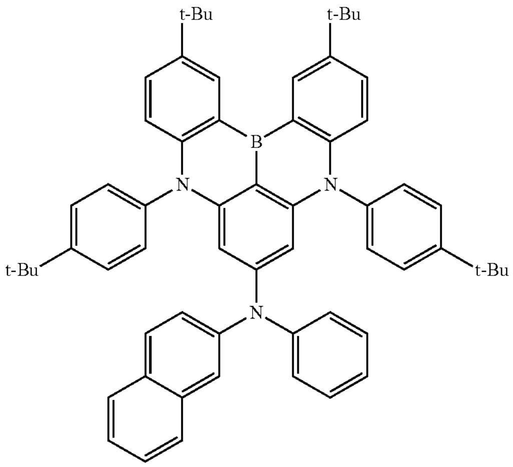

-continued
C-328
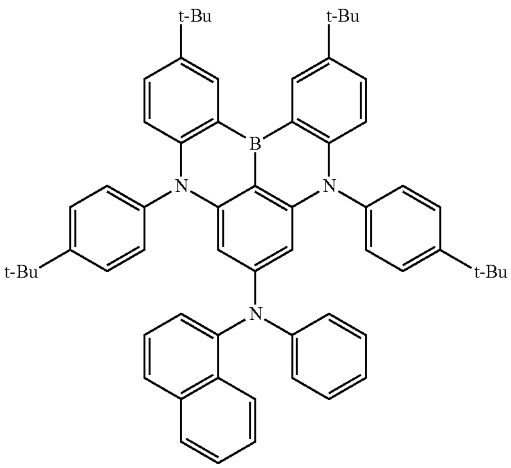
C-329
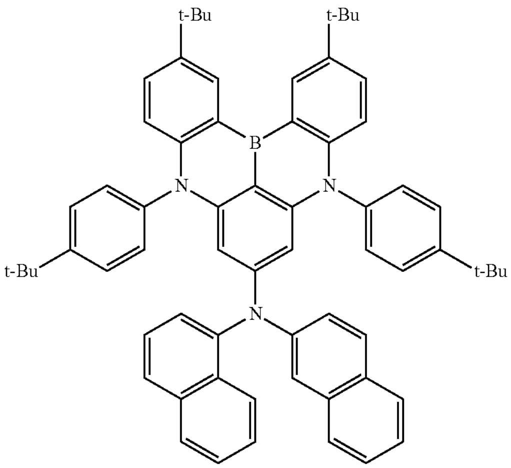
C-330
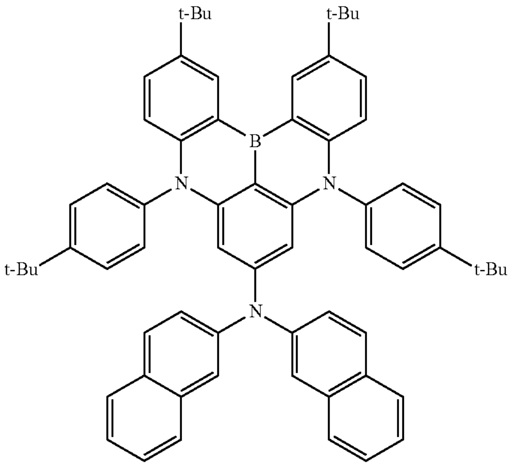
-continued
C-331
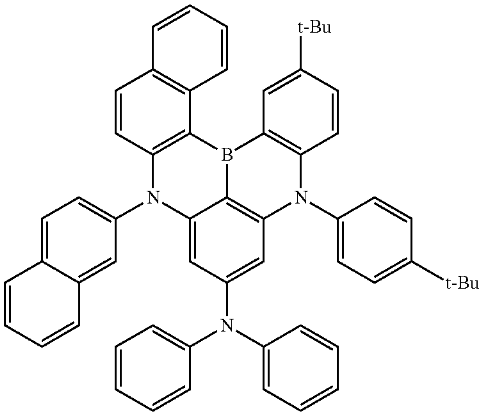
C-332
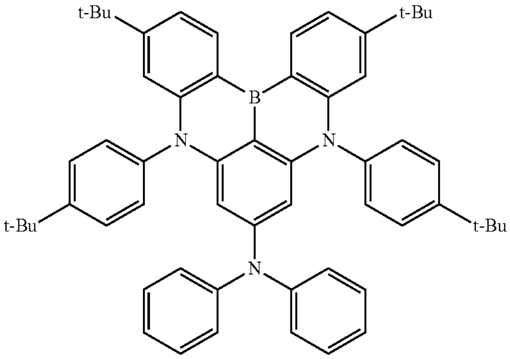
C-333
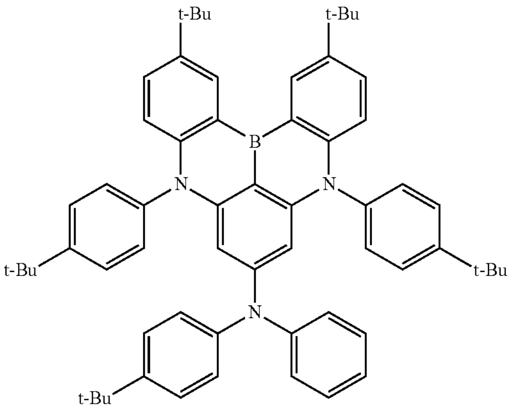
C-334
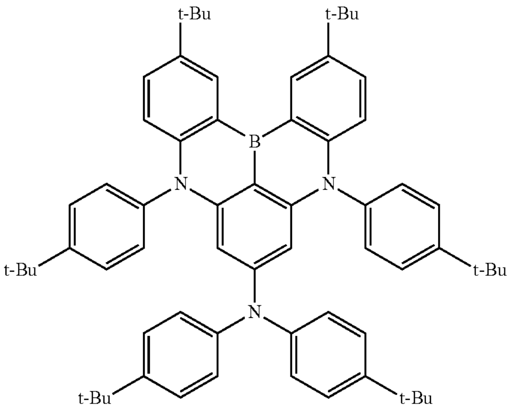

-continued
C-335
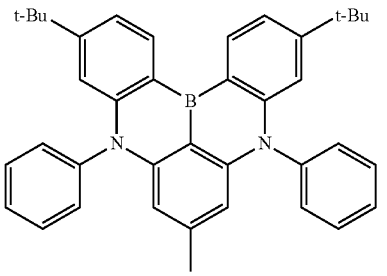
C-336
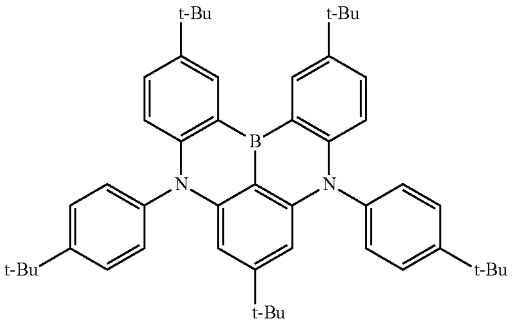
C-337
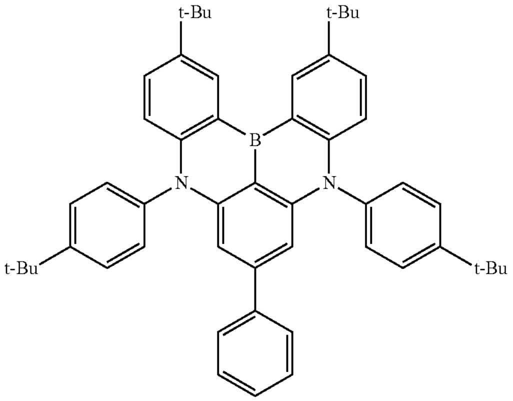
C-338
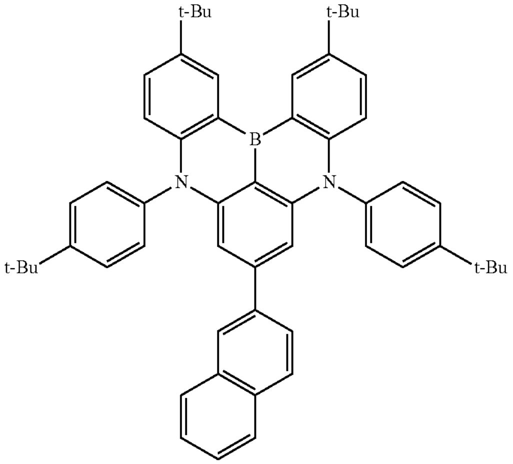
-continued
C-339
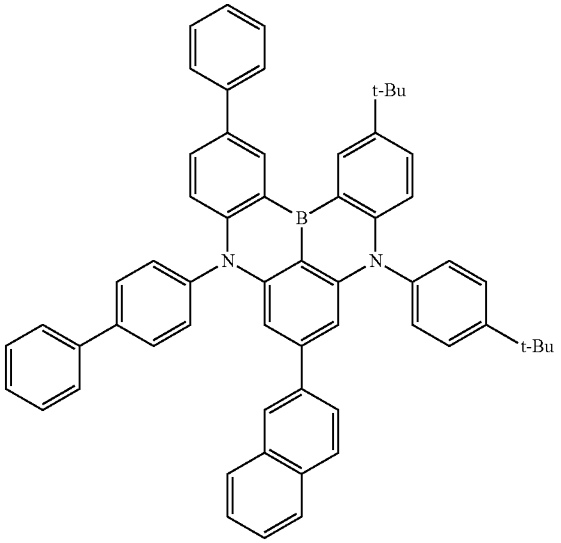
C-340
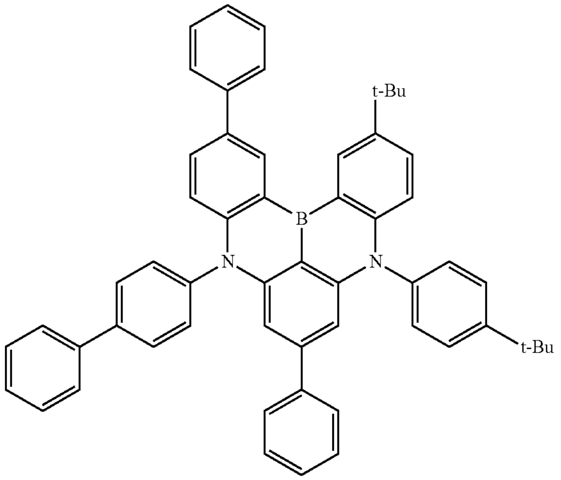
C-341
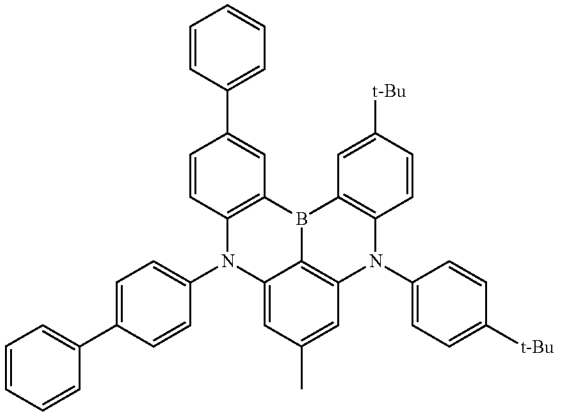

-continued
C-342
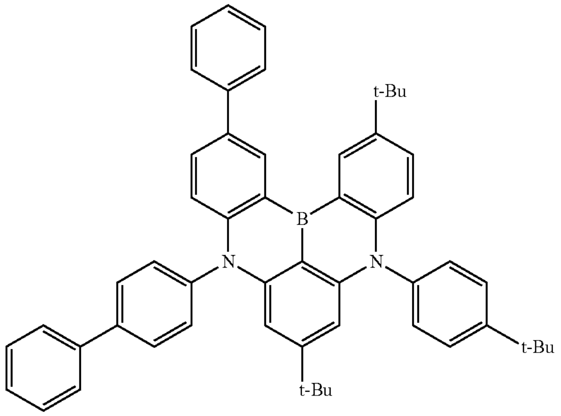
C-343
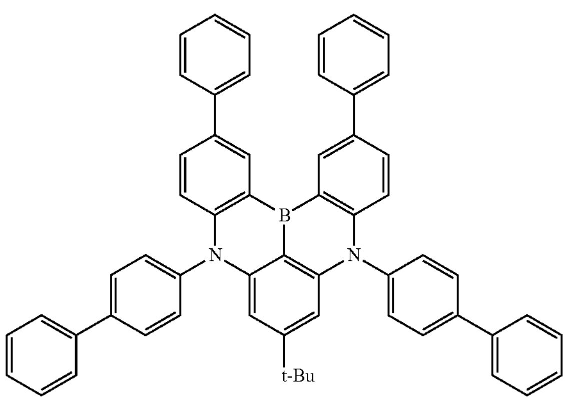
C-344
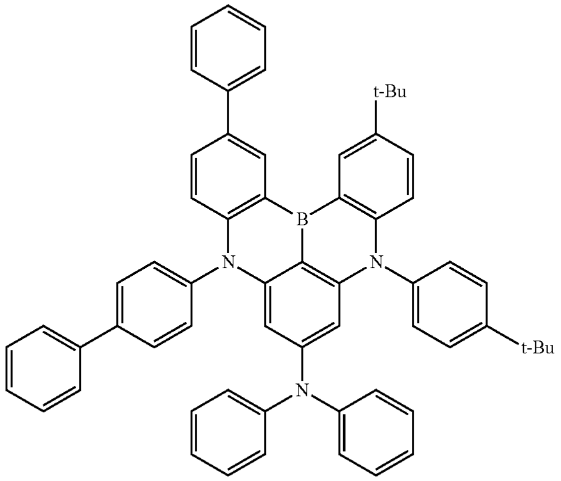
-continued
C-345
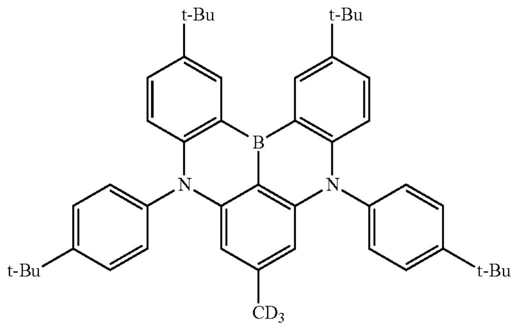
C-346
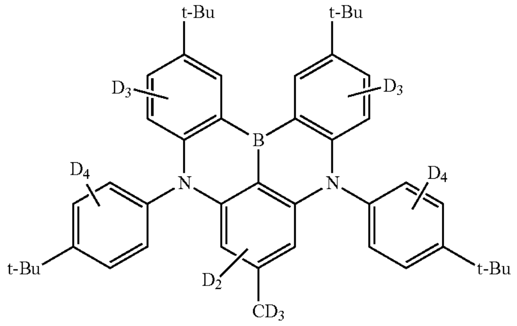
C-347
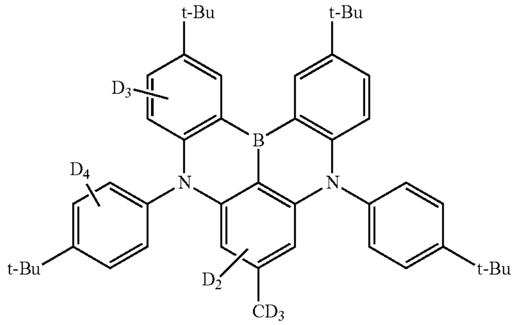
C-348
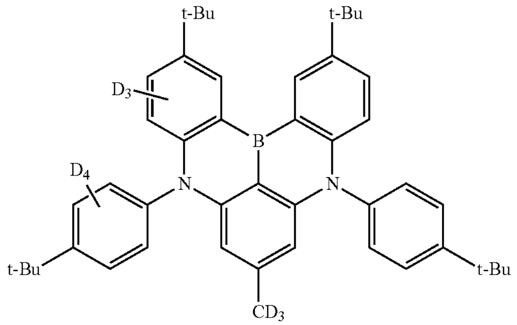

-continued
C-349
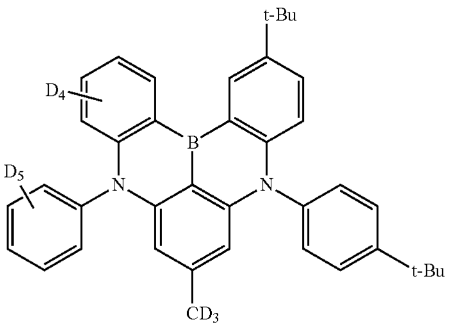
C-350
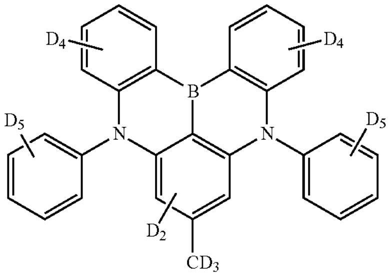
C-351
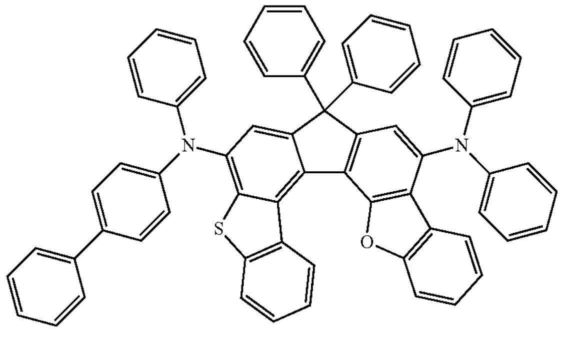
C-352
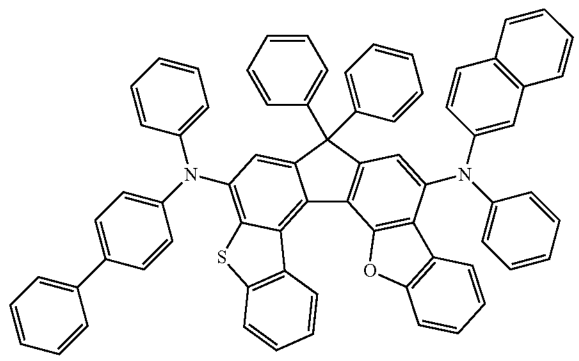
-continued
C-353
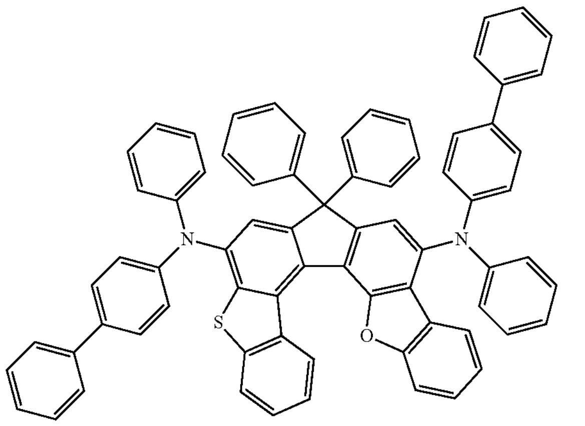
C-354
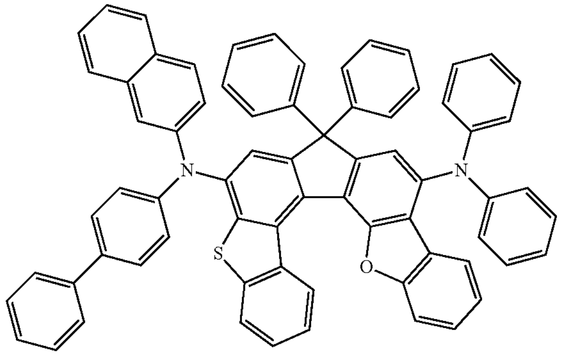
C-355
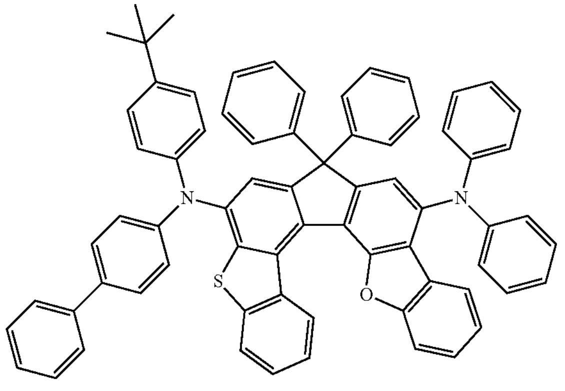
C-356
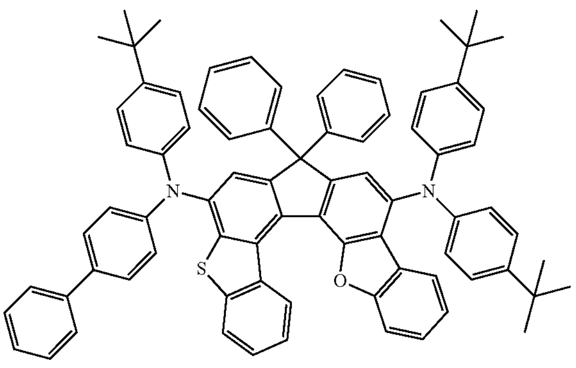

-continued
C-357
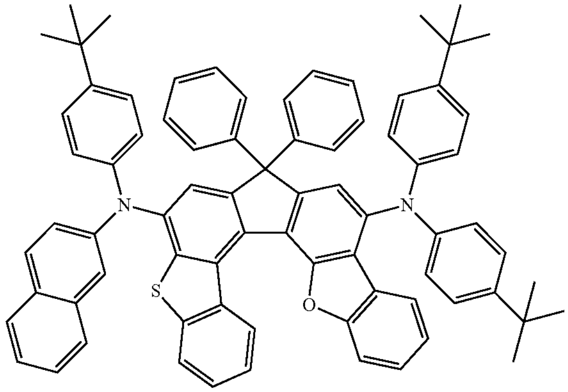
C-358
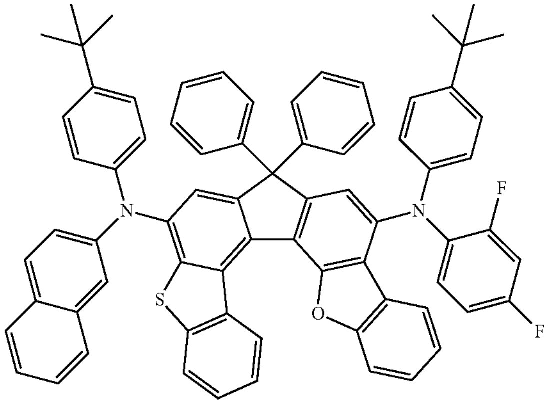
C-359
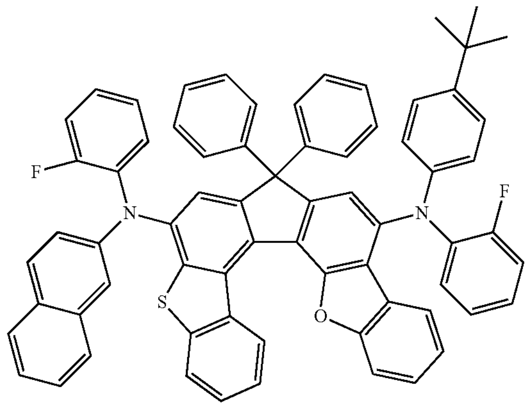
-continued
C-360
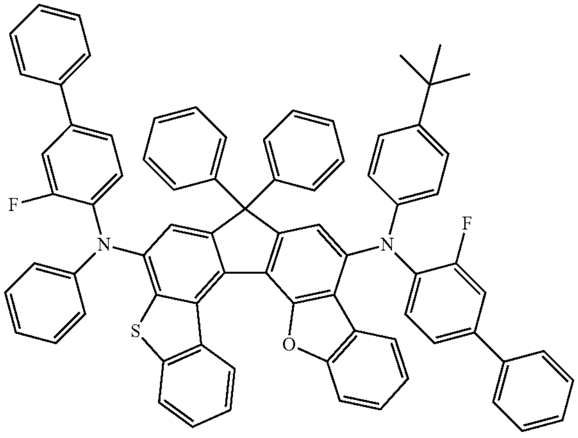
C-361
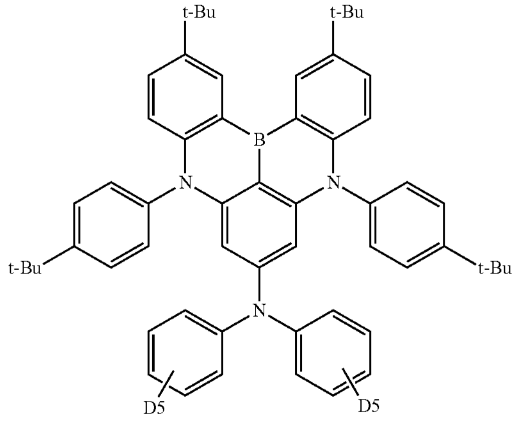
C-362
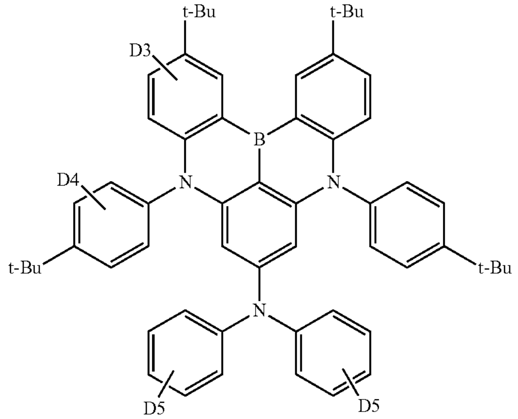

-continued
C-363
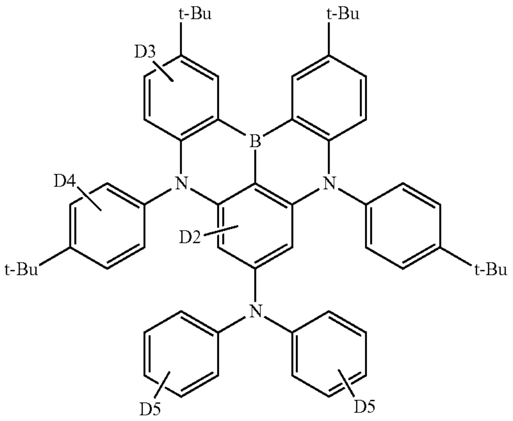
C-364
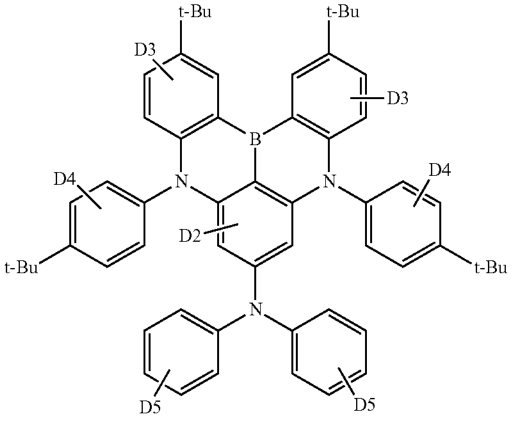
C-365
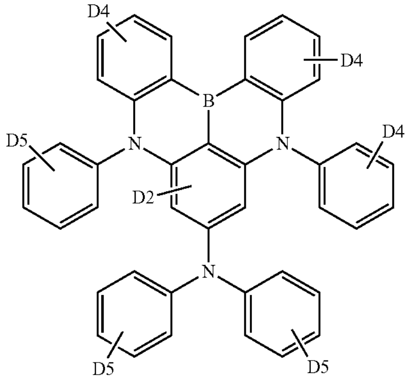
-continued
C-366
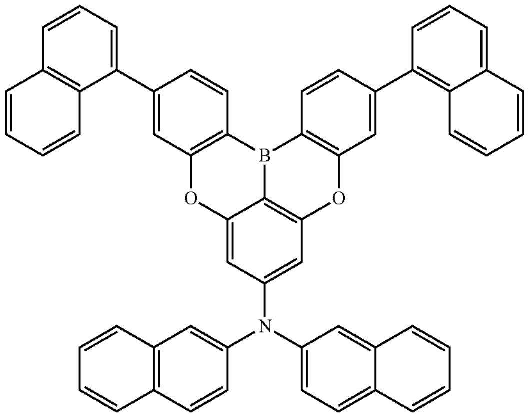
C-367
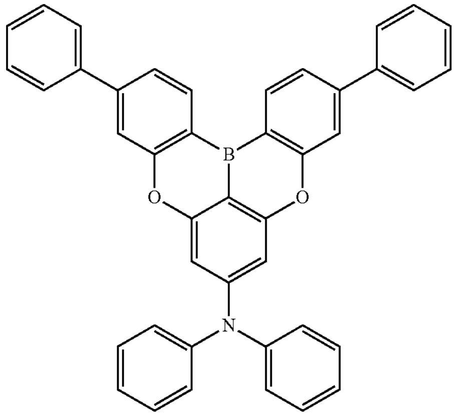
C-368
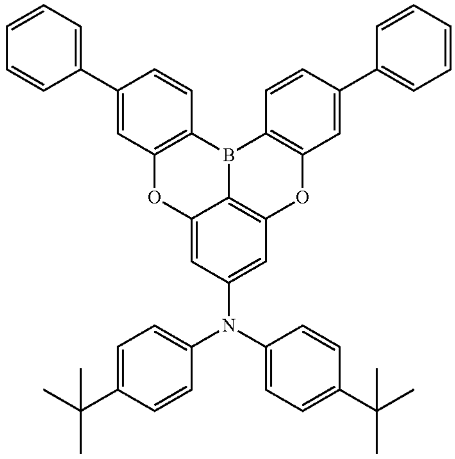

-continued
C-369
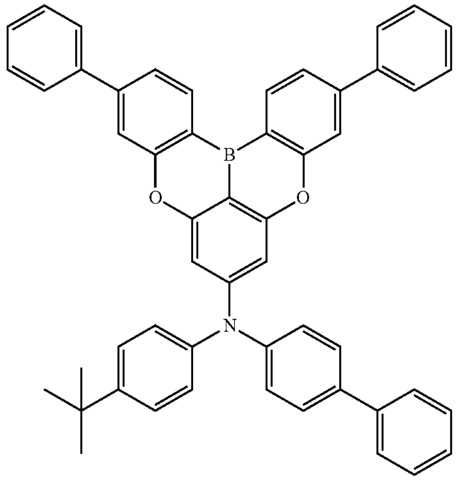
C-370
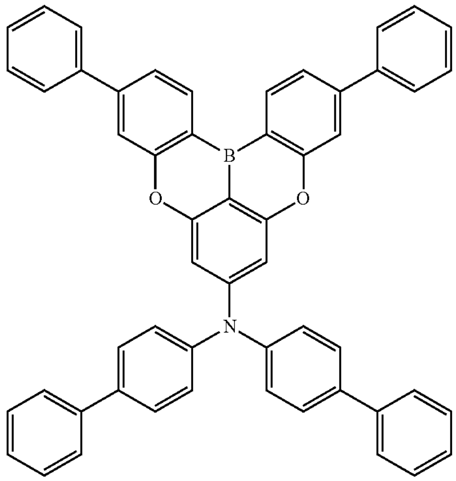
C-371
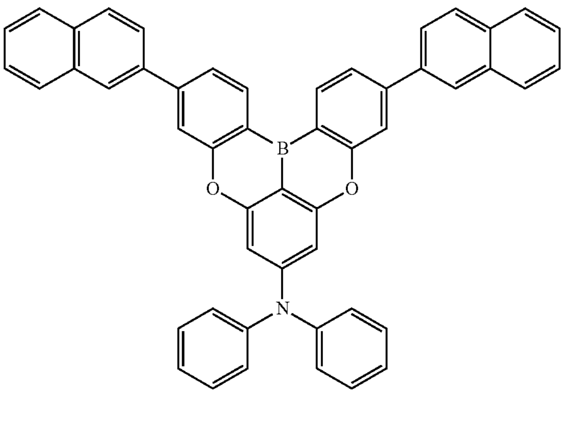
-continued
C-372
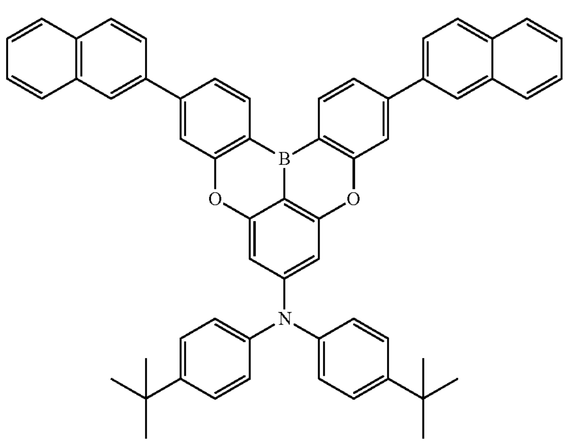
C-373
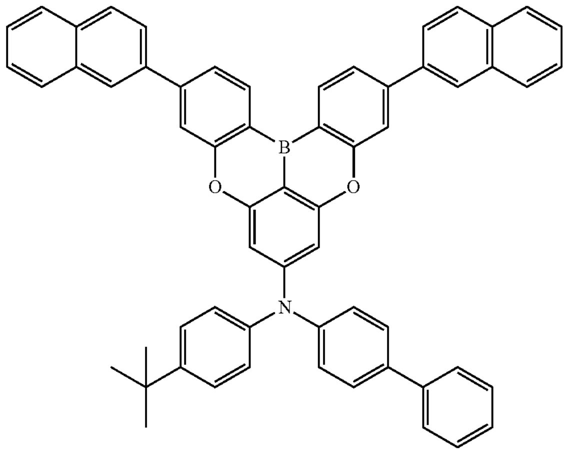
C-374
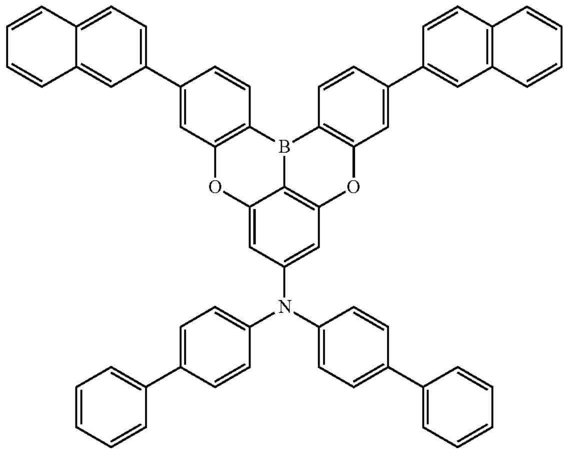

-continued
C-375
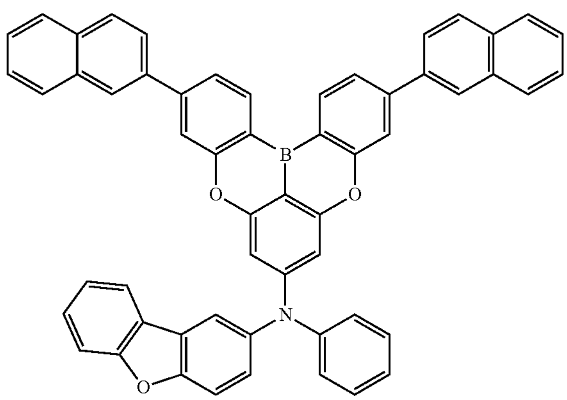
C-376
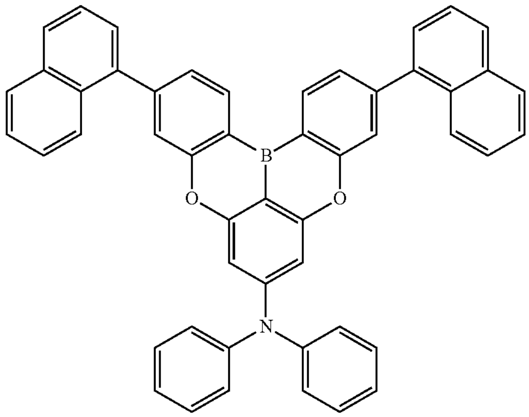
C-377
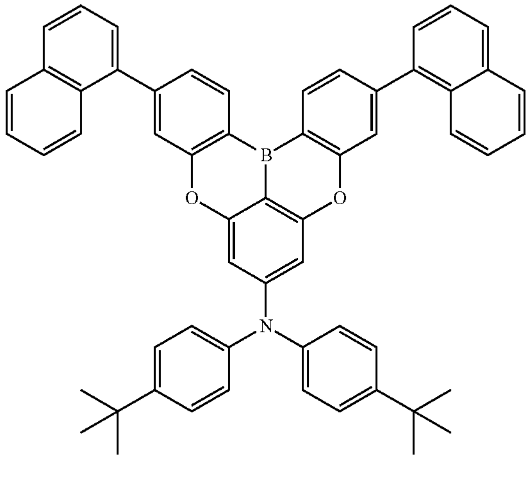
-continued
C-378
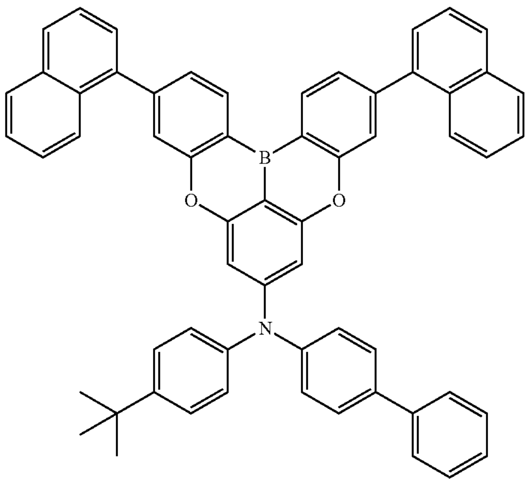
C-379
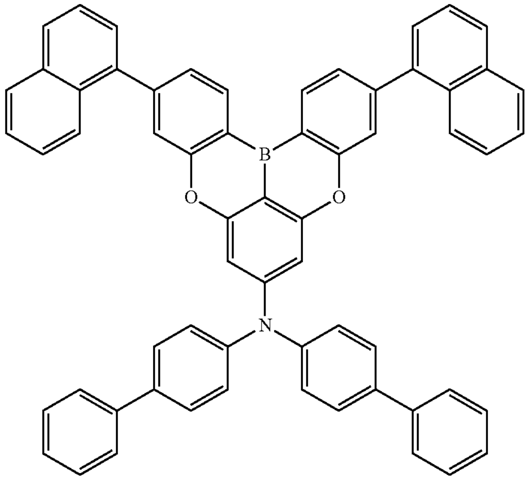
C-380
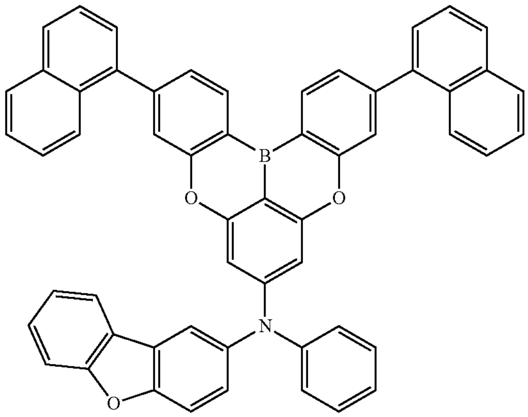

-continued
C-381
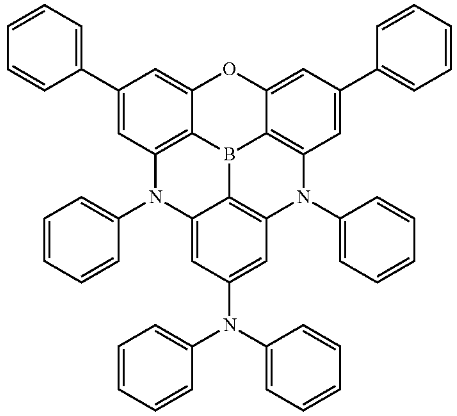
C-382
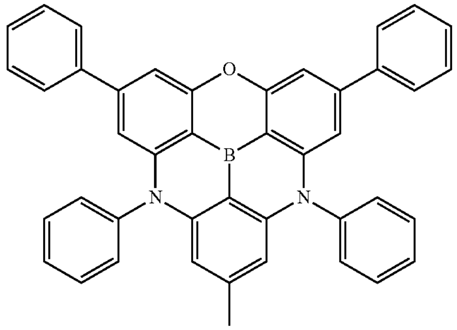
C-383
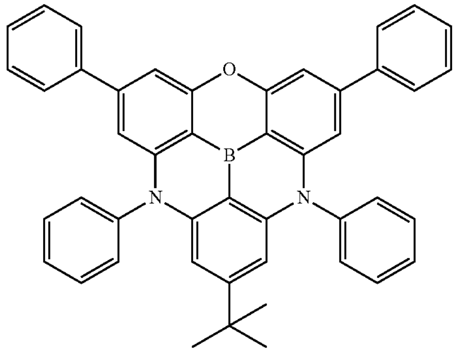
C-384
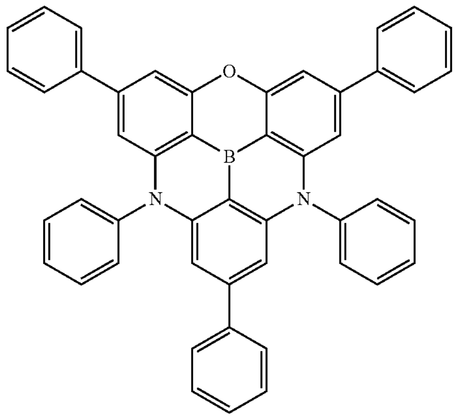
-continued
C-385
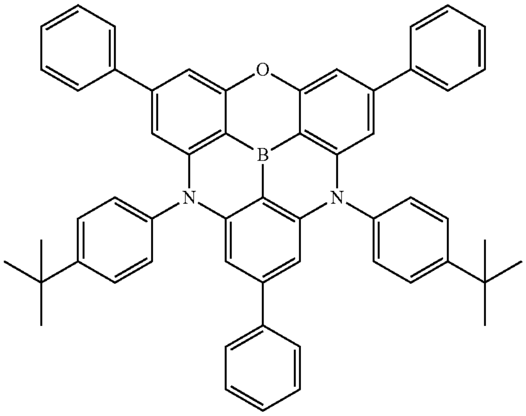
C-386
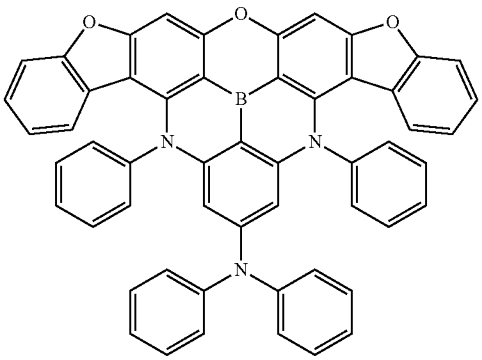
C-387
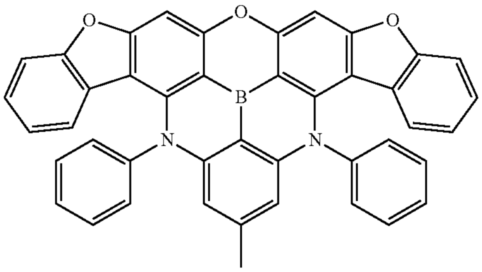
C-388
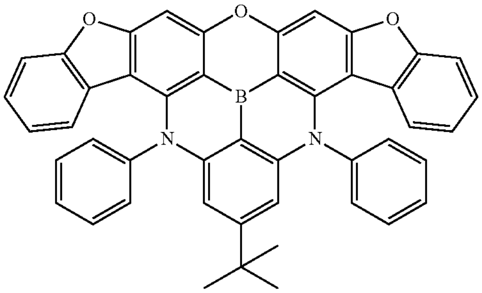

-continued
C-389
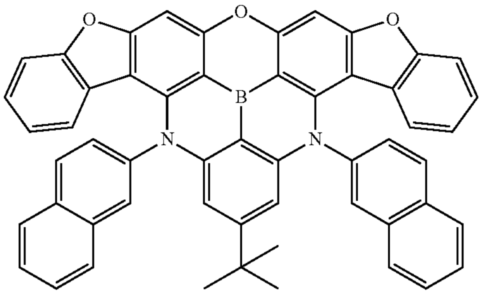
C-390
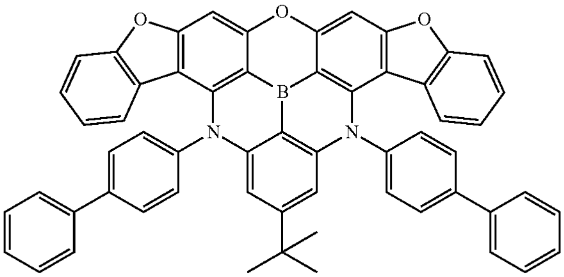
C-391
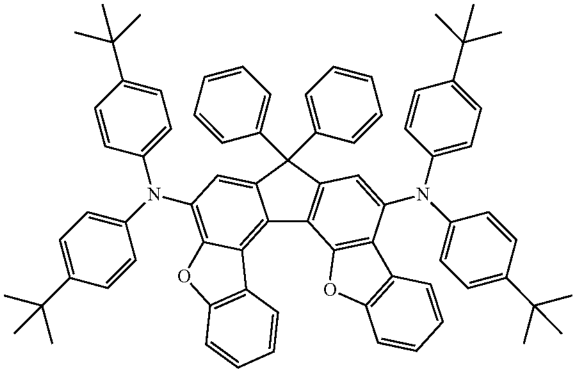
C-392
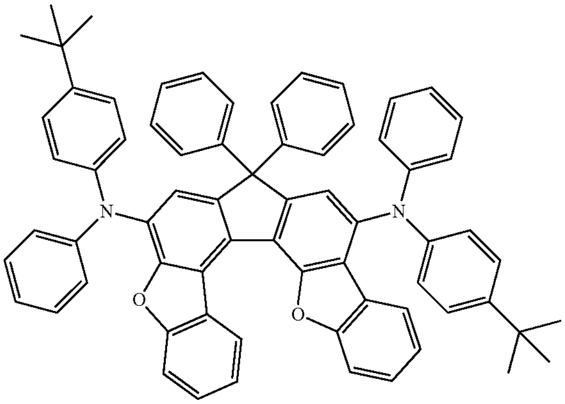
-continued
C-393
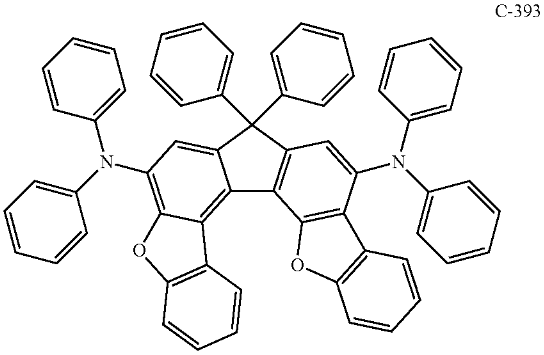
C-394
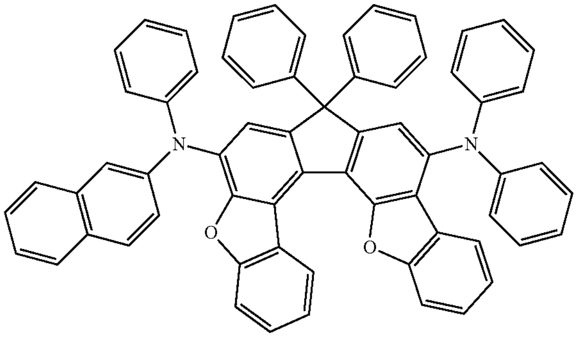
C-395
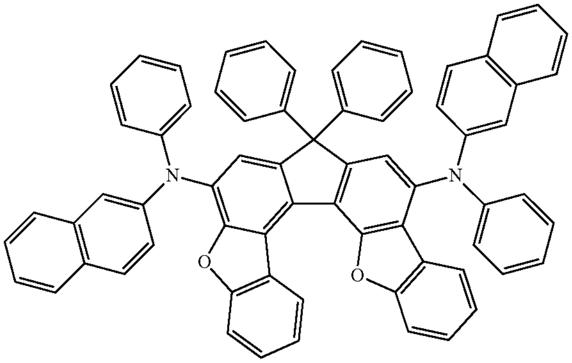
C-396
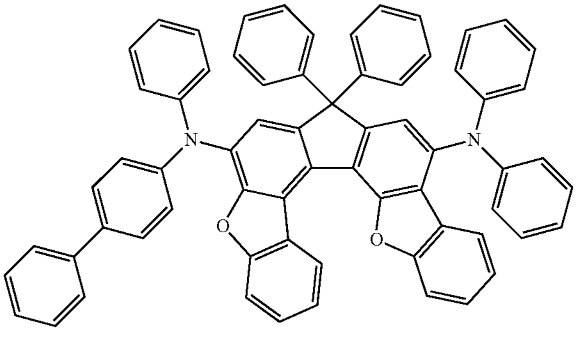

-continued
C-397
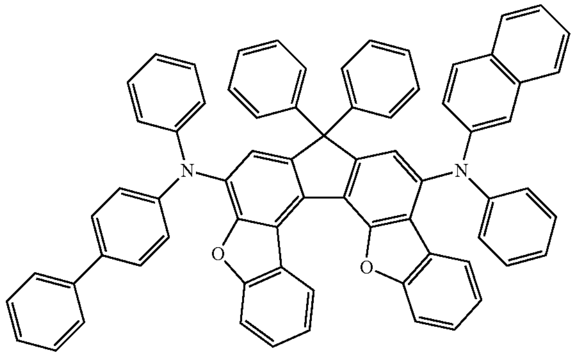
C-398
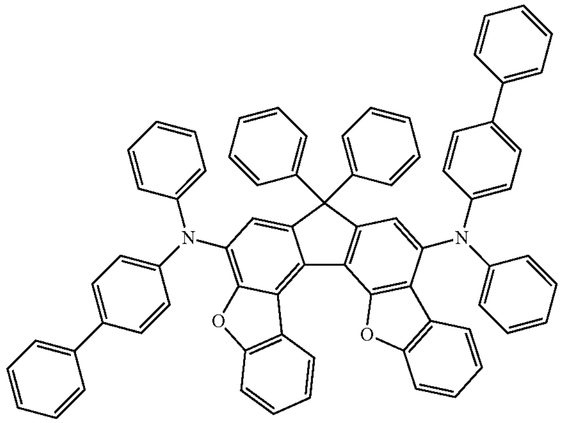
C-399
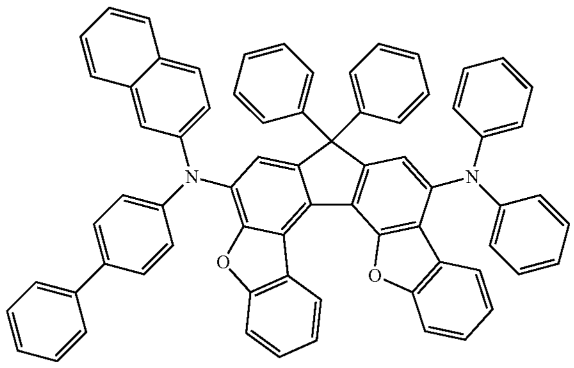
C-400
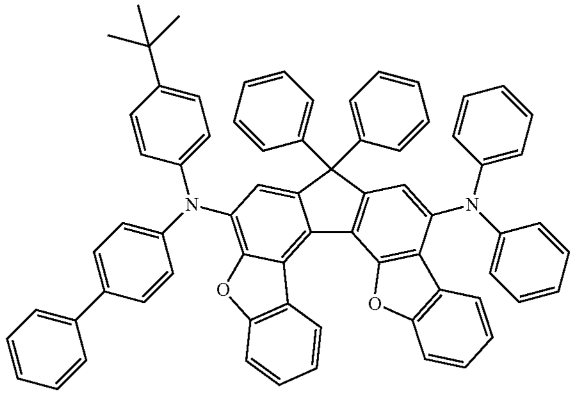
-continued
C-401
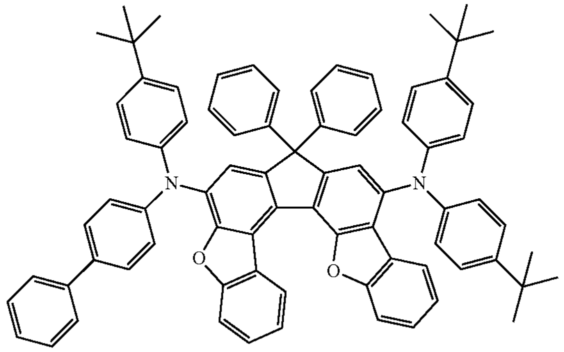
C-402
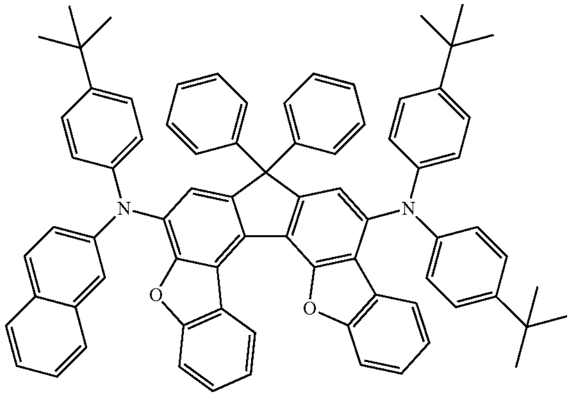
C-403
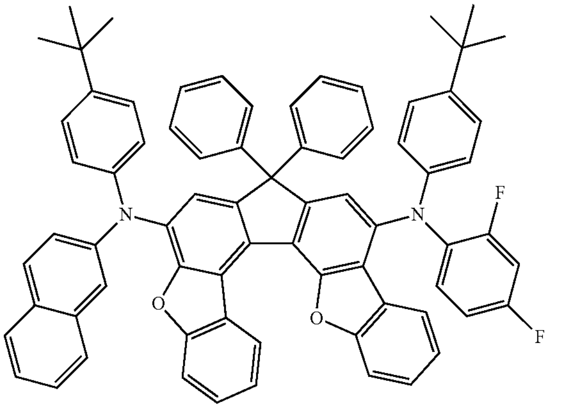
C-404
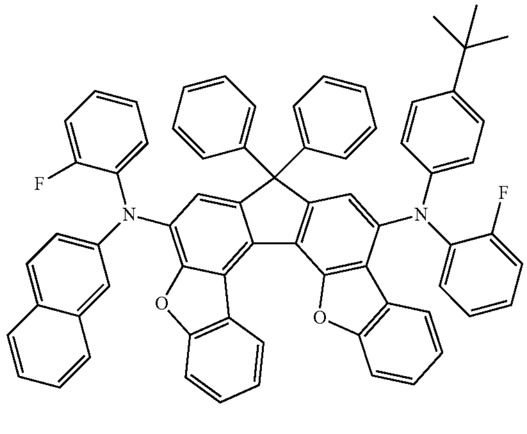

-continued
C-405
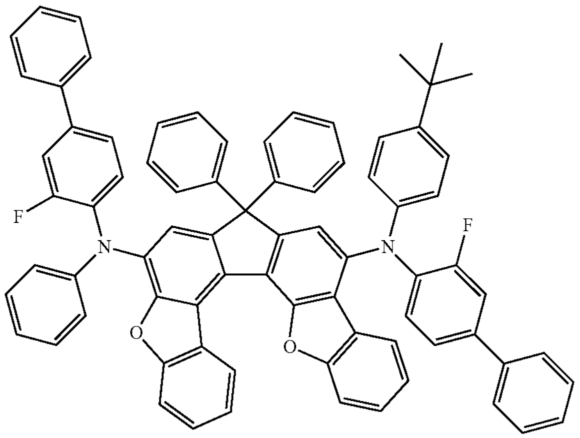
C-406
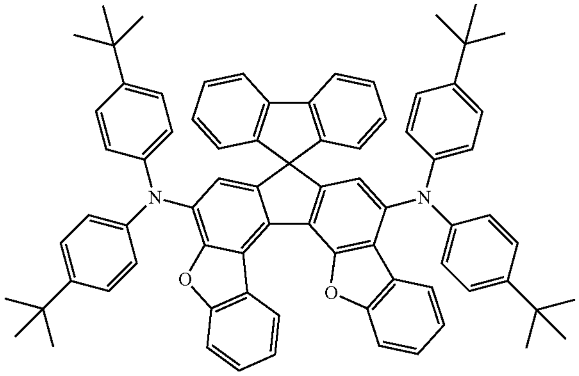
C-407
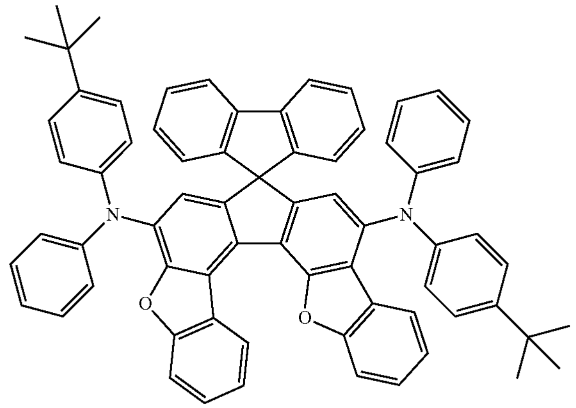
C-408
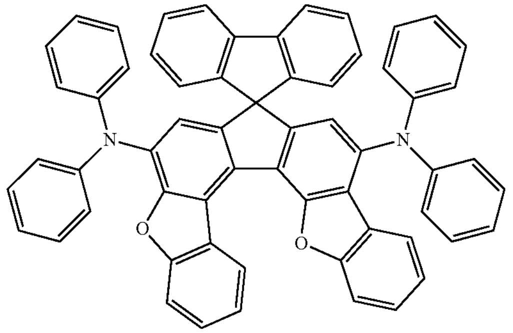
-continued
C-409
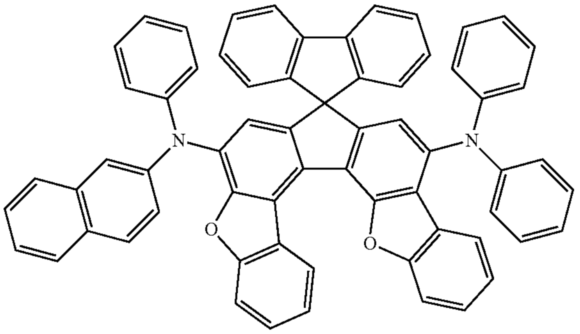
C-410
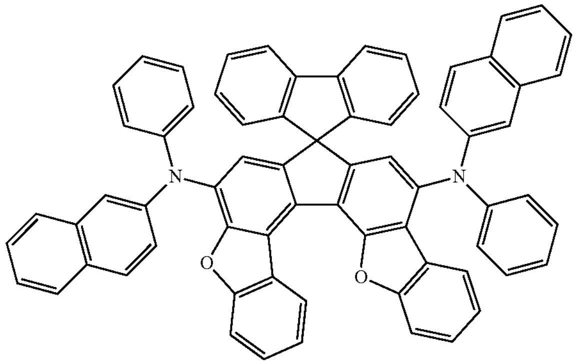
C-411
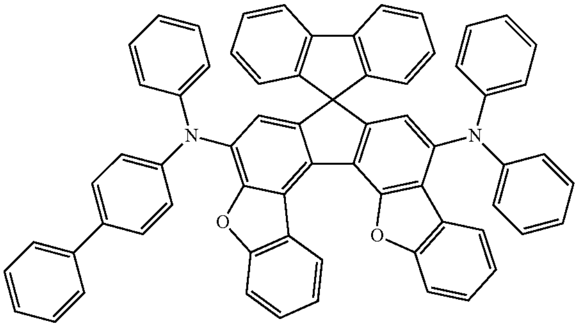
C-412
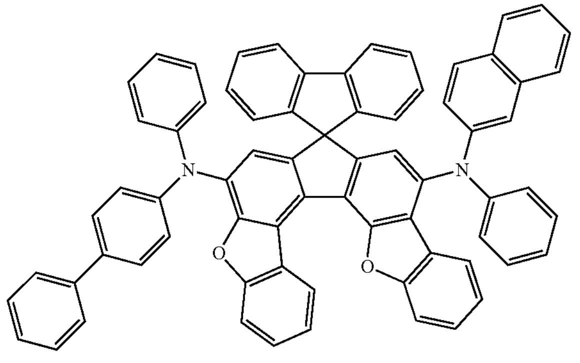

-continued
C-413
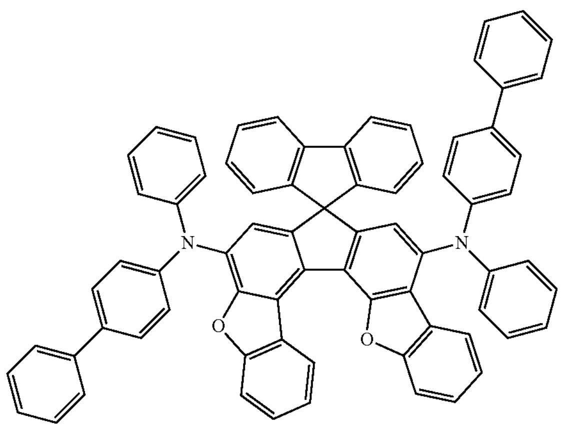
C-414
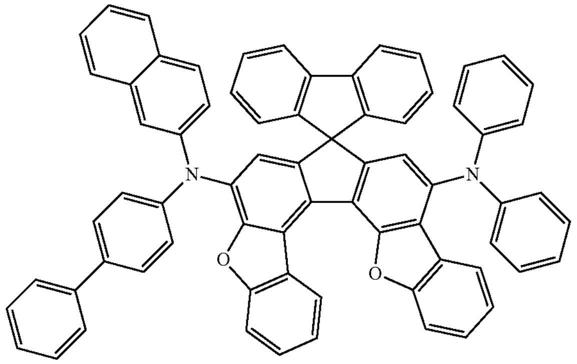
C-415
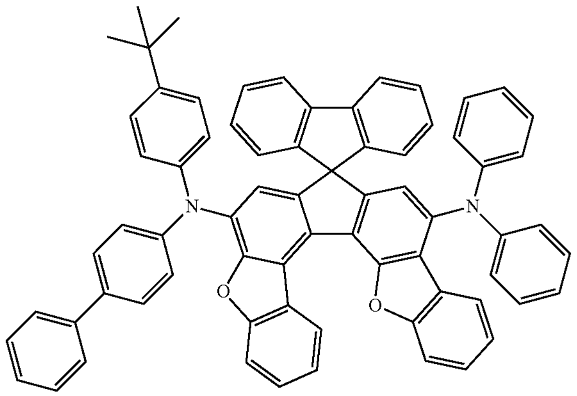
C-416
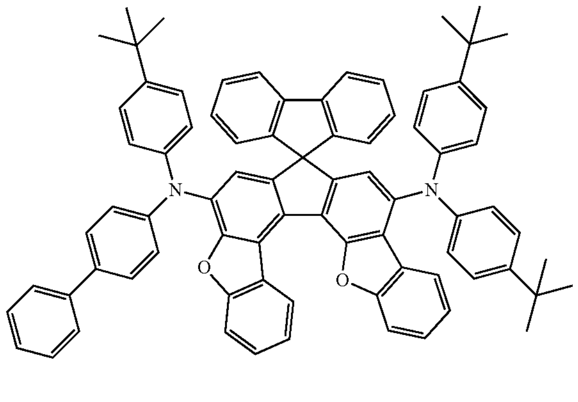
-continued
C-417
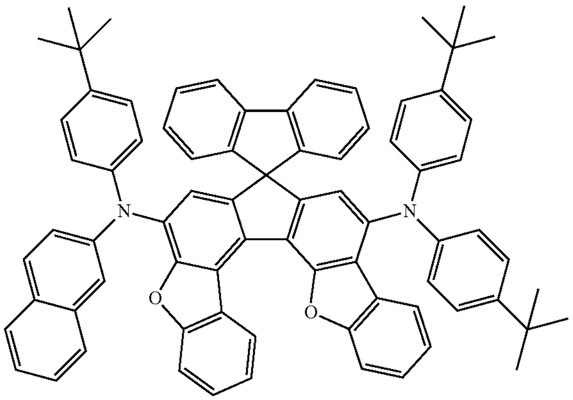
C-418
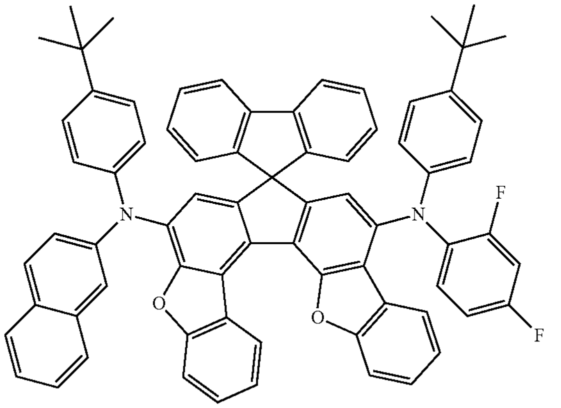
C-419
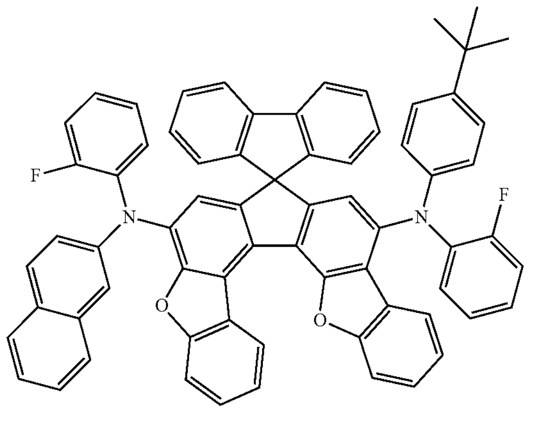

-continued
C-420
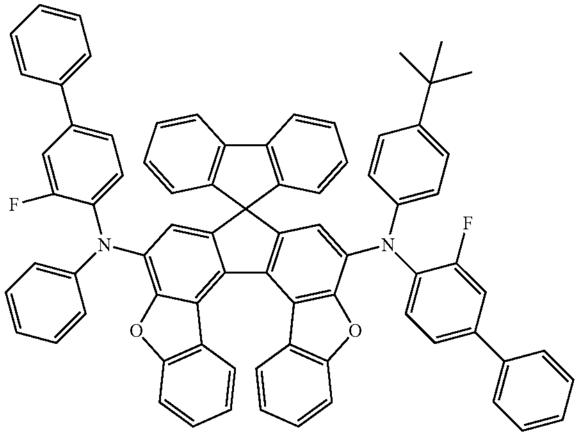
C-421
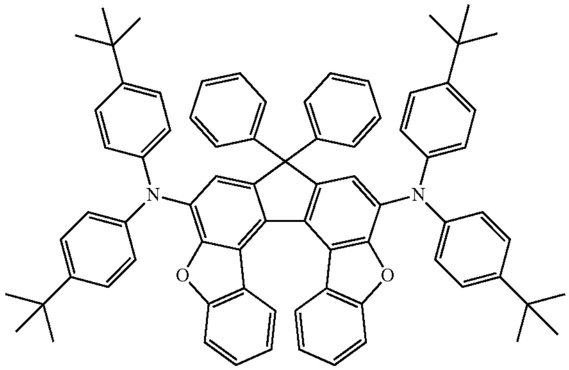
C-422
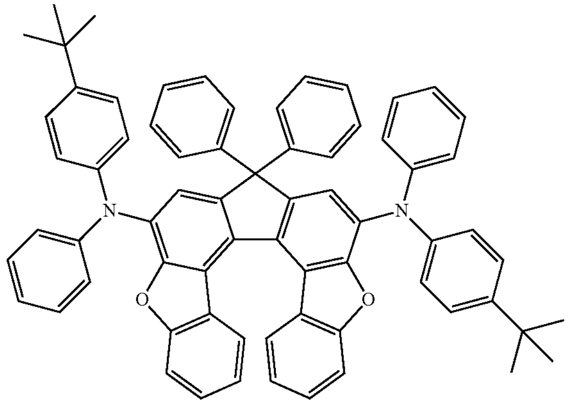
C-423
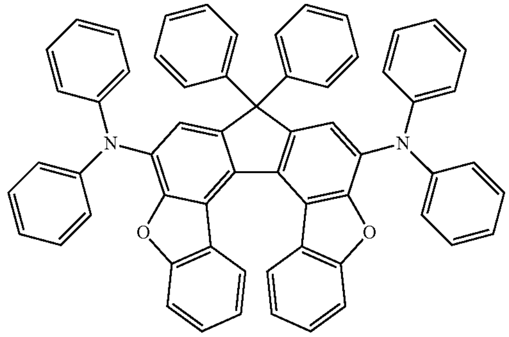
-continued
C-424
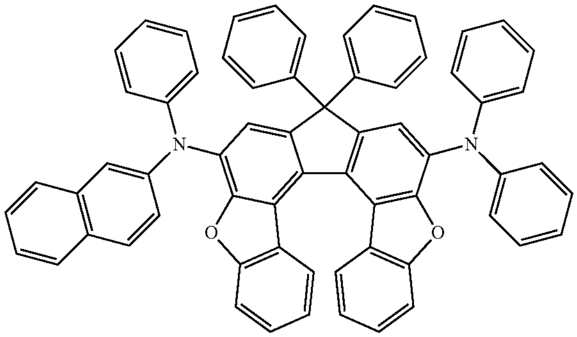
C-425
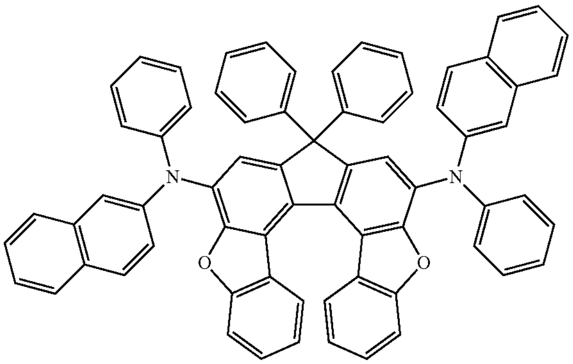
C426
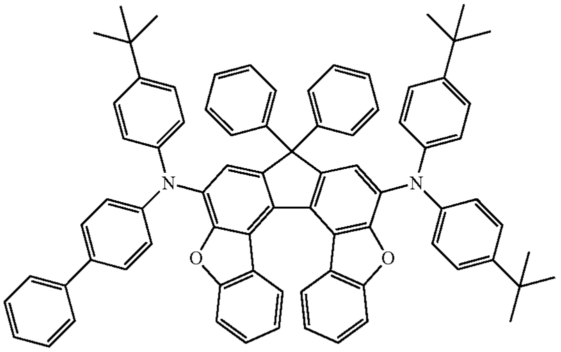
C-427
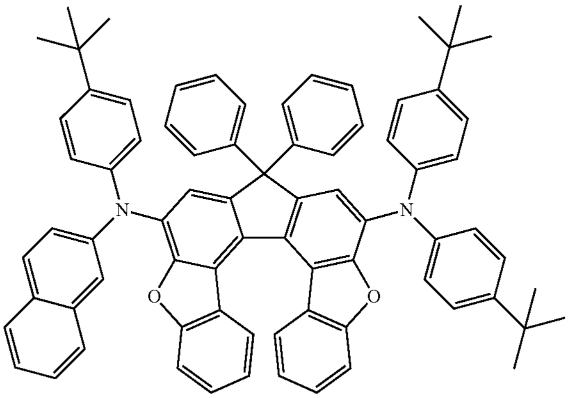

-continued
C-428
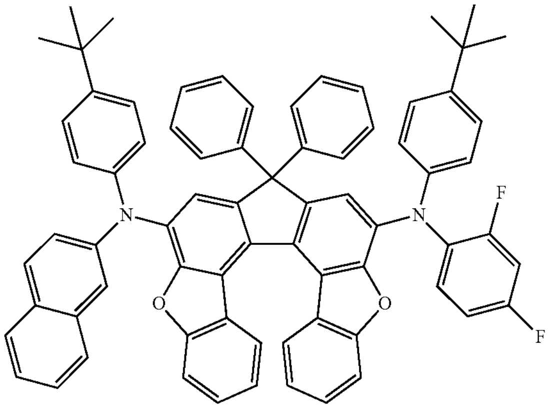
C-429
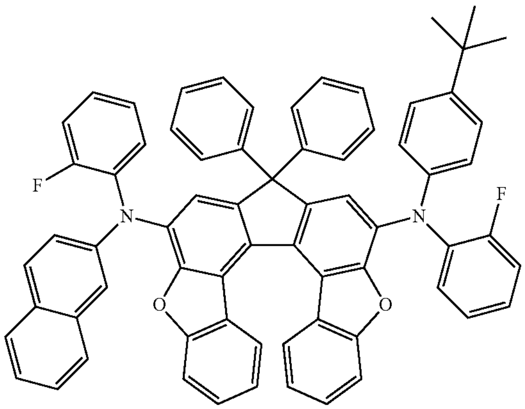
C-430
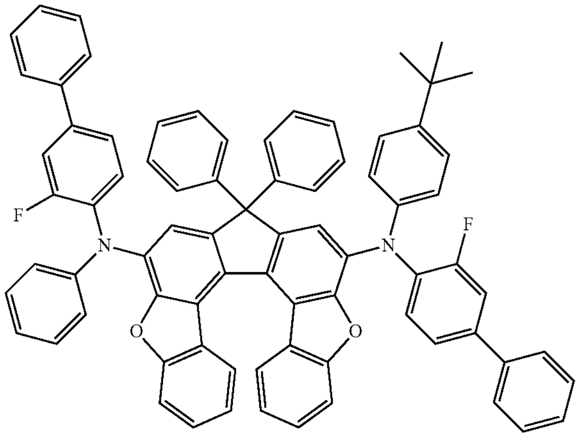
-continued
C-431
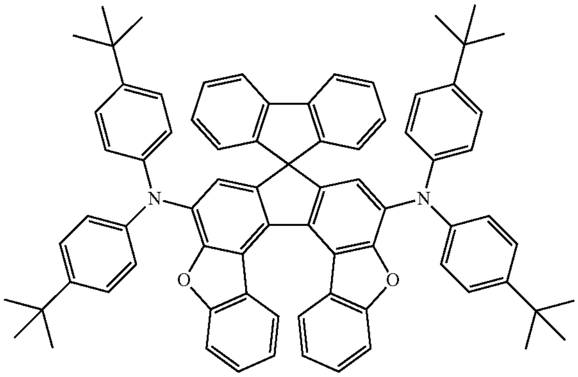
C-432
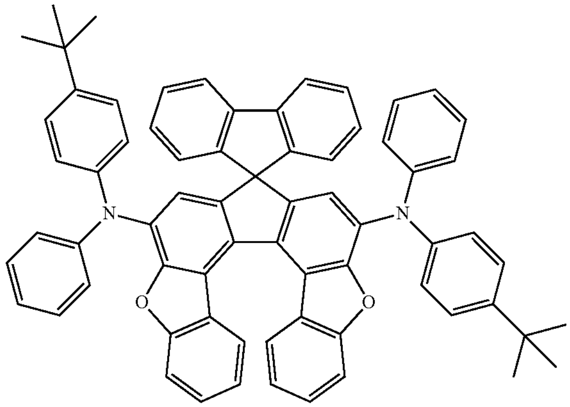
C-433
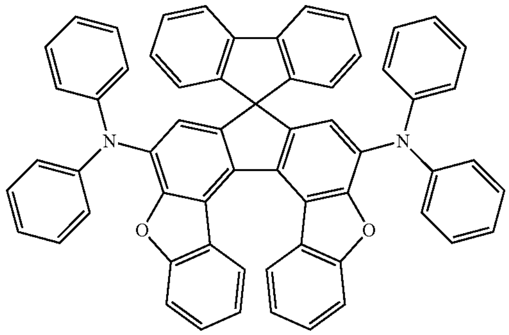
C-434
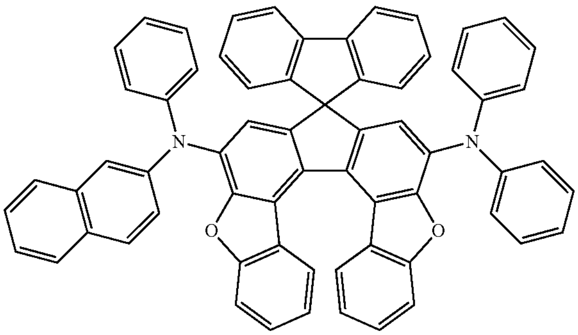

-continued
C-435
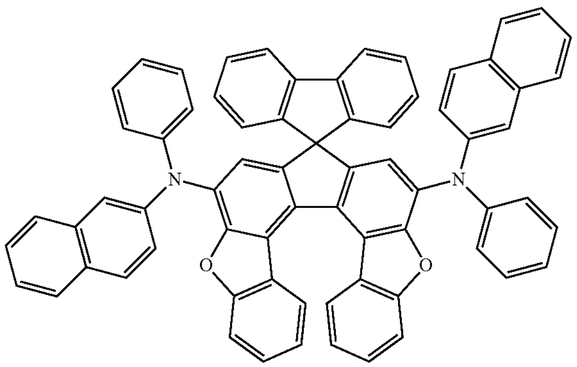
C-436
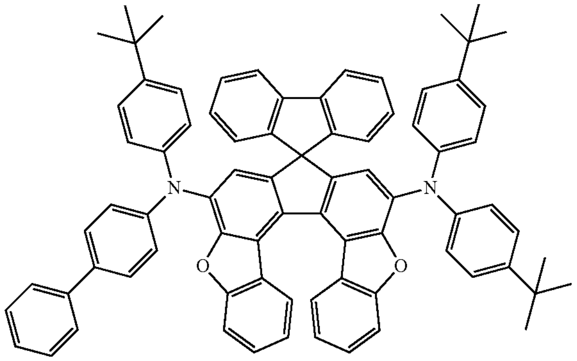
C-437
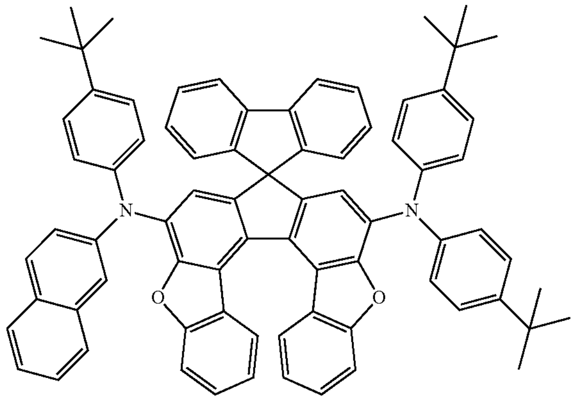
C-438
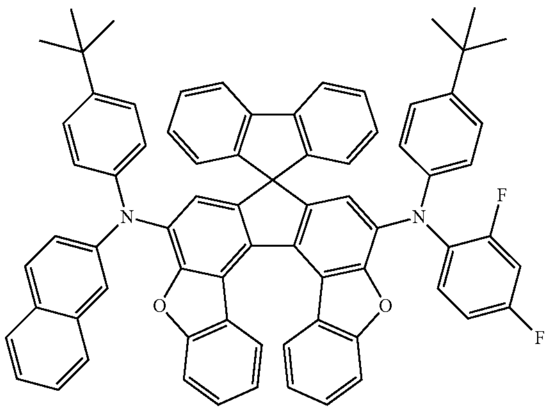
-continued
C-439
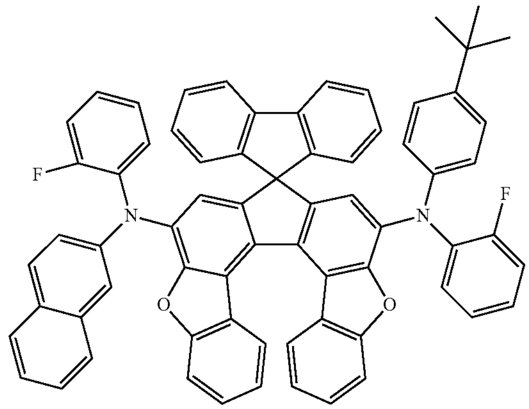
C-440
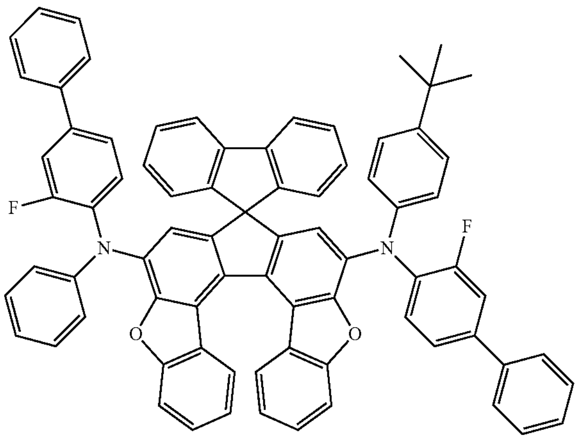
C-441
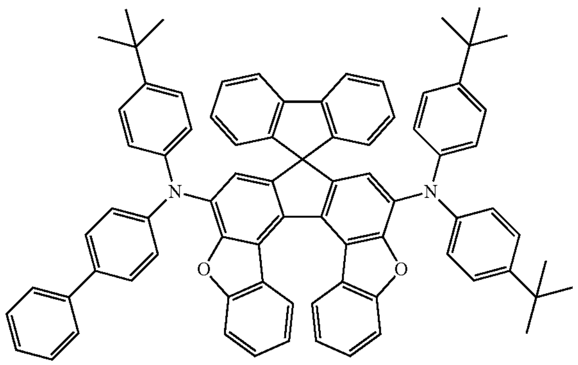

-continued
C-442
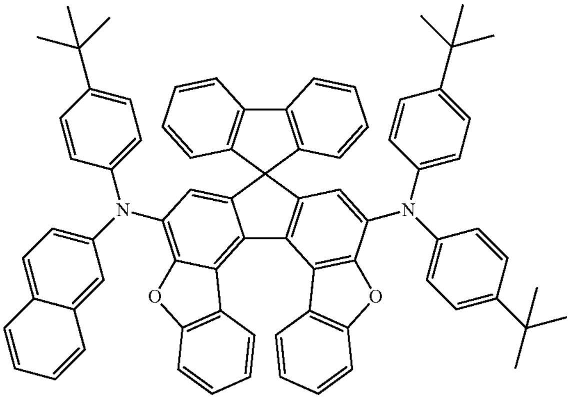
C-443
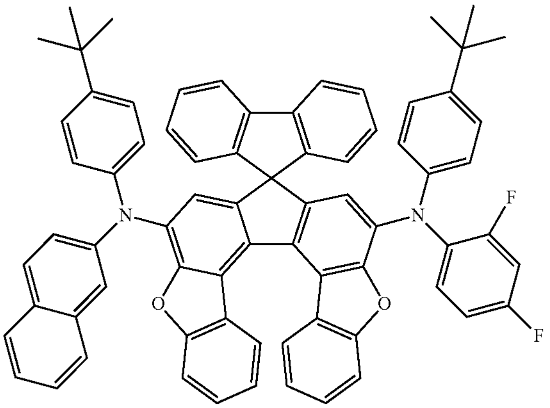
C-444
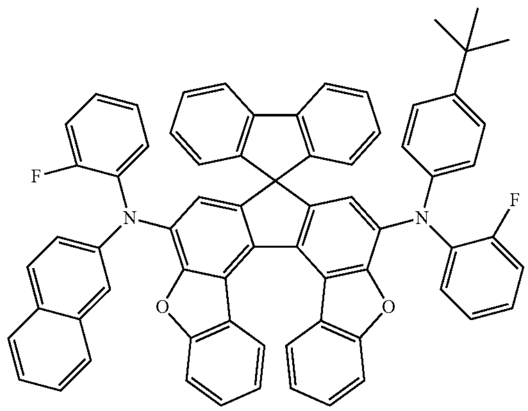
-continued
C-445
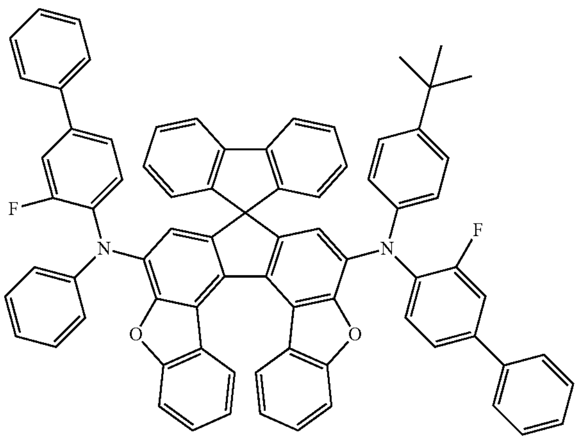
C-446
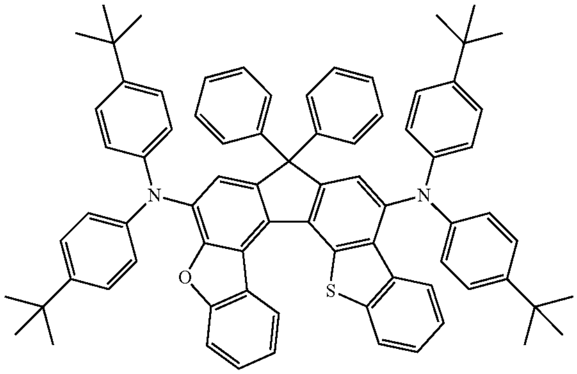
C-447
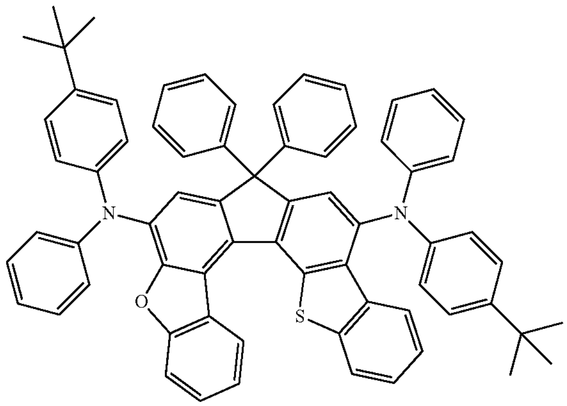
C-448
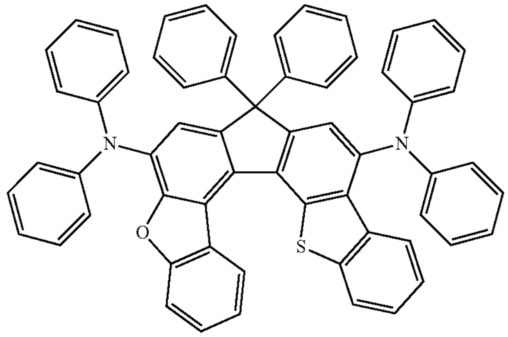

-continued
C-449
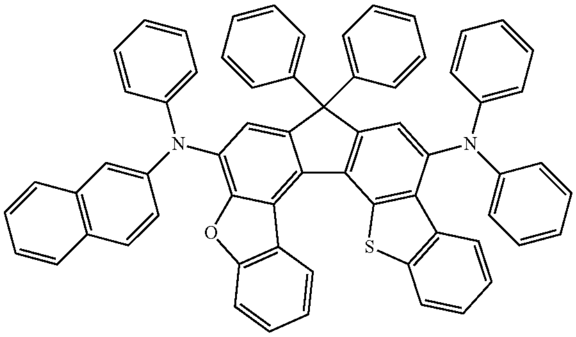
C-450
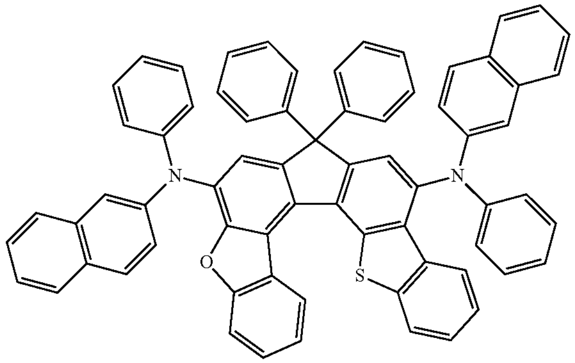
C-451
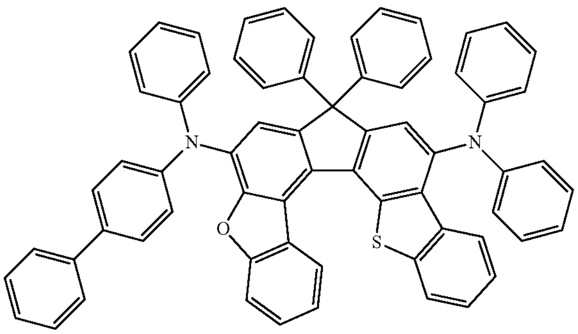
C-452
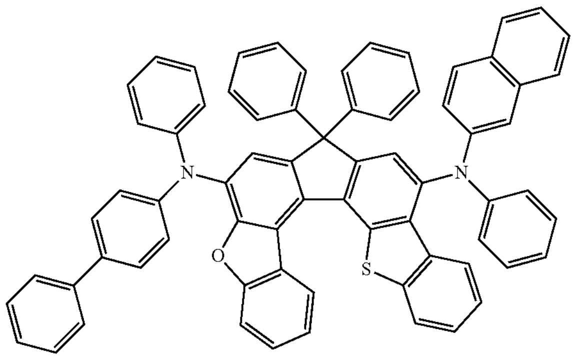
-continued
C-453
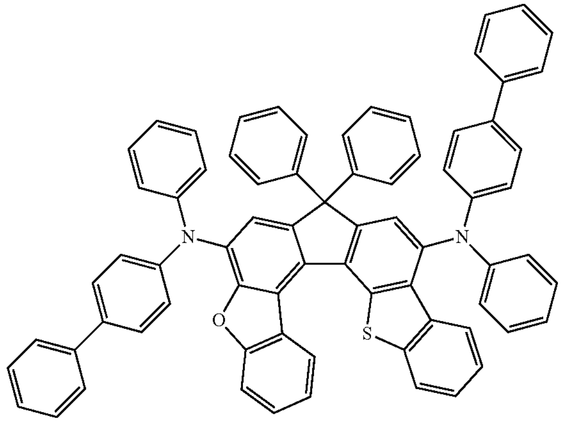
C-454
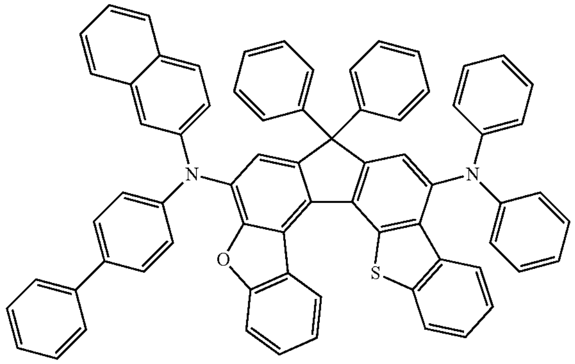
C-455
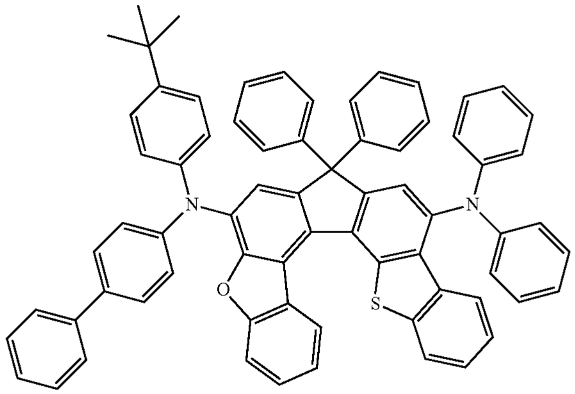
C-456
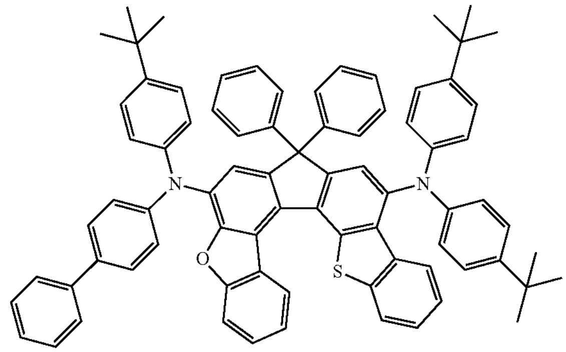

-continued
C-457
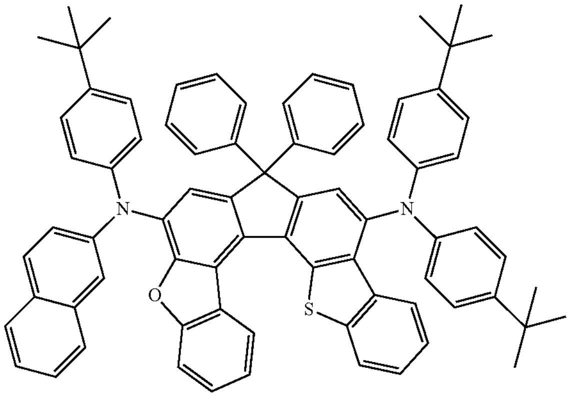
C-458
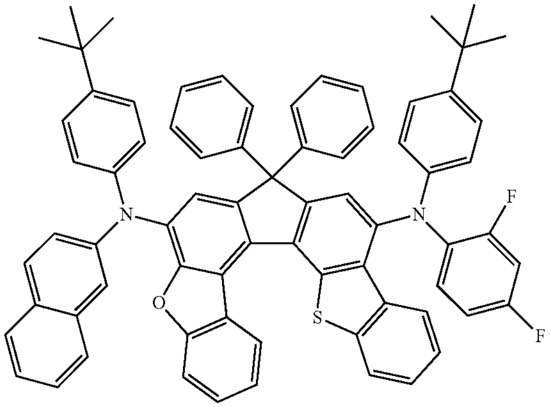
C-459
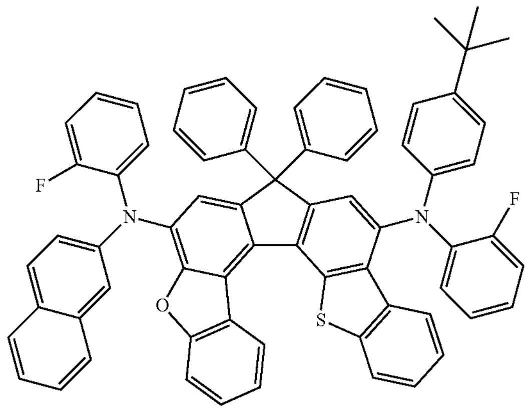
-continued
C-460
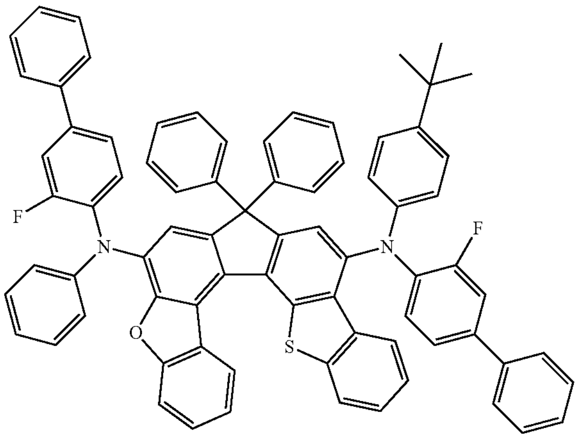
C-461
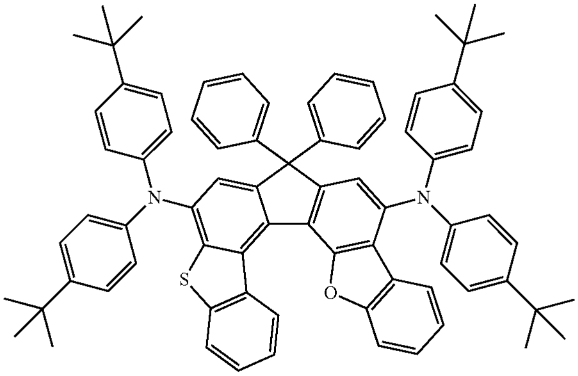
C-462
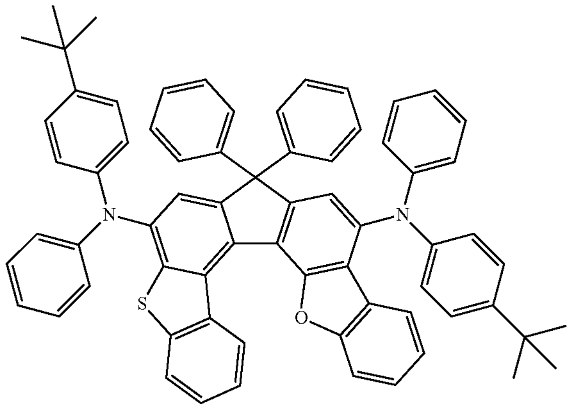
C-463
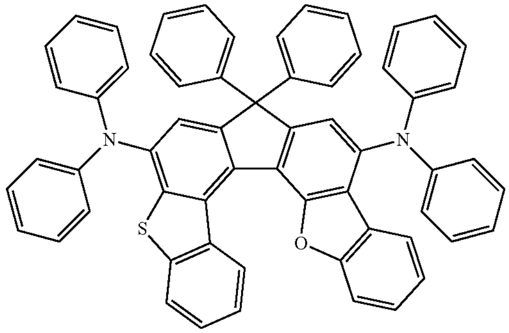

-continued

C-464

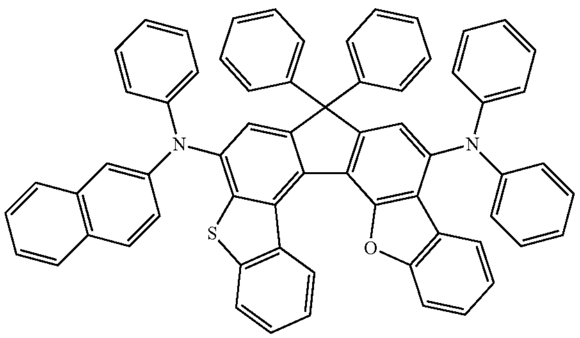

C-465

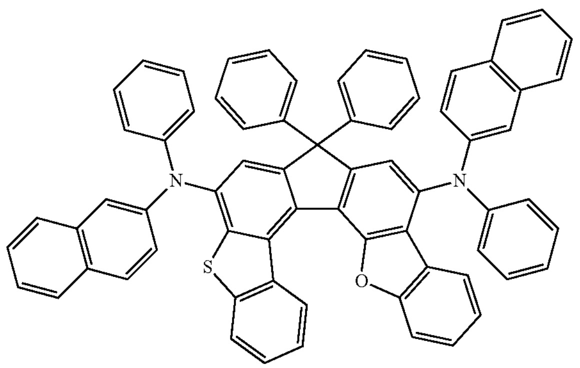

A combination of at least one of Compounds H1-1 to H1-295 and at least one of Compounds C-1 to C-465 may be used in an organic electroluminescent device. According to one embodiment, at least one of Compounds H1-1 to H1-295 may be applied as a host material, and at least one of Compounds C-1 to C-465 may be applied as a dopant material.

The present disclosure provides an organic electroluminescent compound represented by the following formula 11:

(11)

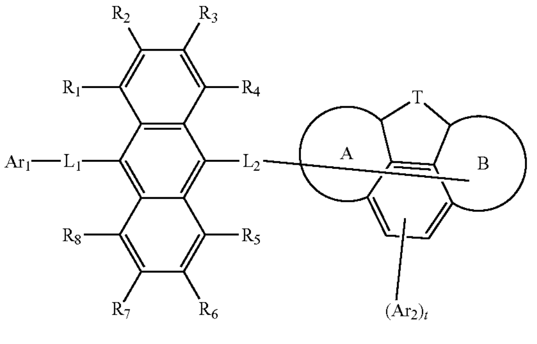

wherein,

T represents O, S, or $CR_9R_{10}$;

ring A and ring B, each independently, represent a substituted or unsubstituted (C6-C30)aryl, or a substituted or unsubstituted (3- to 30-membered) heteroaryl;

$R_1$ to $R_{10}$, each independently, represent hydrogen, deuterium, a halogen, a cyano, a substituted or unsubstituted (C1-C30)alkyl, a substituted or unsubstituted (C6-C30)aryl, a substituted or unsubstituted (3- to 30-membered) heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri (C6-C30)arylsilyl, a substituted or unsubstituted fused ring group of a (C3-C30) aliphatic ring(s) and a (C6-C30) aromatic ring(s), or $-L_3-N(Ar_{11})(Ar_{12})$;

$L_1$ to $L_3$, each independently, represent a single bond, a substituted or unsubstituted (C6-C30)arylene, or a substituted or unsubstituted (3- to 30-membered) heteroarylene;

$Ar_1$, each independently, represents a substituted or unsubstituted (C6-C30)aryl, or a substituted or unsubstituted (3- to 30-membered) heteroaryl;

$Ar_2$, $Ar_{11}$, and $Ar_{12}$, each independently, represent hydrogen, deuterium, a halogen, a cyano, a substituted or unsubstituted (C1-C30)alkyl, a substituted or unsubstituted (C2-C30)alkenyl, a substituted or unsubstituted (C6-C30)aryl, a substituted or unsubstituted (3- to 30-membered) heteroaryl, a substituted or unsubstituted (C3-C30)cycloalkyl, a substituted or unsubstituted (C1-C30)alkoxy, a substituted or unsubstituted fused ring group of a (C3-C30) aliphatic ring(s) and a (C6-C30) aromatic ring(s), a substituted or unsubstituted tri (C1-C30)alkylsilyl, a substituted or unsubstituted di(C1-C30)alkyl(C6-C30)arylsilyl, a substituted or unsubstituted (C1-C30)alkyldi(C6-C30)arylsilyl, or a substituted or unsubstituted tri (C6-C30)arylsilyl; and t represents an integer of 1 or 2, in which if t is 2, each of $Ar_2$ may be the same or different;

with the proviso that if both ring A and ring B represent a C6 aryl and $L_2$ represents a single bond, at least one of $L_1$, $Ar_1$, $Ar_2$, $R_1$ to $R_{10}$, ring A, and ring B comprises at least one deuterium.

If in formula 11, both ring A and ring B represent a C6 aryl and $L_2$ represents a single bond, at least one of $L_1$, $Ar_1$, $Ar_2$, $R_1$ to $R_{10}$, ring A, and ring B may be deuterium, or the substituent of at least one of $L_1$, $Ar_1$, $Ar_2$, $R_1$ to $R_{10}$, ring A, and ring B may be deuterium. The number of deuterium is preferably 1 to 50, more preferably 4 to 45, and even more preferably 6 to 40.

In formula 11, specific embodiments of ring A, ring B, $R_1$ to $R_{10}$, $L_1$, $L_2$, $Ar_1$, and $Ar_2$, each independently, are as disclosed in formula 1.

Specifically, the compound represented by formula 11 may be at least one selected from the group consisting of Compounds H1-151 to H1-170, H1-201 to H1-250, and H1-256 to H1-295, but is not limited thereto.

According to one embodiment of the present disclosure, an organic electroluminescent device comprising the organic electroluminescent compound represented by formula 11 may be provided, and the organic electroluminescent compound may be comprised in a light-emitting layer, preferably as a host material.

The non-deuterated analogues of the compound represented by formula 1 or 11 can be prepared by known coupling and substitution reactions. Also, the compound of formula 1 or 11 may be prepared in a similar manner by using deuterated precursor materials, or more generally may be prepared by treating the non-deuterated compound with a deuterated solvent or D6-benzene in the presence of an H/D exchange catalyst such as a Lewis acid, e.g., aluminum trichloride or ethyl aluminum chloride, a trifluoromethanesulfonic acid, or a trifluoromethanesulfonic acid-D. In addition, the degree of deuteration can be controlled by changing the reaction conditions such as the reaction temperature. For example, the number of deuterium in formula 1 or 11 can be controlled by adjusting the reaction temperature and time, the equivalent of the acid, etc.

The compound represented by formula 1 or 11 according to the present disclosure may be prepared by a synthetic method known to one skilled in the art. For example, the compound represented by formula 1 or 11 can be prepared by referring to Chinese Patent Appl. Laid-Open No. 110294663 A (published on Oct. 1, 2019), but is not limited thereto.

The compound represented by formula 1 or 11 in which hydrogens are replaced with deuterium and $L_2$ is not single bond, may be prepared by referring to the following reaction schemes, but is not limited thereto.

[Reaction Scheme 1]

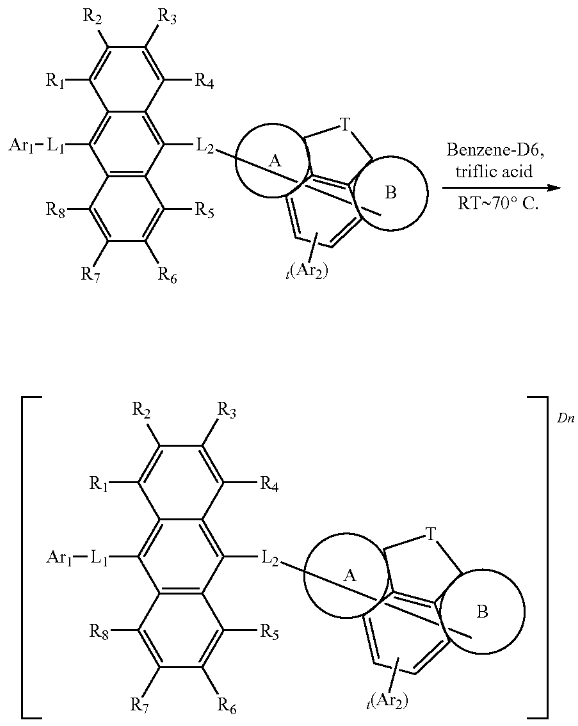

[Reaction Scheme 2]

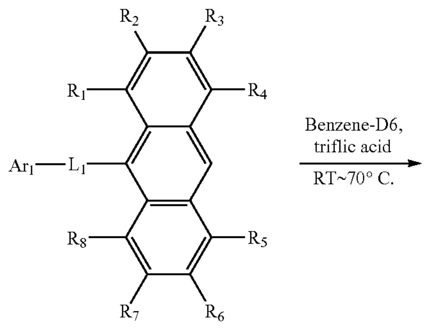

-continued

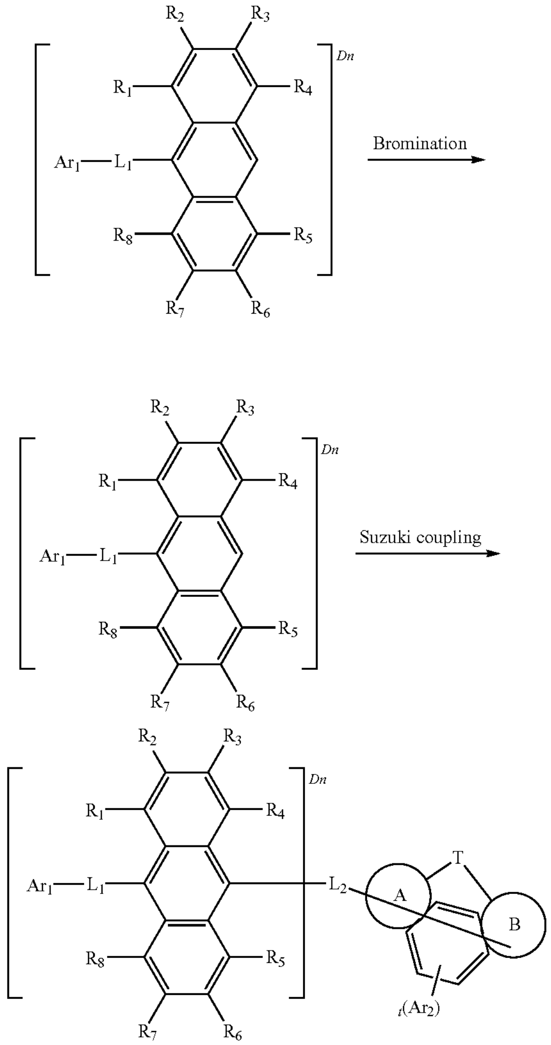

[Reaction Scheme 3]

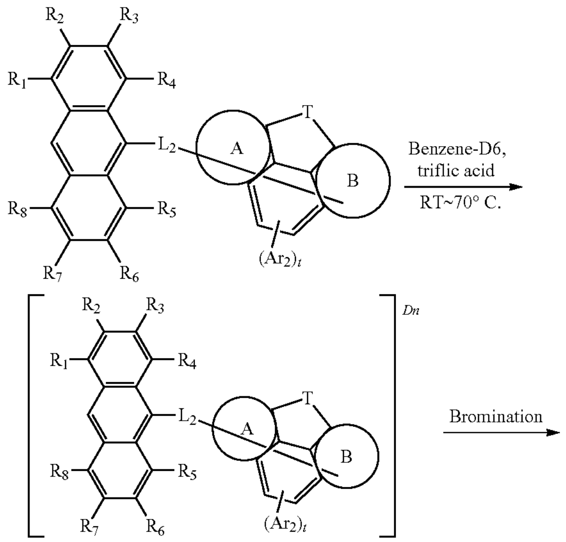

-continued

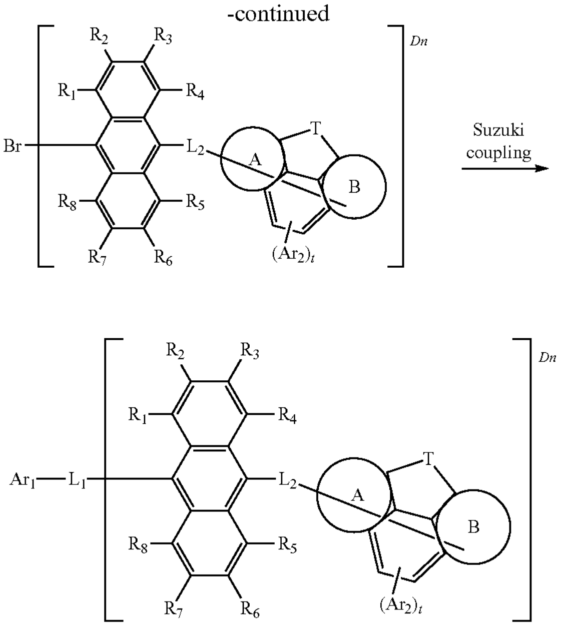

In reaction schemes 1 to 3, T, ring A, ring B, $R_1$ to $R_8$, $L_1$, $L_2$, $Ar_1$, $Ar_2$, t, and $D_n$ are as defined in formula 1.

In reaction scheme 4, T, ring A, ring B, $R_1$ to $R_8$, $L_1$, $Ar_1$, $Ar_2$, and t are as defined in formula 1, and $L_2$ represents a substituted or unsubstituted (C6-C30)arylene, or a substituted or unsubstituted (5- to 30-membered) heteroarylene.

Although illustrative synthesis examples of the compound represented by formula 1 or 11 are described above, one skilled in the art will be able to readily understand that all of them are based on a Buchwald-Hartwig cross-coupling reaction, an N-arylation reaction, a Miyaura borylation reaction, a Suzuki cross-coupling reaction, a Pd(II)-catalyzed oxidative cyclization reaction, a Heck reaction, a Cyclic Dehydration reaction, an $SN_1$ substitution reaction, an $SN_2$ substitution reaction, a Phosphine-mediated reductive cyclization reaction, a Ullmann reaction, a Wittig reaction, etc., and the reactions above proceed even when substituents, which are defined in formulas 1 or 11 above, but are not specified in the specific synthesis examples above, are bonded.

The compound represented by formula 2 according to the present disclosure may be prepared by a synthetic method known to one skilled in the art. For example, the compound represented by formula 2 can be prepared by referring to Korean Patent Publication No. 1955647 B (published on Mar. 7, 2019), Korean Patent Appl. Laid-Open No. 2019-0117531 A (published on Oct. 16, 2019), Korean Patent Publication No. 1423070 B (published on Jul. 28, 2014), Korean Patent Appl. Laid-Open No. 2017-0056422 A (pub-

[Reaction Scheme 4]

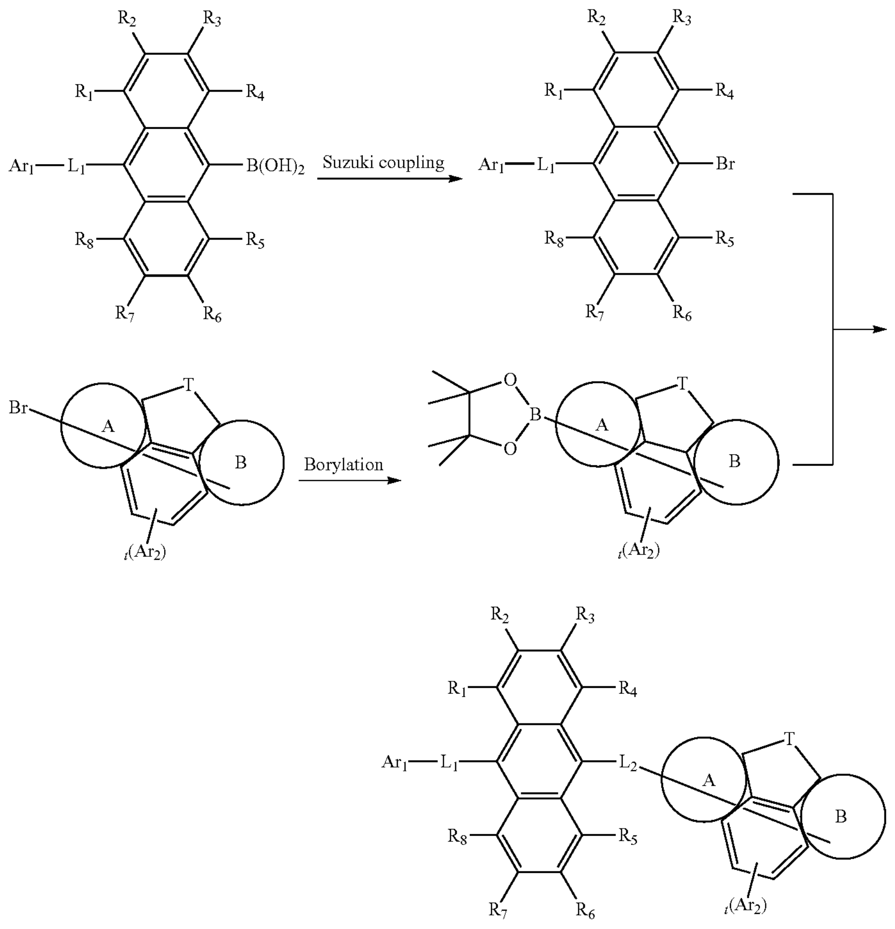

lished on May 23, 2017), Korean Patent Appl. Laid-Open No. 2014-0131898 A (published on Nov. 14, 2014), etc., but is not limited thereto.

Hereinafter, an organic electroluminescent device comprising the aforementioned plurality of light-emitting materials will be described.

The organic electroluminescent device according to one embodiment of the present disclosure comprises a first electrode, a second electrode, and at least one organic layer between the first and second electrodes. The organic layer may comprise a light-emitting layer, and the light-emitting layer may include a plurality of light-emitting materials. The plurality light-emitting materials comprises at least one first compound and at least one second compound, and the first compound is represented by the formula 1, and the second compound is represented by the formula 2. The first compound may be represented by the formula 11. According to one embodiment of the present disclosure, the light-emitting layer may include the organic electroluminescent compound represented by the formula 11, and the organic electroluminescent compound may be comprised in the light-emitting layer.

The light-emitting layer is a layer comprising a host(s) and a dopant(s) from which light is emitted, and may be a single layer or a multi-layer in which two or more layers are stacked. Here, the host mainly has a function of promoting recombination of electrons and holes and confining excitons in the light-emitting layer, and the dopant has a function of efficiently emitting light of excitons obtained by recombination. In the plurality of light-emitting materials of the present disclosure, the first compound and the second compound may be included in the same layer, or may be included in different layers, respectively. The dopant compound of the light-emitting layer may be doped to less than 25% by weight, preferably less than 20% by weight, more preferably less than 17% by weight based on the total amount of the host and dopant compounds.

One of the first and second electrodes may be an anode, and the other may be a cathode. The second electrode may be a transflective electrode or a reflective electrode, and may be a top emission type, a bottom emission type, or a both-sides emission type, depending on the materials. The organic layer comprises a light-emitting layer and may further comprise at least one layer selected from a hole injection layer, a hole transport layer, a hole auxiliary layer, a light-emitting auxiliary layer, an electron transport layer, an electron injection layer, an interlayer, a hole blocking layer, an electron blocking layer, and an electron buffer layer.

The organic layer may further comprise an amine-based compound and/or an azine-based compound in addition to the light-emitting material(s) of the present disclosure. Specifically, the hole injection layer, the hole transport layer, the hole auxiliary layer, the light-emitting layer, the light-emitting auxiliary layer, and/or the electron blocking layer may comprise an amine-based compound, e.g., an arylamine-based compound, a styrylarylamine-based compound, etc., as a hole injection material, a hole transport material, a hole auxiliary material, a light-emitting material, a light-emitting auxiliary material, and/or an electron blocking material. In addition, the electron transport layer, the electron injection layer, the electron buffer layer, and/or the hole blocking layer may comprise an azine-based compound as an electron transport material, an electron injection material, an electron buffer material, and/or a hole blocking material.

In addition, the organic layer may further comprise at least one metal selected from the group consisting of metals of Group 1, metals of Group 2, transition metals of the 4th period, transition metals of the 5th period, lanthanides and organic metals of d-transition elements of the Periodic Table, or at least one complex compound comprising said metal.

A hole injection layer, a hole transport layer, or an electron blocking layer, or a combination thereof may be used between the anode and the light-emitting layer. The hole injection layer may be multilayers in order to lower the hole injection barrier (or hole injection voltage) from the anode to the hole transport layer or the electron blocking layer, wherein each of the multilayers may use two compounds simultaneously. The electron blocking layer may be located between the hole transport layer (or the hole injection layer) and the light-emitting layer, and may block the overflow of electrons from the light-emitting layer to trap the excitons in the light-emitting layer to prevent light leakage. The hole transport layer or the electron blocking layer may be multilayers, wherein each of the multilayers may use a plurality of compounds.

An electron buffer layer, a hole blocking layer, an electron transport layer, or an electron injection layer, or a combination thereof may be used between the light-emitting layer and the cathode. The electron buffer layer may be multilayers in order to control the injection of the electrons and improve the interfacial properties between the light-emitting layer and the electron injection layer, wherein each of the multilayers may use two compounds simultaneously. The hole blocking layer or the electron transport layer may also be multilayers, wherein each of the multilayers may use a plurality of compounds.

A light-emitting auxiliary layer may be placed between the anode and the light-emitting layer, or between the cathode and the light-emitting layer. When the light-emitting auxiliary layer is placed between the anode and the light-emitting layer, it can be used for promoting the hole injection and/or the hole transport, or for preventing the overflow of electrons. When the light-emitting auxiliary layer is placed between the cathode and the light-emitting layer, it can be used for promoting the electron injection and/or the electron transport, or for preventing the overflow of holes.

In addition, the hole auxiliary layer may be placed between the hole transport layer (or hole injection layer) and the light-emitting layer, and may be effective to promote or block the hole transport rate (or the hole injection rate), thereby enabling the charge balance to be controlled. When an organic electroluminescent device includes two or more hole transport layers, the hole transport layer, which is further included, may be used as a hole auxiliary layer or an electron blocking layer. The light-emitting auxiliary layer, the hole auxiliary layer or the electron blocking layer may have an effect of improving the efficiency and/or the lifetime of the organic electroluminescent device.

In the organic electroluminescent device of the present disclosure, at least one layer selected from a chalcogenide layer, a metal halide layer and a metal oxide layer (hereinafter, "a surface layer") may be preferably placed on an inner surface(s) of one or both electrodes. Specifically, a chalcogenide (including oxides) layer of silicon or aluminum is preferably placed on an anode surface of an electroluminescent medium layer, and a metal halide layer or a metal oxide layer is preferably placed on a cathode surface of an electroluminescent medium layer. Such a surface layer may provide operation stability for the organic electroluminescent device. Preferably, the chalcogenide includes $SiO_x$ ($1 \le X \le 2$), $AlO_x$ ($1 \le X \le 1.5$), SiON, SiAlON, etc.; the metal halide includes LiF, $MgF_2$, $CaF_2$, a rare earth metal fluoride, etc.; and the metal oxide includes $Cs_2O$, $Li_2O$, MgO, SrO, BaO, CaO, etc.

In the organic electroluminescent device of the present disclosure, a mixed region of an electron transport compound and a reductive dopant, or a mixed region of a hole transport compound and an oxidative dopant is preferably placed on at least one surface of a pair of electrodes. In this case, the electron transport compound is reduced to an anion, and thus it becomes easier to inject and transport electrons from the mixed region to an electroluminescent medium. Further, the hole transport compound is oxidized to a cation, and thus it becomes easier to inject and transport holes from the mixed region to the electroluminescent medium. Preferably, the oxidative dopant includes various Lewis acids and acceptor compounds; and the reductive dopant includes alkali metals, alkali metal compounds, alkaline earth metals, rare-earth metals, and mixtures thereof. A reductive dopant layer may be used as a charge-generating layer to prepare an organic electroluminescent device having two or more light-emitting layers and emitting white light.

Various structures have been proposed for the white organic electroluminescent device, for example, a side-by-side structure or a stacking structure depending on the arrangement of R (red), G (green) or YG (yellow green), and B (blue) light emitting parts, or a color conversion material (CCM) method, etc. The plurality of light-emitting materials of the present disclosure may also be applied to such white organic electroluminescent device.

The plurality of light-emitting materials according to one embodiment of the present disclosure may also be applied to the organic electroluminescent device comprising a QD (quantum dot).

The present disclosure may provide a display system by using a plurality of light-emitting materials according to one embodiment of the present disclosure. That is, it is possible to produce a display system or a lighting system by using the compound(s) of the present disclosure or the combination of the compounds of the present disclosure. Specifically, it is possible to produce a display system, e.g., a display system for smartphones, tablets, notebooks, PCs, TVs, or cars, or a lighting system, e.g., an outdoor or indoor lighting system, by using the compound(s) of the present disclosure or the combination of the compounds of the present disclosure.

In order to form each layer of the organic electroluminescent device of the present disclosure, dry film-forming methods such as vacuum evaporation, sputtering, plasma and ion plating methods, or wet film-forming methods such as ink jet printing, nozzle printing, slot coating, spin coating, dip coating, and flow coating methods may be used. When using a wet film-forming method, a thin film may be formed by dissolving or diffusing materials forming each layer into any suitable solvent such as ethanol, chloroform, tetrahydrofuran, dioxane, etc. The solvent may be any solvent where the materials forming each layer can be dissolved or diffused, and where there are no problems in film-formation capability.

The dopant and host compounds of the present disclosure may be co-evaporated or mixture-evaporated. The co-evaporation is a mixed deposition method in which two or more isomer materials are placed in a respective individual crucible source and a current is applied to both cells at the same time to evaporate the materials. The mixture-evaporation is a mixed deposition method in which two or more isomer materials are mixed in one crucible source before evaporating them, and a current is applied to the cell to evaporate the materials.

Hereinafter, the preparation method of the compound of the present disclosure and the properties thereof will be explained in detail with reference to the representative compounds of the present disclosure. However, the present disclosure is not limited by the following examples.

Example 1: Preparation of Compound H1-226-D8

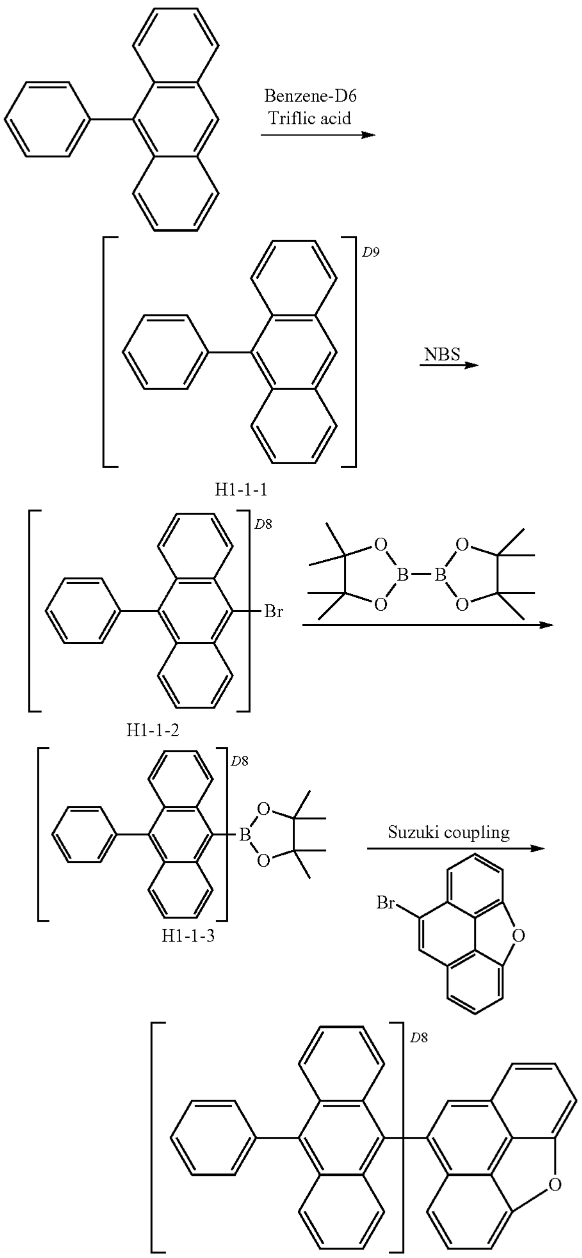

H1-1-1

H1-1-2

H1-1-3

H1-226-D8

Synthesis of Compound H1-1-1

9-phenylanthracene (5 g, 19.67 mmol) and benzene-D6 (100 mL, 1128.9 mmol) were added in a flask, and stirred under reflux. Triflic acid (2.55 g, 16.99 mmol) was added thereto at 35° C. After 3 hours, the mixture was cooled to ambient temperature. 10 ml of deuterium oxide ($D_2O$) was added thereto, and the mixture was stirred for 10 minutes. The mixture was neutralized with an aqueous $K_3PO_4$ solution, and an organic layer was extracted with ethyl acetate. The residual moisture was removed with magnesium sulfate, and the residue was distilled under reduced pressure and separated by column chromatography to obtain 3.7 g of compound H1-1-1 (yield: 71.52%).

Synthesis of Compound H1-1-2

In a flask, compound H1-1-1 (66 g, 250.9 mmol) was dissolved in dichloromethane (1700 mL), N-bromosuccinimide (67 g, 377.86 mmol) was added, and the mixture was stirred under reflux. After 4 hours, the mixture was cooled to ambient temperature. The organic layer was washed with an aqueous $K_2CO_3$ solution, and washed again with an aqueous sodium thiosulfate solution. The residual moisture was removed with magnesium sulfate, and the organic layer was distilled under reduced pressure. The resulting mixture was separated by column chromatography to obtain 75 g of compound H1-1-2 (yield: 87.61%).

Synthesis of Compound H1-1-3

Compound H1-1-2 (75 g, 220.58 mmol), 4,4,4',4',5,5,5',5'-octamethyl-2,2'-bi (1,3,2-dioxaborolane) (72.8 g, 286.7 mmol), $PdCl_2(PPh_3)_2$ (7.74 g, 11.03 mmol), KOAc (43.4 g, 441.17 mmol), and 1,4-dioxane (1200 mL) were added in a flask. The mixture was heated to 155° C. After 4 hours, the mixture was cooled to ambient temperature. Distilled water was added and an organic layer was extracted with ethyl acetate. The residual moisture was removed with magnesium sulfate, and the residue was distilled under reduced pressure and separated by column chromatography to obtain 46 g of compound H1-1-3 (yield: 53.70%).

Synthesis of Compound H1-226-D8

Compound H1-1-3 (6.3 g, 16.23 mmol), 8-bromophenanthro[4,5-bcd]furan (4.0 g, 14.75 mmol), $Pd_2(dba)_3$ (0.54 g, 0.59 mmol), S-Phos (0.72 g, 1.77 mmol), $K_3PO_4$ (7.8 g, 36.88 mmol), toluene (100 mL), distilled water (18 mL) and ethanol (25 mL) were stirred in a flask, and the mixture was heated to 140° C. After 3 hours, the mixture was cooled to ambient temperature, distilled water was added, and the organic layer was extracted with ethyl acetate. The residual moisture was removed with magnesium sulfate, and the residue was distilled under reduced pressure and separated by column chromatography to obtain 5.2 g of compound H1-226-D8 (yield: 77.96%).

| Compound | MW | M.P. |
|---|---|---|
| H1-226-D8 | 452 | 250° C. |

Example 2: Preparation of Compound H1-202

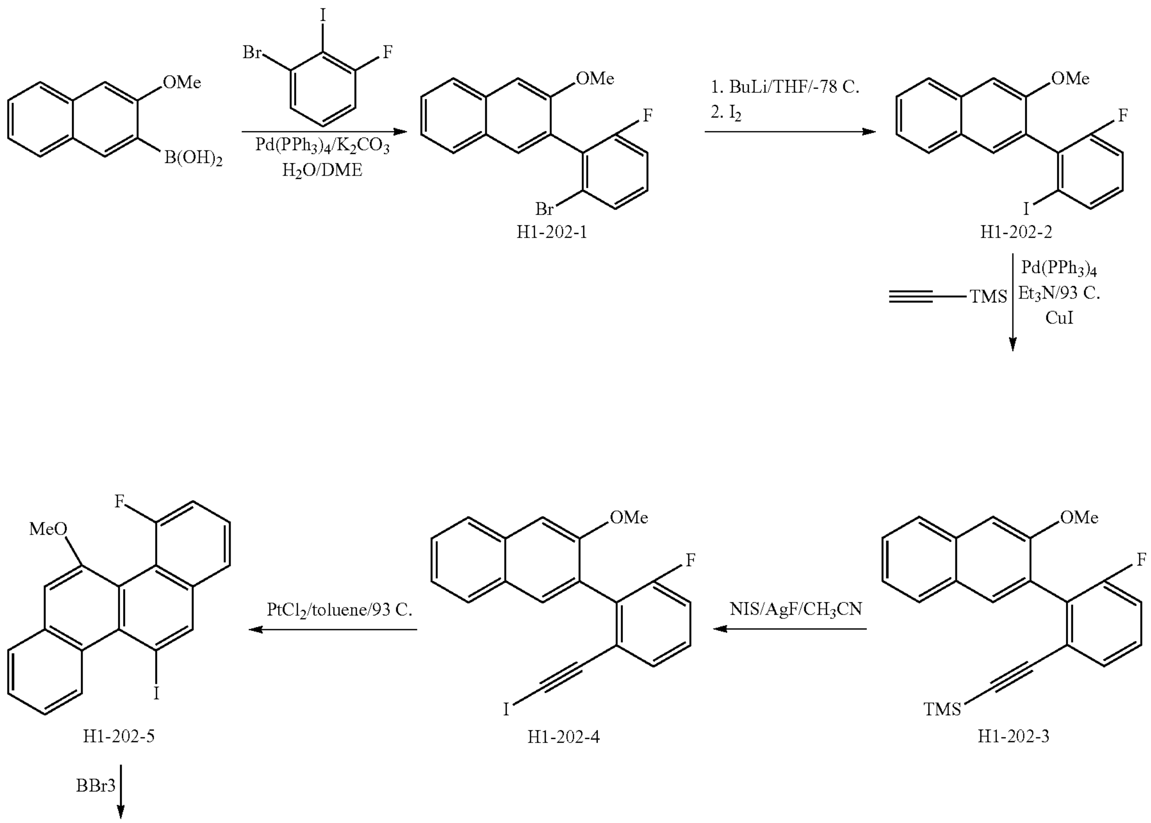

H1-202-1
H1-202-2
H1-202-3
H1-202-4
H1-202-5

-continued

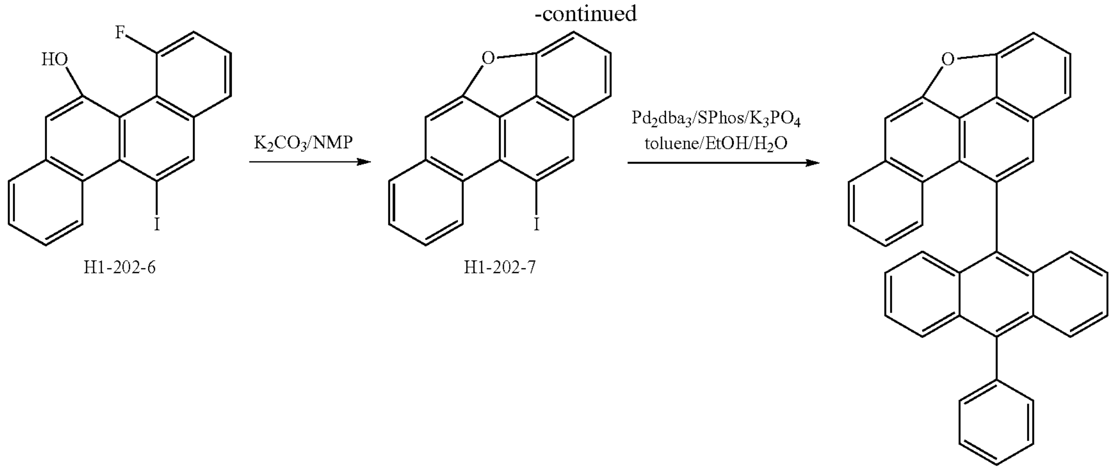

H1-202-6 H1-202-7 H1-202

Synthesis of Compound H1-202-1

A mixture of 3-methoxynaphthalene-2-boronic acid (10.253 g, 50.75 mmol), 1-bromo-3-fluoro-2-iodobenzene (20.2 g, 67 mmol), $Pd(PPh_3)_4$ (2.99 g, 2.59 mmol), $K_2CO_3$ (10.5 g, 76.1 mmol), 1,2-dimethoxyethane (235 mL) and water (137 mL) was degassed and stirred under nitrogen atmosphere at 78° C. for 20 hours. After that the mixture was cooled down, diluted with water (200 mL), and extracted with dichloromethane (3 times). Thereafter, the extract was dried with anhydrous sodium sulfate, and dichloromethane was evaporated to obtain 25.8 g of a mixture. The mixture was dissolved in dichloromethane, absorbed onto celite, and separated by chromatography on silica gel column using hexane and dichloromethane. The solvent was evaporated under reduced pressure and dried in vacuum to obtain 12.7 g of compound H1-202-1 (yield: 75.59%).

Synthesis of Compound H1-202-2

Compound H-202-1 (31.7 g, 95.71 mmol) was dissolved in anhydrous tetrahydrofuran (610 mL), and the solution was stirred and cooled with acetone/dry ice bath under nitrogen atmosphere. nBuLi (62.8 mL of 1.6 M solution in hexanes, 100.5 mmol) was added dropwise to the mixture, and internal temperature was maintained below −70° C. After that the mixture was stirred at −78° C. for 60 minutes, then iodine (26.73 g, 105.3 mmol) was added to the mixture at once. The mixture was stirred overnight while cooling with a dry ice/acetone bath. After that the reaction mixture was warmed to ambient temperature using a water bath, and water and sodium bisulfate solution were slowly added, the tetrahydrofuran layer was separated, and the aqueous layer was extracted with ether. The resulting organic layer was passed through a filter filled with silica gel, and further passed through ether. The solvent was distilled off using a rotary evaporator. After partial evaporation of ether, the precipitates were collected portion-wise. The pure portions were combined to obtain 28.8 g of compound H1-202-2 (yield: 79.55%).

Synthesis of Compound H1-202-3

A mixture of compound H1-202-2 (28.8 g, 76.16 mmol), trimethylsilylacetylene (43.4 g, 442 mmol), $Pd(PPh_3)_4$ (9.81 g, 8.50 mmol), CuI (14.5 g, 76.16 mmol) and triethylamine (750 ml) was degassed and stirred at 93° C. for 4 hours under nitrogen atmosphere. The reaction mixture was cooled down, passed through a filter filled with silica gel, and further passed through dichloromethane. After evaporating solvents dissolved in dichloromethane, the residue was absorbed onto celite, and separated by column chromatography with hexane-dichloromethane. The solvent was evaporated, and the residue was dried in vacuum to obtain 19.6 g of compound H1-202-3 (yield: 73.85%).

Synthesis of Compound H1-202-4

Compound H1-202-3 (19.6 g, 56.24 mmol) was dissolved in anhydrous acetonitrile (800 mL) under nitrogen atmosphere. Silver fluoride (10.33 g, 81.4 mmol) was added to the solution, followed by addition after 10 minutes of N-iodosuccinimide (18.31 g, 81.4 mmol). The resulting mixture was stirred at ambient temperature for 1 hour, and filtered. The precipitates were washed with acetonitrile, and acetonitrile was distilled off using a rotary evaporator. The residue was mixed with approximately 100 mL of hot dichloromethane, and passed through a short column filled with silica gel. Dichloromethane was distilled off using a rotary evaporator, and the residue was dried in vacuum to obtain 22.2 g of compound H1-202-4 (yield: 98.14%).

Synthesis of Compound H1-202-5

A mixture of compound H1-202-4 (22.2 g, 55.2 mmol), platinum chloride (0.734 g, 2.76 mmol) and anhydrous toluene (800 mL) was degassed, and stirred at 93° C. for 3 hours. The reaction mixture was cooled down, and filtered through a pad of silica gel. Toluene was distilled off using a rotary evaporator to obtain 25.9 g of dark-red oil. The resulting mixture was dissolved in dichloromethane, absorbed onto celite, and separated by chromatography on silica gel column using hexanes-dichloromethane mixtures. The solvent was evaporated, and the residue was dried in vacuum to obtain 9.56 g of compound H1-202-5 (yield: 43.06%).

Synthesis of Compound H1-202-6

Compound H1-202-5 (10.1 g, 25.1 mmol) and dichloromethane (232 mL) were stirred under nitrogen atmosphere, and boron tribromide (8.81 g, 35.16 mmol) was slowly added to the stirred solution. The reaction mixture was stirred under nitrogen atmosphere at ambient temperature for 1.5 hours. The reaction mixture was slowly added to approximately 115 mL of water, and stirred under nitrogen atmosphere for 30 minutes. The precipitates were filtered, and the filtrate was filtered again. The precipitates were washed several times with water, and dried to obtain 8.77 g of compound H1-202-6 (yield: 90.04%).

Synthesis of Compound H1-202-7

A mixture of compound H1-202-6 (8.0 g, 20.61 mmol), potassium carbonate (14.24 g, 103 mmol) and anhydrous N-methylpyrrolidinone (250 mL) was stirred with heating at 120° C. for 1 hour. The reaction mixture was cooled down, and water (100 mL) was added. The precipitates were filtered, washed with water and methanol, and dried in vacuum to obtain 7.2 g of compound H1-202-7 (yield: 94.98%).

Synthesis of Compound H1-202

A mixture of compound H1-202-7 (7.10 g, 19.28 mmol), 4,4,5,5-tetramethyl-2-(10-phenylanthracen-9-yl)-1,3,2-dioxaborolane (7.70 g, 20.25 mmol), $Pd_2(dba)_3$ (353 mg, 0.386 mmol), SPhos (396 mg, 0.964 mmol), and $K_3PO_4$ (12.28 g, 57.84 mmol) in toluene (470 mL), ethanol (188 mL) and water (94 mL) was degassed, and stirred at slight reflux (at 94° C.) for 16 hours. The reaction mixture was cooled down, and stirred with 200 ml of water for 10 minutes. Toluene was separated, and the aqueous layer was extracted with toluene. The resulting organic layer was passed through small filter filled with florisil and silica gel, and the solvent was concentrated using a rotary evaporator. The residue was dissolved with heating in approximately 1100 mL of dichloromethane, and filtered through a filter filled with silica gel. Dichloromethane was evaporated, and the precipitates were collected by filtration after 30 minutes and dried to obtain 8.15 g of solids of the product. The resulting product was dissolved in approximately 700 mL of hot toluene at 90° C., and toluene was evaporated to a volume of approximately 110 mL, and allowed to stand at room temperature for 2 hours. The resulting products were collected by filtration, washed with toluene and hexane, and dried in vacuum to obtain 6.76 g of compound H1-202 (yield: 86.66%).

| Compound | MW | M.P. |
|---|---|---|
| H1-202 | 494 | 343° C. |

Example 3: Preparation of Compound H1-226-D16

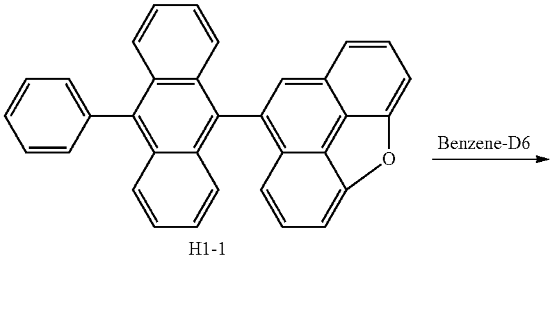

H1-1

-continued

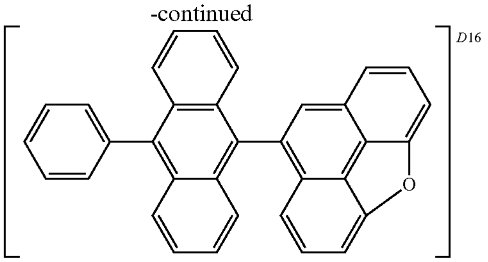

H1-226-D16

Compound H1-1 (1 g, 2.25 mmol) and benzene-D6 (25 mL, 280.37 mmol) were added in a flask, and heated to dissolve compound H1-1. Triflic acid (0.3 mL, 3.39 mmol) was added thereto at 60° C. After 3 hours, the mixture was cooled to ambient temperature. 1 mL of deuterium oxide ($D_2O$) was added thereto, and the mixture was stirred for 10 minutes. The mixture was neutralized with an aqueous $K_3PO_4$ solution, and an organic layer was extracted with ethyl acetate. The residual moisture was removed with magnesium sulfate, and the residue was distilled under reduced pressure and separated by column chromatography to obtain 0.6 g of compound H1-226-D16 (yield: 57.91%).

Hereinafter, a method of producing an organic electroluminescent device (OLED) comprising the compound according to the present disclosure and the properties thereof will be explained in detail. However, the following examples merely illustrate the properties of an OLED according to the present disclosure in detail, but the present disclosure is not limited to the following examples.

Device Example 1: Producing an OLED Using the Compound According to the Present Disclosure An OLED was produced using the organic electroluminescent compound according to the present disclosure, as follows: A transparent electrode indium tin oxide (ITO) thin film (10 Ω/sq) on a glass substrate for an OLED (GEOMATEC CO., LTD., Japan) was subjected to an ultrasonic washing with acetone, ethanol and distilled water, sequentially, and then was stored in isopropanol. The ITO substrate was mounted on a substrate holder of a vacuum vapor deposition apparatus. Compound HI-1 was introduced into a cell of the vacuum vapor deposition apparatus, and the pressure in the chamber of the apparatus was then controlled to 10-6 torr. Thereafter, an electric current was applied to the cell to evaporate the above-introduced material, thereby forming a first hole injection layer having a thickness of 60 nm on the ITO substrate. Next, compound HI-2 was introduced into another cell of the vacuum vapor deposition apparatus and was evaporated by applying an electric current to the cell, thereby forming a second hole injection layer having a thickness of 5 nm on the first hole injection layer. Compound HT-1 was then introduced into another cell of the vacuum vapor deposition apparatus and was evaporated by applying an electric current to the cell, thereby forming a first hole transport layer having a thickness of 20 nm on the second hole injection layer. Compound HT-2 was then introduced into another cell of the vacuum vapor deposition apparatus and was evaporated by applying an electric current to the cell, thereby forming a second hole transport layer having a thickness of 5 nm on the first hole transport layer. After forming the hole injection layers and the hole transport layers, a light-emitting layer was formed thereon as follows: Compound H1-1 was introduced into a cell of the vacuum vapor deposition apparatus as a host and compound C-326 was introduced into another cell as a dopant. The two materials were evaporated and the dopant was doped in a doping amount of 2 wt % based on the total amount of the host and dopant to form a light-emitting layer having a thickness of 20 nm on the second hole transport layer. Next, compound EI-1 and compound ET-1 were evaporated at a rate of 1:1 in two other cells to deposit an electron transport layer having a thickness of 35 nm on the light-emitting layer. After depositing compound EI-1 as an electron injection layer having a thickness of 2 nm on the electron transport layer, an Al cathode having a thickness of 80 nm was deposited on the electron injection layer by another vacuum vapor deposition apparatus. Thus, an OLED was produced.

Device Examples 2 to 4: Producing an OLED Using the Compound According to the Present Disclosure An OLED was produced in the same manner as in Device Example 1, except that the dopant compound shown in Table 1 was used instead of compound C-326 as the dopant of the light-emitting layer.

Device Examples 5 to 7: Producing an OLED Using the Compound According to the Present Disclosure An OLED was produced in the same manner as in Device Example 1, except that the host compound shown in Table 1 was used instead of compound H1-1 as the host of the light-emitting layer.

Comparative Example 1: Producing an OLED Using a Conventional Compound

An OLED was produced in the same manner as in Device Example 1, except that compound D-1 was used instead of compound C-326 as the dopant of the light-emitting layer.

Table 1 shows the driving voltage, current efficiency [cd/A], and CIE color coordinate based on a luminance of 1,000 nit, and the minimum time taken to be reduced from 100% to 95% of the luminance (lifetime; T95) based on specific luminances (each luminance disclosed in Table 1) of the OLED produced in Device Examples 1 to 7 and Comparative Example 1 above.

TABLE 1

| | Host | Dopant | Driving Voltage [V] | Current Efficiency [cd/A] | CIE Color Coordinate (x, y) | Lifetime (T95) [hr] |
|---|---|---|---|---|---|---|
| Device Example 1 | H1-1 | C-326 | 3.6 | 5.0 | (0.141, 0.057) | 71.3 @1280 nit |
| Device Example 2 | H1-1 | C-286 | 3.5 | 7.2 | (0.131, 0.084) | 88.5 @1890 nit |
| Device Example 3 | H1-1 | C-390 | 3.4 | 9.2 | (0.136, 0.109) | 88.5 @2500 nit |
| Device Example 4 | H1-1 | C-144 | 3.5 | 8.6 | (0.136, 0.109) | 46.0 @2500 nit |
| Device Example 5 | H1-226-D8 | C-326 | 3.6 | 5.0 | (0.141, 0.056) | 113.3 @1280 nit |
| Device Example 6 | H1-202 | C-326 | 3.5 | 5.2 | (0.139, 0.064) | 49.8 @1280 nit |
| Device Example 7 | H1-226-D16 | C-326 | 3.7 | 5.3 | (0.138, 0.062) | 236.8 @1280 nit |
| Comparative Example 1 | H1-1 | D-1 | 4.4 | 2.1 | (0.152, 0.075) | 0.33 @1650 nit |

From Table 1, it can be seen that an OLED using a plurality of light-emitting materials comprising the compound represented by formula 1 of the present disclosure and the compound represented by formula 2 of the present disclosure has excellent current efficiency and lifetime properties while having a low driving voltage compared to an OLED using a conventional compound. In addition, the lifetime of a blue organic electroluminescent device can be improved significantly by comprising the plurality of light-emitting materials of the present disclosure. Thus, the blue organic electroluminescent device can also exhibit a competitive performance, which can be comparable to the lifetime performance of red or green organic electroluminescent devices. Accordingly, it is expected that the blue organic electroluminescent device comprising the plurality of light-emitting materials of the present disclosure can be applied to various fields, as well as displays.

The compounds used in the Device Examples and the Comparative Example are shown in Table 2.

TABLE 2
| | |
|---|---|
| Hole Injection Layer/ Hole Transport Layer | 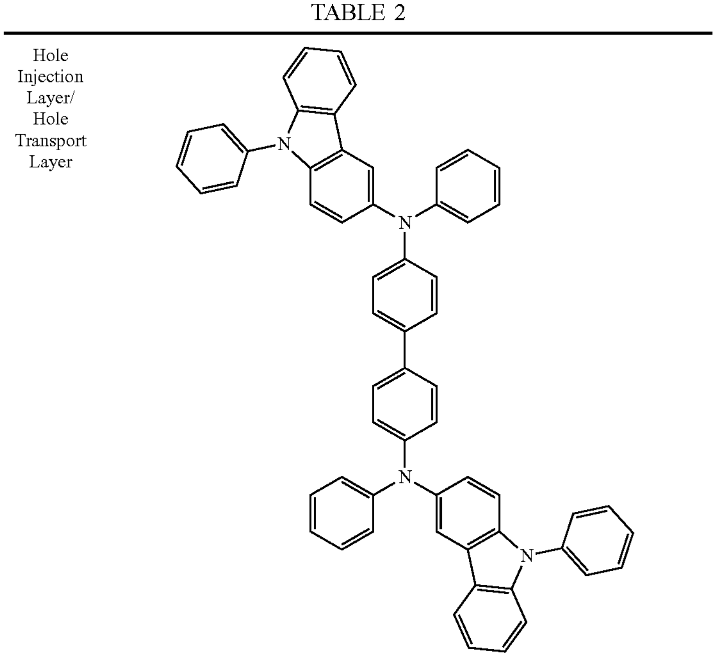 HI-1 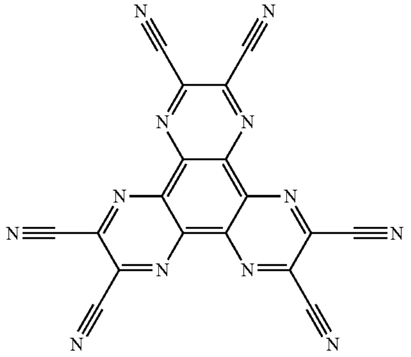 HI-2 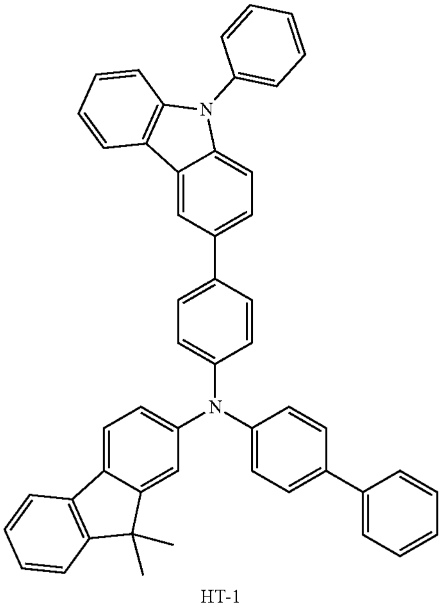 HT-1 |

TABLE 2-continued
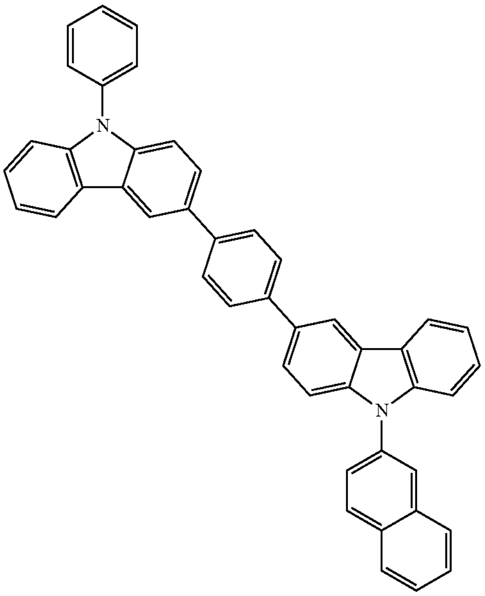
HT-2
Light-Emitting Layer
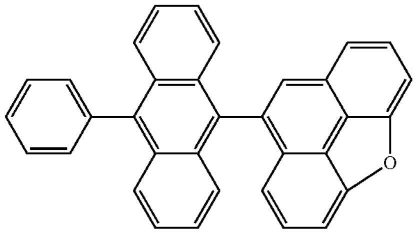
H1-1
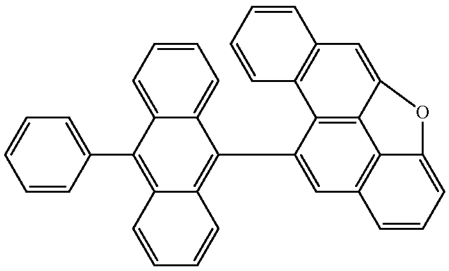
H1-202
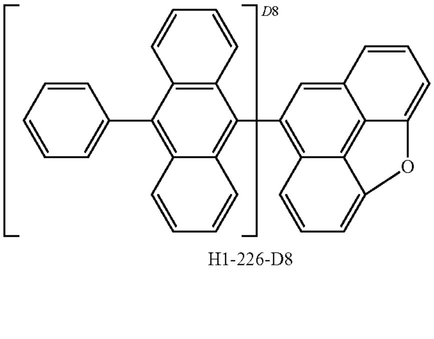
H1-226-D8

TABLE 2-continued
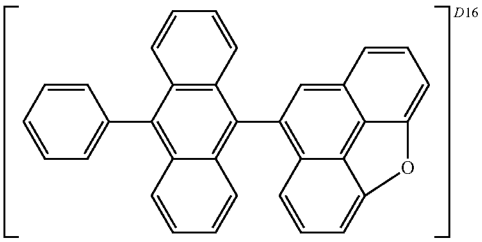
H1-226-D16
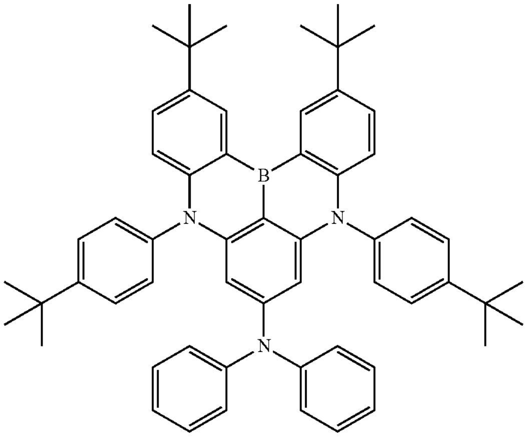
C-326
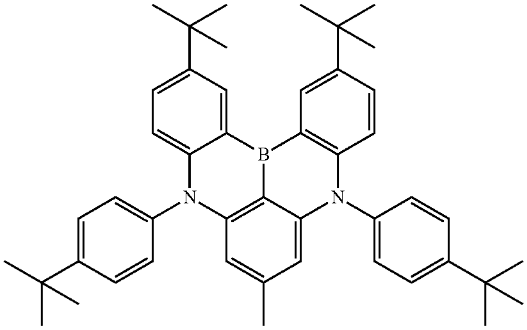
C-286
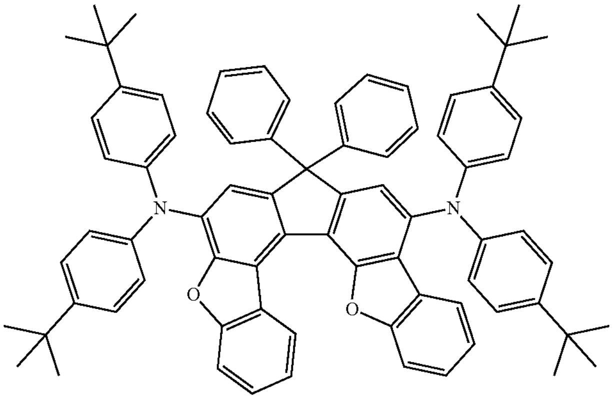
C-391

TABLE 2-continued
| | |
|---|---|
| | 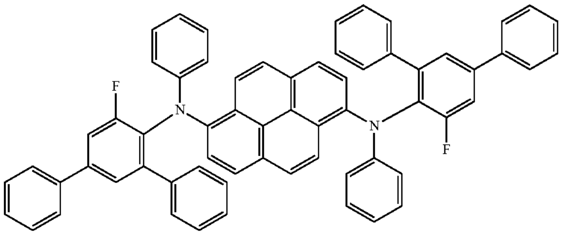<br>C-144 |
| | 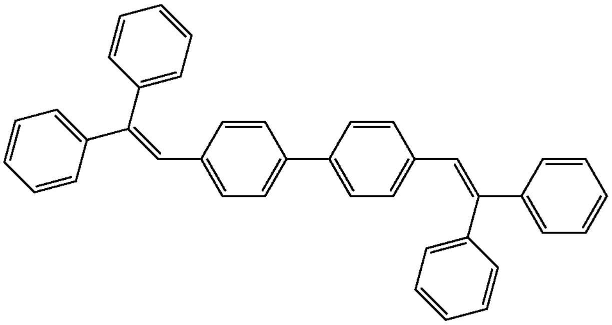<br>D-1 |
| Electron Transport Layer/ Electron Injection Layer | 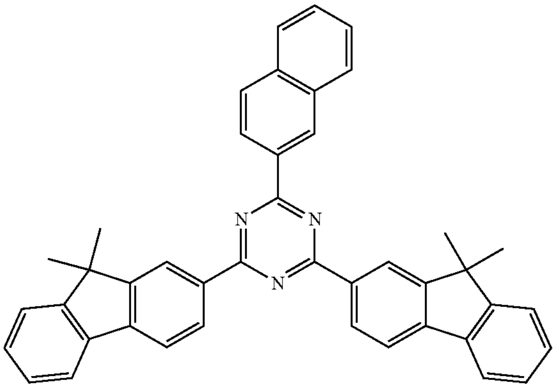<br>ET-1 |
| | 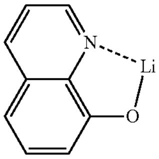<br>EI-1 |

The invention claimed is:

1. A plurality of light-emitting materials comprising at least one first compound and at least one second compound, wherein the first compound is represented by the following formula 1 and the second compound is represented by at least one of the following formulas 2 and 2-13 to 2-15:

(1)

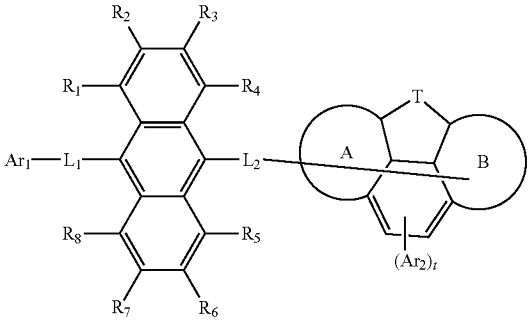

wherein,

T represents O, S, or $CR_9R_{10}$;

ring A and ring B, each independently, represent a substituted or unsubstituted (C6-C30)aryl, or a substituted or unsubstituted (3- to 30-membered) heteroaryl;

$R_1$ to $R_{10}$, each independently, represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted fused ring group of a (C3-C30) aliphatic ring(s) and a (C6-C30) aromatic ring(s), or $-L_3-N(Ar_{11})(Ar_{12})$;

$L_1$ to $L_3$, each independently, represent a single bond, a substituted or unsubstituted (C6-C30)arylene, or a substituted or unsubstituted (3- to 30-membered) heteroarylene;

$Ar_1$ represents a substituted or unsubstituted (C6-C30) aryl, or a substituted or unsubstituted (3- to 30-membered) heteroaryl;

$Ar_2$, $Ar_{11}$, and $Ar_{12}$, each independently, represent hydrogen, deuterium, a halogen, a cyano, a substituted or unsubstituted (C1-C30)alkyl, a substituted or unsubstituted (C2-C30)alkenyl, a substituted or unsubstituted (C6-C30)aryl, a substituted or unsubstituted (C3-C30) heteroaryl, a substituted or unsubstituted (C3-C30) cycloalkyl, a substituted or unsubstituted (C1-C30) alkoxy, a substituted or unsubstituted fused ring group of a (C3-C30) aliphatic ring(s) and a (C6-C30) aromatic ring(s), a substituted or unsubstituted tri(C1-C30) alkylsilyl, a substituted or unsubstituted di(C1-C30) alkyl(C1-C30)arylsilyl, a substituted or unsubstituted (C1-C30)alkyldi(C6-C30)arylsilyl, or a substituted or unsubstituted tri(C6-C30)arylsilyl; and t represents an integer of 1 or 2, in which if t is 2, each of $Ar_2$ may be the same or different;

(2)

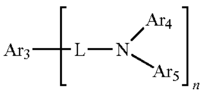

(2-13)

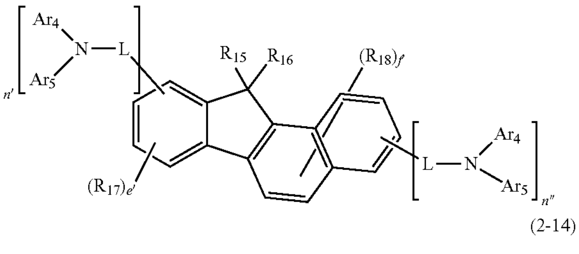

(2-14)

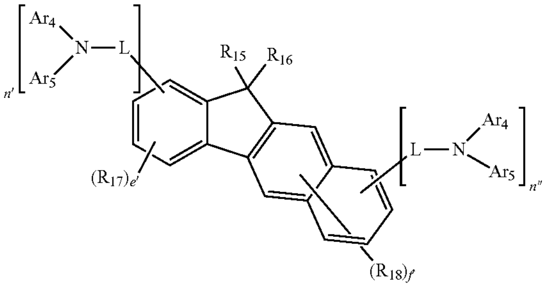

(2-15)

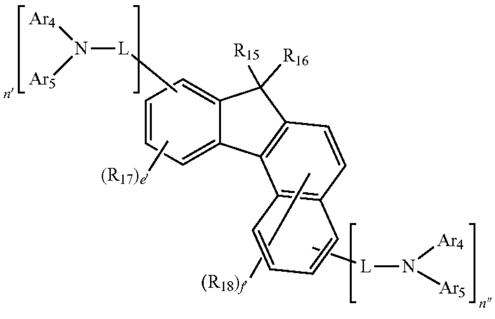

wherein

L, each independently, represents a single bond, a substituted or unsubstituted (C6-C30)arylene, or a substituted or unsubstituted (3- to 30-membered)heteroarylene;

$Ar_4$ and $Ar_5$, each independently, represent a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted fused ring group of a (C3-C30) aliphatic ring(s) and a (C6-C30) aromatic ring(s), or $-L_4-N(Ar_{13})(Ar_{14})$; or $Ar_4$ and $Ar_5$ may be linked to each other to form a ring(s);

n represents an integer of 0 to 2, in which if n is 0, $Ar_5$ is represented by the following formula 2-1;

if n is 1 or 2, $Ar_3$ is represented by any one of the following formulas 2-1, 2-2, 2-4 and 2-5; and if n is 2,

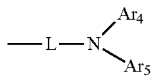

may be the same or different;

with the proviso that if in formula 1, both ring A and ring B represent a C6 aryl, $L_2$ represents a single bond, and T represents $CR_9R_{10}$, then $Ar_3$ is not represented by formula 2-2:

(2-1)

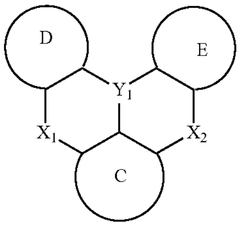

(2-2)

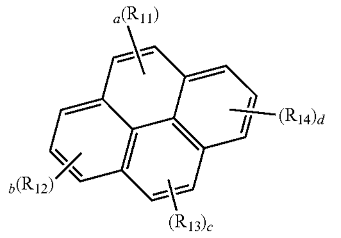

(2-4)

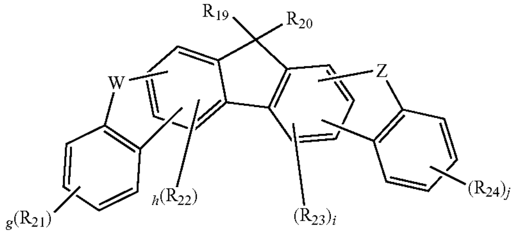

(2-5)

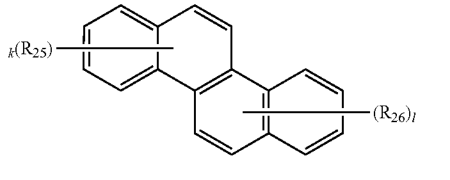

wherein, $Y_1$ represents B;

$X_1$ and $X_2$, each independently, represent NR', O or S;

W and Z, each independently, represent O, S, NR' or $CR_{27}R_{28}$;

R', each independently, represents hydrogen, deuterium, a halogen, a cyano, a substituted or unsubstituted (C1-C30)alkyl, a substituted or unsubstituted (C6-C30)aryl, a substituted or unsubstituted (3- to 30-membered) heteroaryl, a substituted or unsubstituted (C3-C30) cycloalkyl, a substituted or unsubstituted (C1-C30) alkoxy, a substituted or unsubstituted tri(C1-C30) alkylsilyl, a substituted or unsubstituted di(C1-C30) alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted fused ring group of a (C3-C30) aliphatic ring(s) and a (C6-C30) aromatic ring(s), or $-L_4-N(Ar_{13})(Ar_{14})$; and R' in formula 2-1 may be linked to at least one of ring C, ring D and ring E, directly or via B, O, S or $CR_{27}R_{28}$ as a linker, to form a ring(s);

ring C, ring D, and ring E, each independently, represent a substituted or unsubstituted (C6-C30)aryl, or a substituted or unsubstituted (3- to 50-membered)heteroaryl; and ring D and ring E may be linked to each other directly or via B, O, S or $CR_{27}R_{28}$ as a linker to form a ring(s);

$R_{11}$ to $R_{14}$, $R_{17}$, $R_{18}$, and $R_{21}$ to $R_{26}$, each independently, represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30) arylsilyl, a substituted or unsubstituted tri(C6-C30) arylsilyl, a substituted or unsubstituted fused ring group of a (C3-C30) aliphatic ring(s) and a (C6-C30) aromatic ring(s), or $-L_4-N(Ar_{13})(Ar_{14})$;

$R_{15}$, $R_{16}$, $R_{19}$, $R_{20}$, $R_{27}$, and $R_{28}$, each independently, represent a substituted or unsubstituted (C1-C30)alkyl, a substituted or unsubstituted (C6-C30)aryl, or a substituted or unsubstituted (3- to 30-membered)heteroaryl; and at least one of $R_{15}$ and $R_{16}$, $R_{19}$ and $R_{20}$, and $R_{27}$ and $R_{28}$ may be fused to each other to form a spiro structure;

$L_4$, each independently, represents a single bond, a substituted or unsubstituted (C6-C30)arylene, a substituted or unsubstituted (3- to 30-membered)heteroarylene, a substituted or unsubstituted divalent (C2-C30) aliphatic hydrocarbon group, or a substituted or unsubstituted divalent fused ring group of a (C3-C30) aliphatic ring(s) and a (C6-C30) aromatic ring(s);

$Ar_{13}$ and $Ar_{14}$, each independently, represent a substituted or unsubstituted (C1-C30)alkyl, a substituted or unsubstituted (C2-C30) alkenyl, a substituted or unsubstituted (C6-C30)aryl, or a substituted or unsubstituted (3- to 30-membered)heteroaryl; and n' and n'', each independently, represent 0 or 1, in which at least one of n' and n'' is 1;

a, c, h, and i, each independently, represent an integer of 1 or 2; b and d, each independently, represent an integer of 1 to 3; f', k, and l, each independently, represent an integer of 1 to 6; and e', g, and j, each independently, represent an integer of 1 to 4, in which if a to d, e', f, g to l, each independently, are an integer of 2 or more, each of $R_{11}$, each of $R_{12}$, each of $R_{13}$, each of $R_{14}$, each of $R_{17}$, each of $R_{18}$, each of $R_{21}$, each of $R_{22}$, each of $R_{23}$, each of $R_{24}$, each of $R_{25}$, or each of $R_{26}$ may be the same or different.

2. The plurality of light-emitting materials according to claim 1, wherein the substituents of the substituted alkyl, the substituted alkenyl, the substituted aryl(ene), the substituted heteroaryl(ene), the substituted cycloalkyl, the substituted alkoxy, the substituted trialkylsilyl, the substituted dialkylarylsilyl, the substituted alkyldiarylsilyl, the substituted triarylsilyl, the substituted divalent aliphatic hydrocarbon group, and the substituted fused ring group of a aliphatic ring(s) and an aromatic ring(s), each independently, are at least one selected from the group consisting of deuterium; a halogen; a cyano; a carboxyl; a nitro; a hydroxyl; a phosphineoxide; a (C1-C30)alkyl unsubstituted or substituted with at least one of deuterium(s) and a halogen(s); a halo (C1-C30)alkyl; a (C2-C30) alkenyl; a (C2-C30) alkynyl; a (C1-C30)alkoxy; a (C1-C30)alkylthio; a (C3-C30)cycloalkyl; a (C3-C30) cycloalkenyl; a (3- to 7-membered) heterocycloalkyl; a (C6-C30)aryloxy; a (C6-C30)arylthio; a (3- to 30-membered)heteroaryl unsubstituted or substituted with at least one of a (C1-C30)alkyl(s), a (C6-C30)aryl(s) and a di(C6-C30)arylamino(s); a (C6-C30)aryl unsubstituted or substituted with at least one of deuterium(s), a (C1-C30) alkyl(s), a (3- to 30-membered)heteroaryl(s) and a di(C6-C30)arylamino(s); a tri(C1-C30)alkylsilyl; a tri(C6-C30) arylsilyl; a di(C1-C30)alkyl(C6-C30)arylsilyl; a (C1-C30) alkyldi(C6-C30)arylsilyl; an amino; a mono- or di-(C1-C30) alkylamino; a mono- or di-(C2-C30) alkenylamino; a mono- or di-(C6-C30)arylamino unsubstituted or substituted with at least one of a (C1-C30)alkyl(s), a (3- to 30-membered) heteroaryl(s) and a di(C6-C30)arylamino(s); a mono- or di-(3- to 30-membered)heteroarylamino; a (C1-C30)alkyl (C2-C30) alkenylamino; a (C1-C30)alkyl(C6-C30)arylamino; a (C1-C30)alkyl(3- to 30-membered)heteroarylamino; a (C2-C30) alkenyl (C6-C30)arylamino; a (C2-C30) alkenyl (3- to 30-membered)heteroarylamino; a (C6-C30) aryl (3- to 30-membered)heteroarylamino unsubstituted or substituted with a (C6-C30)aryl(s); a (C1-C30)alkylcarbonyl; a (C1-C30)alkoxycarbonyl; a (C6-C30)arylcarbonyl; a (C6-C30)arylphosphine; a di(C6-C30)arylboronyl; a di(C1-C30)alkylboronyl; a (C1-C30)alkyl(C6-C30)arylboronyl; a (C6-C30)aryl (C1-C30)alkyl; and a (C1-C30)alkyl(C6-C30) aryl.

3. The plurality of light-emitting materials according to claim 1, wherein the formula 1 is represented by at least one of the following formulas 1-1 and 1-2:

(1-1)

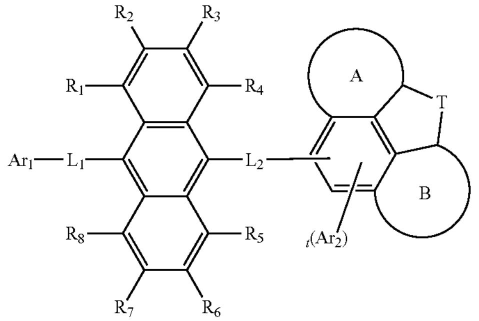

(1-2)

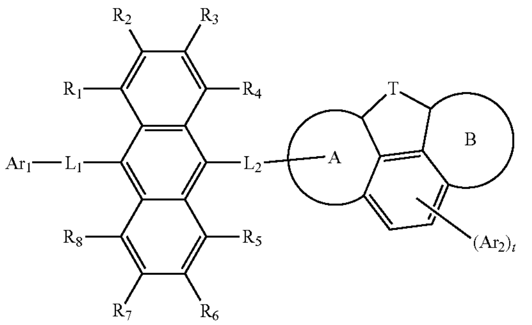

wherein, $L_1$, $L_2$, $Ar_1$, $Ar_2$, T, ring A, ring B, $R_1$ to $R_8$, and t are as defined in claim 1.

4. The plurality of light-emitting materials according to claim 1, wherein the formula 2 is represented by at least one of the following formulas 2-11, 2-12 and 2-16 to 2-18:

(2-11)

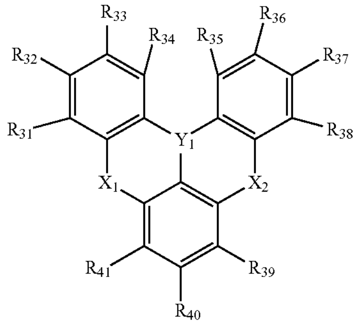

(2-12)

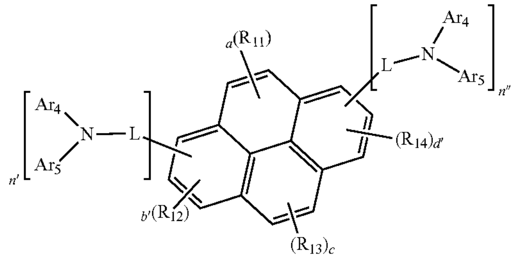

(2-16)

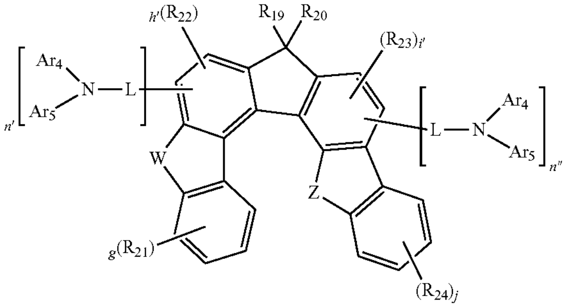

(2-17)

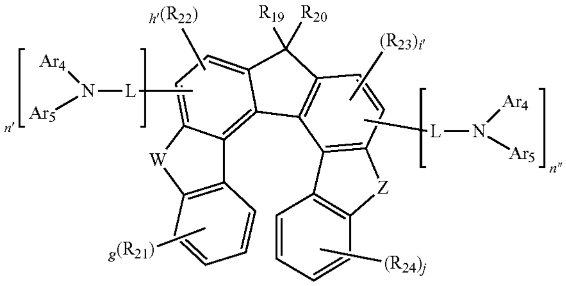

-continued (2-18)

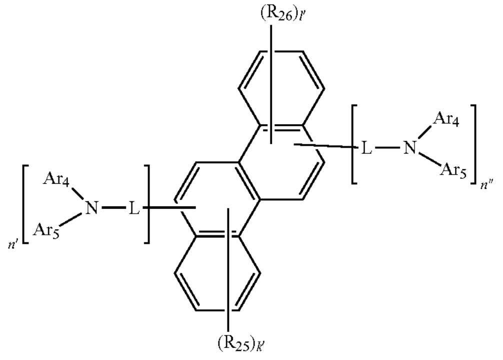

wherein, $R_{31}$ to $R_{41}$, each independently, represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted fused ring group of a (C3-C30) aliphatic ring(s) and a (C6-C30) aromatic ring(s), or $-L_4-N(Ar_{13})(Ar_{14})$; or at least two adjacent ones of $R_{31}$ to $R_{41}$ and R' may be linked to each other directly or via B, O, S or $CR_{27}R_{28}$ as a linker to form a ring(s);

n' and n'', each independently, represent 0 or 1, in which at least one of n' and n'' is 1;

b' and d', each independently, represent an integer of 1 to 3; k', and l', each independently, represent an integer of 1 to 6; and h' and i', each independently, represent an integer of 1 or 2; and $Y_1$, $X_1$, $X_2$, W, Z, $R_{11}$ to $R_{14}$, $R_{19}$ to $R_{28}$, L, $Ar_4$, $Ar_5$, $L_4$, $Ar_{13}$, $Ar_{14}$, a, c, g, and j, each independently, are as defined in claim 1.

5. The plurality of light-emitting materials according to claim 1, wherein the compound represented by formula 1 is at least one selected from the group consisting of the following compounds:

H1-1

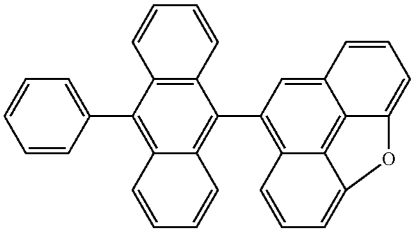

-continued

H1-2

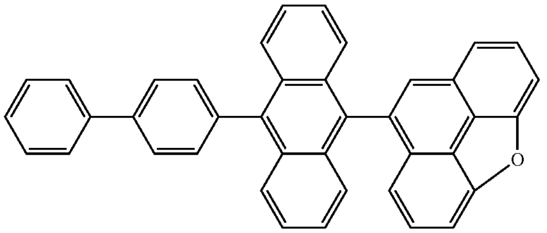

H1-3

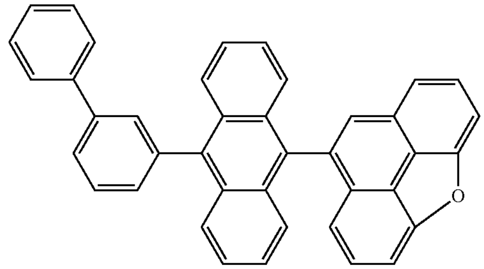

H1-4

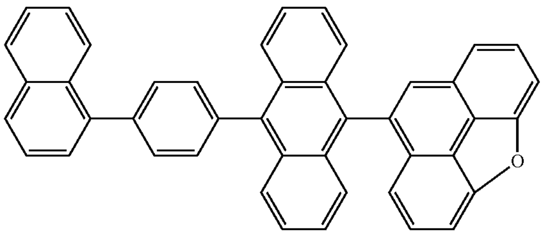

H1-5

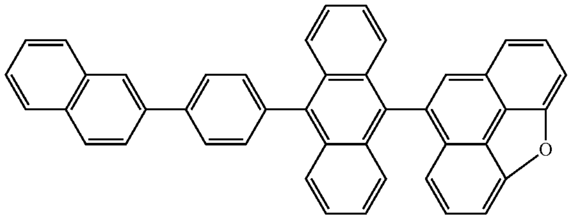

H1-6

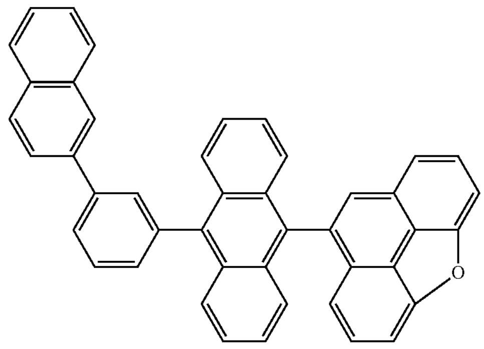

-continued
H1-7
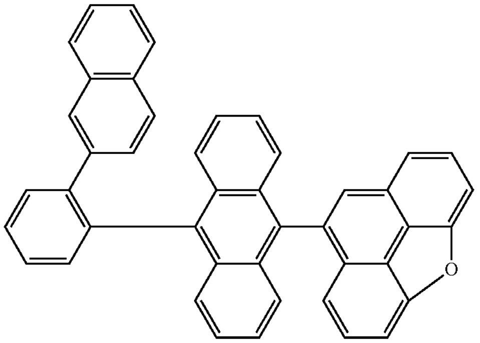
H1-8
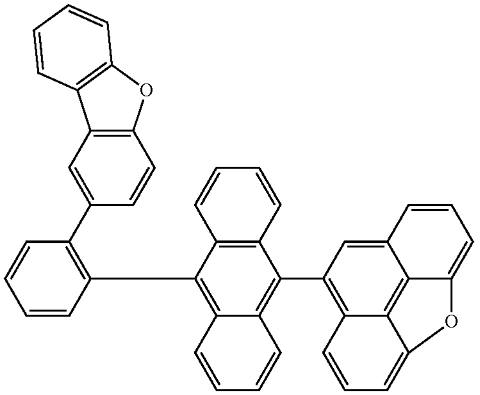
H1-9
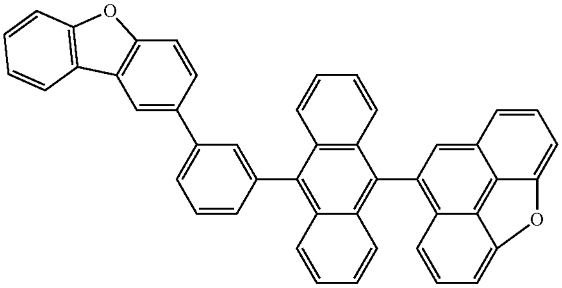
H1-10
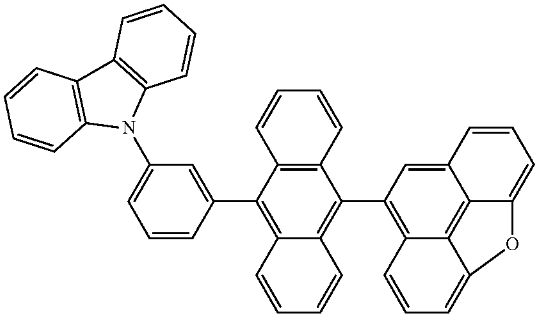
-continued
H1-11
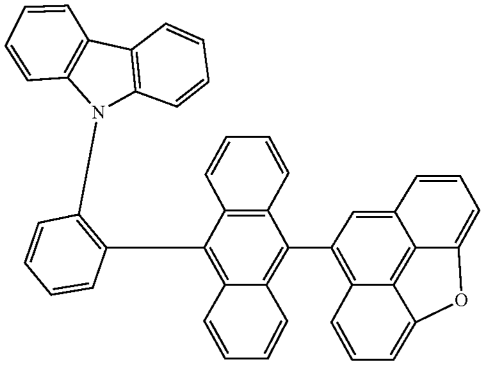
H1-12
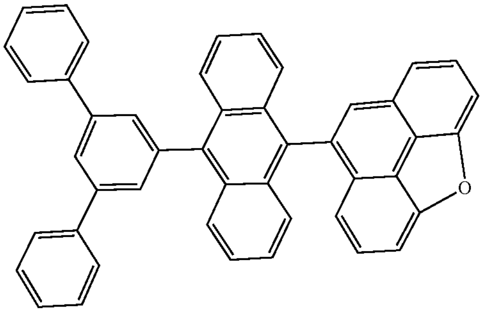
H1-13
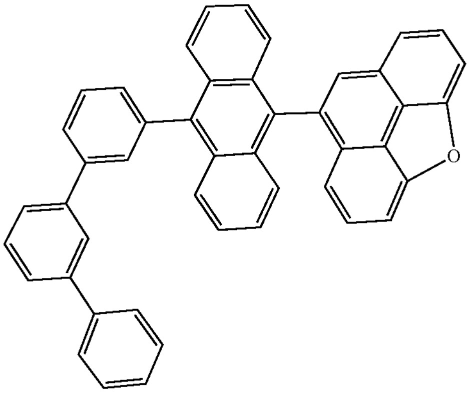
H1-14
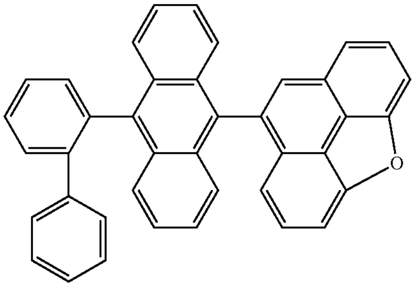

-continued
H1-15
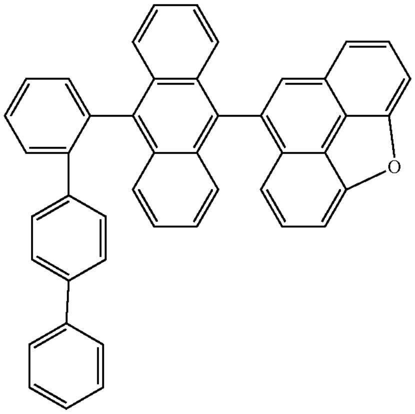
H1-16
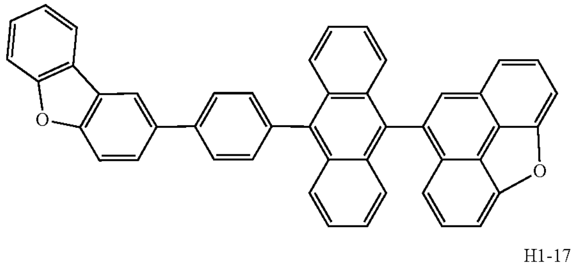
H1-17
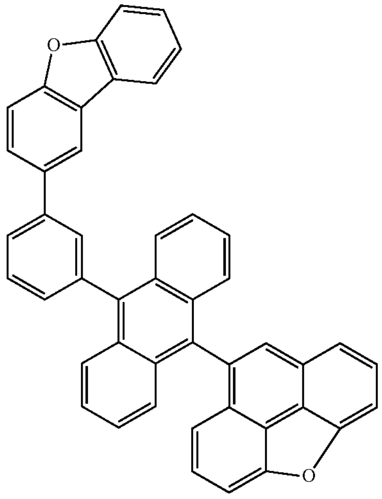
H1-18
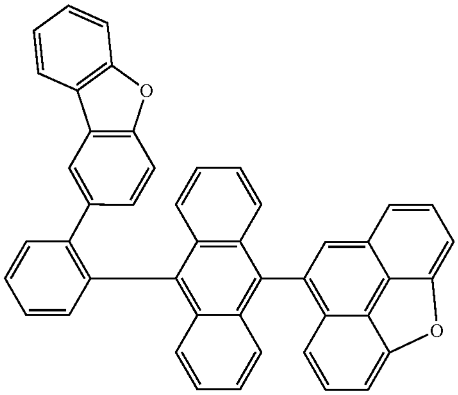
-continued
H1-19
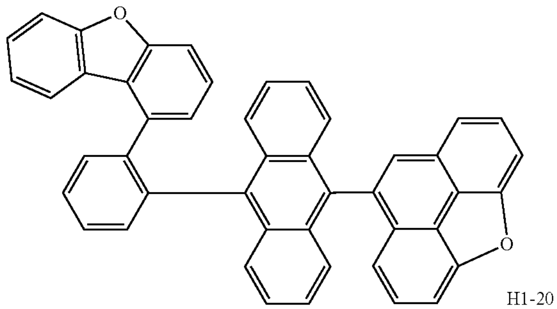
H1-20
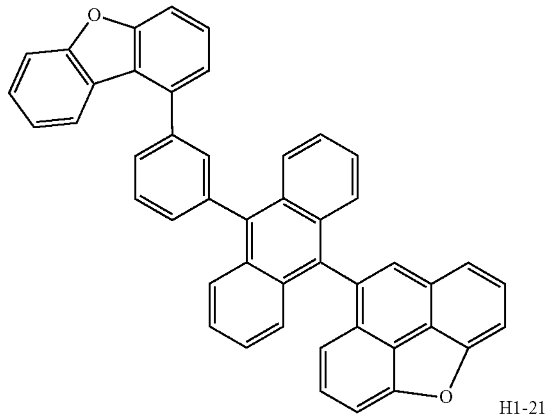
H1-21
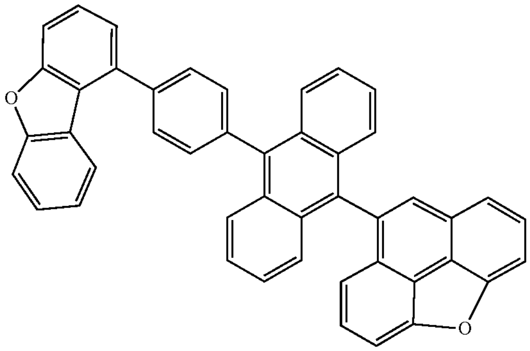
H1-22
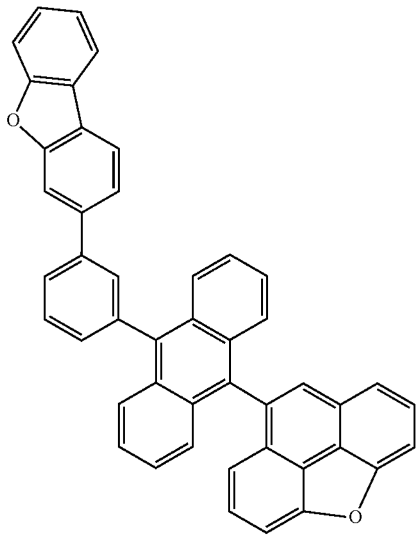

-continued
H1-23
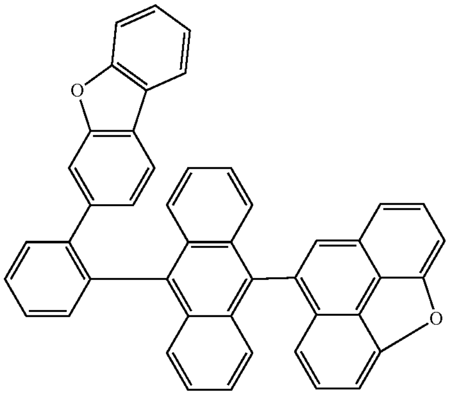
H1-24
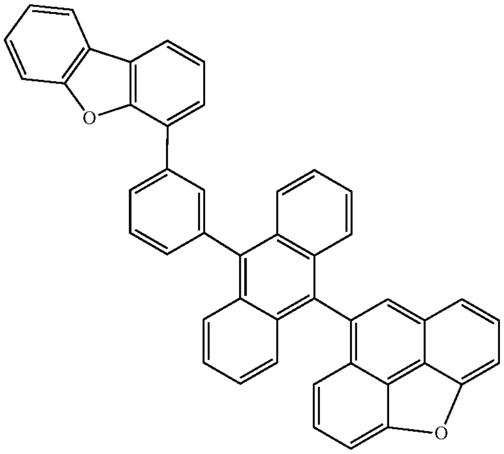
H1-25
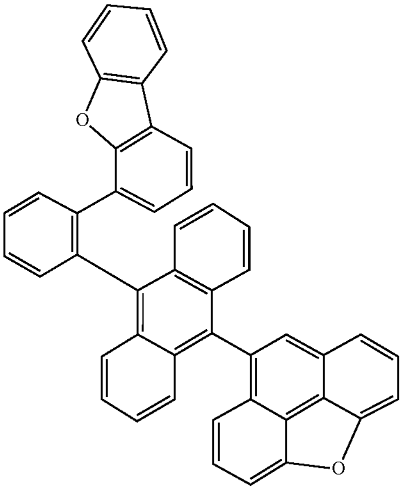
H1-26
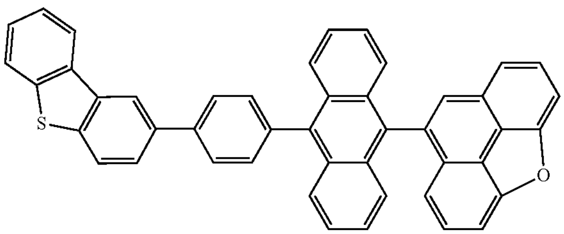
-continued
H1-27
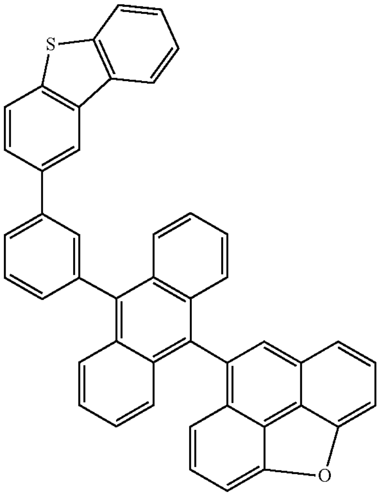
H1-28
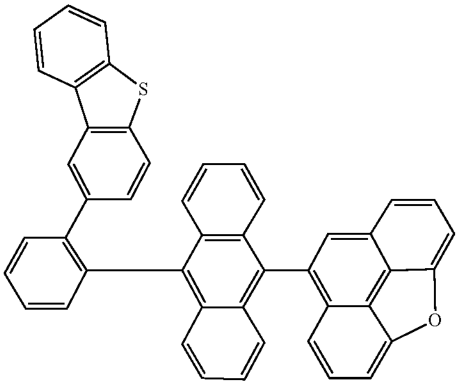
H1-29
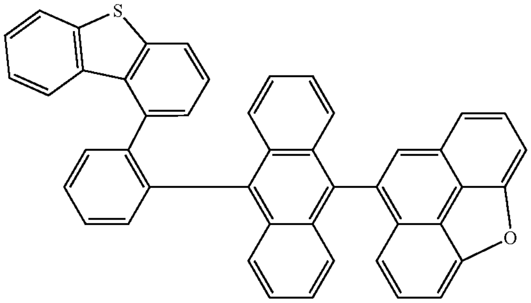
H1-30
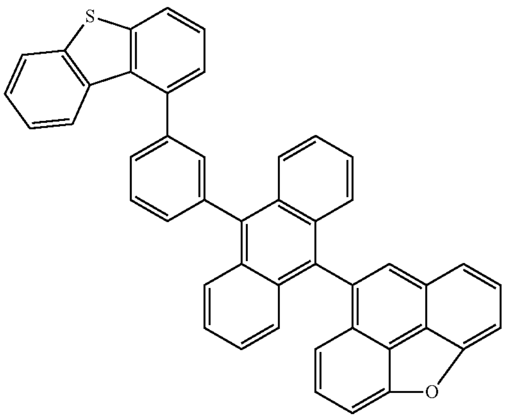

-continued
H1-31
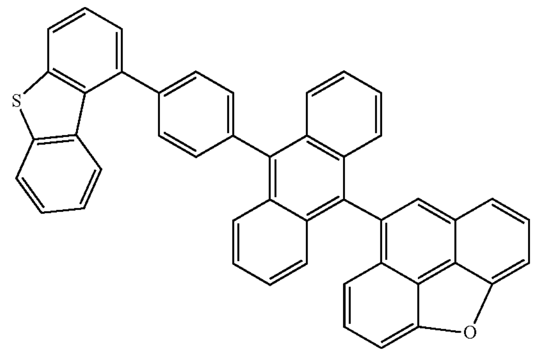
H1-32
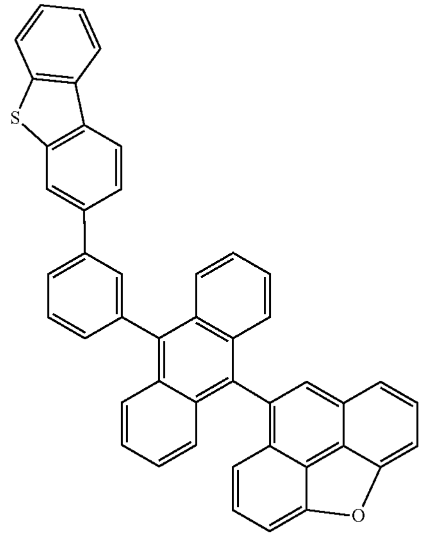
H1-33
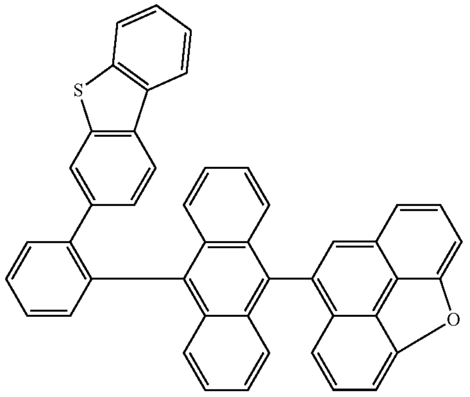
-continued
H1-34
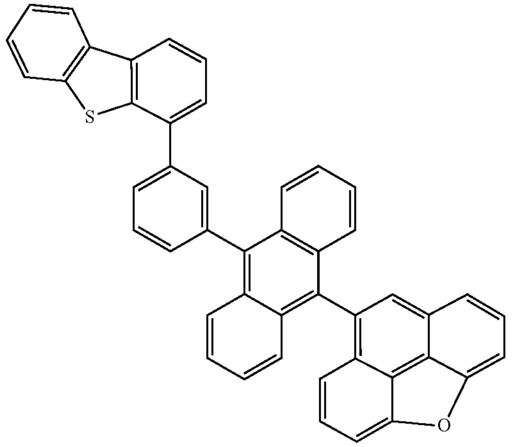
H1-35
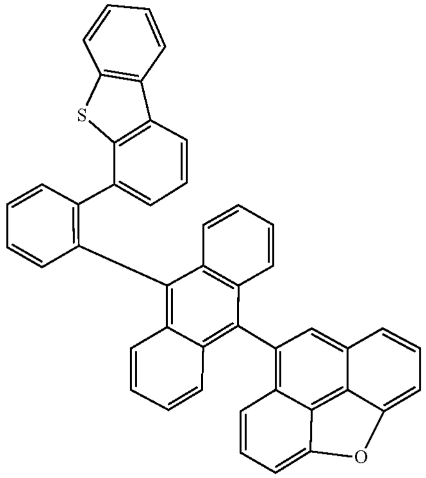
H1-36
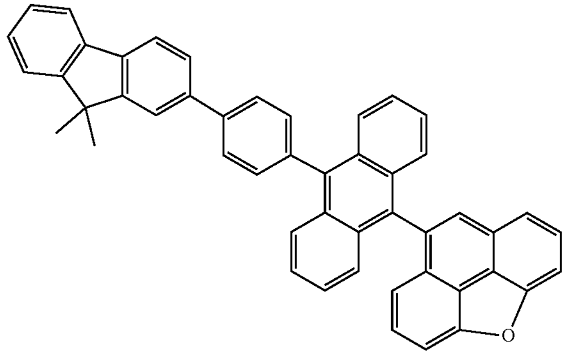

-continued
H1-37
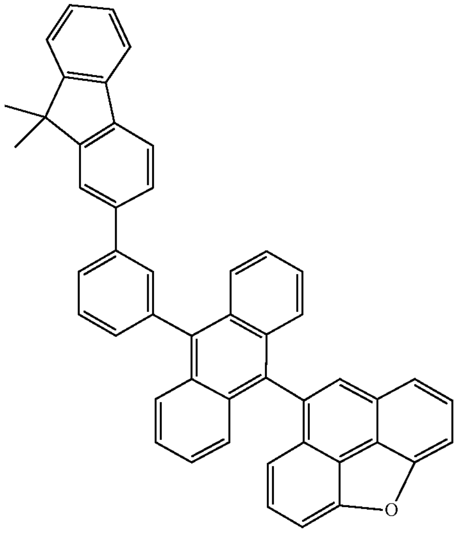
H1-38
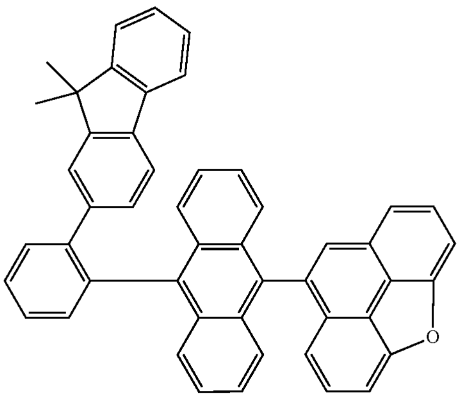
H1-39
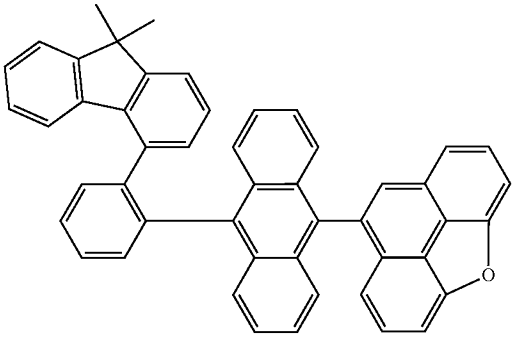
-continued
H1-40
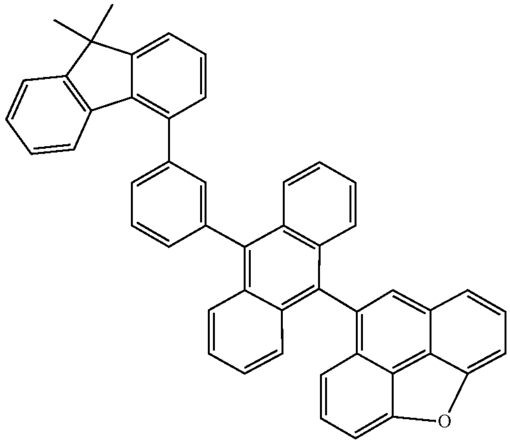
H1-41
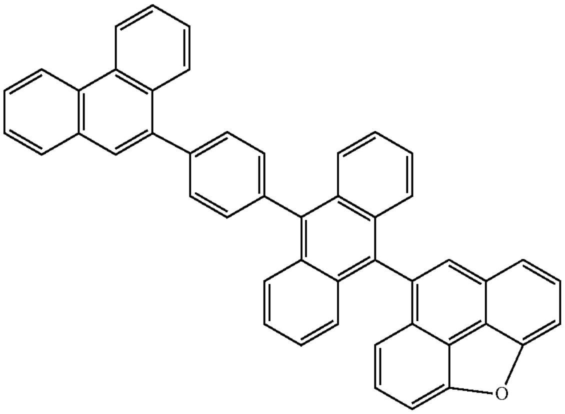
H1-42
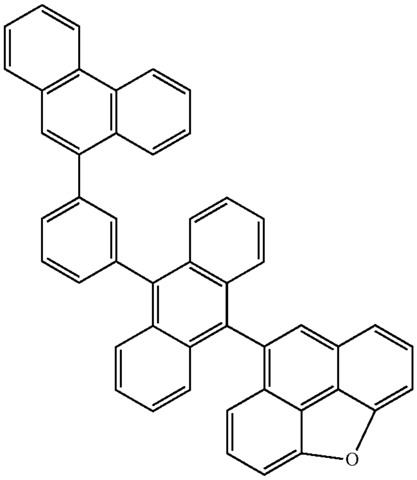

-continued
H1-43
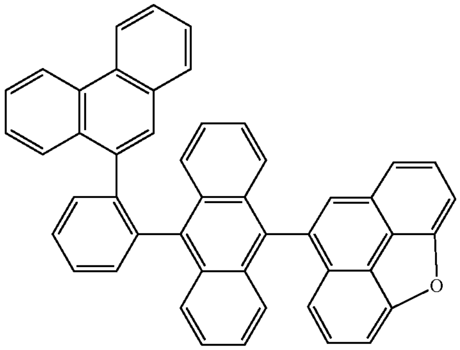
H1-44
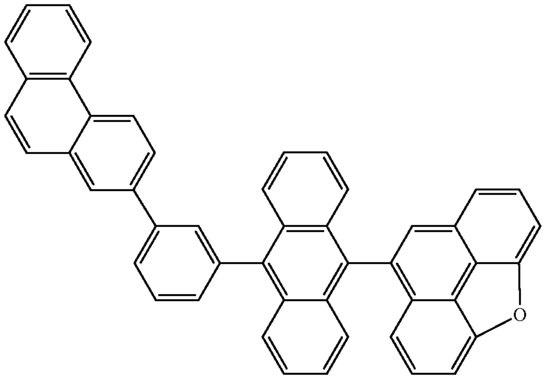
H1-45
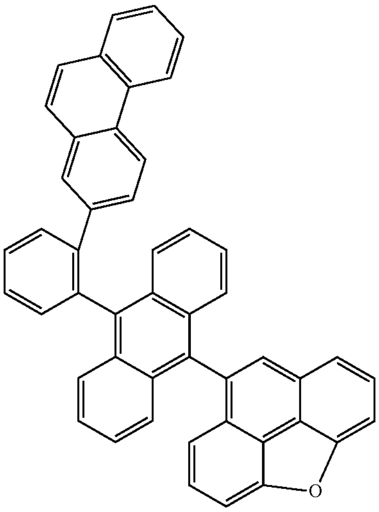
H1-46
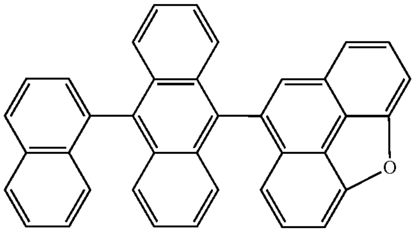
-continued
H1-47
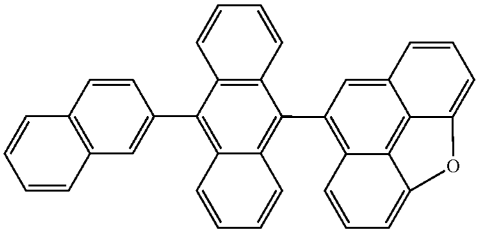
H1-48
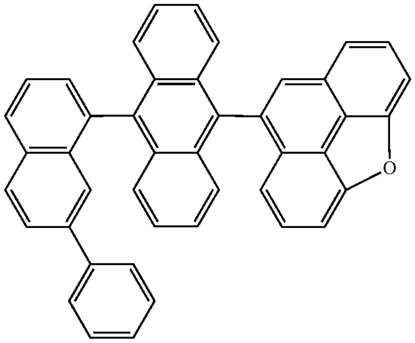
H1-49
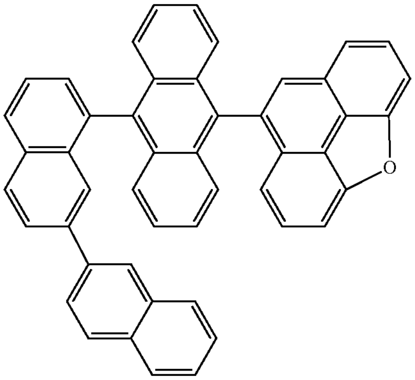
H1-50
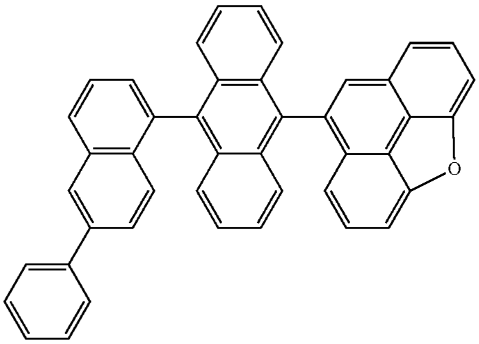

-continued
H1-51
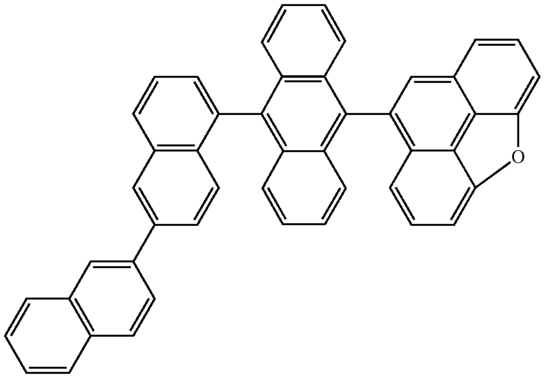
H1-52
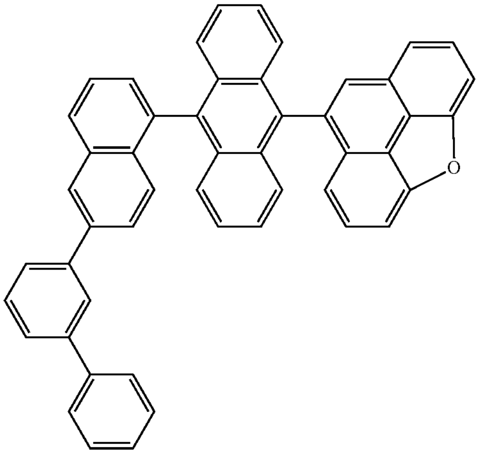
H1-53
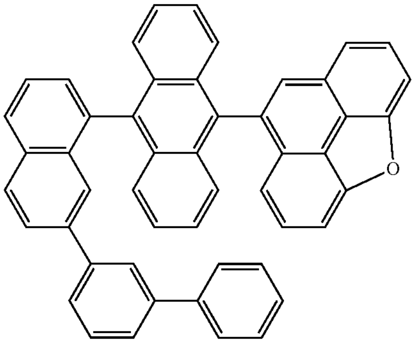
H1-54
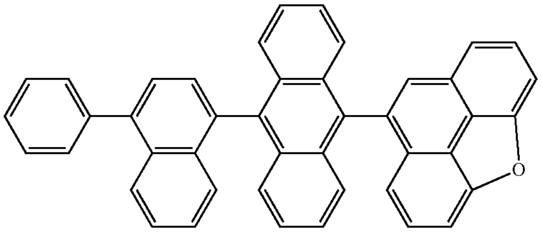
-continued
H1-55
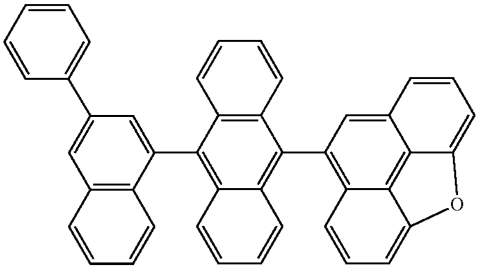
H1-56
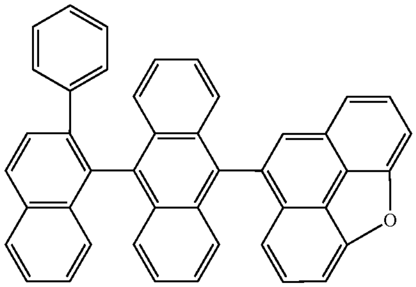
H1-57
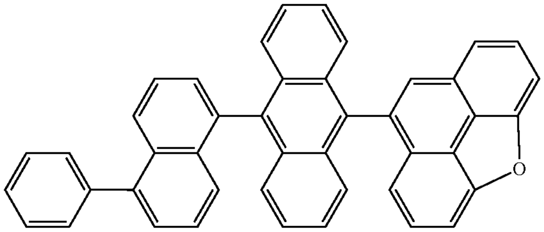
H1-58
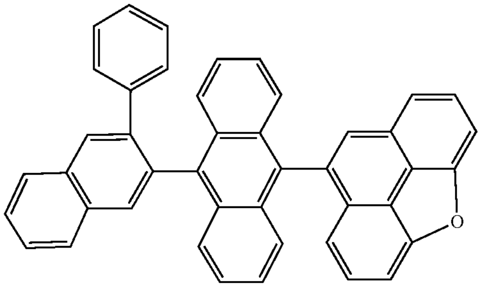
H1-59
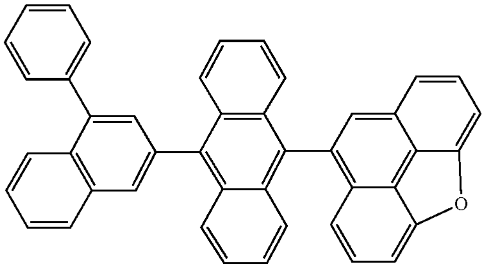
H1-60
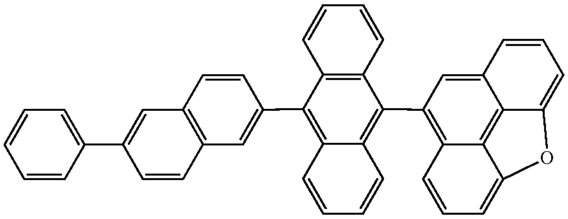

-continued
H1-61
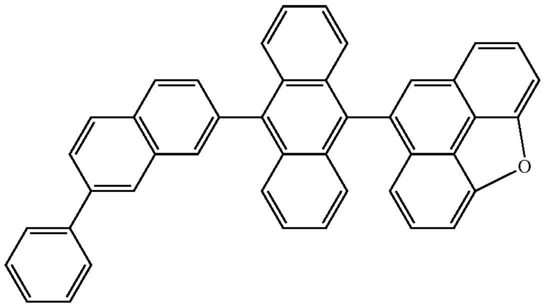
H1-62
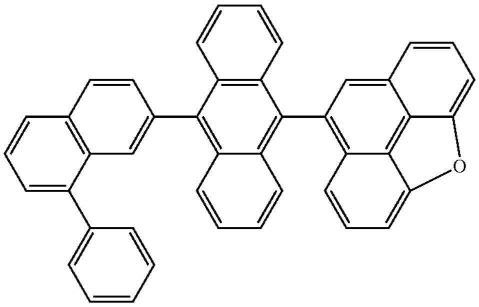
H1-63
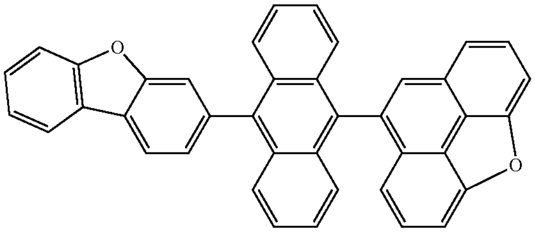
H1-64
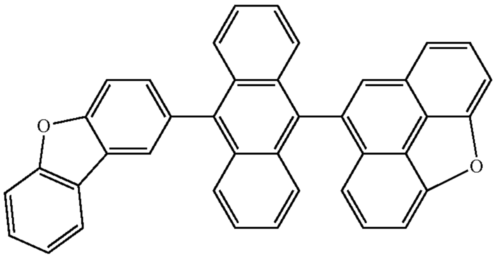
H1-65
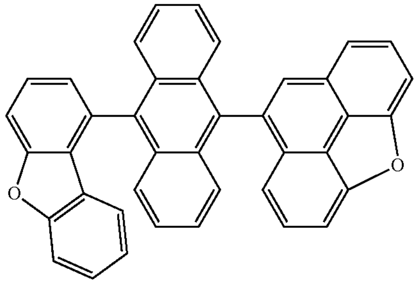
-continued
H1-66
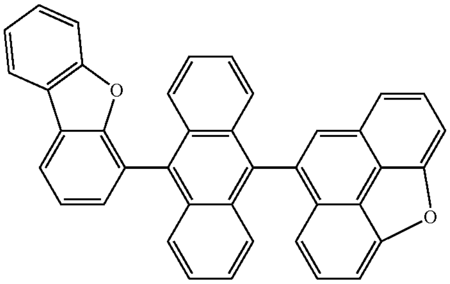
H1-67
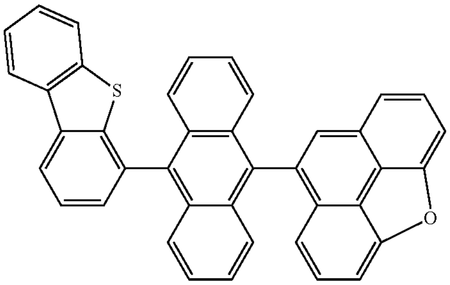
H1-68
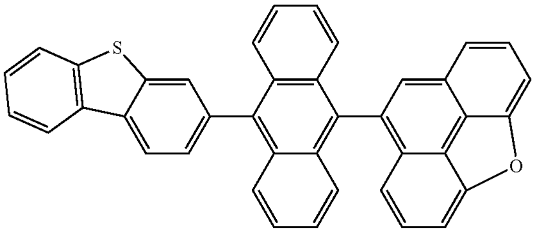
H1-69
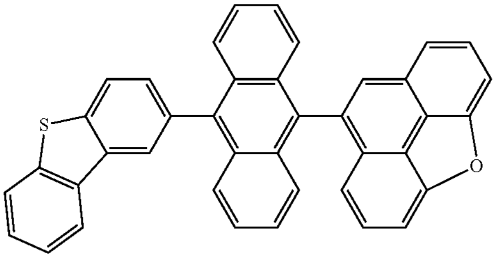
H1-70
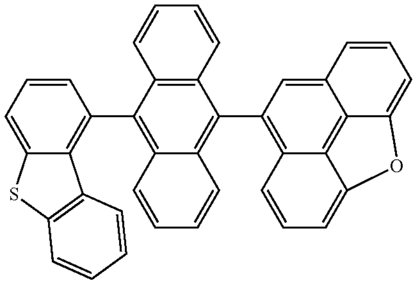
H1-71
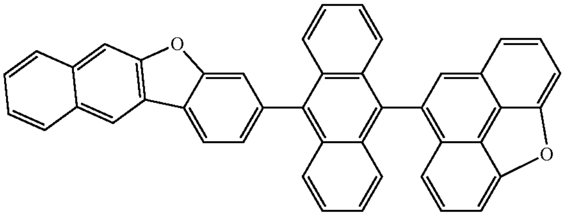

-continued
H1-72
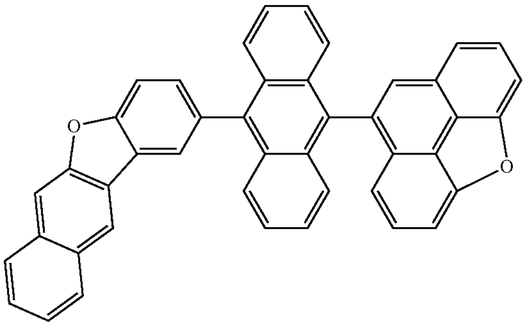
H1-73
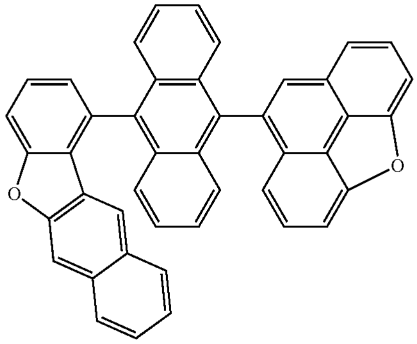
H1-74
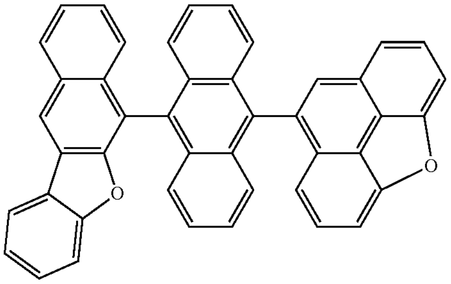
H1-75
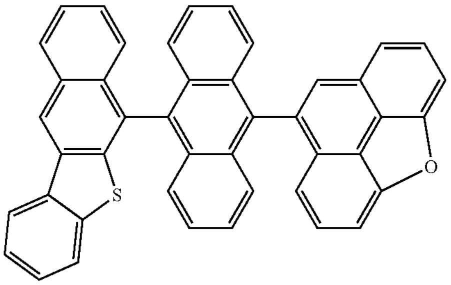
H1-76
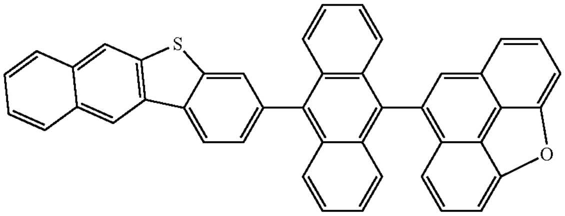
-continued
H1-77
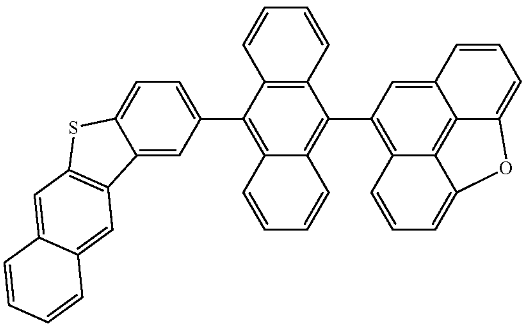
H1-78
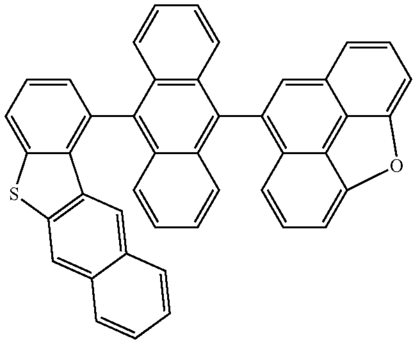
H1-79
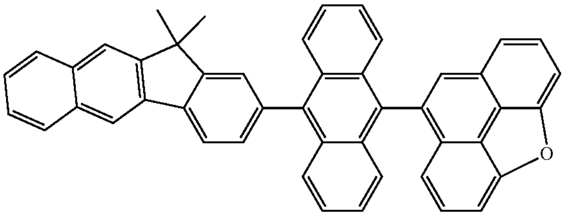
H1-80
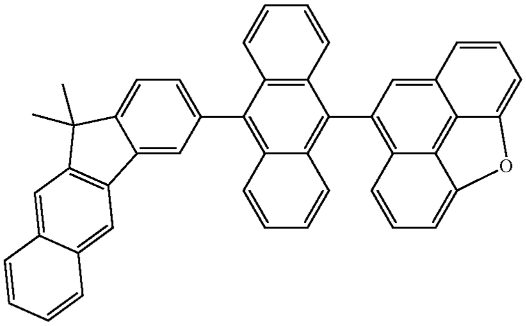
H1-81
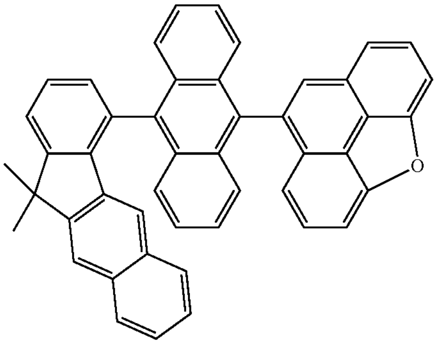

-continued
H1-82
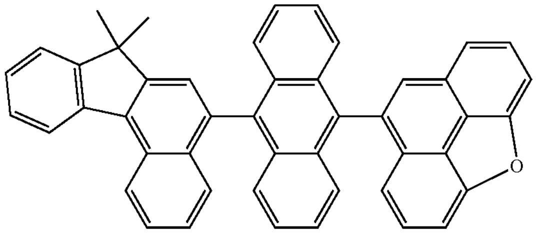
H1-83
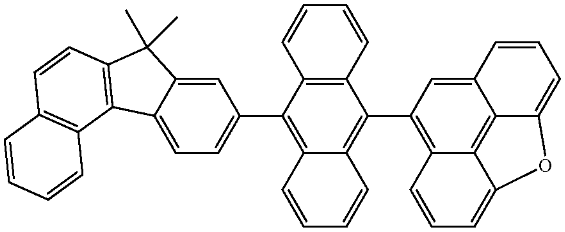
H1-84
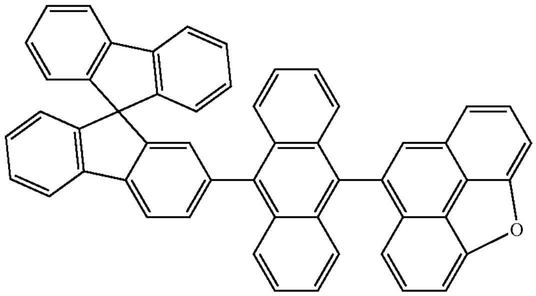
H1-85
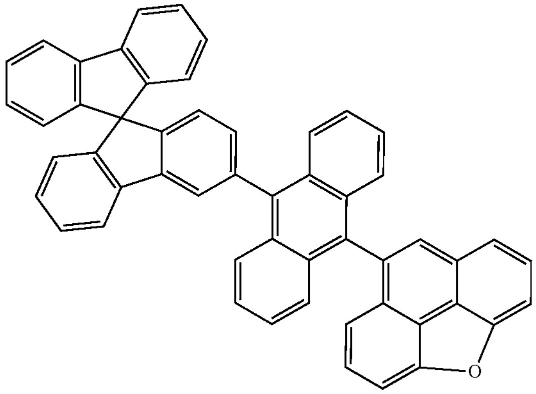
H1-86
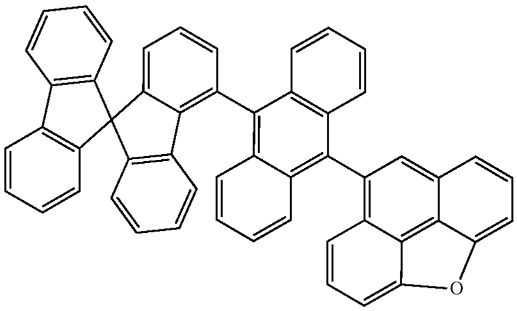
-continued
H1-87
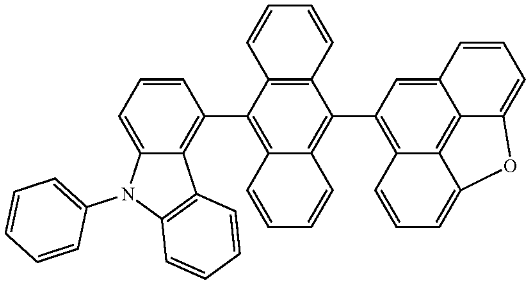
H1-88
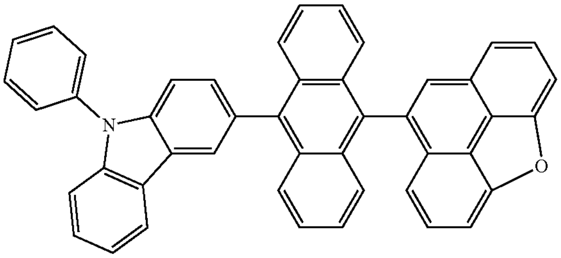
H1-89
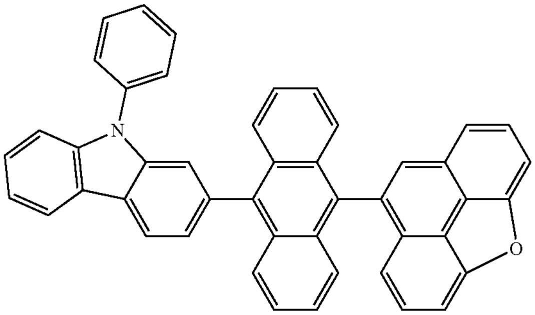
H1-90
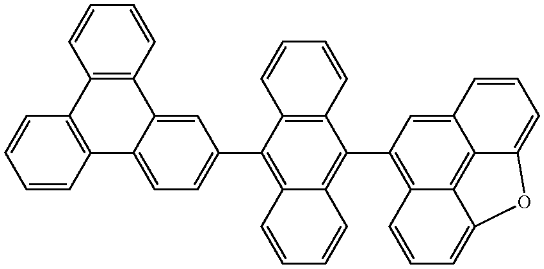
H1-91
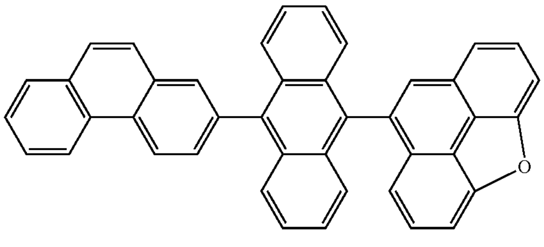

-continued
H1-92
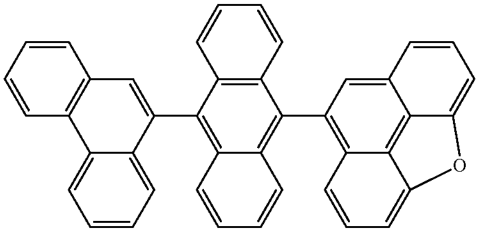
H1-93
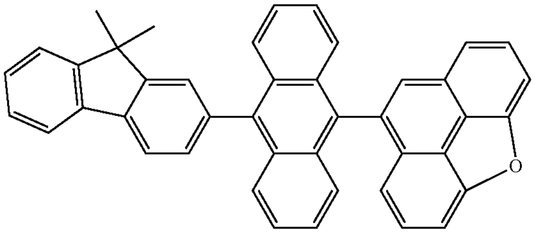
H1-94
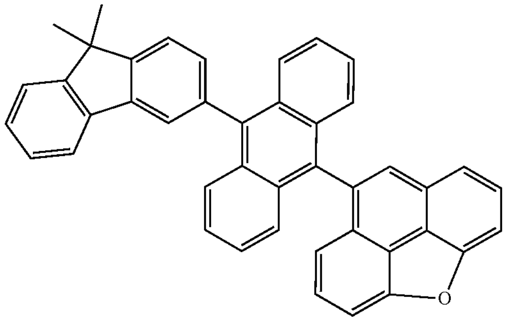
H1-95
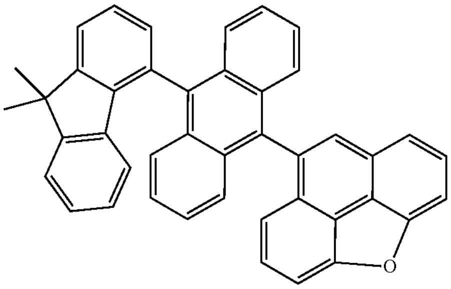
H1-96
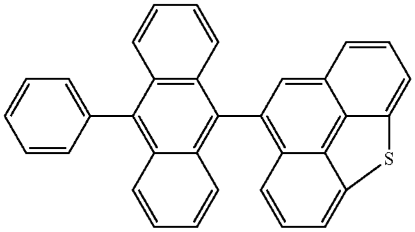
H1-97
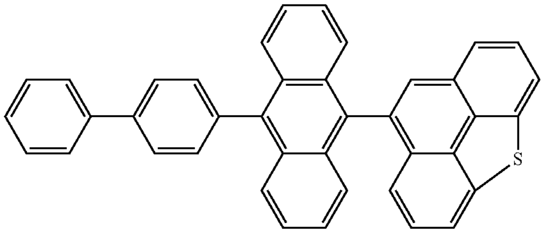
-continued
H1-98
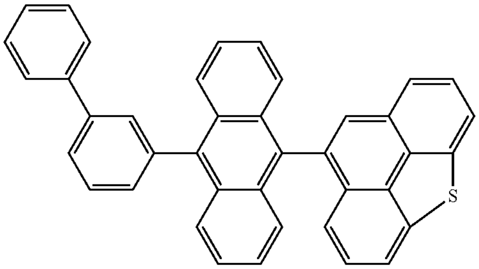
H1-99
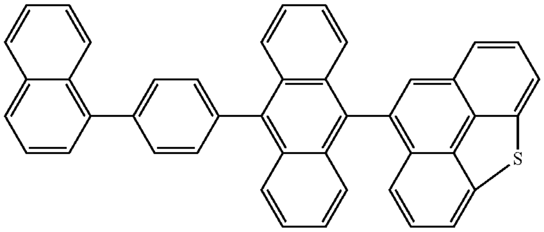
H1-100
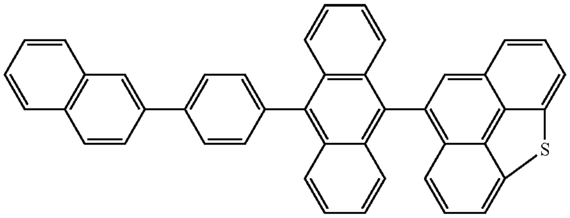
H1-101
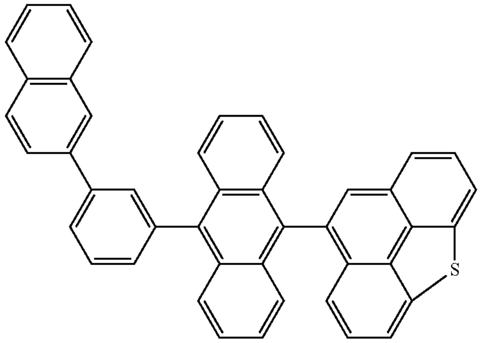
H1-102
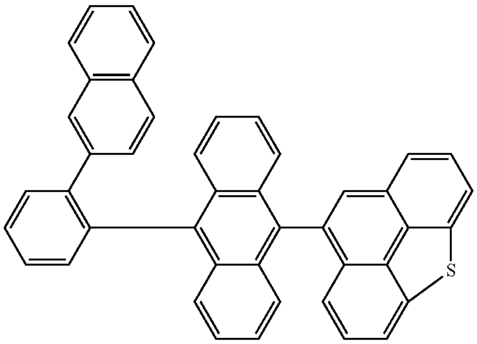

-continued
H1-103
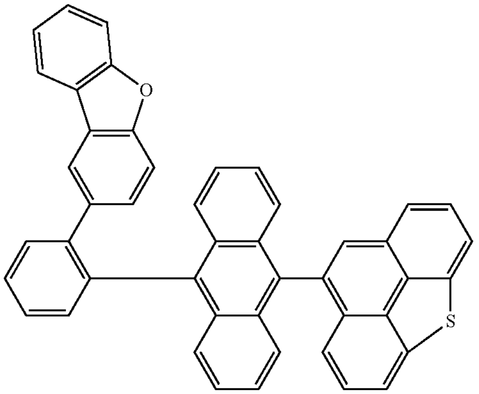
H1-104
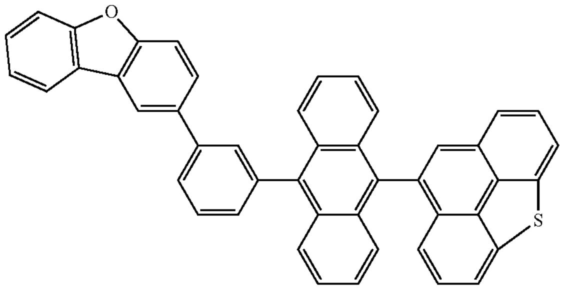
H1-105
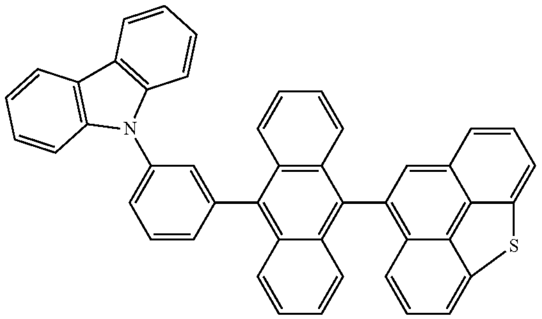
H1-106
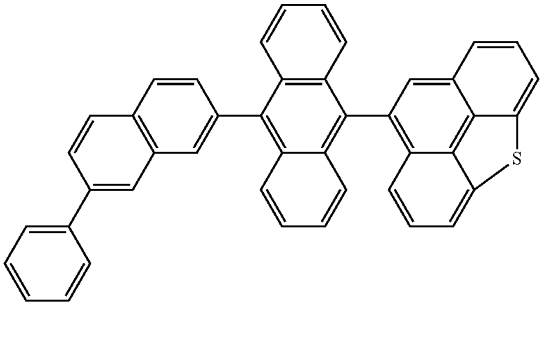
-continued
H1-107
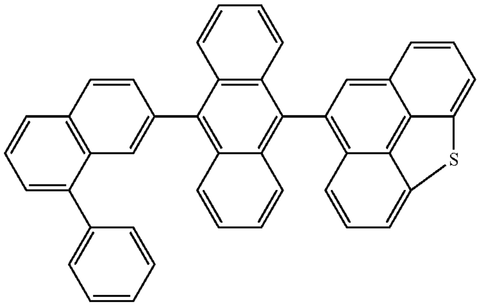
H1-108
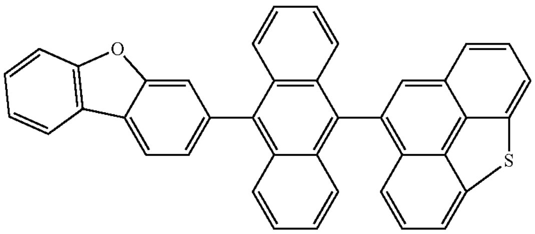
H1-109
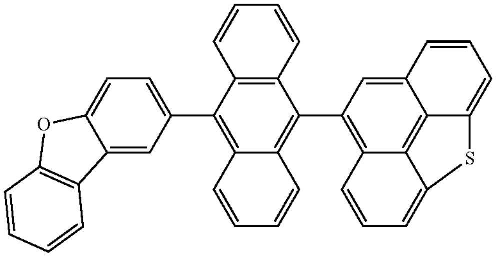
H1-110
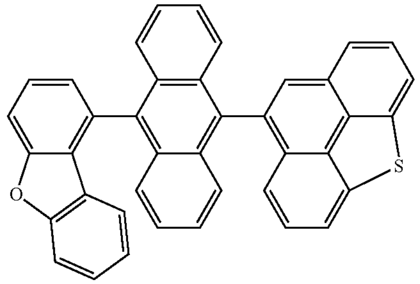
H1-111
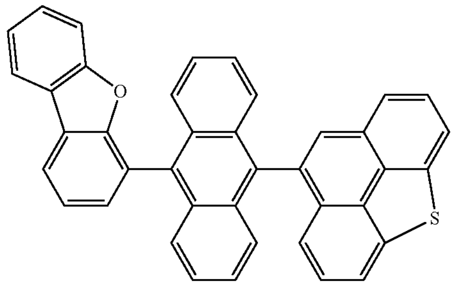

-continued
H1-112
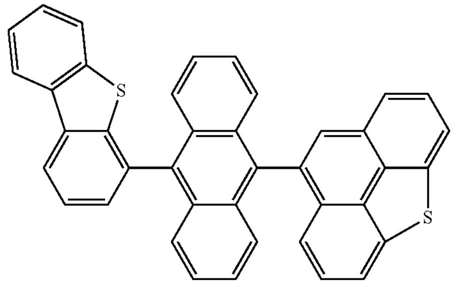
H1-113
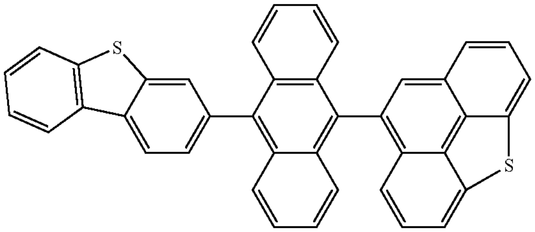
H1-114
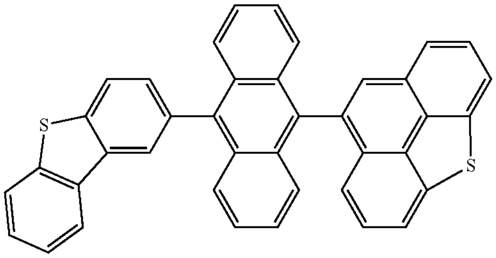
H1-115
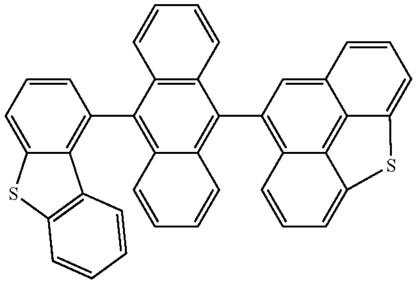
H1-116
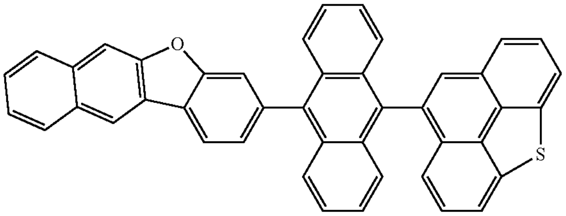
-continued
H1-117
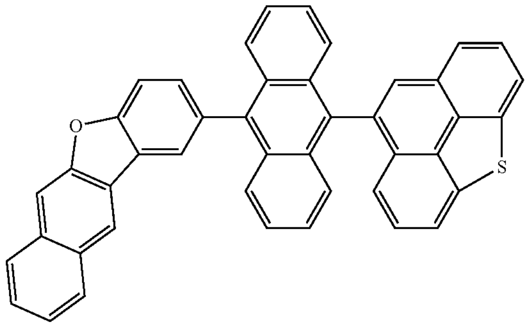
H1-118
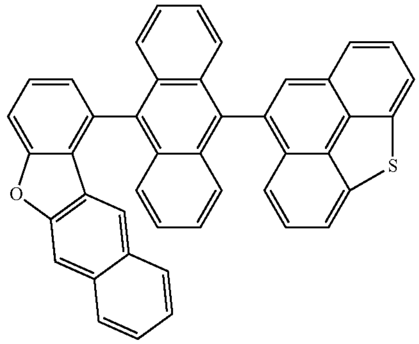
H1-119
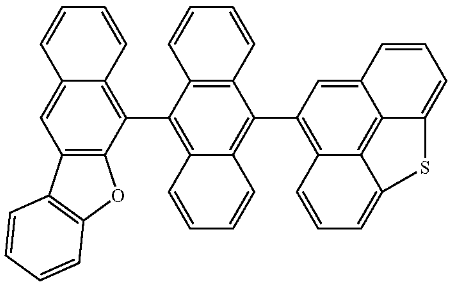
H1-120
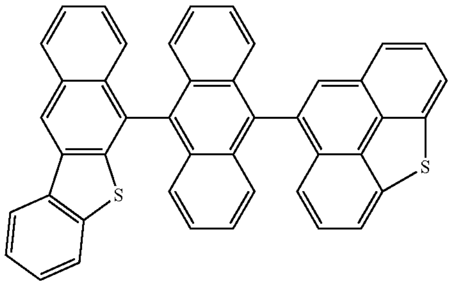
H1-121
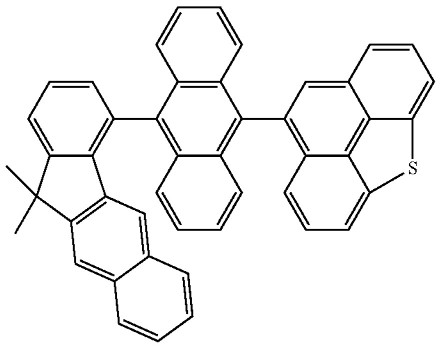

-continued
H1-122
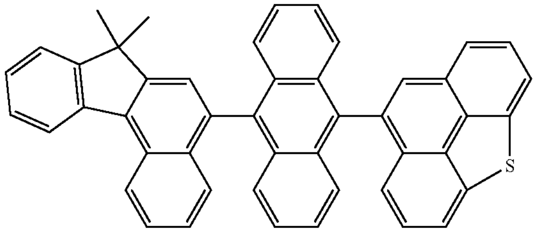
H1-123
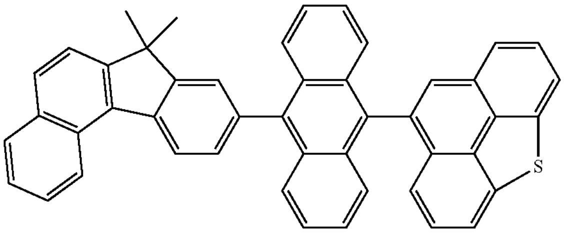
H1-124
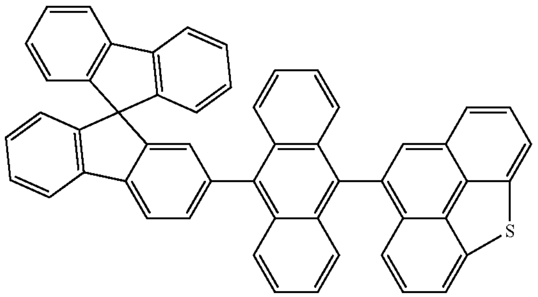
H1-125
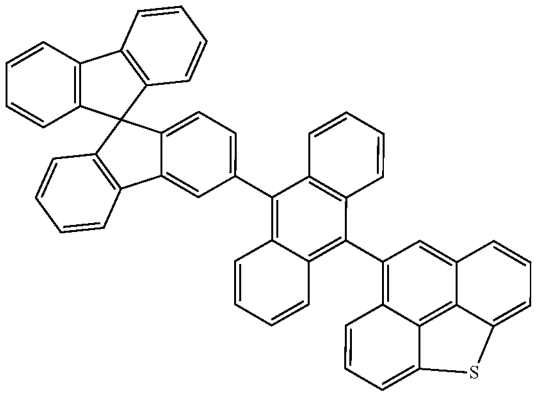
H1-126
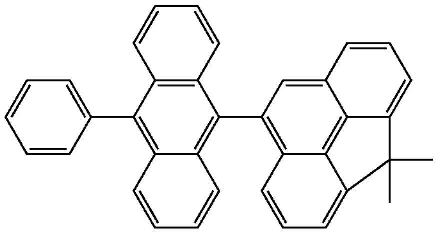
-continued
H1-127
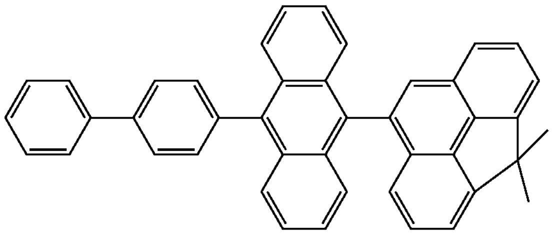
H1-128
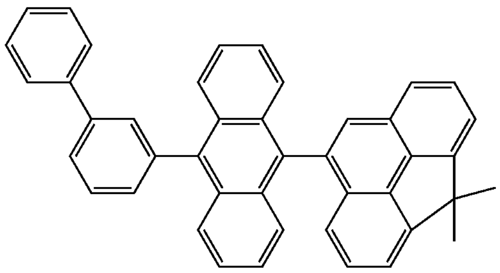
H1-129
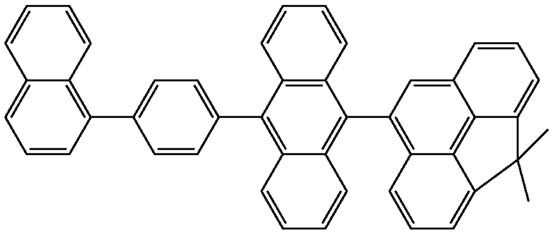
H1-130
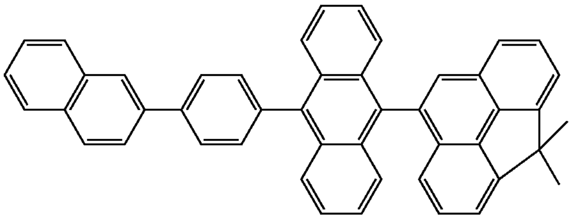
H1-131
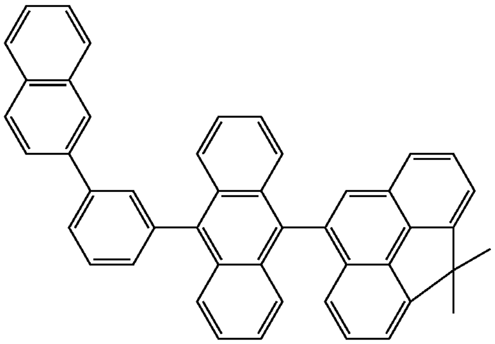

-continued
H1-132
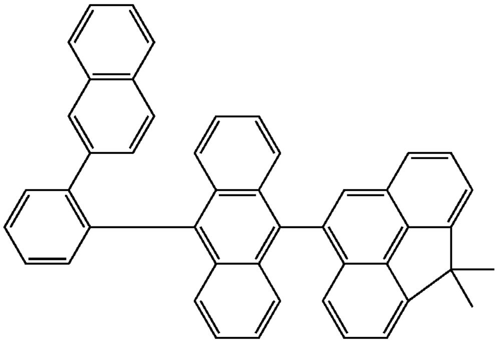
H1-133
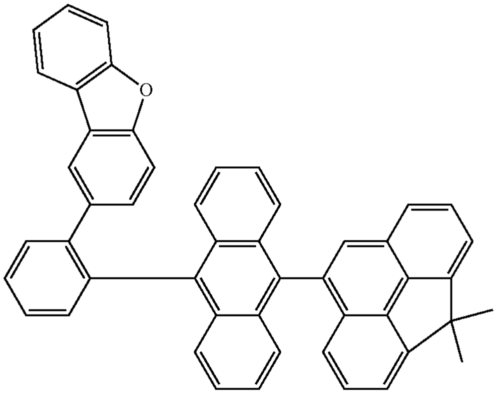
H1-134
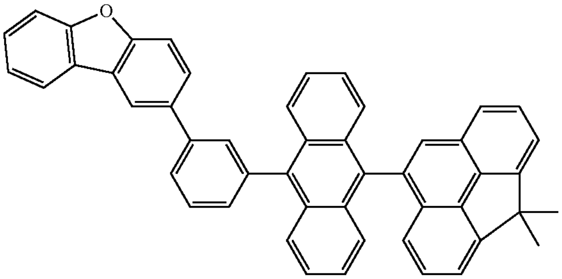
H1-135
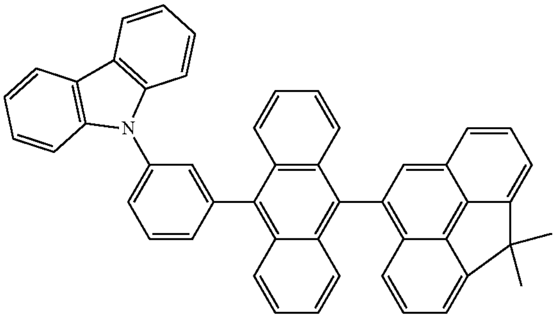
-continued
H1-136
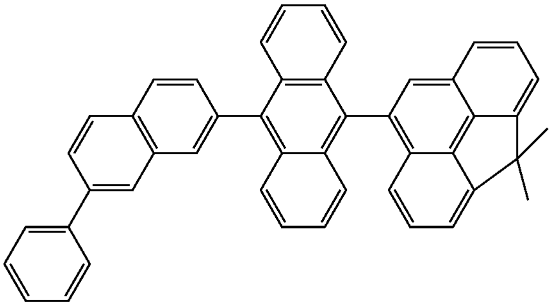
H1-137
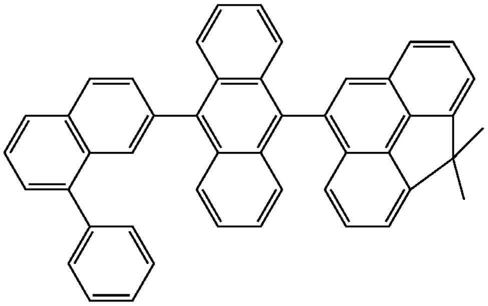
H1-138
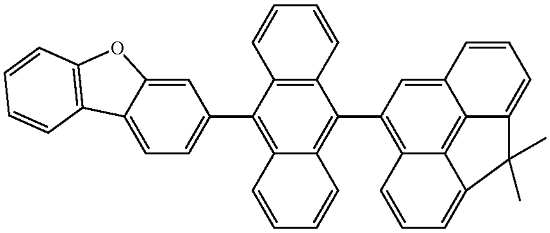
H1-139
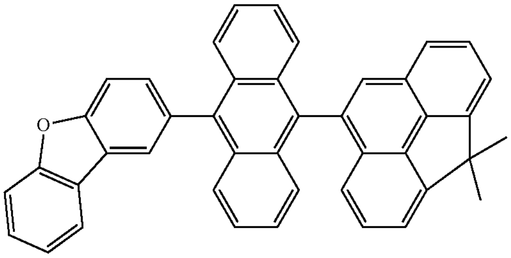
H1-140
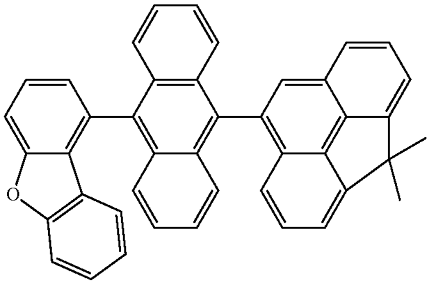

-continued
H1-141
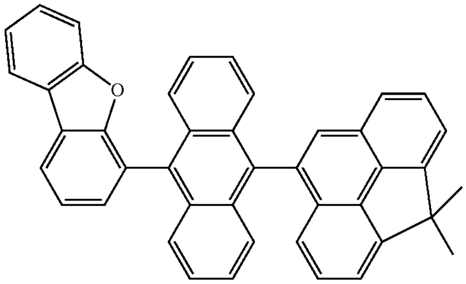
H1-142
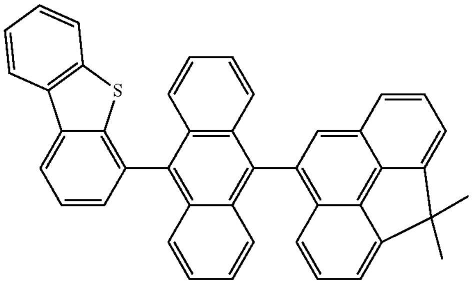
H1-143
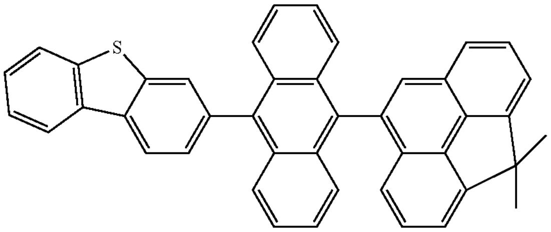
H1-144
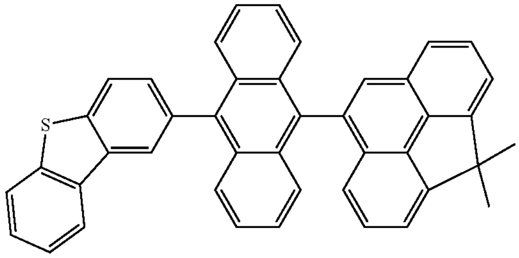
H1-145
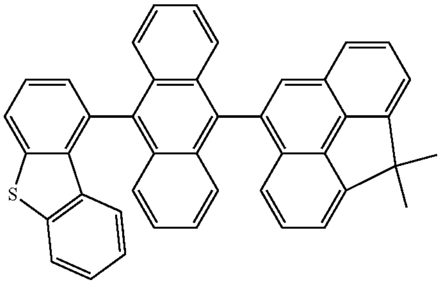
-continued
H1-146
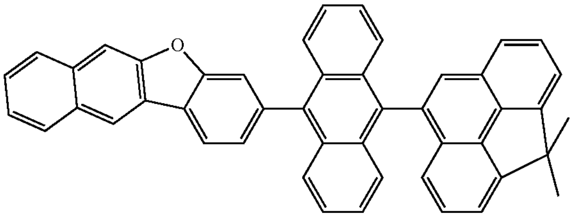
H1-147
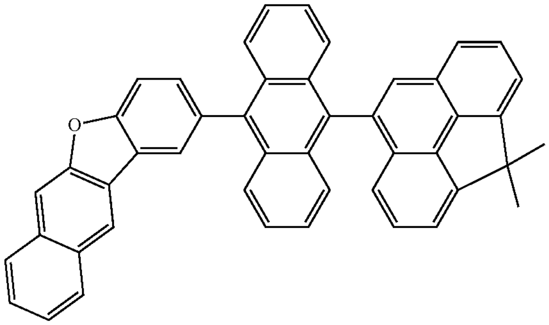
H1-148
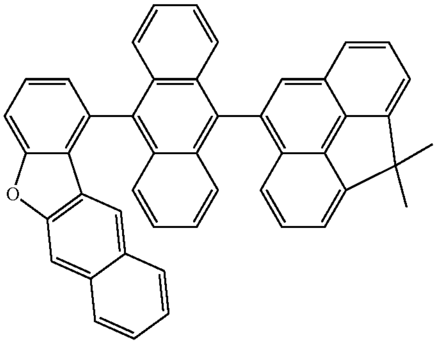
H1-149
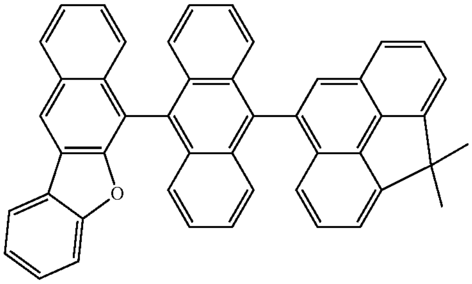
H1-150
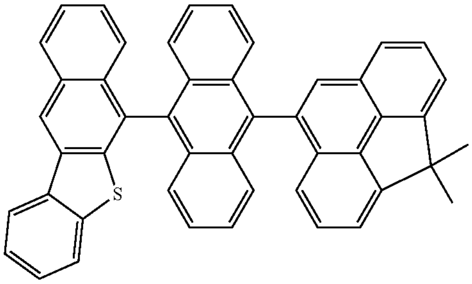

-continued
H1-151
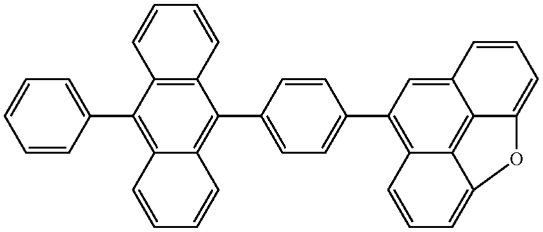
H1-152
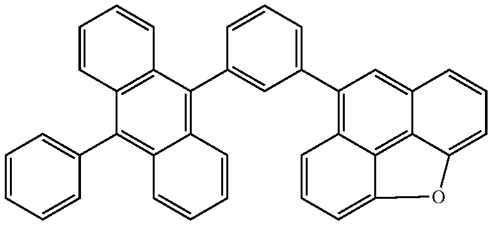
H1-153
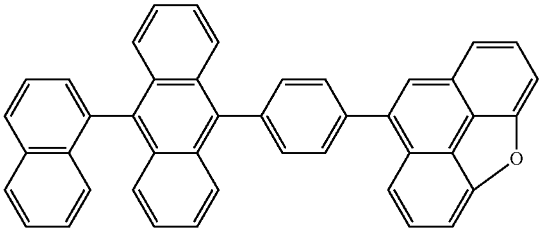
H1-154
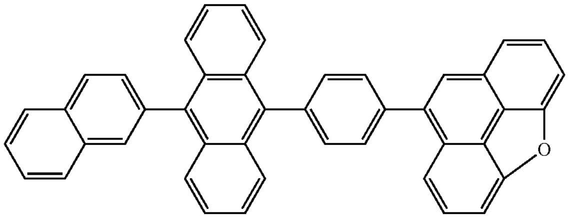
H1-155
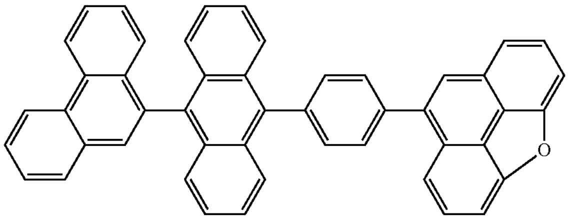
H1-156
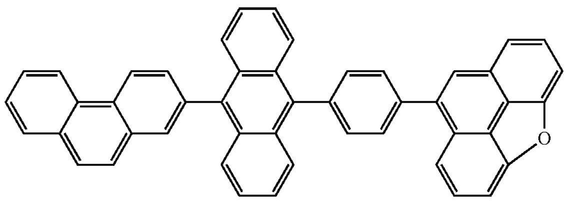
-continued
H1-157
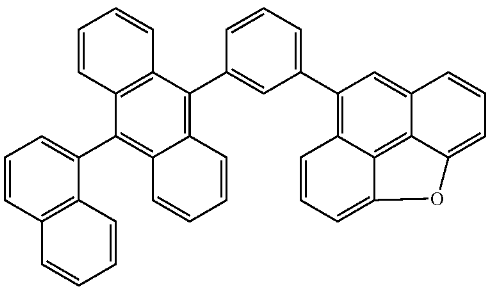
H1-158
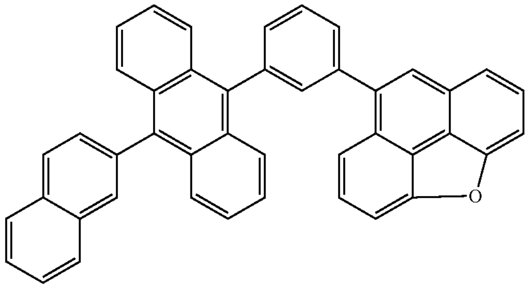
H1-159
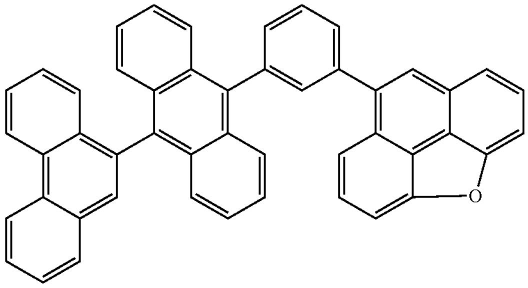
H1-160
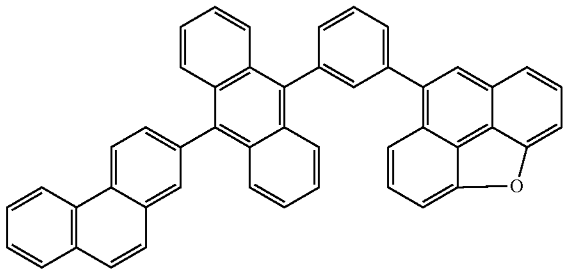
H1-161
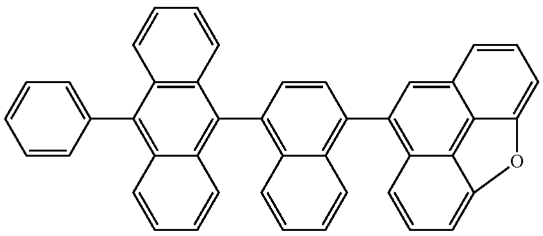

-continued
H1-162
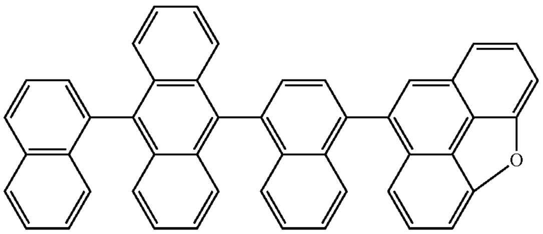
H1-163
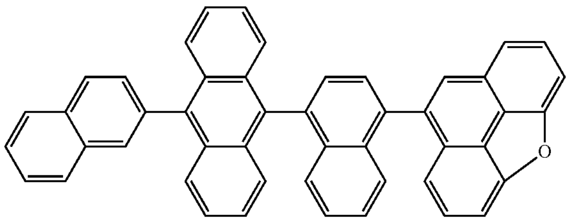
H1-164
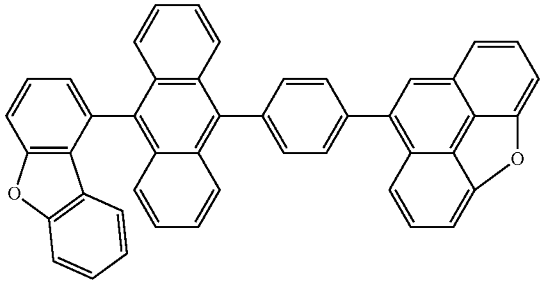
H1-165
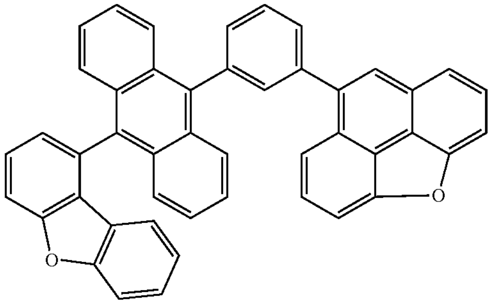
H1-166
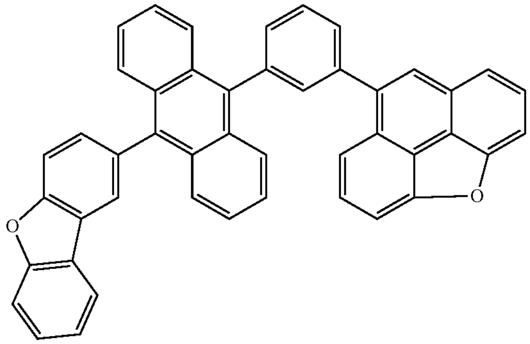
-continued
H1-167
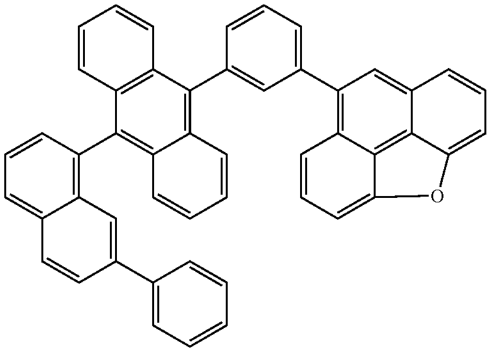
H1-168
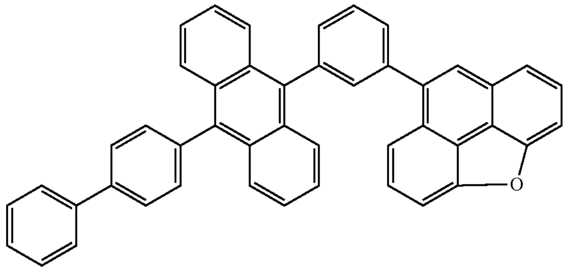
H1-169
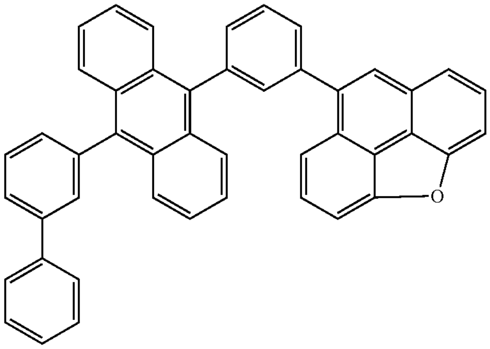
H1-170
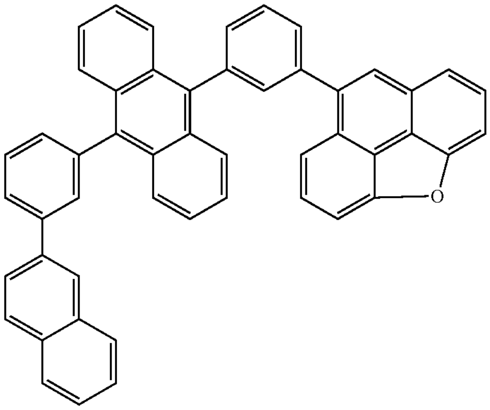

-continued
H1-171
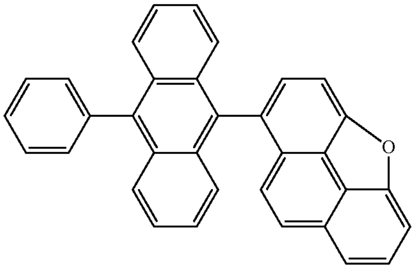
H1-172
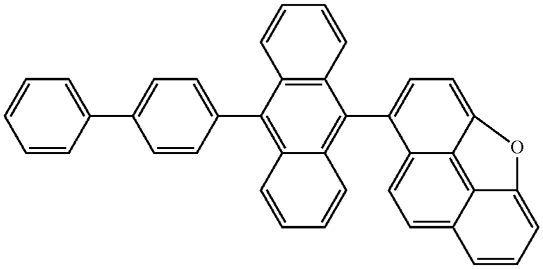
H1-173
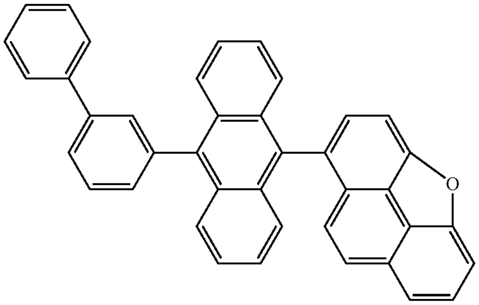
H1-174
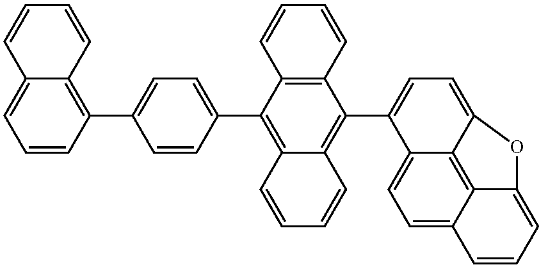
H1-175
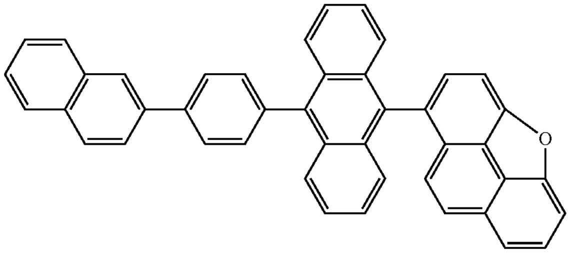
-continued
H1-176
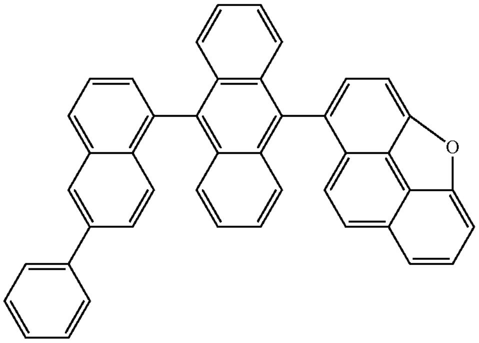
H1-177
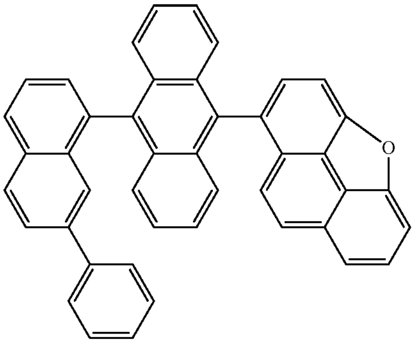
H1-178
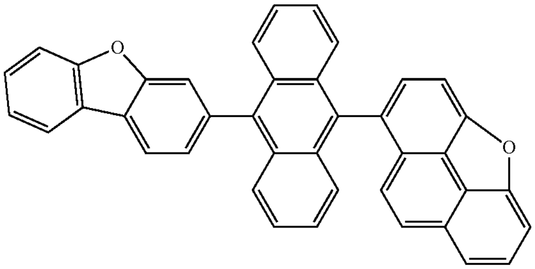
H1-179
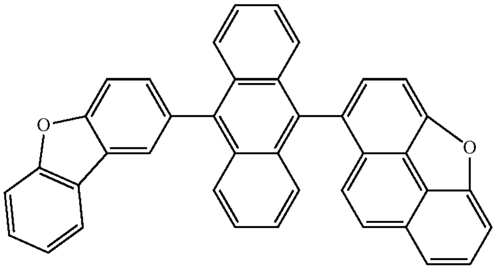
H1-180
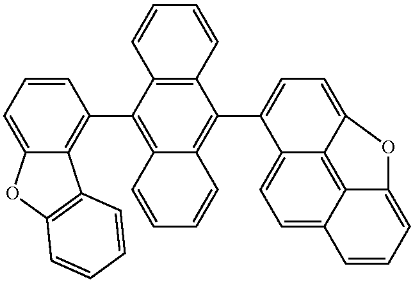

-continued
H1-181
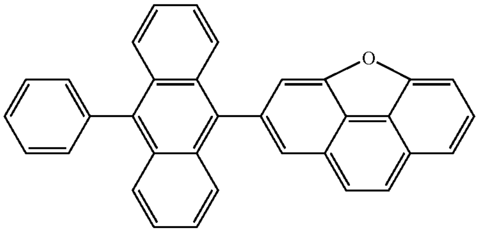
H1-182
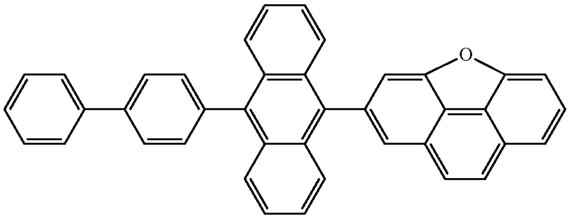
H1-183
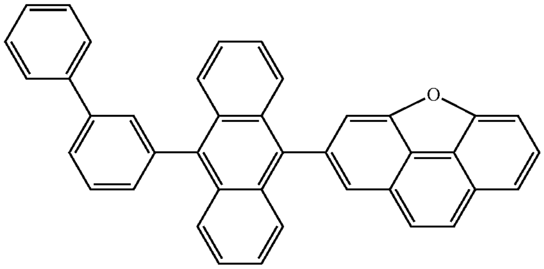
H1-184
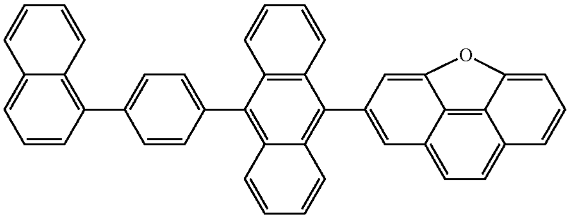
H1-185
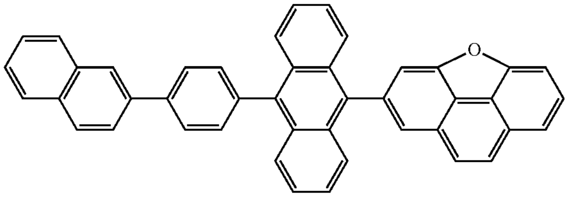
H1-186
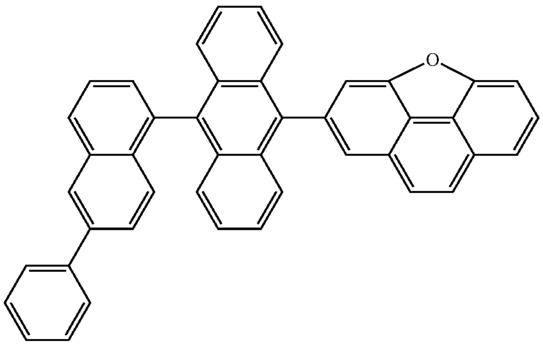
-continued
H1-187
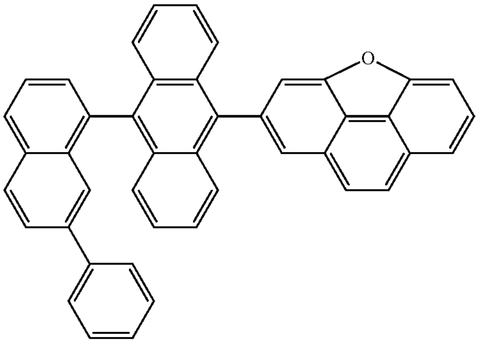
H1-188
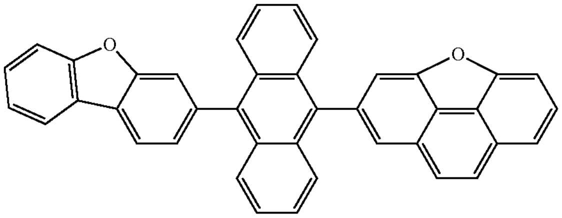
H1-189
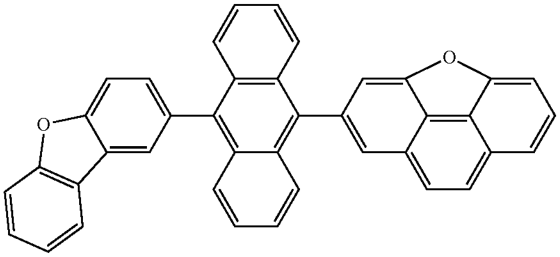
H1-190
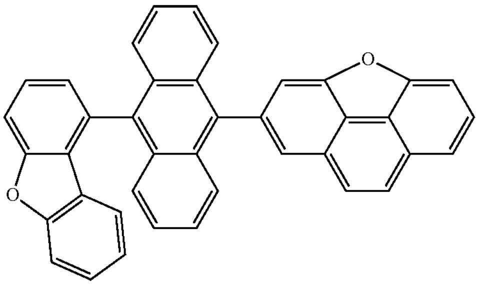
H1-191
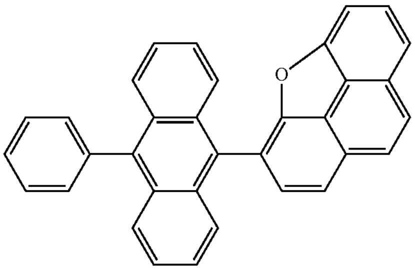

-continued
H1-192
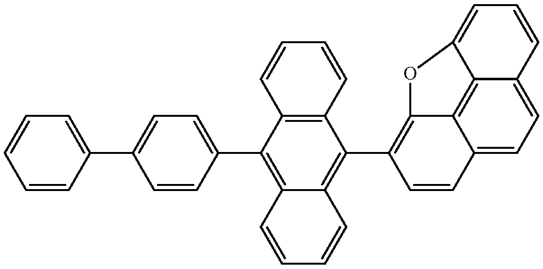
H1-193
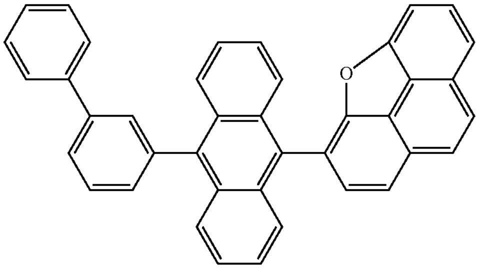
H1-194
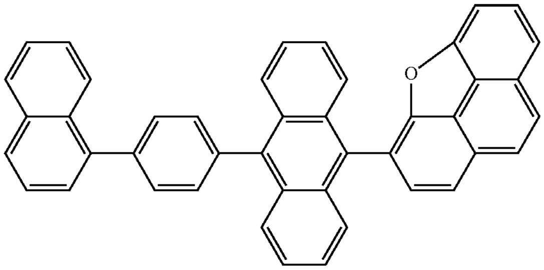
H1-195
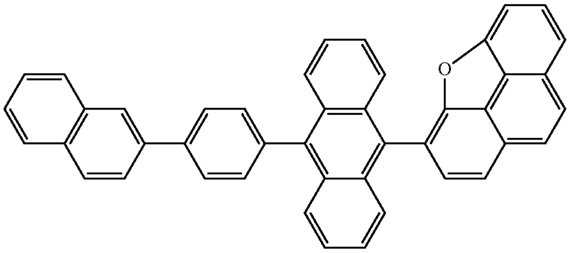
H1-196
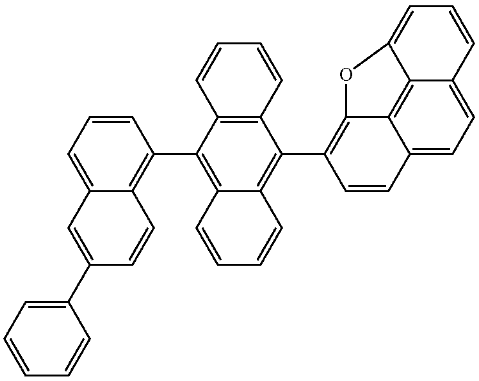
-continued
H1-197
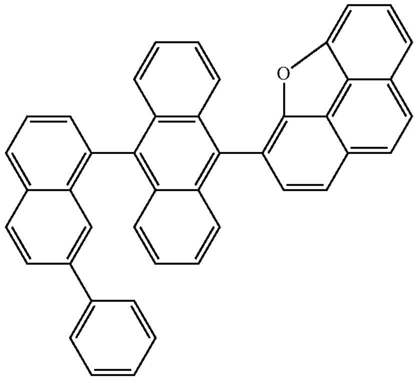
H1-198
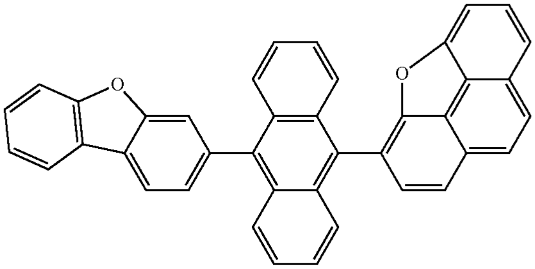
H1-199
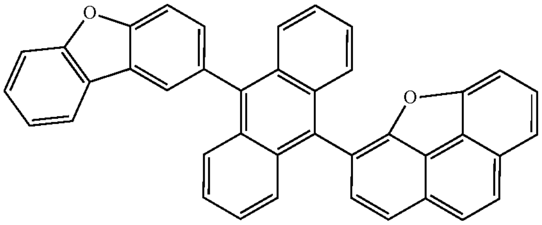
H1-200
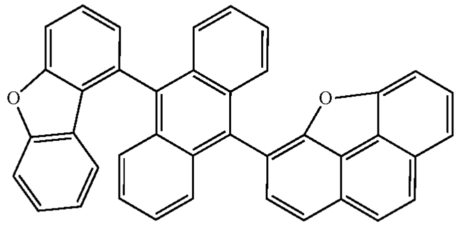
H1-201
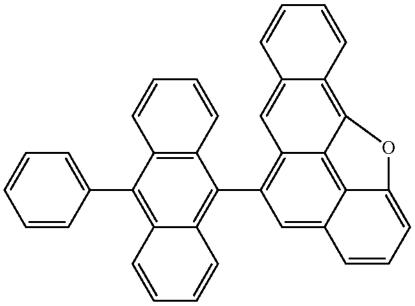

-continued
H1-202
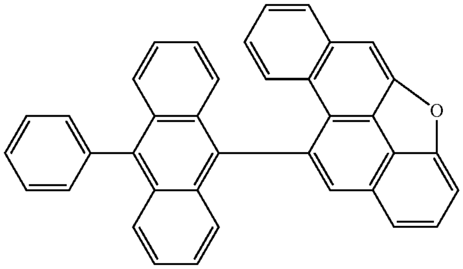
H1-203
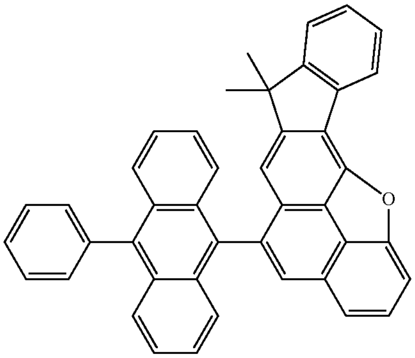
H1-204
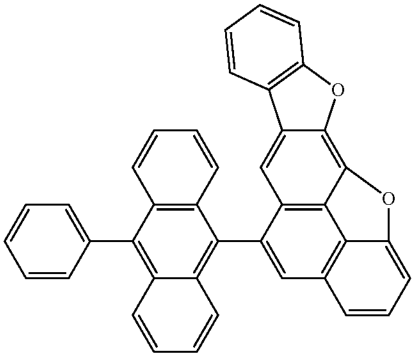
H1-205
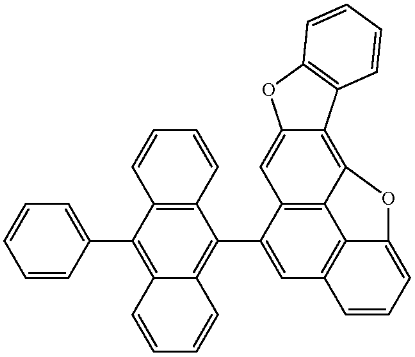
-continued
H1-206
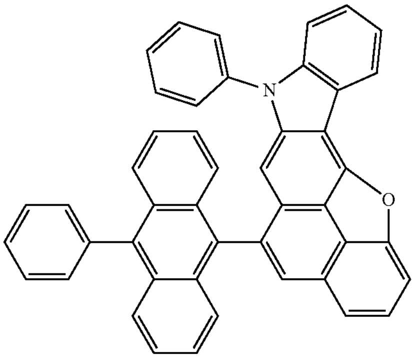
H1-207
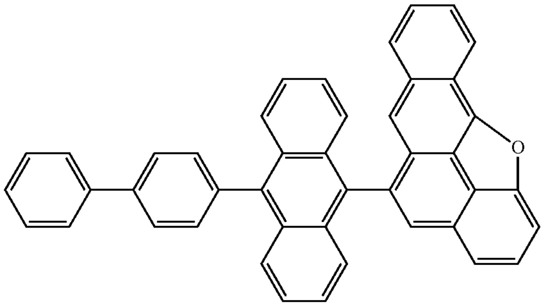
H1-208
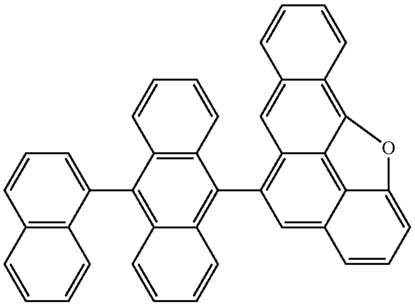
H1-209
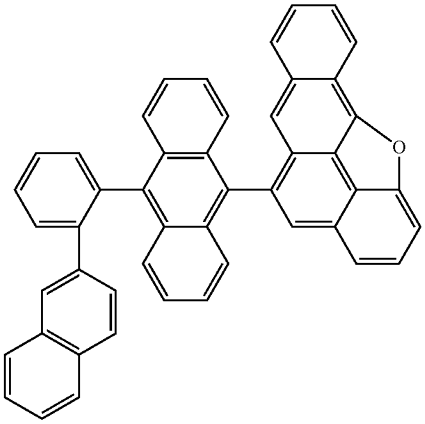

-continued
H1-210
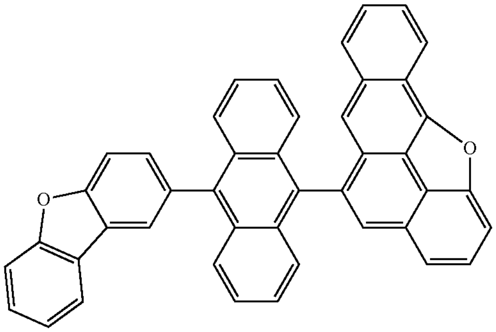
H1-211
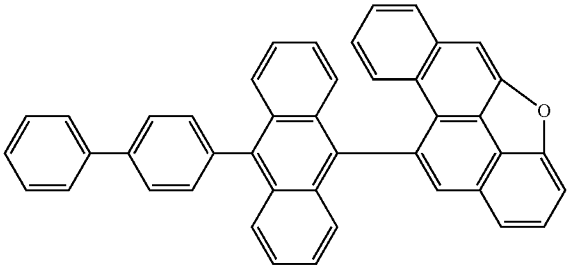
H1-212
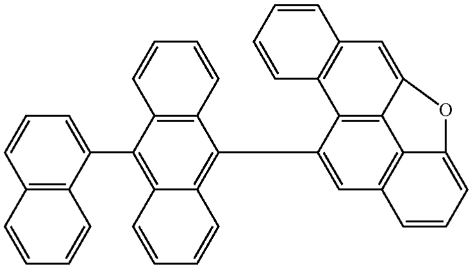
H1-213
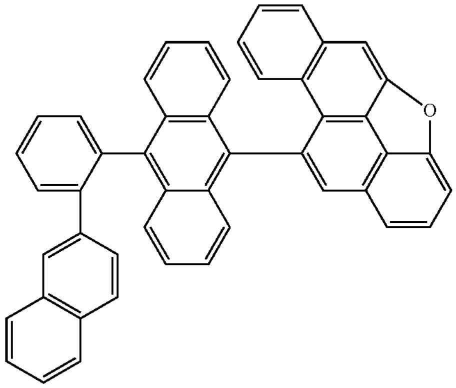
H1-214
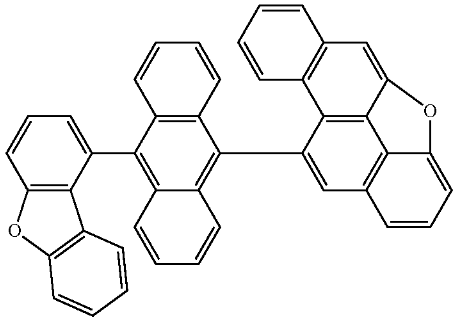
-continued
H1-215
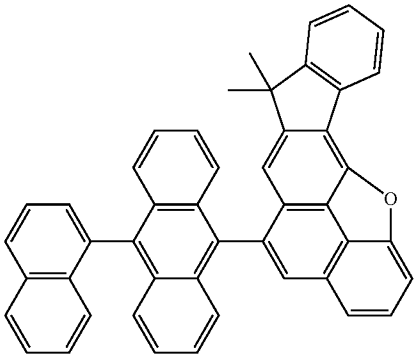
H1-216
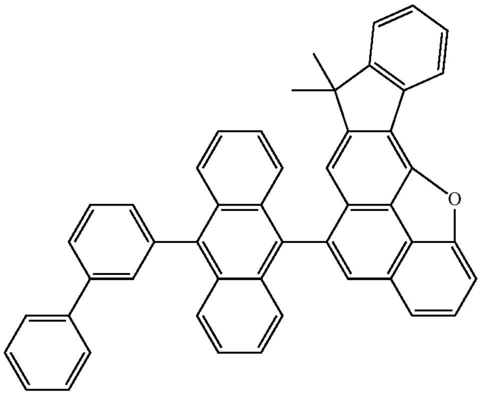
H1-217
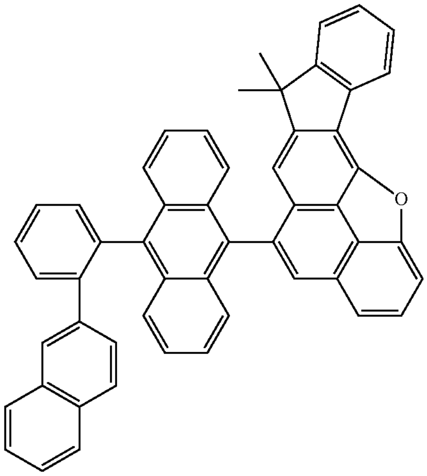
H1-218
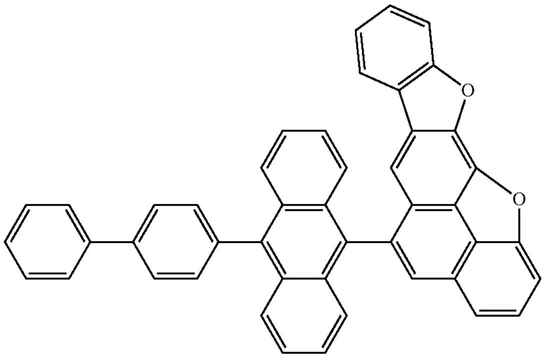

-continued
H1-219
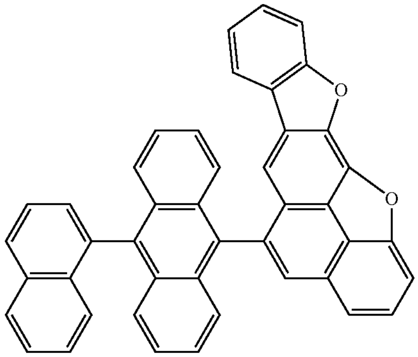
H1-220
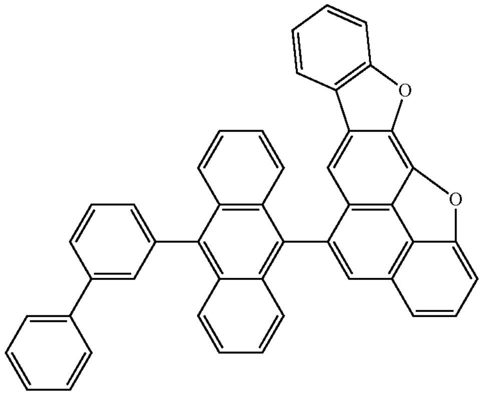
H1-221
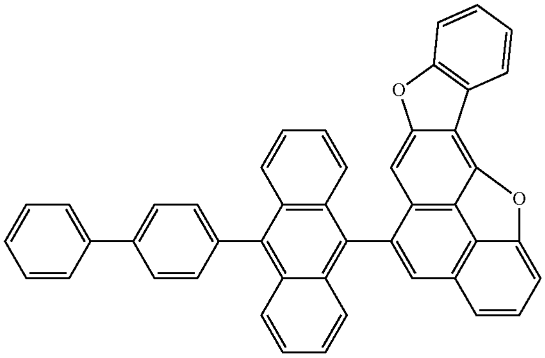
H1-222
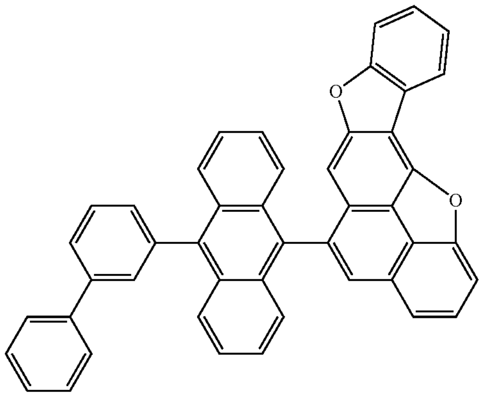
-continued
H1-223
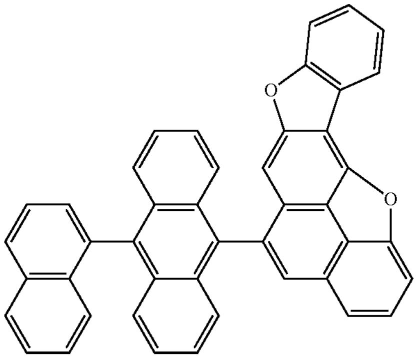
H1-224
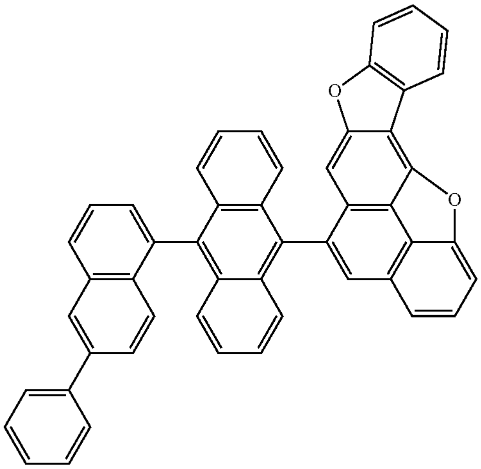
H1-225
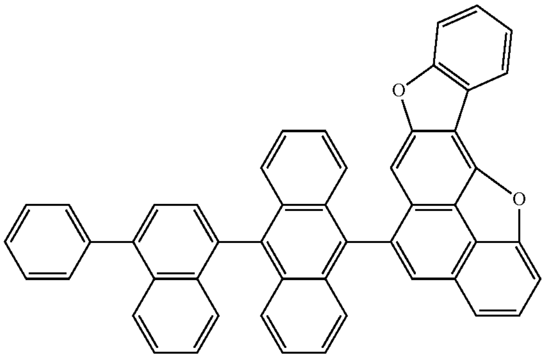
H1-226
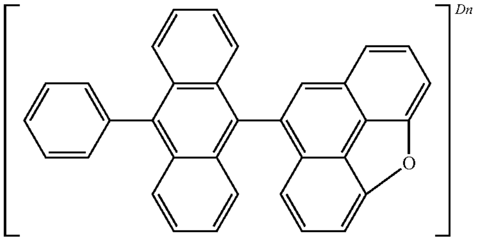

-continued
H1-227
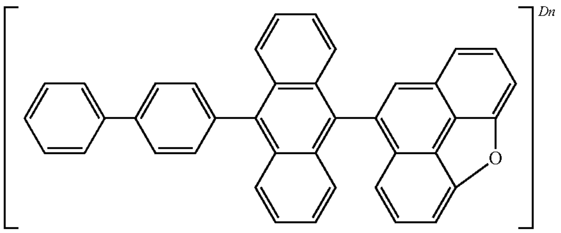
H1-228
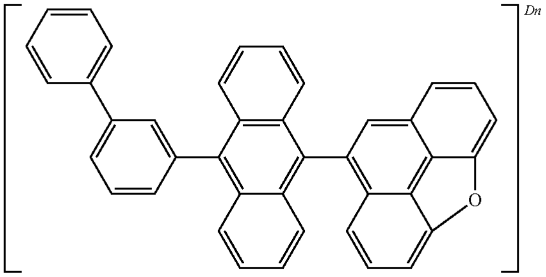
H1-229
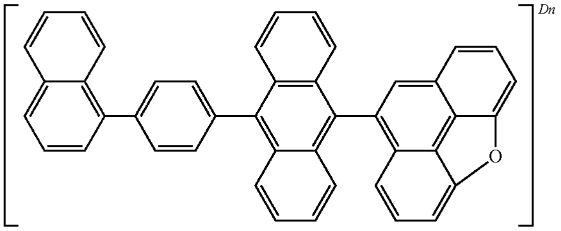
H1-230
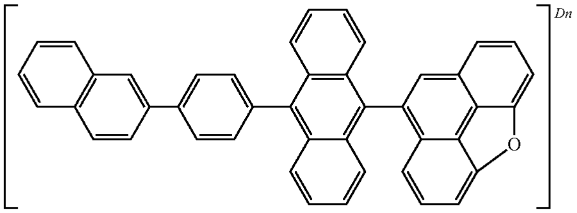
H1-231
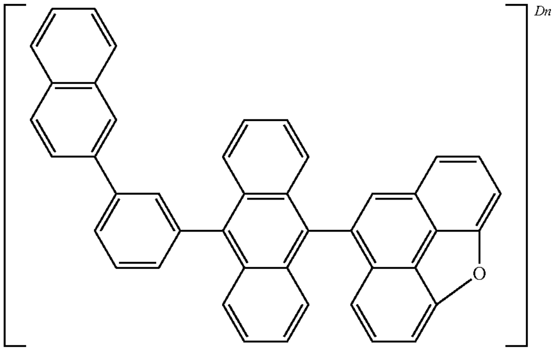
-continued
H1-232
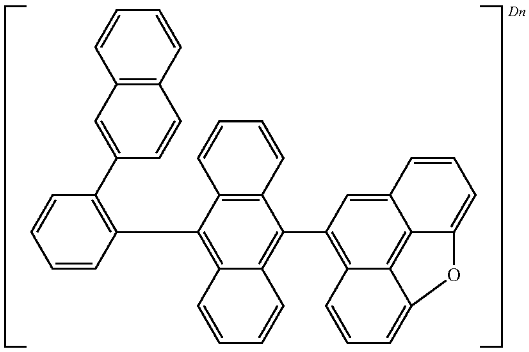
H1-233
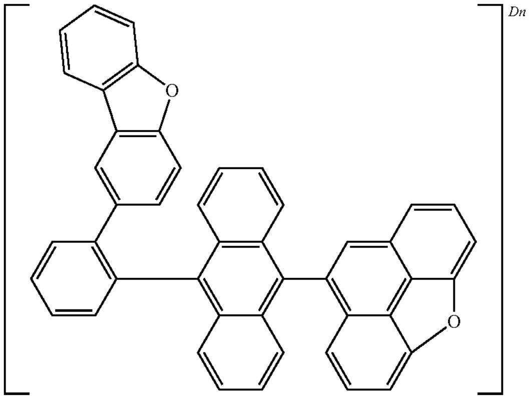
H1-234
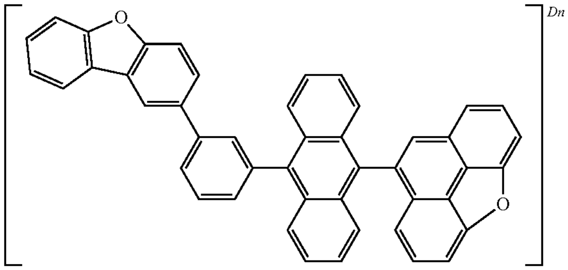
H1-235
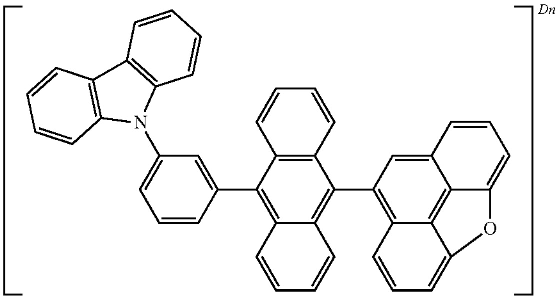

-continued
H1-236
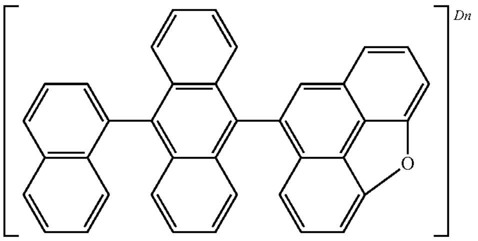
H1-237
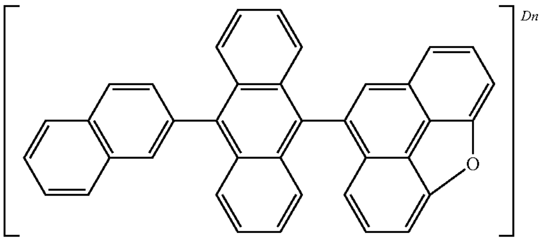
H1-238
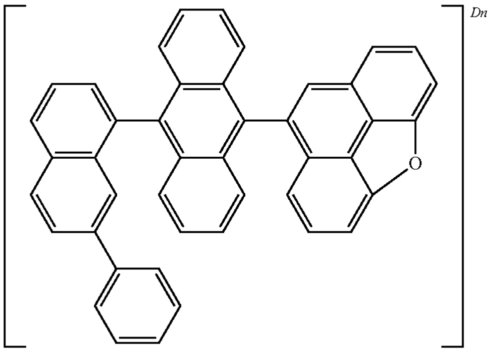
H1-239
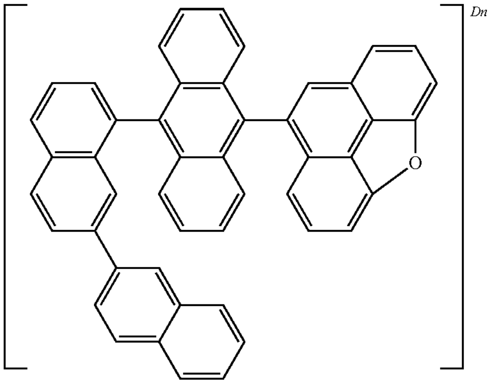
-continued
H1-240
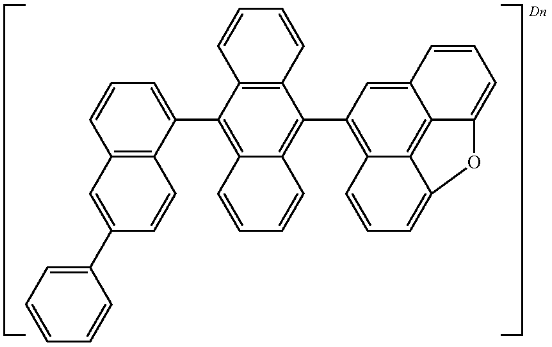
H1-241
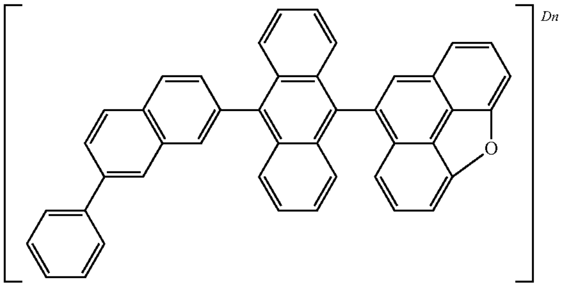
H1-242
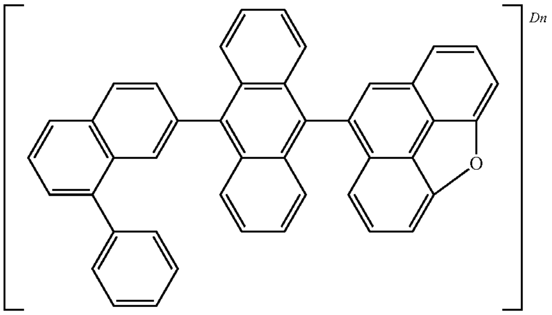
H1-243
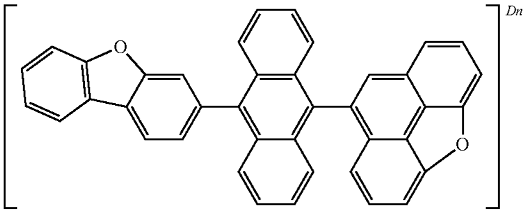
H1-244
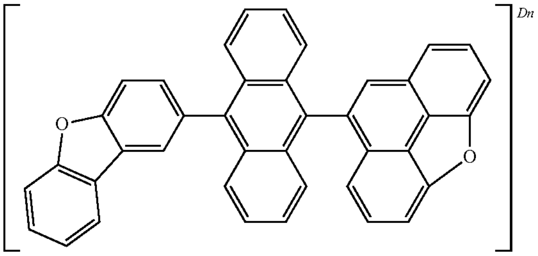

-continued
H1-245
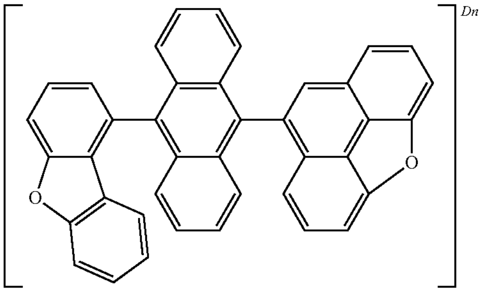
H1-246
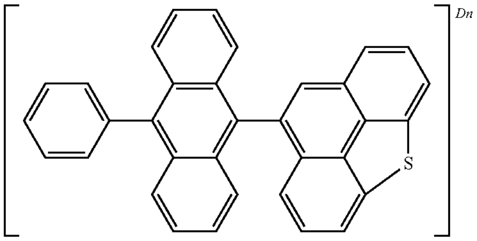
H1-247
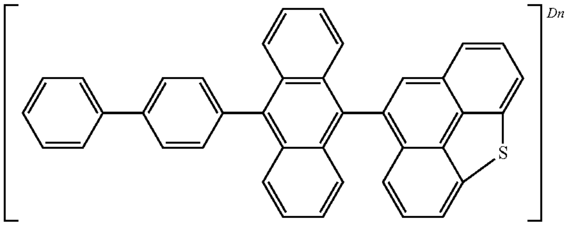
H1-248
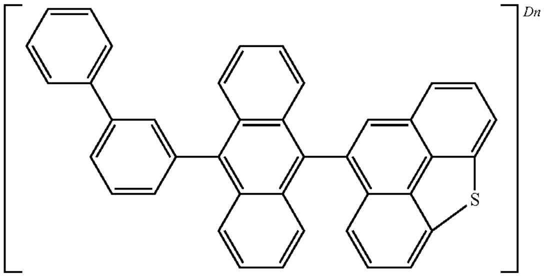
H1-249
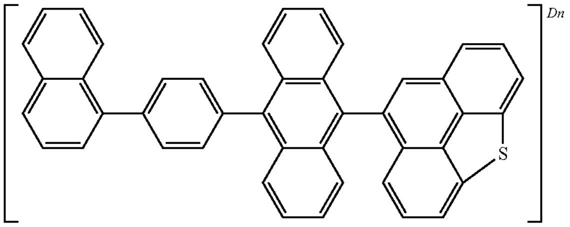
H1-250
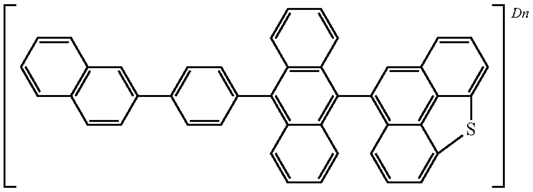
-continued
H1-251
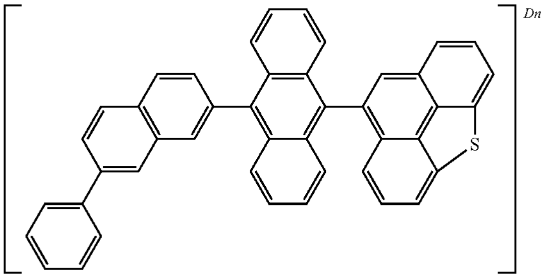
H1-252
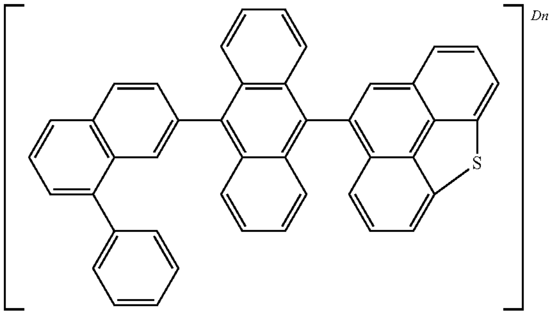
H1-253
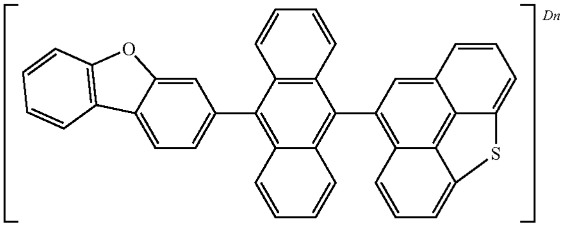
H1-254
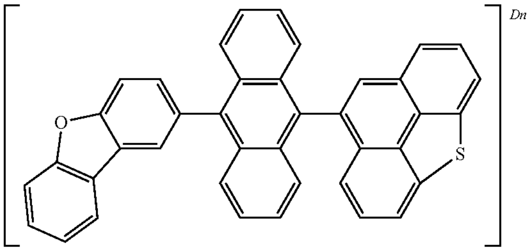
H1-255
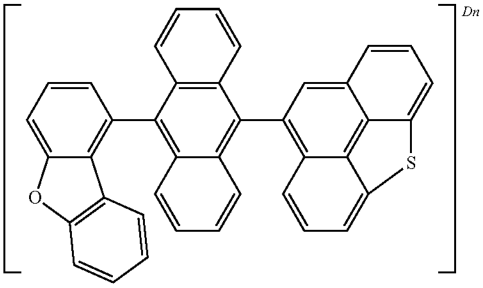

-continued
H1-256
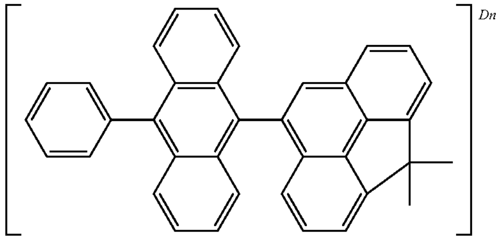
H1-257
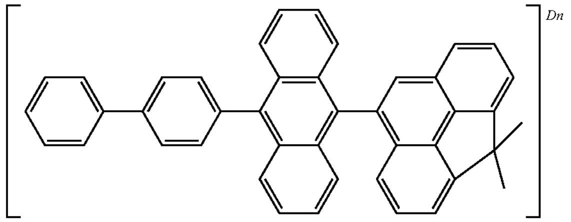
H1-258
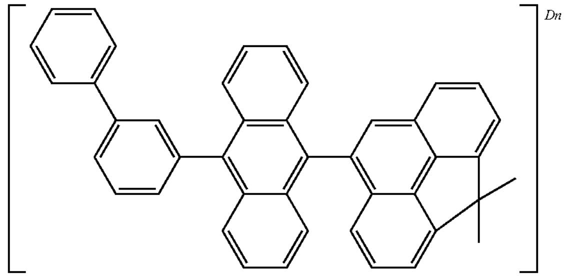
H1-259
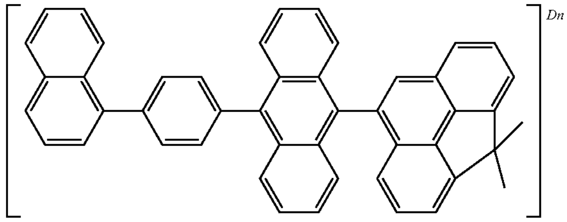
H1-260
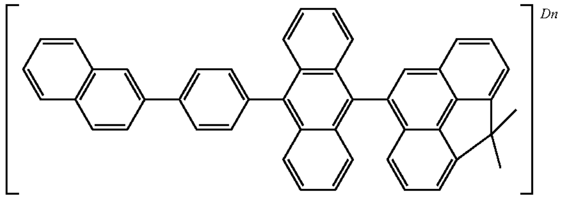
H1-261
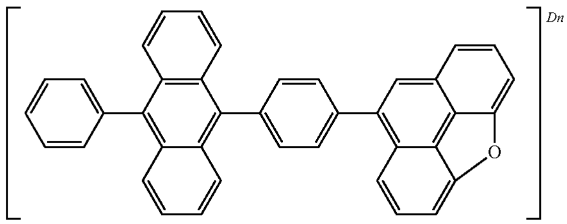
-continued
H1-262
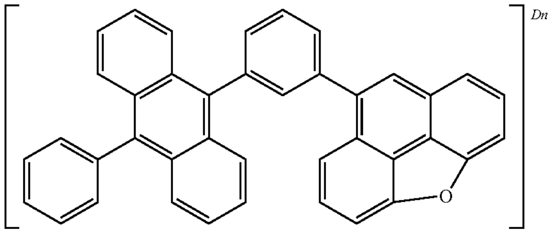
H1-263
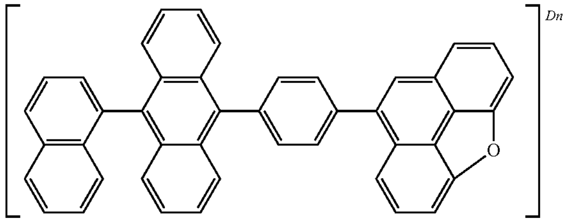
H1-264
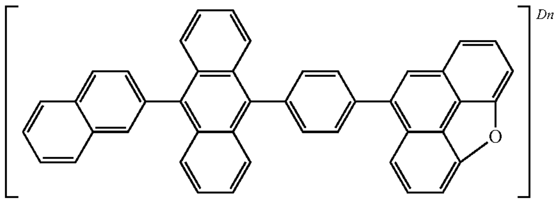
H1-265
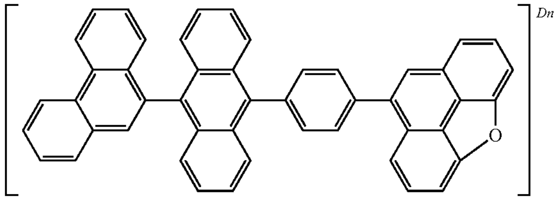
H1-266
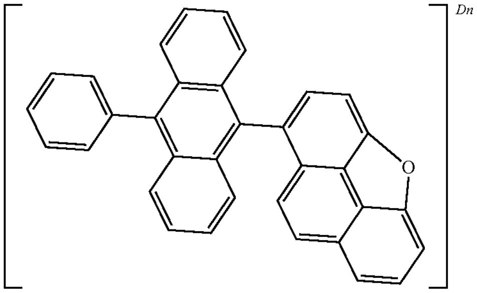
H1-267
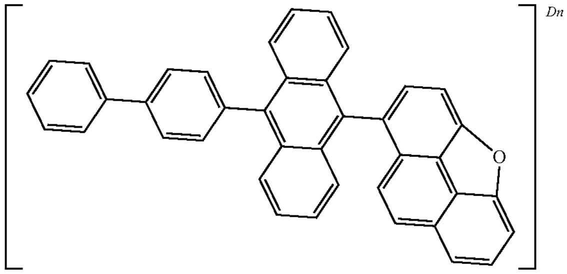

-continued
H1-268
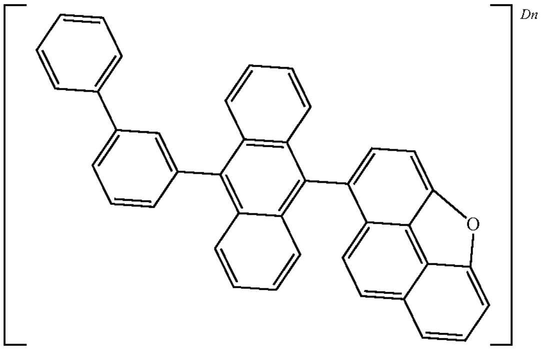
H1-269
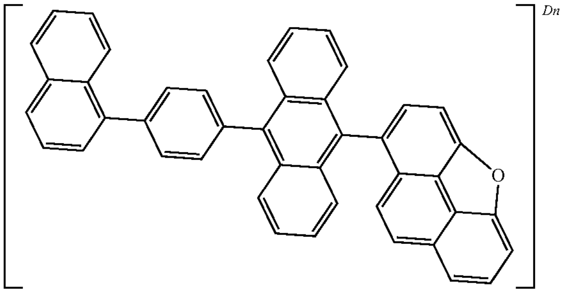
H1-270
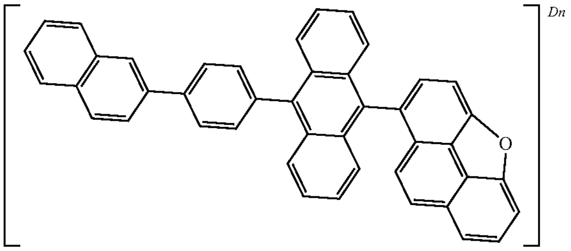
H1-271
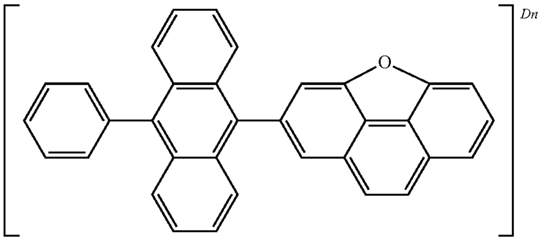
H1-272
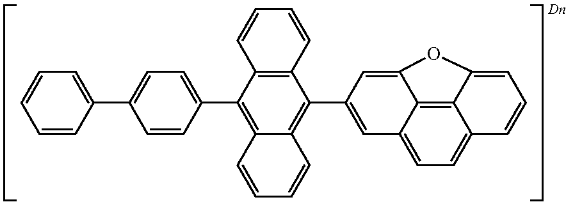
-continued
H1-273
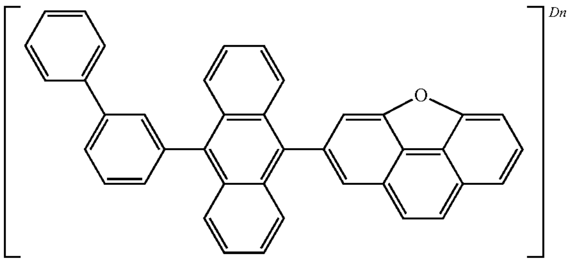
H1-274
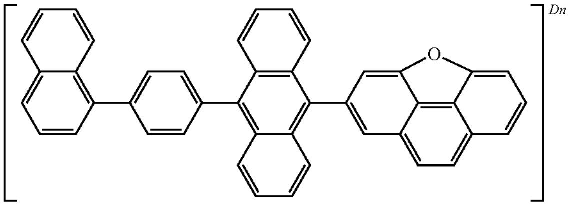
H1-275
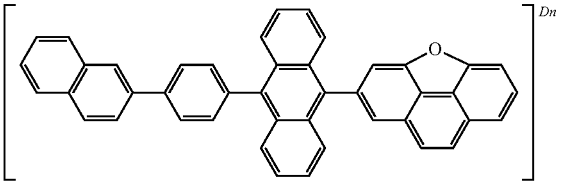
H1-276
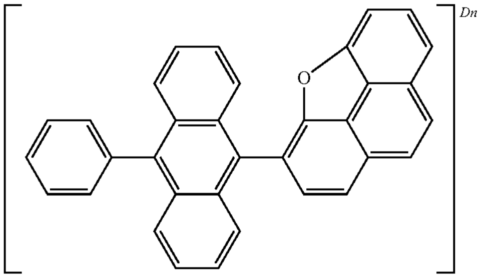
H1-277
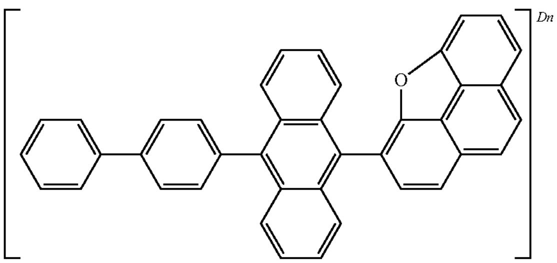

-continued
H1-278
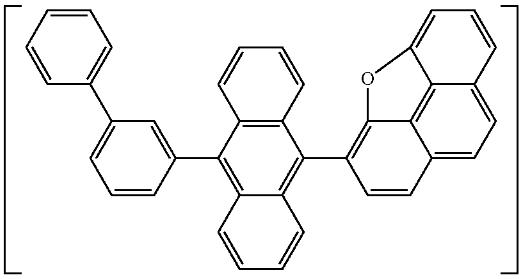
H1-279
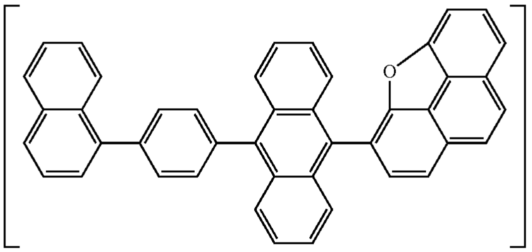
H1-280
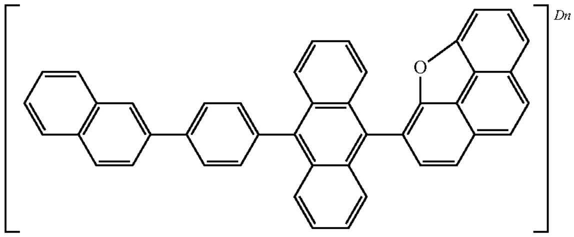
H1-281
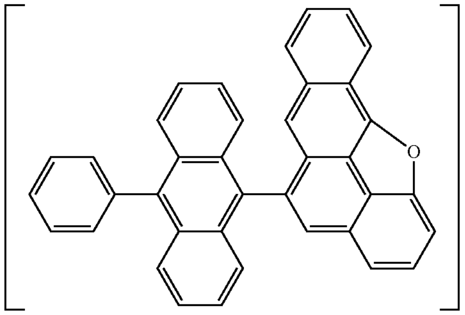
H1-282
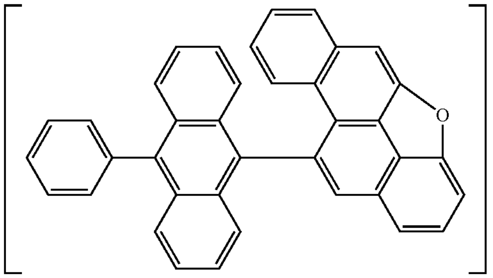
-continued
H1-283
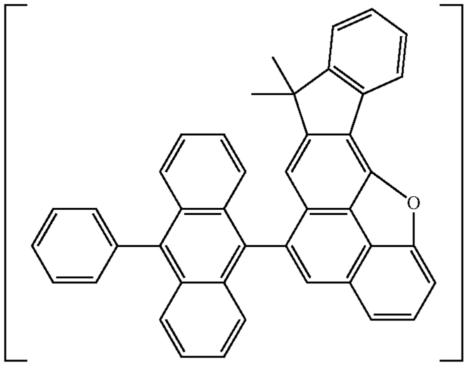
H1-284
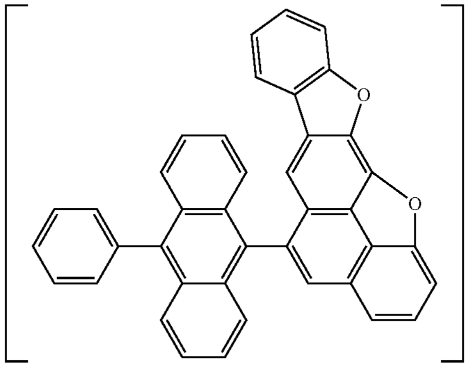
H1-285
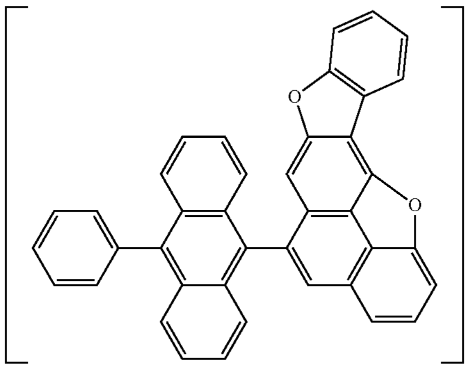

-continued
H1-286
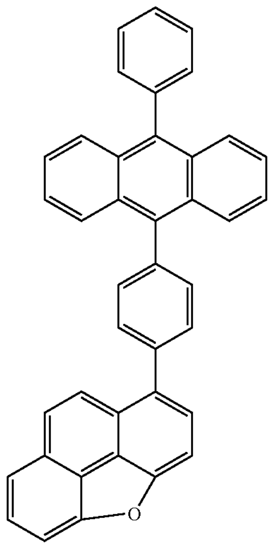
-continued
H1-288
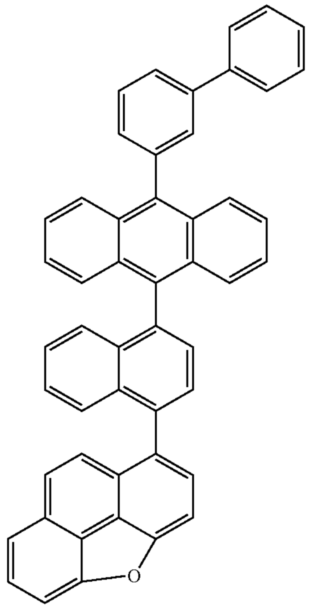
H1-287
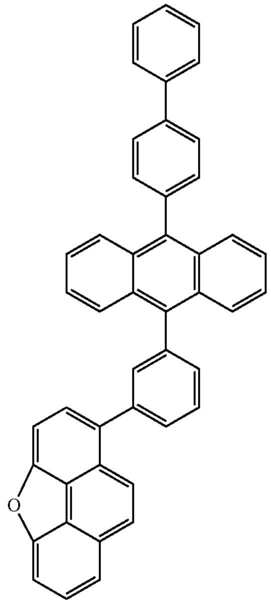
H1-289
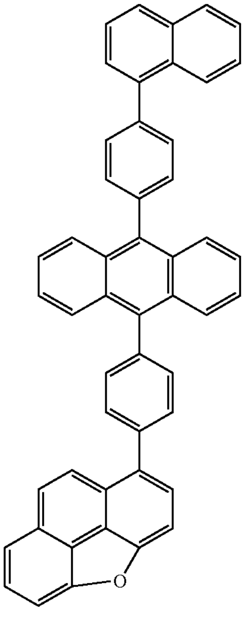

-continued
-continued
H1-290
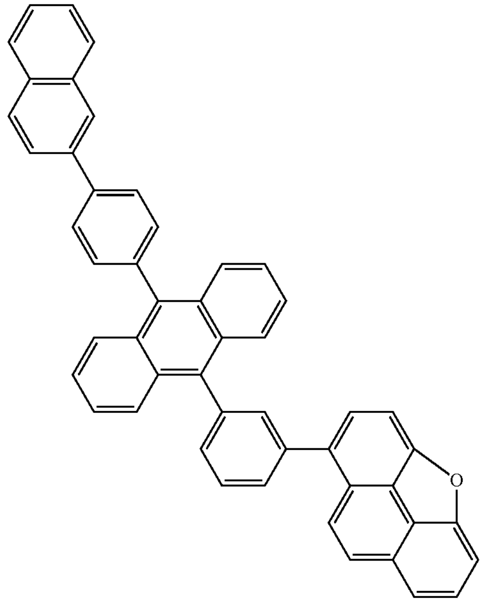
H1-292
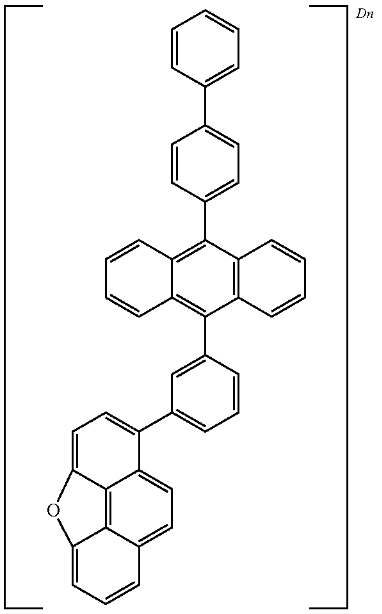
H1-291
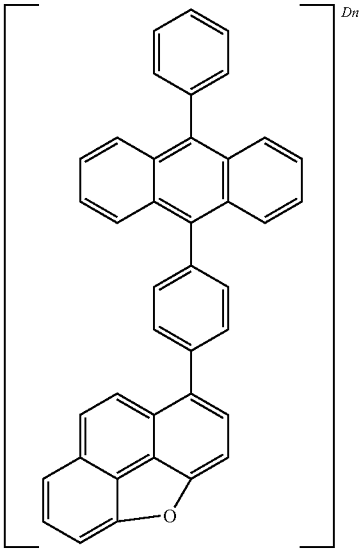
H1-293
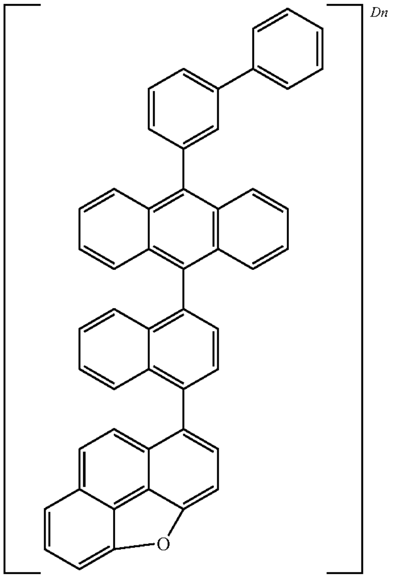

-continued
H1-294
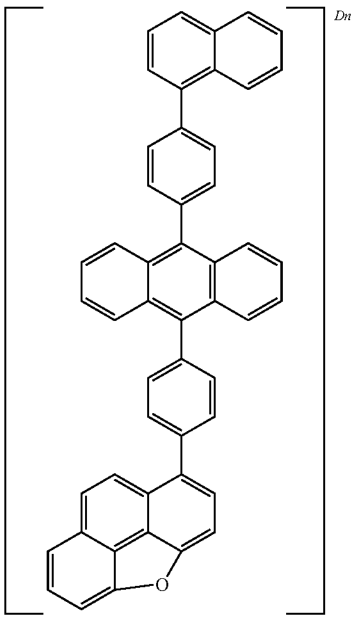
and
H1-295
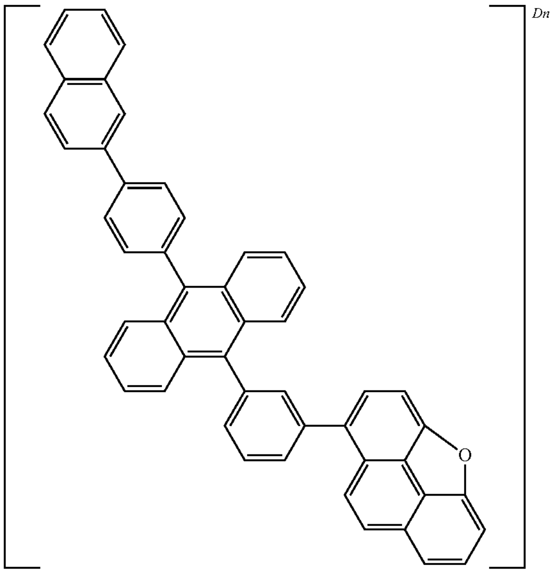
wherein, $D_n$ represents that n hydrogens are replaced with deuterium; and n represents an integer of 1 to 50.
6. The plurality of light-emitting materials according to claim 1, wherein the second compound is at least one selected from the group consisting of the following compounds:
C-1
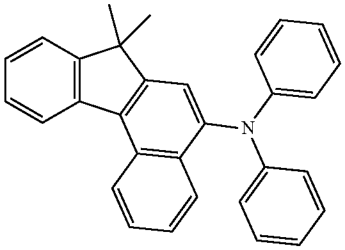
C-2
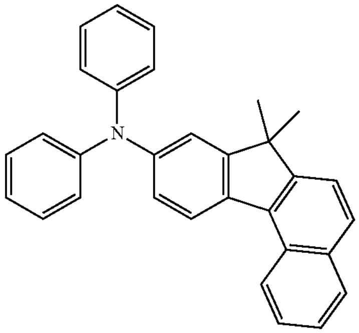
C-3
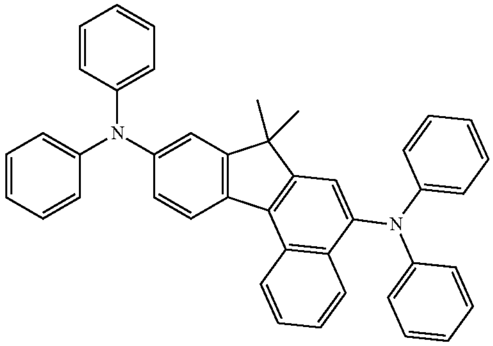
C-4
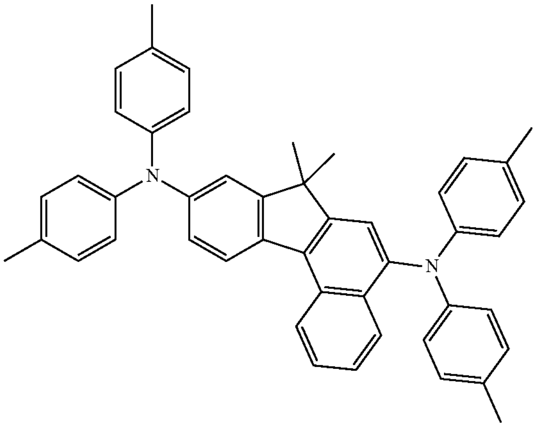

-continued
C-5
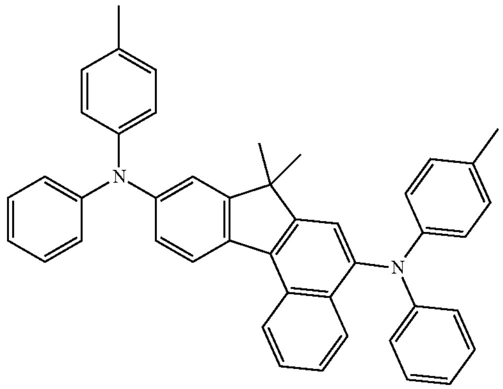
C-6
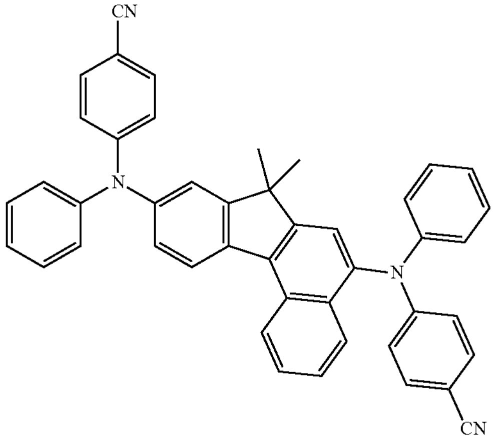
C-7
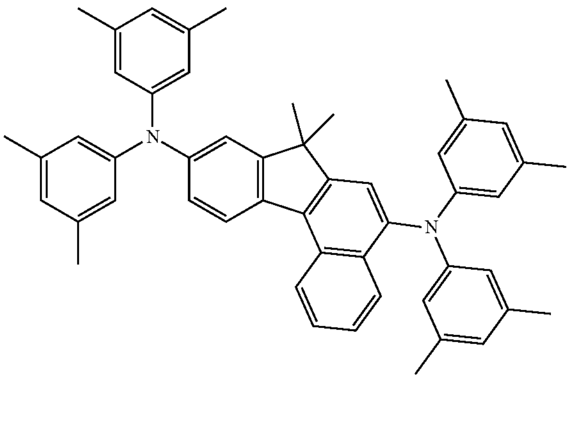
-continued
C-8
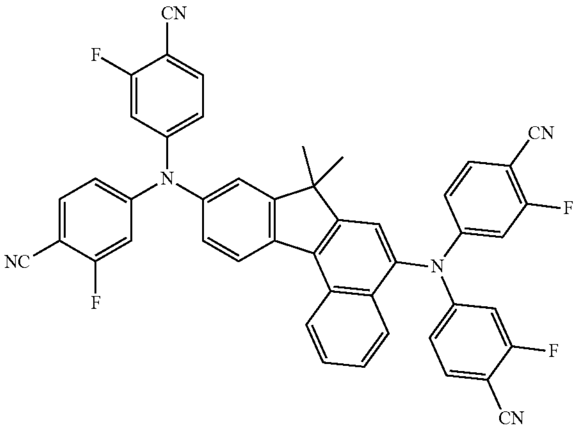
C-9
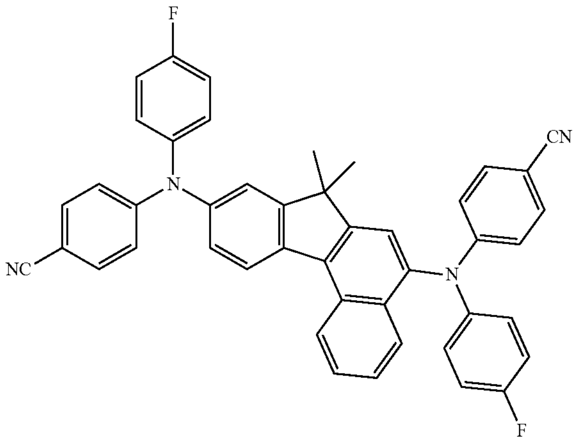
C-10
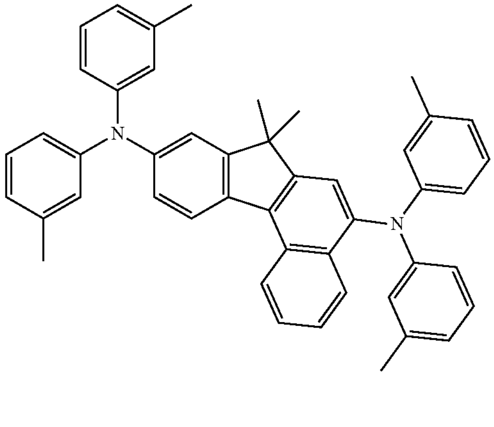

C-11
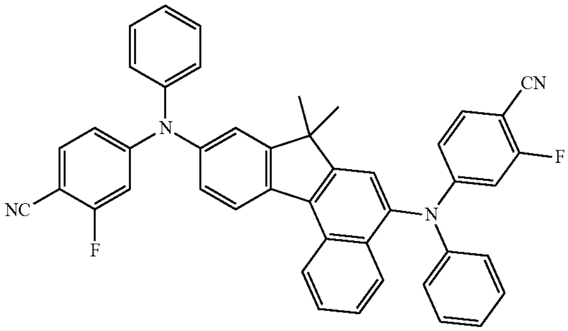
C-12
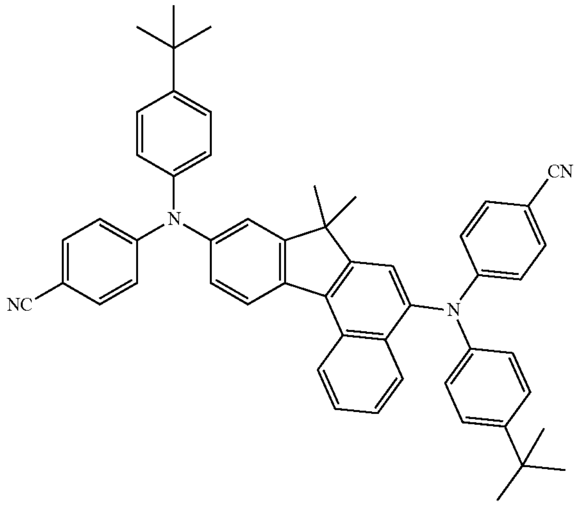
C-13
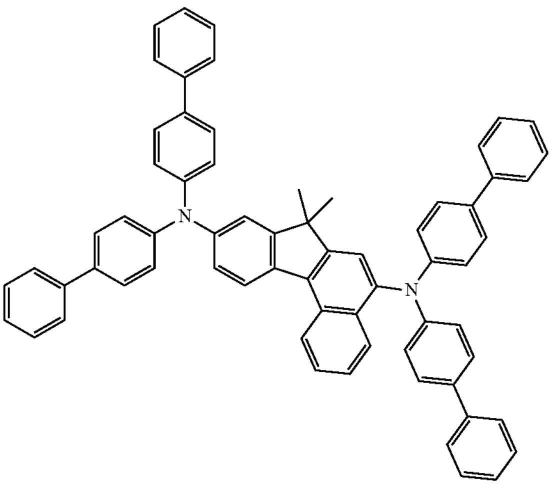
C-14
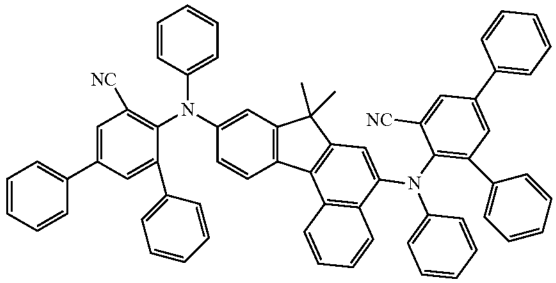
C-15
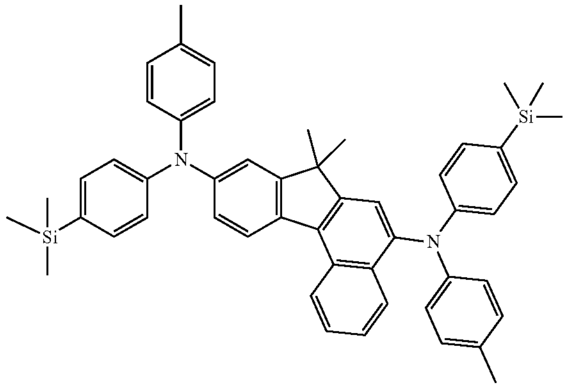
C-16
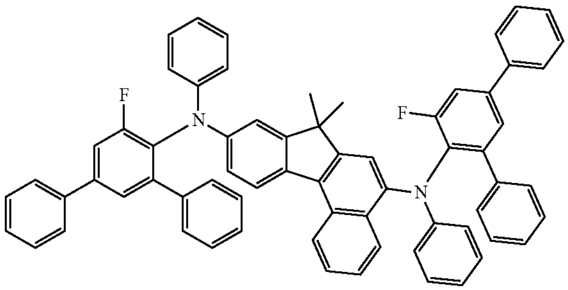
C-17
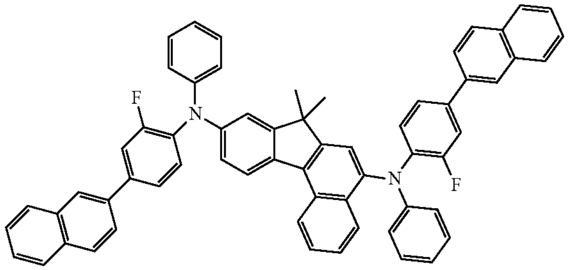

-continued
C-18
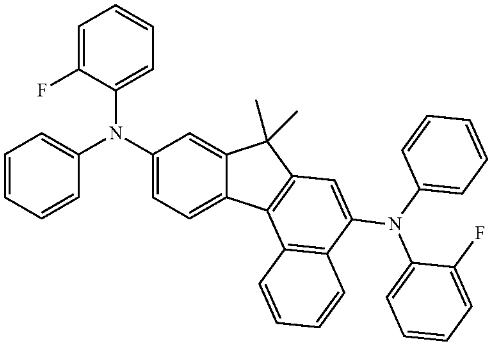
C-19
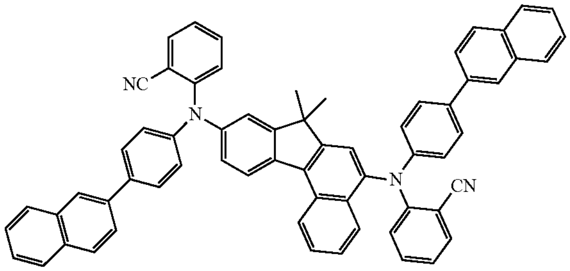
C-20
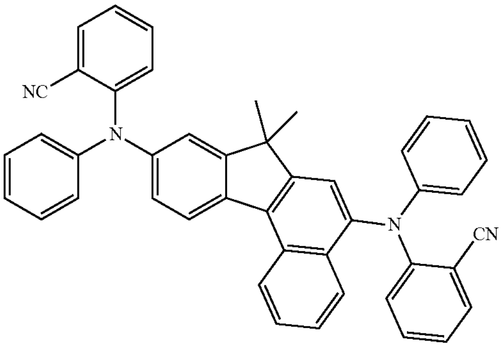
C-21
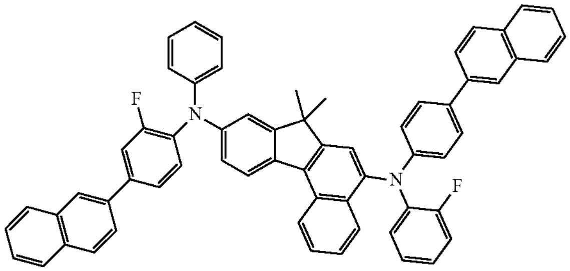
C-22
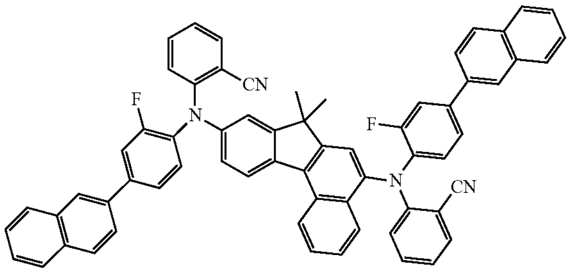
-continued
C-23
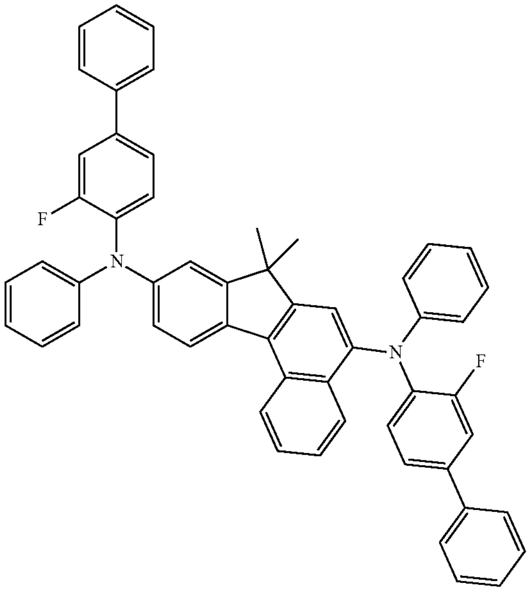
C-24
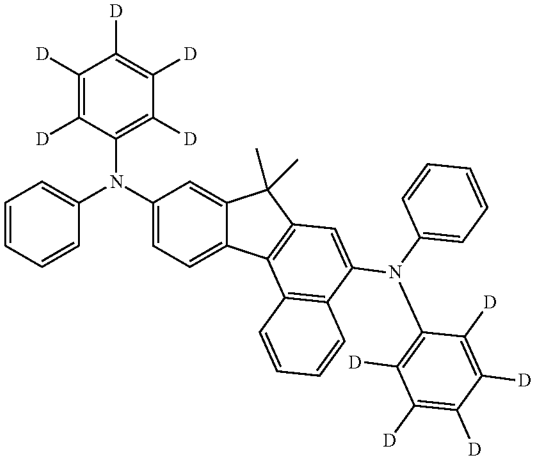
C-25
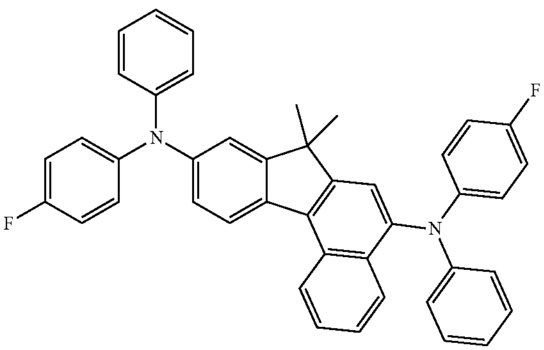

-continued
C-26
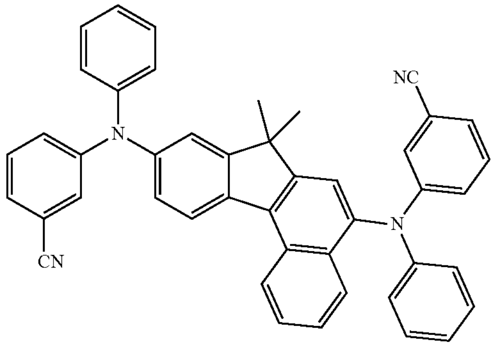
C-27
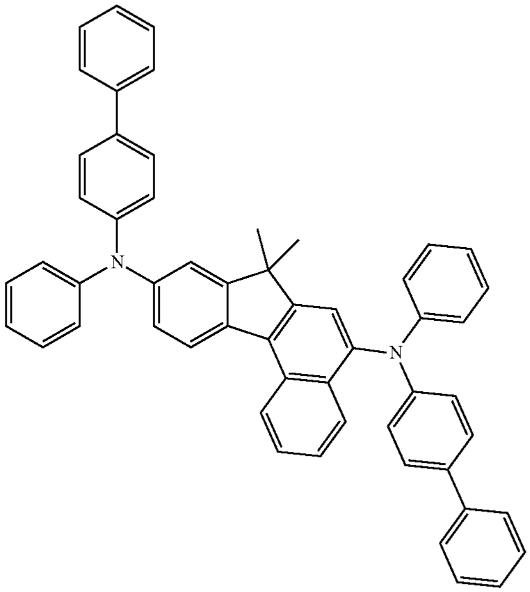
C-28
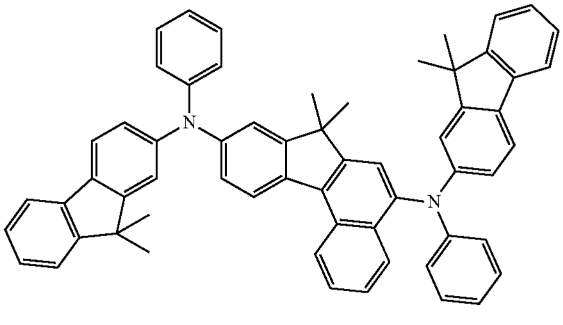
-continued
C-29
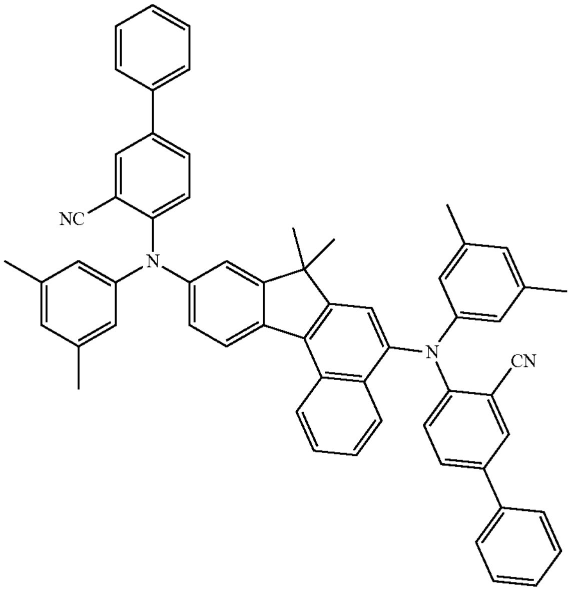
C-30
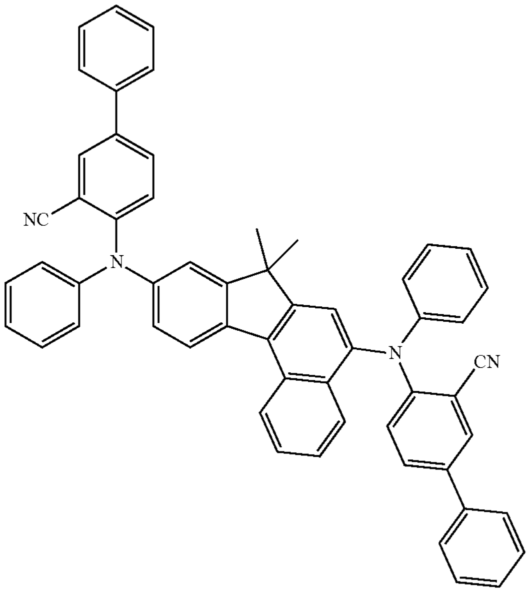
C-31
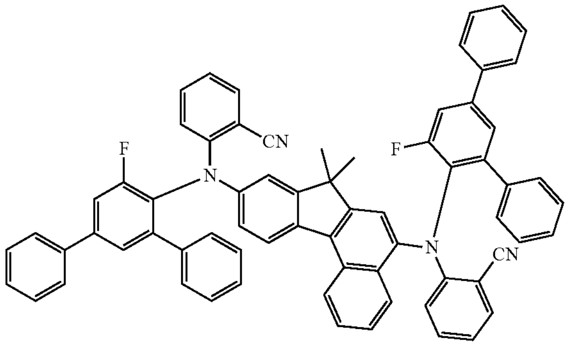

C-32
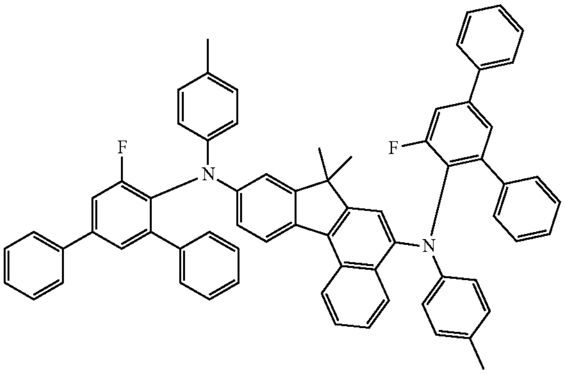
C-33
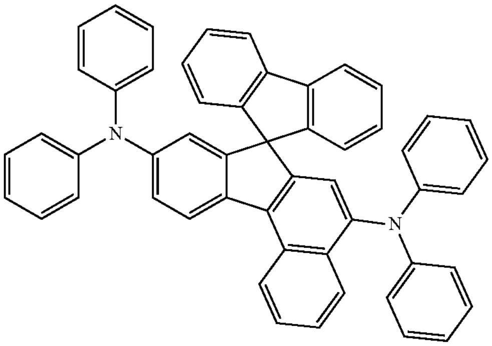
C-34
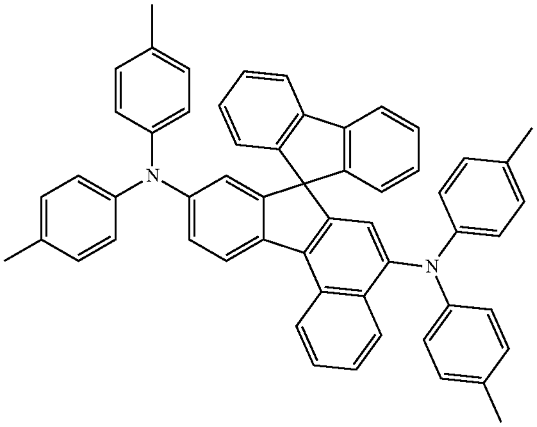
C-35
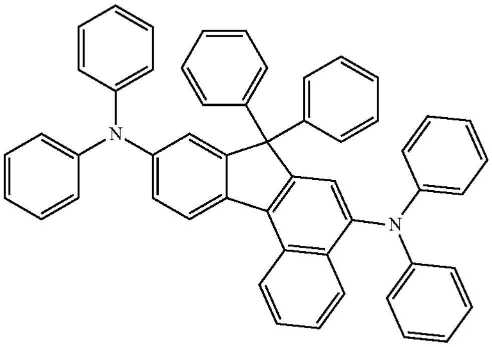
C-36
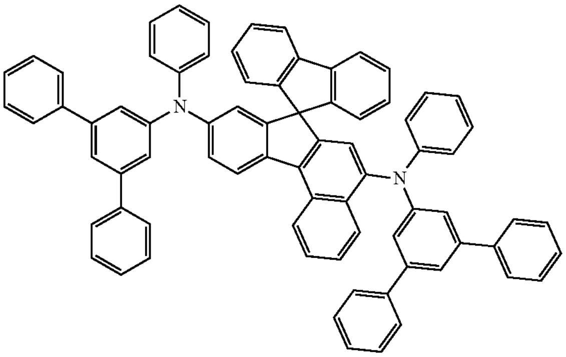
C-37
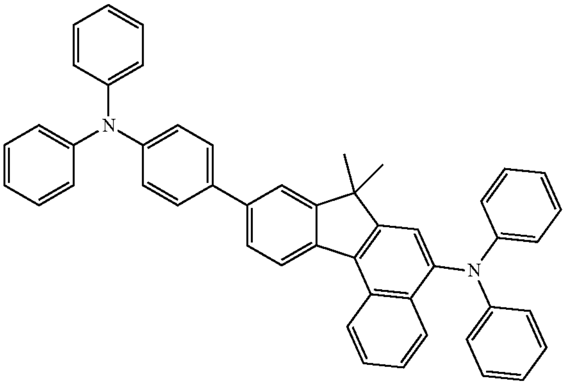
C-38
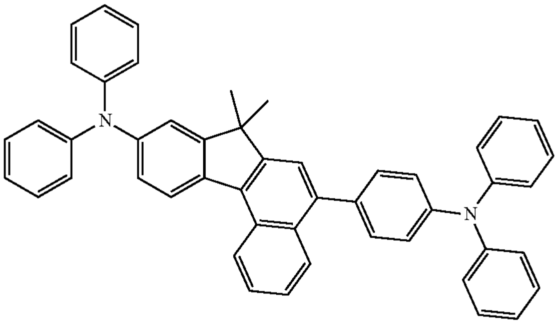
C-39
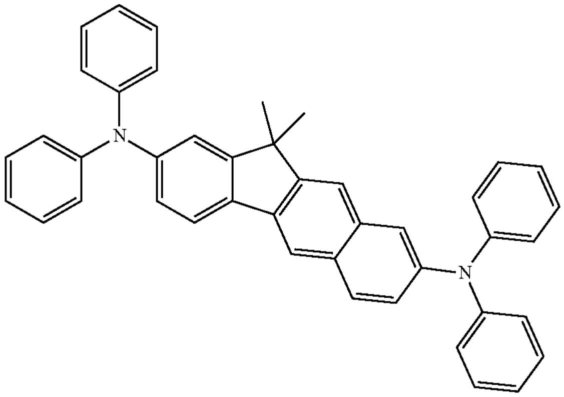

-continued
C-40
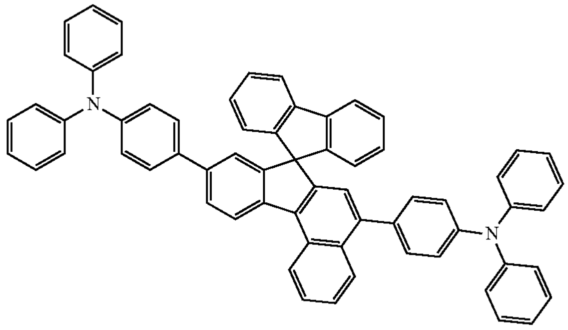
C-41
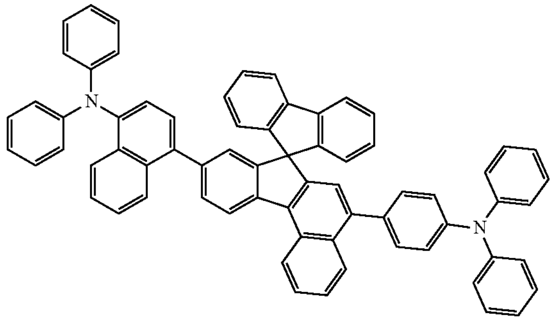
C-42
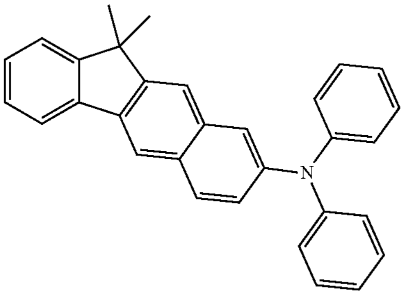
C-43
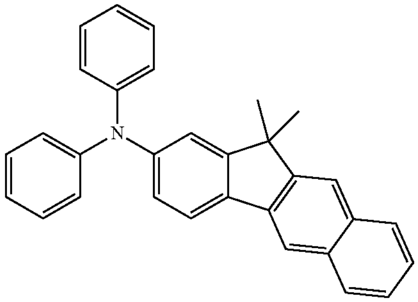
-continued
C-44
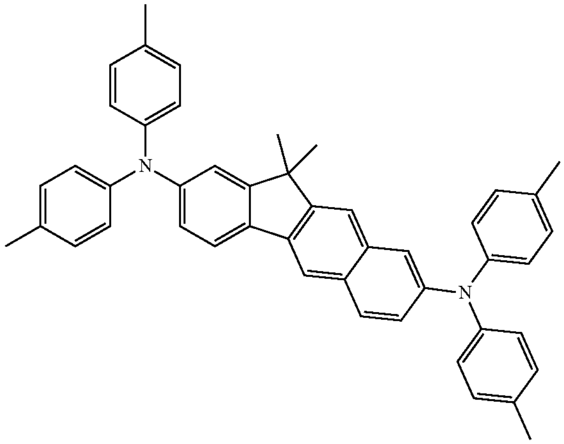
C-45
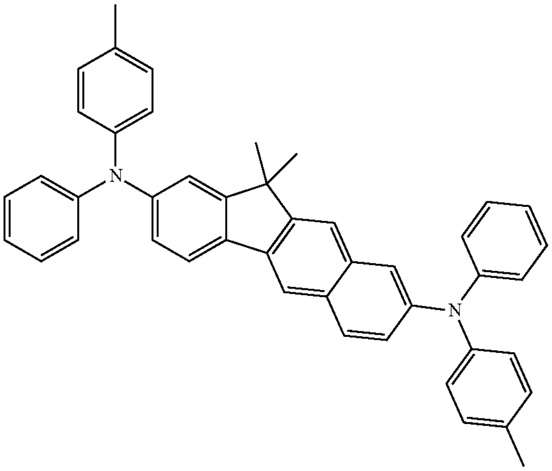
C-46
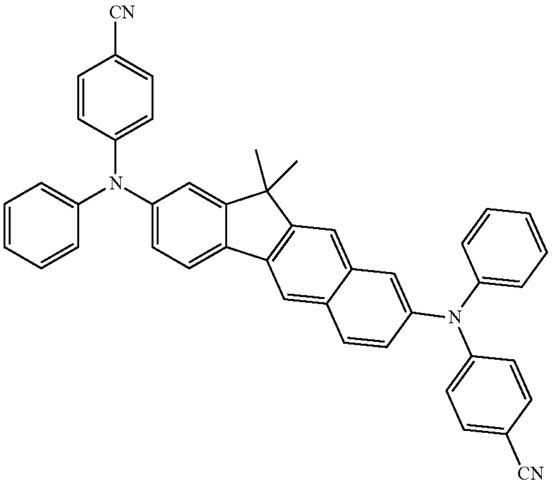

-continued
C-47
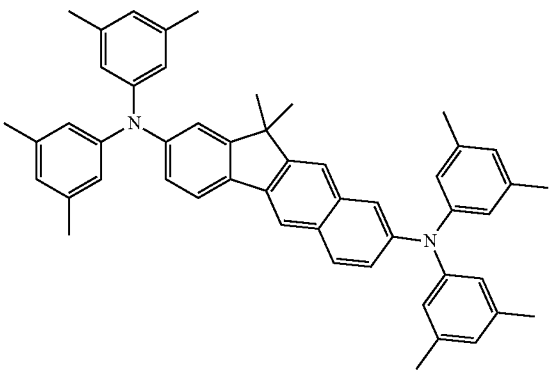
C-48
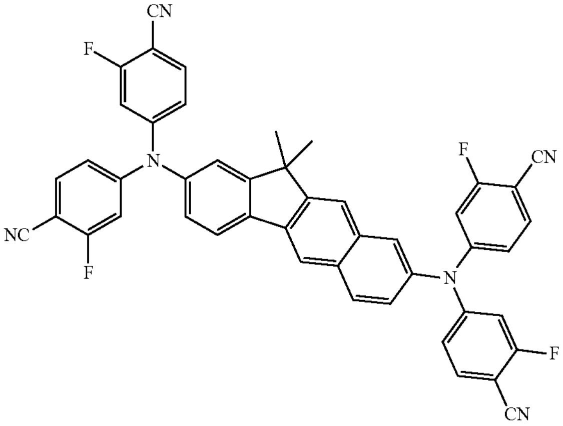
C-49
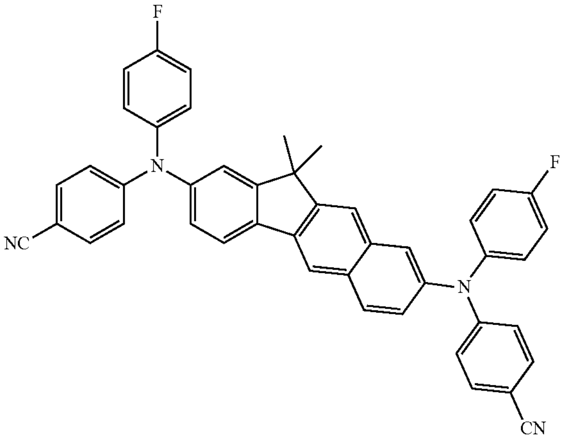
-continued
C-50
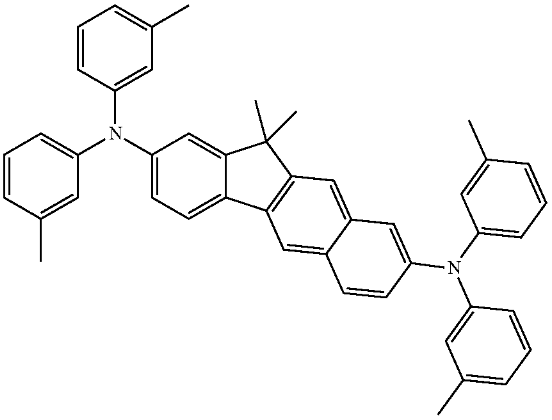
C-51
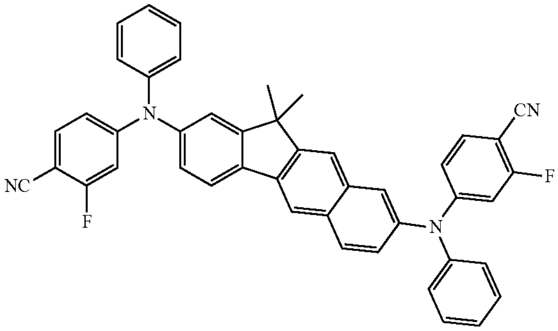
C-52
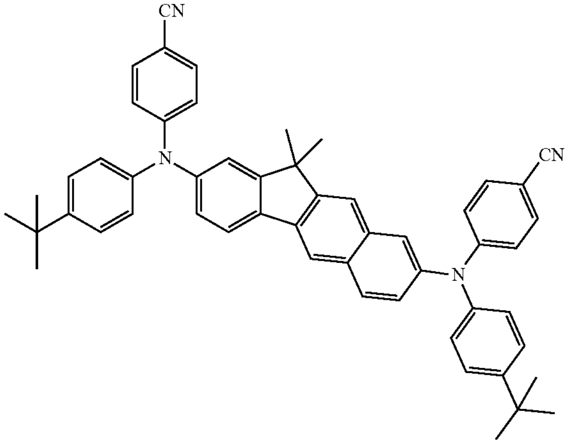

-continued
C-53
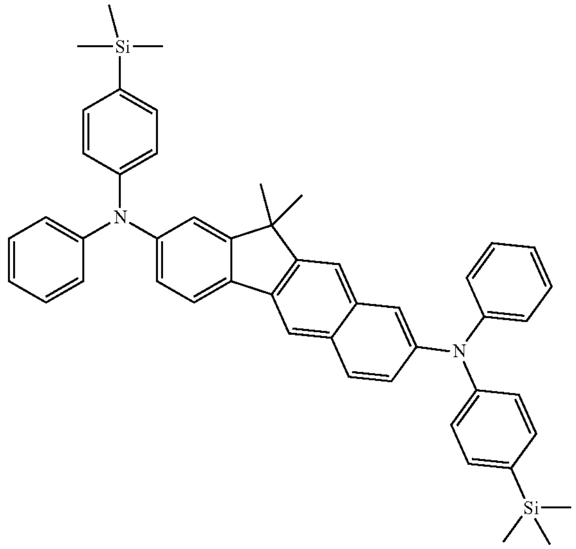
C-54
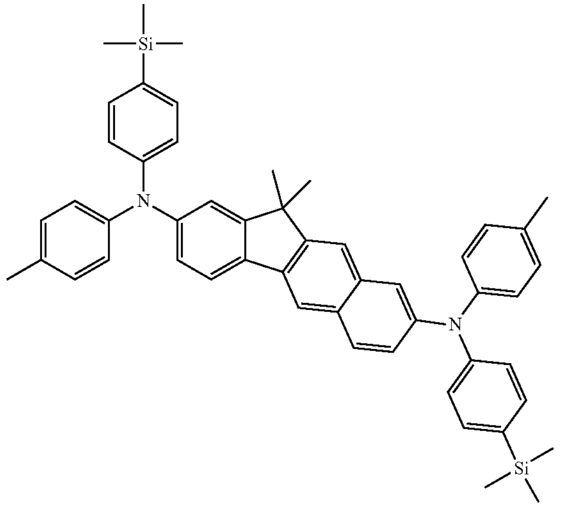
C-55
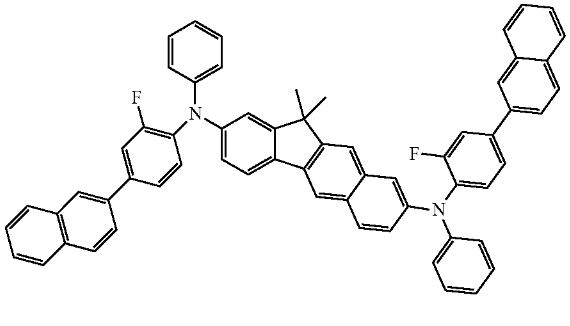
-continued
C-56
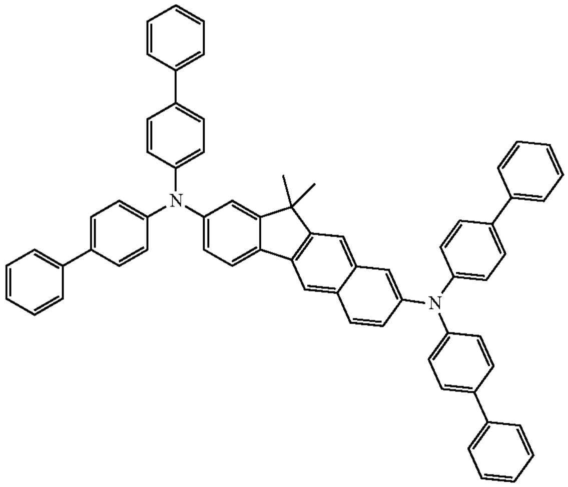
C-57
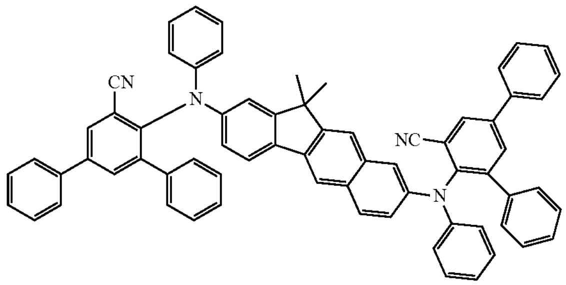
C-58
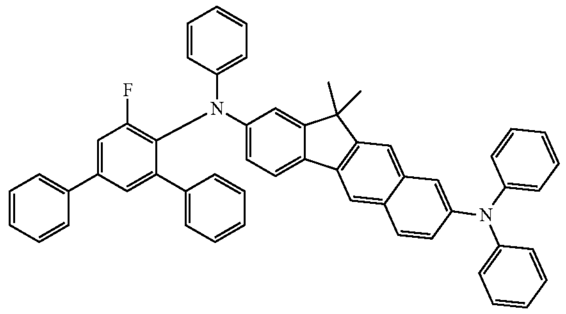
C-59
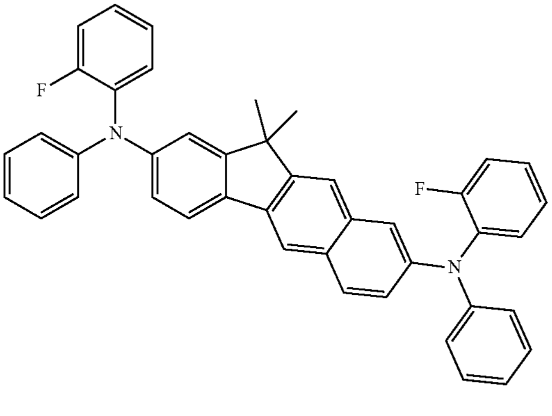

-continued
C-60
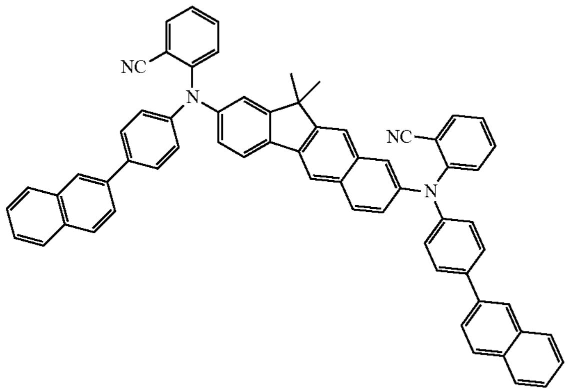
C-61
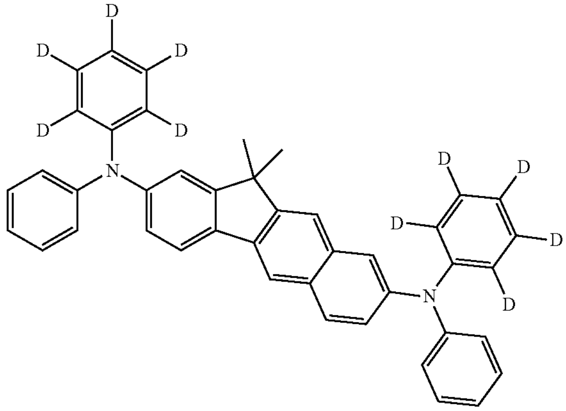
C-62
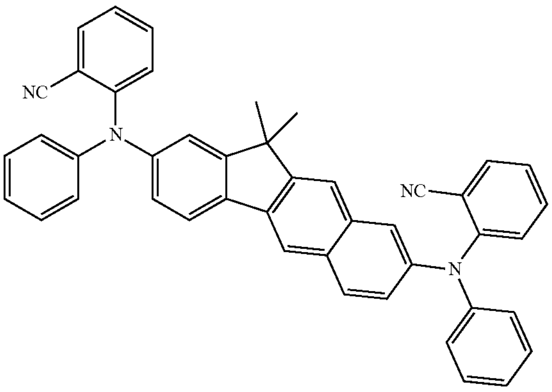
C-63
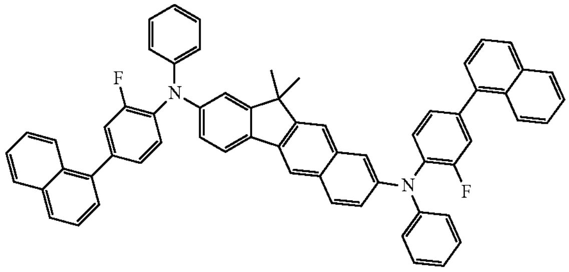
-continued
C-64
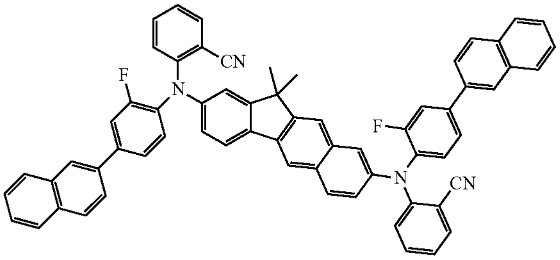
C-65
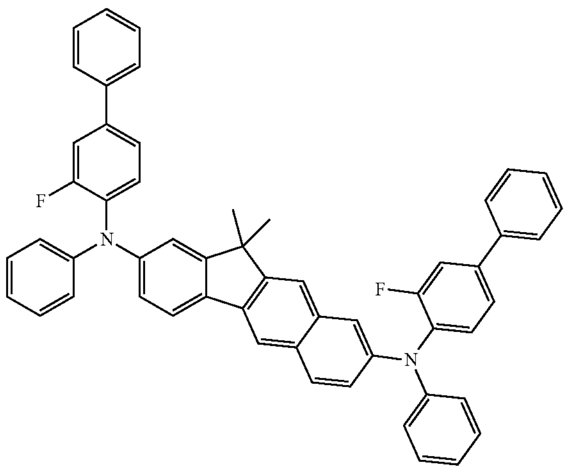
C-66
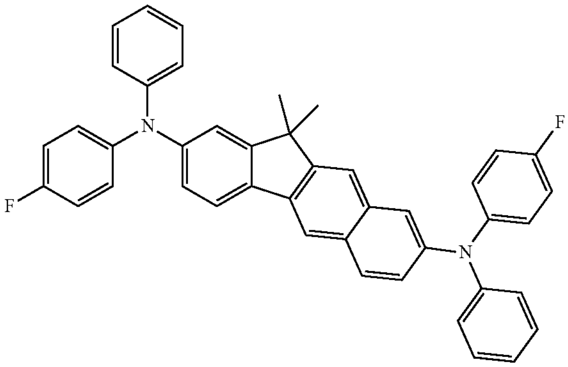
C-67
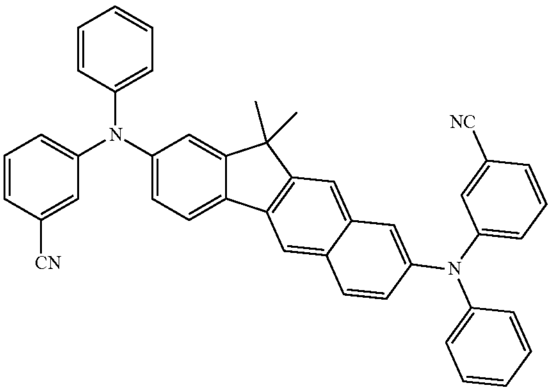

-continued
C-68
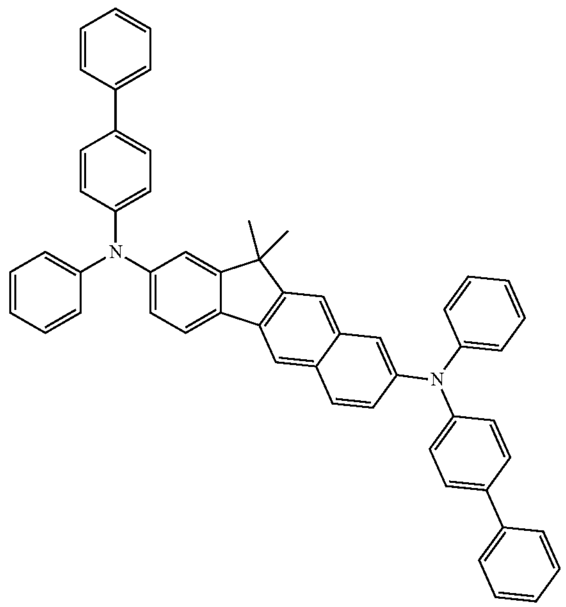
C-69
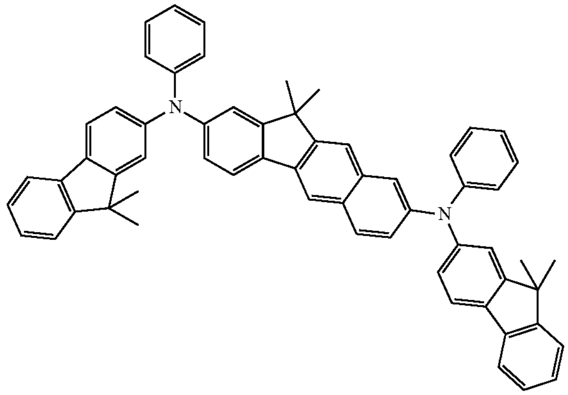
C-70
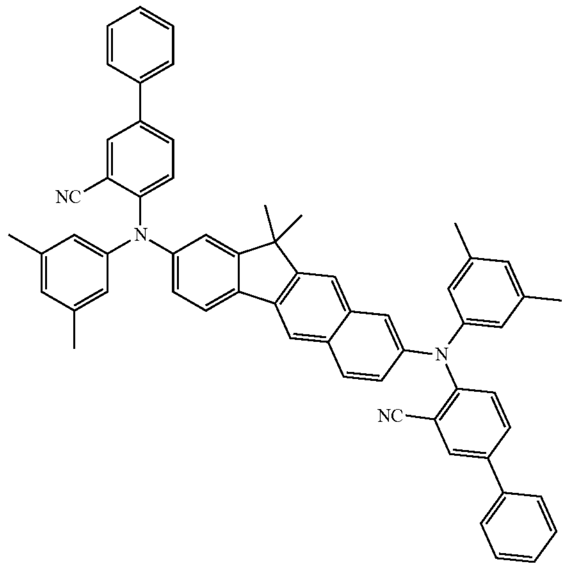
-continued
C-71
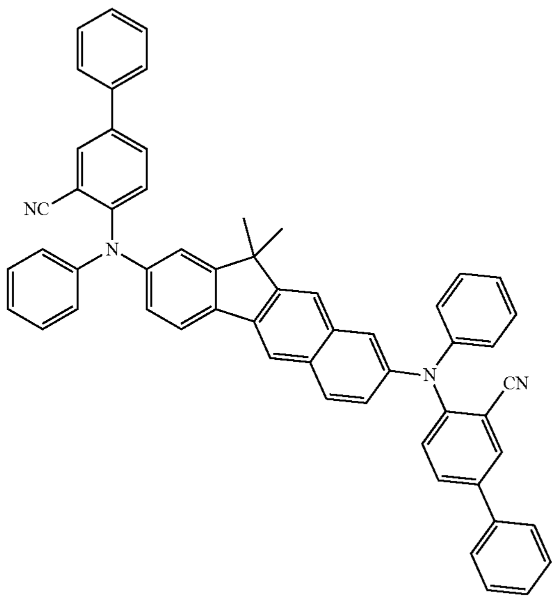
C-72
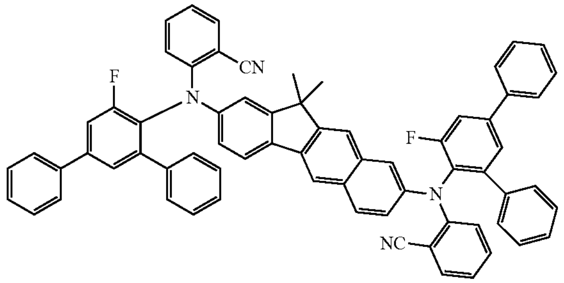
C-73
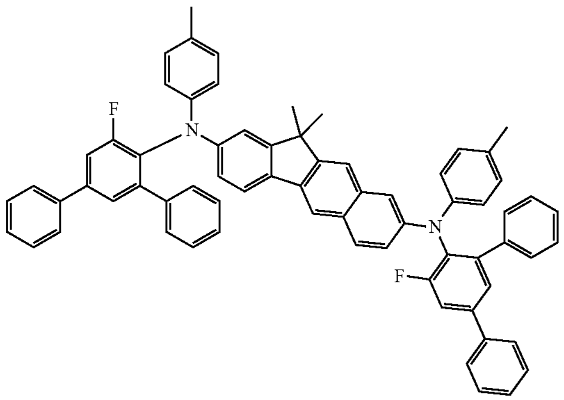

C-74
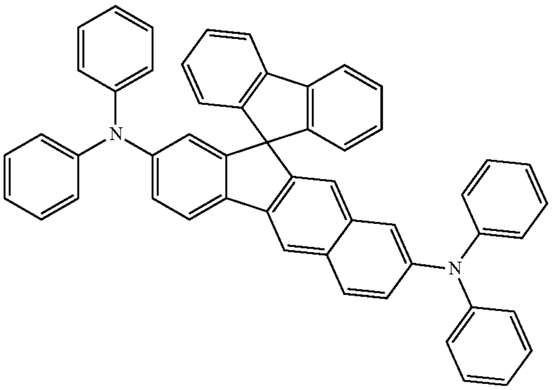
C-75
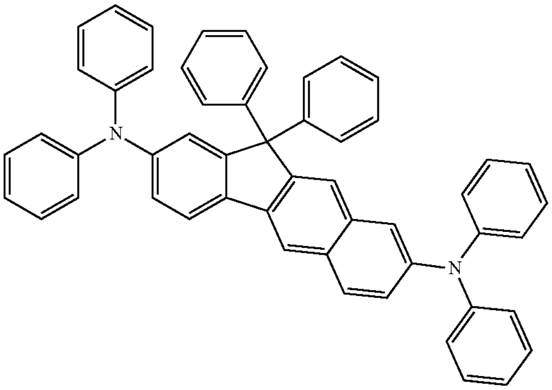
C-76
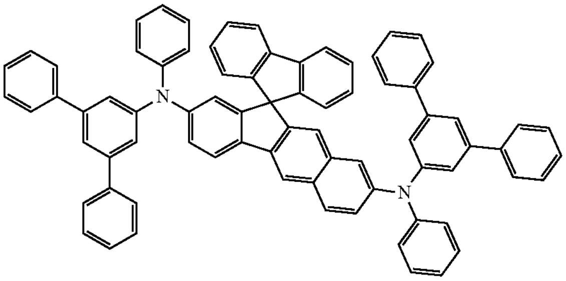
C-77
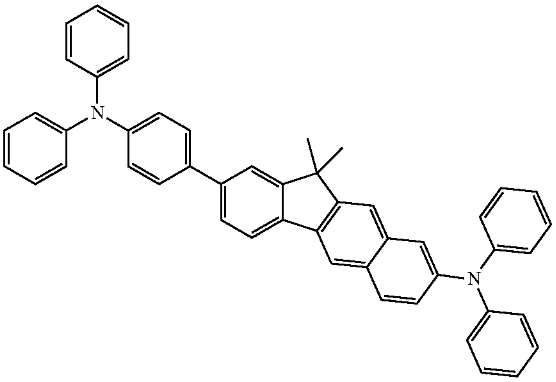
C-78
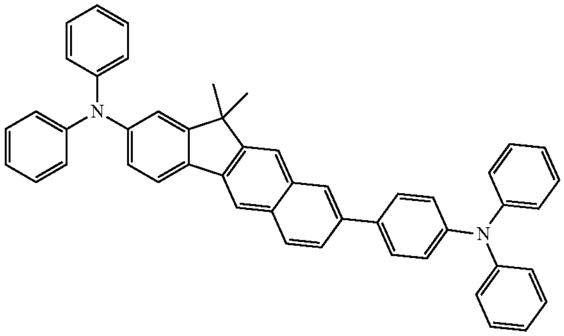
C-79
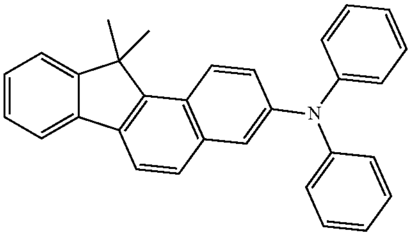
C-80
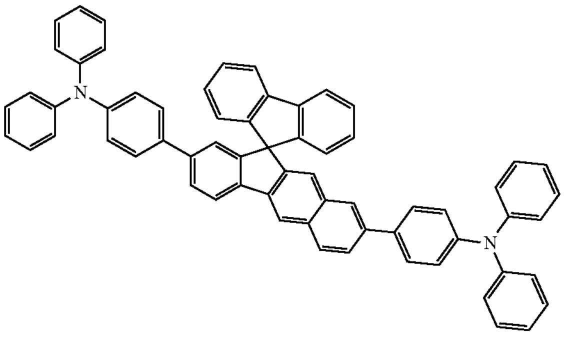
C-81
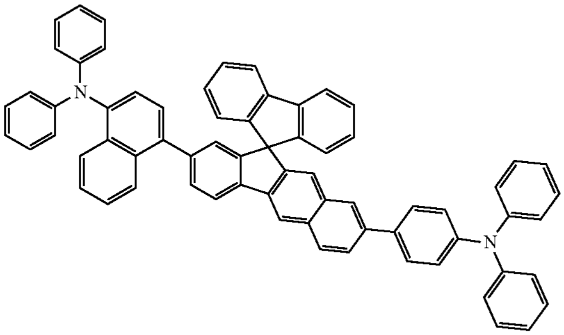

-continued
C-82
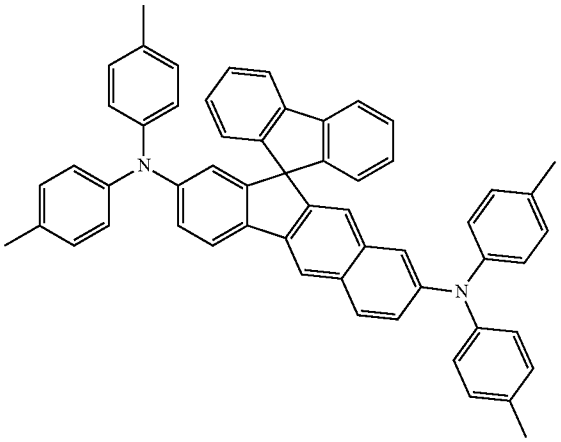
C-83
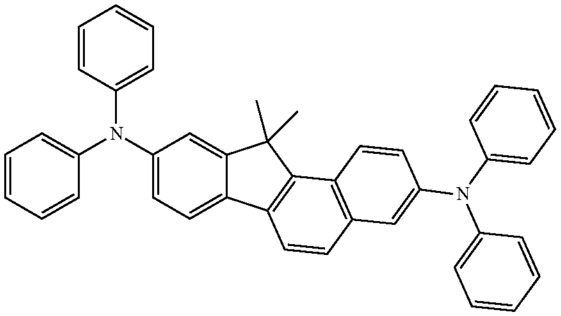
C-84
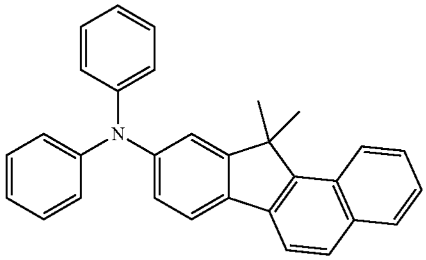
C-85
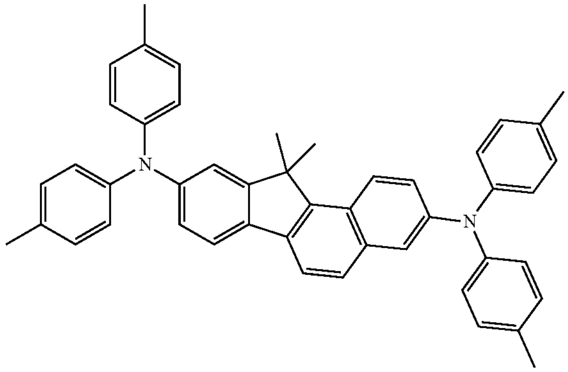
-continued
C-86
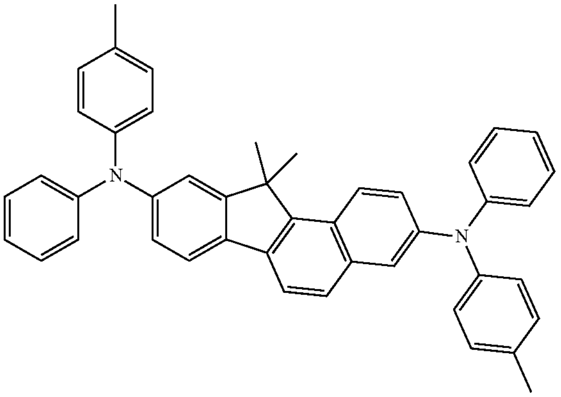
C-87
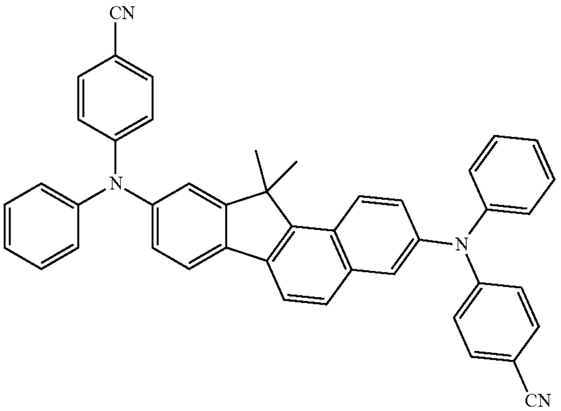
C-88
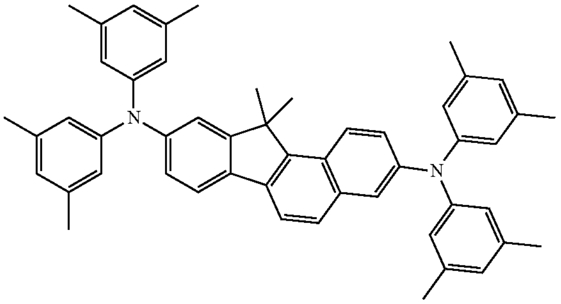
C-89
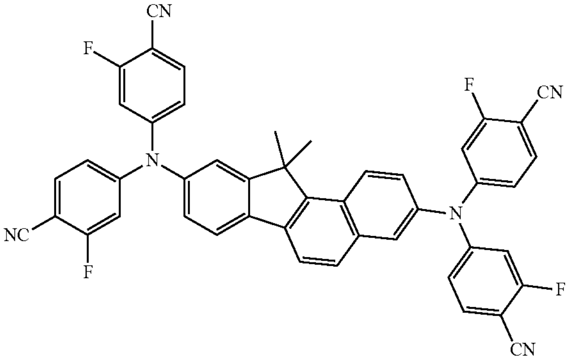

-continued
C-90
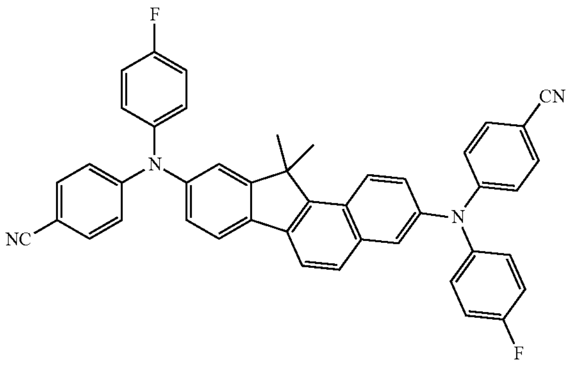
C-91
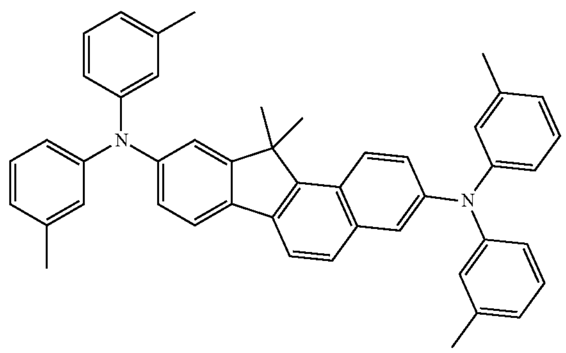
C-92
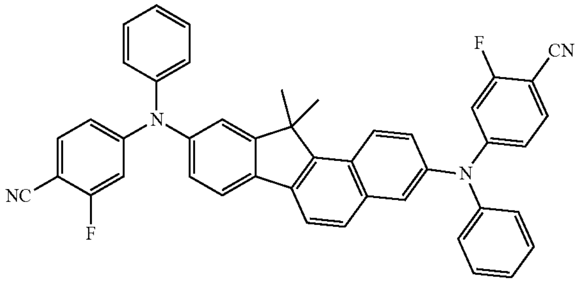
C-93
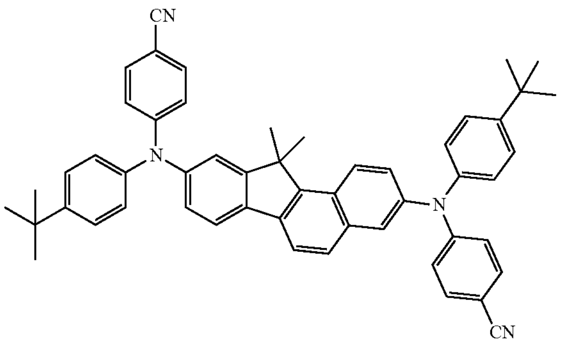
-continued
C-94
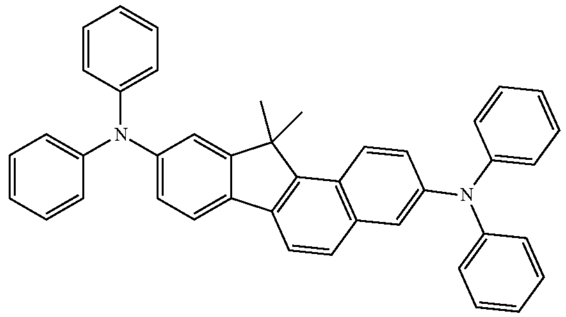
C-95
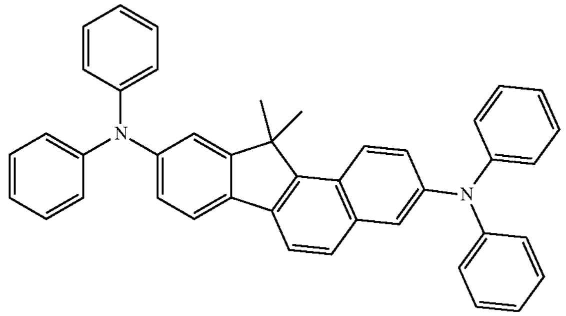
C-96
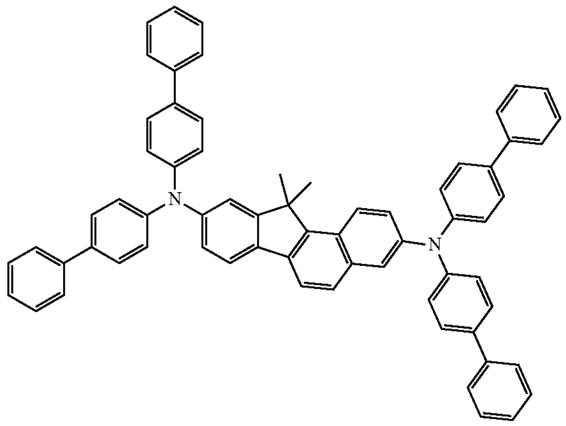
C-97
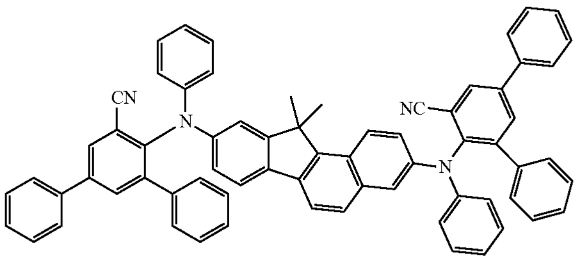

C-98
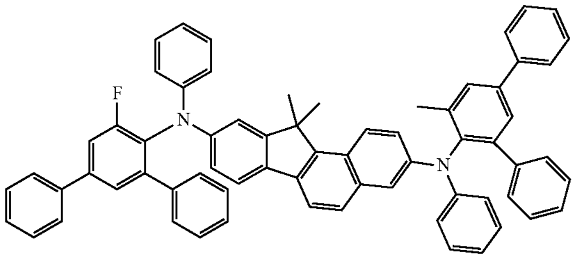
C-99
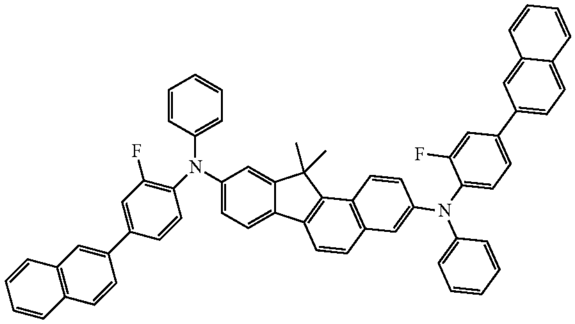
C-100
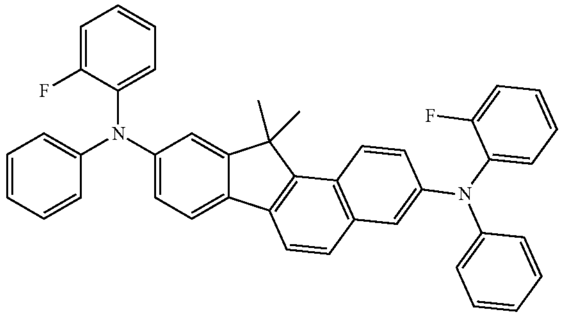
C-101
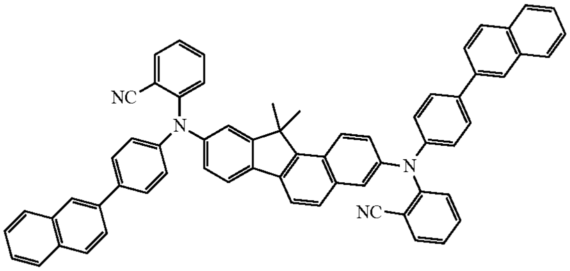
C-102
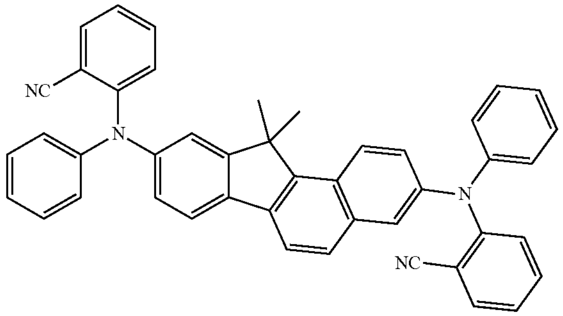
C-103
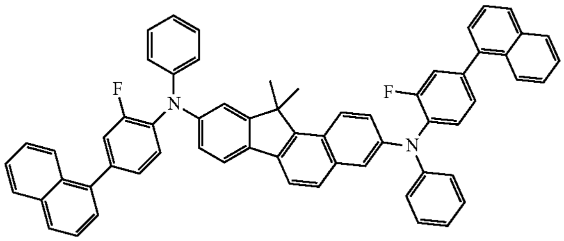
C-104
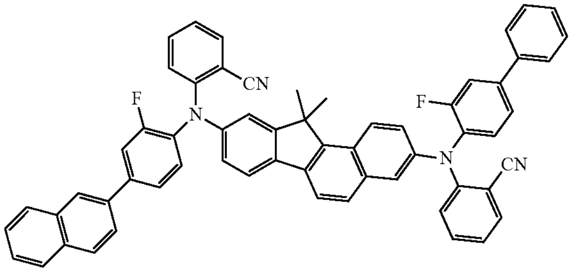
C-105
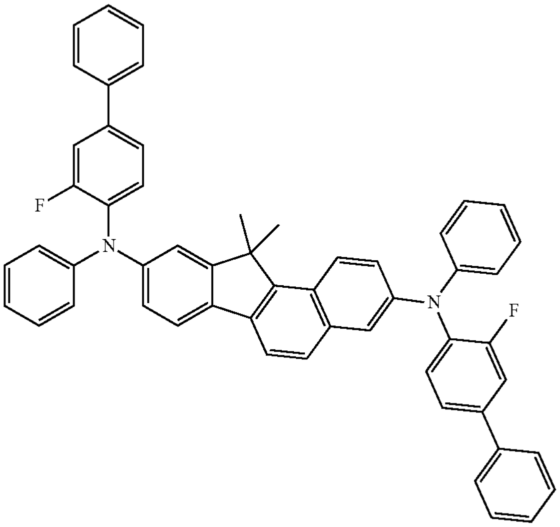
C-106
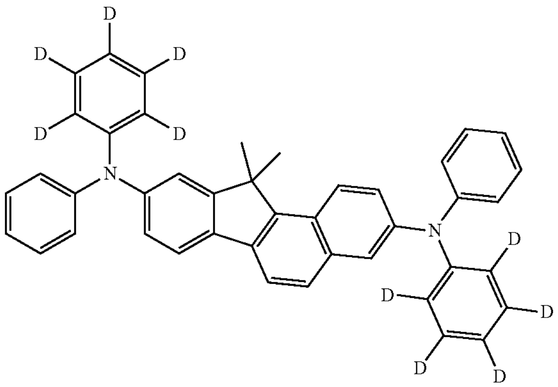

-continued
C-107
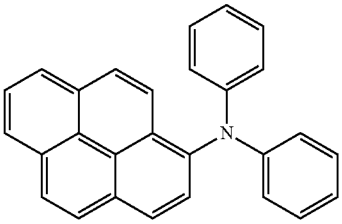
C-108
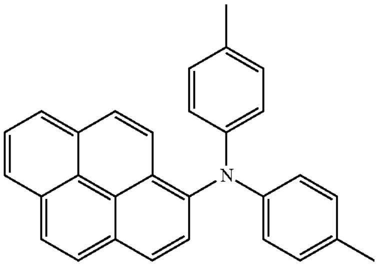
C-109
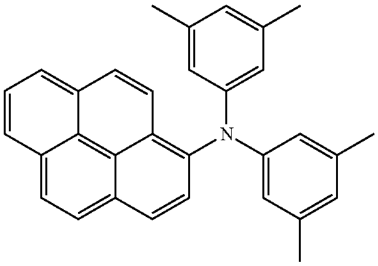
C-110
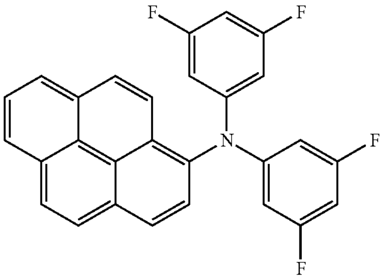
C-111
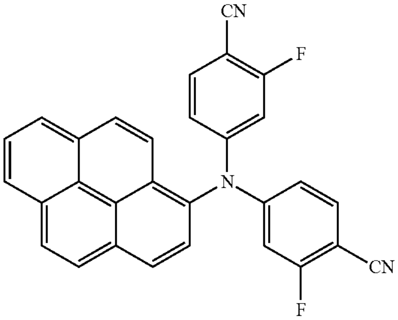
-continued
C-112
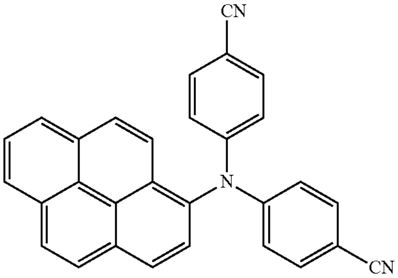
C-113
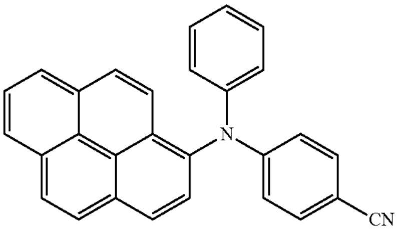
C-114
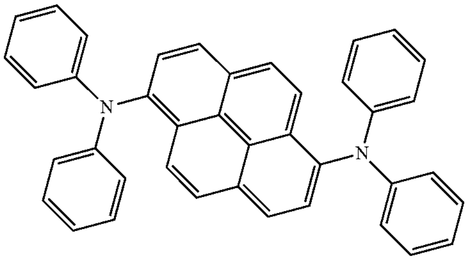
C-115
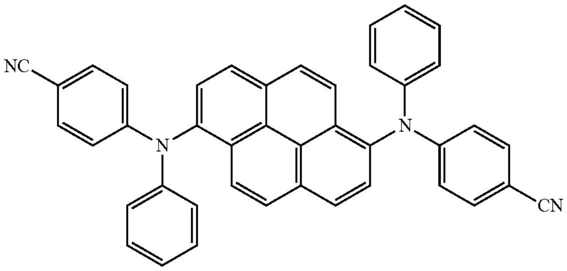
C-116
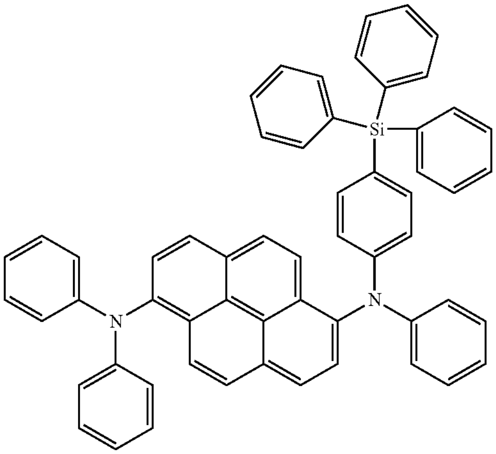

-continued
C-117
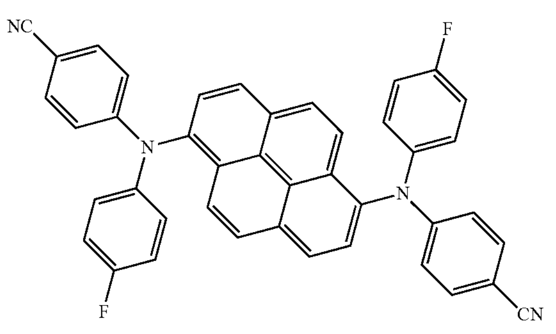
C-118
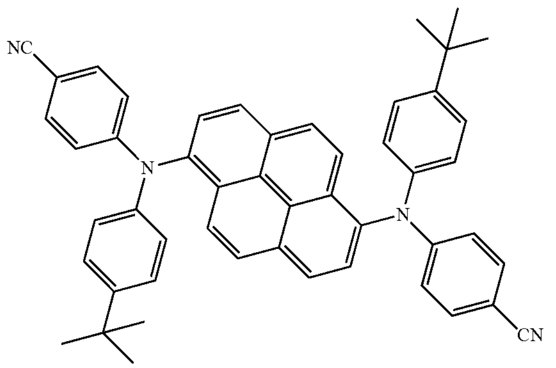
C-119
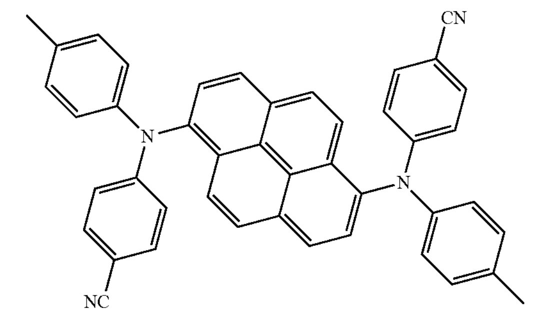
C-120
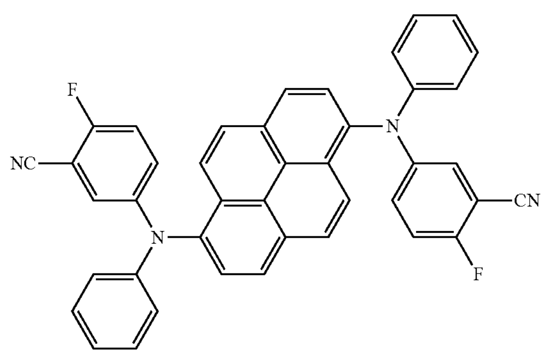
-continued
C-121
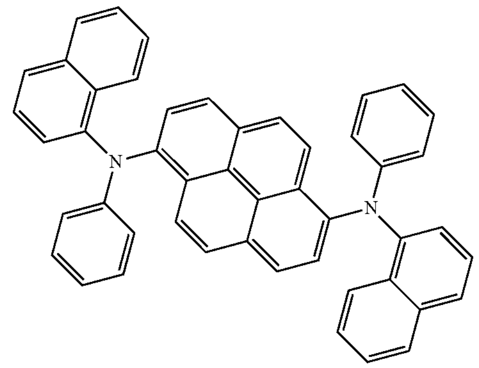
C-122
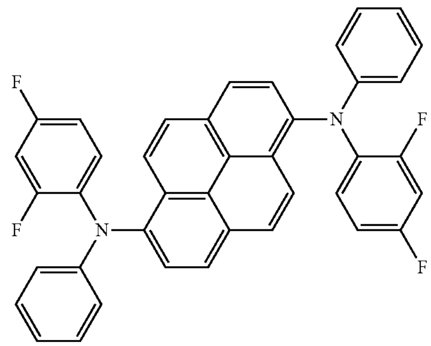
C-123
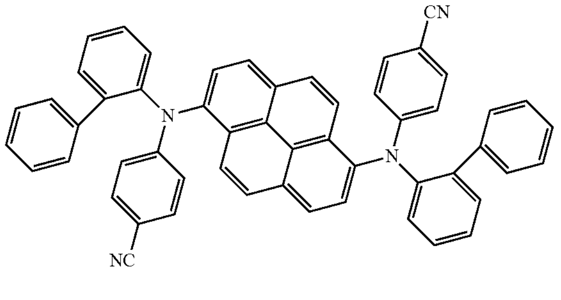
C-124
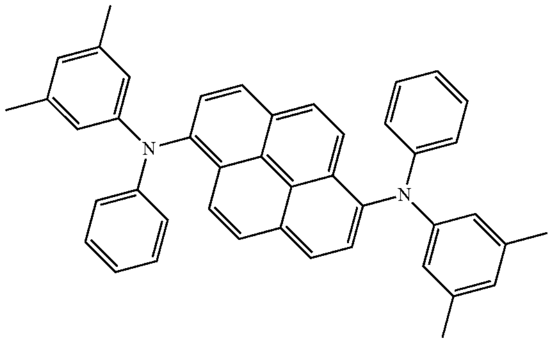

-continued
C-125
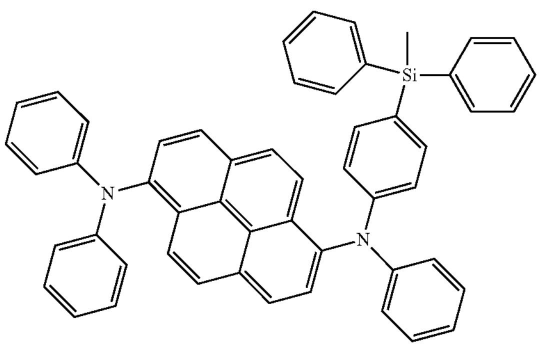
C-126
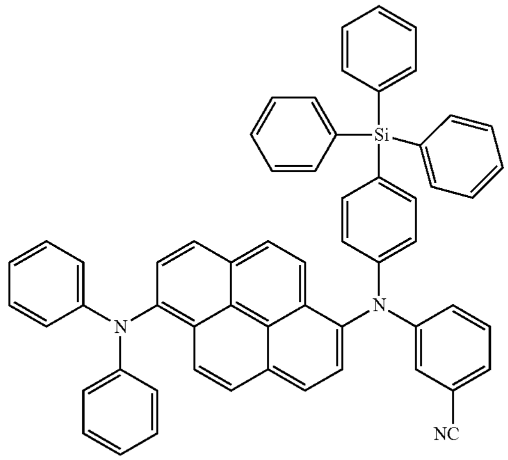
C-127
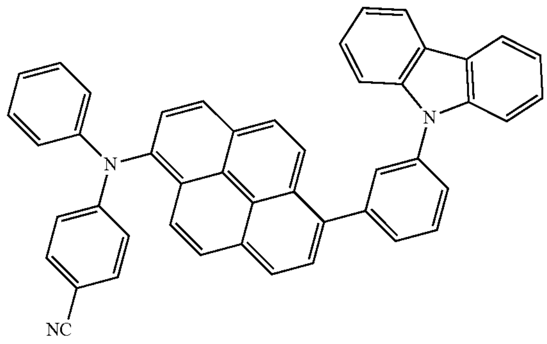
C-128
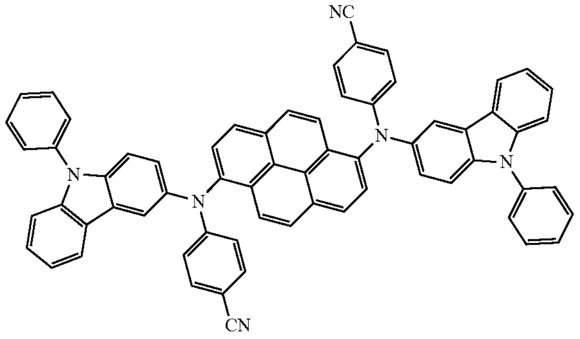
-continued
C-129
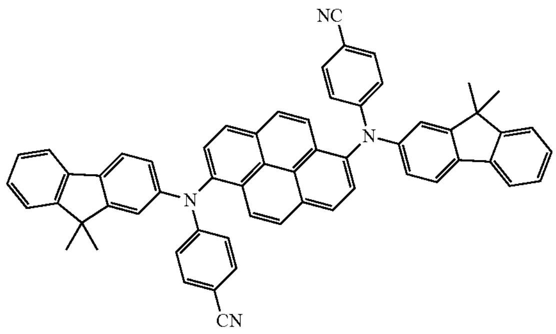
C-130
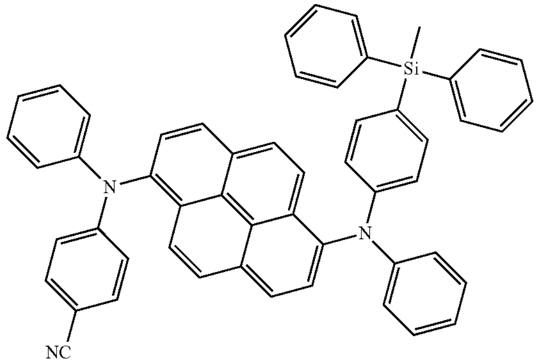
C-131
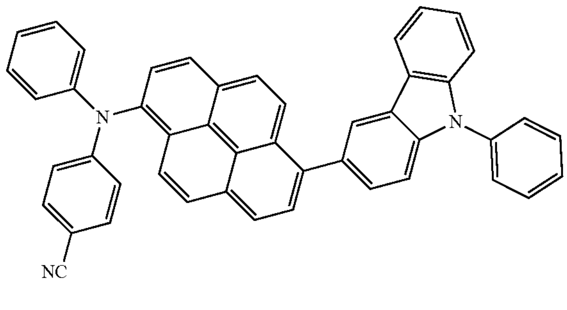
C-132
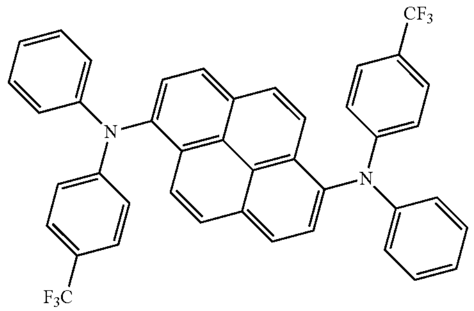

-continued
C-133
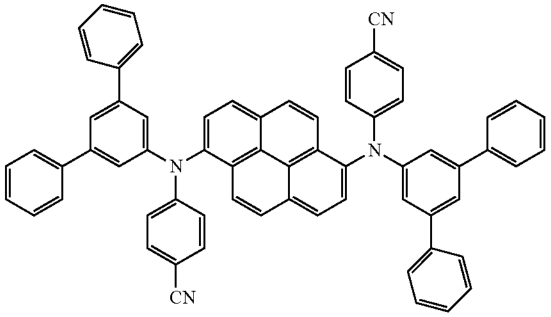
C-134
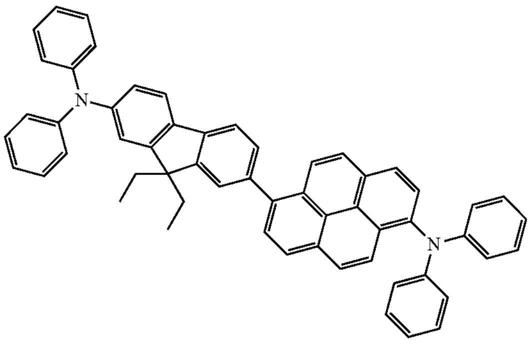
C-135
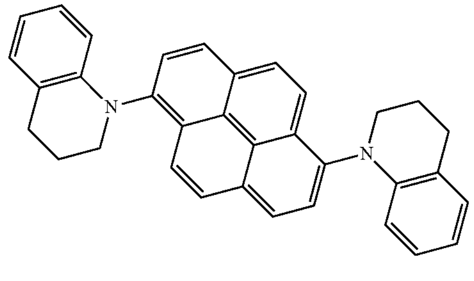
C-136
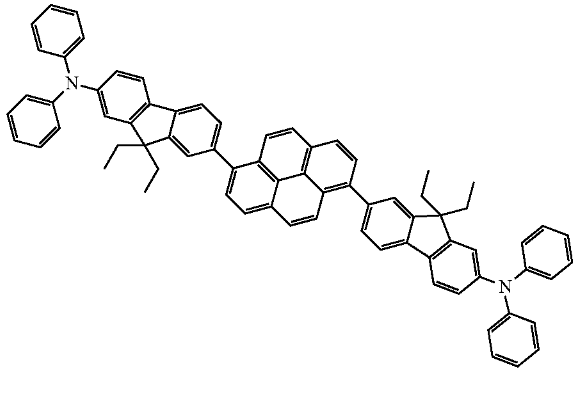
-continued
C-137
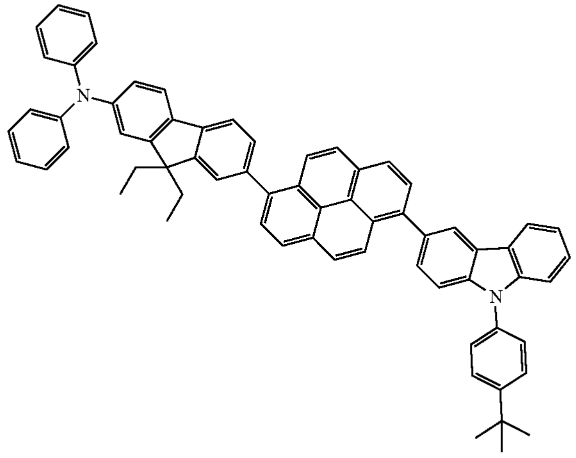
C-138
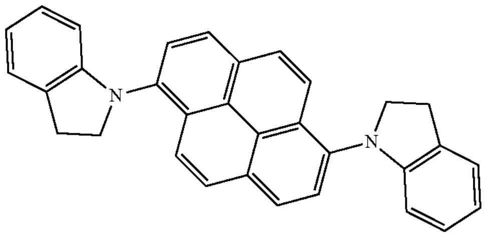
C-139
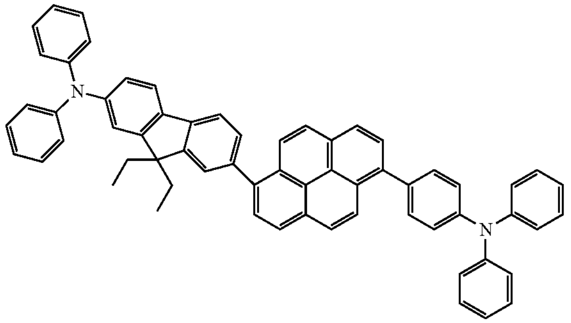
C-140
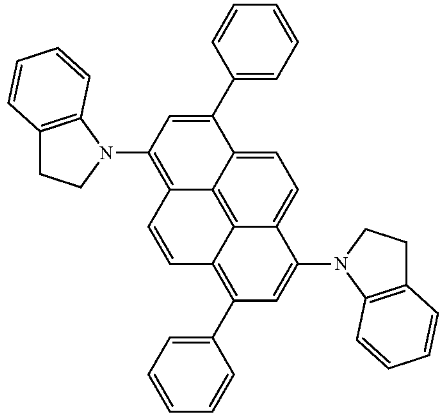

-continued
C-141
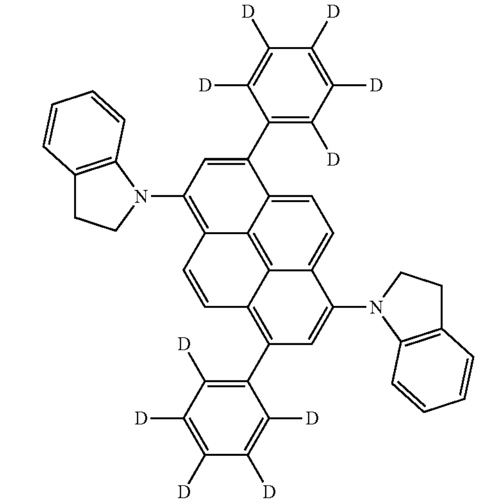
C-142
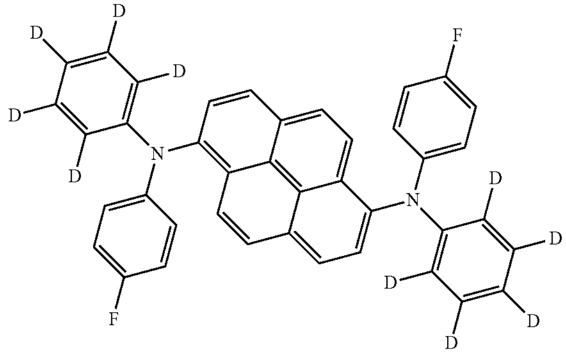
C-143
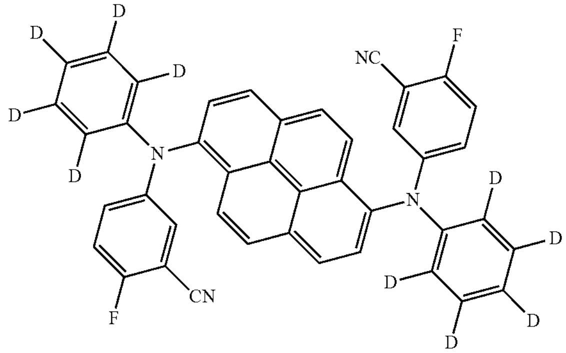
-continued
C-144
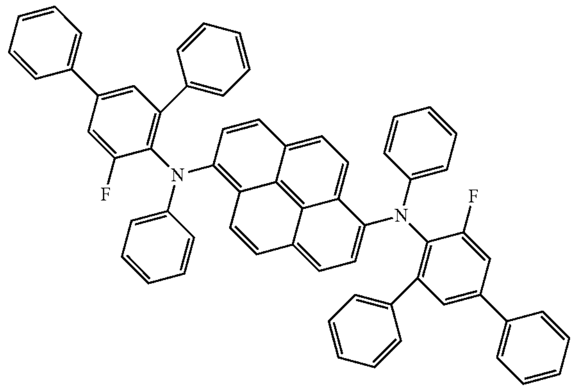
C-145
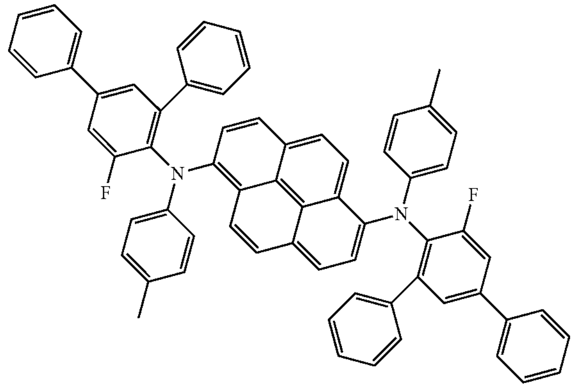
C-146
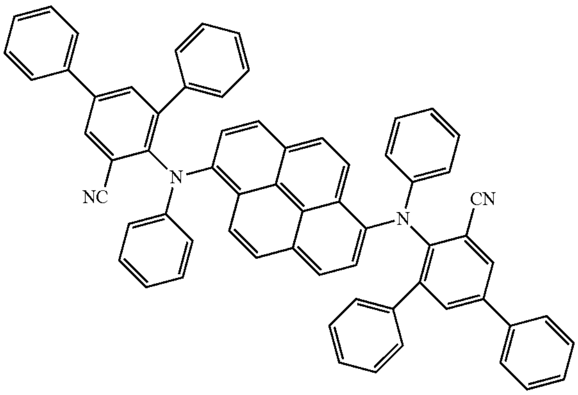
C-147
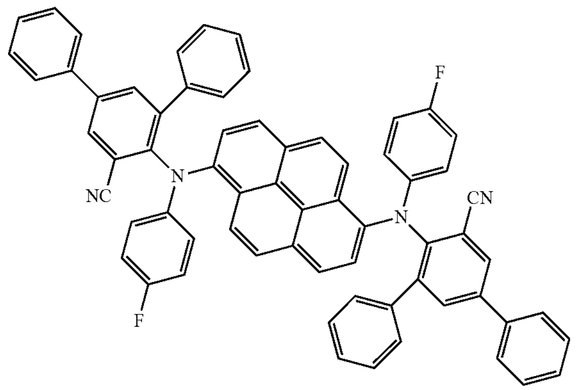

-continued
C-148
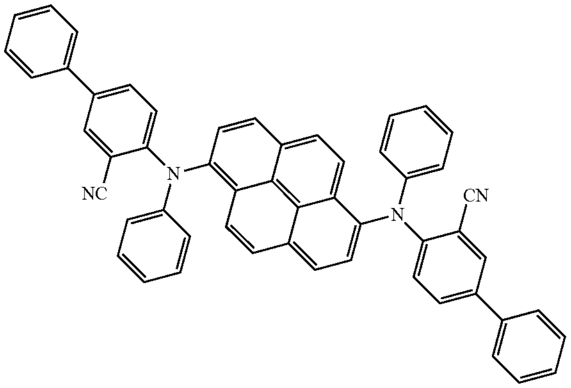
C-149
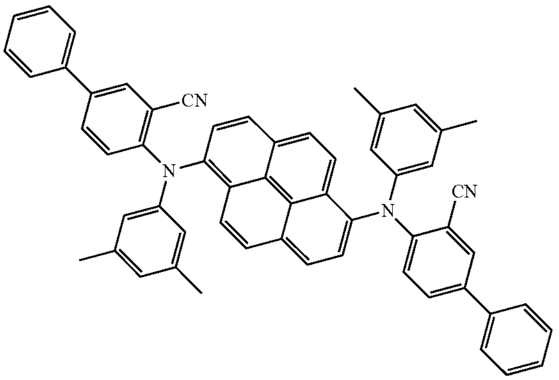
C-150
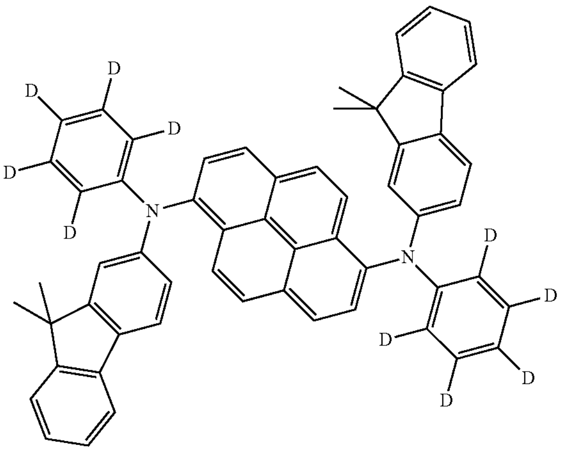
-continued
C-151
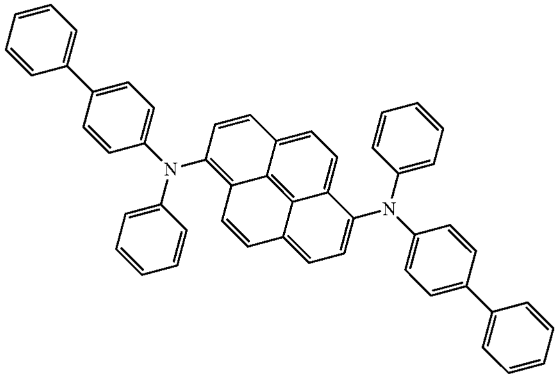
C-152
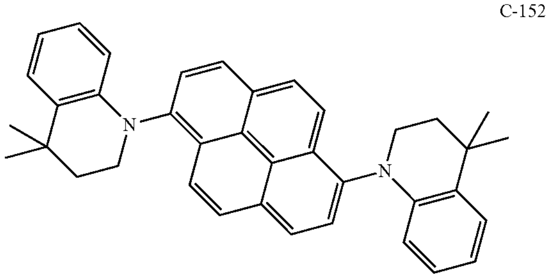
C-153
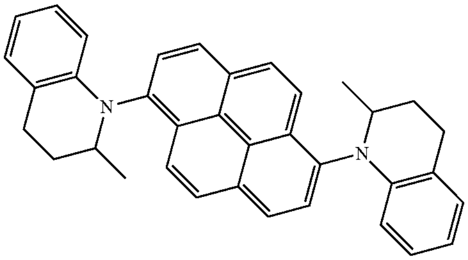
C-154
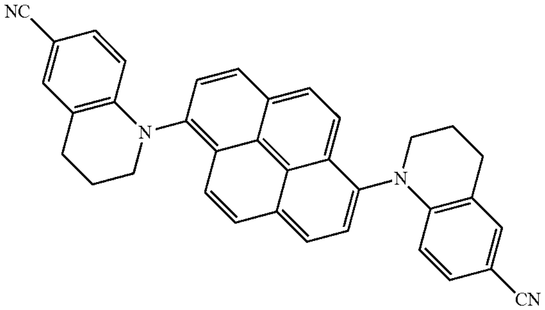
C-155
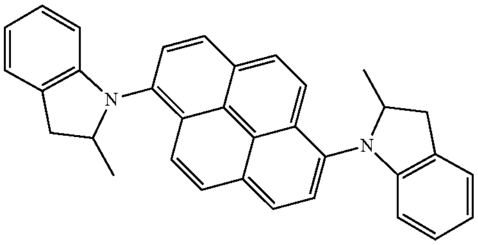

-continued
C-156
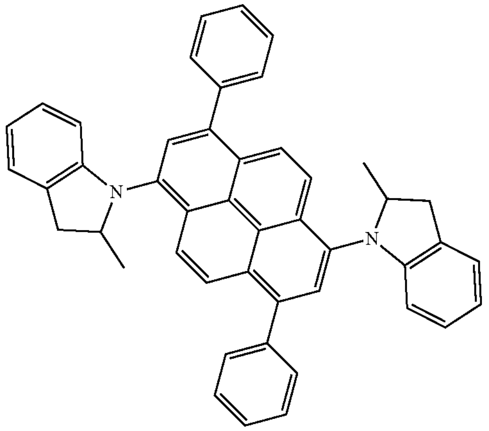
C-157
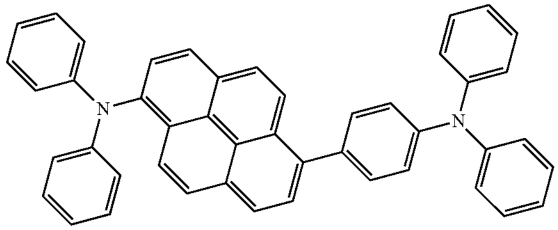
C-158
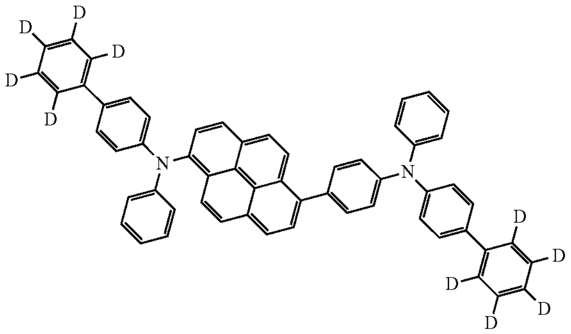
C-159
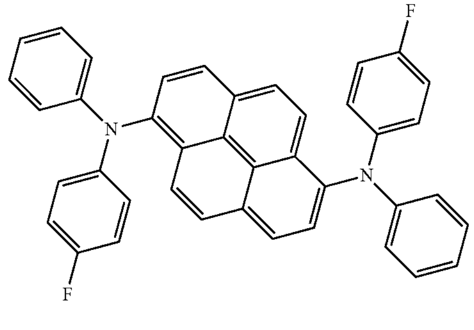
-continued
C-160
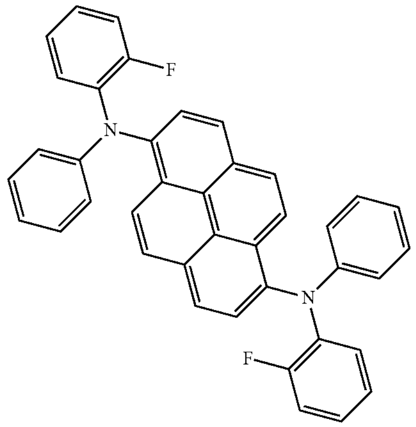
C-161
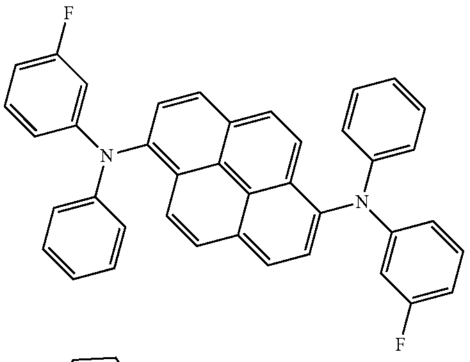
C-162
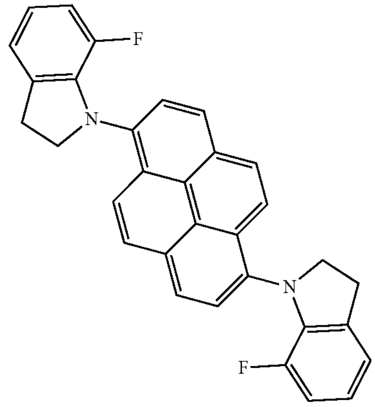
C-163
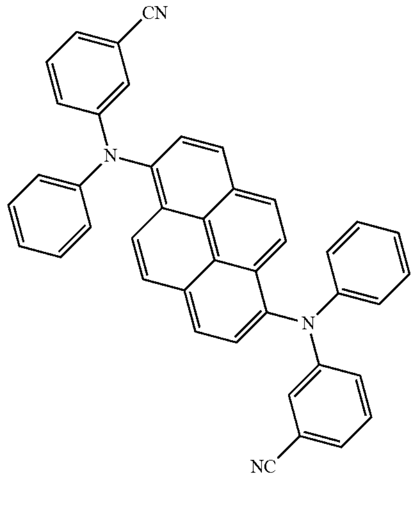

-continued
C-164
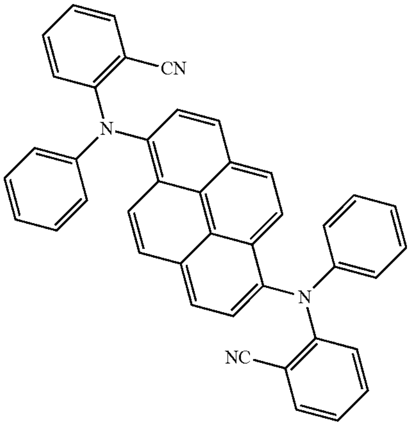
C-165
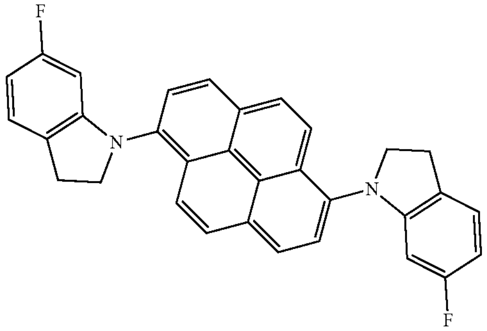
C-166
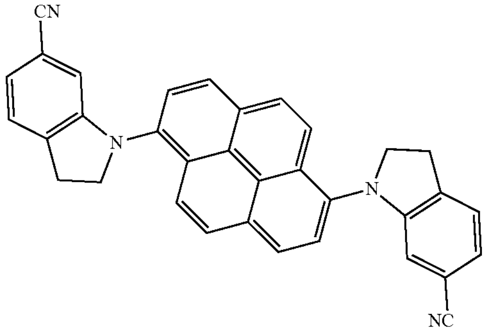
-continued
C-167
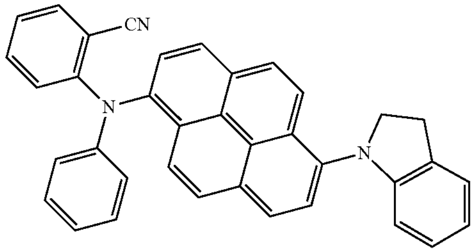
C-168
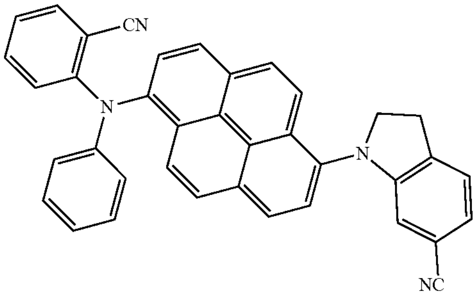
C-169
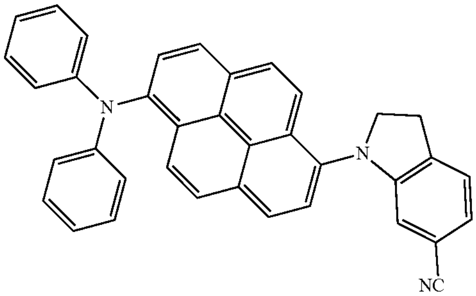
C-170
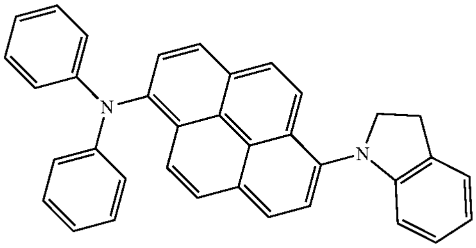
C-171
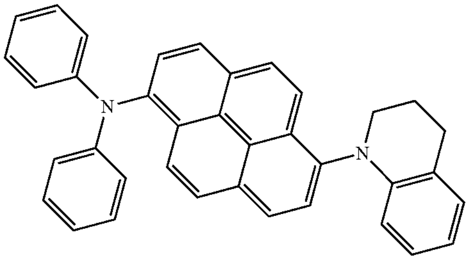
C-172
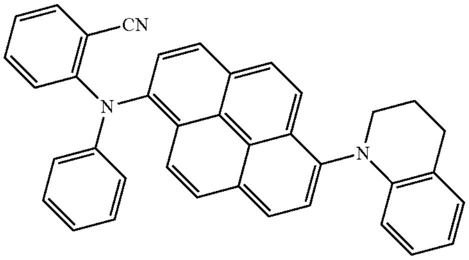

-continued
C-173
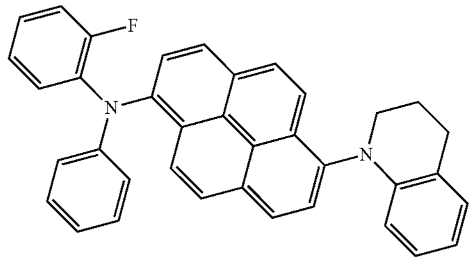
C-174
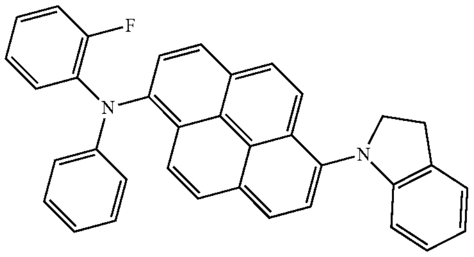
C-175
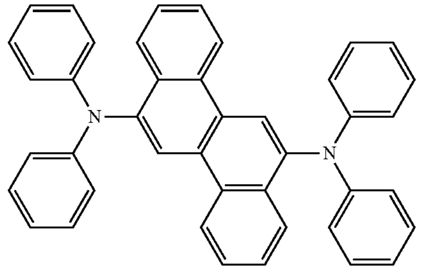
C-176
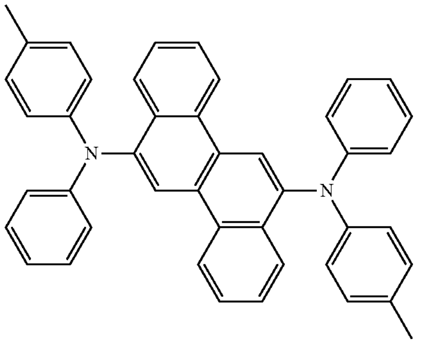
C-177
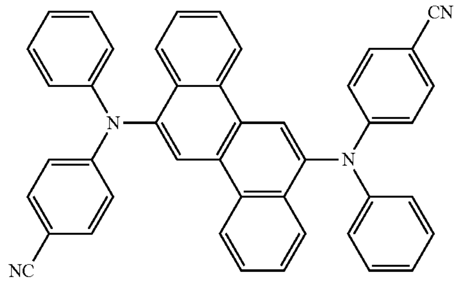
C-178
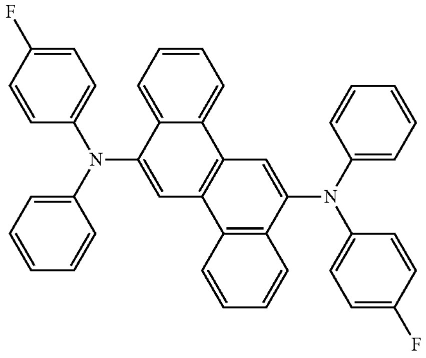
C-179
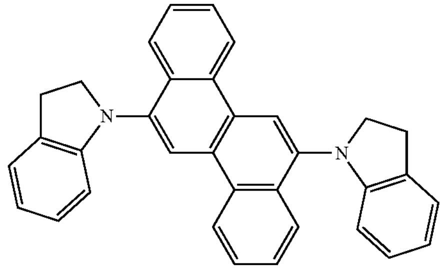
C-180
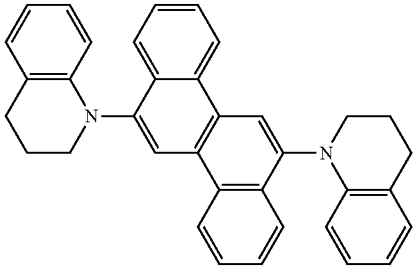

-continued
C-181
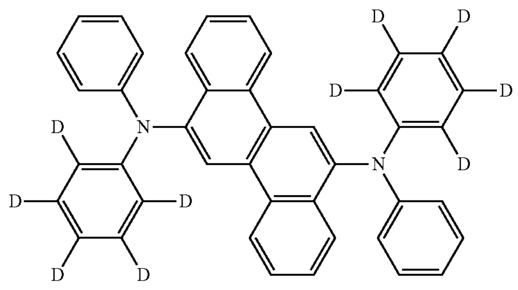
C-182
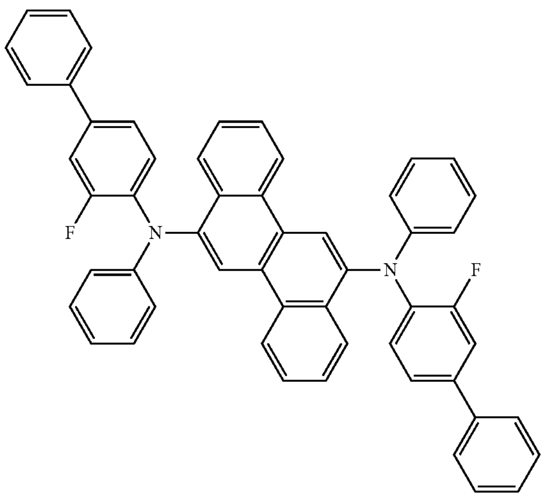
C-183
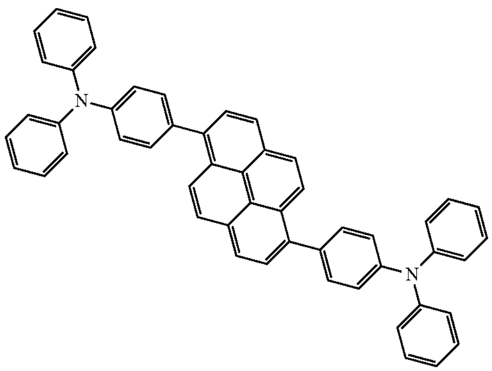
C-184
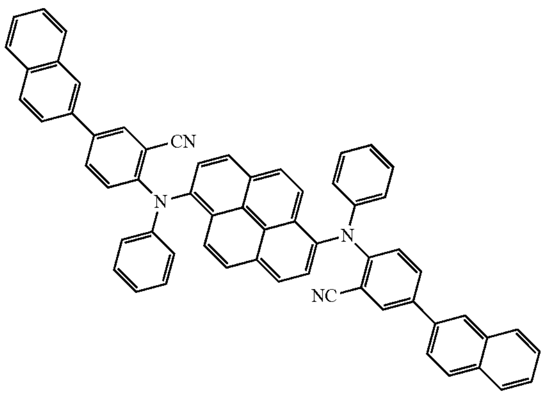
C-185
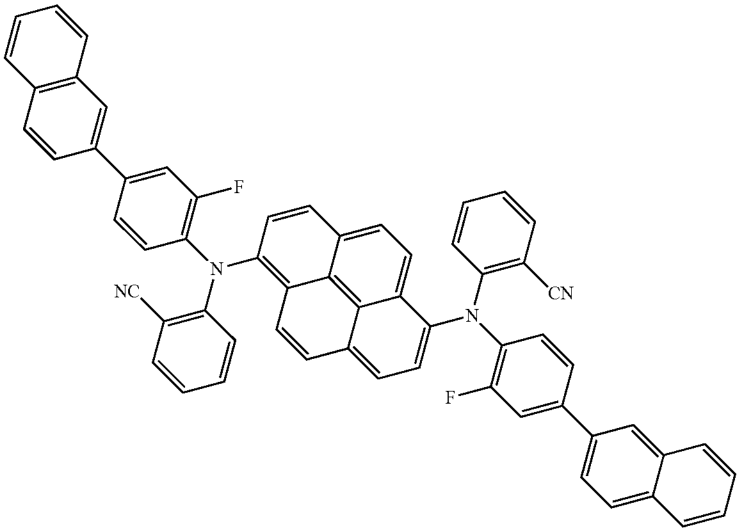

-continued
C-186
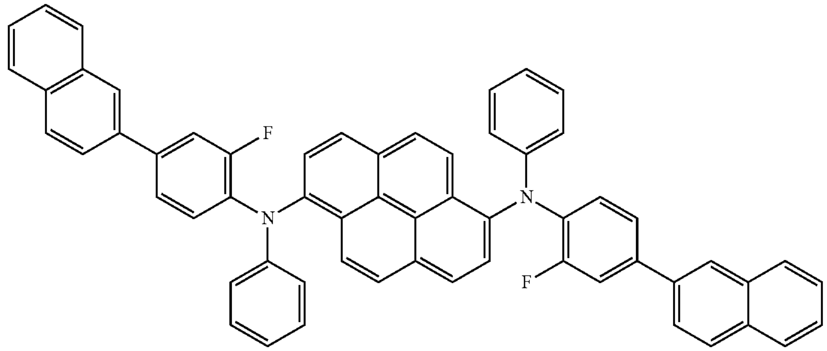
C-187
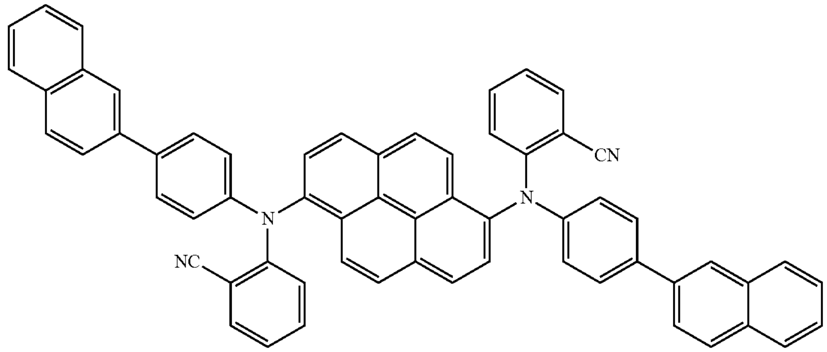
C-188
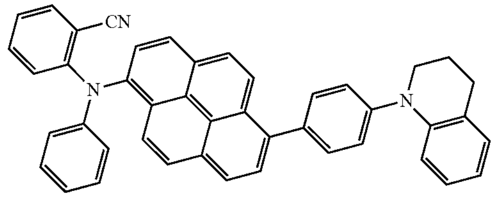
C-189
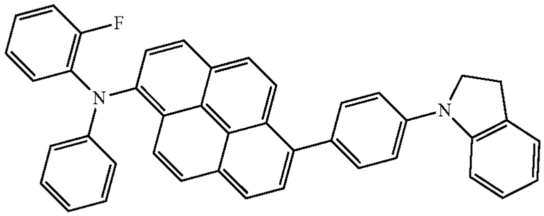
C-190
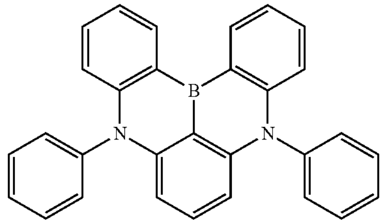
C-191
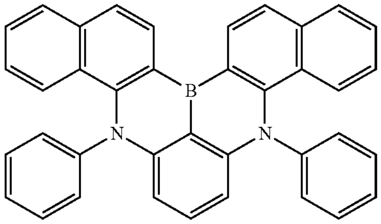
C-192
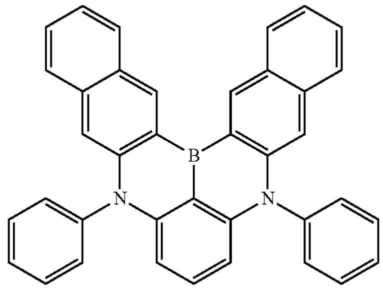
C-193
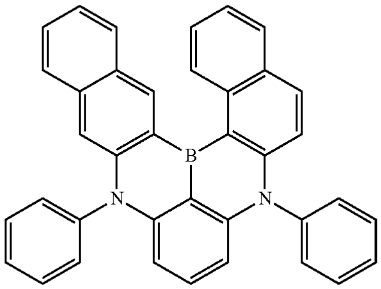

-continued
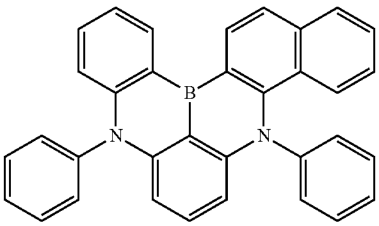
C-194
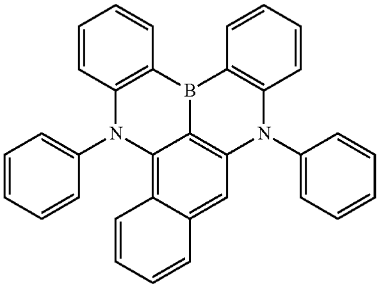
C-195
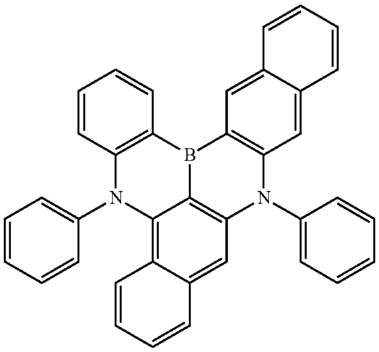
C-196
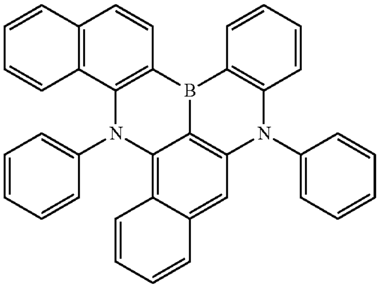
C-197
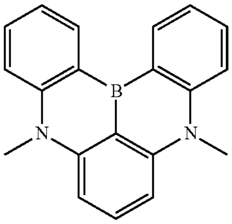
C-198
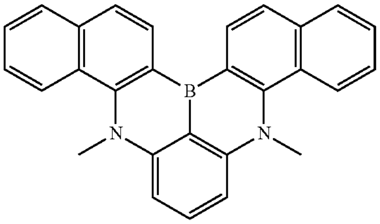
C-199
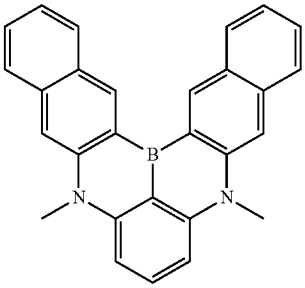
C-200
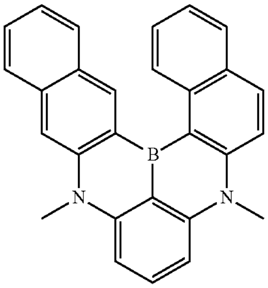
C-201
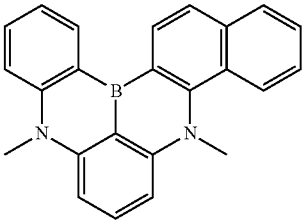
C-202
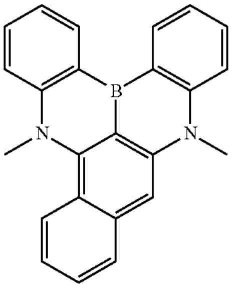
C-203

-continued
C-204
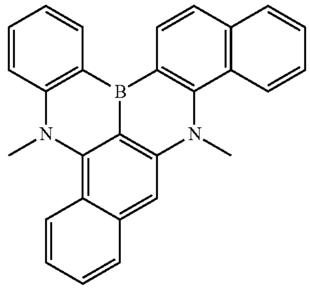
C-205
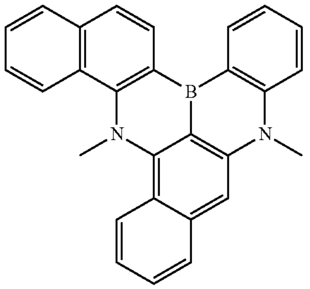
C-206
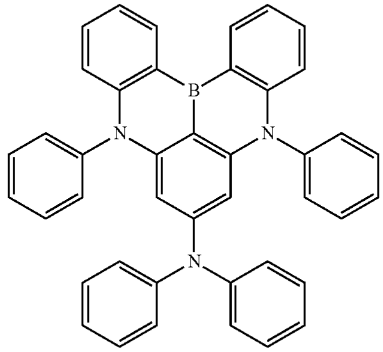
C-207
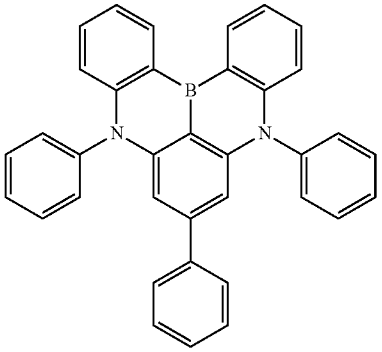
C-208
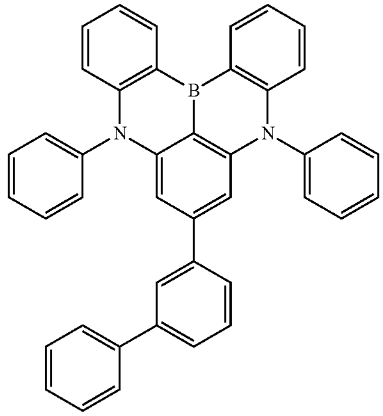
C-209
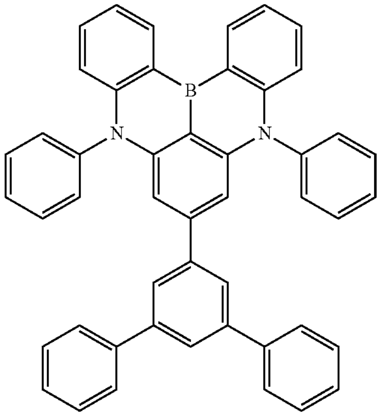
C-210
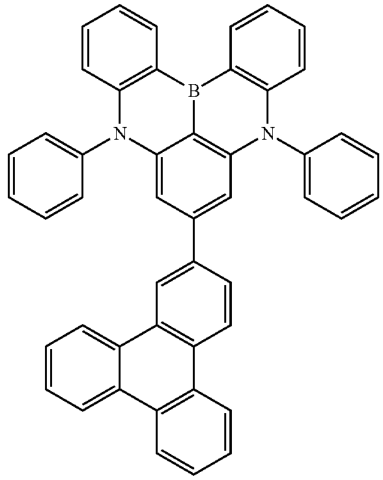
C-211
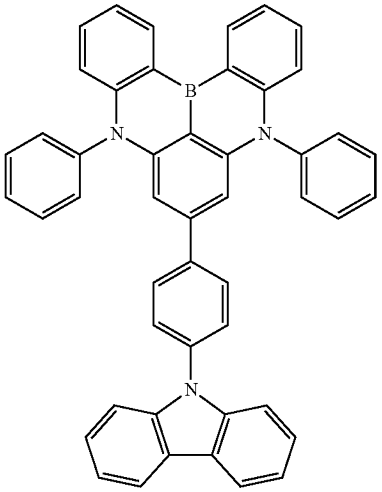

-continued
C-212
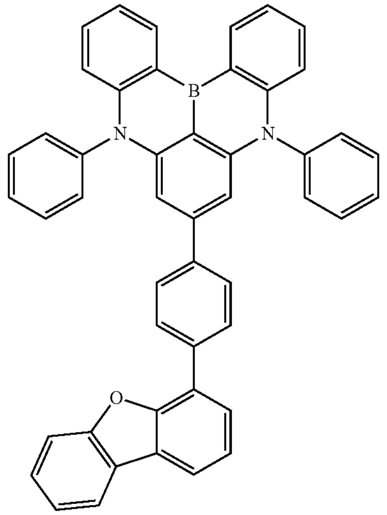
C-213
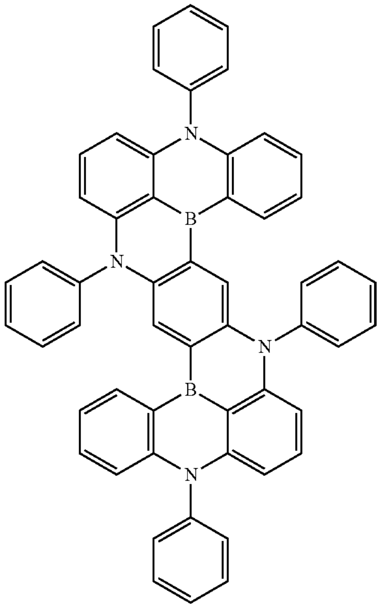
C-214
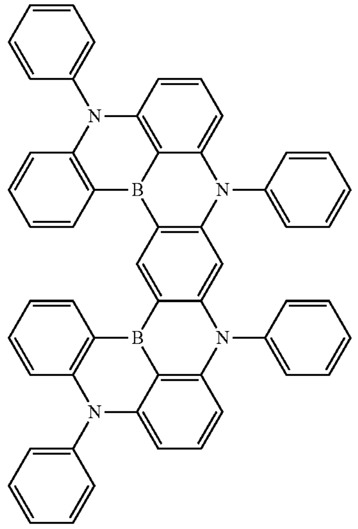
C-215
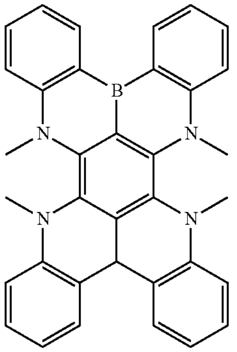
C-216
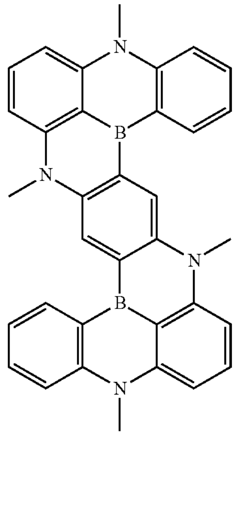
C-217
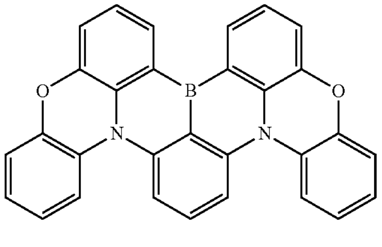

-continued
C-218
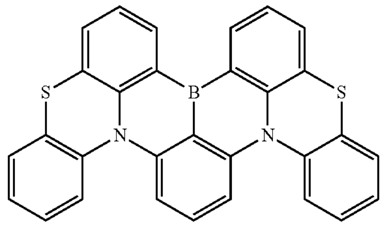
C-219
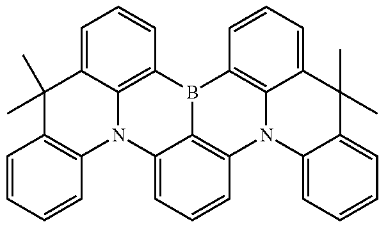
C-220
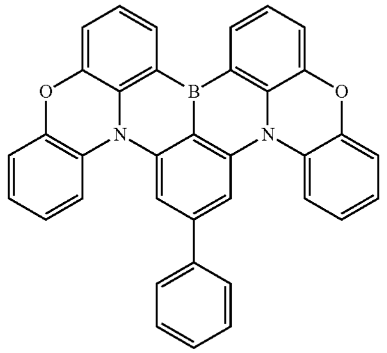
C-221
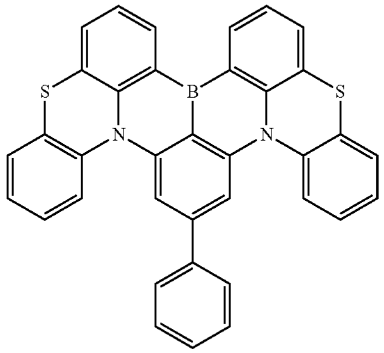
C-222
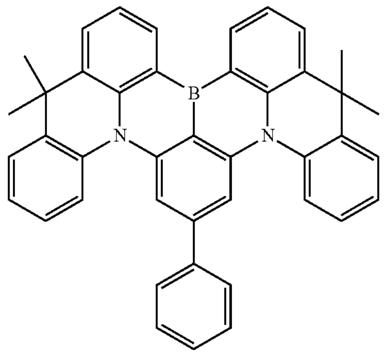
C-223
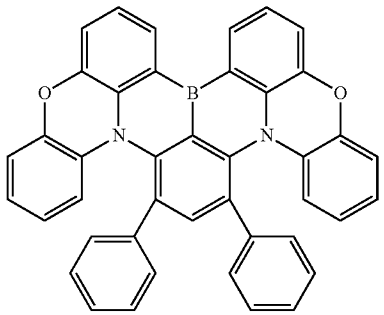
C-224
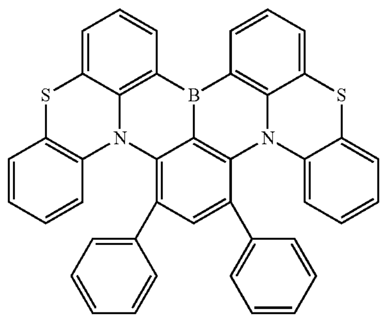
C-225
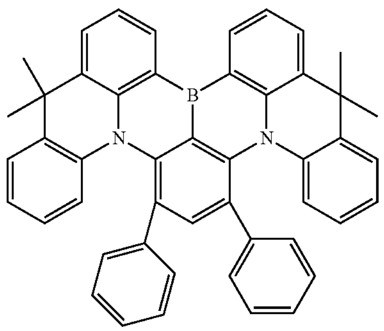

-continued
C-226
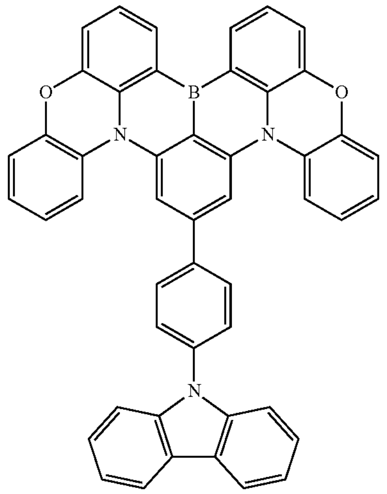
C-227
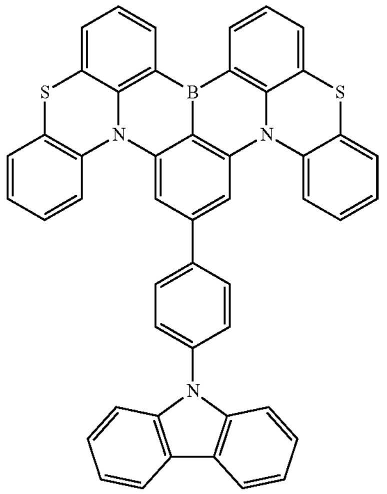
C-228
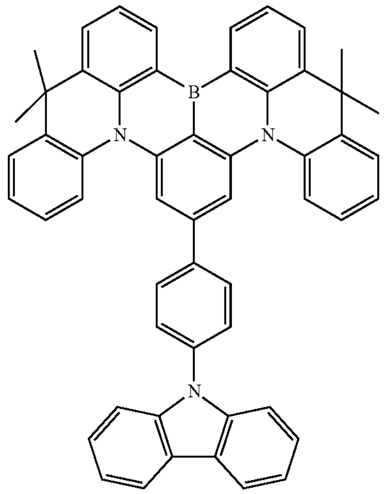
C-229
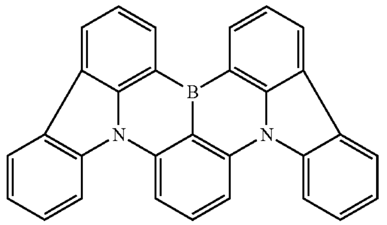
C-230
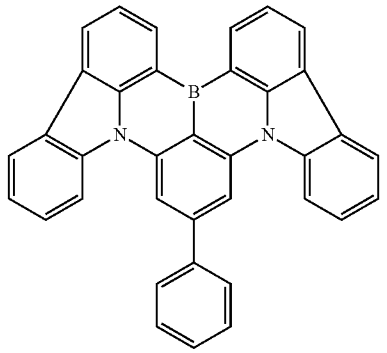
C-231
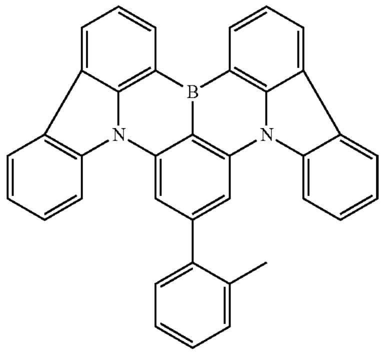

-continued
C-232
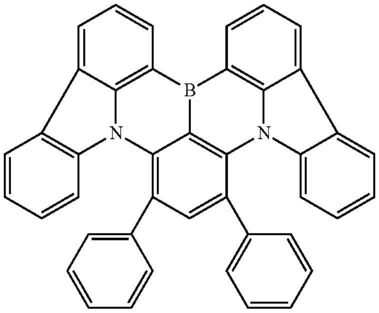
C-233
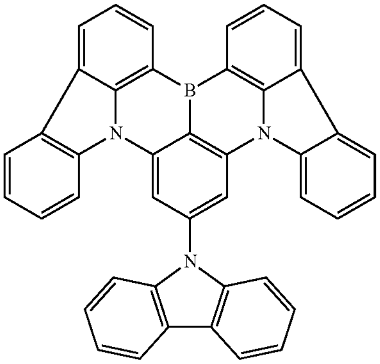
C-234
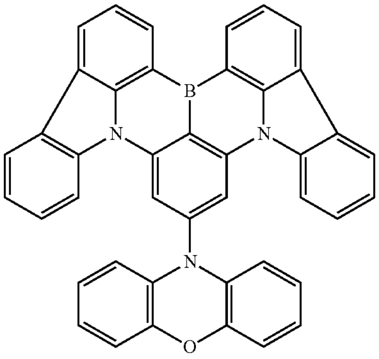
C-235
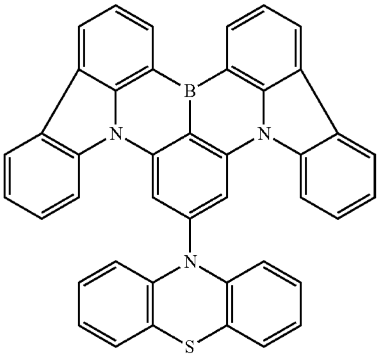
C-236
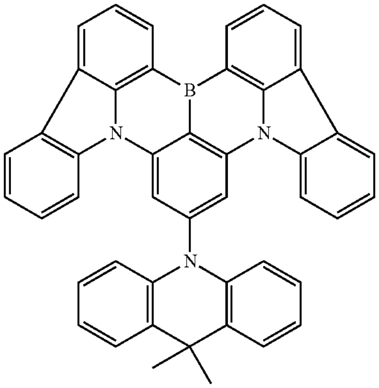
C-237
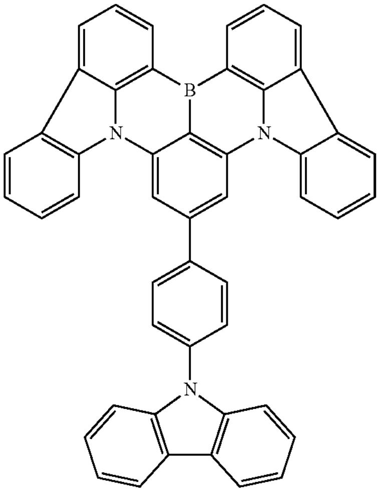

-continued
C-238
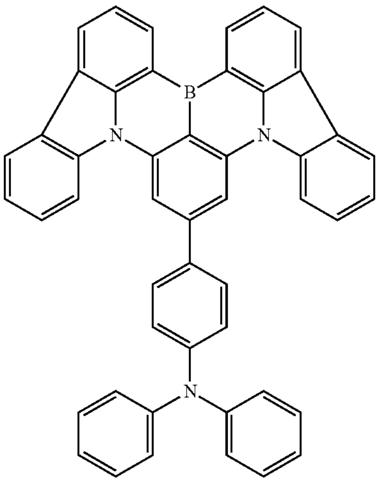
C-239
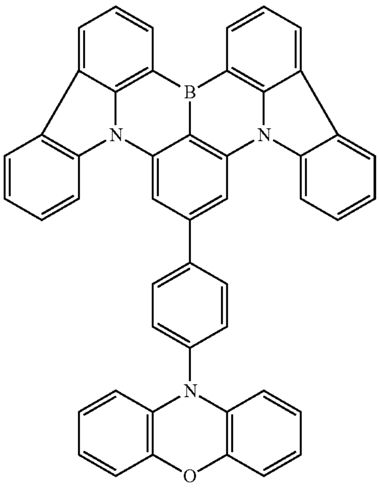
C-240
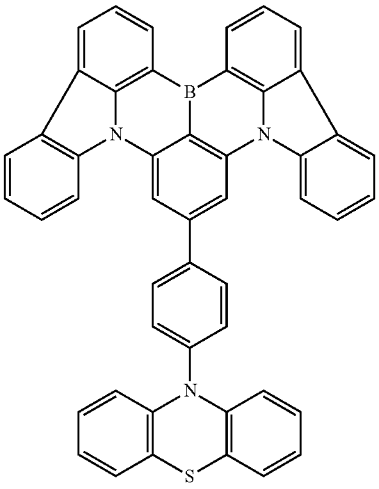
C-241
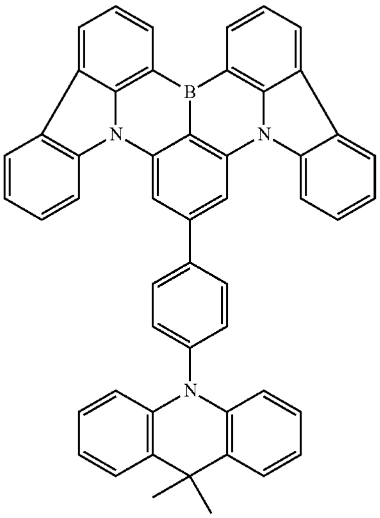
C-242
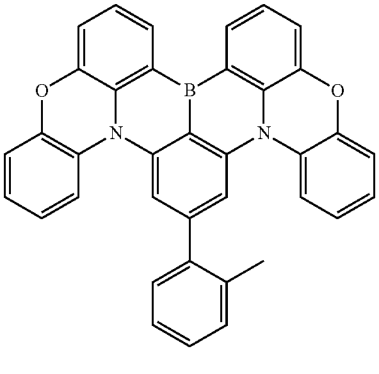
C-243
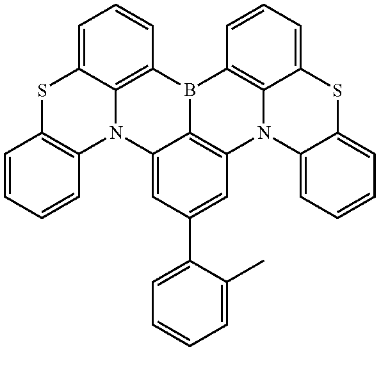

-continued
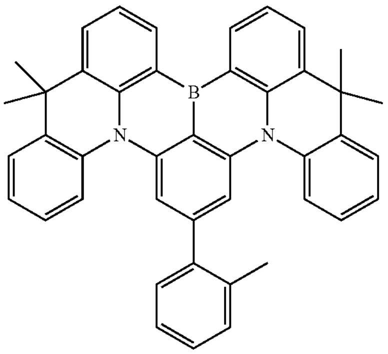
C-244
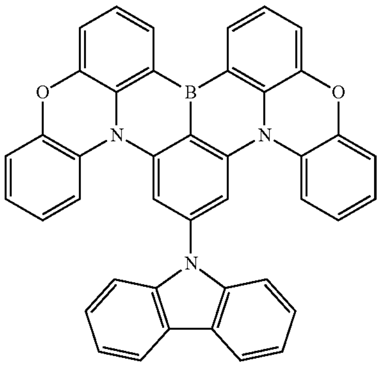
C-245
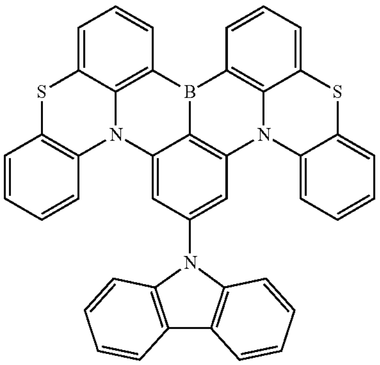
C-246
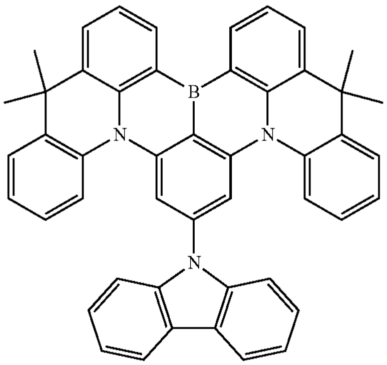
C-247
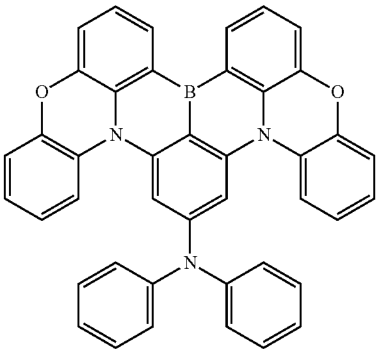
C-248
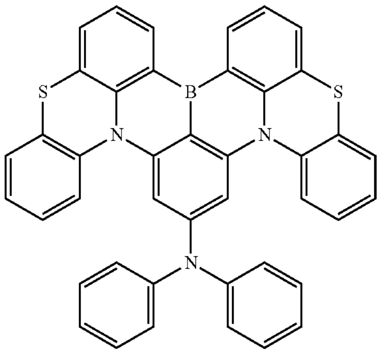
C-249
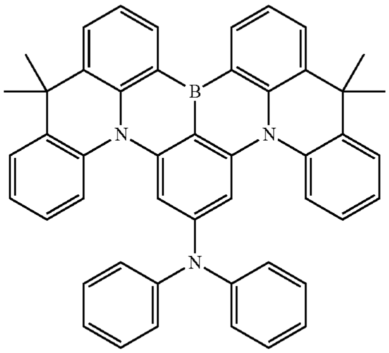
C-250
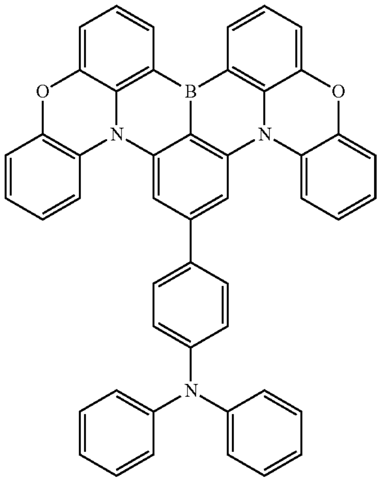
C-251

-continued
C-252
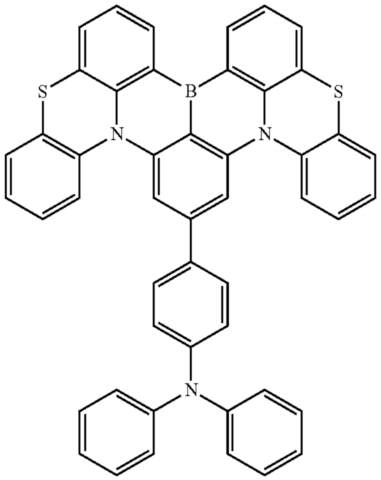
C-253
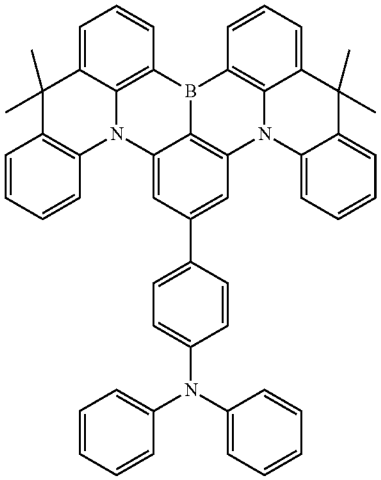
C-254
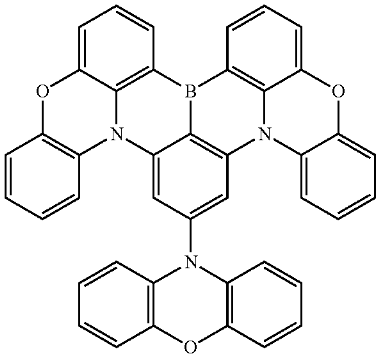
C-255
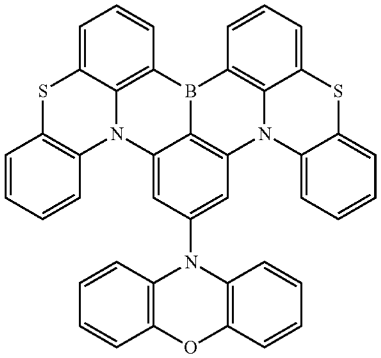
C-256
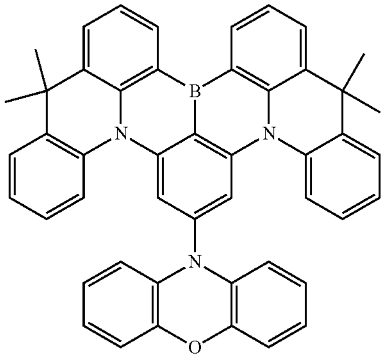
C-257
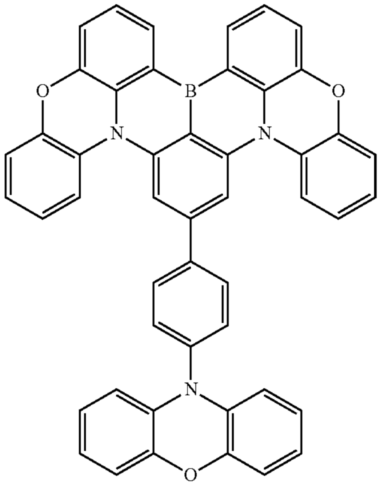

-continued
C-258
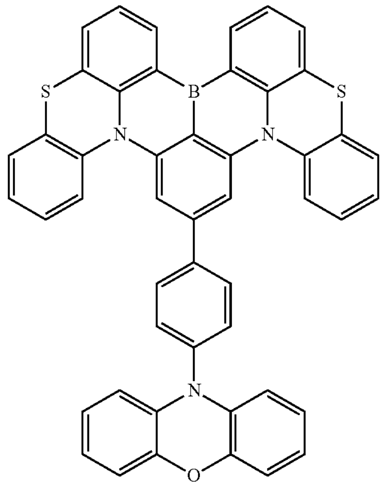
C-259
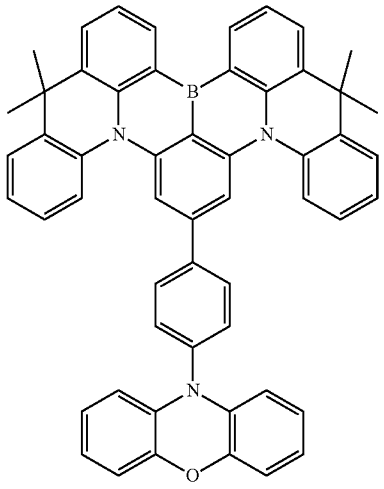
C-260
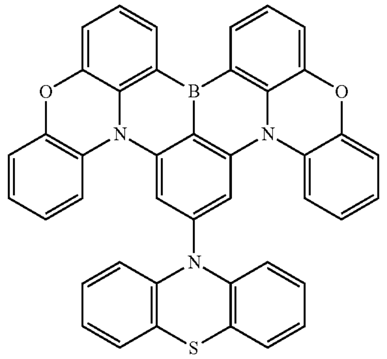
C-261
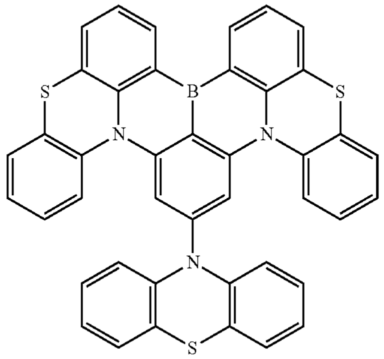
C-262
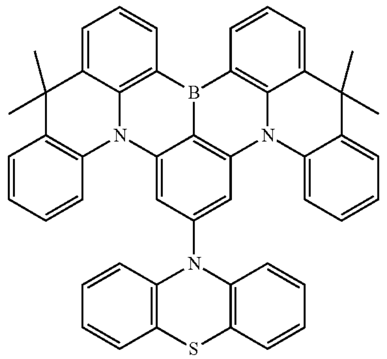
C-263
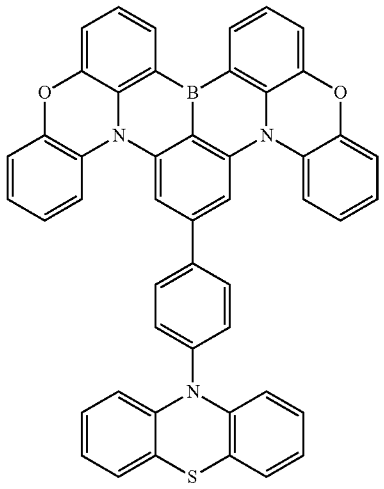

-continued
C-264
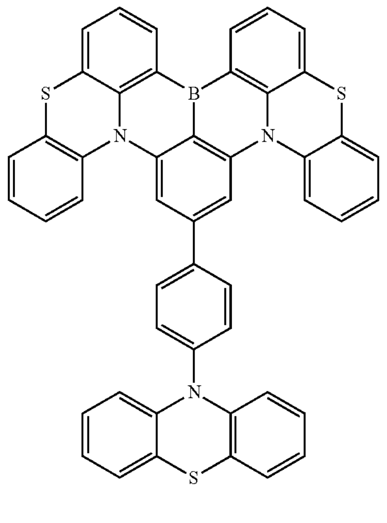
C-265
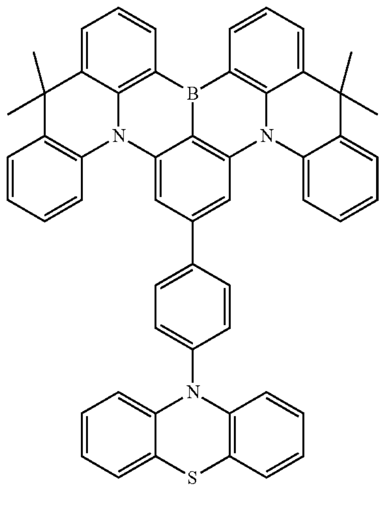
C-266
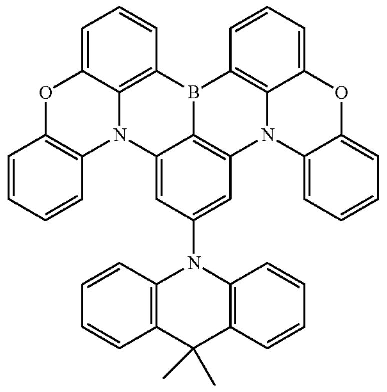
C-267
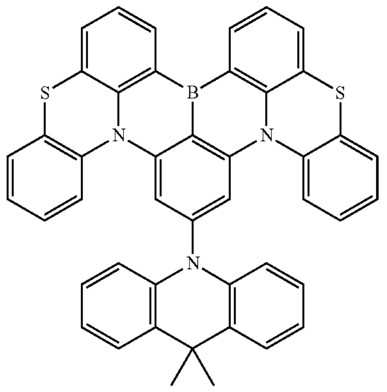
C-268
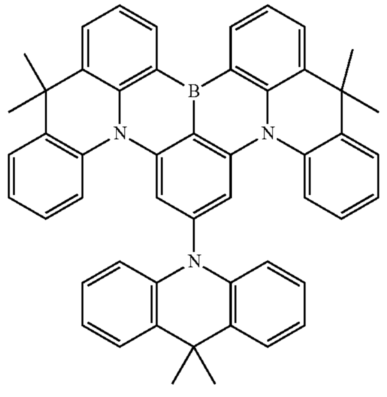
C-269
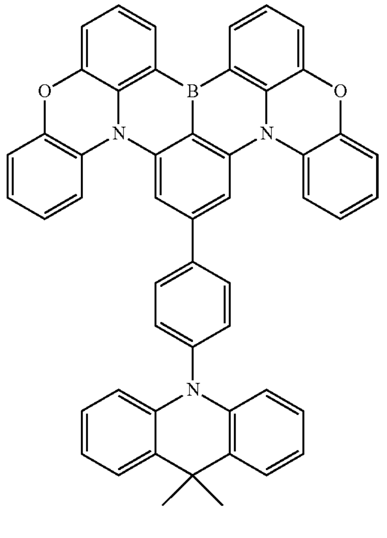

-continued
C-270
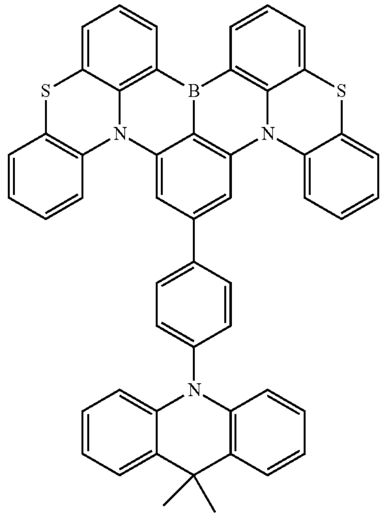
C-271
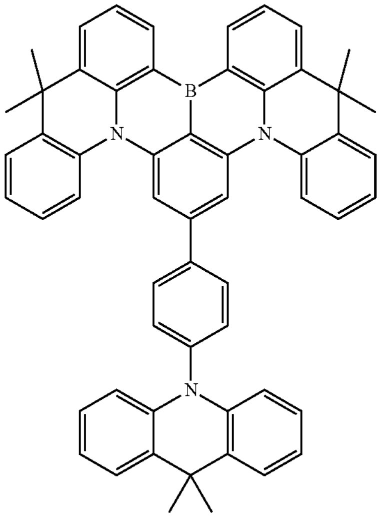
C-272
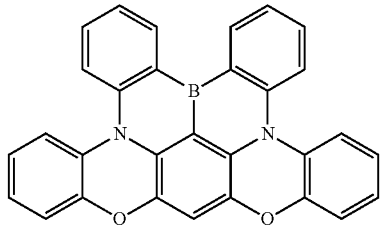
C-273
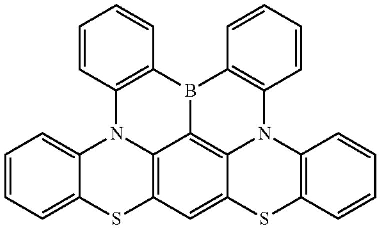
C-274
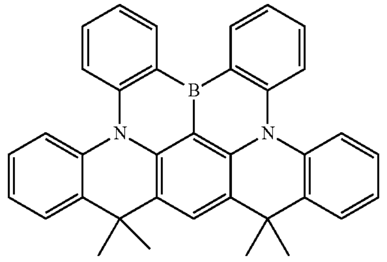
C-275
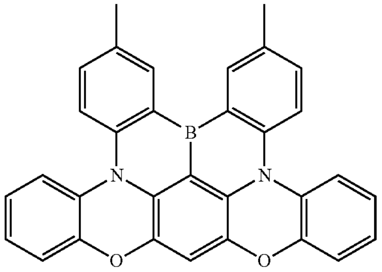
C-276
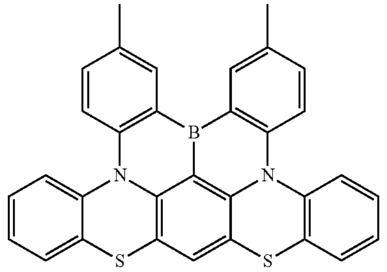
C-277
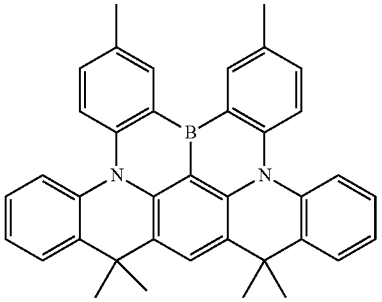

-continued
C-278
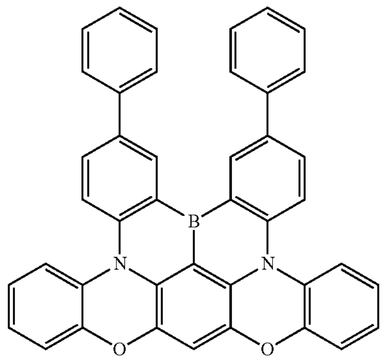
C-279
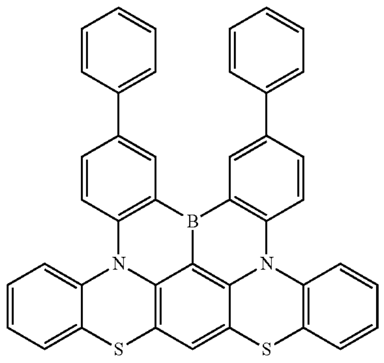
C-280
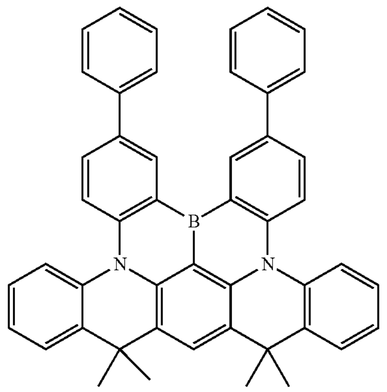
C-281
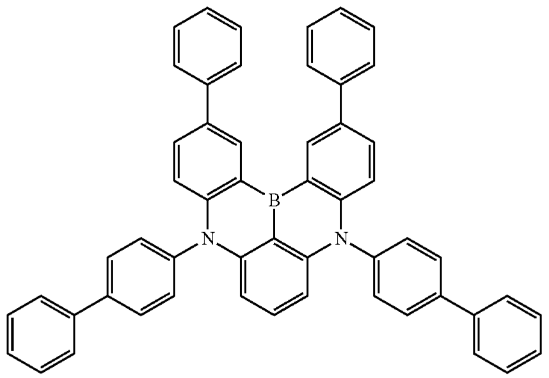
C-282
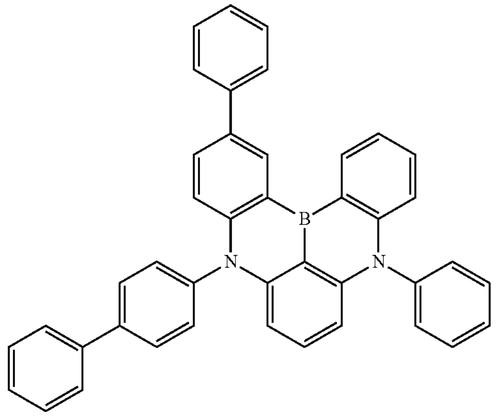
C-283
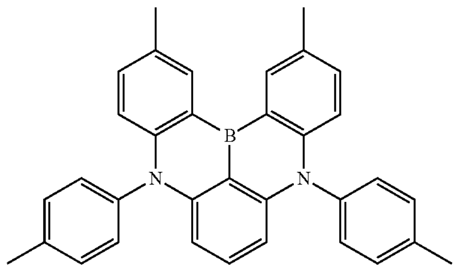
C-284
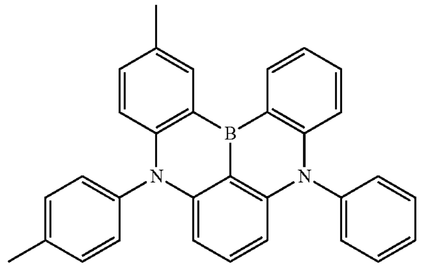
C-285
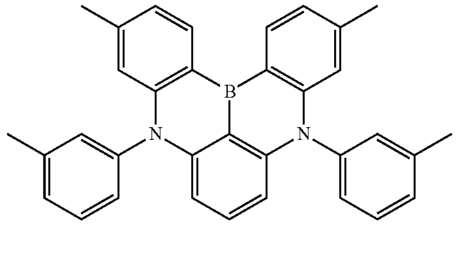

-continued
C-286
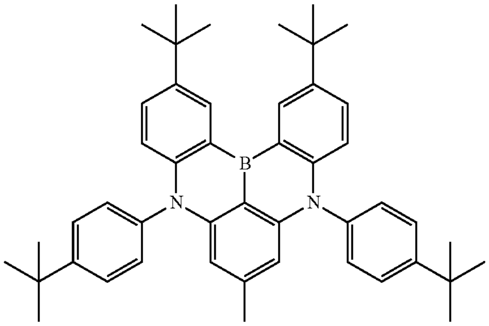
C-287
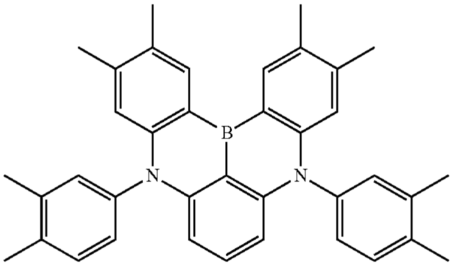
C-288
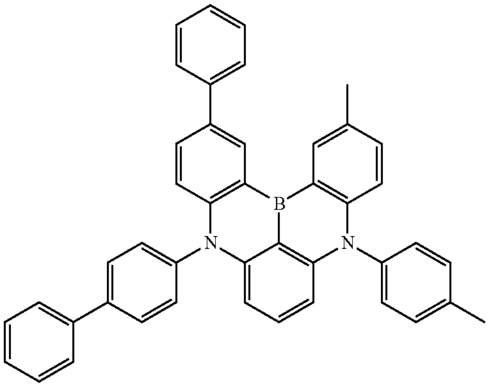
C-289
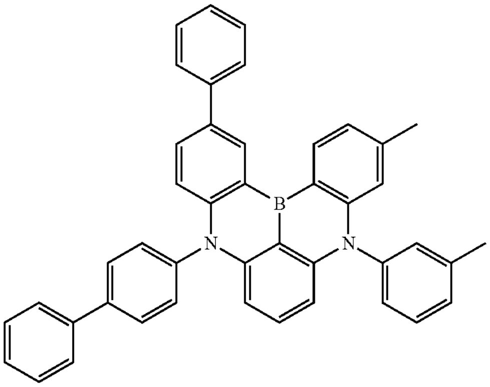
C-290
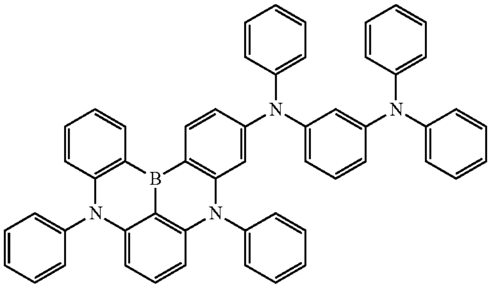
C-291
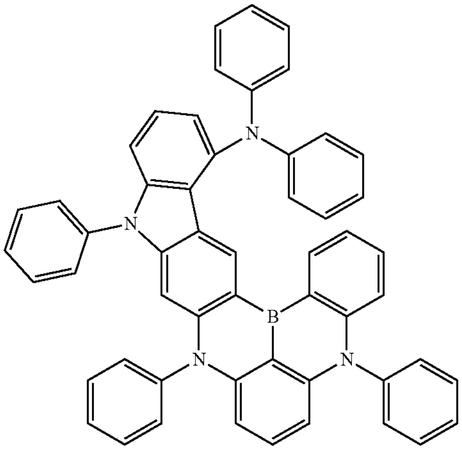
C-292
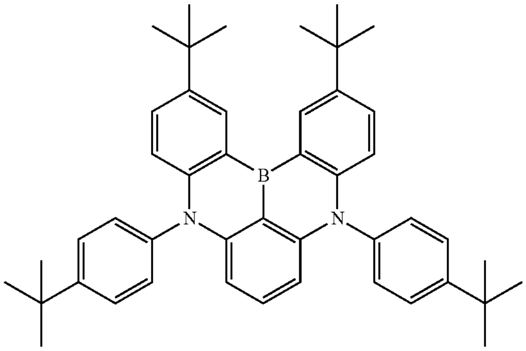
C-293
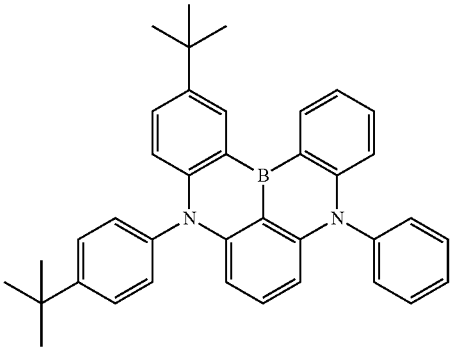

-continued
C-294
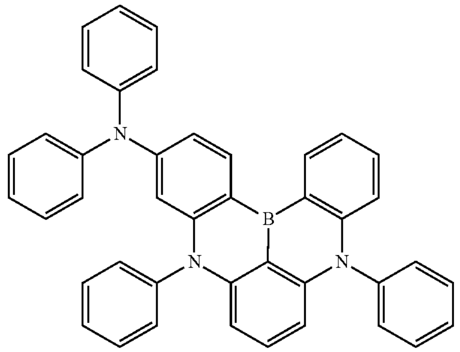
C-295
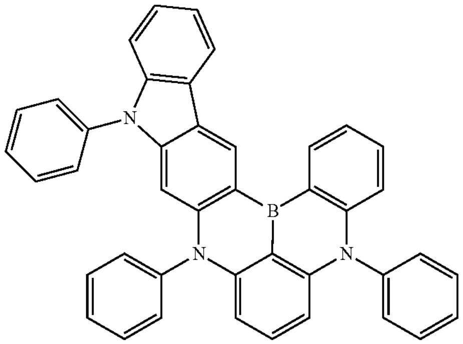
C-296
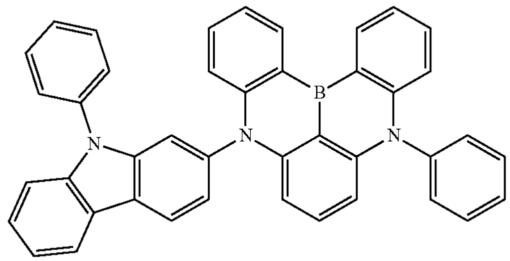
C-297
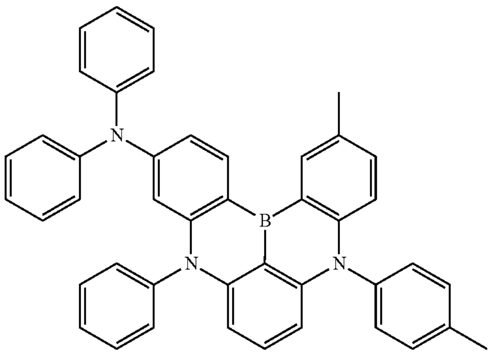
C-298
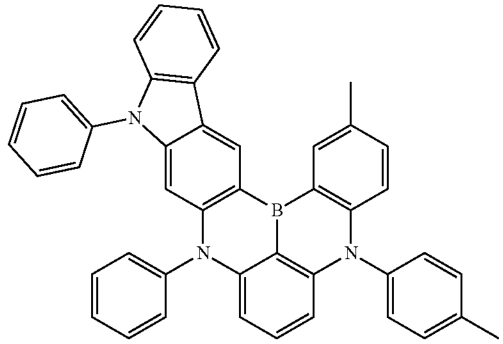
C-299
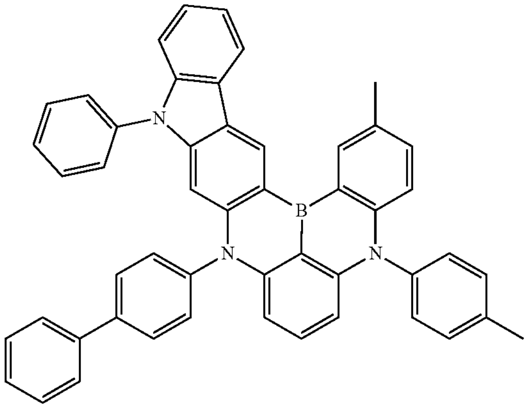
C-300
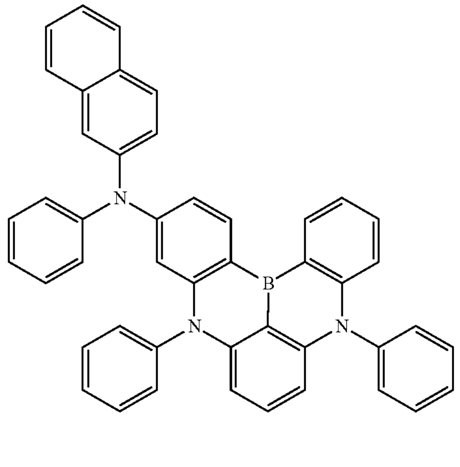

-continued
C-301
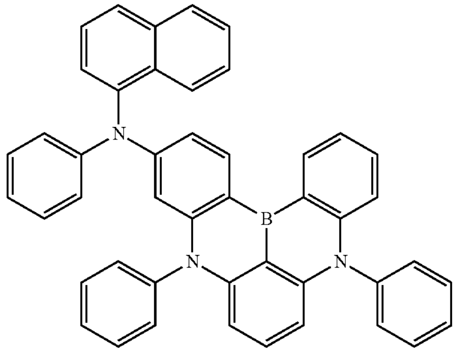
C-302
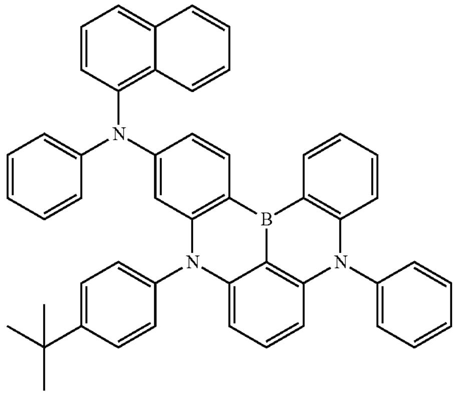
C-303
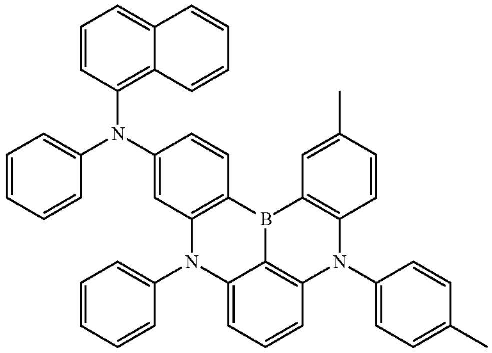
C-304
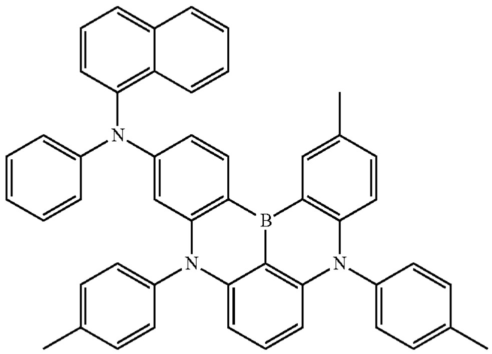
C-305
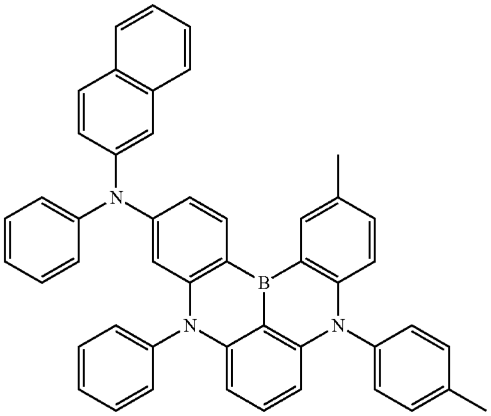
C-306
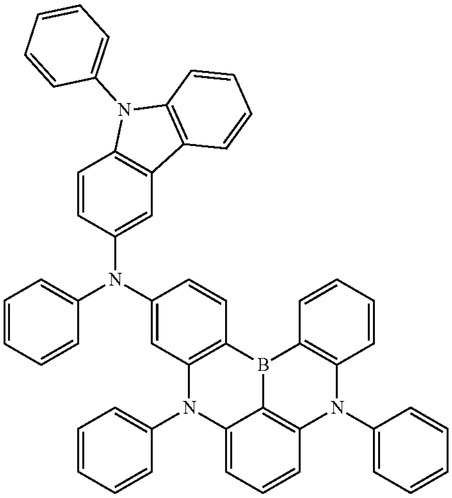
C-307
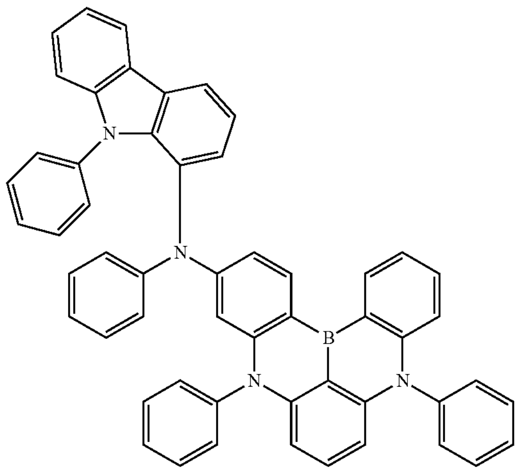

-continued
C-308
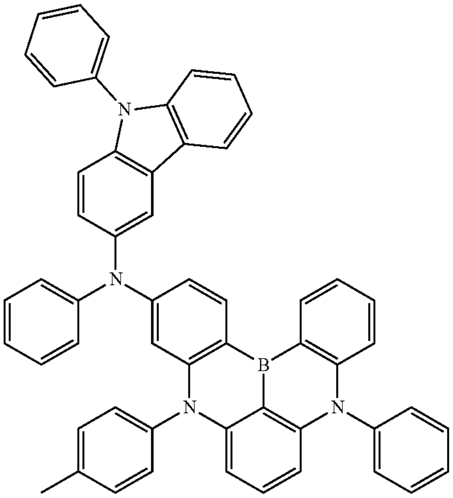
C-309
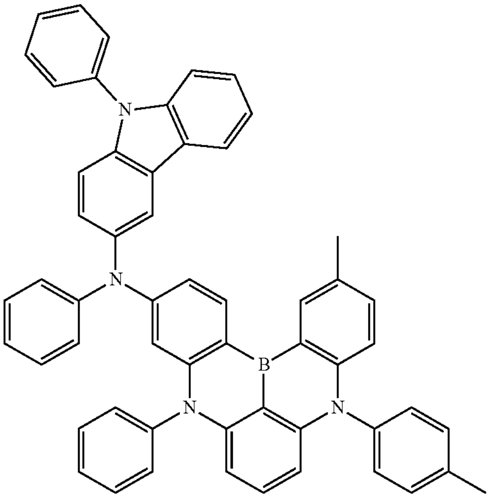
C-310
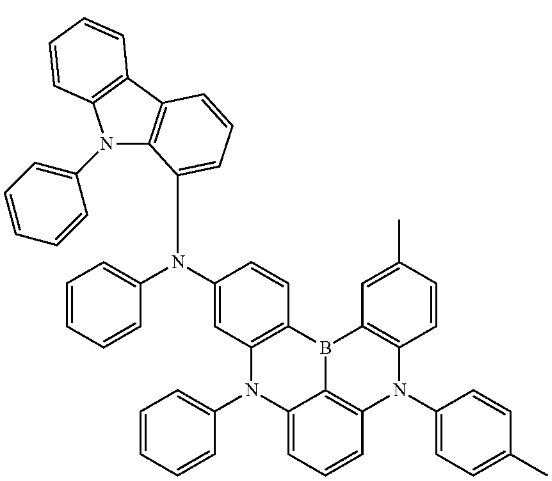
-continued
C-311
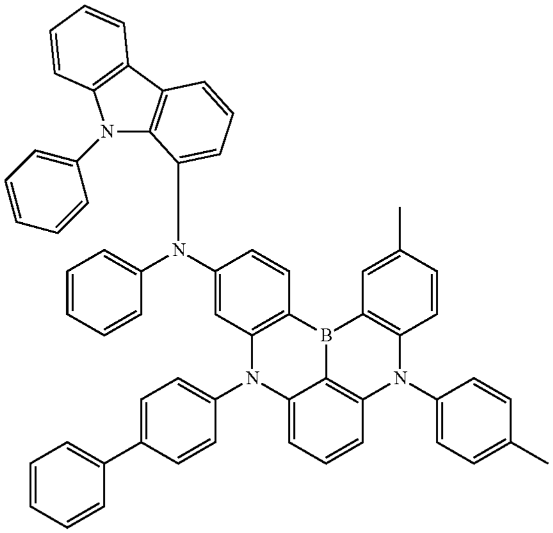
C-312
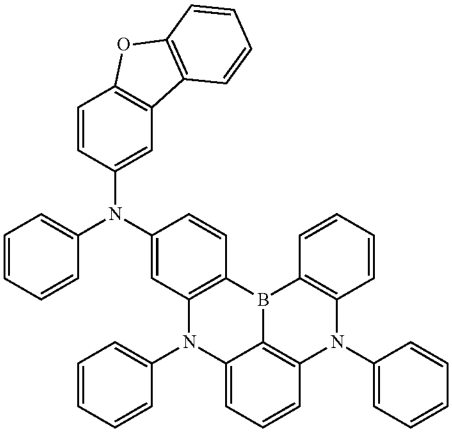
C-313
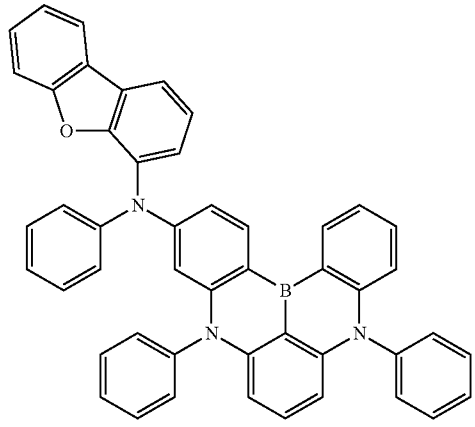

-continued
C-314
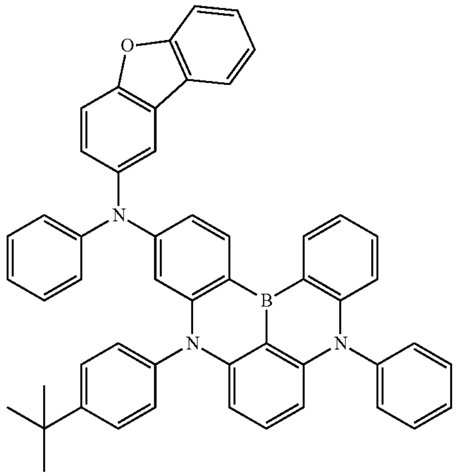
C-315
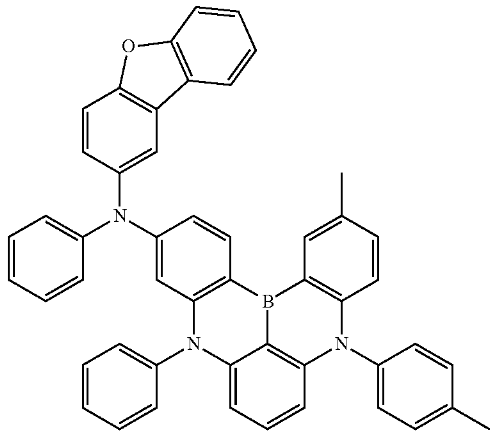
C-316
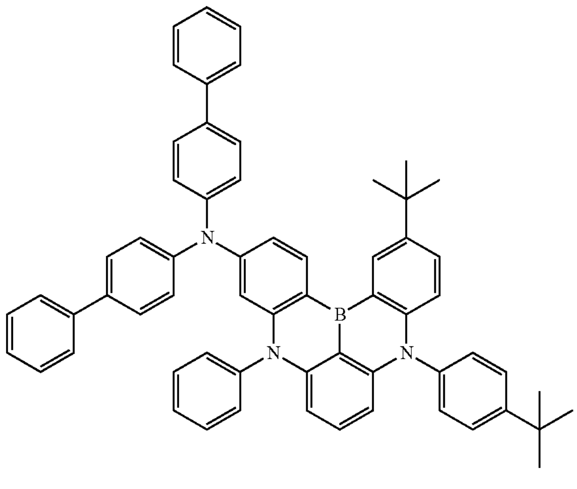
-continued
C-317
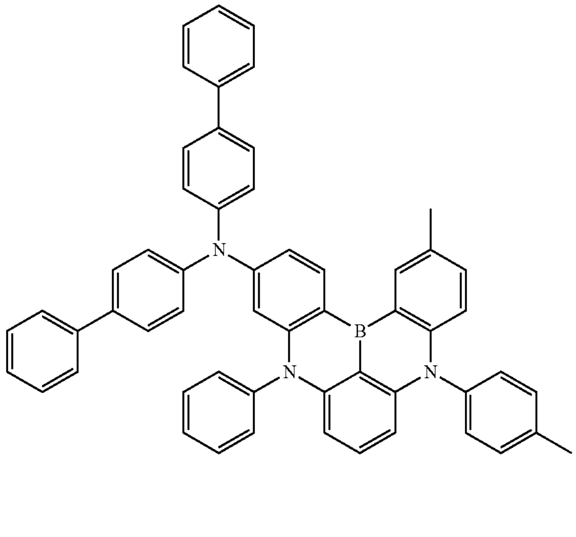
C-318
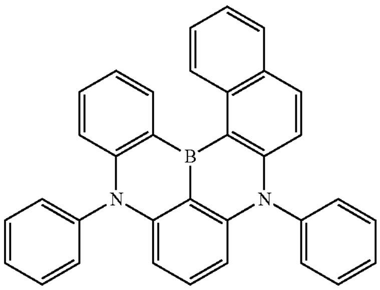
C-319
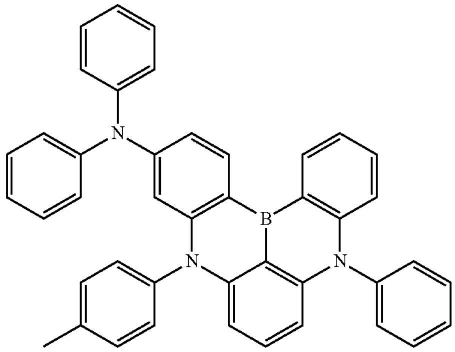
C-320
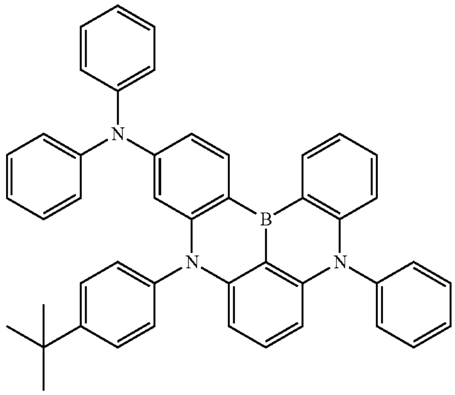

-continued
C-321
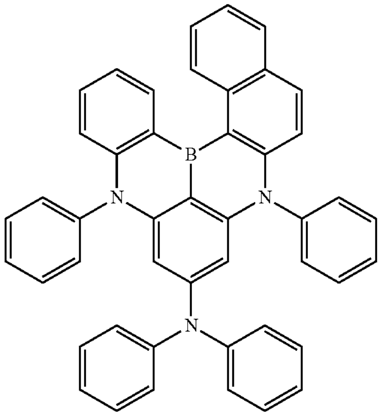
C-322
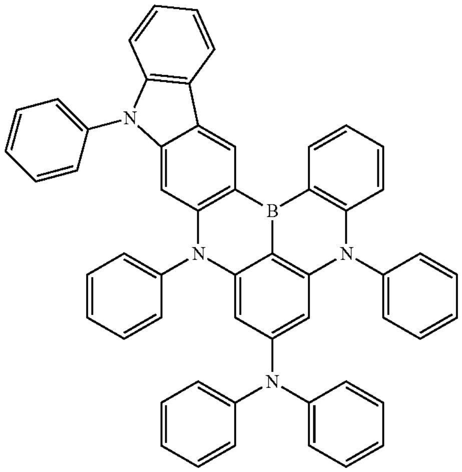
C-323
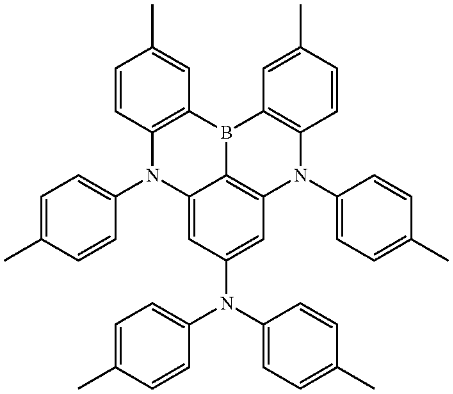
-continued
C-324
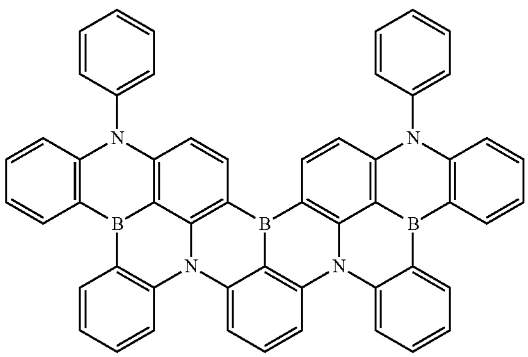
C-325
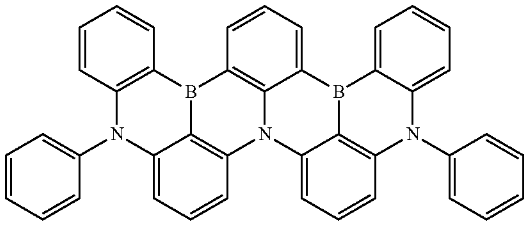
C-326
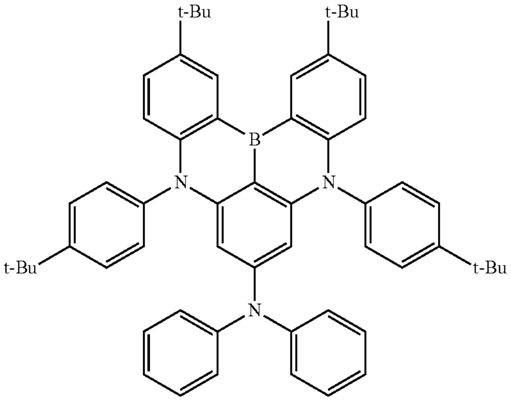
C-327
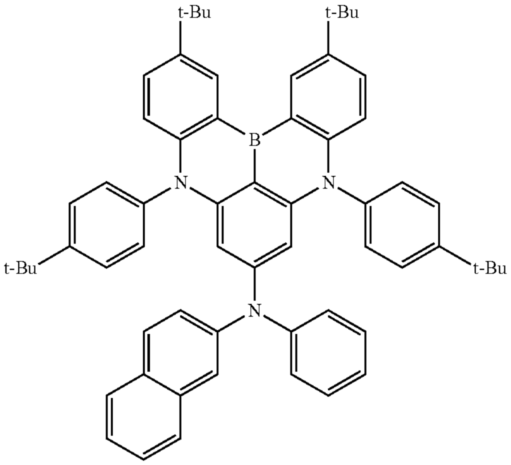

-continued
C-328
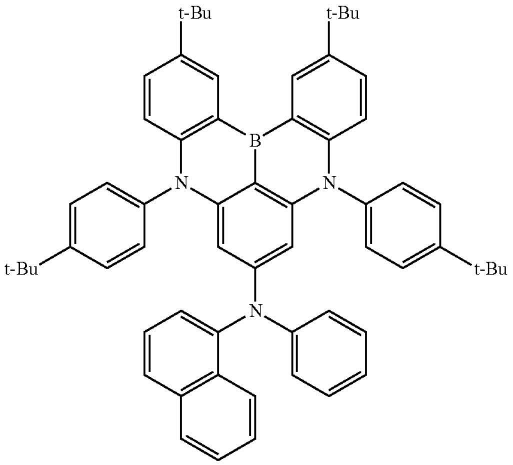
C-329
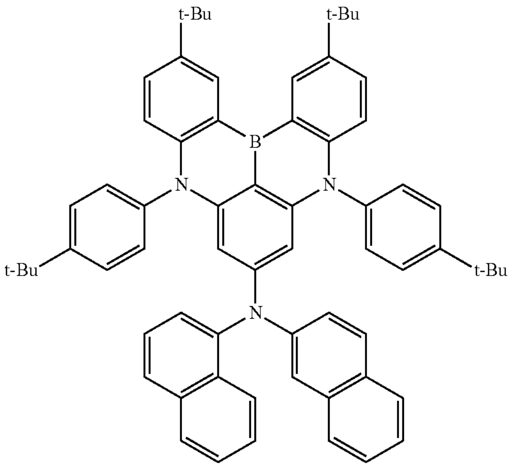
C-330
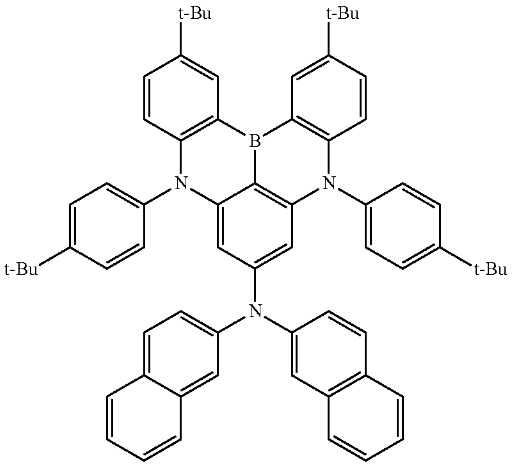
-continued
C-331
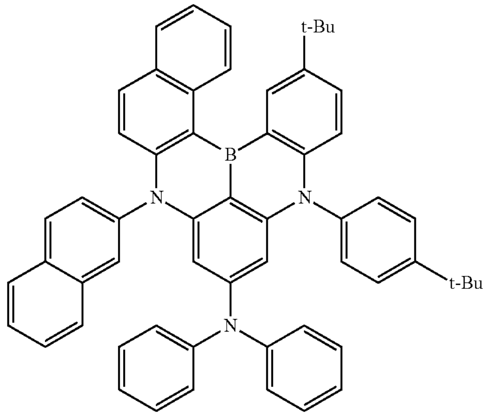
C-332
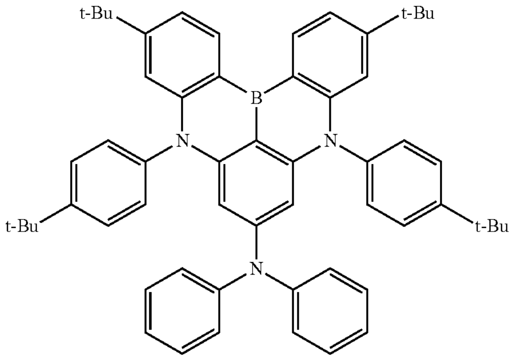
C-333
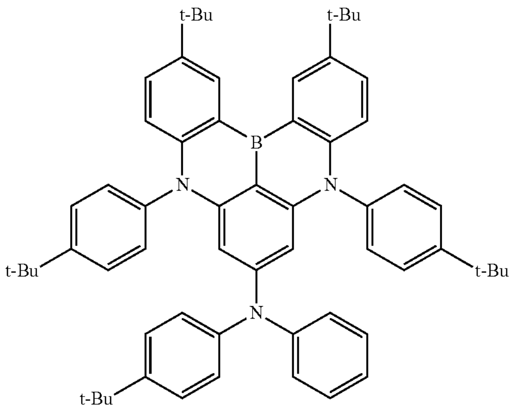
C-334
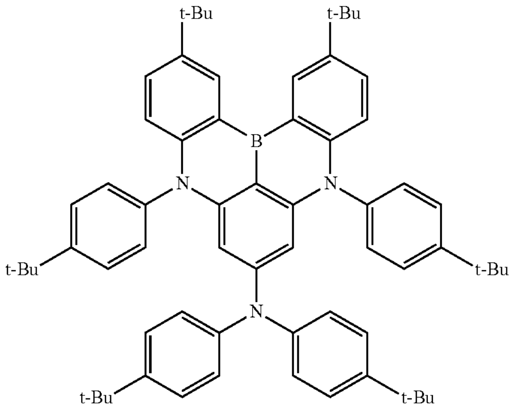

-continued
C-335
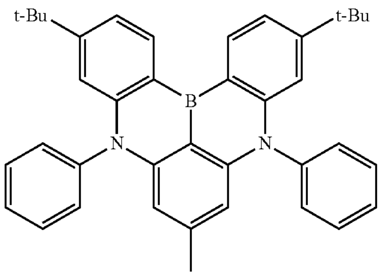
C-336
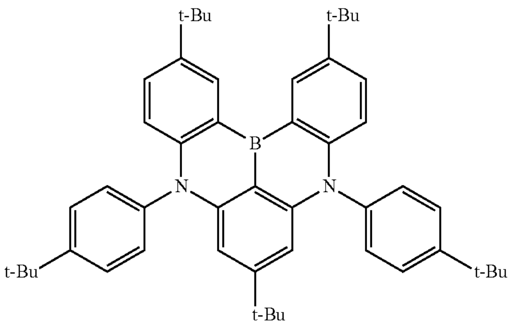
C-337
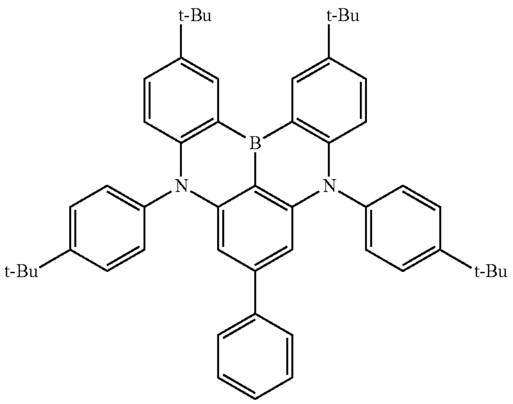
C-338
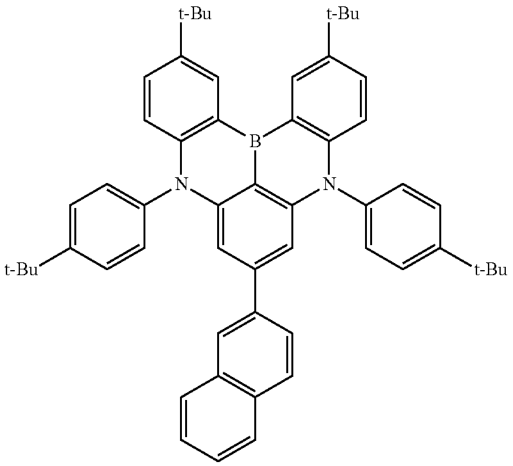
-continued
C-339
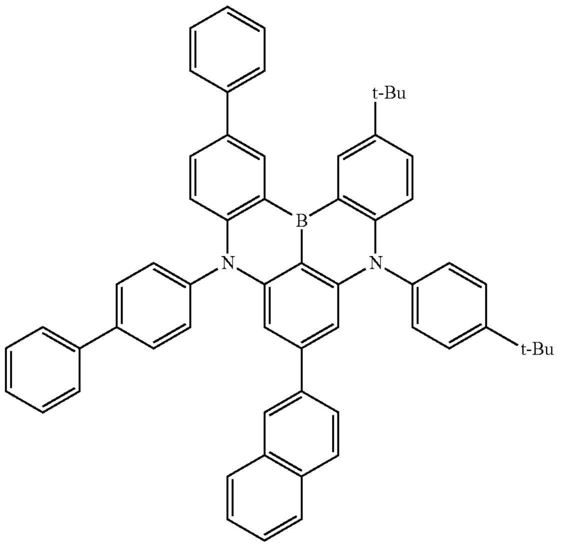
C-340
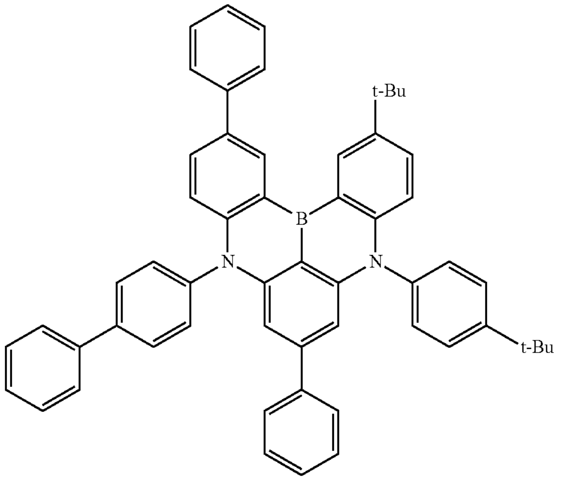
C-341
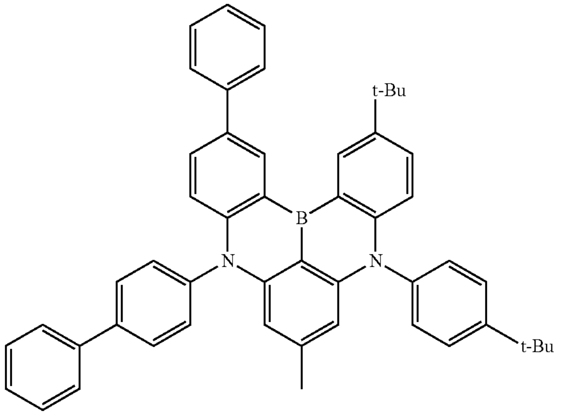

-continued
C-342
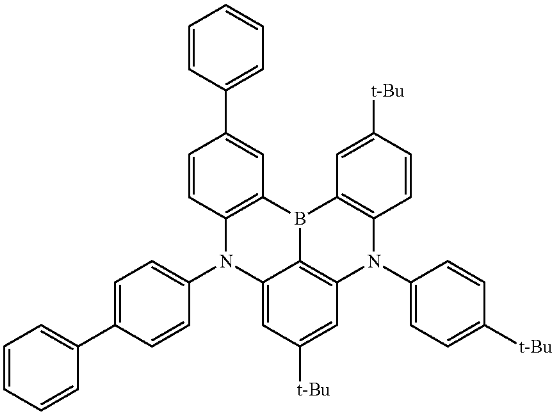
C-343
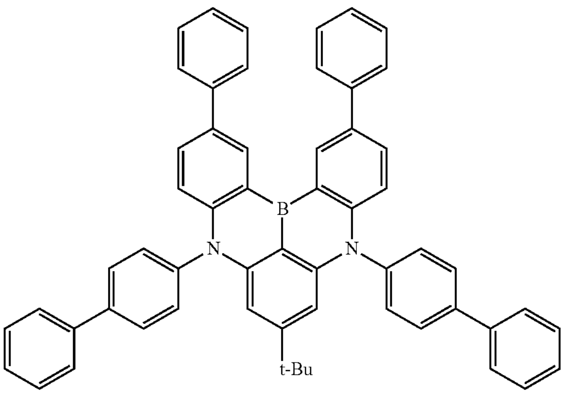
C-344
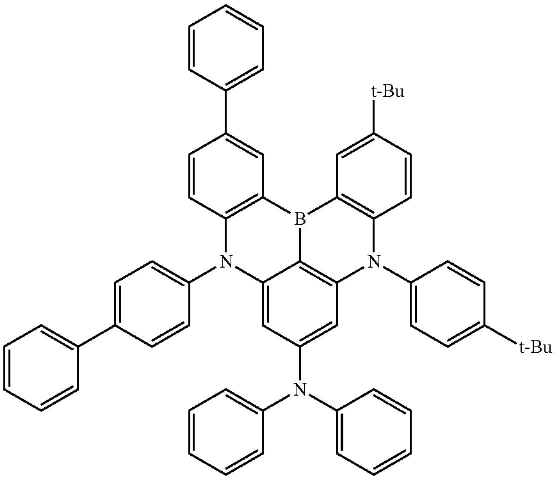
-continued
C-345
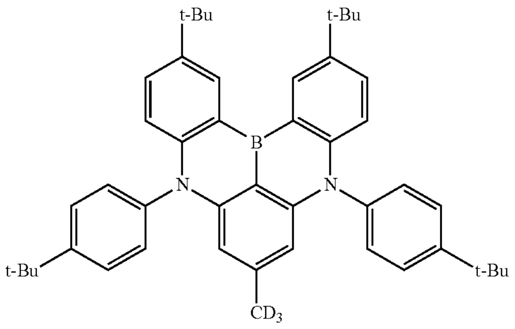
C-346
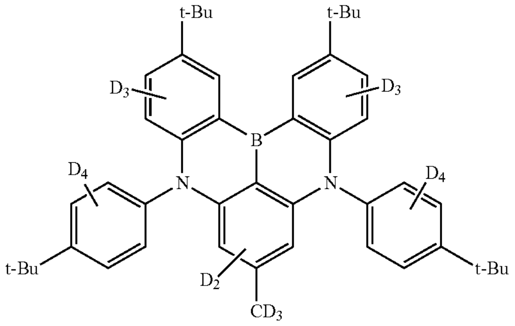
C-347
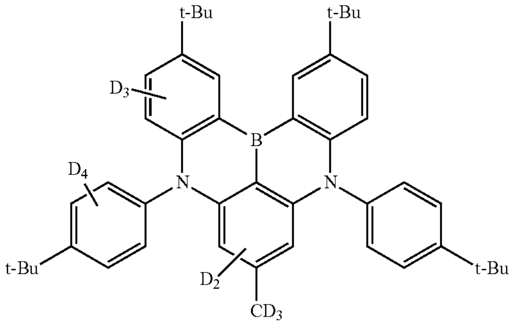
C-348
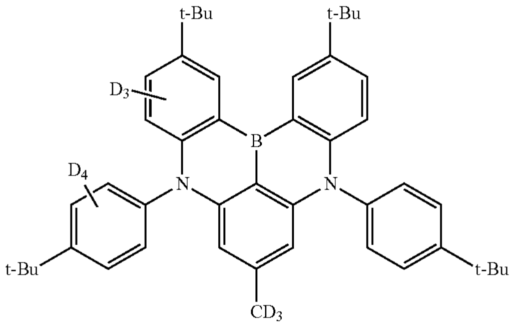

-continued
C-349
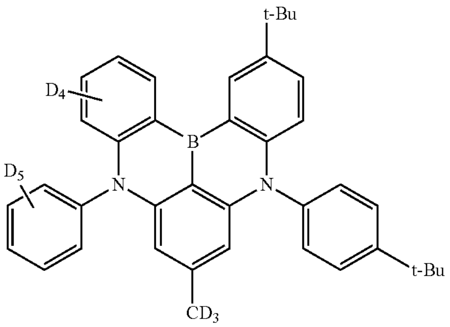
C-350
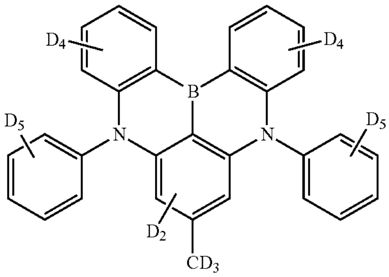
C-351
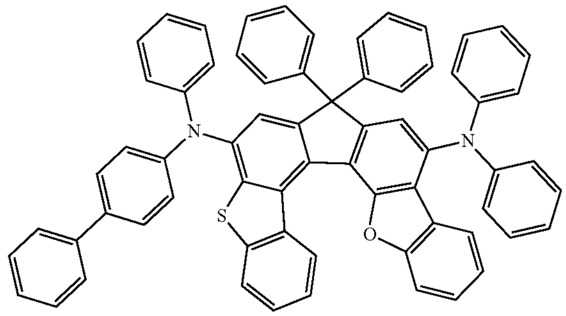
C-352
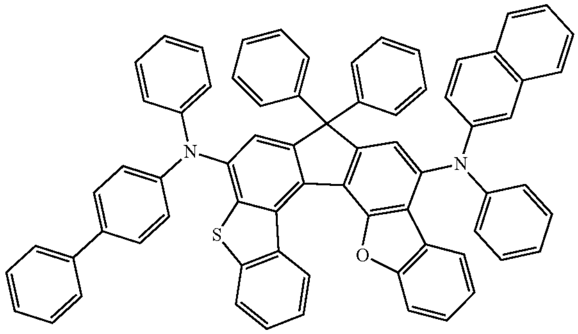
-continued
C-353
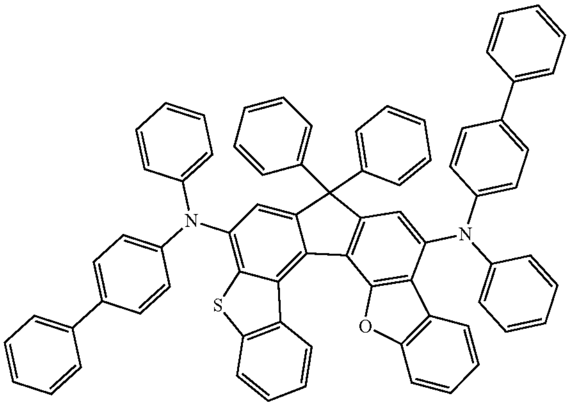
C-354
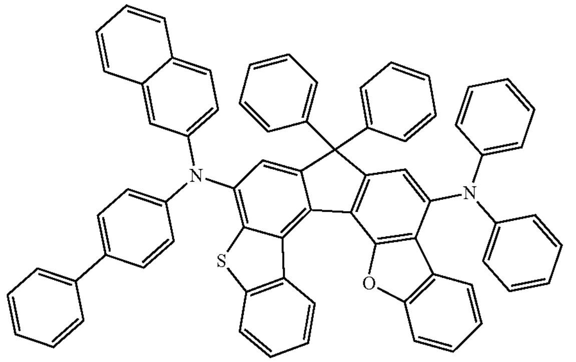
C-355
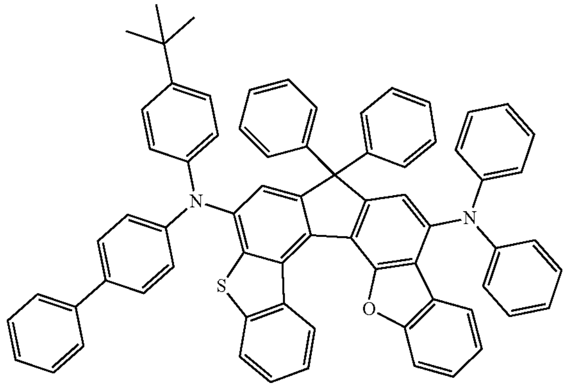
C-356
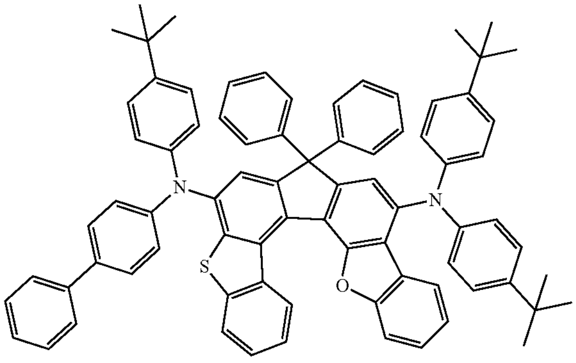

-continued
C-357
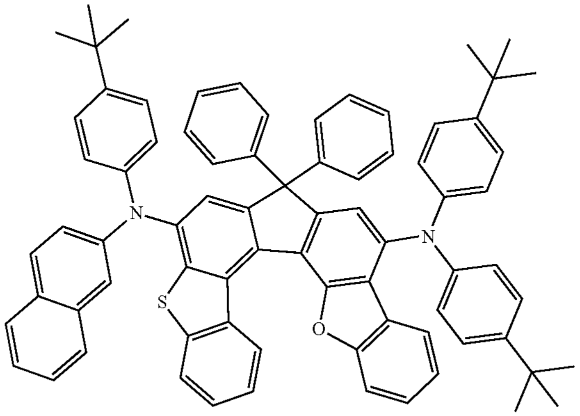
C-358
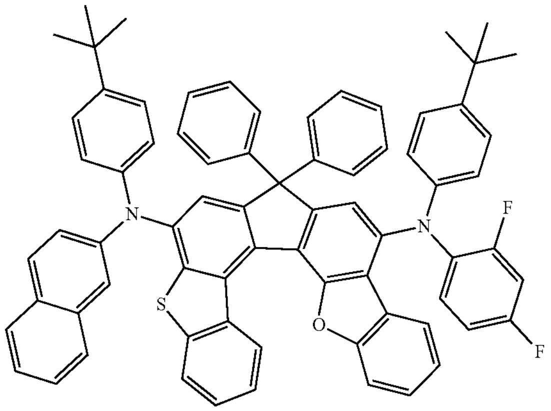
C-359
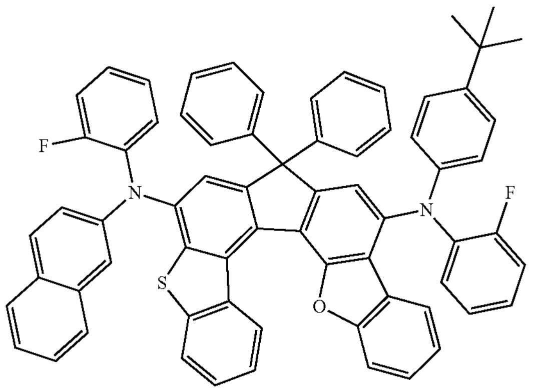
-continued
C-360
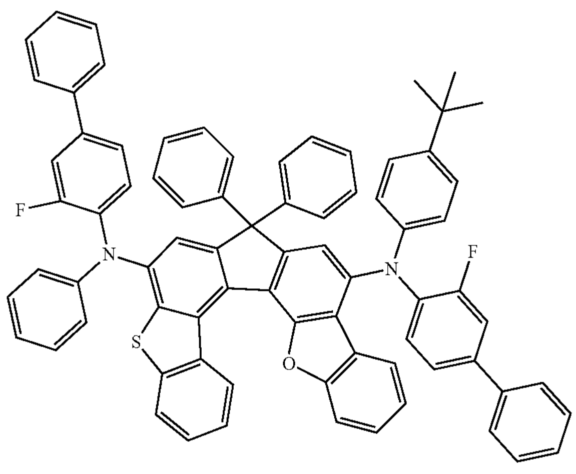
C-361
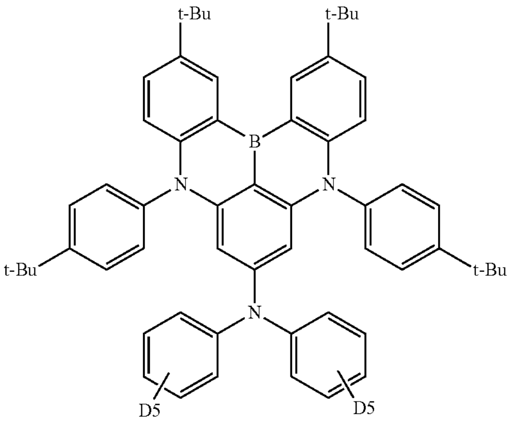
C-362
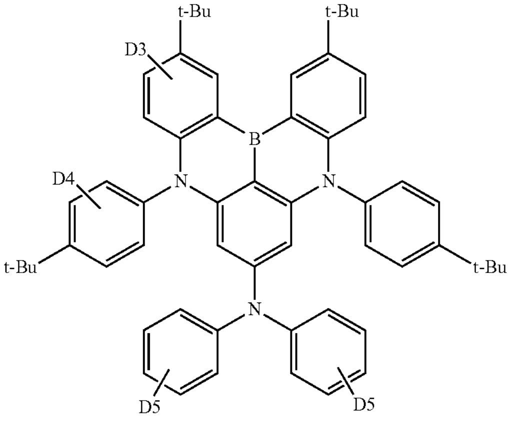

-continued
C-363
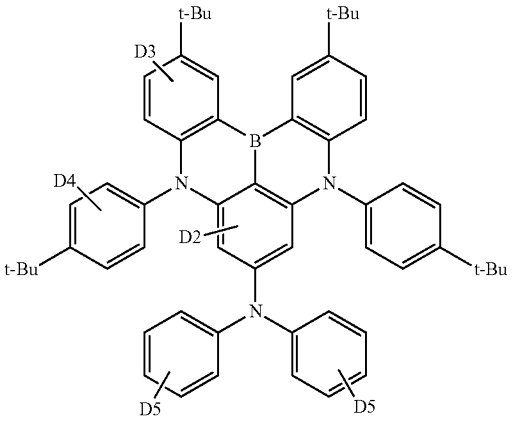
C-364
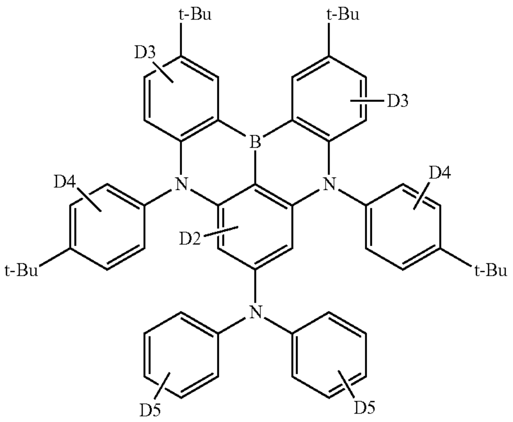
C-365
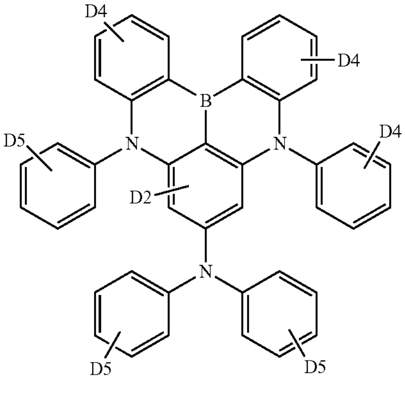
-continued
C-366
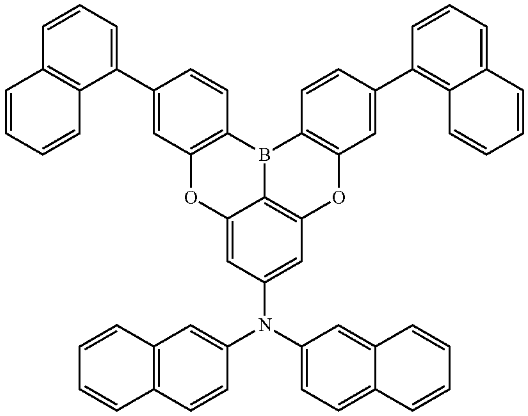
C-367
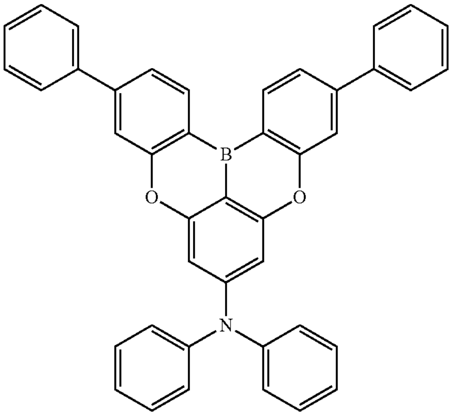
C-368
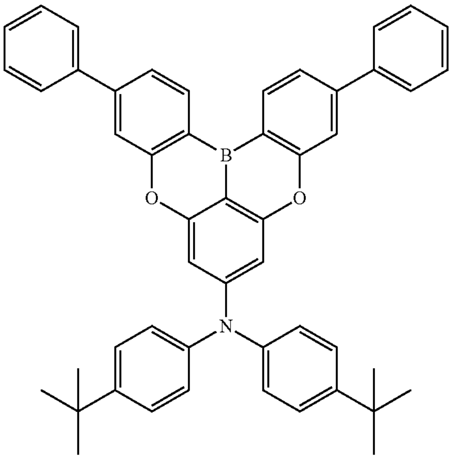

-continued
C-369
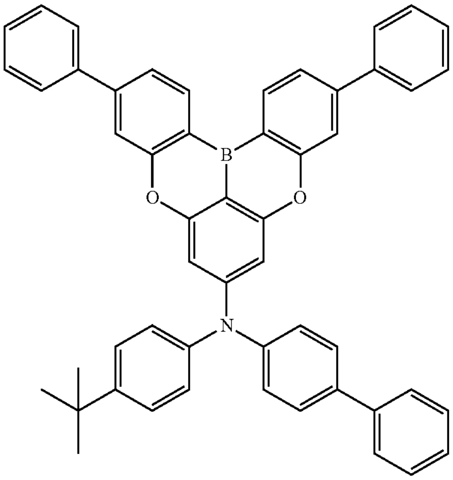
C-370
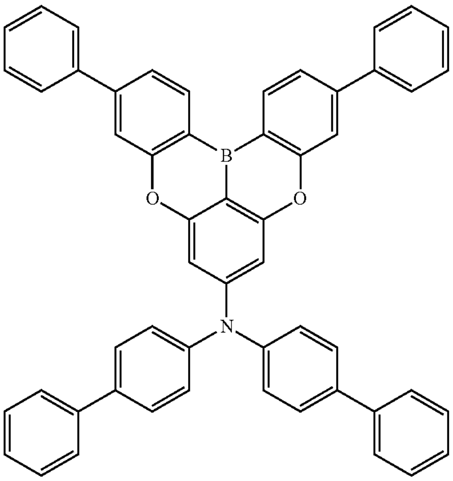
C-371
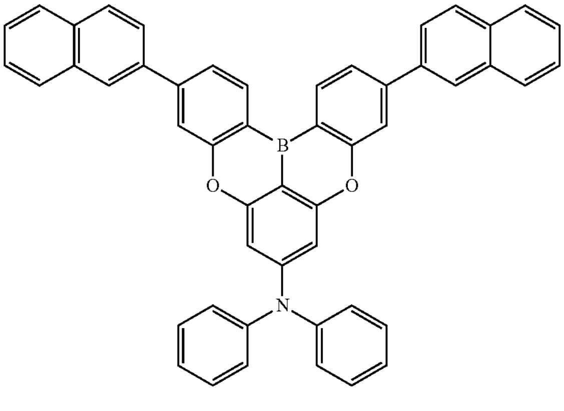
-continued
C-372
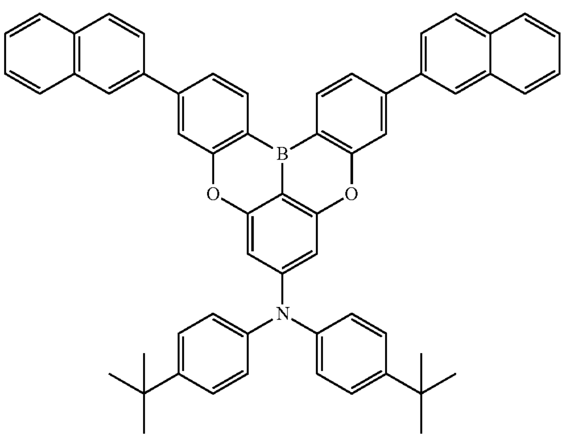
C-373
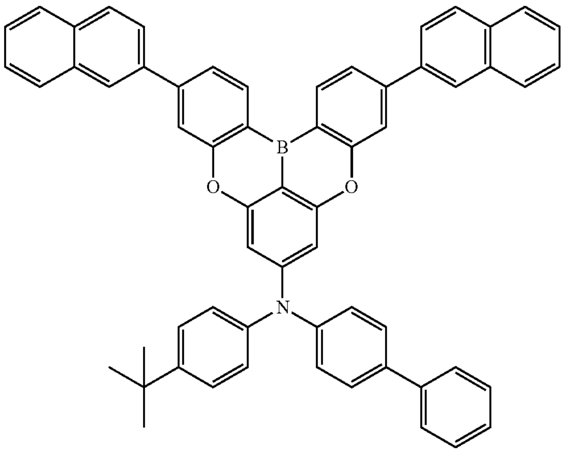
C-374
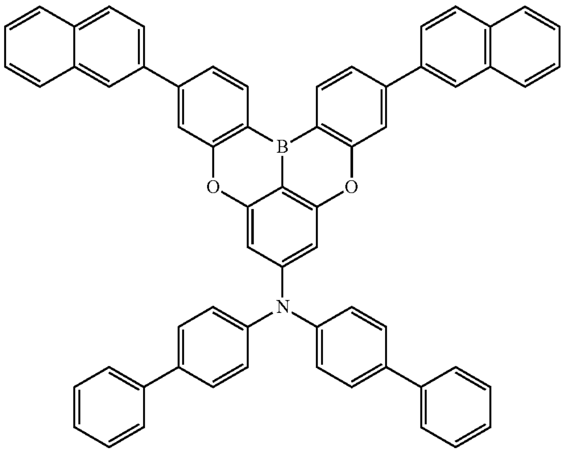

-continued
C-375
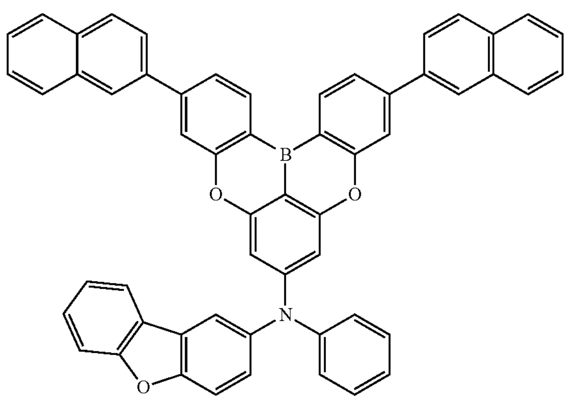
C-376
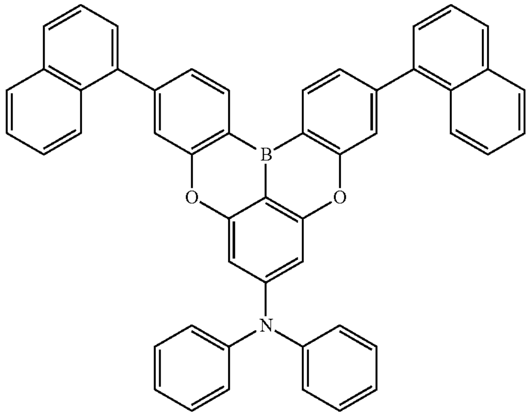
C-377
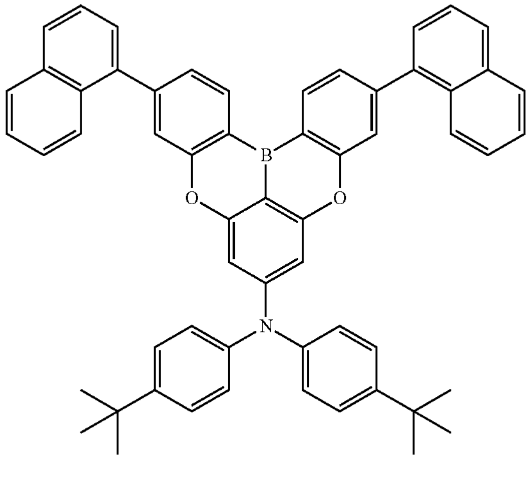
-continued
C-378
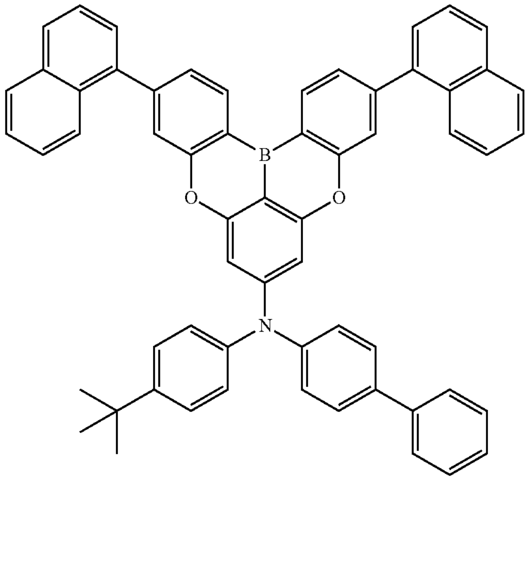
C-379
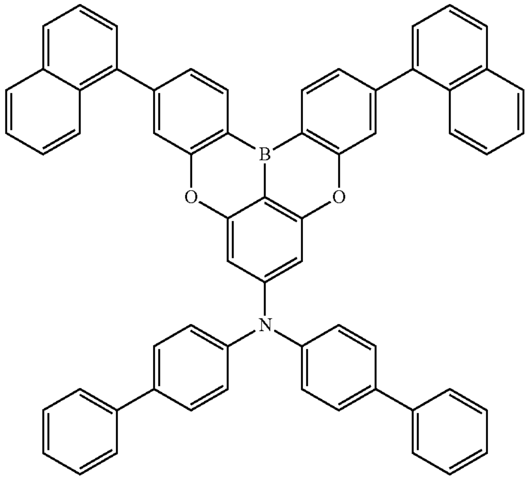
C-380
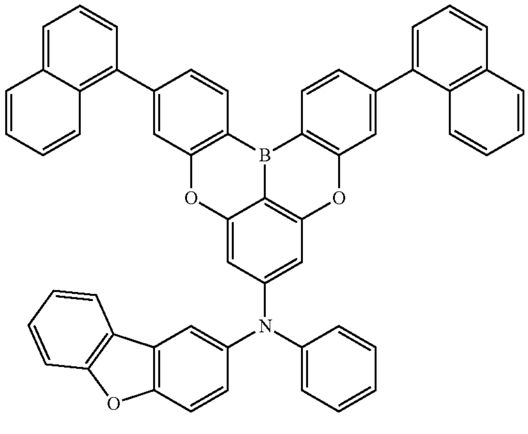

-continued
C-381
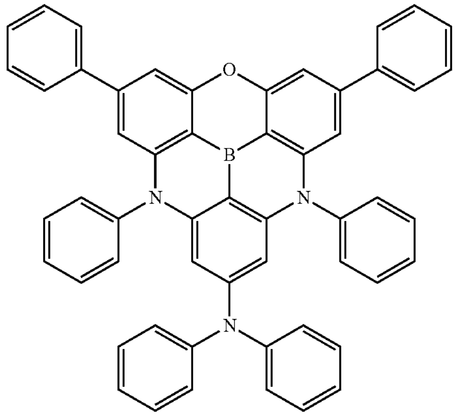
C-382
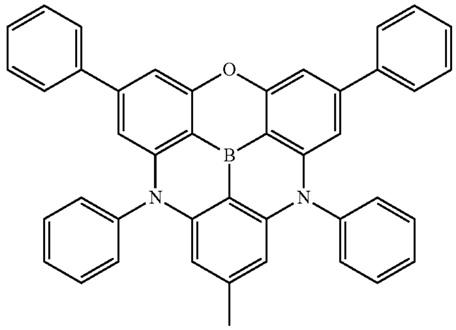
C-383
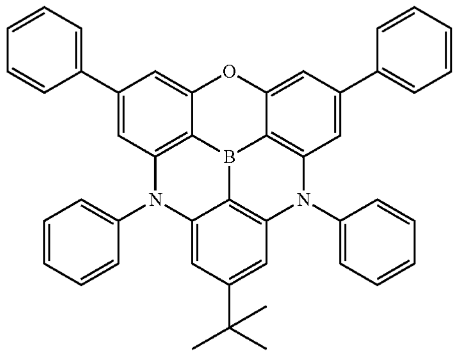
C-384
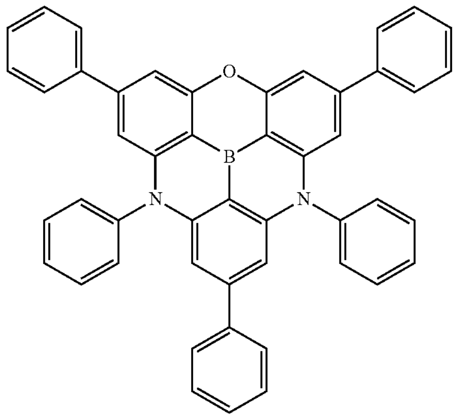
-continued
C-385
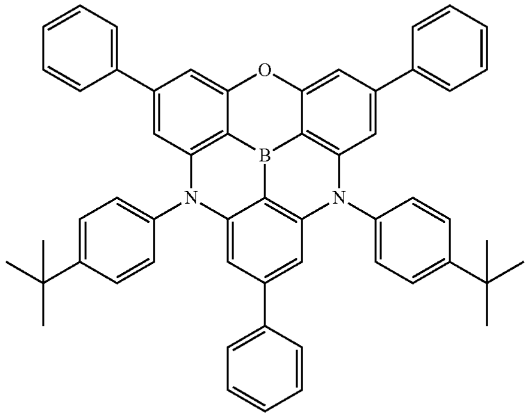
C-386
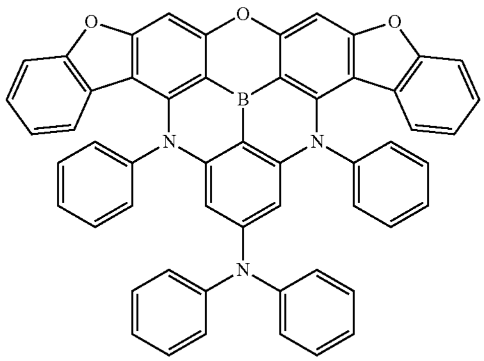
C-387
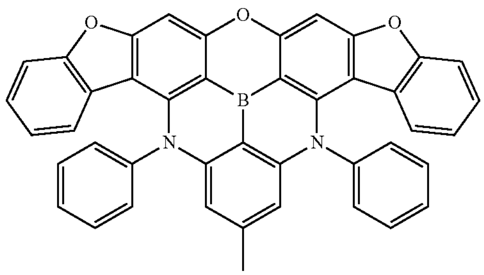
C-388
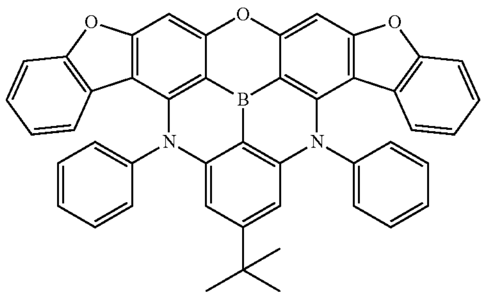

-continued
C-389
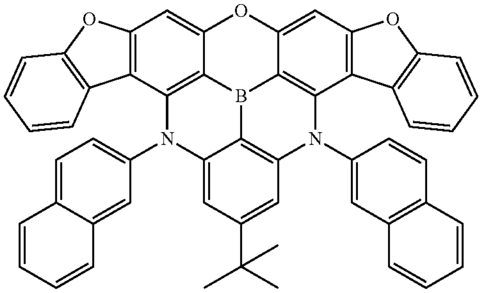
C-390
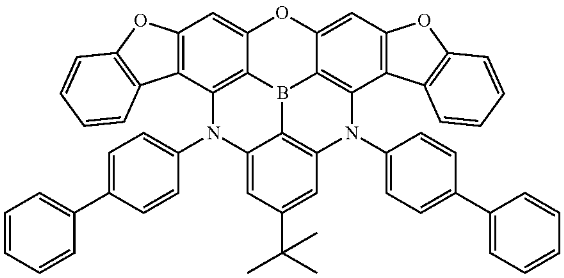
C-391
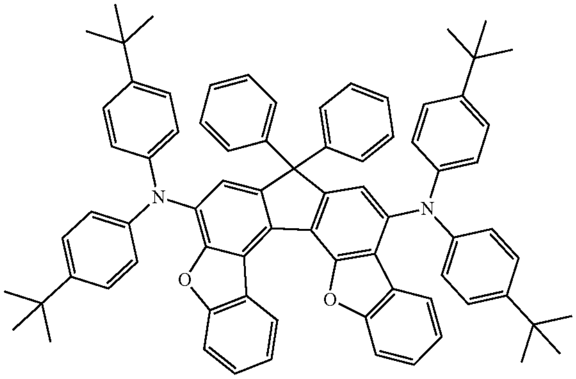
C-392
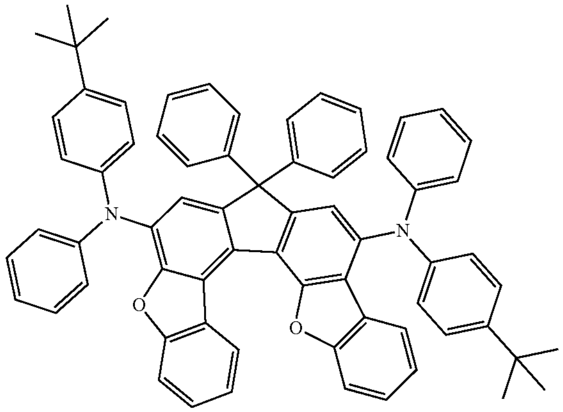
-continued
C-393
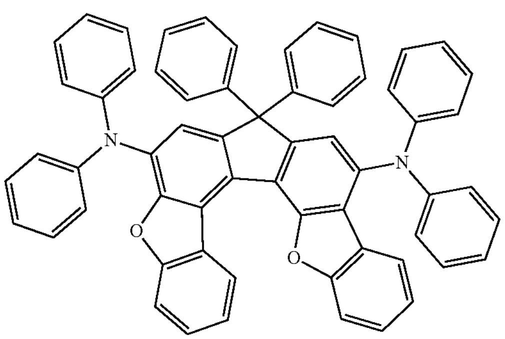
C-394
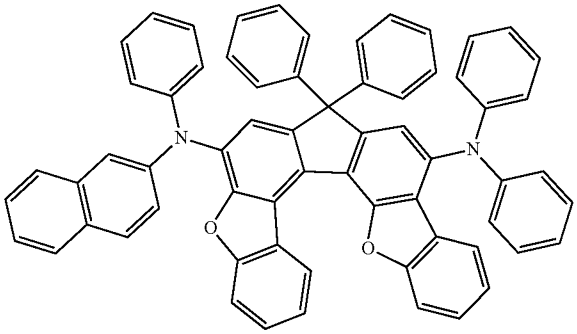
C-395
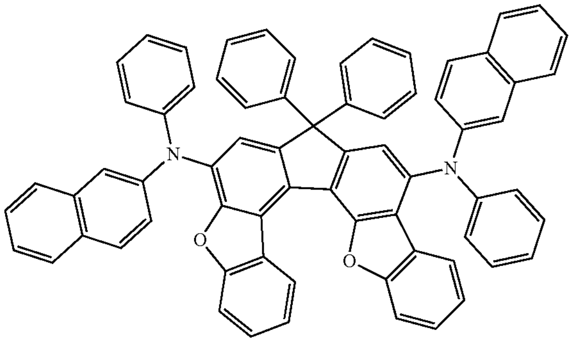
C-396
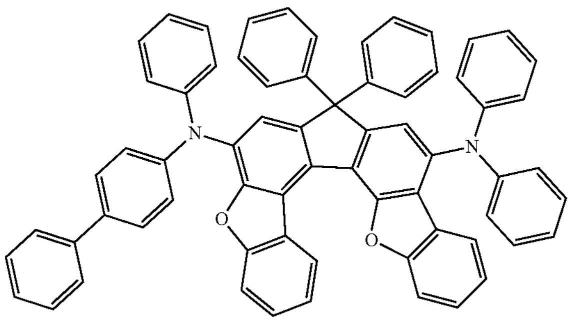

-continued
C-397
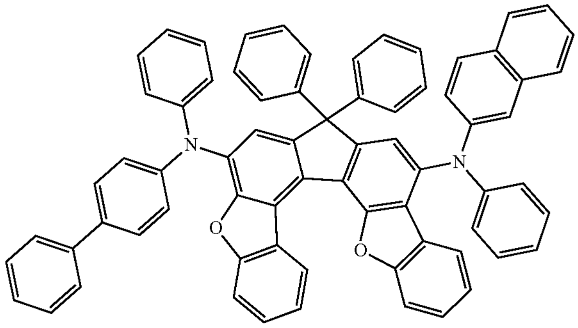
C-398
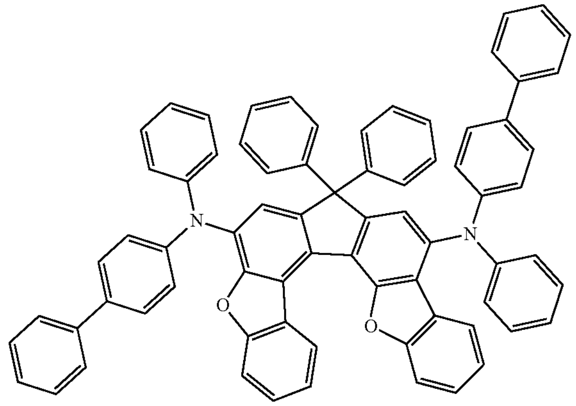
C-399
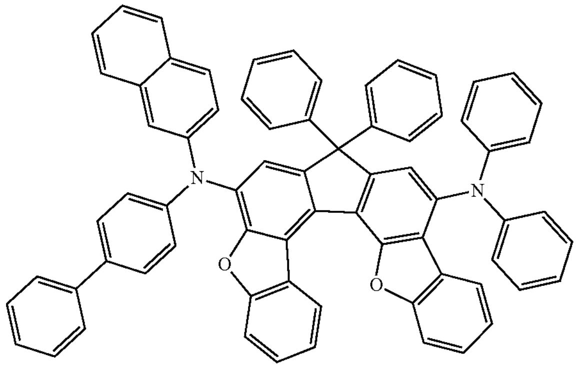
C-400
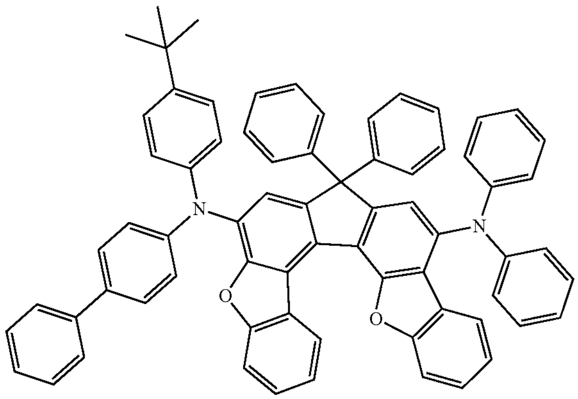
-continued
C-401
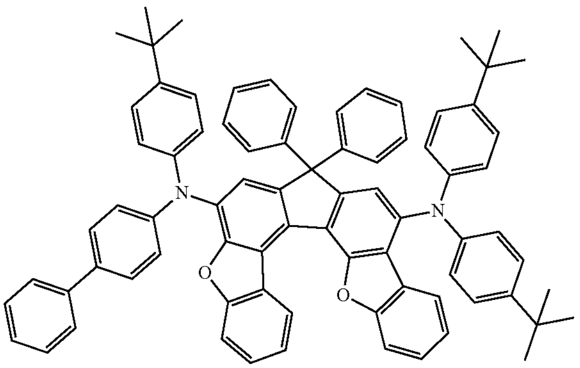
C-402
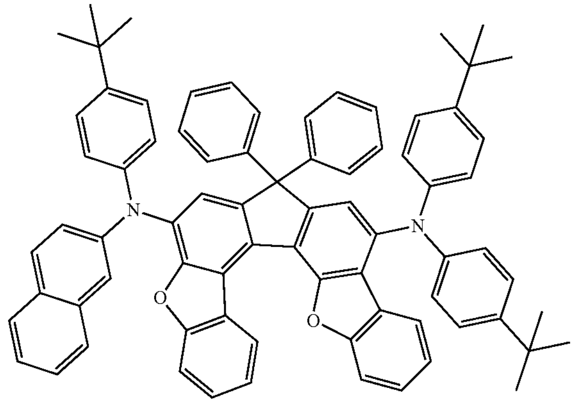
C-403
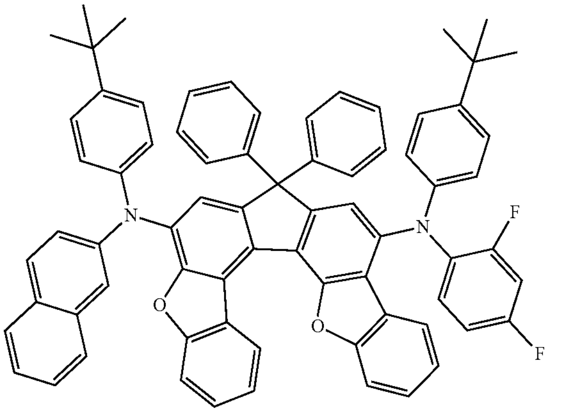
C-404
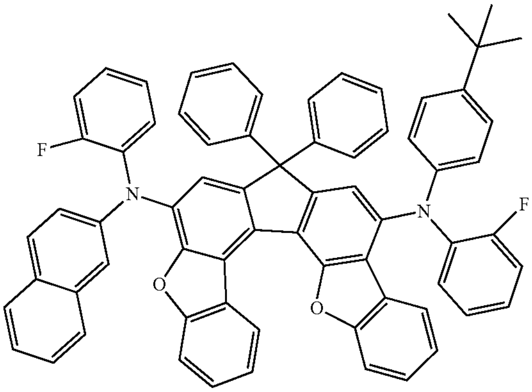

-continued
C-405
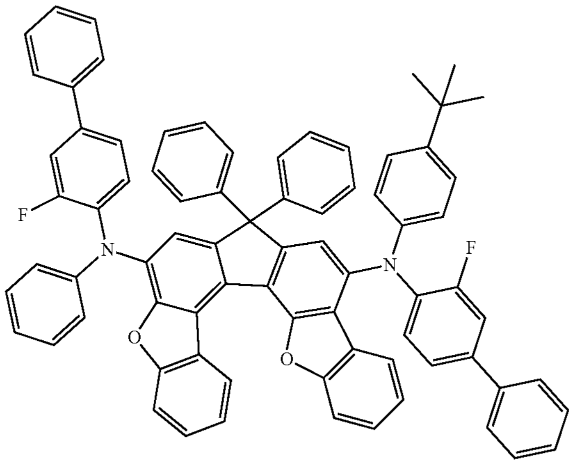
C-406
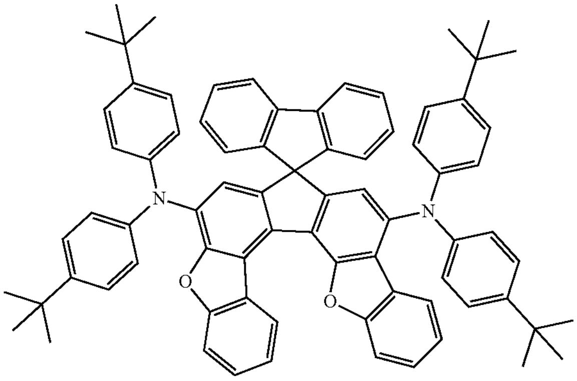
C-407
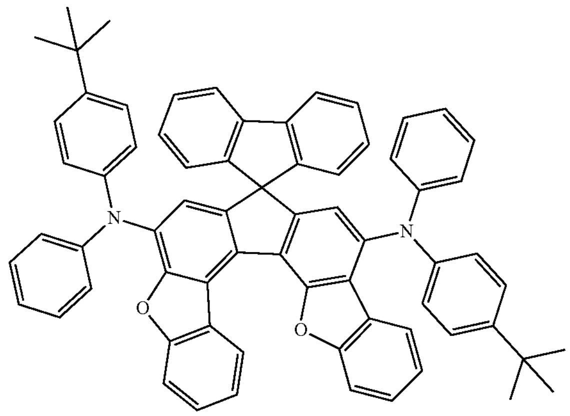
-continued
C-408
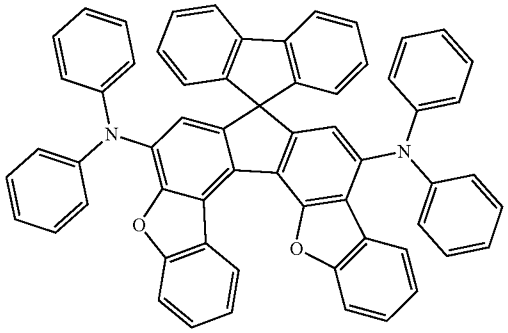
C-409
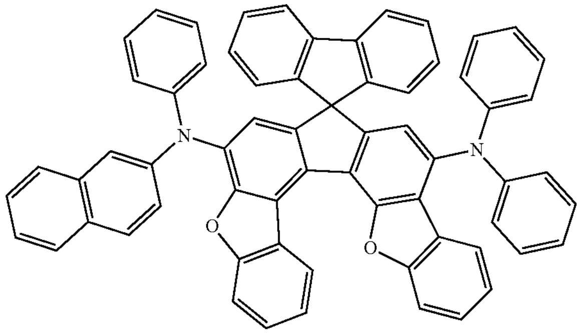
C-410
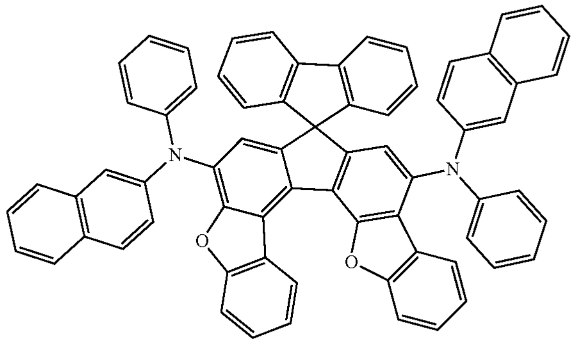
C-411
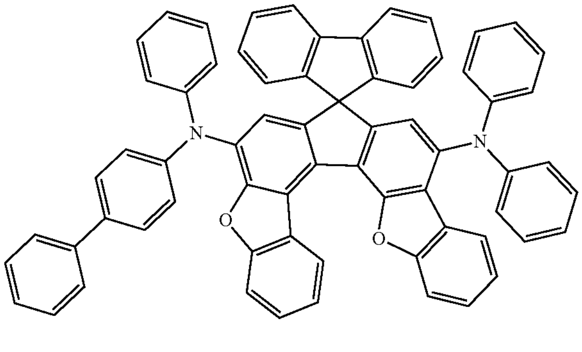

-continued
C-412
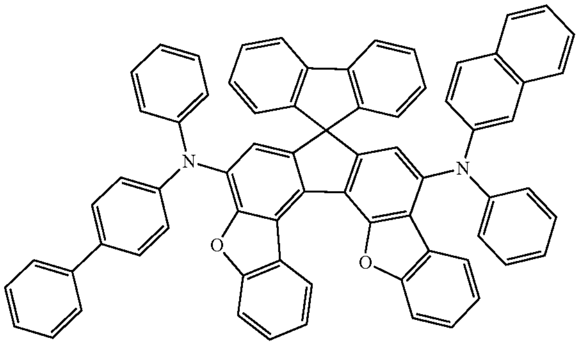
C-413
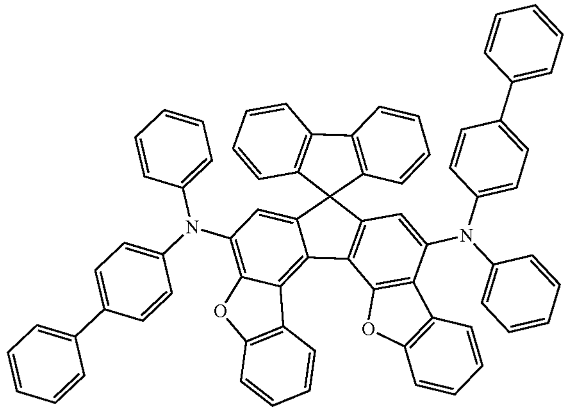
C-414
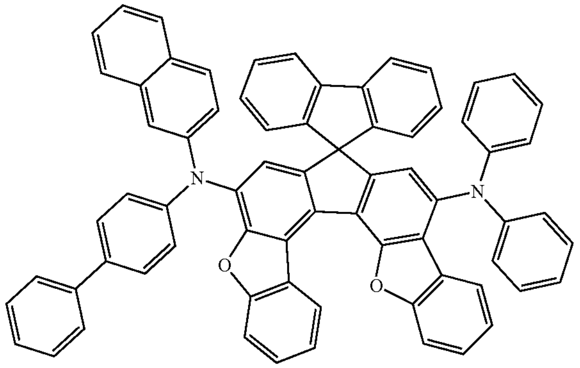
C-415
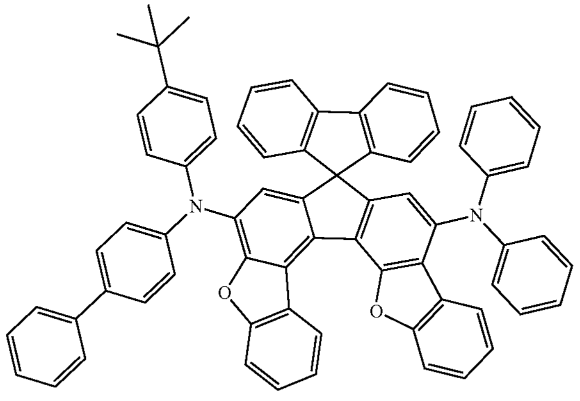
-continued
C-416
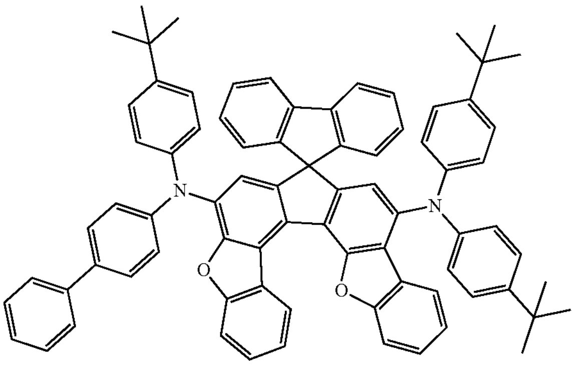
C-417
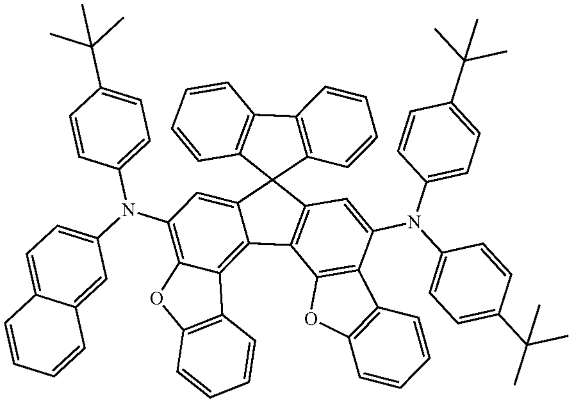
C-418
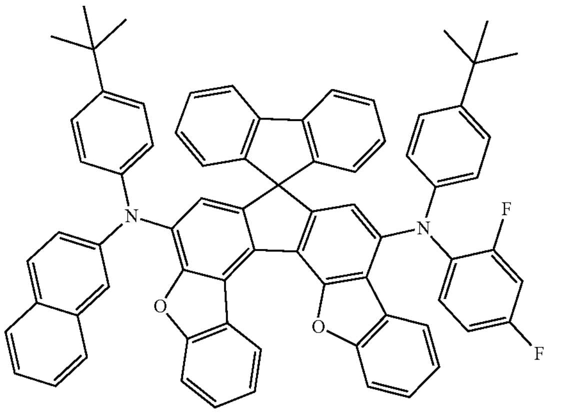

-continued
C-419
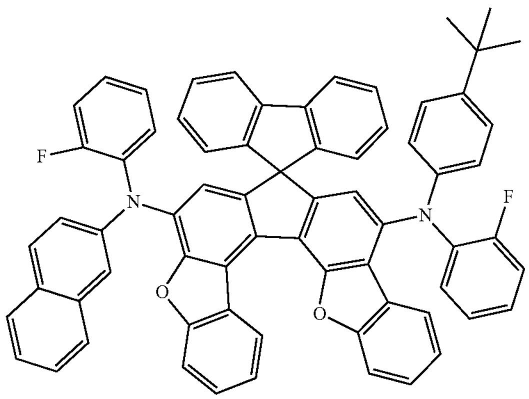
C-420
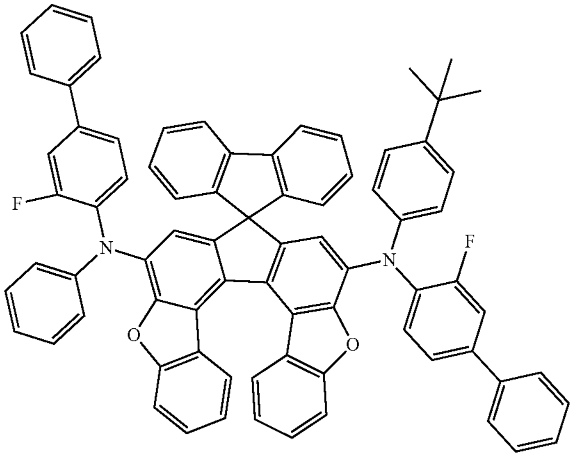
C-421
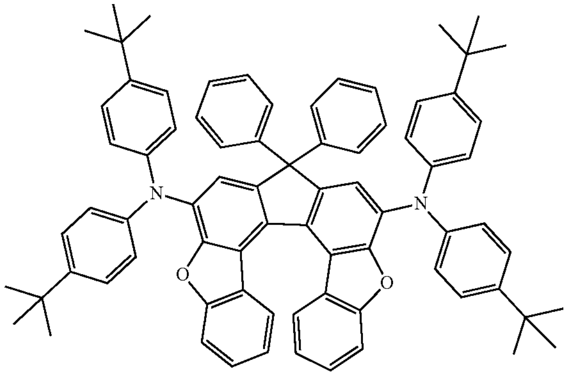
-continued
C-422
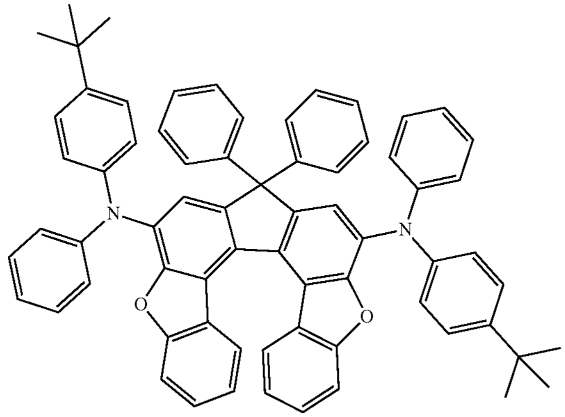
C-423
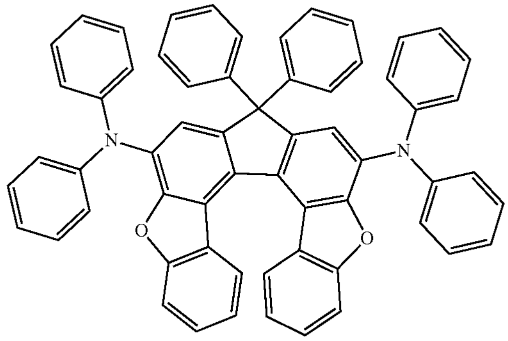
C-424
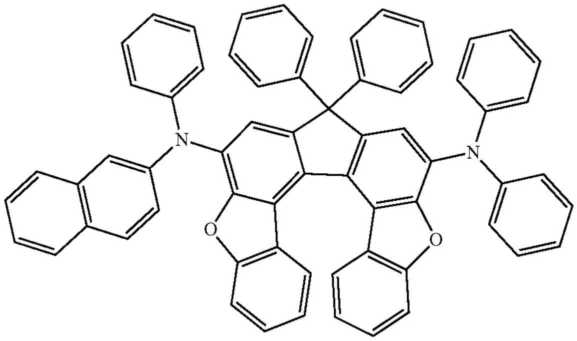
C-425
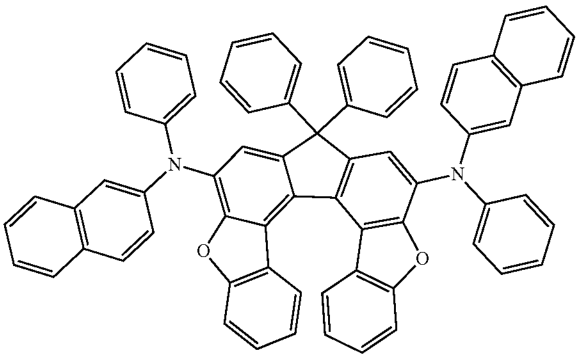

-continued
C-426
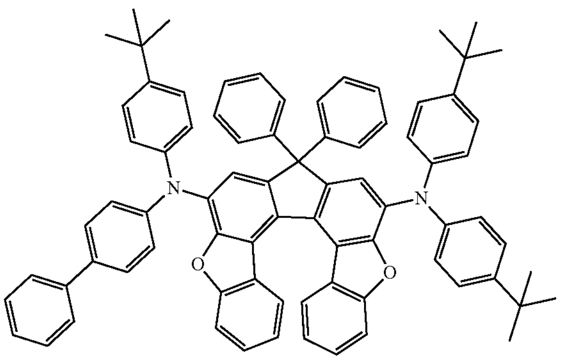
C-427
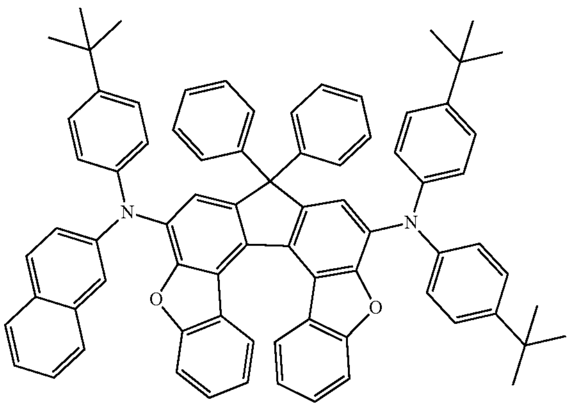
C-428
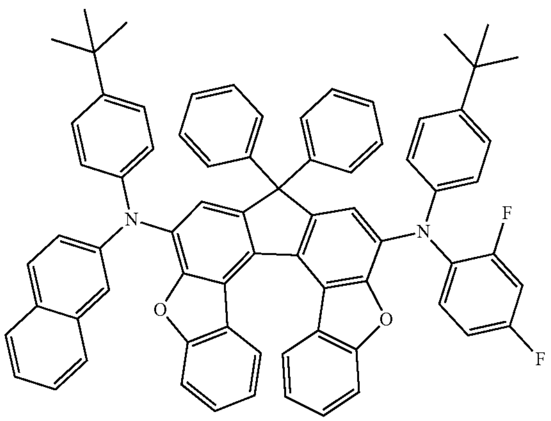
-continued
C-429
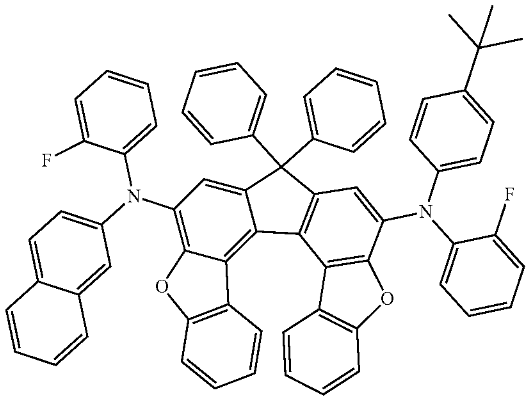
C-430
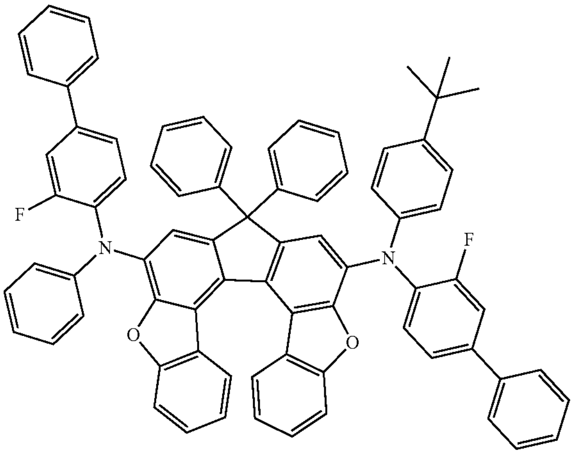
C-431
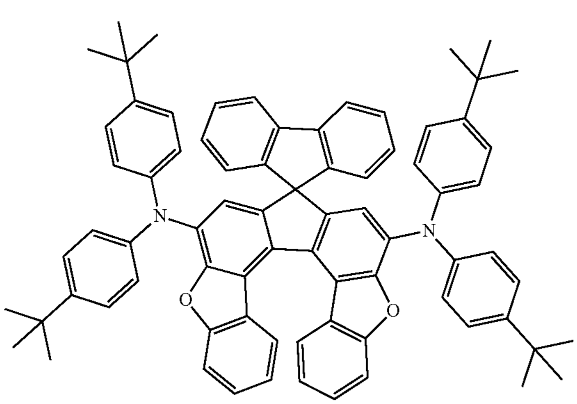

-continued
C-432
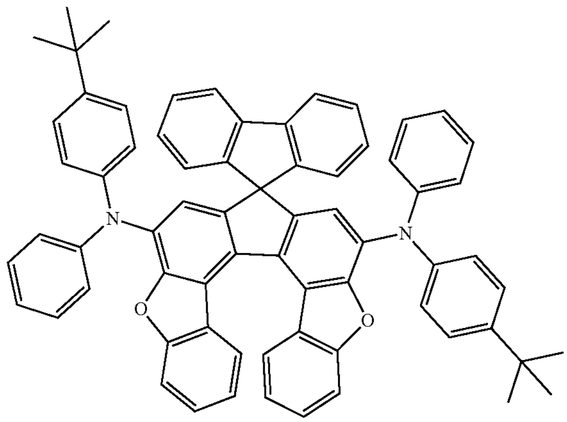
C-433
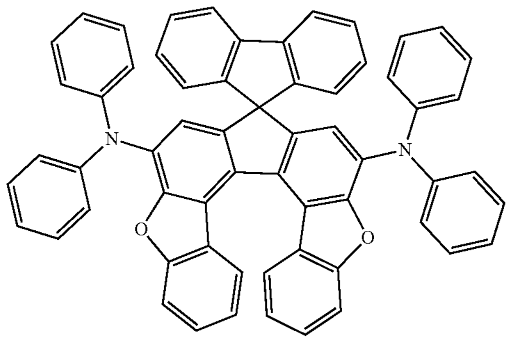
C-434
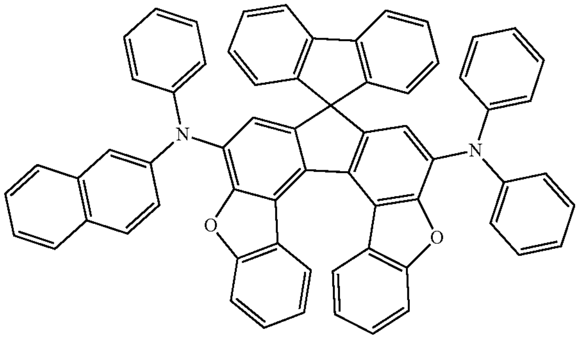
C-435
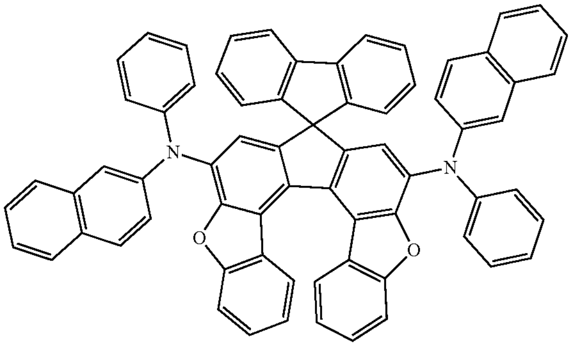
-continued
C-436
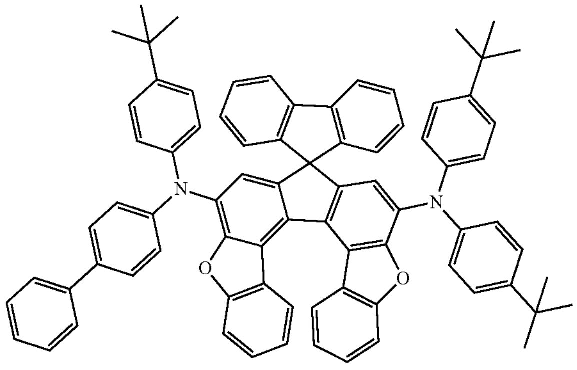
C-437
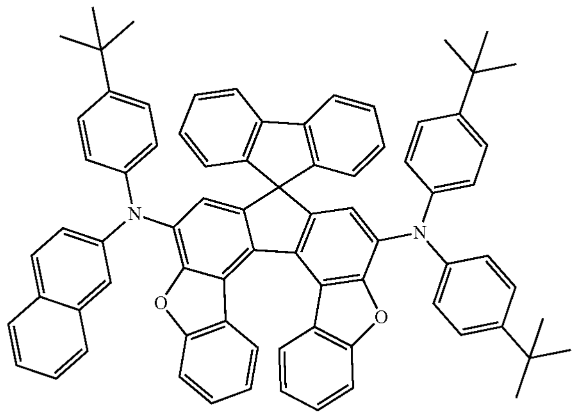
C-438
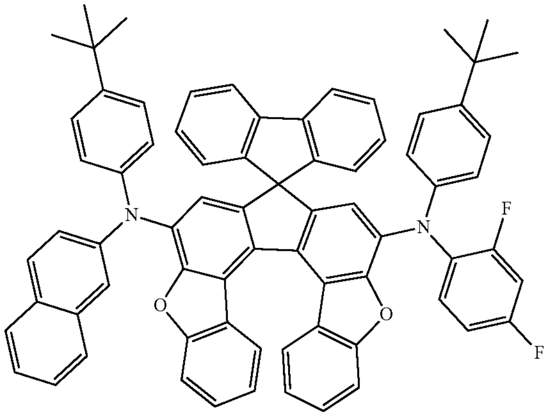

-continued
C-439
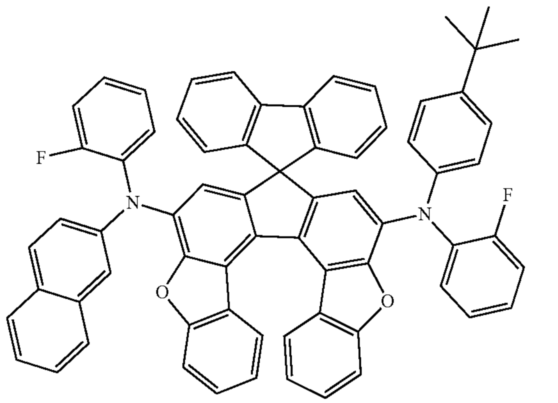
C-440
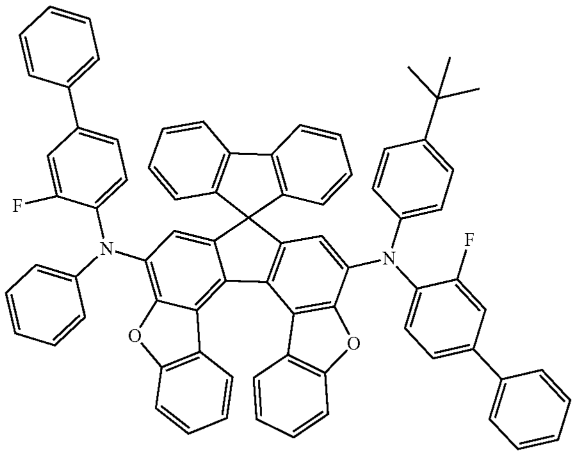
C-441
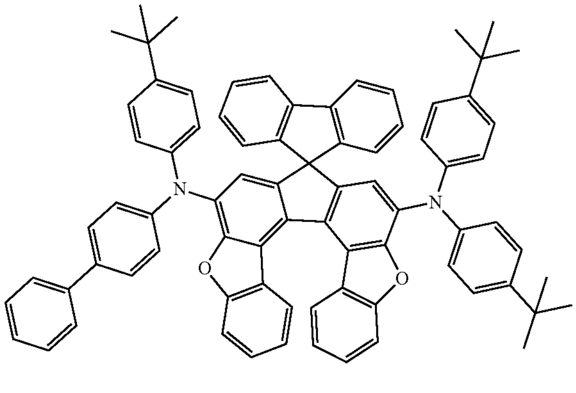
-continued
C-442
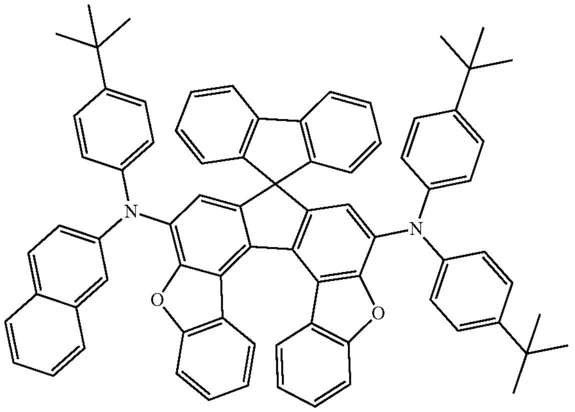
C-443
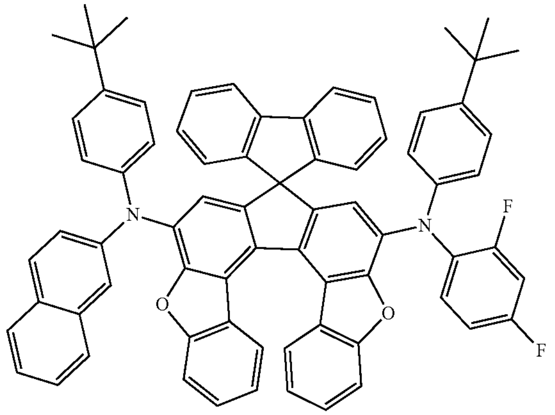
C-444
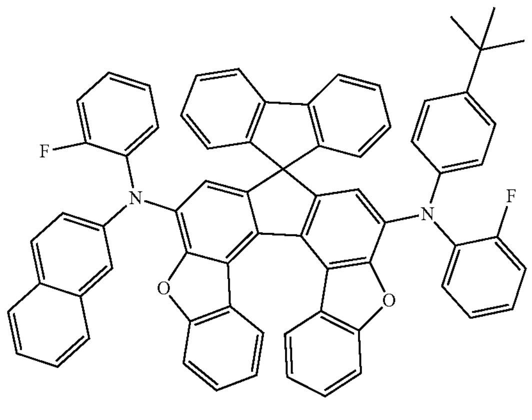

-continued
C-445
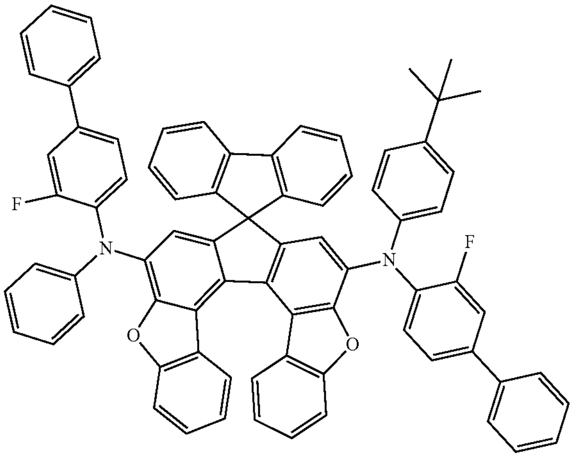
C-446
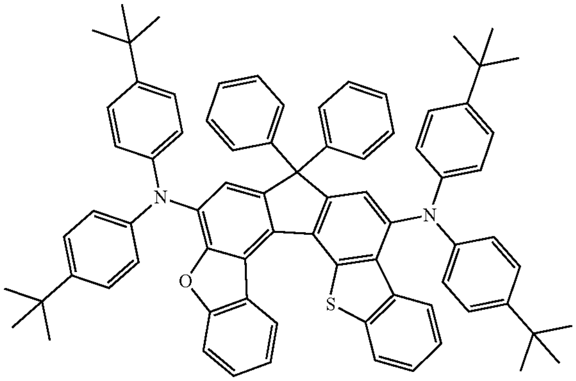
C-447
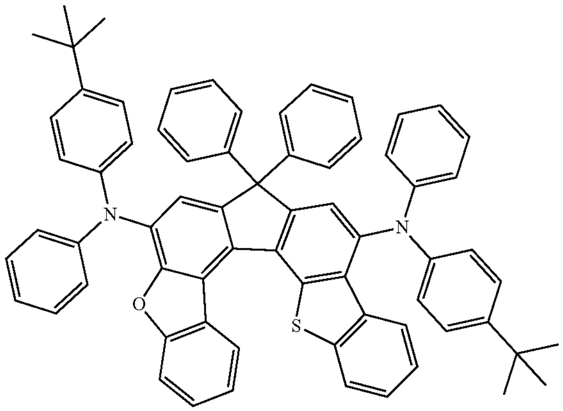
-continued
C-448
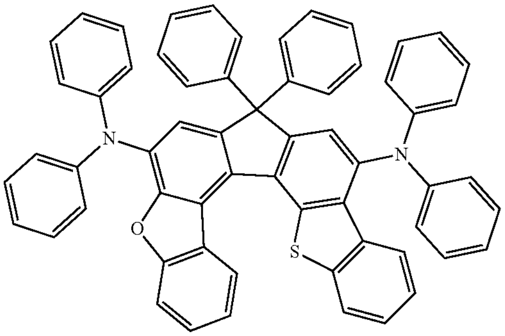
C-449
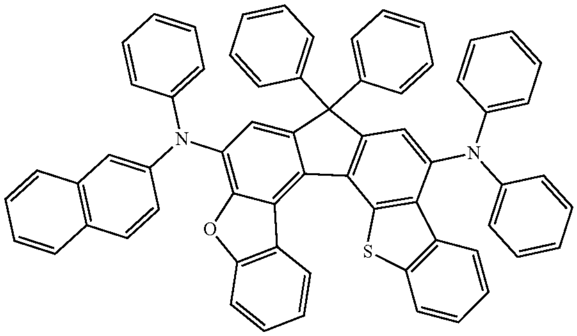
C-450
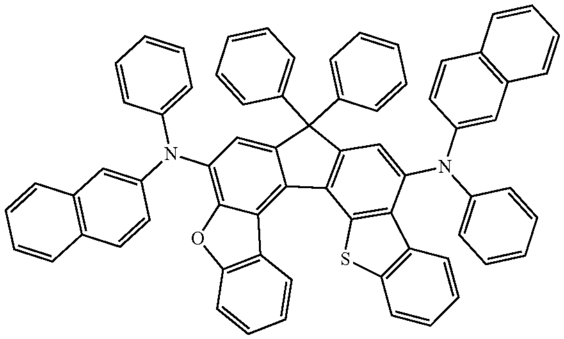
C-451
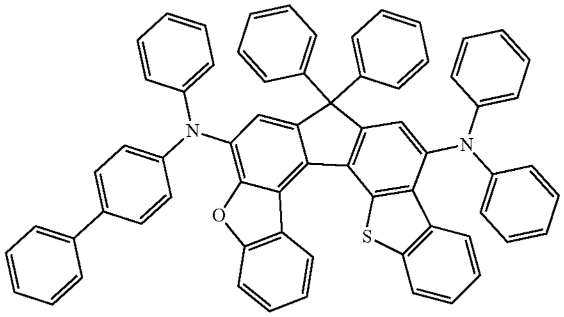

-continued
C-452
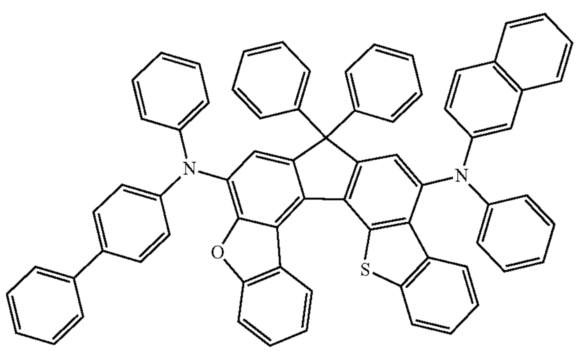
C-453
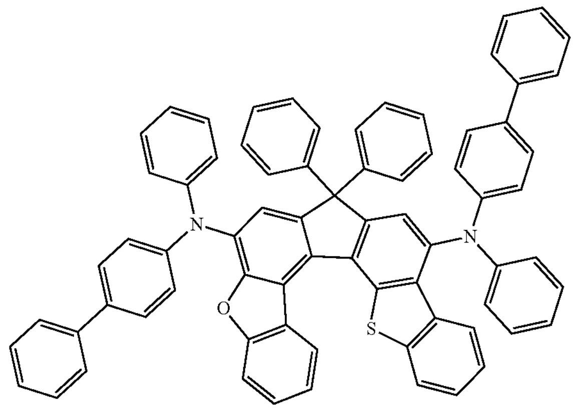
C-454
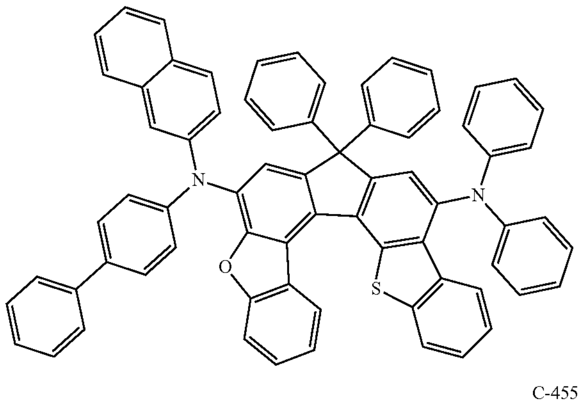
C-455
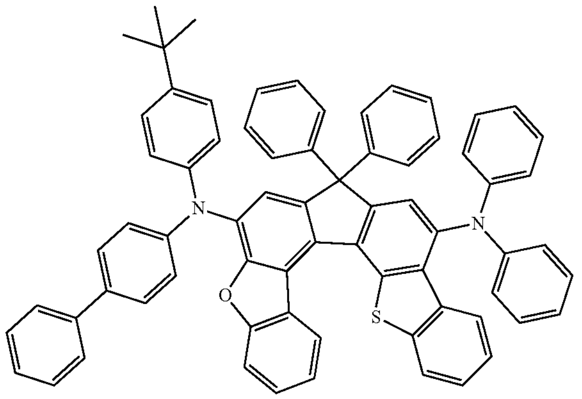
-continued
C-456
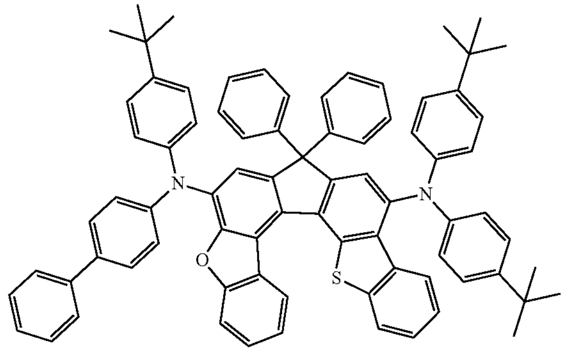
C-457
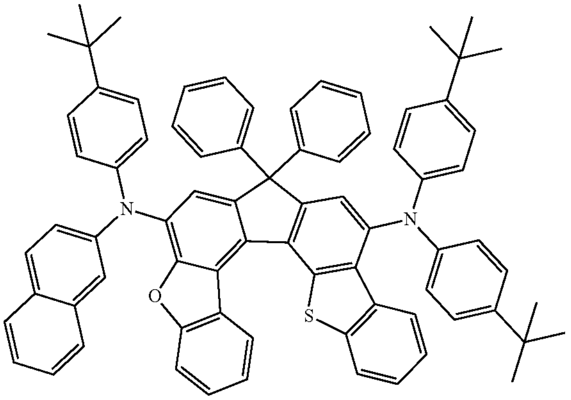
C-458
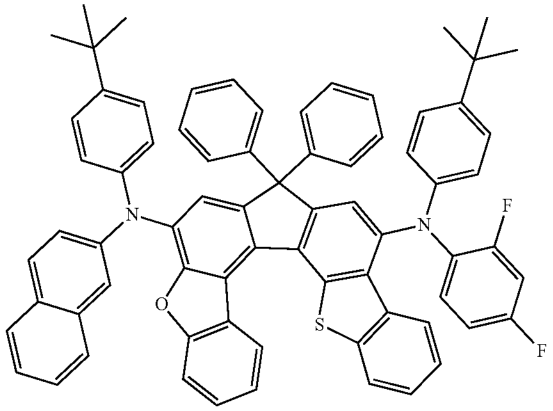
C-459
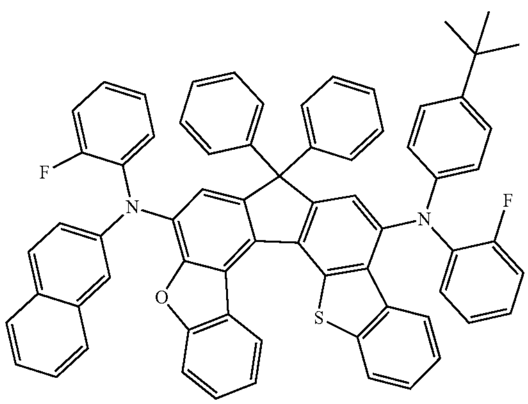

-continued
C-460
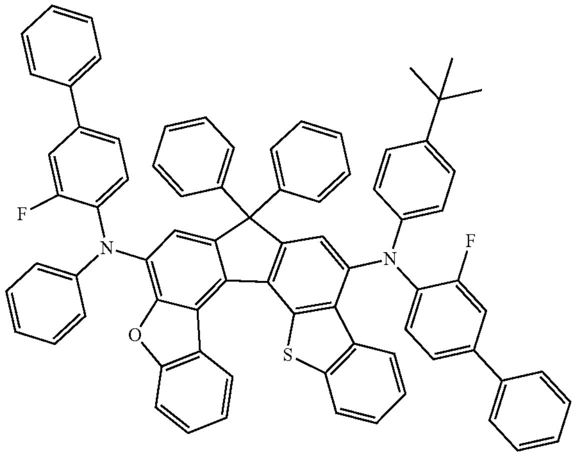
C-461
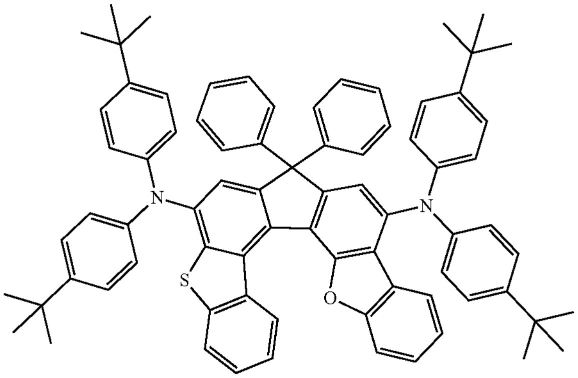
C-462
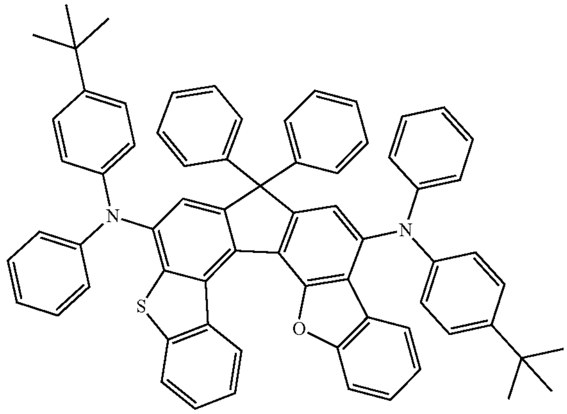
-continued
C-463
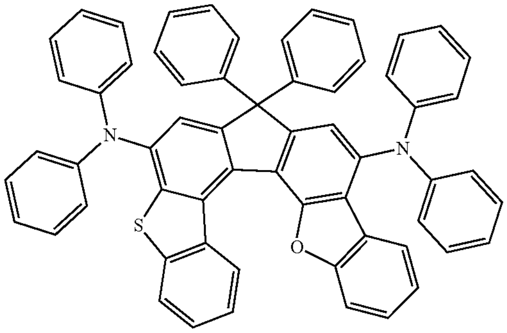
C-464
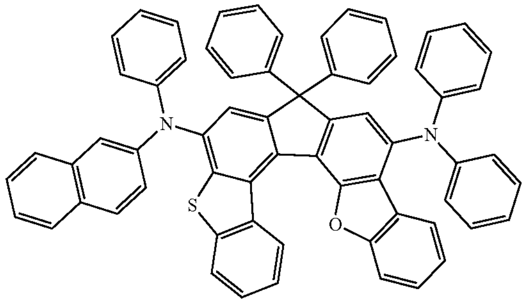
and
C-465
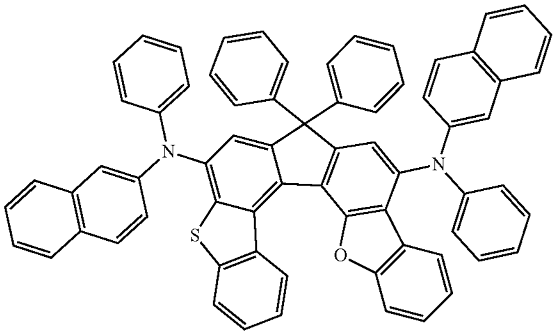
.
7. An organic electroluminescent device comprising the plurality of light-emitting materials according to claim 1.
8. The organic electroluminescent device according to claim 7, wherein the first compound is comprised as a host material, and the second compound is comprised as a dopant material.
* * * * *